United States Patent
Cai et al.

(10) Patent No.: US 11,207,420 B2
(45) Date of Patent: Dec. 28, 2021

(54) CYTOTOXIN AND CONJUGATE, USES OF SAME AND PREPARATION METHOD THEREFOR

(71) Applicant: SICHUAN KELUN-BIOTECH BIOPHARMACEUTICAL CO., LTD., Chengdu (CN)

(72) Inventors: Jiaqiang Cai, Chengdu (CN); Tongtong Xue, Chengdu (CN); Shuai Song, Chengdu (CN); Jing Wang, Chengdu (CN); Qiang Tian, Chengdu (CN); Liang Xiao, Chengdu (CN); Hanwen Deng, Chengdu (CN); Liping Liu, Chengdu (CN); Zujian Tang, Chengdu (CN); Hong Zeng, Chengdu (CN); Rongrong Long, Chengdu (CN); Hongmei Song, Chengdu (CN); Qiang Zhang, Chengdu (CN); Guoqing Zhong, Chengdu (CN); Dengnian Liu, Chengdu (CN); Haitao Huang, Chengdu (CN); Ruibin Hu, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 0 days.

(21) Appl. No.: 16/497,415

(22) PCT Filed: Apr. 12, 2018

(86) PCT No.: PCT/CN2018/082809
§ 371 (c)(1),
(2) Date: Feb. 3, 2020

(87) PCT Pub. No.: WO2018/192407
PCT Pub. Date: Oct. 25, 2018

(65) Prior Publication Data
US 2020/0179529 A1 Jun. 11, 2020

(30) Foreign Application Priority Data

Apr. 19, 2017 (CN) .................. 201710258500.9
Jan. 30, 2018 (CN) .................. 201810086794.6
Jan. 30, 2018 (CN) .................. 201810087078.X

(51) Int. Cl.
| | |
|---|---|
| *A61K 47/68* | (2017.01) |
| *A61K 47/62* | (2017.01) |
| *A61P 35/00* | (2006.01) |
| *A61K 31/5386* | (2006.01) |
| *A61K 38/07* | (2006.01) |
| *C07K 7/02* | (2006.01) |
| *A61K 38/08* | (2019.01) |
| *A61K 39/00* | (2006.01) |

(52) U.S. Cl.
CPC ...... *A61K 47/6849* (2017.08); *A61K 31/5386* (2013.01); *A61K 38/07* (2013.01); *A61K 38/08* (2013.01); *A61K 47/62* (2017.08); *A61P 35/00* (2018.01); *C07K 7/02* (2013.01); *A61K 2039/505* (2013.01)

(58) Field of Classification Search
CPC ............ A61K 47/6803; A61K 47/6849; A61K 38/08; A61K 35/00; C07K 7/02
See application file for complete search history.

(56) References Cited

U.S. PATENT DOCUMENTS

| | | | |
|---|---|---|---|
| 5,410,024 | A | 4/1995 | Pettit et al. |
| 5,767,237 | A | 6/1998 | Sakakibara et al. |
| 2011/0020343 | A1 | 1/2011 | Senter et al. |
| 2014/0017265 | A1 | 1/2014 | Yurkovetskiy et al. |

FOREIGN PATENT DOCUMENTS

| | | | |
|---|---|---|---|
| CA | 3080236 | * | 6/2019 |
| CN | 1938046 | | 3/2007 |
| CN | 104379168 | | 2/2015 |
| CN | 106729743 | | 5/2017 |
| CN | 107029244 | | 8/2017 |
| CN | 201810230346.9 | * | 3/2018 |
| CN | 110903395 A | | 3/2020 |
| WO | WO 2009/117531 | | 9/2009 |
| WO | WO 2011/097627 | | 8/2011 |
| WO | WO 2013/072813 | | 5/2013 |
| WO | WO 2014/144878 A2 | | 9/2014 |
| WO | WO 2016/205738 A2 | | 12/2016 |
| WO | WO 2017/004144 A1 | | 1/2017 |

(Continued)

OTHER PUBLICATIONS

Fosgerau. Drug Discovery Today, 2015, 29 (1), 122-128 (Year: 2015).*
International Search Report for International Application No. PCT/CN2018/082809, dated Jul. 9, 2018.
Written Opinion of the International Searching Authority for International Application No. PCT/CN2018/082809, dated Jul. 9, 2018.
Extended European Search Report for EP Application No. 18787805.3, dated Mar. 12, 2021.
International Search Report for International Application No. PCT/CN2018/120125, dated Mar. 18, 2019.
Written Opinion of the International Searching Authority for International Application No. PCT/CN2018/120125, dated Mar. 18, 2019.

(Continued)

*Primary Examiner* — Noble E Jarrell
(74) *Attorney, Agent, or Firm* — Finnegan Henderson Farabow Garrett & Dunner LLP

(57) ABSTRACT

Provided is a method for modifying a chimeric antigen receptor-modified T cell (CAR-T cell). The method comprises expressing an SCFV-CDS TM-4-1BB-CD3ζ molecule in a T cell. The CAR-T cell prepared using the method can specifically recognize and bind to a tumor cell with elevated expression of a ROBO1 protein, and can be used to prevent and treat a corresponding tumor-related disease.

36 Claims, 10 Drawing Sheets

Specification includes a Sequence Listing.

(56) References Cited

FOREIGN PATENT DOCUMENTS

| WO | WO 2018/183041 A1 | 10/2018 |
| WO | WO 2019/114666 A1 | 6/2019 |

OTHER PUBLICATIONS

Narihiro Toda et al., "Rapid, Stable, Chemoselective Labeling of Thiols with Julia-Kocienski-Like Reagents: A Serum-Stable Alternative to Maleimide-Based Protein Conjugation," *Angew. Chem. Int. Ed.* 2013, vol. 52(48), pp. 12592-12596.

Xiuling Li et al., "Site-Specific Dual Antibody Conjugation via Engineered Cysteine and Selenocysteine Residues," *Bioconjug Chem.* 2015, vol. 26(11), pp. 2243-2248.

James T. Patterson et al., "Improving the Serum Stability of Site-Specific Antibody Conjugates with Sulfone Linkers," *Bioconjugate Chem.* 2014, vol. 25, pp. 1402-1407.

Xiaofei Liang et al., "Discovery of 2-((3-Amino-4-methylphenyl)amino)-N-(2-methyl-5-(3-(trifluoromethyl)benzamido)phenyl)-4-(methylamino)pyrimidine-5-carboxamide (CHMFL-ABL-053) as a Potent, Selective, and Orally Available BCR-ABL/SRC/p38 Kinase Inhibitor for Chronic Myeloid Leukemia," *J. Med. Chem.* 2016, vol. 59, pp. 1984-2004.

Sung-Ju Moon et al., "Antibody Conjugates of 7-Ethyl-10-hydroxycamptothecin (SN-38) for Targeted Cancer Chemotherapy," *J. Med. Chem.*, 2008, vol. 51 (21), 6916-6926.

\* cited by examiner

SEQUENCE LISTING

```
<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Synthetic peptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic peptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

CYTOTOXIN AND CONJUGATE, USES OF SAME AND PREPARATION METHOD THEREFOR

This application is a national stage filing under 35 U.S.C. § 371 of International Application No. PCT/CN2018/082809, filed on Apr. 12, 2018, which claims the benefit of the filing date of Chinese Patent Application No. 201710258500.9, filed on Apr. 19, 2017; Chinese Patent Application No. 201810087078.X, filed on Jan. 30, 2018; and Chinese Patent Application No. 201810086794.6, filed on Jan. 30, 2018; each of which is incorporated herein by reference.

TECHNICAL FIELD

The present invention belongs to the technical field of medicine, relates to a cytotoxin, a linker and a conjugate, a method for preparing the cytotoxin and the conjugate, and uses of the cytotoxin and of the conjugate in preventing and/or treating a tumor disease.

BACKGROUND ART

Chemotherapy was a conventional therapy for cancer, but the small molecule drugs with high-killing rate can also kill normal cells and cause serious side effects. Targeted anti-tumor drugs have become a hot spot in the field of cancer research due to their simultaneous tumor-targeting and anti-tumor activities. Since the 20$^{th}$ century, biomacromolecules (such as therapeutic antibodies or antibody fragments) have made breakthroughs in the targeted therapy of tumors. Nevertheless, biomacromolecules, though highly targeting, have limited therapeutic effects on solid tumors; while cytotoxic drugs, though having a high killing effect on cancer cells, lack targeting and often injure normal cells, causing serious toxic side effects.

In recent years, studies have found that therapeutic antibodies can be linked to cytotoxic drugs to form antibody-drug conjugates (ADCs). The ADC combines the targeting characteristic of antibodies with the cytotoxicity of small molecule cytotoxic drugs to become a "bio-missile". The antibody directs the ADC to bind to the targeted cell, then the ADC is internalized by the cell, consequently, the conjugated drug is released to treat diseases. Because the antibody has specificity and targeting to tumor cell-related targets, its application value is not only reflected in therapy, but also becomes an ideal carrier for drug targeted delivery, which reduces the side effects of the drug.

Typically, an ADC consists of an antibody, a cytotoxic drug, and a linker. A cytotoxic drug is covalently coupled to a monoclonal antibody via a linker; the antibody (e.g., monoclonal antibody) can specifically recognize a specific target on the surface of a tumor cell, thereby directing the ADC to the surface of the cancer cell, and allowing the ADC to enter the cancer cell through endocytosis; then, the cytotoxic drug can be released intracellularly, thereby achieving the effect of specifically killing the cancer cell without damaging the normal tissue cell. Some ADCs can specifically release toxins in a tumor microenvironment, and the toxins enter the cell in various ways to exert a killing effect.

Currently, there are four ADCs already on the market: Mylotarg (Gemtuzumab Ozogamicin), Adcetris (Brentuximab Vedotin, CD30 mAb-MMAE), Kadcyla (Trastuzumab Emtansine, trastuzumab-maytansinoid) and Besponsa (Inotuzumab ozogamicin, CD22 mAb-calicheamicin). Due to its high toxic side effects and limited efficacy, Mylotarg has been withdrawn from the market by Pfizer on its own initiative.

CONTENTS OF THE INVENTION

In the present invention, the scientific and technical terms used herein have the meanings commonly understood by those skilled in the art, unless otherwise stated. Moreover, the cell culture, molecular genetics, nucleic acid chemistry, and immunology laboratory operating procedures used herein are all routine procedures widely used in the corresponding art. Also, for better understanding of the present invention, definitions and explanations of related terms are provided below.

In the present invention, the term "conjugate" refers to a substance obtained by linking a small molecule drug with a targeting moiety. In some embodiments of the present invention, the small molecule drug is linked to the targeting moiety via a linker. The linker can be cleaved in a specific environment (e.g., an intracellular low pH environment, a slightly acidic tumor microenvironment) or under a specific action (e.g., the action of a lysosomal protease), thereby causing the small molecule drug to separate from the targeting moiety. In some embodiments of the present invention, the linker comprises a cleavable or non-cleavable unit, such as a peptide or a disulfide bond. In some embodiments of the present invention, the small molecule drug is linked directly to the targeting moiety by a covalent bond that is capable of cleavage in a specific environment or under a specific action, thereby causing the small molecule drug to be separated from the targeting moiety.

In some embodiments of the present invention, the small molecule drug in the conjugate is a cytotoxic agent.

In the present invention, the term "cytotoxic agent" refers to a substance which inhibits or prevents the function of a cell and/or causes cell death or destruction, for example, radioisotopes such as $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioisotopes of Lu; chemotherapeutic agents, such as methotrexate, adriamycin, vincaalkaloids, vincristine, vinblastine, etoposide, doxorubicin, melphalan, mitomycin C, chlorambucil, daunorubicin or other intercalators; enzymes and fragments thereof, such as ribozymes; antibiotics; and toxins, such as small molecule toxins or enzymatically active toxins originated from bacteria, fungi, plant or animal, including fragments and/or variants thereof; growth inhibitors; drug modules; and a compound of formula (I) of the present invention or a pharmaceutically acceptable salt, solvate, hydrate, isomer thereof, or any crystalline form or racemate thereof. The term "toxin" refers to a substance that is capable of producing a detrimental effect on the growth or proliferation of a cell.

The term "small molecule" is defined herein as a small molecule drug having cytotoxic activity.

In the present invention, the term "linker" refers to a fragment that links a small molecule drug with a targeting moiety.

In the present invention, the term "targeting moiety" refers to a moiety in a conjugate that is capable of specifically binding to a target (or a portion of a target) on the surface of a cell. The conjugate can be delivered to a specific cell population by interaction of the targeting moiety with the target.

In the present invention, when the targeting moiety in the conjugate is an antibody, the conjugate may be referred to as a "drug-antibody conjugate". In the present invention, "drug-antibody conjugate" and "immunoconjugate" are used interchangeably.

As used herein, the term "antibody" is used in its broadest sense and includes intact monoclonal antibodies, polyclonal antibodies, and multispecific antibodies (e.g., bispecific antibodies) formed from at least two intact antibodies, as long as they have the desired biological activity. As used herein, "antibody" and "immunoglobulin" are used interchangeably.

As used herein, the term "monoclonal antibody" refers to an antibody from a population of substantially homogeneous antibodies, i.e., the individual antibodies constituting the population are completely identical except for a few natural mutations that may be present. Monoclonal antibody has a high specificity against one determinant (epitope) of an antigen, while polyclonal antibodies contain different antibodies against different determinants (epitopes). In addition to high specificity, monoclonal antibody has the advantage of being free from contamination by other antibodies during synthesis. The modifier "monoclonal" as used herein indicates that the character of the antibody as being obtained from a substantially homogeneous population of antibodies, and shall not be construed as being necessarily prepared by a particular method.

In some embodiments of the present invention, the monoclonal antibody also specifically includes a chimeric antibody, i.e., an antibody wherein a portion of the heavy and/or the light chain is identical or homologous to a certain antibody, a certain class or a certain subclass of antibodies, and the rest is identical or homologous to another antibody, another class or another subclass of antibodies, as long as they have the desired biological activity (see, for example, U.S. Pat. No. 4,816,567; and Morrison et al., 1984, PNAS, 81: 6851-6855). A chimeric antibody useful in the present invention includes a primatized antibody comprising a variable region of antigen binding sequence from non-human primates (e.g., ancient monkeys, orangutans and the like) and a human constant region sequence.

The term "antibody fragment" refers to a portion of an antibody, preferably an antigen binding region or variable region. Examples of the antibody fragment include Fab, Fab', F(ab')2, Fd, Fv, dAb and complementarity determining region fragment, diabody, linear antibodys and single chain antibody molecule.

The term "bispecific antibody", also referred to as "bifunctional antibody conjugate", refers to a conjugate formed by a first antibody (fragment) and a second antibody (fragment) through a coupling arm. The conjugate exhibits the activities of individual antibodies and thus is bifunctional and bispecific.

The term "multispecific antibody" includes, for example, trispecific antibody and tetraspecific antibody, wherein the former refers to an antibody having three different antigen binding specificities and the latter refers to an antibody having four different antigen binding specificities.

The term "intact antibody" refers to an antibody comprising an antigen-binding variable region, a light chain constant region (CL) and a heavy chain constant region (CH1, CH2 and CH3). The constant region can be a native sequence (e.g., a human native constant region sequence) or an amino acid sequence variant thereof. An intact antibody is preferably an intact antibody having one or more effector functions.

The term "probody" is a modified antibody comprising an antibody or an antibody fragment which specifically binds to its target and is capable of coupling to a masking group, wherein the masking group is such a group that the dissociation constant for binding the antibody or antibody fragment to its target in the presence of said group is at least 100-fold or 1000-fold, or 10,000-fold greater than that in absence of said group.

In the present invention, a "humanized" form of a non-human (e.g., murine) antibody refers to a chimeric antibody comprising a minimal amount of non-human immunoglobulin sequences. Most humanized antibodies are obtained by replacing residues in hypervariable region of human recipient immunoglobulin with residues in hypervariable region of a non-human (e.g., mice, rat, rabbit, or non-human primate) (donor antibody) having the desired specificity, affinity, and function. In some embodiments, the framework region (FR) residues of the human immunoglobulin are also replaced with the residues of the non-human antibody. Moreover, a humanized antibody may also comprise residues that are not found in the recipient antibody or in the donor antibody. These modifications are intended to further optimize the performance of the humanized antibody. A humanized antibody generally comprise at least one, usually two variable regions, wherein all or nearly all of hypervariable loops correspond to those of the non-human immunoglobulin, while FRs are completely or almost completely the sequences of the human immunoglobulin. A humanized antibody can also comprise at least a portion of an immunoglobulin constant region (Fc, typically human immunoglobulin Fc). For details, see, for example, Jones et al, 1986, Nature, 321: 522-525; Riechmann et al, 1988, Nature, 332: 323-329; and Presta, 1992, Curr Op Struct Bwl 2: 593-596.

Intact antibody can be divided into different "classes" based on the amino acid sequence of the heavy chain constant region. The main five classes are IgA, IgD, IgE, IgG and IgM, several of which can further be divided into different "subclasses" (isotypes), such as IgG1, IgG2, IgG3, IgG4, IgA1 and IgA2. The heavy chain constant regions of the five classes of antibodies are called α, β, ε, γ and μ, respectively. Subunit structures and three-dimensional configurations of different classes of immunoglobulins are well known in the art.

In the present invention, although the amino acid substitution in the antibody is, in most cases, but not limited to substitution by L-amino acid. In some embodiments, one or more D-amino acids can be included in the peptide chain of the antibody. It is believed that a peptide comprising D-amino acids is more stable and not readily degradable in mouth, intestine or plasma than a peptide comprising only L-amino acids.

The monoclonal antibodies used in the present invention can be produced by a number of methods. For example, monoclonal antibodies for use in the present invention can be obtained by hybridoma methods using a variety of species (including cells of mice, hamsters, rats, and humans) (see, for example, Kohler et al., 1975, Nature, 256: 495), or alternatively by recombinant DNA techniques (see, for example, U.S. Pat. No. 4,816,567), or isolated from phage antibody libraries (see, for example, Clackson et al, 1991, Nature, 352: 624-628; and Marks et al, 1991, Journal of Molecular Biology, 222: 581-597). Monoclonal antibodies useful in the present invention include, but are not limited to, monoclonal antibodies against Her 2, such as trastuzumab, pertuzumab, or monoclonal antibodies against Trop-2, such as Sacituzumab (i.e., Isactuzumab or hRS7 antibody).

In some embodiments of the present invention, the targeting moiety is trastuzumab or pertuzumab. Trastuzumab is a monoclonal antibody against Her 2 of which the amino acid sequence is known to those skilled in the art, and the schematic sequence of which can be seen in, for example, CN103319599, wherein the Lys at the terminal is easily deleted, but such a deletion does not affect the biological activity, see Dick, L. W. et al., Biotechnol. Bioeng., 100: 1132-1143.

Exemplary heavy chain sequences and light chain sequences of trastuzumab may include, for example, SED ID NO: 1 and SED ID NO: 2. In the present invention, when the heavy chain sequence and light chain sequence of trastuzumab are mentioned or involved, they are described using the sequences shown by SED ID NO: 1 and SED ID NO: 2, respectively. Exemplary heavy chain sequences and light chain sequences of pertuzumab may include SEQ ID No. 16 and SEQ ID No. 15 that are described in U.S. Pat. No. 7,560,111.

In some embodiments of the present invention, the targeting moiety is an anti-Trop-2 antibody which is RS7 (i.e., Sacituzumab of the present invention) as described in U.S. Pat. No. 7,517,964, or hRS7 (i.e., Sacituzumab of the present invention) as described in US 2012/0237518. Anti-Trop-2 antibodies useful in the present invention can also be screened through vector designing, constructing and approaches to construct antibody libraries that display antibodies, as disclosed in CN103476941A, or obtained by screening G-MAB® library of Sorrento Therapeutics, Inc.

In the present invention, ErbB2 and Her2 are used interchangeably, both of which represent a human Her2 protein with a native sequence (Genebank accession number: X03363, see, for example, Semba et al., 1985, PNAS, 82: 6497-6501; and Yamamoto et al., 1986, Nature, 319: 230-234), and a functional derivative thereof, such as amino acid sequence variant. ErbB2 represents the gene encoding human Her2, and neu represents the gene encoding rat p185neu. In some embodiments, the compound or conjugate of the present invention is capable of inhibiting or killing a cell expressing ErbB2 receptor, such as breast cancer cell, ovarian cancer cell, gastric cancer cell, endometrial cancer cell, salivary gland cancer cell, lung cancer cell, renal cancer cell, colon cancer cell, thyroid cancer cell, pancreatic cancer cell, bladder cancer cell or liver cancer cell.

In the present invention, Trop-2 or TROP2 refers to human trophoblast cell-surface antigens 2, also known as TACSTD2, M1S1, GA733-1, EGP-1, which is a cell surface receptor expressed by many human tumor (such as breast cancer, colorectal cancer, lung cancer, pancreatic cancer, ovarian cancer, prostate cancer, cervical cancer) cells. In some embodiments, the compound or conjugate of the present invention is capable of inhibiting or killing a cell expressing TROP2 receptor, such as breast cancer cell, colorectal cancer cell, lung cancer cell, pancreatic cancer cell, ovarian cancer cell, prostate cancer cell, cervical cancer cell.

As used herein, the term "$C_{1-6}$ alkyl" refers to a linear or branched alkyl group having 1 to 6 carbon atoms, and includes, for example, "$C_{1-4}$ alkyl", "$C_{1-3}$ alkyl" and the like. Specific examples thereof include, but are not limited to, methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, and the like.

As used herein, the term "$C_{2-6}$ alkenyl" refers to a linear, branched or cyclic alkenyl group containing at least one double bond and having 2 to 6 carbon atoms, including, for example, "$C_{2-4}$ alkenyl" and the like. Examples thereof include, but are not limited to, vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl, 1,4-cyclohexadienyl and the like.

As used herein, the term "$C_{2-6}$ alkynyl" refers to a linear or branched alkynyl group containing at least one triple bond and having 2 to 6 carbon atoms, including, for example, "$C_{2-4}$ alkynyl" and the like. Examples thereof include, but are not limited to, ethynyl, propynyl, 2-butynyl, 2-pentynyl, 3-pentynyl, 4-methyl-2-pentynyl, 2-hexynyl, 3-hexynyl, 5-methyl-2-hexynyl and the like.

As used herein, the term "halogen" includes fluoro, chloro, bromo, iodo.

As used herein, the term "3-8 membered cycloalkyl" or "$C_{3-8}$ cycloalkyl" refers to a saturated cyclic alkyl group containing from 3 to 8 carbon atoms, including, for example, "3-6 membered cycloalkyl", "4-6 membered cycloalkyl group", "5-7 membered cycloalkyl group" or "5-6 membered cycloalkyl group" and the like. Specific examples thereof include, but are not limited to, cyclopropyl, cyclobutyl, cyclopentyl, cyclohexyl, cycloheptyl, cyclooctyl and the like.

As used herein, the term "3-7 membered aliphatic heterocyclic group" refers to a cyclic group containing from 3 to 7 ring atoms wherein at least one ring atom is a hetero atom such as a nitrogen atom, an oxygen atom or a sulfur atom. Optionally, a ring atom (e.g., a carbon atom, a nitrogen atom, or a sulfur atom) in the cyclic structure may be substituted with an oxygen atom. The "3-7 membered heterocyclic group" includes, for example, "3-7 membered nitrogen-containing heterocyclic group", "3-7 membered oxygen-containing heterocyclic group", "3-6 membered heterocyclic group", "3-6 membered oxygen-containing heterocyclic group", "4-7 membered heterocyclic group", "4-6 membered heterocyclic group", "5-7 membered heterocyclic group", "5-6 membered heterocyclic group", "5-6 membered nitrogen-containing heterocyclic group", including but not limited to oxiranyl, oxocyclobutyl, pyrrolidinyl, tetrahydrofuranyl, piperidinyl, piperazinyl, tetrahydropyranyl, homopiperazinyl and the like.

As used herein, the term "6-12 membered spiro ring group" refers to a cyclic structure containing from 6 to 12 ring carbon atoms formed by two or more cyclic structures that share one carbon atom with each other. Optionally, a carbon atom in the cyclic structure can be substituted with an oxygen atom. The "6-12 membered spiro ring group" includes, for example, "6-11 membered spiro ring group", "6-10 membered spiro ring group", "7-10 membered spiro ring group", "7-9 membered spiro ring group" "7-8 membered spiro ring group", "9-10 membered spiro ring group", "3-10 membered spiro ring group" and the like. Specific examples thereof include, but are not limited to:

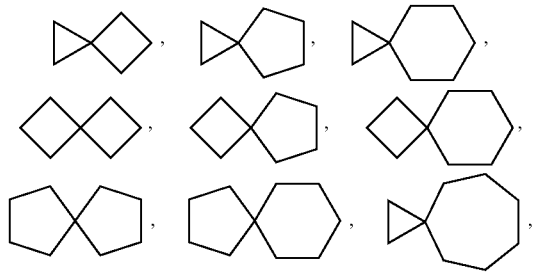

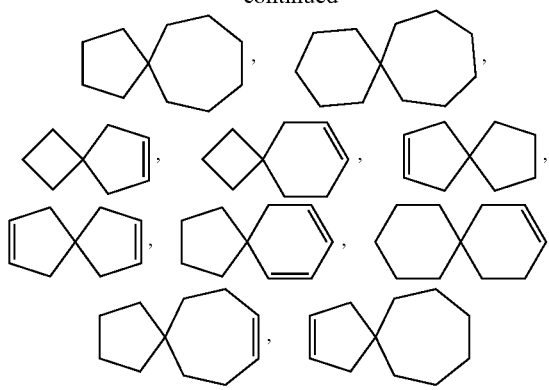

and the like.

As used herein, the term "6-12 membered bridged ring group" refers to a cyclic structure containing from 6 to 12 ring carbon atoms formed by two or more ring structures that share two non-adjacent carbon atoms with each other. Optionally, a carbon atom in the cyclic structure can be substituted with an oxygen atom. The "6-12 membered bridged ring group" includes, for example, "6-11 membered bridged ring group", "5-10 membered bridged ring group", "7-10 membered bridged ring group", "7-9 membered bridged ring group", "7-8 membered bridged ring group", "9-10 membered bridged ring group", "3-10 membered bridged ring group" and the like. Specific examples thereof include, but are not limited to:

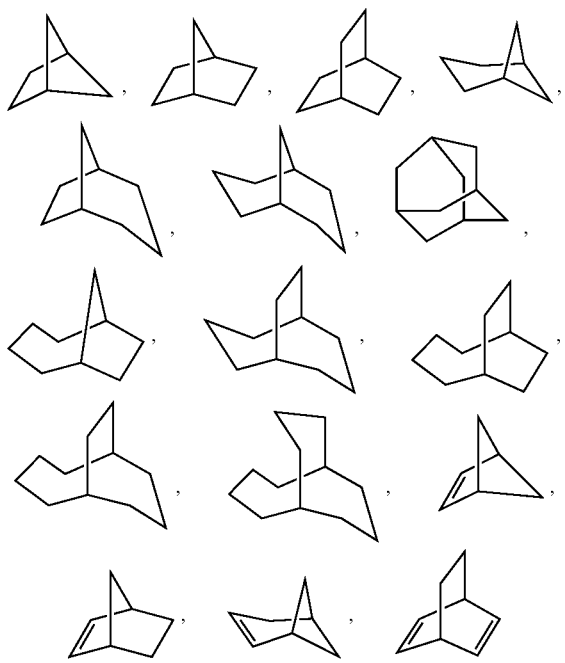

and the like.

As used herein, the term "6-12 membered fused ring group" refers to a cyclic structure containing 6 to 12 ring carbon atoms formed by two or more ring structures that share two adjacent atoms with each other, including "6-11 membered fused ring group", "6-10 membered fused ring group", "6-8 membered fused ring group", "10-12 membered fused ring group", "7-10 membered fused ring group". Examples thereof include, but are not limited to:

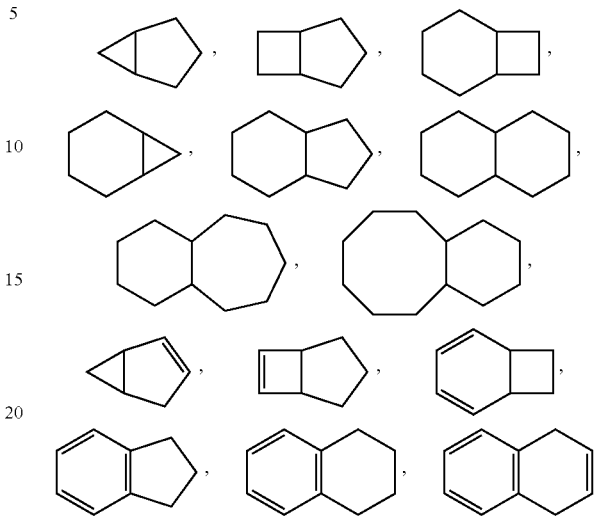

and the like.

As used herein, the term "6-12 membered spiro heterocyclic group" refers to a cyclic structure containing from 6 to 12 ring atoms, wherein at least one ring atom is a hetero atom such as a nitrogen atom, an oxygen atom or a sulfur atom, formed by two or more ring structures that share one ring atom with each other. Optionally, a ring atom (e.g., a carbon atom, a nitrogen atom, or a sulfur atom) in the cyclic structure can be substituted with an oxygen atom. The "6-12 membered spiro heterocyclic group" includes, for example, "6-11 membered spiro heterocyclic group", "5-10 membered spiro heterocyclic group", "7-11 membered spiro heterocyclic group", "7-10 spiro heterocyclic group", "7-9 membered spiro heterocyclic group", "7-8 membered spiro heterocyclic group", "9-10 membered spiro heterocyclic group", "3-10 membered spiro heterocyclic group" and the like. Specific examples thereof include, but are not limited to:

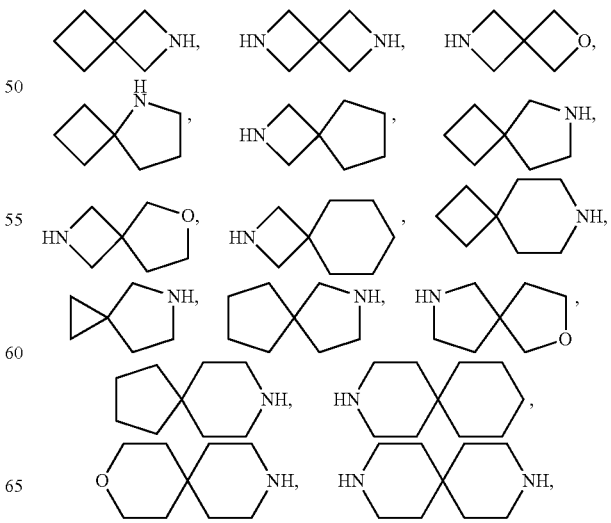

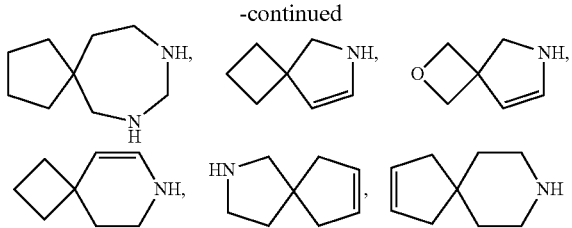

and the like.

As used herein, the term "6-12 membered bridged heterocyclic group" refers to a cyclic structure containing from 6 to 12 ring atoms, wherein at least one ring atom is a hetero atom such as a nitrogen atom, an oxygen atom or a sulfur atom, formed by two or more ring structures that share two non-adjacent ring atoms with each other. Optionally, a ring atom (e.g., a carbon atom, a nitrogen atom, or a sulfur atom) in the cyclic structure can be substituted with an oxygen atom. The "6-12 membered bridged heterocyclic group" includes, for example, "6-11 membered bridged heterocyclic group", "6-9 membered bridged heterocyclic group", "6-10 membered bridged heterocyclic group", and "7-10 membered bridged heterocyclic group", "7-9 membered bridged heterocyclic group", "7-8 membered bridged heterocyclic group", "8 membered bridged heterocyclic group", "9-10 membered bridged heterocyclic group", "3-10 membered bridged heterocyclic group" and the like. Specific examples thereof include, but are not limited to:

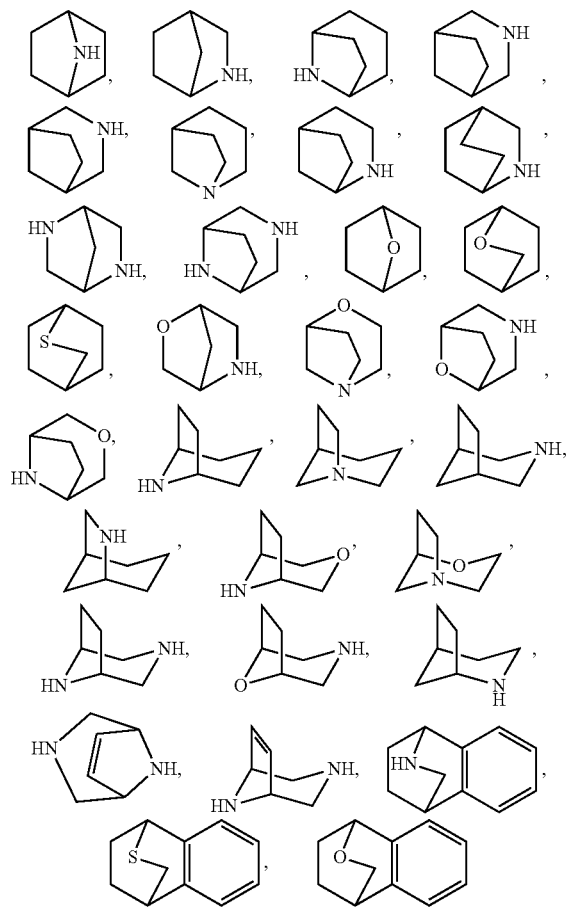

and the like.

As used herein, the term "6-12 membered fused heterocyclic group" refers to a cyclic structure containing from 6 to 12 ring atoms, wherein at least one ring atom is a hetero atom such as a nitrogen atom, an oxygen atom or a sulfur atom, formed by two or more ring structures that share two adjacent atoms with each other. Optionally, a ring atom (e.g., a carbon atom, a nitrogen atom, or a sulfur atom) in the cyclic structure can be substituted with an oxygen atom. The "6-12 membered fused heterocyclic group" includes, for example, "6-11 membered fused heterocyclic group", "5-10 membered fused heterocyclic group", "7-10 membered fused heterocyclic group", "3-10 membered fused heterocyclic group", "3-10 membered nitrogen-containing fused heterocyclic group", "9-10 membered fused heterocyclic group", "9-10 membered nitrogen-containing fused heterocyclic group", "6-12 membered oxygen-containing fused heterocyclic group" and the like. Specific examples thereof include, but are not limited to, tetrahydroimidazo[4,5-c]pyridyl, 3,4-dihydroquinazolinyl, 1,2-dihydroquinoxalinyl, benzo[d][1,3]dioxolyl, 1,3-dihydroisobenzofuranyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, benzoimidazolidinyl, octahydro-benzo[d]imidazolyl, decahydroquinolyl, hexahydrothienoimidazolyl, hexahydrofuroimidazolyl, 4,5,6,7-tetrahydro-1H-benzo[d]imidazolyl, octahydrocyclopenteno[c]pyrrolyl, indolinyl, dihydroisoindolyl, benzoxazolidinyl, benzothiazolidinyl, 1,2,3,4-tetrahydroisoquinolinyl, 1,2,3,4-tetrahydroquinolinyl, 4H-1,3-benzoxazinyl and the like.

As used herein, the term "aryl" refers to an aromatic monocyclic or polycyclic hydrocarbon group, for example, 6-20 membered aryl group, 6-10 membered aryl group, 5-8 membered aryl group and the like. Specific examples thereof include, but are not limited to, phenyl, naphthyl, anthracenyl, phenanthryl, and the like. The "6-20 membered aryl group" refers to an aryl group having 6 to 20 ring atoms.

As used herein, the term "heteroaryl" refers to an aromatic cyclic group wherein at least one ring atom is a hetero atom such as a nitrogen atom, an oxygen atom or a sulfur atom. Optionally, a ring atom (e.g., a carbon atom, a nitrogen atom, or a sulfur atom) in the cyclic structure can be substituted with an oxygen atom. Specific examples thereof include, but are not limited to, 5-10 membered heteroaryl group, 5-10 membered nitrogen-containing heteroaryl group, 6-10 membered oxygen-containing heteroaryl group, 6-8 membered nitrogen-containing heteroaryl group, 5-8 membered oxygen-containing heteroaryl group and the like, such as furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl 1,3,4-oxadiazolyl, pyridyl, 2-pyridinone, 4-pyridinone, pyrimidinyl, 1,4-dioxino, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azacyclohep-tatrienyl, 1,3-diazacyclohep-tatrienyl, azocinyl and the like.

Optionally, the hydrogen in the groups involved in the present invention may be replaced by deuterium.

As used herein, the term "reactive group" refers to a group capable of being converted or derivatized or bonded to other functional groups.

The group mentioned in the present invention is obtained by replacing 1, 2 or 3 hydrogen atoms in the compound corresponding to the group with other atoms, and the number of the replaced hydrogen atoms may be determined by the number of valence bonds formed in the compound or conjugate of the present invention. For example, an alkyl group is a group obtained by replacing one hydrogen atom in an alkane, and an alkylene group is a group obtained by replacing two hydrogen atoms in an alkane, methyl group and ethyl group are respectively obtained by replacing one hydrogen atom in methane and ethane, and methylene group and ethylene group are respectively obtained by replacing two hydrogen atoms in methane and ethane.

As used herein, the term "solvate" refers to a substance formed by association of a compound with a solvent molecule. The solvent may be an organic solvent (for example, methanol, ethanol, propanol, acetonitrile and the like) or the like. For example, the compound of the present invention may form an ethanolate with ethanol.

As used herein, the term "hydrate" refers to a substance formed by association of a compound with a water molecule.

In an embodiment of the present invention, if the compound has a chiral carbon, the present invention includes isomers formed based on any stereo configuration of the chiral carbon, for example, including racemates or any mirror isomers. Moreover, the present invention includes all other stereoisomers that may be present. That is, the compounds of the present invention include all enantiomers, diastereomers, cis and trans isomers, racemates and the like.

After intensive research, the inventors have unexpectedly discovered a toxin molecule which has obvious in vitro cytotoxic activity, good stability, can be prepared by a simple method, and can be efficiently coupled with an antibody by different coupling methods. A linker has also been discovered which can efficiently couple a toxin molecule with an antibody, and a drug-antibody conjugate has also been discovered, which can smoothly release a toxin molecule in a cell and has good inhibitory effect on a tumor cell. Thus, the following invention is provided.

After intensive research, the inventors have unexpectedly discovered a toxin molecule which has obvious in vitro cytotoxic activity, good stability, can be prepared by a simple method, and can be efficiently coupled with an antibody by different coupling methods. A linker has also been discovered which can efficiently couple a toxin molecule with an antibody, and a drug-antibody conjugate has also been discovered, which can smoothly release a toxin molecule in a cell and has good inhibitory effect on a tumor cell. Thus, the following invention is provided.

In one aspect, the present invention provides a compound of formula (I), or a pharmaceutically acceptable salt, solvate, hydrate, isomer thereof, or any crystalline form or racemate thereof,

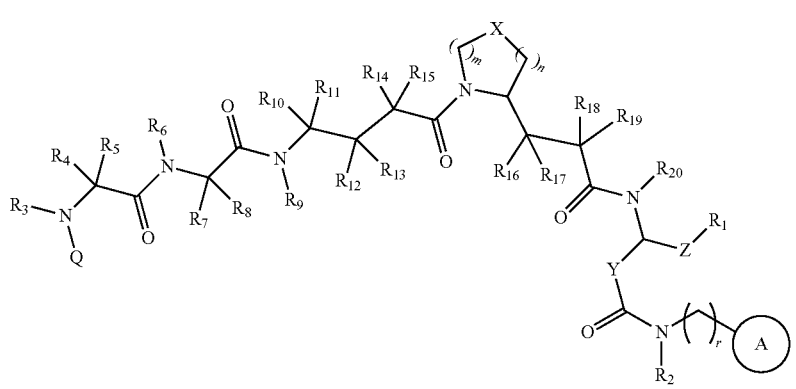

(I)

wherein,

X is selected from: $CH_2$, S, S=(O), $S(O)_2$, C=(O), CHF, CHCN, $CHN_3$, CH—OH, CH—$ONHR_w$ or $CHOR_w$, wherein $R_w$ is H (hydrogen), D (deuterium) or a $C_{1-6}$ alkyl group optionally substituted by $M_1$;

Y is absent or selected from the following groups optionally substituted by $M_2$: $C_{1-6}$ alkyl, $C_{3-6}$ cycloalkyl, 3-7 membered aliphatic heterocyclic group, $C_{2-6}$ alkynyl, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group;

Z is absent or selected from the following groups optionally substituted by $M_3$: $C_{1-6}$alkyl, $C_{3-6}$ cycloalkyl, 3-7 membered aliphatic heterocyclic group, aryl, heteroaryl, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group;

m=0, 1, 2 or 3;
n=0, 1, 2 or 3;
r=1, 2, 3, 4, 5 or 6;

$R_1$ is selected from H (hydrogen), D (deuterium), $N_3$, CN, $NHR_a$, $N(R_a)_2$, $OR_a$, $SR_a$, $S(O)R_a$, $S(O)_2R_a$, and the following groups optionally substituted by $M_4$: $C_{1-6}$ alkyl, $C_{1-6}$ alkoxy, $C_{3-6}$ cycloalkyl, 3-7 membered aliphatic heterocyclic group, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group, $C_{2-6}$ alkynyl, aryl, heteroaryl;

$R_2$ is selected from: H (hydrogen), D (deuterium), and the following groups optionally substituted by $M_5$: $C_{1-6}$ alkyl, $C_{3-6}$ cycloalkyl, 6-12 membered bridged ring group, 6-12 membered spiro ring group, 6-12 fused ring group, —$(CH_2CH_2O)_{j1}$—$(CH_2)_{j2}R_a$;

$R_a$ is independently selected from: H (hydrogen), D (deuterium), $C_{1-6}$ alkyl optionally substituted by $M_5$, $N_3$, OH, CN, $NR_bR_c$;

$R_b$ and $R_c$, independently of each other, are selected from: H (hydrogen), D (deuterium), and the following groups optionally substituted by $M_5$: $C_{1-6}$ alkyl, $C_{3-6}$ cycloalkyl, 3-7 membered aliphatic heterocyclic group, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group;

j1 and j2, independently of each other, are selected from 0, 1, 2, 3;

$R_3$ is selected from: H (hydrogen), D (deuterium), and the following groups optionally substituted by $M_6$: $C_{1-6}$ alkyl, $C_{2-6}$ alkenyl, $C_{2-6}$ alkynyl, $C_{3-8}$ cycloalkyl, 3-7 membered aliphatic heterocyclic group, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group, —(CH$_2$CH$_2$O)$_{q1}$—(CH$_2$)$_{q2}$—R$_d$, aryl, heteroaryl;

$R_4$-$R_{20}$, independently of each other, are selected from: H (hydrogen), D (deuterium), halogen, and the following groups optionally substituted by $M_7$: $C_{1-6}$ alkyl, $C_{1-6}$ alkoxy, $C_{2-6}$ alkenyl, $C_{2-6}$ alkynyl, $C_{3-8}$ cycloalkyl, 3-7 membered aliphatic heterocyclic group, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group, —(CH$_2$CH$_2$O)$_{q3}$—(CH$_2$)$_{q4}$—R$_c$, aryl, heteroaryl;

Optionally, $R_3$ and $R_5$ together with the atoms to which they are attached form a 5-7 membered ring optionally substituted by J;

Optionally, $R_4$ and $R_5$ together with the atom to which they are attached form a 3-6 membered ring optionally substituted by J;

Optionally, $R_4$ and $R_6$ together with the atoms to which they are attached form a 5-7 membered ring optionally substituted by J;

Optionally, $R_6$ and $R_7$ together with the atoms to which they are attached form a 3-6 membered ring optionally substituted by J;

Optionally, $R_7$ and $R_8$ together with the atom to which they are attached form a 3-6 membered ring optionally substituted by J;

Optionally, $R_7$ and $R_9$ together with the atoms to which they are attached form a 5-7 membered ring optionally substituted by J;

Optionally, $R_9$ and $R_{10}$ together with the atoms to which they are attached form a 3-6 membered ring optionally substituted by J;

Optionally, $R_9$ and $R_{12}$ together with the atoms to which they are attached form a 5-7 membered ring optionally substituted by J;

Optionally, $R_{10}$ and $R_{11}$ together with the atom to which they are attached form a 3-6 membered ring optionally substituted by J;

Optionally, $R_{10}$ and $R_{12}$ together with the atoms to which they are attached form a 5-7 membered ring optionally substituted by J;

Optionally, $R_{12}$ and $R_{13}$ together with the atom to which they are attached form a 3-6 membered ring optionally substituted by J;

Optionally, $R_{12}$ and $R_{14}$ together with the atoms to which they are attached form a 5-7 membered ring optionally substituted by J;

Optionally, $R_{14}$ and $R_{15}$ together with the atom to which they are attached form a 3-6 membered ring optionally substituted by J;

Optionally, $R_{16}$ and $R_{18}$ together with the atoms to which they are attached form a 5-7 membered ring optionally substituted by J;

Optionally, $R_{16}$ and $R_{17}$ together with the atom to which they are attached form a 3-6 membered ring optionally substituted by J;

Optionally, $R_{18}$ and $R_{19}$ together with the atom to which they are attached form a 3-6 membered ring optionally substituted by J;

Optionally, $R_{18}$ and $R_{20}$ together with the atoms to which they are attached form a 5-7 membered ring optionally substituted by J;

$R_d$, $R_e$, independently of each other, are selected from: H (hydrogen), D (deuterium), N$_3$, OH, CN, NR$_f$R$_g$;

$R_f$ and $R_g$, independently of each other, are selected from: H (hydrogen), D (deuterium), $C_{1-6}$ alkyl;

q1, q2, q3, q4, independently of each other, are selected from 0, 1, 2, 3, 4, 5 and 6;

A is selected from aryl substituted by reactive group $M_5$, heteroaryl substituted by reactive group $M_8$;

Q is selected from H (hydrogen), D (deuterium), and the following groups optionally substituted by $M_9$: $C_{1-6}$ alkyl, $C_{2-6}$ alkenyl, $C_{2-6}$ alkynyl, $C_{3-8}$ cycloalkyl, 3-7 membered aliphatic heterocyclic group, aryl, heteroaryl, 6-12 membered bridged ring group, 6-12 membered spiro ring group, 6-12 membered fused ring group, 6-12 membered bridged heterocyclic group, 6-12 membered spiro heterocyclic group, 6-12 membered fused heterocyclic group, or, Q and $R_3$ together with the atom to which they are attached form a 5-7 membered ring optionally substituted by $M_9$;

Optionally, Q is substituted by reactive group $M_{10}$;

The $M_1$-$M_7$, $M_9$, J, independently of each other, are selected from: H (hydrogen), D (deuterium), hydroxy, methylsulfonyl, amino, carboxy, halogen, CF$_3$, CN, $C_{1-6}$ alkyl, $C_{1-6}$ alkoxy, $C_{2-10}$ alkynyl;

The $M_8$ and $M_{10}$, independently of each other, are selected from the following groups substituted by a substituent: hydroxy, amino, hydrazine or hydroxyamino, wherein the substituent is selected from H (hydrogen), D (deuterium), $C_{1-6}$ alkyl, $C_{2-6}$ alkenyl, $C_{2-6}$ alkynyl, $C_{3-8}$ cycloalkyl, hydroxy substituted $C_{1-6}$ alkyl, cyano substituted $C_{1-6}$ alkyl, N$_3$ substituted $C_{1-6}$ alkyl, halogen substituted $C_{1-6}$ alkyl, 3-7 membered aliphatic heterocyclic group, 5-7 membered heteroaryl, OH.

In some embodiments, the compound of formula (I), or a pharmaceutically acceptable salt, solvate, hydrate, isomer thereof, or any crystalline form or racemate thereof has one or more of the following characteristics:

(1) X is CH$_2$;

(2) Y is absent, or is selected from $C_{1-6}$ alkylene and deuterated $C_{1-6}$ alkylene;

(3) Z is absent, or is selected from $C_{1-6}$ alkyl optionally substituted by deuterium, $C_{1-4}$ alkyl, hydroxy or methoxy (for example, methyl or ethyl, deuterated methyl or ethyl, hydroxy substituted methyl or ethyl, methoxy substituted methyl or ethyl, deuterium and hydroxy substituted methyl or ethyl);

(4) m=1;

(5) n=1;

(6) r=1, r=2 or r=3; preferably, r=1;

(7) $R_2$ is selected from H (hydrogen), D (deuterium) and $C_{1-6}$ alkyl (for example, methyl);

(8) $R_3$ is selected from H (hydrogen), D (deuterium) and $C_{1-6}$ alkyl (for example, methyl);

(9) $R_4$-$R_{20}$, independently of each other, are selected from H (hydrogen), D (deuterium), optionally deuterated $C_{1-6}$ alkyl (for example, methyl, ethyl, isopropyl, sec-butyl, deuterated methyl, deuterated ethyl, deuterated isopropyl, deu terated sec-butyl), and optionally deuterated $C_{1-6}$ alkoxy (for example, methoxy, deuterated methoxy);

(10) Q is methyl.

In some embodiments, the compound has the above characteristics (1), (4), (5), (8) and (9).

In some embodiments, the compound has the above characteristics (1), (4), (5), (8), (9) and (10).

In some embodiments, the compound has one or more of the above characteristics (2), (3), (6) and (7).

In some embodiments, the compound has the above characteristics (1), (2), (3), (4), (5), (6), (7), (8), (9) and (10).

In some embodiments, in the compound of formula (I), or a pharmaceutically acceptable salt, solvate, hydrate, isomer thereof, or any crystalline form or racemate thereof, X is $CH_2$;

Y is absent, or is methylene or ethylene;

Z is absent, or is selected from $C_{1-6}$ alkyl optionally substituted by deuterium, hydroxy, $C_{1-4}$ alkyl or methoxy (for example, methyl or ethyl, deuterated methyl or ethyl, hydroxy substituted methyl or ethyl, methoxy substituted methyl or ethyl, deuterium and hydroxy substituted methyl or ethyl);

m=1;

n=1;

r=1, r=2 or r=3 (preferably, r=1);

$R_2$ is H (hydrogen), D (deuterium), or methyl;

$R_3$ is methyl;

$R_4$-$R_{20}$, independently of each other, are selected from H (hydrogen), D (deuterium), methyl, ethyl, isopropyl, sec-butyl, methoxy;

Q is methyl.

In some embodiments, in the compound of formula (I), or a pharmaceutically acceptable salt, solvate, hydrate, isomer thereof, or any crystalline form or racemate thereof, $R_1$ is selected from: H (hydrogen), D (deuterium), $N_3$, CN, $S(O)_2R_a$, and the following groups optionally substituted by $M_4$: $C_{1-6}$ alkyl, $C_{3-6}$ cycloalkyl, $C_{2-6}$ alkynyl, aryl, heteroaryl.

In some embodiments, $R_a$ is selected from $C_{1-6}$ alkyl.

In some embodiments, $R_1$ is selected from: H (hydrogen), D (deuterium), $N_3$, CN, methyl, ethyl, propyl, isopropyl, cyclopropyl, ethynyl, methylsulfonyl, phenyl optionally substituted by $M_4$, 5-7 membered heteroaryl optionally substituted by $M_4$, 5-7 membered aliphatic heterocyclic group optionally substituted by $M_4$.

In some embodiments, $M_4$ is selected from H (hydrogen), D (deuterium), hydroxy, methylsulfonyl, $C_{1-6}$ alkyl (for example, methyl).

In some embodiments, $R_1$ is selected from: H (hydrogen), D (deuterium), $N_3$, CN, methyl, ethyl, propyl, isopropyl, cyclopropyl, ethynyl, methylsulfonyl, phenyl, p-hydroxyphenyl, p-(methylsulfonyl) phenyl, 5 membered nitrogen-containing heteroaryl, 6 membered nitrogen-containing aliphatic heterocyclic group, 6 membered nitrogen-containing heteroaryl.

Optionally, the 5 membered nitrogen-containing heteroaryl, 6 membered nitrogen-containing aliphatic heterocyclic group or 6 membered nitrogen-containing heteroaryl further contains a sulfur atom and/or an oxygen atom.

In some embodiments, the 5 membered nitrogen-containing heteroaryl is selected from:

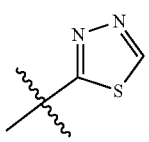 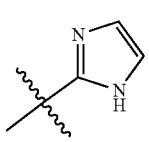 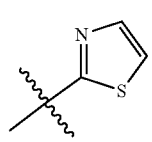

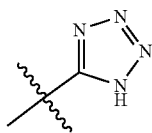 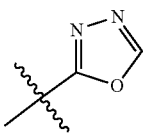 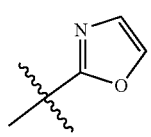

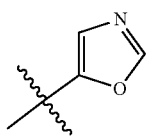 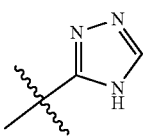 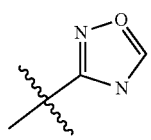

In some embodiments, the 5 membered nitrogen-containing heteroaryl is

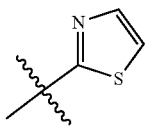 or 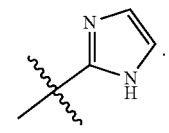.

In some embodiments, the 6 membered nitrogen-containing aliphatic heterocyclic group is selected from:

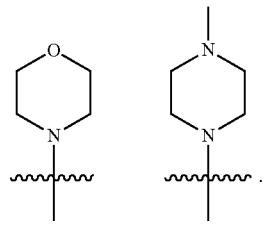

In some embodiments, the 6 membered nitrogen-containing heteroaryl is selected from:

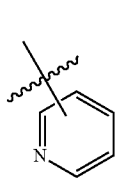  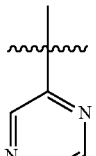

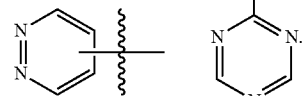

In some embodiments, the 6 membered nitrogen-containing heteroaryl is selected from:

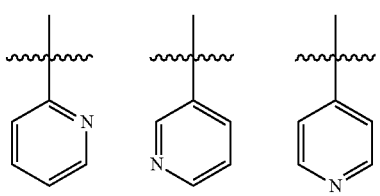

In some embodiments, in the compound of formula (I), or a pharmaceutically acceptable salt, solvate, hydrate, isomer thereof, or any crystalline form or racemate thereof, A is selected from 6-10 membered aryl substituted by $M_8$, and 5-6 membered heteroaryl substituted by $M_8$.

In some embodiments, A is selected from phenyl substituted by $M_8$, 5-6 membered nitrogen-containing heteroaryl substituted by $M_8$, 5-6 membered oxygen-containing heteroaryl substituted by $M_8$, 5-6 membered sulfur-containing heteroaryl substituted by $M_8$.

Optionally, the 5-6 membered nitrogen-containing heteroaryl further contains a sulfur atom and/or an oxygen atom.

In some embodiments, the 5-6 membered nitrogen-containing heteroaryl is selected from:

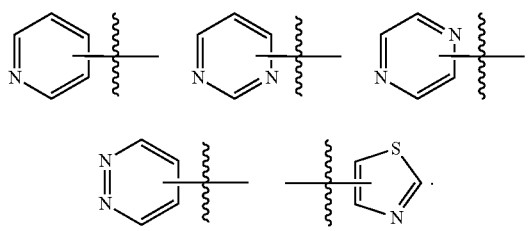

In some embodiments, the 5-6 membered nitrogen-containing heteroaryl is selected from:

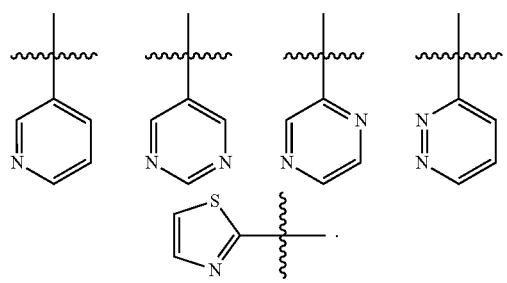

In some embodiments, $M_8$ is selected from hydroxy, amino, hydrazine and hydroxyamino which are substituted by a substitutent, wherein the substituent is selected from H (hydrogen), D (deuterium), $C_{1-6}$ alkyl, $C_{2-6}$ alkenyl, $C_{2-6}$ alkynyl, $C_{3-8}$ cycloalkyl, hydroxy substituted $C_{1-6}$ alkyl, cyano substituted $C_{1-6}$ alkyl, $N_3$ substituted $C_{1-6}$ alkyl, halogen substituted $C_{1-6}$ alkyl, $C_{3-7}$ aliphatic heterocyclic group, $C_{5-7}$ heteroaryl, OH.

In some embodiments, A is selected from:

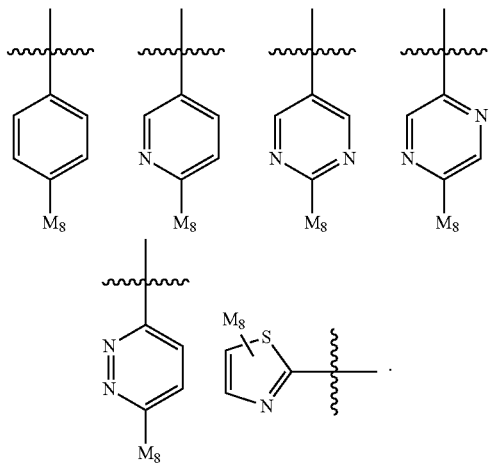

Optionally, A is substituted by 1-4 substituents $R_h$, $R_h$ is independently selected from D (deuterium), halogen, $CF_3$, CN, $C_{1-6}$ alkyl, fluorinated $C_{1-4}$ alkyl, $C_{1-6}$ alkoxy, $C_{3-6}$ cycloalkyl, $C_{2-10}$ alkenyl, $C_{2-10}$ alkynyl.

In some embodiments, A is amino substituted phenyl.

In some embodiments, A is

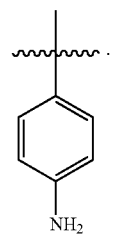

In some embodiments, the compound has the structure of formula (II), (II') or (II");

(II)

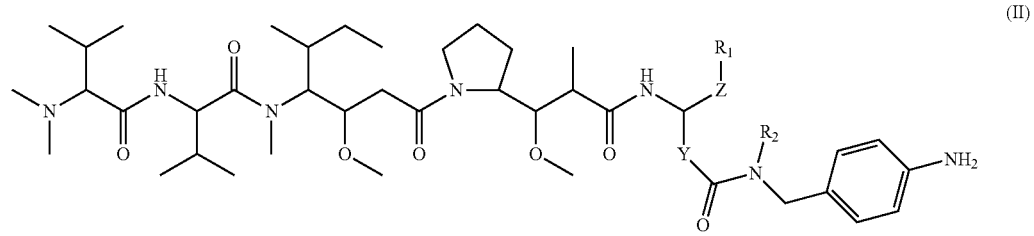

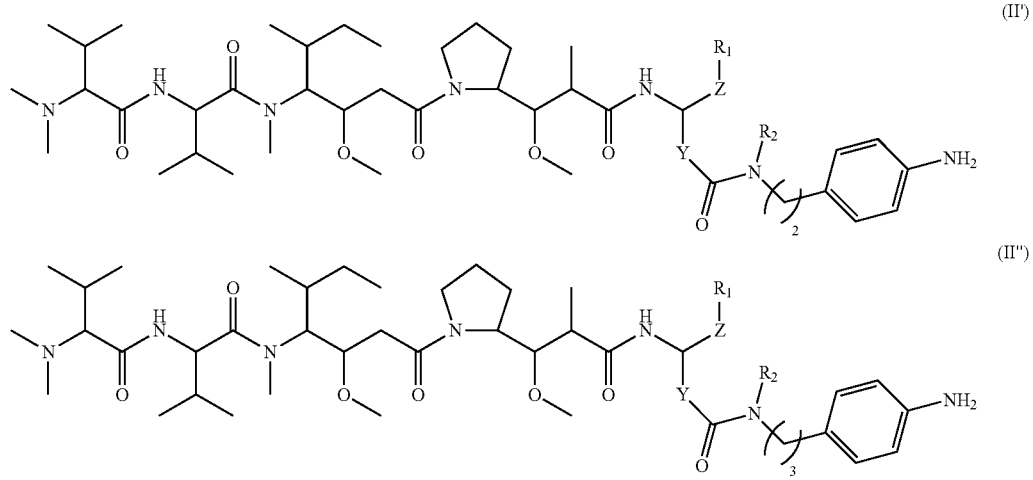

(II')

(II'')

wherein,
Y is absent, or is methylene;
Z is absent, or is methylene or ethylene;
$R_1$ is selected from: H (hydrogen), D (deuterium), $N_3$, CN, methyl, ethyl, propyl, isopropyl, cyclopropyl, ethynyl, methylsulfonyl, phenyl, p-hydroxyphenyl, p-(methylsulfonyl) phenyl,

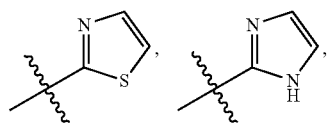 [SMILES: *c1nccs1 ; *c1ncc[nH]1]

oxazolyl, isoxazolyl, triazolyl, oxadiazolyl, pyrazolyl, pyridyl, imidazolyl, pyridazinyl, morpholinyl optionally substituted by =O, piperazinyl optionally substituted by =O and/or $C_{1-6}$ alkyl (for example, methyl), thiomorpholinyl optionally substituted by =O.

Preferably, $R_1$ is selected from: H (hydrogen), D (deuterium), N, CN, methyl, ethyl, propyl, isopropyl, cyclopropyl, ethynyl, methylsulfonyl, phenyl, p-hydroxyphenyl, p-(methylsulfonyl) phenyl,

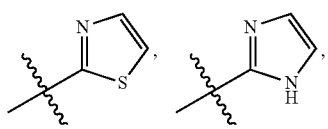 [SMILES: *c1nccs1 ; *c1ncc[nH]1]

oxazolyl, isoxazolyl, pyrazolyl, pyridyl, imidazolyl, pyridazinyl, morpholinyl optionally substituted by =O, piperazinyl optionally substituted by =O and/or $C_{1-6}$ alkyl (for example, methyl), thiomorpholinyl optionally substituted by =O;
$R_2$ is H (hydrogen), D (deuterium) or methyl.

In some embodiments, the compound has the structure of formula (III), (III') or (III'')

(III)

(III')

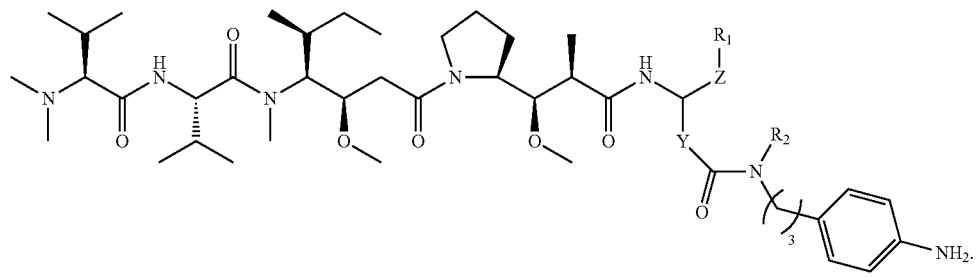
In some embodiments, the compound is selected from:
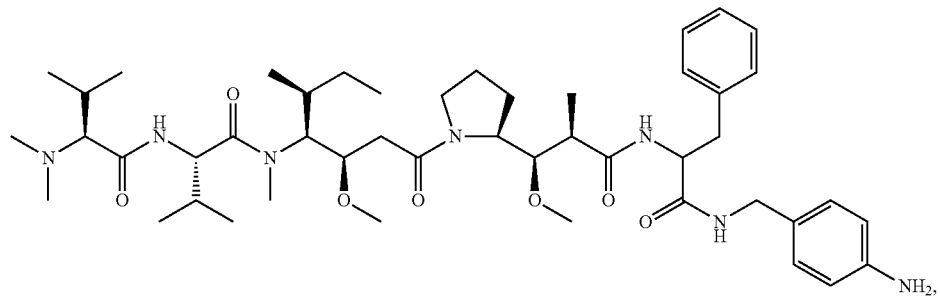
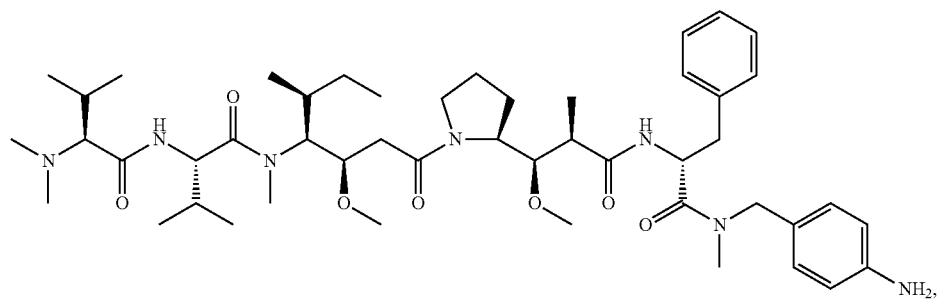
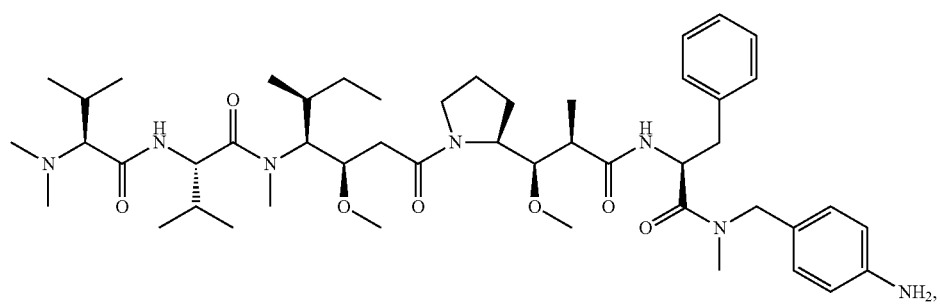
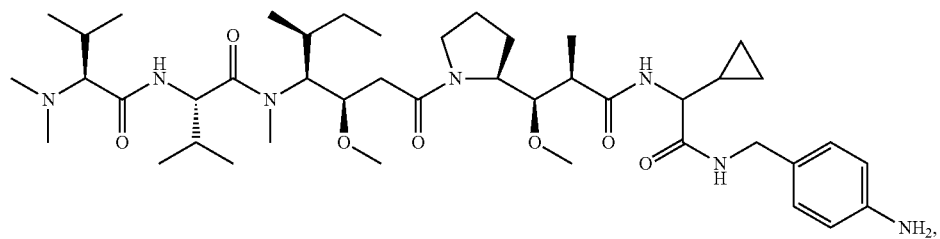

-continued
T005
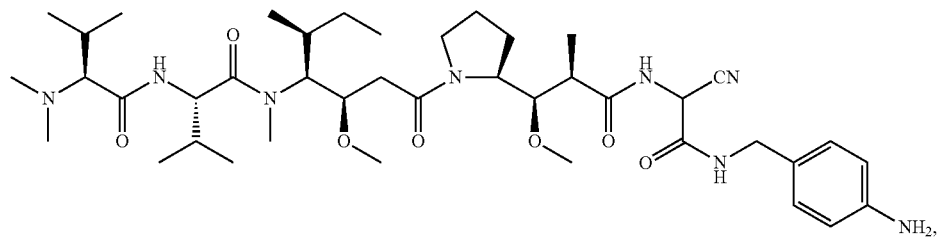
T006
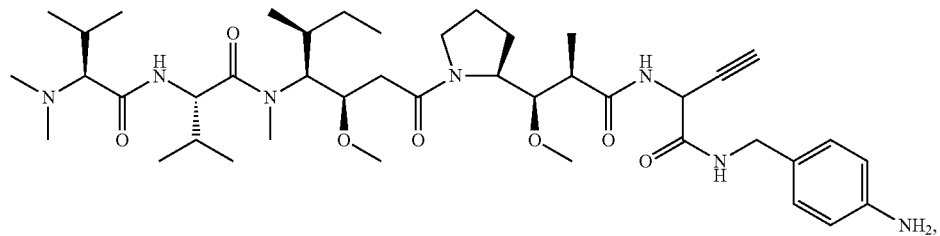
T007
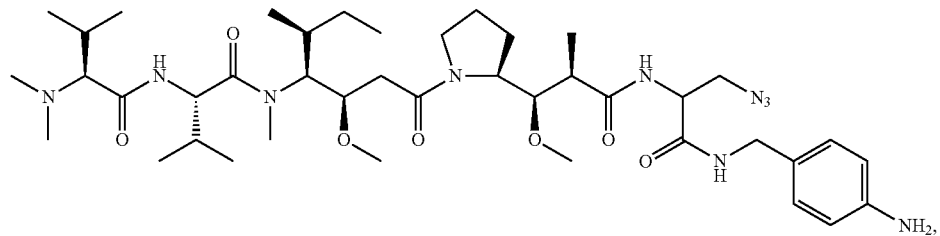
T008
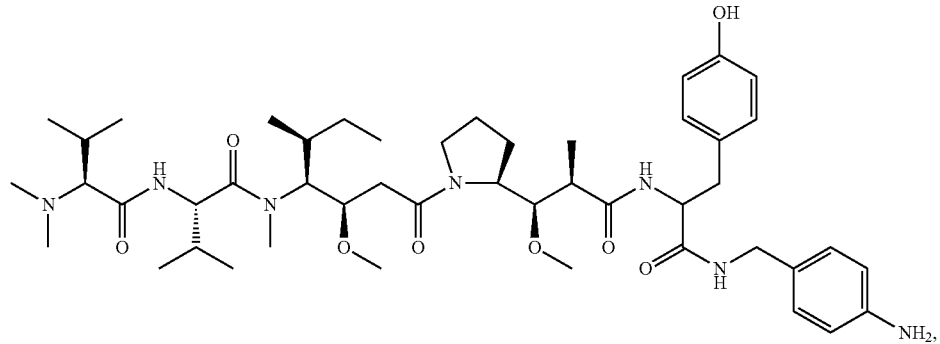
T009
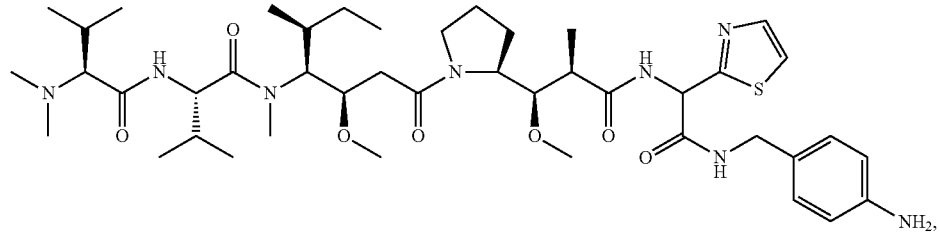
T010
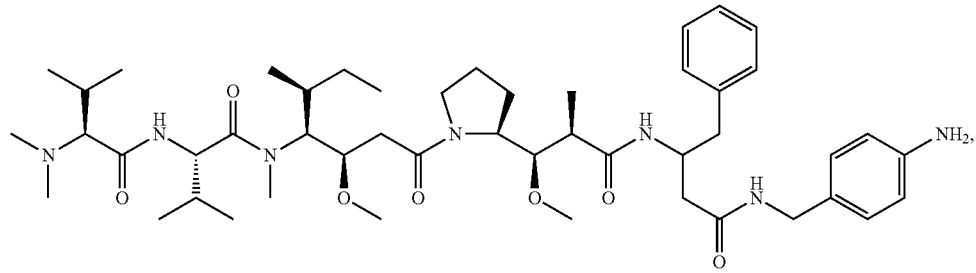

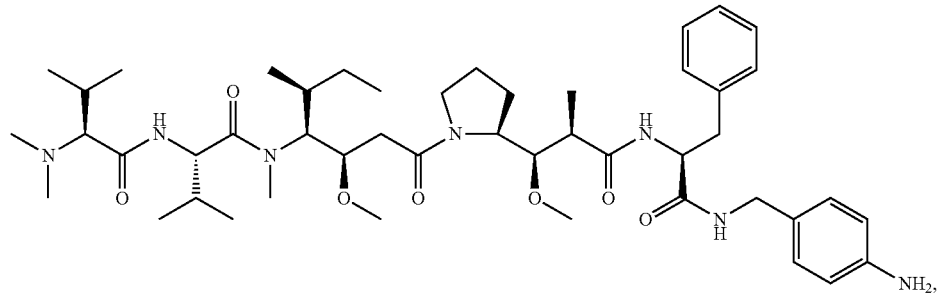
T011
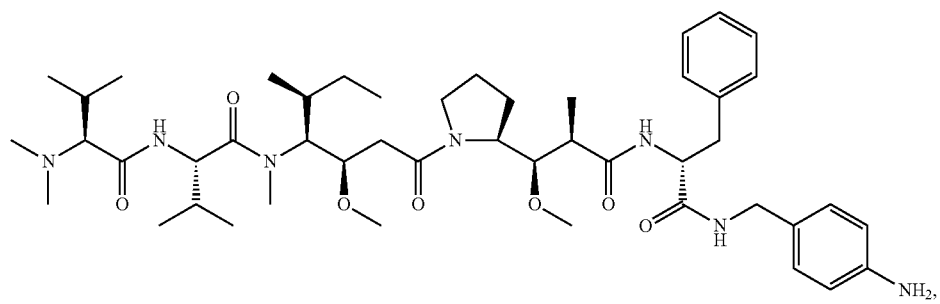
T012
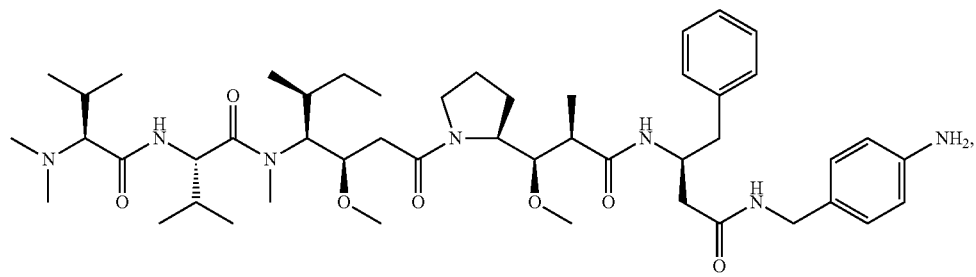
T013
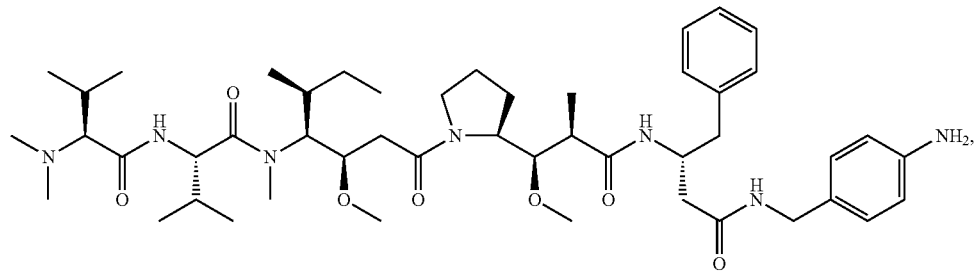
T014
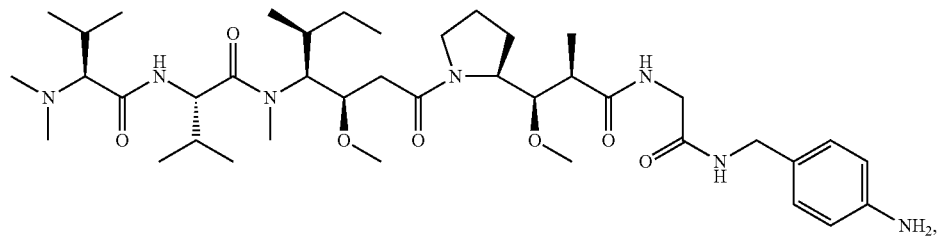
T015

-continued
T016
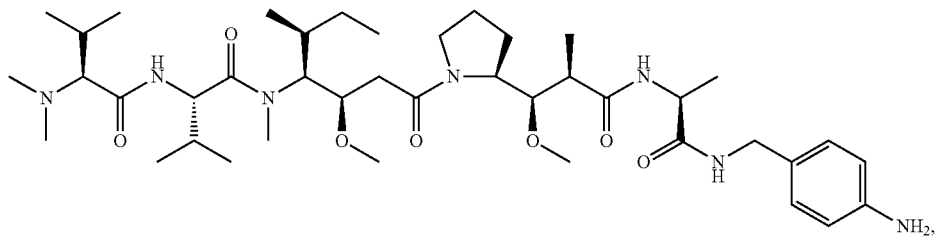
T017
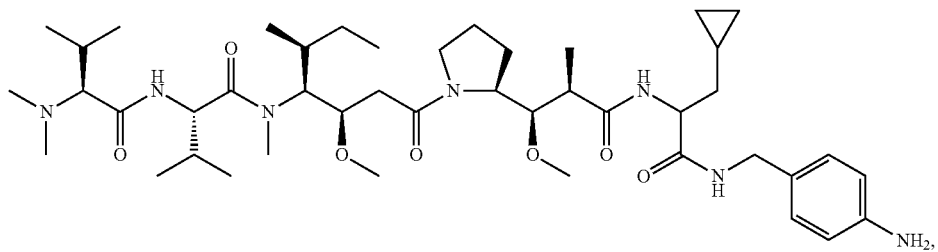
T018
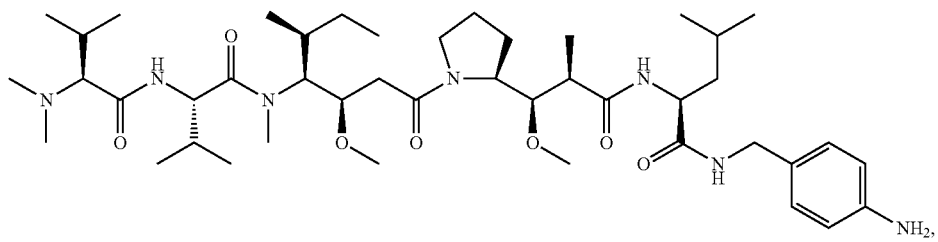
T019
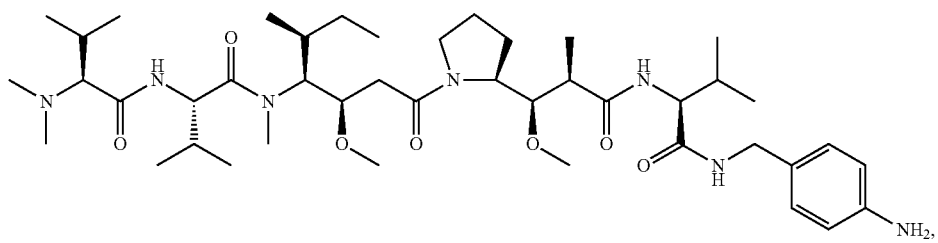
T020
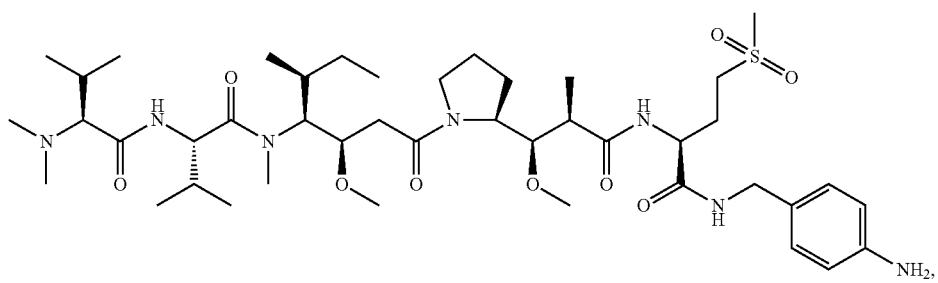
T021
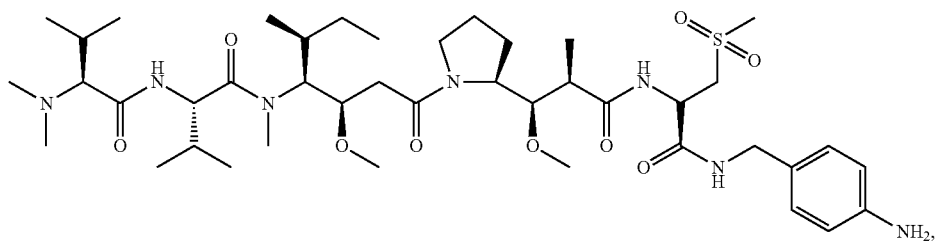

-continued
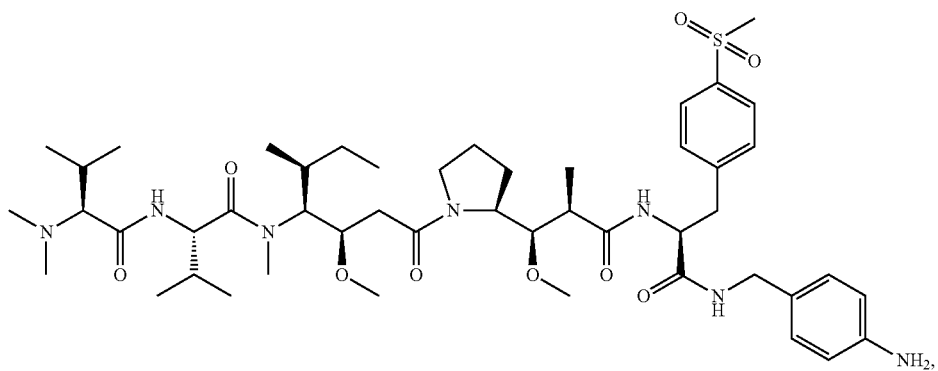
T022
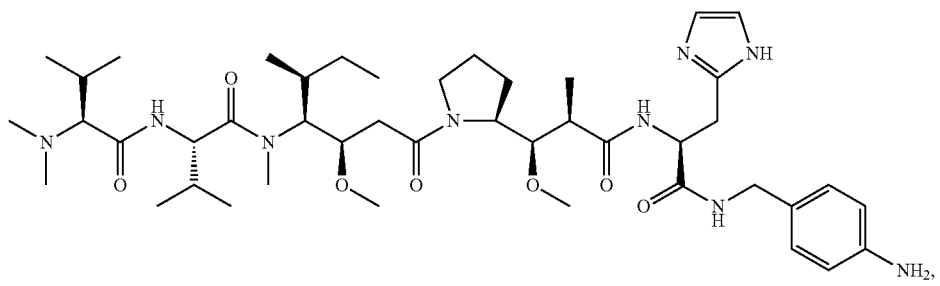
T023
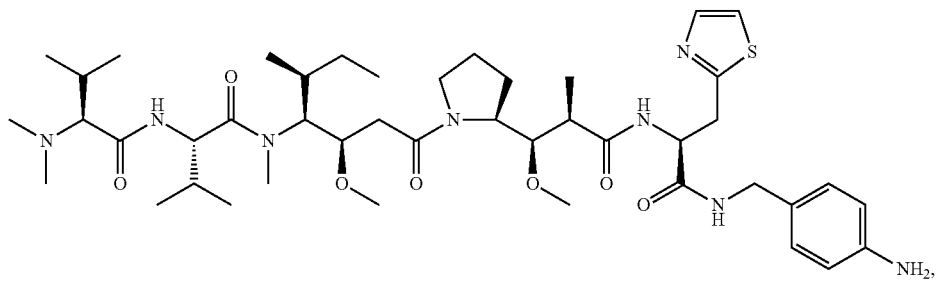
T024
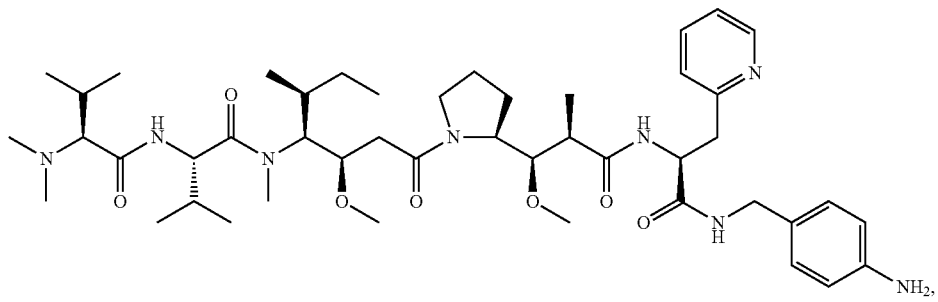
T025
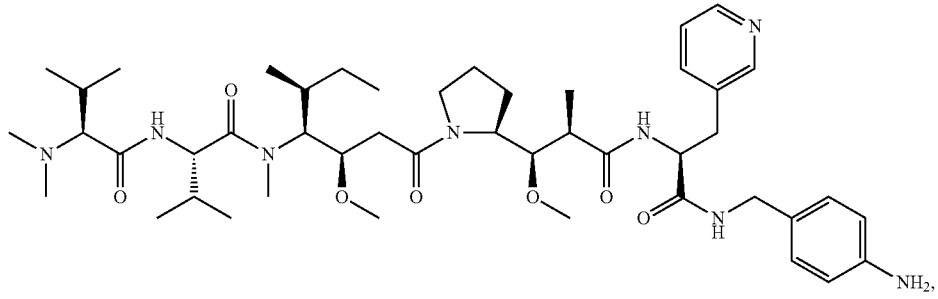
T026

-continued
T027
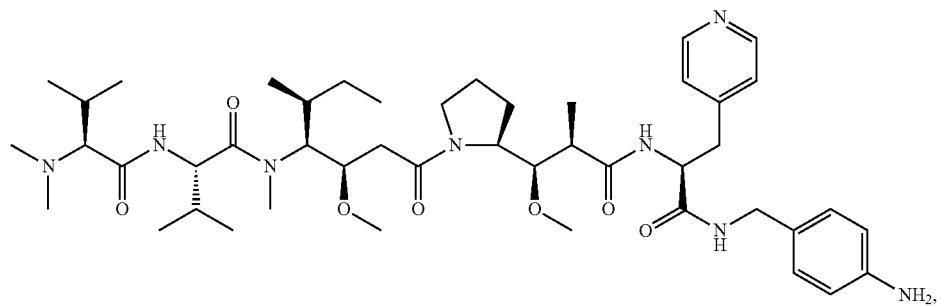
T028
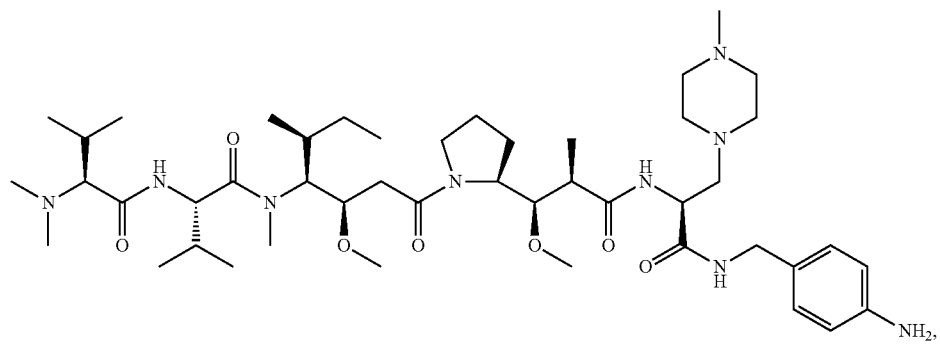
T029
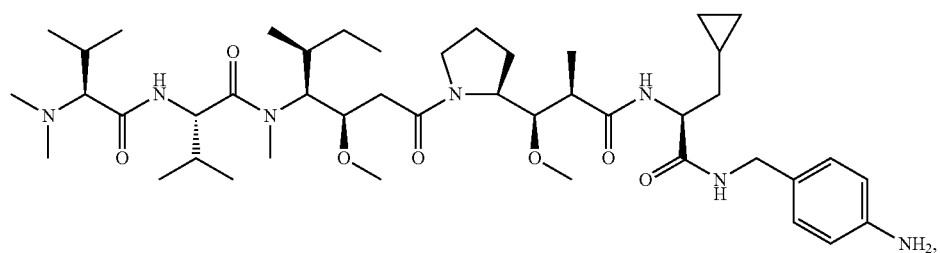
T030
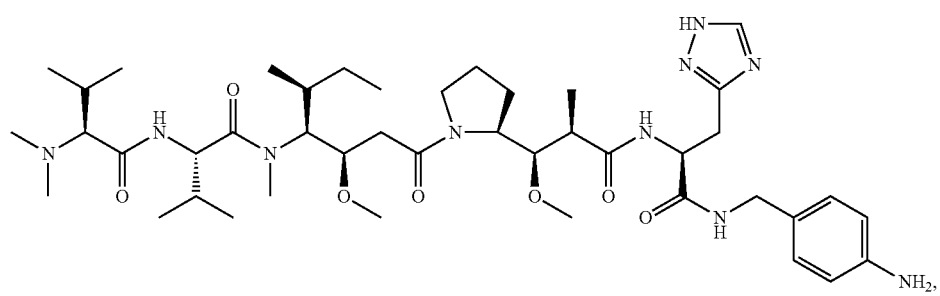
T031
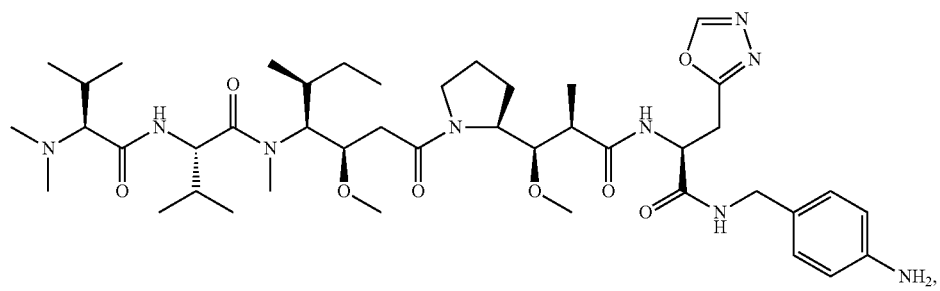

-continued
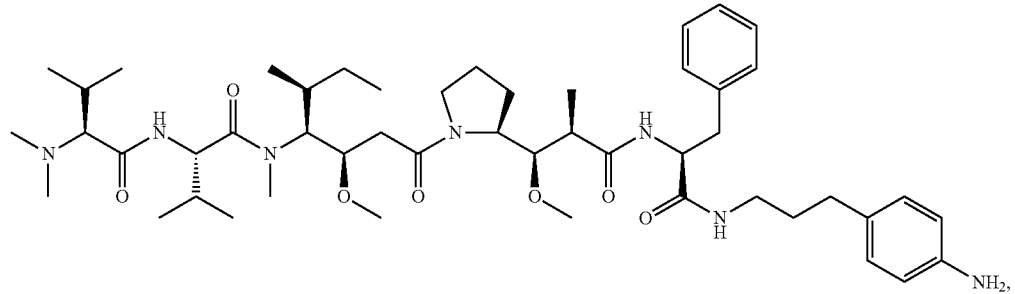
T032
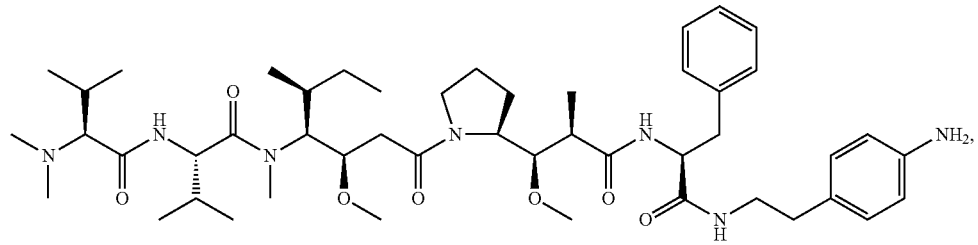
T033
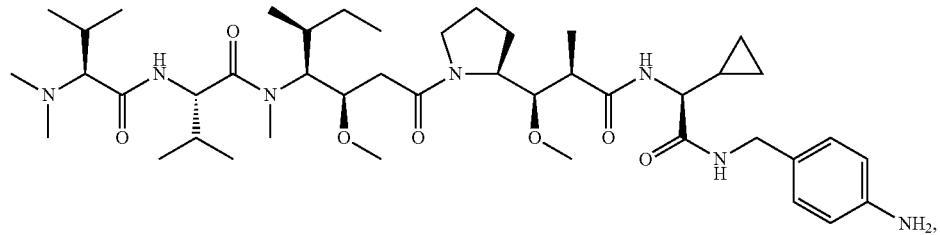
T034
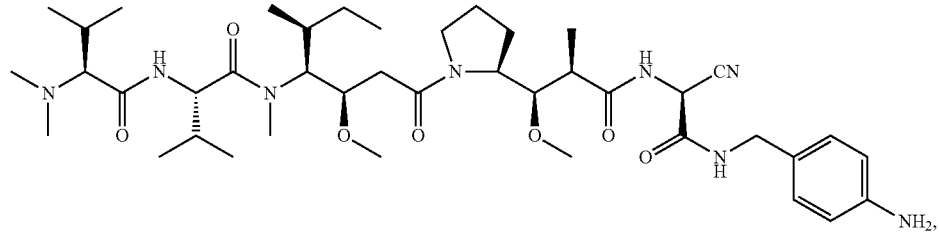
T035
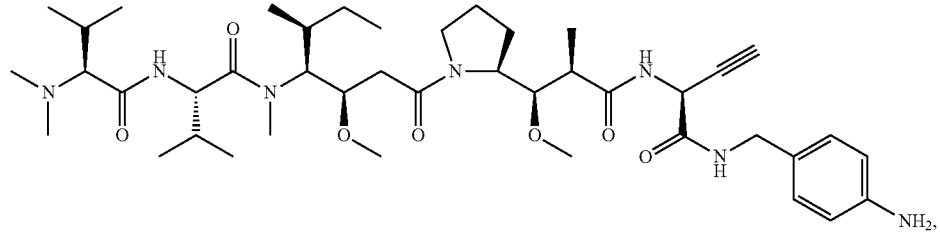
T036
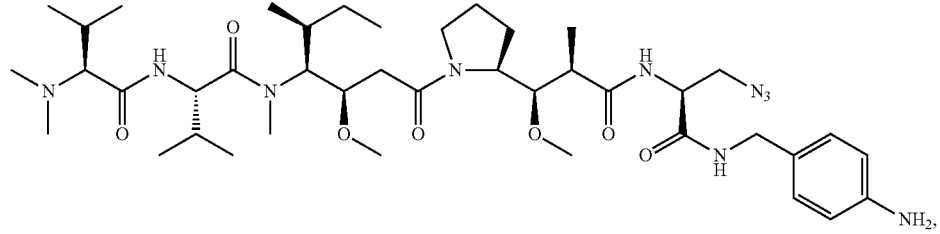
T037

-continued

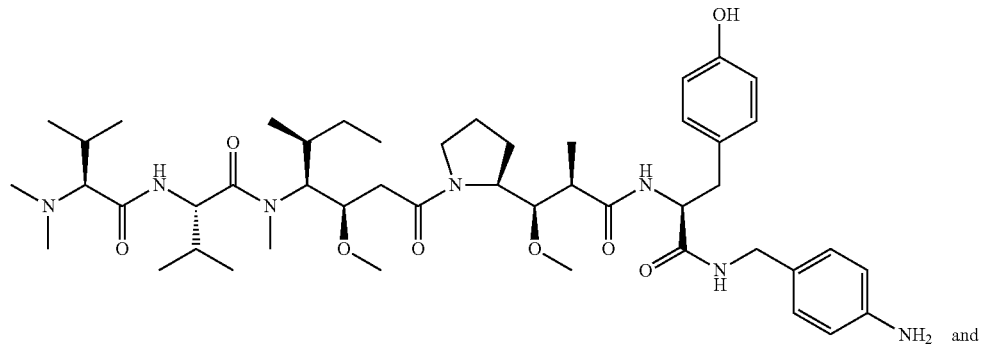
T038

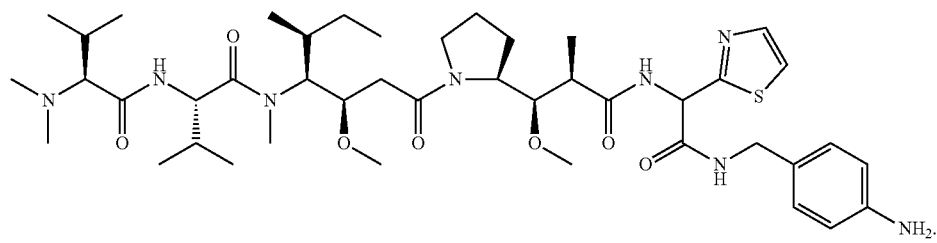
and
T039

The present invention also encompasses a conjugate comprising one or more of the compounds as described above, or a pharmaceutically acceptable salt, solvate, hydrate, isomer thereof, or any crystalline form or racemate thereof, and one or more linkers, wherein the compound or a pharmaceutically acceptable salt, solvate, hydrate, isomer thereof, or any crystalline form or racemate thereof, is linked to the linker via a reactive group.

Optionally, the linker is also covalently linked to a targeting moiety.

In some embodiments, in the conjugate, the compound or a pharmaceutically acceptable salt, solvate, hydrate, isomer thereof, or any crystalline form or racemate thereof, is linked to the linker via $M_8$ and an optional $M_{10}$.

In some embodiments, the conjugate of the present application has the structure:

G-B wherein G is a compound as described above, or a pharmaceutically acceptable salt, solvate, hydrate, isomer thereof, or any crystalline form or racemate thereof, which is linked to B via $M_8$ and an optional $M_{10}$;

B is a linker. In some embodiments, it has the structure:

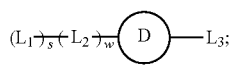

wherein $L_1$ is selected from: peptide, oligose, —$(CH_2)_t$—, —$(CH_2CH_2O)_t$—$(CH_2)_t$—, Val, Cit, Phe, Lys, D-Val, Leu, Lys, Gly, Ala, Asn, Val-Cit, Val-Ala, Val-Lys(Ac), Phe-Lys, Phe-Lys(Ac), D-Val-Leu-Lys, Gly-Gly-Arg, Ala-Ala-Asn, t=1, 2, 3, 4, 5 or 6;

$L_2$ is selected from: —$(CH_2)_y$—, —$(CH_2CH_2O)_y$—$(CH_2)_y$—,

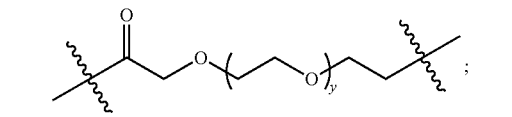

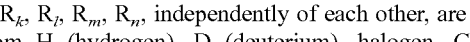

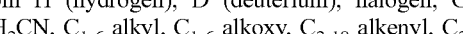

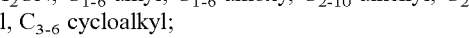

wherein, $R_k$, $R_l$, $R_m$, $R_n$, independently of each other, are selected from H (hydrogen), D (deuterium), halogen, $CF_3$, CN, $CH_2CN$, $C_{1-6}$ alkyl, $C_{1-6}$ alkoxy, $C_{2-10}$ alkenyl, $C_{2-10}$ alkynyl, $C_{3-6}$ cycloalkyl;

y, independently of each other, is 0, 1, 2, 3, 4, 5, 6, 7, 8, 9 or 10;

$L_3$ is selected from the following groups:

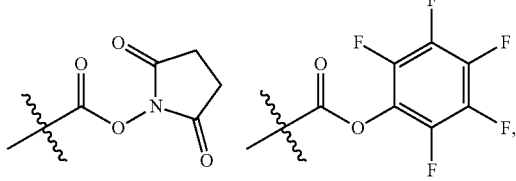

D is selected from the following groups optionally substituted by one or more $R_i$: 3-8 membered cycloalkyl, 3-8 membered aliphatic heterocyclic group, 6-12 membered bridged heterocyclic group, 6-12 membered spiro heterocyclic group, 6-12 membered fused heterocyclic group, aryl, heteroaryl, 3-8 membered cycloalkyl-W—, $R_i$ is independently selected from H (hydrogen), D (deuterium), halogen, =O, $CF_3$, CN, $CH_2CN$, $C_{1-6}$ alkyl, $C_{1-6}$ alkoxy, $C_{2-10}$ alkenyl, $C_{2-10}$ alkynyl, COOH, $SO_3H$; W is O or $NR_j$, $R_j$ is independently selected from H (hydrogen), D (deuterium), $C_{1-6}$ alkyl, $C_{3-6}$ cycloalkyl, $C_{1-6}$ alkoxy, cyano $C_{1-2}$ alkyl.

In some embodiments, the conjugate of the present application has the structure, G-B or (G-B)$_\alpha$-E, wherein, G is a compound as described above, or a pharmaceutically acceptable salt, solvate, hydrate, isomer thereof, or any crystalline form or racemate thereof, which is linked to B via $M_8$ and an optional $M_{10}$;

B is a linker. In some embodiments, it has the structure:

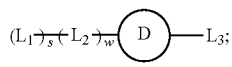

wherein $L_1$ is selected from: peptide, oligose, —(CH$_2$)$_t$—, —(CH$_2$CH$_2$O)$_t$—(CH$_2$)$_t$—, Val, Cit, Phe, Lys, D-Val, Leu, Lys, Gly, Ala, Asn, Val-Cit, Val-Ala, Val-Lys(Ac), Phe-Lys, Phe-Lys(Ac), D-Val-Leu-Lys, Gly-Gly-Arg, Ala-Ala-Asn, t=1, 2, 3, 4, 5 or 6;

$L_2$ is selected from: —(CH$_2$)$_y$—, —(CH$_2$CH$_2$O)$_y$—(CH$_2$)$_y$—,

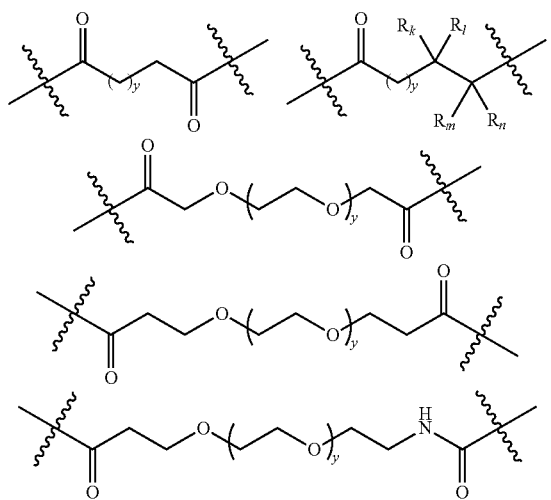

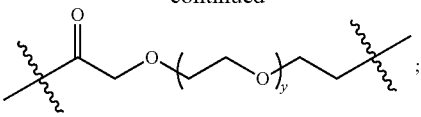

wherein, $R_k$, $R_l$, $R_m$, $R_n$, independently of each other, are selected from H (hydrogen), D (deuterium), halogen, $CF_3$, CN, $CH_2CN$, $C_{1-6}$ alkyl, $C_{1-6}$ alkoxy, $C_{2-10}$ alkenyl, $C_{2-10}$ alkynyl, $C_{3-6}$ cycloalkyl;

y, independently of each other, is 0, 1, 2, 3, 4, 5, 6, 7, 8, 9 or 10;

$L_3$ is selected from the following groups:

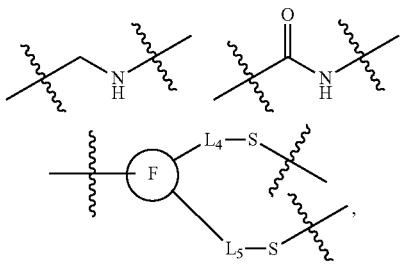

wherein, $L_4$, $L_5$ are absent or, independently of each other, are selected from $C_{1-6}$ alkylene (for example, methylene);

F is selected from:

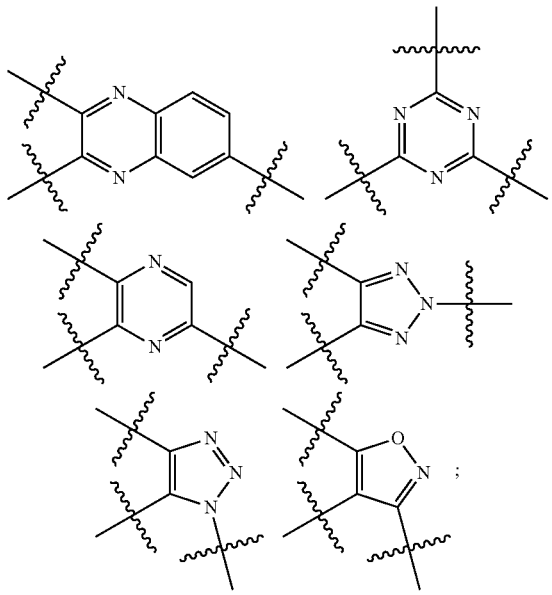

s, w, independently of each other, are selected from 1 or 2 (for example, s and w both are 1);

D is selected from the following groups optionally substituted by one or more $R_i$: 3-8 membered cycloalkyl, 3-8 membered aliphatic heterocyclic group, 6-12 membered bridged heterocyclic group, 6-12 membered spiro heterocyclic group, 6-12 membered fused heterocyclic group, aryl, heteroaryl, 3-8 membered cycloalkyl-W—, $R_i$ is independently selected from H (hydrogen), D (deuterium), halogen, =O, $CF_3$, CN, $CH_2CN$, $C_{1-6}$ alkyl, $C_{1-6}$ alkoxy, $C_{2-10}$ alkenyl, $C_{2-10}$ alkynyl, COOH, $SO_3H$; W is O or $NR_j$, $R_j$ is independently selected from H (hydrogen), D (deuterium), $C_{1-6}$ alkyl, $C_{3-6}$ cycloalkyl, $C_{1-6}$ alkoxy, cyano $C_{1-2}$ alkyl;

E is a targeting moiety;

α is a number (for example, a positive integer) between 1-20 (for example, 1-10, 1-5, 1-4 or 1-3), for example, 1, 2, 3, 4, 5, 6, 7, 8, 9, 10, 11, 12, 13, 14, 15, 16, 17, 18, 19 or 20.

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more nitrogen atoms.

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more quaternized nitrogen atoms.

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more nitrogen atoms, wherein, at least one nitrogen atom is substituted by =O.

In some embodiments, in the linker of the conjugate, $L_1$ is selected from peptide, oligose, Val-Cit, Val-Ala, Val-Lys (Ac), Phe-Lys, Phe-Lys(Ac), D-Val-Leu-Lys, Gly-Gly-Arg, Ala-Ala-Asn.

In some embodiments, $L_1$ is

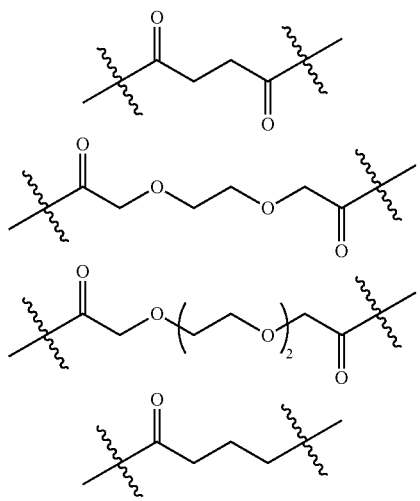

In some embodiments, in the linker of the conjugate, $L_2$ is selected from:

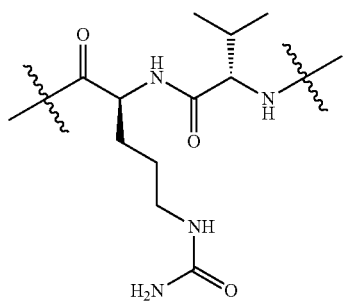

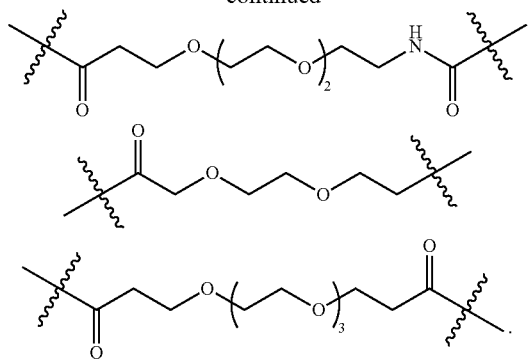

In some embodiments, in the linker of the conjugate, $L_3$ is selected from

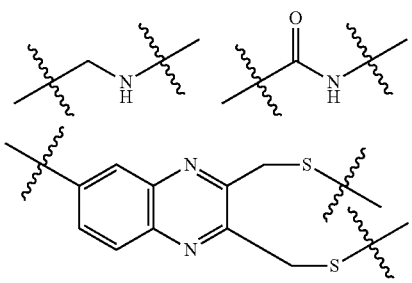

In some embodiments, $L_3$ is

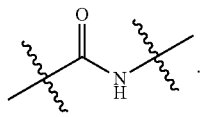 [SMILES: *NC(*)=O]

In some embodiments, in the linker of the conjugate, D is selected from the following groups optionally substituted by one or more $R_i$: 5-7 membered cycloalkyl, 5-7 membered aliphatic heterocyclic group, 8-11 membered bridged heterocyclic group, 8-11 membered spiro heterocyclic group, 8-11 membered fused heterocyclic group, phenyl, 5-6 membered heteroaryl, 5-6 membered cycloalkyl-W—; the 8-11 membered bridged heterocyclic group, 8-11 membered spiro heterocyclic group, 8-11 membered fused heterocyclic group or 5-6 membered heteroaryl contains a nitrogen atom and/or an oxygen atom.

In some embodiments, the 5-7 membered aliphatic heterocyclic group, 8-11 membered bridged heterocyclic group, 8-11 membered spiro heterocyclic group, 8-11 membered fused heterocyclic group or 5-6 membered heteroaryl contains one or more nitrogen atoms.

In some embodiments, the 5-7 membered aliphatic heterocyclic group, 8-11 membered bridged heterocyclic group, 8-11 membered spiro heterocyclic group, 8-11 membered fused heterocyclic group or 5-6 membered heteroaryl contains one or more quaternized nitrogen atoms.

In some embodiments, D is selected from the following groups optionally substituted by one or more $R_i$: 5-7 membered cycloalkyl, 5-7 membered aliphatic heterocyclic group, 5-6 membered heteroaryl, 8 membered bridged heterocyclic group, 11 membered spiro heterocyclic group, 8-11 membered fused heterocyclic group, phenyl, 5-6 membered cycloalkyl-W—; the 5-7 membered aliphatic heterocyclic group, 5-6 membered heteroaryl, 8 membered bridged heterocyclic group, 11 membered spiro heterocyclic group or 8-11 membered fused heterocyclic group contains a nitrogen atom and/or an oxygen atom.

In some embodiments, the 5-7 membered aliphatic heterocyclic group, 5-6 membered heteroaryl, 8 membered bridged heterocyclic group, 11 membered spiro heterocyclic group or 8-11 membered fused heterocyclic group contains one or more nitrogen atoms.

In some embodiments, the 5-7 membered aliphatic heterocyclic group, 5-6 membered heteroaryl, 8 membered bridged heterocyclic group, 11 membered spiro heterocyclic group or 8-11 membered fused heterocyclic group contains one or more quaternized nitrogen atoms.

In some embodiments, D is selected from the following groups optionally substituted by one or more $R_i$: cyclohexyl, 5-7 membered nitrogen-containing aliphatic heterocyclic group, 5-7 membered oxygen-containing aliphatic heterocyclic group, 6 membered nitrogen-containing heteroaryl, 8 membered nitrogen-containing bridged heterocyclic group, 11 membered oxygen-containing spiro heterocyclic group, 8 membered nitrogen-containing fused heterocyclic group, phenyl, cyclohexyl-W—.

In some embodiments, the 5-7 membered nitrogen-containing aliphatic heterocyclic group, 6 membered nitrogen-containing heteroaryl, 8 membered nitrogen-containing bridged heterocyclic group, 11 membered oxygen-containing spiro heterocyclic group or 8 membered nitrogen-containing fused heterocyclic group contains one or more quaternized nitrogen atoms.

In some embodiments, D is selected from the following groups optionally substituted by one or more $R_i$:

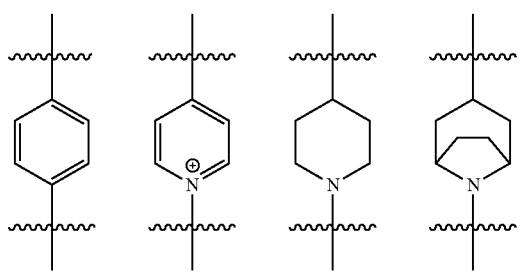

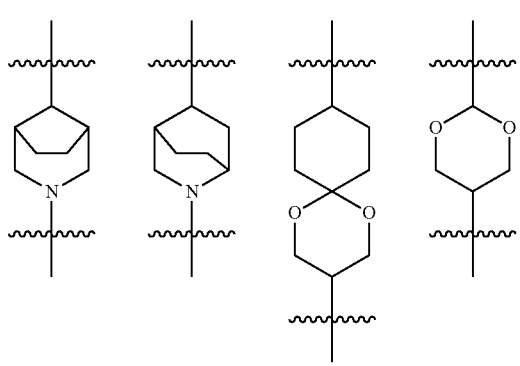

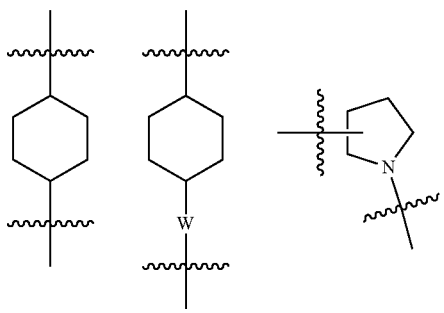

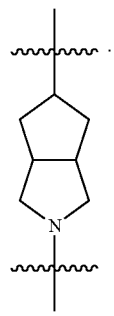

In some embodiments, $R_i$ is independently selected from H (hydrogen), D (deuterium), =O, CN, $CH_2CN$, methyl, $CF_3$.

In some embodiments, D is selected from:

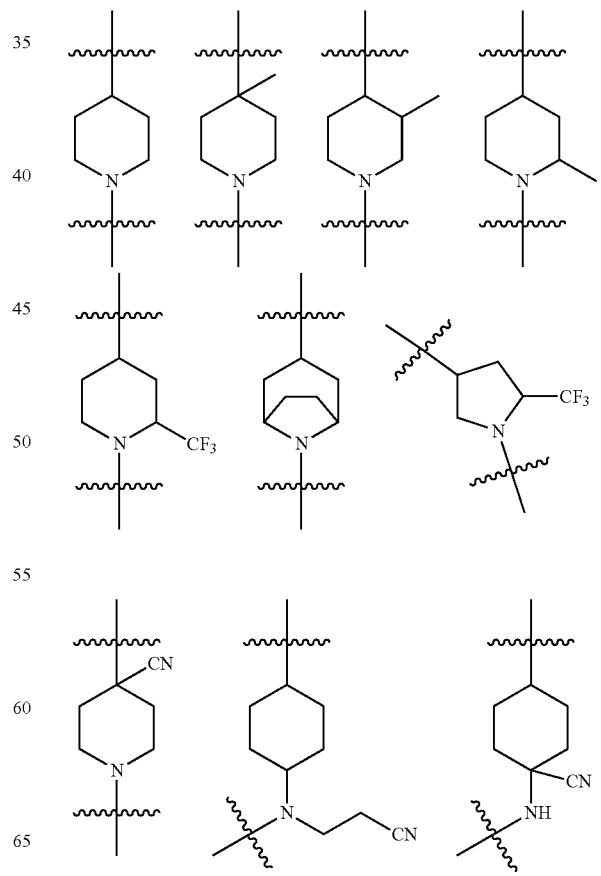

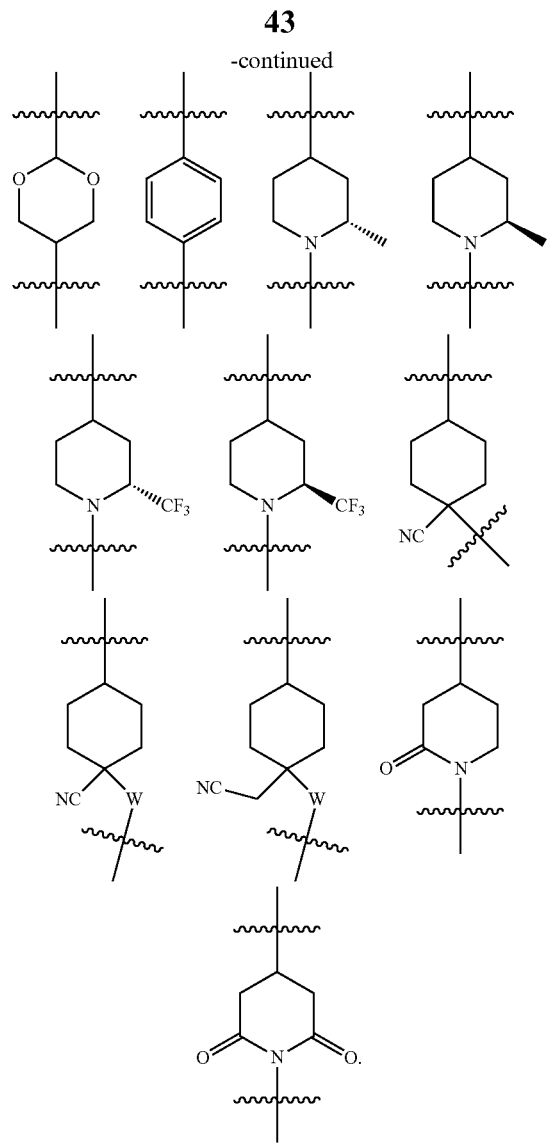
In some embodiments, D is selected from:
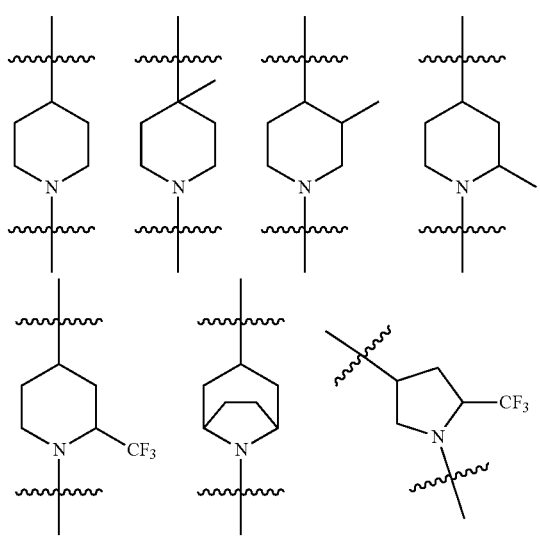
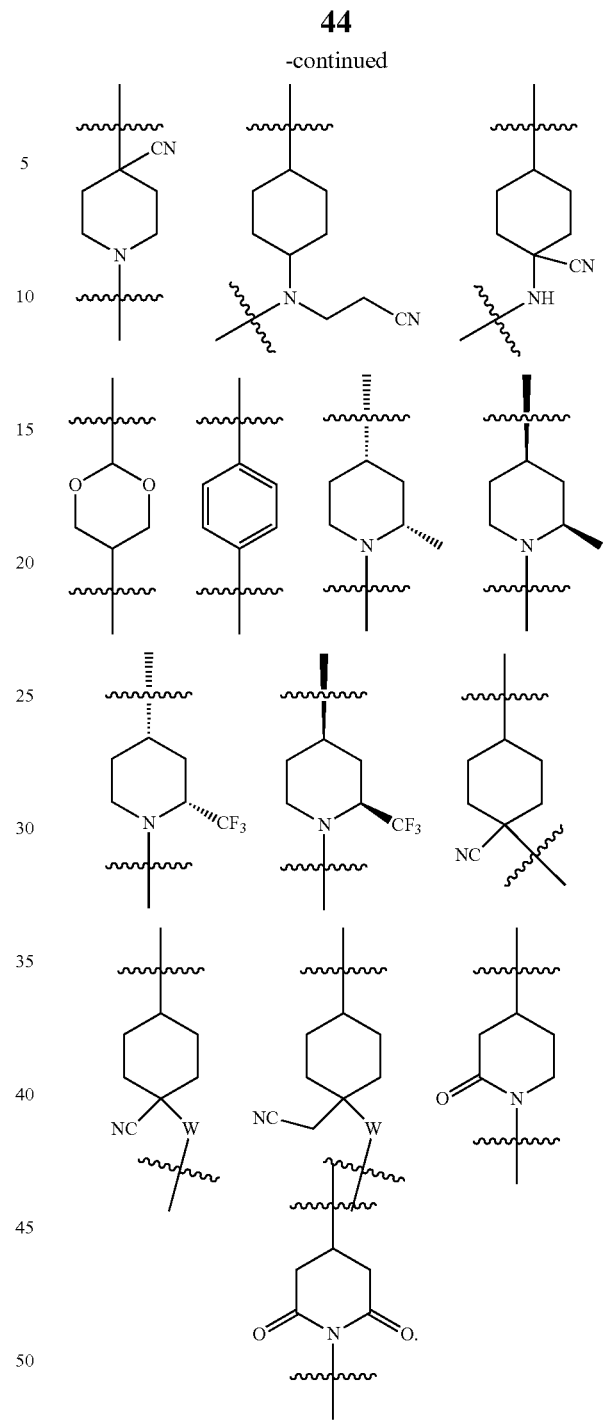
In some embodiments, D is selected from
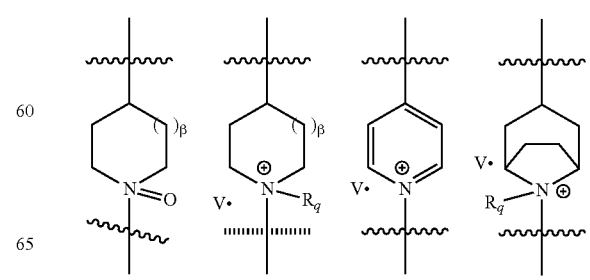

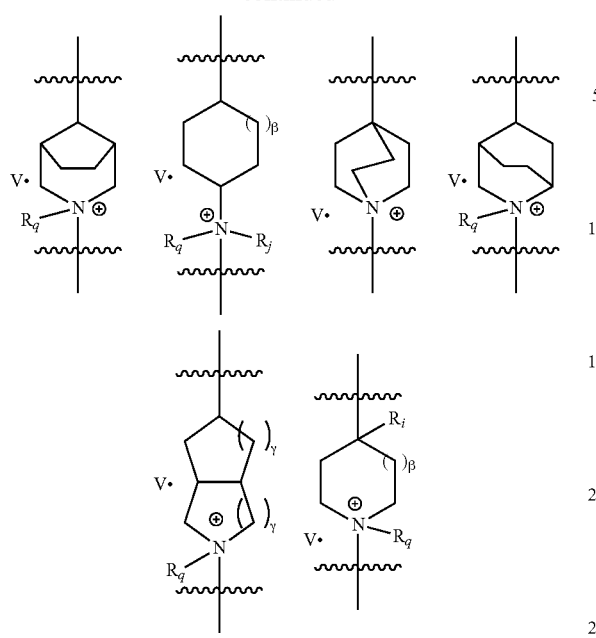

In some embodiments, $R_q$ is independently selected from $C_{1-6}$ alkyl, $C_{2-6}$ alkenyl, $C_{3-6}$ alkynyl, $C_{3-8}$ cycloalkyl; $R_j$ is selected from H (hydrogen), D (deuterium), $CH_2CN$ or $CH_2CH_2CN$; V. is a counterion, preferably a halogen anion, more preferably a chloride ion, a bromide ion or an iodide ion.

In some embodiments, D is selected from

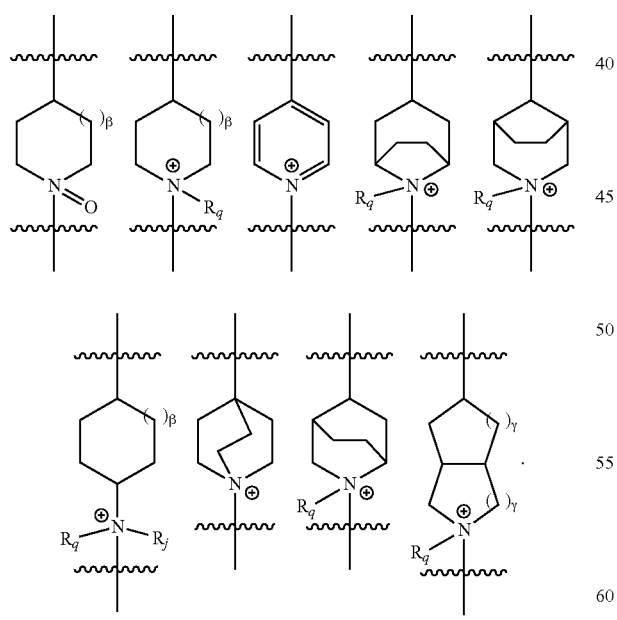

In some embodiments, $R_q$ is independently selected from $C_{1-6}$ alkyl, $C_{2-6}$ alkenyl, $C_{3-6}$ alkynyl, $C_{3-8}$ cycloalkyl;

β=0, 1 or 2;

γ=1, 2 or 3.

In some embodiments, D is selected from:

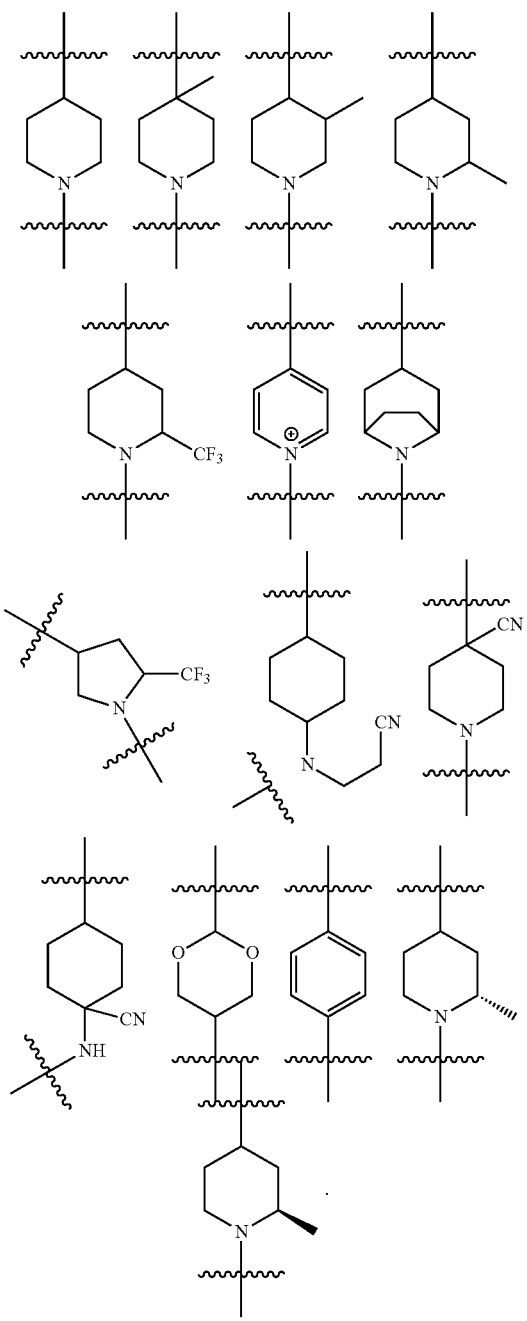

In some embodiments, D is selected from:

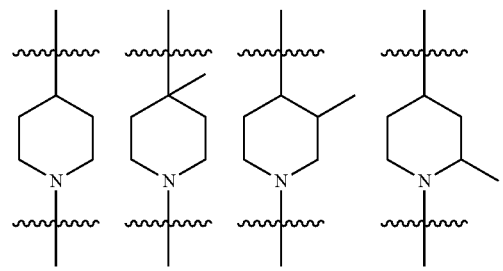

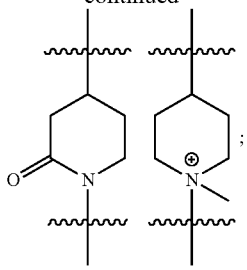

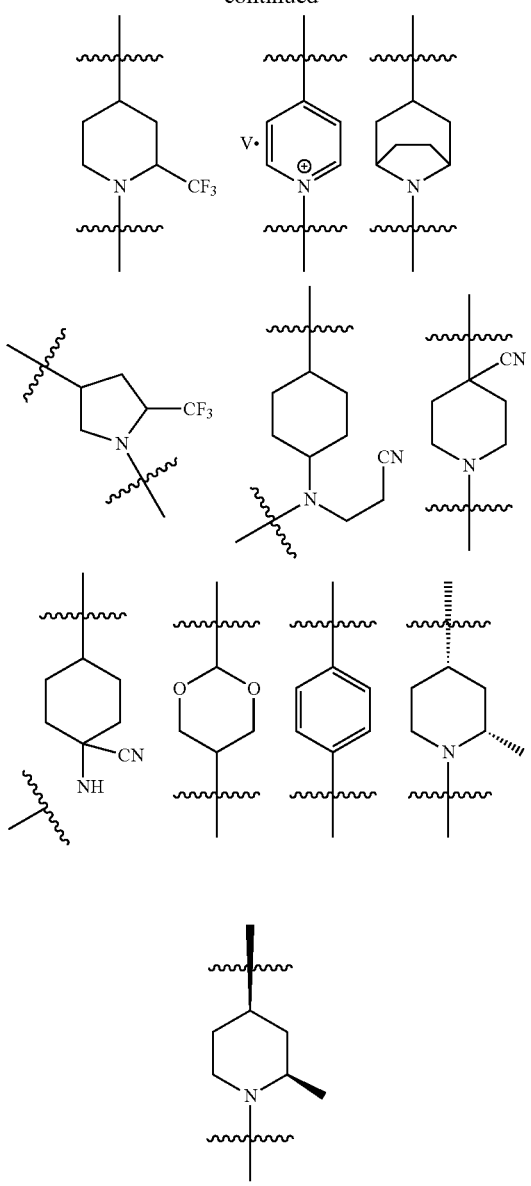

V. is a counterion, preferably a halogen anion, more preferably a chloride ion, a bromide ion or an iodide ion.

In some embodiments, D is selected from

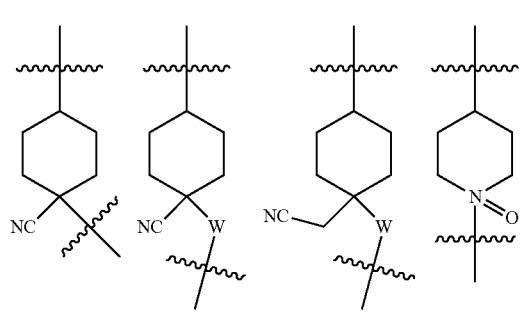

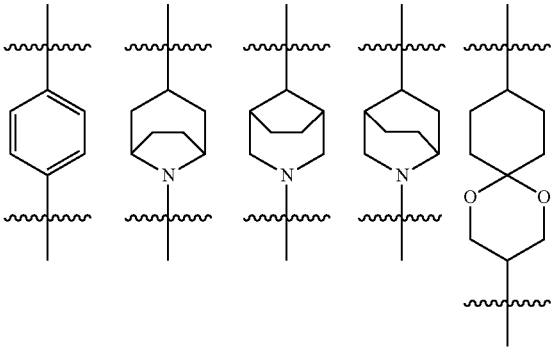

W is $NR_j$, $R_j$ is selected from H (hydrogen), D (deuterium), $CH_2CN$ or $CH_2CH_2CN$.

In some embodiments, in the linker of the conjugate, D is selected from the following groups substituted by one or more $R_i$: 3-8 membered cycloalkyl, 3-8 membered aliphatic heterocyclic group, 6-12 membered bridged heterocyclic group, 6-12 membered spiro heterocyclic group, 6-12 membered fused heterocyclic group, aryl, heteroaryl, 3-8 membered cycloalkyl-W—.

In some embodiments, D is selected from the following groups substituted by one or more $R_i$: 5-6 membered cycloalkyl, 5-6 membered aliphatic heterocyclic group, 8-11 membered nitrogen-containing or oxygen-containing bridged heterocyclic group, 8-11 membered nitrogen-containing or oxygen-containing spiro heterocyclic group, 8-11 membered nitrogen-containing or oxygen-containing fused heterocyclic group, phenyl, 5-6 membered nitrogen-containing heteroaryl, 5-6 membered cycloalkyl-W—.

In some embodiments, D is selected from the following groups substituted by one or more $R_i$: 5-6 membered cycloalkyl, 5-6 membered nitrogen-containing or oxygen-containing aliphatic heterocyclic group, 5-6 membered nitrogen-containing heteroaryl, 8 membered nitrogen-containing or oxygen-containing bridged heterocyclic group, 11 membered nitrogen-containing or oxygen-containing spiro heterocyclic group, 8-11 membered nitrogen-containing or oxygen-containing fused heterocyclic group, phenyl, 5-6 membered cycloalkyl-W—.

In some embodiments, D is selected from the following groups substituted by one or more $R_i$: cyclohexyl, 5-6 membered nitrogen-containing or oxygen-containing aliphatic heterocyclic group, 6 membered nitrogen-containing heteroaryl, 8 membered nitrogen-containing bridged heterocyclic group, 11 membered oxygen-containing spiro heterocyclic group, 8 membered nitrogen-containing fused heterocyclic group, phenyl, cyclohexyl-W—.

In some embodiments, D is selected from the following groups substituted by one or more $R_i$:

-continued
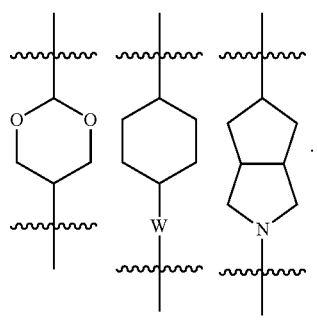
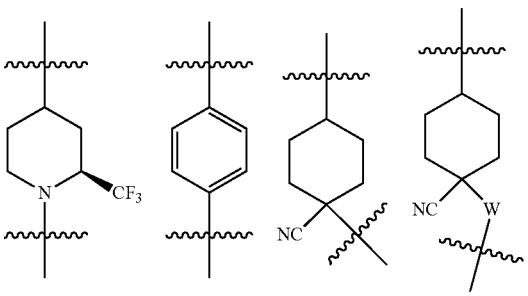
In some embodiments, $R_i$ is independently selected from H (hydrogen), D (deuterium), =O, CN, $CH_2CN$, methyl, $CF_3$.
In some embodiments, D is selected from:
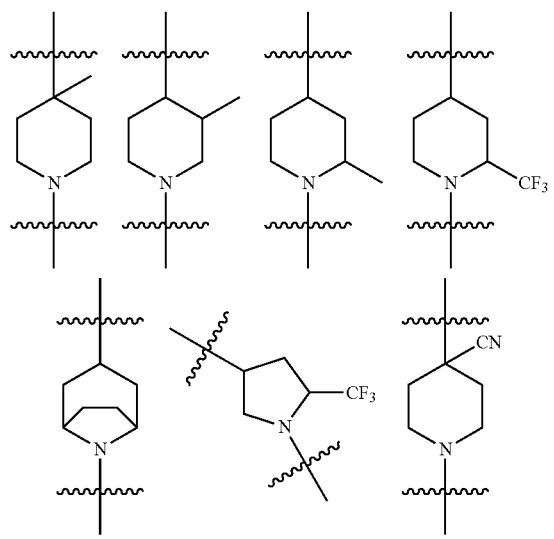
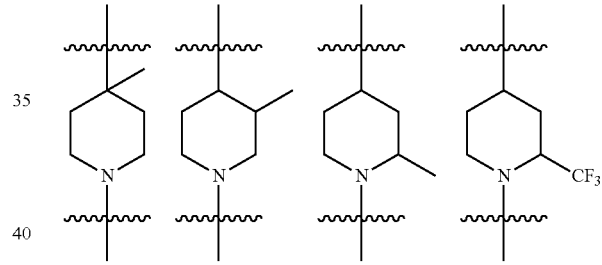
In some embodiments, W is $NR_j$, $R_j$ is selected from H (hydrogen), D (deuterium), $CH_2CN$ or $CH_2CH_2CN$.
In some embodiments, D is selected from:
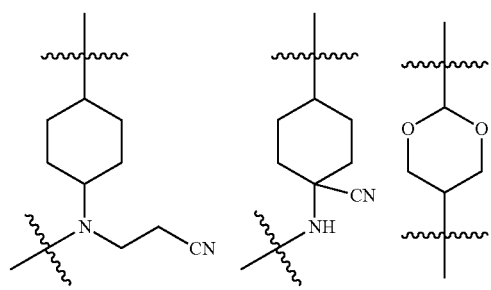
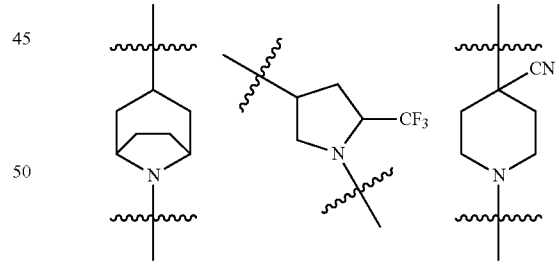
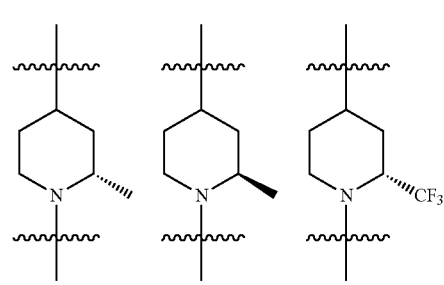
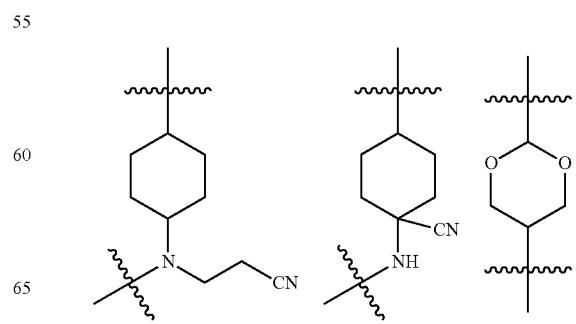

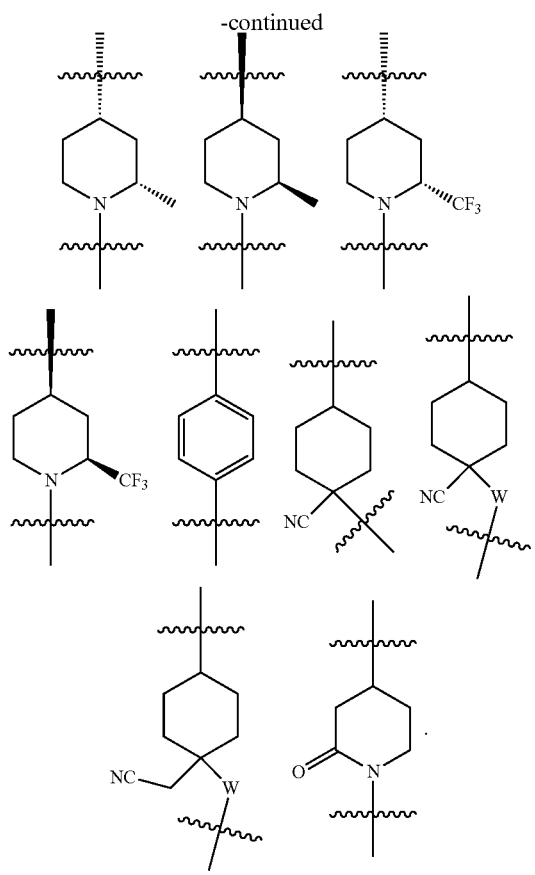

In some embodiments, W is NR$_j$, R$_j$ is selected from H (hydrogen), D (deuterium), CH$_2$CN or CH$_2$CH$_2$CN.

In some embodiments, in the linker of the conjugate, D is selected from the following groups optionally substituted by one or more R$_i$: 3-8 membered nitrogen-containing aliphatic heterocyclic group, 6-12 membered nitrogen-containing bridged heterocyclic group, 6-12 membered nitrogen-containing spiro heterocyclic group, 6-12 membered nitrogen-containing fused heterocyclic group, nitrogen-containing heteroaryl, 3-8 membered cycloalkyl-W—.

In some embodiments, the nitrogen-containing heteroaryl, 3-8 membered nitrogen-containing aliphatic heterocyclic group, 6-12 membered nitrogen-containing bridged heterocyclic group, 6-12 membered nitrogen-containing Spiro heterocyclic group or 6-12 membered nitrogen-containing fused heterocyclic group contains one or more quaternized nitrogen atoms.

In some embodiments, in the 3-8 membered nitrogen-containing aliphatic heterocyclic group, at least one nitrogen atom is substituted by =O.

In some embodiments, D is selected from the following groups optionally substituted by one or more R$_i$: 5-6 membered nitrogen-containing aliphatic heterocyclic group, 8-11 membered nitrogen-containing bridged heterocyclic group, 8-11 membered nitrogen-containing spiro heterocyclic group, 8-11 membered nitrogen-containing fused heterocyclic group, 5-6 membered nitrogen-containing heteroaryl.

In some embodiments, the 5-6 membered nitrogen-containing aliphatic heterocyclic group, 8-11 membered nitrogen-containing bridged heterocyclic group, 8-11 membered nitrogen-containing spiro heterocyclic group, 8-11 membered nitrogen-containing fused heterocyclic group or 5-6 membered nitrogen-containing heteroaryl contains one or more quaternized nitrogen atoms; preferably, D is selected from the following groups optionally substituted by one or more R$_i$: 5-6 membered nitrogen-containing aliphatic heterocyclic group, 5-6 membered nitrogen-containing heteroaryl (for example, pyridyl), 8 membered nitrogen-containing bridged heterocyclic group, 11 membered nitrogen-containing spiro heterocyclic group, 8-11 membered nitrogen-containing fused heterocyclic group.

In some embodiments, the 5-6 membered nitrogen-containing aliphatic heterocyclic group, 5-6 membered nitrogen-containing heteroaryl (for example, pyridyl), 8 membered nitrogen-containing bridged heterocyclic group, 11 membered nitrogen-containing spiro heterocyclic group or 8-11 membered nitrogen-containing fused heterocyclic group contains one or more quaternized nitrogen atoms.

In some embodiments, D is selected from the following groups optionally substituted by one or more R$_i$: 5-6 membered nitrogen-containing aliphatic heterocyclic group, 6 membered nitrogen-containing heteroaryl, 8 membered nitrogen-containing bridged heterocyclic group, 11 membered nitrogen-containing spiro heterocyclic group, 8 membered nitrogen-containing fused heterocyclic group.

In some embodiments, the 5-6 membered nitrogen-containing aliphatic heterocyclic group, 6 membered nitrogen-containing heteroaryl, 8 membered nitrogen-containing bridged heterocyclic group, 11 membered nitrogen-containing spiro heterocyclic group, 8 membered nitrogen-containing fused heterocyclic group contains one or more quaternized nitrogen atoms.

In some embodiments, in the 5-6 membered nitrogen-containing aliphatic heterocyclic group, at least one nitrogen atom is substituted by =O.

In some embodiments, D is selected from the following groups substituted by one or more R$_i$:

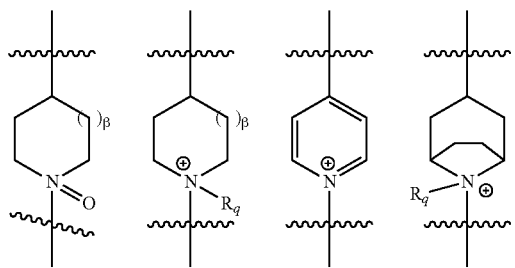

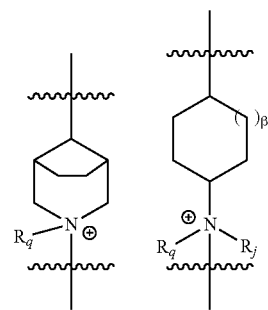

-continued

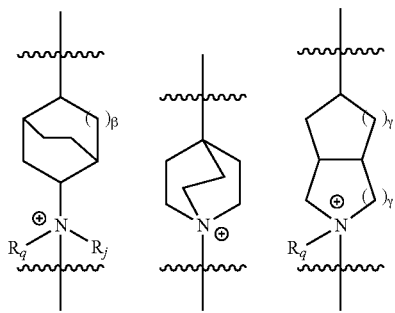

In some embodiments, D is selected from the following groups substituted by one or more $R_i$:

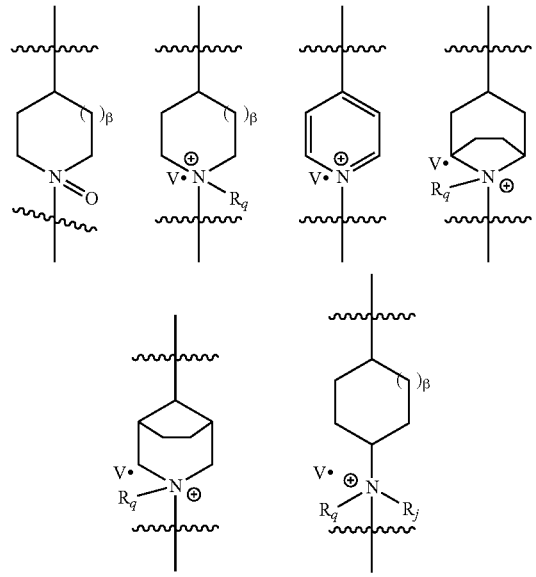

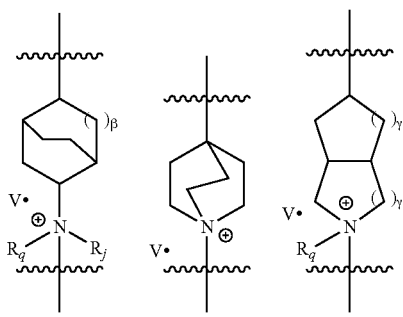

V. is a counterion, preferably a halogen anion, more preferably a chloride ion, a bromide ion or an iodide ion.

In some embodiments, $R_q$ is independently selected from $C_{1-6}$ alkyl, $C_{2-6}$ alkenyl, $C_{3-6}$ alkynyl, $C_{3-8}$ cycloalkyl.

β=0, 1 or 2;

γ=1, 2 or 3.

In some embodiments, $R_i$ is independently selected from H (hydrogen), D (deuterium), =O, CN, $CH_2CN$, methyl, $CF_3$.

In some embodiments, in the linker of the conjugate, D is selected from the following groups:

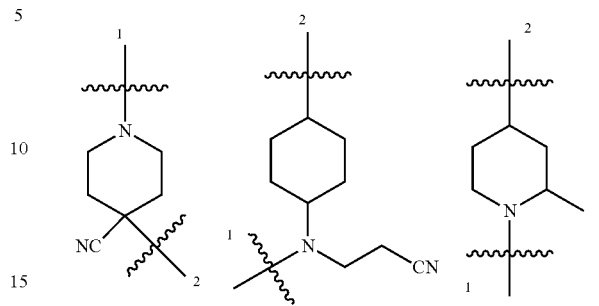

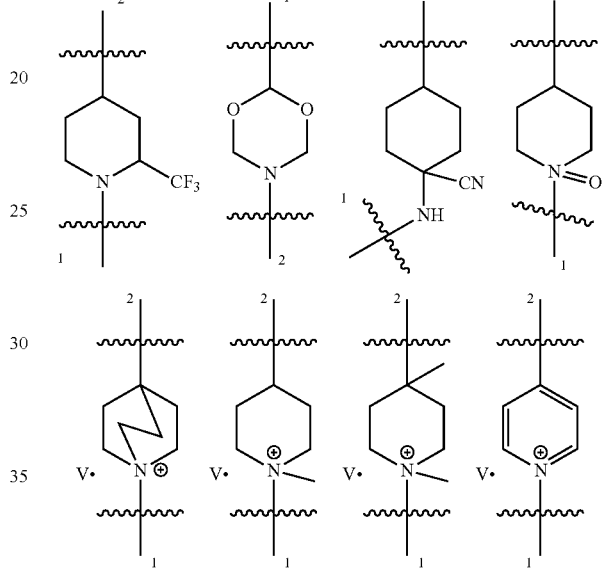

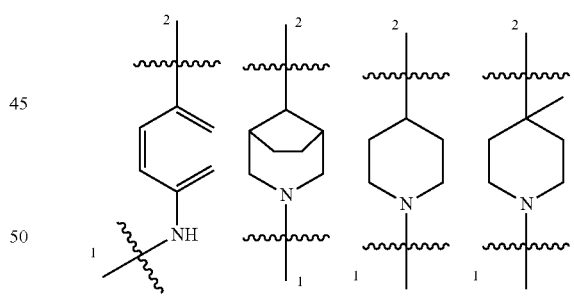

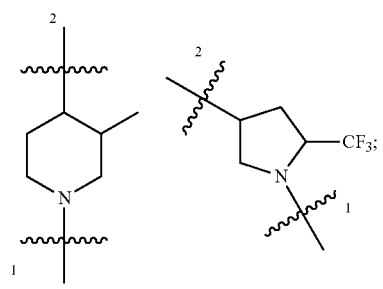

wherein,

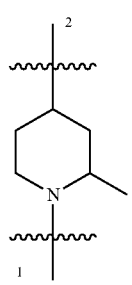

is optionally further selected from

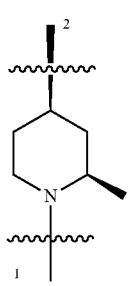

is optionally further selected from

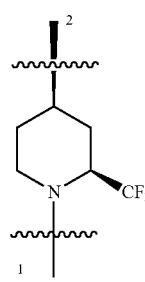

The above group is linked to $L_2$ at one of the two positions marked by 1 or 2, and linked to $L_3$ at the other position; preferably, the above group is linked to $L_2$ at the position marked by 1, and linked to $L_3$ at the position marked by 2;

V. is a counterion, preferably a halogen anion, more preferably a chloride ion, a bromide ion or an iodide ion.

In some embodiments, in the linker of the conjugate, $L_2$ is selected from:

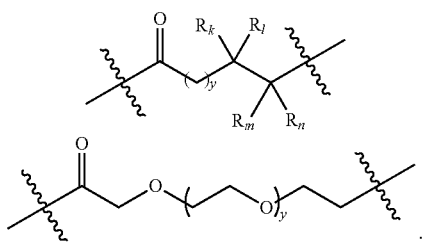

In some embodiments, y=1.
In some embodiments, $R_k$, $R_l$, $R_m$, $R_n$ are all hydrogen.

In one aspect, the present invention provides a linker having the following structure:

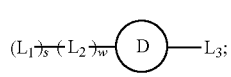

wherein, $L_1$ is selected from: peptide, oligose, —(CH$_2$)$_t$—, —(CH$_2$CH$_2$O)$_t$—(CH$_2$)$_t$—, Val, Cit, Phe, Lys, D-Val, Leu, Lys, Gly, Ala, Asn, Val-Cit, Val-Ala, Val-Lys(Ac), Phe-Lys, Phe-Lys(Ac), D-Val-Leu-Lys, Gly-Gly-Arg, Ala-Ala-Asn, t=1, 2, 3, 4, 5 or 6;
s is selected from 1 or 2;
$L_2$ is selected from: —(CH$_2$)$_y$—, —(CH$_2$CH$_2$O)$_y$—(CH$_2$)$_y$—,

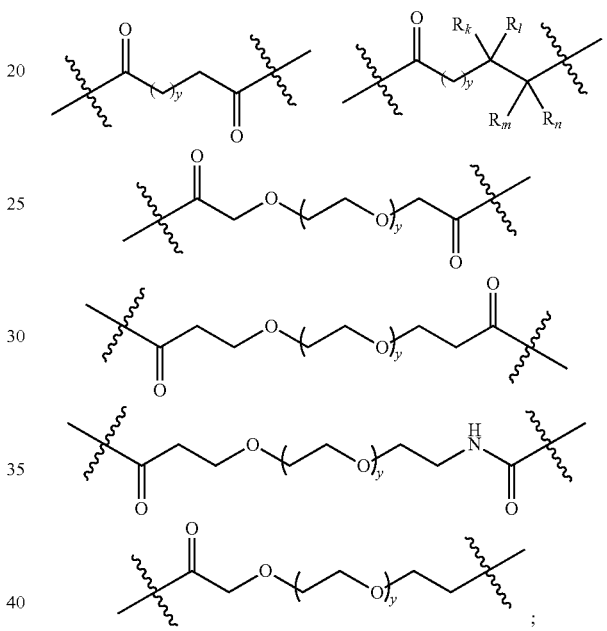

$R_k$, $R_l$, $R_m$, $R_n$, independently of each other, are selected from H (hydrogen), D (deuterium), halogen, CF$_3$, CN, CH$_2$CN, C$_{1-6}$ alkyl, C$_{1-6}$ alkoxy, C$_{2-10}$ alkenyl, C$_{2-10}$ alkynyl, C$_{3-6}$ cycloalkyl;
y, independently of each other, is 0, 1, 2, 3, 4, 5, 6, 7, 8, 9 or 10;
w is selected from 1 or 2;
$L_3$ is selected from the following groups:

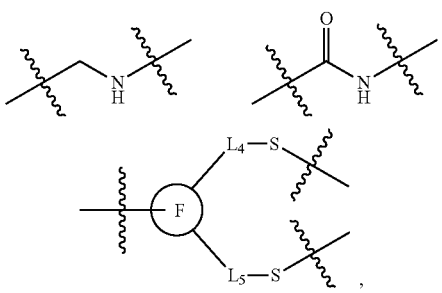

wherein,
$L_4$, $L_5$ are absent or, independently of each other, are selected from C$_{1-6}$ alkylene (for example, methylene);

F is selected from:

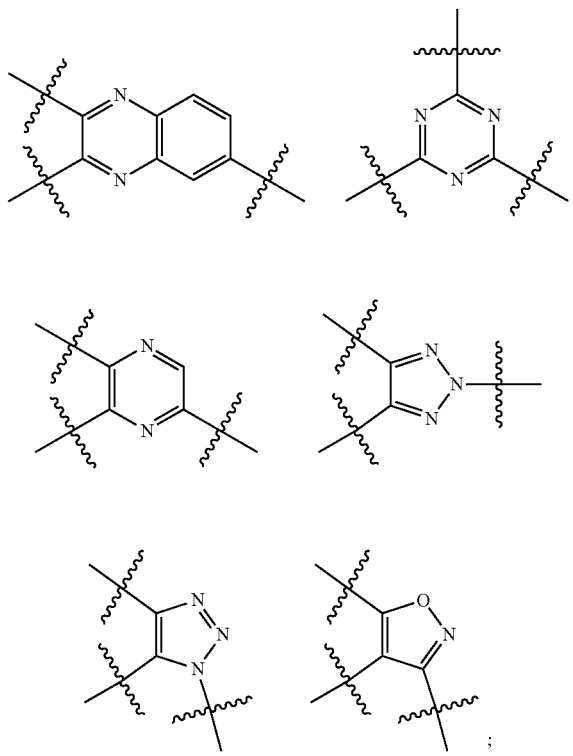

;

D is selected from the following groups substituted by one or more $R_i$: 3-8 membered cycloalkyl, 3-8 membered aliphatic heterocyclic group, 6-12 membered bridged heterocyclic group, 6-12 membered spiro heterocyclic group, 6-12 membered fused heterocyclic group, aryl, heteroaryl, 3-8 membered cycloalkyl-W—;

W is O or $NR_j$, $R_j$ is independently selected from H (hydrogen), D (deuterium), $C_{1-6}$ alkyl, $C_{3-6}$ cycloalkyl, $C_{1-6}$ alkoxy, cyano $C_{1-2}$ alkyl;

$R_i$ is independently selected from H (hydrogen), D (deuterium), halogen, =O, $CF_3$, CN, $CH_2CN$, $C_{1-6}$ alkyl, $C_{1-6}$ alkoxy, $C_{2-10}$ alkynyl, COOH, $SO_3H$.

In some embodiments, $L_1$ is selected from peptide, oligose, Val-Cit, Val-Ala, Val-Lys(Ac), Phe-Lys, Phe-Lys(Ac), D-Val-Leu-Lys, Gly-Gly-Arg, Ala-Ala-Asn.

In some embodiments, $L_1$ is

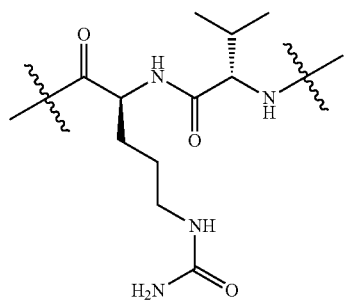 [SMILES: *N[C@H](C(=O)N[C@@H](CCCNC(N)=O)C(*)=O)C(C)C]

In some embodiments, $L_1$ is

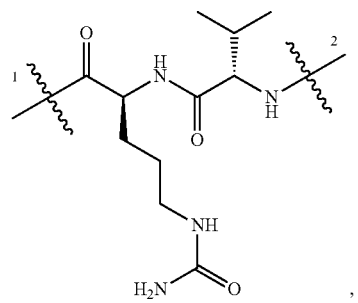 [SMILES: *N[C@H](C(=O)N[C@@H](CCCNC(N)=O)C(*)=O)C(C)C]

and s=1;

wherein, the group $L_1$ is linked to G at the position marked by 1, and linked to $L_2$ at the position marked by 2.

In some embodiments, $L_2$ is selected from:

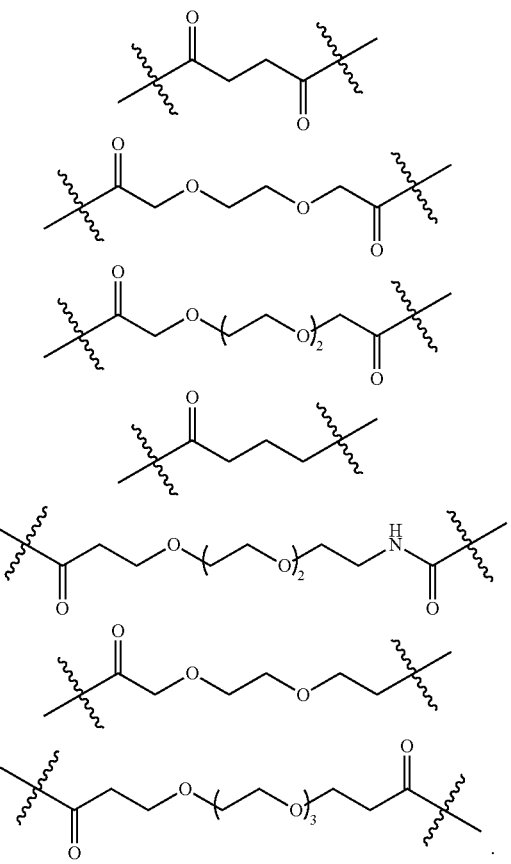

In some embodiments, $L_2$ is selected from:

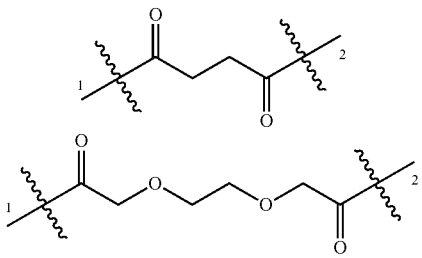

-continued

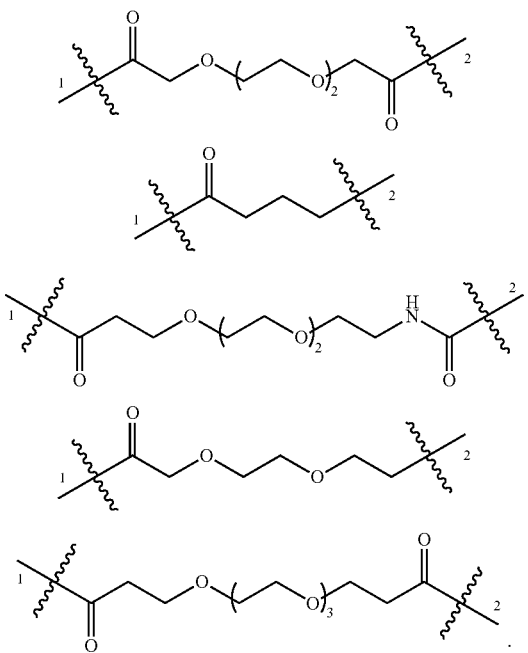

and w=1;
wherein, the group $L_2$ is linked to $L_1$ at the position marked by 1, and linked to D at the position marked by 2.

In some embodiments, $L_3$ is selected from:

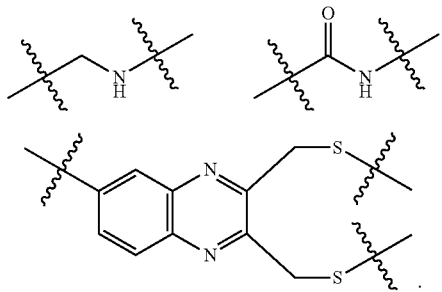

In some embodiments, $L_3$ is selected from:

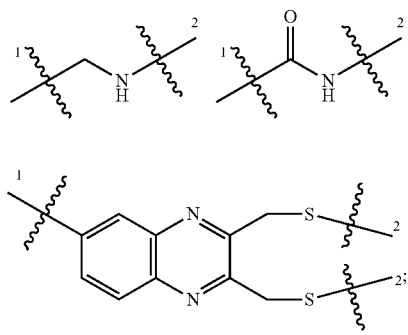

wherein, the group $L_3$ is linked to D at the position marked by 1, and linked to E at the position marked by 2.

In some embodiments, $L_3$ is

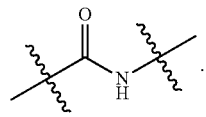

In some embodiments, $L_3$ is

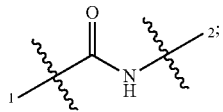

wherein, the group $L_3$ is linked to D at the position marked by 1, and linked to E at the position marked by 2.

In some embodiments, D is selected from the following groups substituted by one or more $R_i$: 5-6 membered cycloalkyl, 5-6 membered aliphatic heterocyclic group, 8-11 membered nitrogen-containing or oxygen-containing bridged heterocyclic group, 8-11 membered nitrogen-containing or oxygen-containing spiro heterocyclic group, 8-11 membered nitrogen-containing or oxygen-containing fused heterocyclic group, phenyl, 5-6 membered nitrogen-containing heteroaryl, 5-6 membered cycloalkyl-W—.

In some embodiments, D is selected from the following groups substituted by one or more $R_i$: 5-6 membered cycloalkyl, 5-6 membered nitrogen-containing or oxygen-containing aliphatic heterocyclic group, 5-6 membered nitrogen-containing heteroaryl, 8 membered nitrogen-containing or oxygen-containing bridged heterocyclic group, 11 membered nitrogen-containing or oxygen-containing spiro heterocyclic group, 8-11 membered nitrogen-containing or oxygen-containing fused heterocyclic group, phenyl, 5-6 membered cycloalkyl-W—.

In some embodiments, D is selected from the following groups substituted by one or more $R_i$: cyclohexyl, 5-6 membered nitrogen-containing or oxygen-containing aliphatic heterocyclic group, 6 membered nitrogen-containing heteroaryl, 8 membered nitrogen-containing bridged heterocyclic group, 11 membered oxygen-containing spiro heterocyclic group, 8 membered nitrogen-containing fused heterocyclic group, phenyl, cyclohexyl-W—.

In some embodiments, D is selected from the following groups substituted by one or more $R_i$:

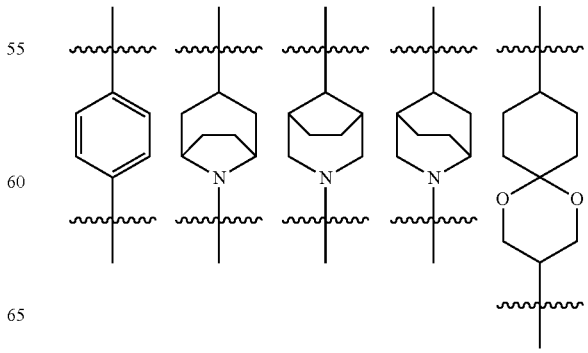

-continued
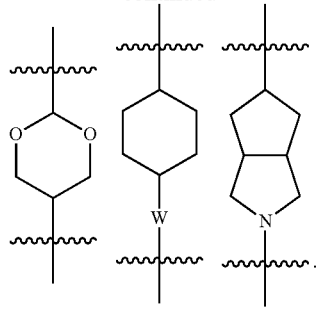
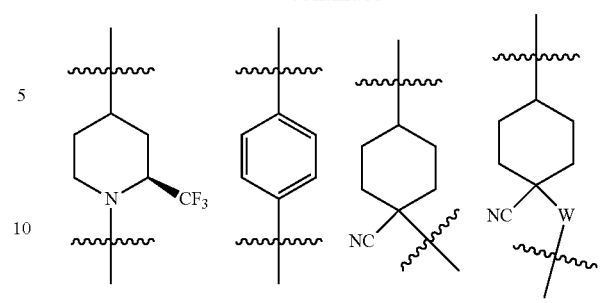
In some embodiments, $R_i$ is independently selected from H (hydrogen), D (deuterium), =O, CN, CH$_2$CN, methyl, CF$_3$.
In some embodiments, D is selected from:
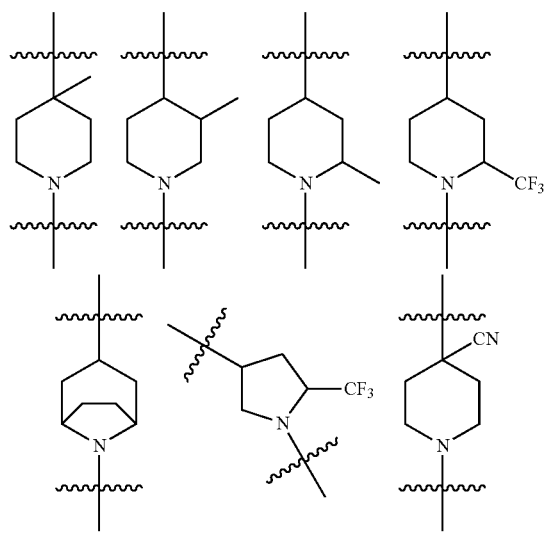
In some embodiments, W is NR$_j$, R$_j$ is selected from H (hydrogen), D (deuterium), CH$_2$CN or CH$_2$CH$_2$CN.
In some embodiments, D is selected from:
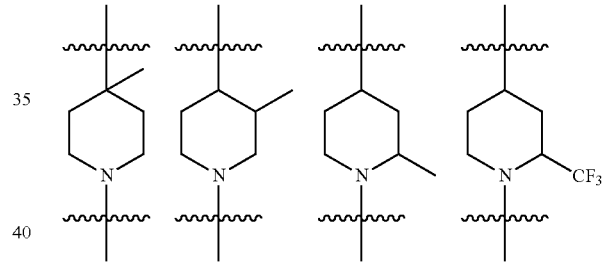
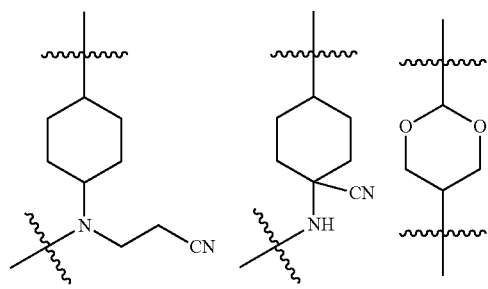
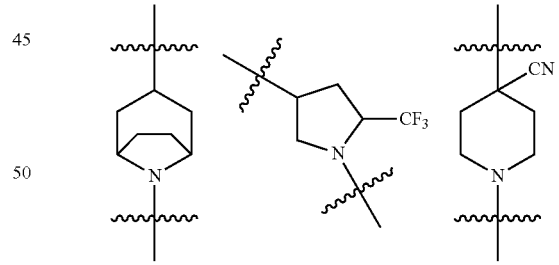
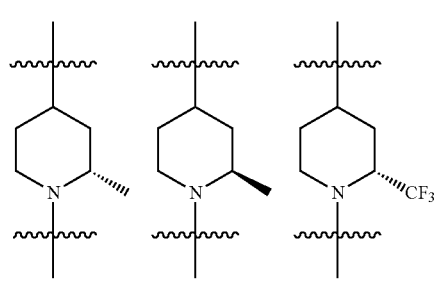
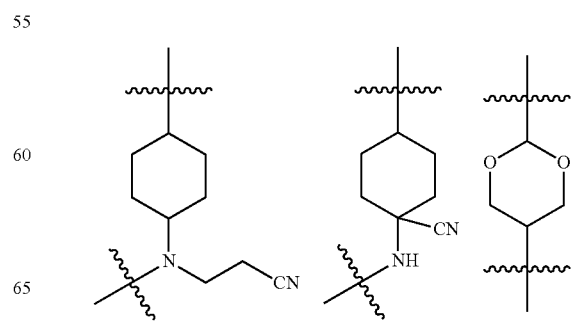

-continued

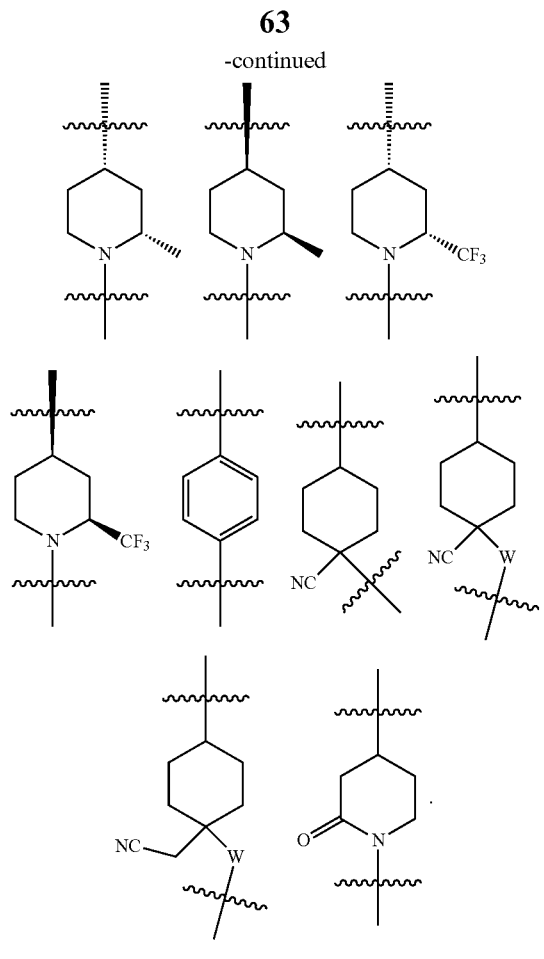

In some embodiments, W is NR$_j$, R$_j$ is selected from H (hydrogen), D (deuterium), CH$_2$CN or CH$_2$CH$_2$CN.

In one aspect, the present invention provides a linker having the following structure:

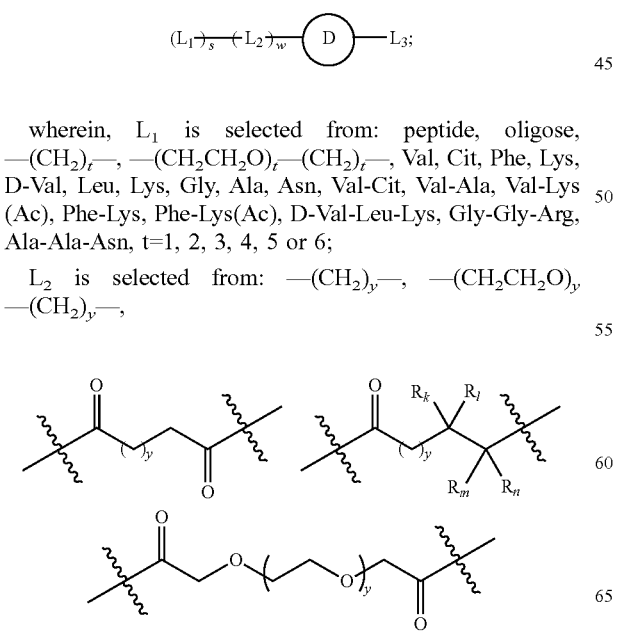

wherein, L$_1$ is selected from: peptide, oligose, —(CH$_2$)$_t$—, —(CH$_2$CH$_2$O)$_t$—(CH$_2$)$_t$—, Val, Cit, Phe, Lys, D-Val, Leu, Lys, Gly, Ala, Asn, Val-Cit, Val-Ala, Val-Lys (Ac), Phe-Lys, Phe-Lys(Ac), D-Val-Leu-Lys, Gly-Gly-Arg, Ala-Ala-Asn, t=1, 2, 3, 4, 5 or 6;

L$_2$ is selected from: —(CH$_2$)$_y$—, —(CH$_2$CH$_2$O)$_y$, —(CH$_2$)$_y$—,

-continued

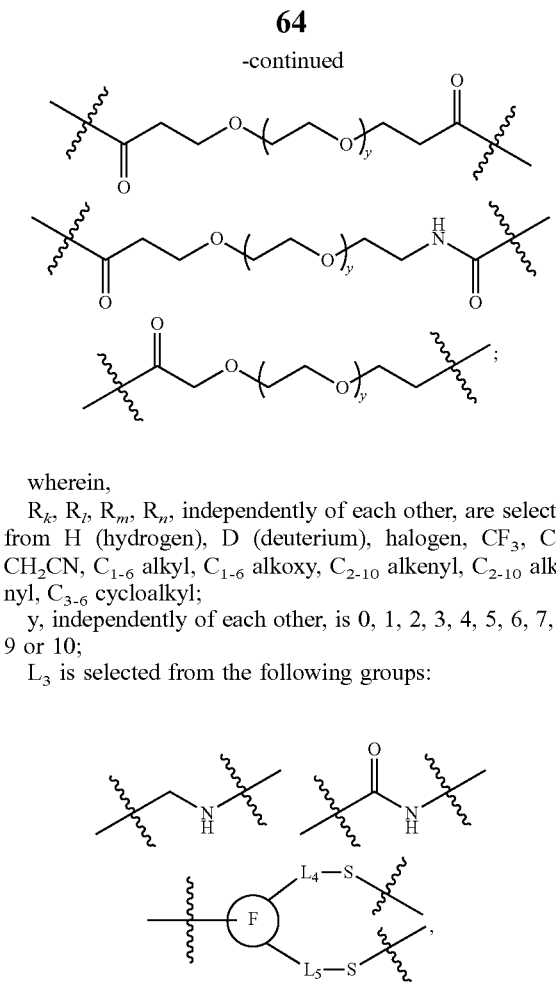

wherein,

R$_k$, R$_l$, R$_m$, R$_n$, independently of each other, are selected from H (hydrogen), D (deuterium), halogen, CF$_3$, CN, CH$_2$CN, C$_{1-6}$ alkyl, C$_{1-6}$ alkoxy, C$_{2-10}$ alkenyl, C$_{2-10}$ alkynyl, C$_{3-6}$ cycloalkyl;

y, independently of each other, is 0, 1, 2, 3, 4, 5, 6, 7, 8, 9 or 10;

L$_3$ is selected from the following groups:

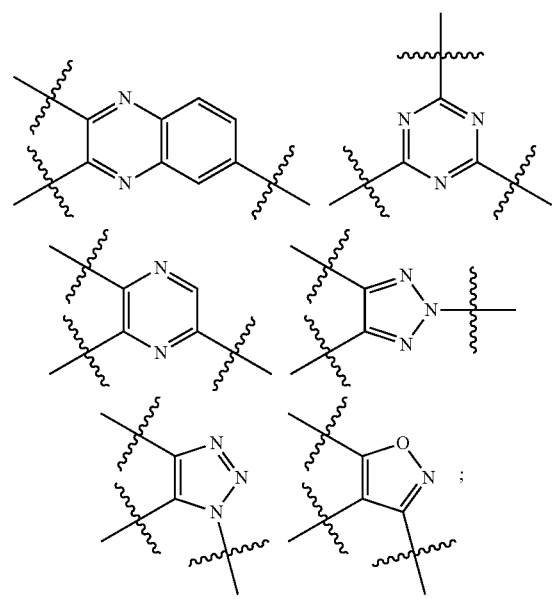

wherein,

L$_4$, L$_5$ are absent or, independently of each other, are selected from C$_{1-6}$ alkylene (for example, methylene);

F is selected from:

s, w, independently of each other, are selected from 1 or 2 (for example, s and w both are 1);

D is selected from the following groups optionally substituted by one or more $R_i$: 3-8 membered nitrogen-containing aliphatic heterocyclic group, 6-12 membered nitrogen-containing bridged heterocyclic group, 6-12 membered nitrogen-containing spiro heterocyclic group, 6-12 membered nitrogen-containing fused heterocyclic group, nitrogen-containing heteroaryl, 3-8 membered cycloalkyl-W—;

W is O or $NR_j$, $R_j$ is independently selected from H (hydrogen), D (deuterium), $C_{1-6}$ alkyl, $C_{3-6}$ cycloalkyl, $C_{1-6}$ alkoxy, cyano $C_{1-2}$ alkyl;

$R_i$ is independently selected from D (deuterium), halogen, =O, $CF_3$, CN, $CH_2CN$, $C_{1-6}$ alkyl, $C_{1-6}$ alkoxy, $C_{2-10}$ alkynyl, COOH, $SO_3H$.

In some embodiments, $L_1$ is selected from peptide, oligose, Val-Cit, Val-Ala, Val-Lys(Ac), Phe-Lys, Phe-Lys(Ac), D-Val-Leu-Lys, Gly-Gly-Arg, Ala-Ala-Asn.

In some embodiments, $L_1$ is

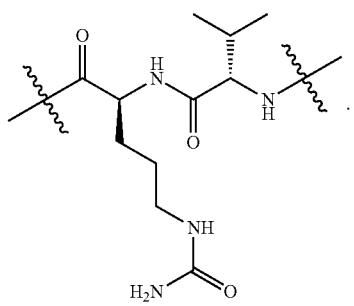 [SMILES: *N[C@H](C(=O)N[C@@H](CCCNC(N)=O)C(*)=O)C(C)C]

In some embodiments, $L_2$ is selected from:

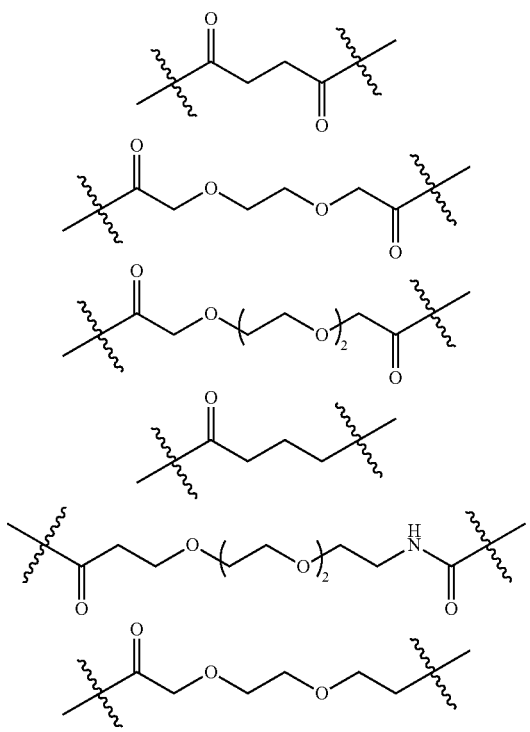

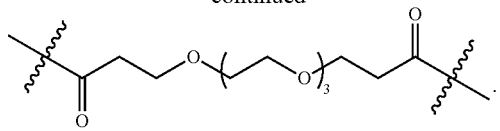

In some embodiments, $L_3$ is selected from:

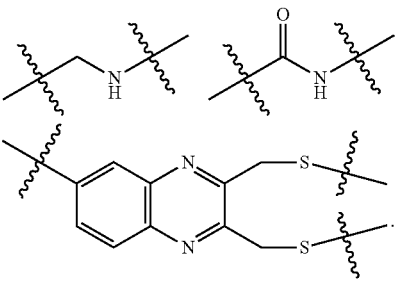

In some embodiments, $L_3$ is

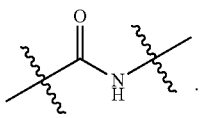

In some embodiments, the nitrogen-containing heteroaryl, 3-8 membered nitrogen-containing aliphatic heterocyclic group, 6-12 membered nitrogen-containing bridged heterocyclic group, 6-12 membered nitrogen-containing Spiro heterocyclic group or 6-12 membered nitrogen-containing fused heterocyclic group contains one or more quaternized nitrogen atoms.

In some embodiments, in the 3-8 membered nitrogen-containing aliphatic heterocyclic group, at least one nitrogen atom is substituted by =O.

In some embodiments, D is selected from the following groups optionally substituted by one or more $R_i$: 5-6 membered nitrogen-containing aliphatic heterocyclic group, 8-11 membered nitrogen-containing bridged heterocyclic group, 8-11 membered nitrogen-containing spiro heterocyclic group, 8-11 membered nitrogen-containing fused heterocyclic group, 5-6 membered nitrogen-containing heteroaryl.

In some embodiments, the 5-6 membered nitrogen-containing aliphatic heterocyclic group, 8-11 membered nitrogen-containing bridged heterocyclic group, 8-11 membered nitrogen-containing spiro heterocyclic group, 8-11 membered nitrogen-containing fused heterocyclic group or 5-6 membered nitrogen-containing heteroaryl contains one or more quaternized nitrogen atoms; preferably, D is selected from the following groups optionally substituted by one or more $R_i$: 5-6 membered nitrogen-containing aliphatic heterocyclic group, 5-6 membered nitrogen-containing heteroaryl (for example, pyridyl), 8 membered nitrogen-containing bridged heterocyclic group, 11 membered nitrogen-containing spiro heterocyclic group, 8-11 membered nitrogen-containing fused heterocyclic group.

In some embodiments, the 5-6 membered nitrogen-containing aliphatic heterocyclic group, 5-6 membered nitrogen-containing heteroaryl (for example, pyridyl), 8 membered nitrogen-containing bridged heterocyclic group, 11 membered nitrogen-containing spiro heterocyclic group or 8-11 membered nitrogen-containing fused heterocyclic group contains one or more quaternized nitrogen atoms.

In some embodiments, D is selected from the following groups optionally substituted by one or more $R_i$: 5-6 membered nitrogen-containing aliphatic heterocyclic group, 6 membered nitrogen-containing heteroaryl, 8 membered nitrogen-containing bridged heterocyclic group, 11 membered nitrogen-containing spiro heterocyclic group, 8 membered nitrogen-containing fused heterocyclic group.

In some embodiments, the 5-6 membered nitrogen-containing aliphatic heterocyclic group, 6 membered nitrogen-containing heteroaryl, 8 membered nitrogen-containing bridged heterocyclic group, 11 membered nitrogen-containing spiro heterocyclic group, 8 membered nitrogen-containing fused heterocyclic group contains one or more quaternized nitrogen atoms.

In some embodiments, in the 5-6 membered nitrogen-containing aliphatic heterocyclic group, at least one nitrogen atom is substituted by =O.

In some embodiments, D is selected from the following groups substituted by one or more $R_i$:

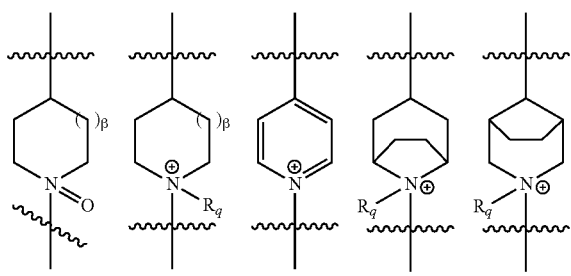

In some embodiments, D is selected from the following groups substituted by one or more $R_i$:

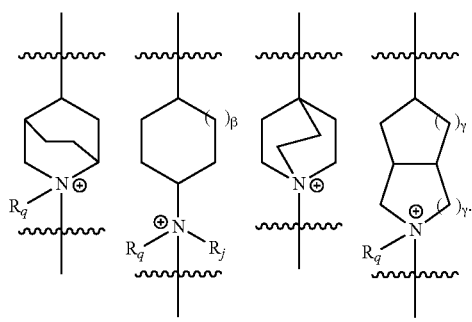

In some embodiments, D is selected from the following groups substituted by one or more $R_i$:

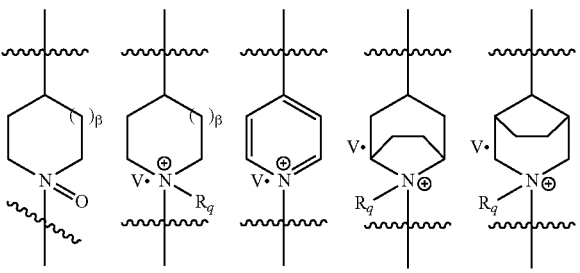

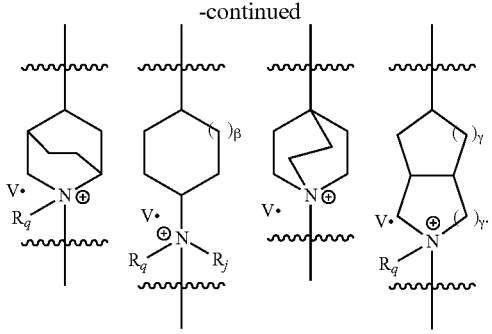

V. is a counterion, preferably a halogen anion, more preferably a chloride ion, a bromide ion or an iodide ion;

In some embodiments, $R_q$ is independently selected from $C_{1-6}$ alkyl, $C_{2-6}$ alkenyl, $C_{3-6}$ alkynyl, $C_{3-8}$ cycloalkyl;

$\beta$=0, 1 or 2;

$\gamma$=1, 2 or 3.

In some embodiments, $R_j$ is independently selected from D (deuterium), =O, CN, CH$_2$CN, methyl, CF$_3$.

In one aspect, the present invention provides a linker having the following structure:

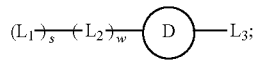

wherein, $L_1$ is selected from: peptide, oligose, —(CH$_2$)$_t$—, —(CH$_2$CH$_2$O)$_t$—(CH$_2$)$_t$—, Val, Cit, Phe, Lys, D-Val, Leu, Lys, Gly, Ala, Asn, Val-Cit, Val-Ala, Val-Lys(Ac), Phe-Lys, Phe-Lys(Ac), D-Val-Leu-Lys, Gly-Gly-Arg, Ala-Ala-Asn, t=1, 2, 3, 4, 5 or 6;

$L_2$ is selected from:

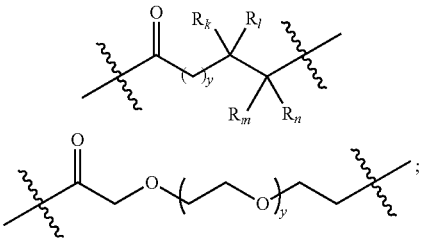

y=1;

$R_k$, $R_l$, $R_m$, $R_n$ are all hydrogen;

$L_3$ is selected from the following groups:

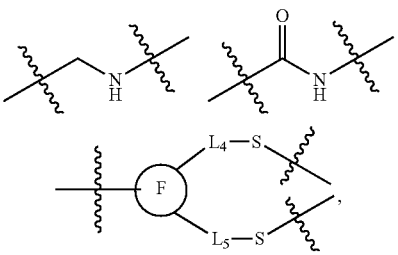

wherein, $L_4$, $L_5$ are absent or, independently of each other, are selected from $C_{1-6}$ alkylene (for example, methylene);

F is selected from:

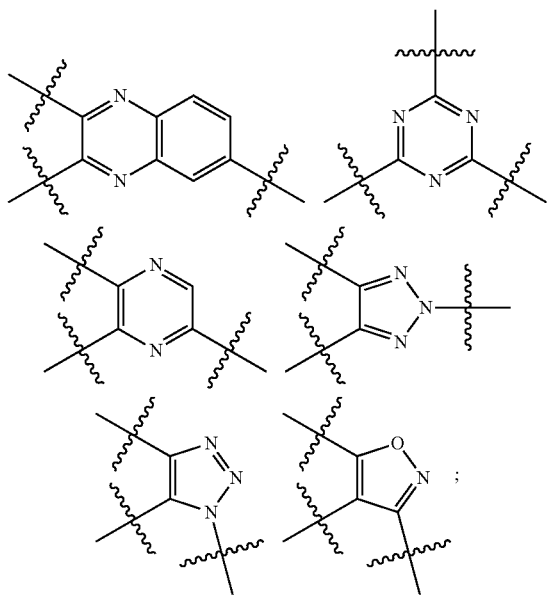

s, w, independently of each other, are selected from 1 or 2 (for example, s and w both are 1);

D is selected from the following groups optionally substituted by one or more $R_i$: 3-8 membered cycloalkyl, 3-8 membered aliphatic heterocyclic group, 6-12 membered bridged heterocyclic group, 6-12 membered spiro heterocyclic group, 6-12 membered fused heterocyclic group, aryl, heteroaryl, 3-8 membered cycloalkyl-W—, $R_i$ is independently selected from D (deuterium), halogen, =O, $CF_3$, CN, $CH_2CN$, $C_{1-6}$ alkyl, $C_{1-6}$ alkoxy, $C_{2-10}$ alkynyl, COOH, $SO_3H$; W is O or $NR_j$, $R_j$ is independently selected from $C_{1-6}$ alkyl, $C_{3-6}$ cycloalkyl, $C_{1-6}$ alkoxy, cyano$C_{1-2}$ alkyl.

In some embodiments, $L_1$ is selected from peptide, oligose, Val-Cit, Val-Ala, Val-Lys(Ac), Phe-Lys, Phe-Lys(Ac), D-Val-Leu-Lys, Gly-Gly-Arg, Ala-Ala-Asn.

In some embodiments, $L_1$ is

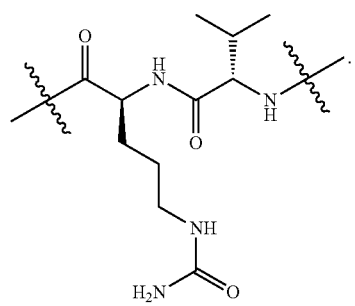 [SMILES: *N[C@H](C(=O)N[C@@H](CCCNC(N)=O)C(*)=O)C(C)C]

In some embodiments, $L_3$ is selected from:

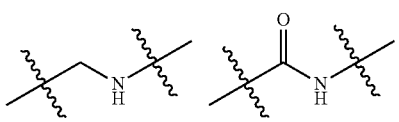

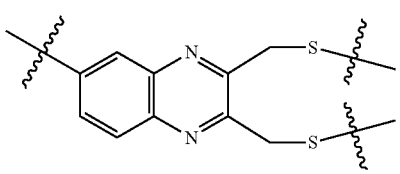

In some embodiments, $L_3$ is

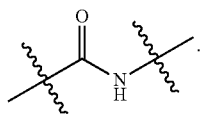 [SMILES: *NC(*)=O]

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more nitrogen atoms.

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more quaternized nitrogen atoms.

In some embodiments, the heteroaryl, 3-8 membered aliphatic heterocyclic group, 6-12 membered bridged heterocyclic group, 6-12 membered spiro heterocyclic group or 6-12 membered fused heterocyclic group contains one or more nitrogen atoms, wherein, at least one nitrogen atom is substituted by =O.

The present invention also provides a conjugate comprising a drug and a linker, and optionally a targeting moiety, wherein the linker is as defined above.

In some embodiments, the drug is selected from the compound as defined above, or a pharmaceutically acceptable salt, solvate, hydrate, isomer thereof, or any crystalline form or racemate thereof.

In some embodiments, the targeting moiety (E) of the conjugate of the present invention is a substance capable of specifically binding to a site on a cell surface, and the targeting moiety (E) may be selected from small molecule ligands, proteins, polypeptides, as well as non-proteinaceous agents such as sugars, RNA or DNA.

In some embodiments of the present invention, the targeting moiety (E) is an antibody, such as a monoclonal antibody or an antigen-binding fragment thereof, wherein the monoclonal antibody or antigen-binding fragment thereof comprises Fab, Fab', F(ab')2, Fd, Fv, dAb, complementarity determining region fragment, single chain antibody (e.g., scFv), non-human antibody, humanized antibody, chimeric antibody, fully human antibody, probody, bispecific antibody or multispecific antibody.

In some embodiments of the present invention, the targeting moiety (E) may be an arginine-glycine-aspartate ("RGD") peptide that recognizes a cell surface integrin receptor; a growth factor that recognizes a cell surface growth factor receptor, for example, EGF, PDGF, VEGF; a peptide that recognizes a functional plasminogen activator on a cell surface, bombesin, bradykinin, somatostatin or a prostate specific membrane antigen receptor. Suitable targeting moieties (E) include: CD40 ligand, CD30 ligand, CD40 ligand, OX40 ligand, PD-1 ligand, ErbB ligand, Her2 ligand, TACSTD2 ligand, DR5 ligand, polyene linking two aliphatic indoles, cyanine dye, IR-783 or a derivative thereof (CN 102099059B).

In some embodiments of the present invention, the targeting moiety (E) is directed to a target selected from the group consisting of: epidermal growth factor, CD37, HER2, CD70, EGFRvIII, Mesothelin, Folate receptor1, Mucin 1, CD138, CD20, CD19, CD30, SLTRK6, Nectin 4, Tissue factor, Mucin16, Endothelinreceeptor, STEAP1, SLC39A6, Guanylylcyclase C, PSMA, CCD79b, CD22, Sodium phosphate cotransporter 2B, GPNMB, Trophoblast glycoprotein, AGS-16, EGFR, CD33, CD66e, CD74, CD56, PD-L1, TACSTD2, DR5, BMPR1B, E16, STEAP1, 0772P, MPF, Napi3b, Sema 5b, PSCA hlg, ETBR, MSG783, STEAP2, TrpM4, CRIPTO, CD79b, FcRH2, NCA, MDP, IL20Rα, Brevican, EphB2R, ASLG659, PSCA, GEDA, BAFF-R, CD22, CD79a, CXCR5, HLA-DOB, P2X5, CD72, LY64, FcRH1, IRTA2, TENB2, integrin α5β6, α4β7, FGF2, FGFR2, Her3, CD70, CA6, DLL3, EpCAM, pCAD, CD223, LYPD3, LY6E, EFNA4, ROR1, SLITRK6, 5T4, ENPP3, SLC39A6, BMPR1B (bone morphogenetic protein receptor-IB type, Genbank accession no. NM_001203), E16 (LAT1, SLC7A5, Genbank accession no. NM_003486), STEAP1 (six-transmembrane epithelial antigen of prostate1, Genbank accession no. NM_012449), 0772P (CA125, MUC16, Genbank accession no. AF361486), MPF (MPF, MSLN, SMR, Megakaryocyte strengthening factor, mesothelin, Genbank accession no. NM_005823), Napi3b (NAPI-3B, NPTIIb, SLC34A2, Solute carrier family 34 (sodium phosphate), member 2, type II sodium-dependent phosphate transporter 3b, Genbank accession no. NM 006424), Sema 5b (FLJ10372, KIAA1445, Mm.42015, SEMA5B, SEMAG, brain signaling protein 5b Hlog, sema domain, seven thrombospondin repeats (type 1 and type 1-like), transmembrane domain (TM) and short cytoplasmic domain, (brain signaling protein) 5B, Genbank accession no. AB040878), PSCA hlg (2700050C12Rik, C530008016Rik, RIKEN cDNA 2700050C12, RIKEN cDNA 2700050C12 gene, Genbank accession no. AY358628), ETBR (endothelin type B receptor, Genbank accession no. AY275463), MSG783 (RNF124, hypothetical protein FLJ20315, Genbank accession no. NM_017763), STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138), TrpM4 (BR22450, FLJ20041, TRPM4, TRPM4B, transient receptor potential cation channel, subfamily M, member 4, Genbank accession no. NM_017636), CRIPTO (CR, CR1, CRGF, CRIPTO, TDGF1, teratogenic cancer-derived growth factor, Genbank accession no. NP_003203 or NM_003212), CD21 (CR2 (complement receptor 2) or C3DR (C3d/Eba virus receptor) or Hs.73792 Genbank accession no. M26004), CD79b (CD79B, CD790, IGb (immunoglobulin-related beta), B29, Genbank accession no. NM_000626), FcRH2 IFGP4, IRTA4, SPAP1A (phosphatase-anchored protein 1a containing SH2 domain), SPAP1B, SPAP1C, Genbank accession no. NM_030764), NCA (Genbank accession no. M18728), MDP (Genbank accession no. BC017023), IL20Rα (Genbank accession no. AF184971), Brevican (Genbank accession no. AF229053), EphB2R (Genbank accession no. NM_004442), ASLG659 (Genbank accession no. AX092328), PSCA (Genbank accession no. AJ297436), GEDA (Genbank accession no. AY260763, BAFF-R (B cell activating factor receptor, BlyS receptor 3, BR3, NP_443177.1), CD22 (B cell receptor CD22-B isoform, NP-001762.1), CD79a (CD79A, CD79α, immunoglobulin-related alpha, and B cell-specific protein that covalently interacts with Ig beta (CD79B) and forms a complex with Ig M molecule on the surface, transducing signals involved in B cell differentiation, Genbank accession no. NP_001774.1), CXCR5 (Burkitt lymphoma receptor 1, G-protein coupled receptor activated by CXCL13 chemokine, which plays a role in lymphocyte migration and humoral defense, and plays a role in HIV-2 infection and possibly in the development of AIDS, lymphoma, myeloma, and leukemia, Genbank accession no. NP_001707.1), HLA-DOB (Beta subunit of MHC type II molecule (Ia antigen), which binds to peptide and presents it to CD4+ T lymphocytes, Genbank accession no. NP_002111.1), P2X5 (purine receptor P2X ligand-gated ion channel 5, extracellular ATP-gated ion channel, which may be involved in synaptic transmission and neurogenesis, and the defect of which may lead to pathophysiological status of idiopathic detrusor instability, Genbank accession no. NP_002552.2), CD72 (B cell differentiation antigen CD72, Lyb-2, Genbank accession no. NP_001773.1), LY64 (lymphocyte antigen 64 (RP105), type I membrane protein family rich in leucine repeats (LRR), which regulates B cell activation and apoptosis, and the loss of its function is related to enhanced disease activity in patients with systemic lupus erythematosus, Genbank accession no. NP_005573.1), FcRH1 (Fc receptor-like protein 1, putative receptor for immunoglobulin Fc domain, including C2 type Ig-like and ITAM domains, possibly playing a role in B lymphocyte differentiation, Genbank accession no. NP_443170.1), IRTA2 (translocation-associated immunoglobulin superfamily receptor 2, putative immunoreceptor, which possibly plays a role in B cell development and lymphoma; gene dysregulation caused by translocation occurs in some B cell malignant diseases, Genbank accession no. NP_112571.1), and TENB2 (putative transmembrane proteoglycan, associated with EGF of growth factor/modulin family and follistatin of growth factor, Genbank accession no. AF179274) and the like.

In some embodiments of the present invention, the targeting moiety (E) is a monoclonal antibody against Her 2, such as trastuzumab, pertuzumab, or the targeting moiety (E) is a monoclonal antibody against Trop-2, such as sacituzumab (i.e., isactuzumab or hRS7 antibody).

In some embodiments of the present invention, the targeting moiety (E) is selected from the group consisting of: somatostatin, a folic acid derivative, such as a folic acid derivative having the structure of:

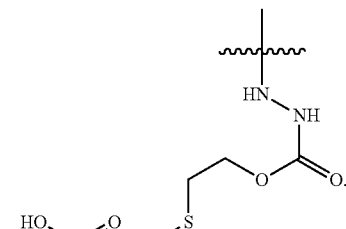
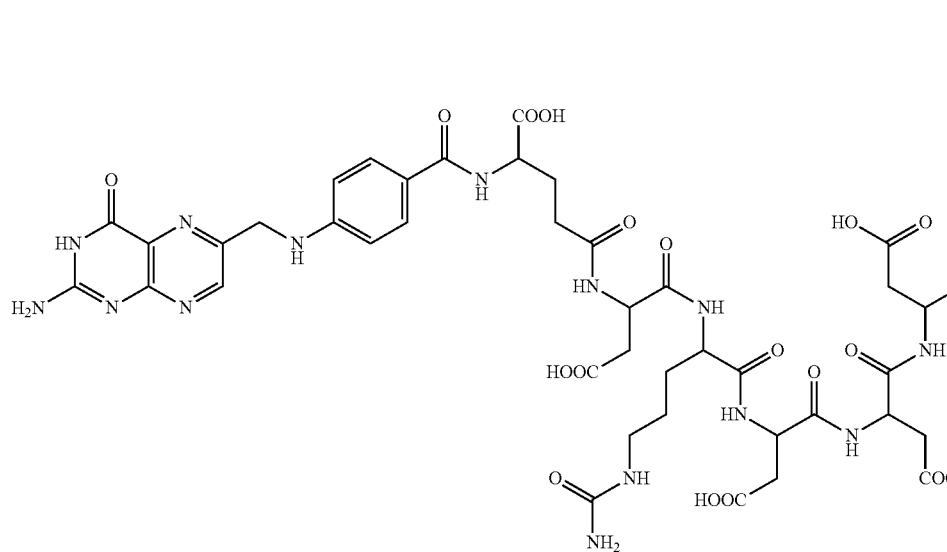
In some embodiments, the conjugate comprises a targeting moiety (E), wherein the targeting moiety (E) comprises a lysine residue or a cysteine residue and is linked to the linker via the lysine residue or the cysteine residue.
In some embodiments, the conjugate of the present invention is selected from:
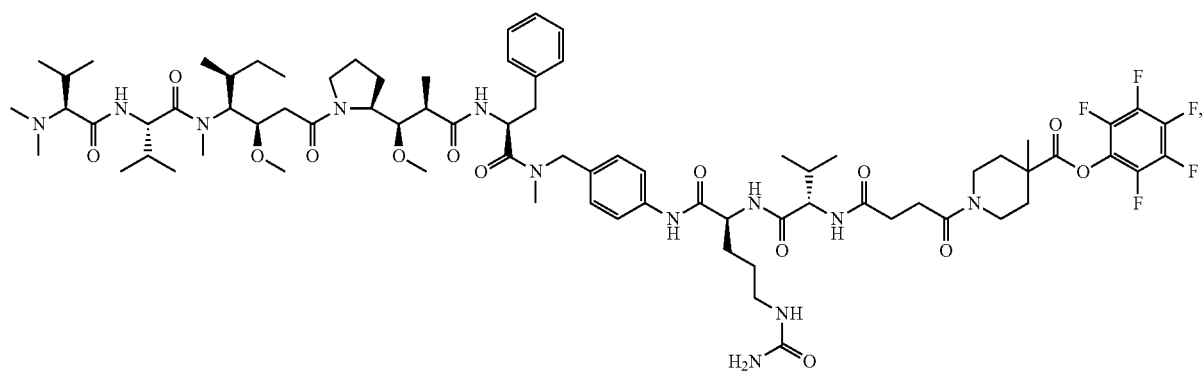
TL001
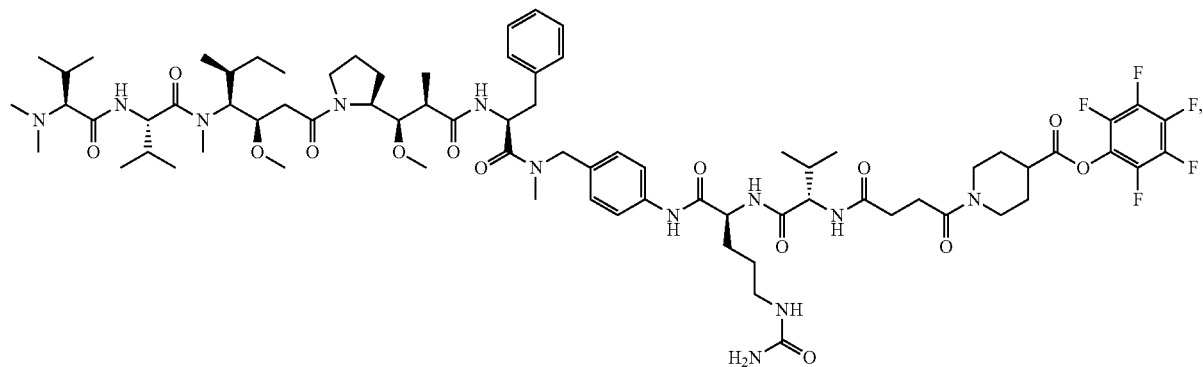
TL004

TL005
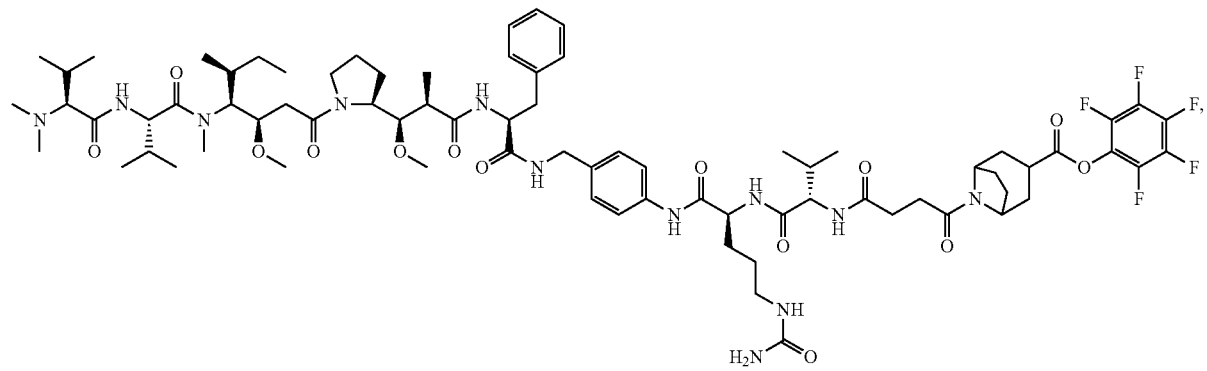
TL006
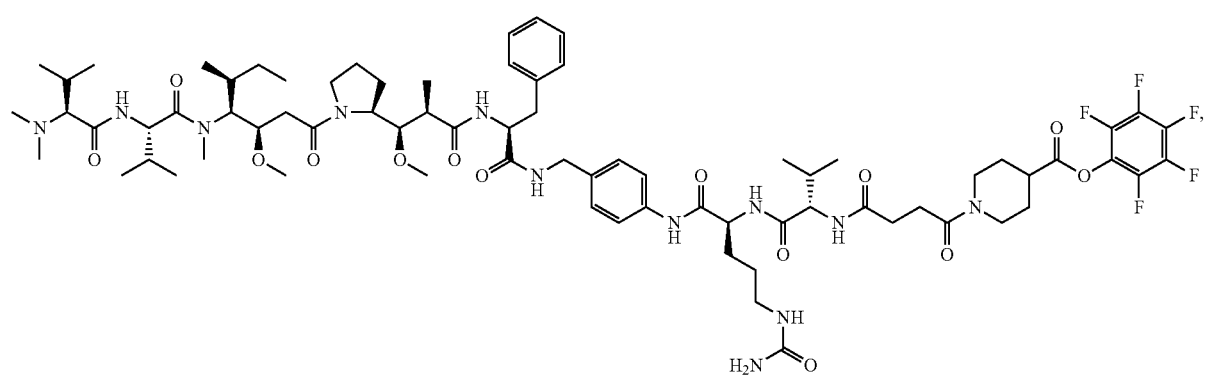
TL07
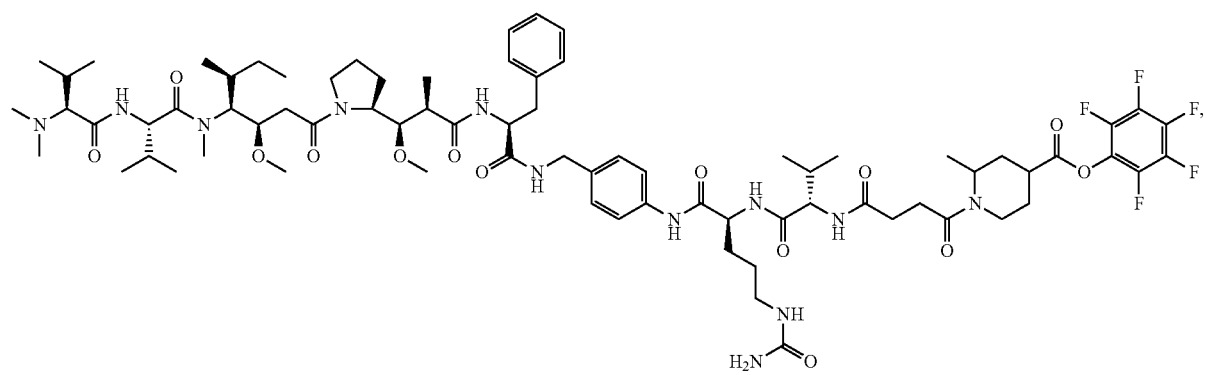
TL008
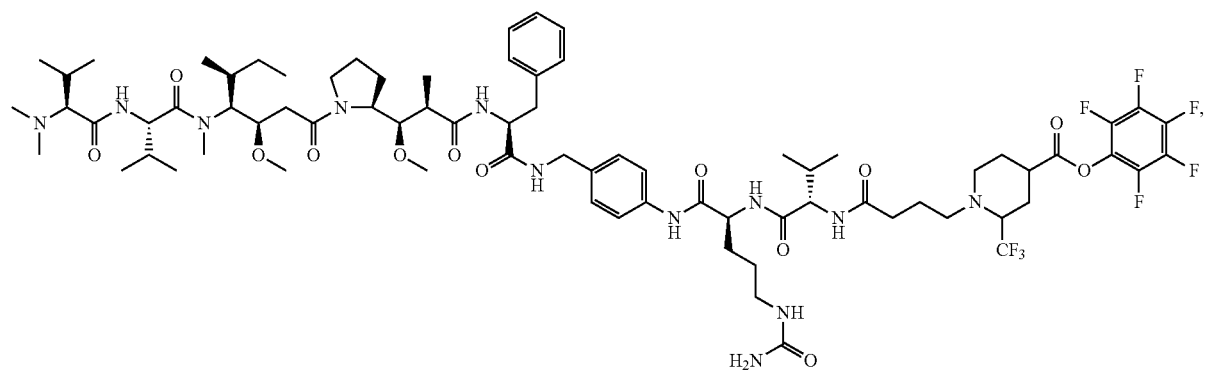

-continued
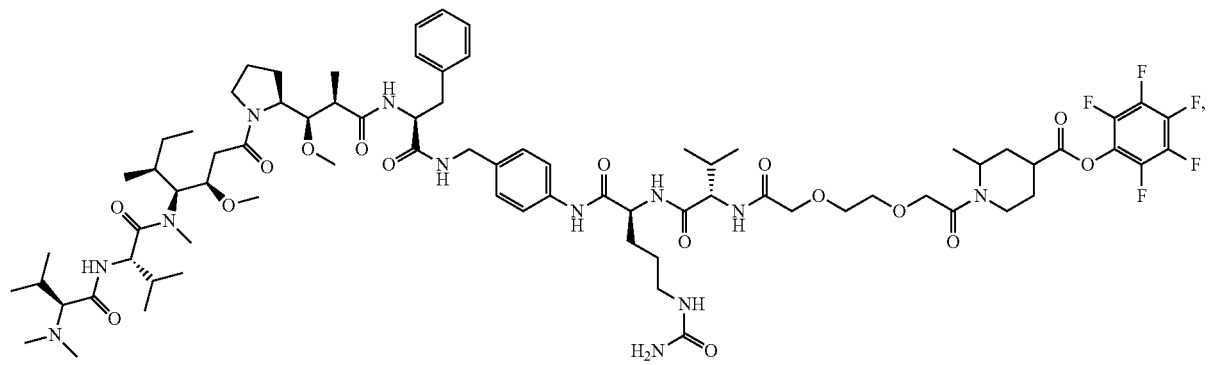
TL009
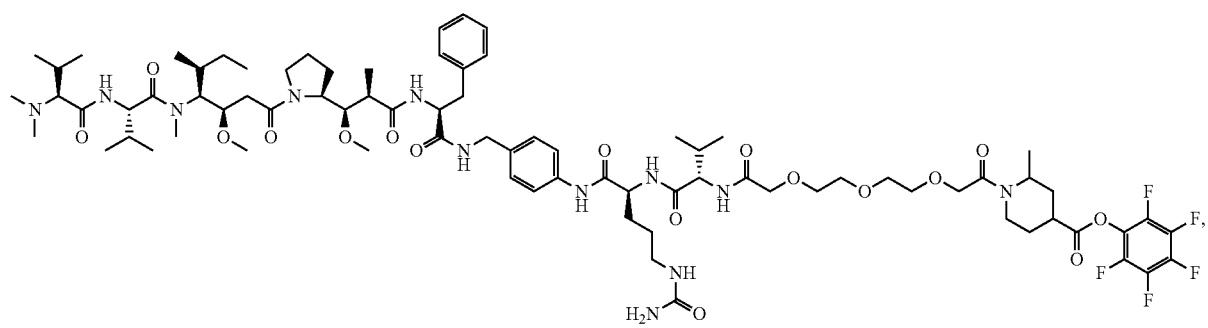
TL010
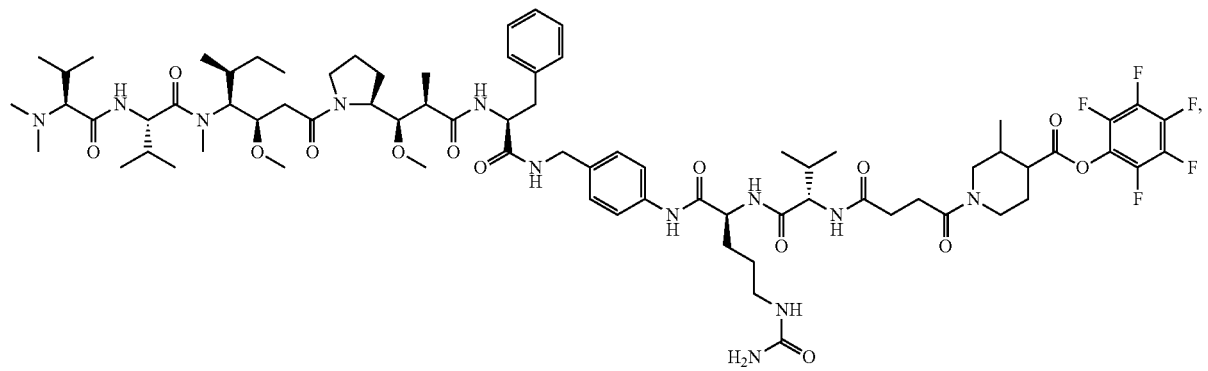
TL011
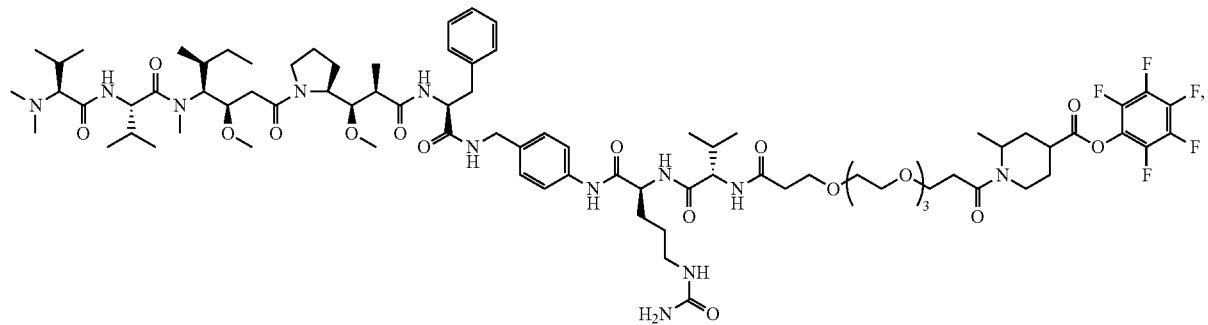
TL012

-continued
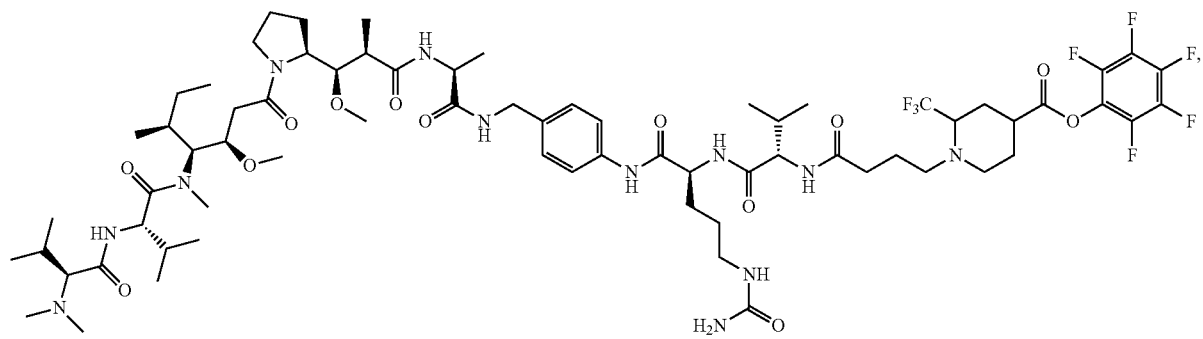
TL013
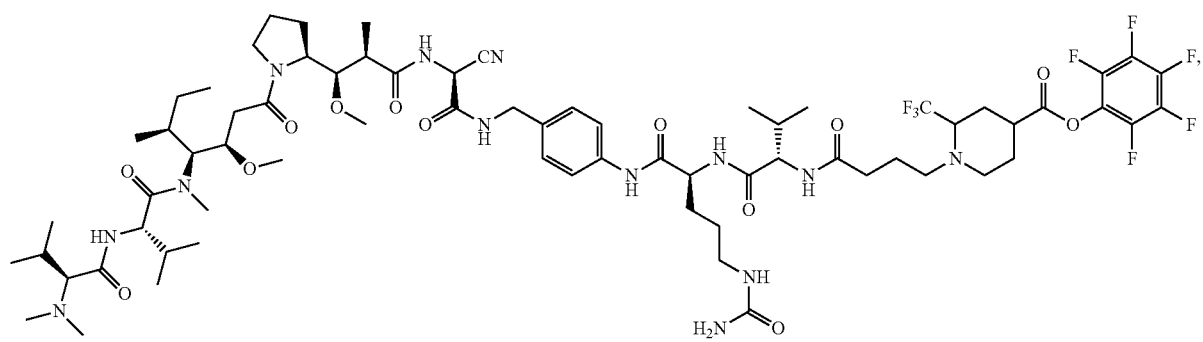
TL014
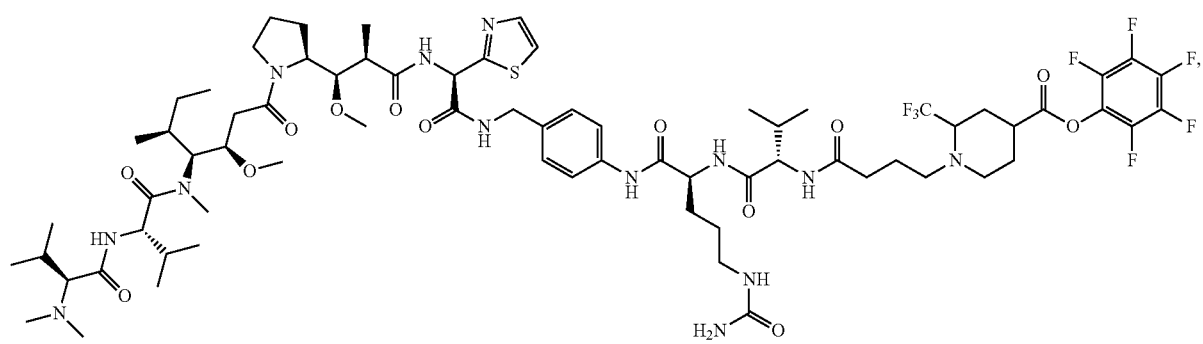
TL015
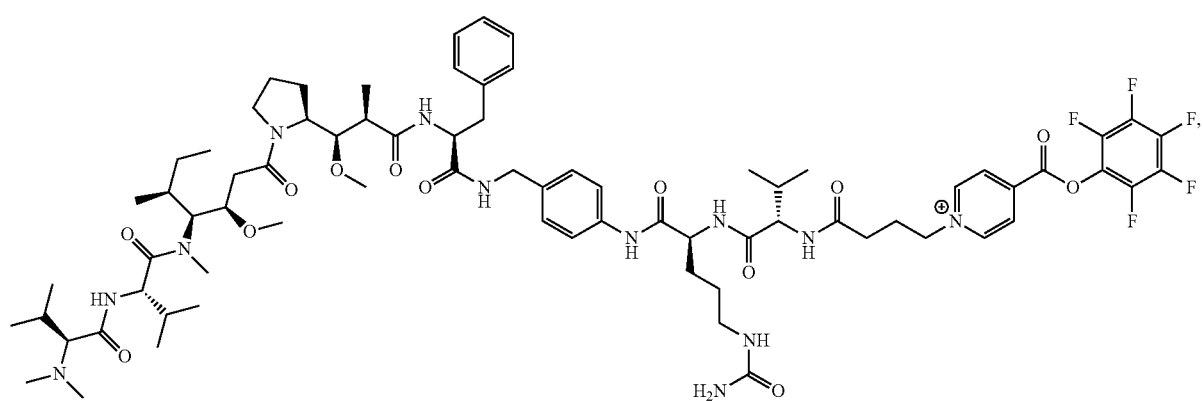
TL016

TL017
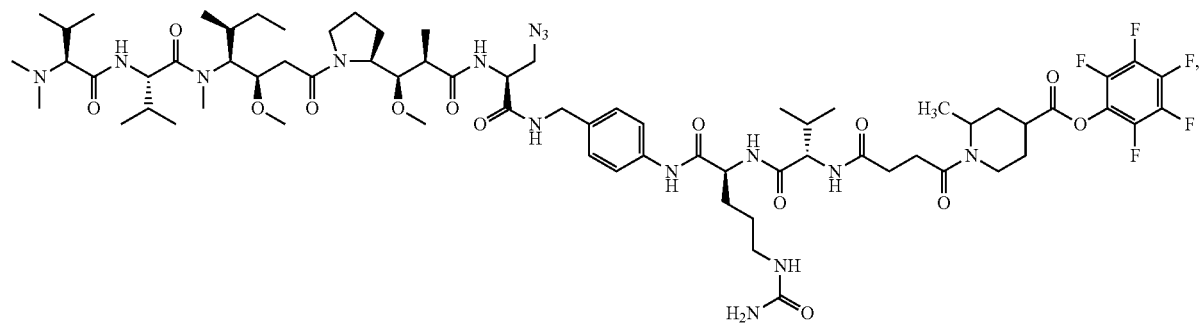
TL018
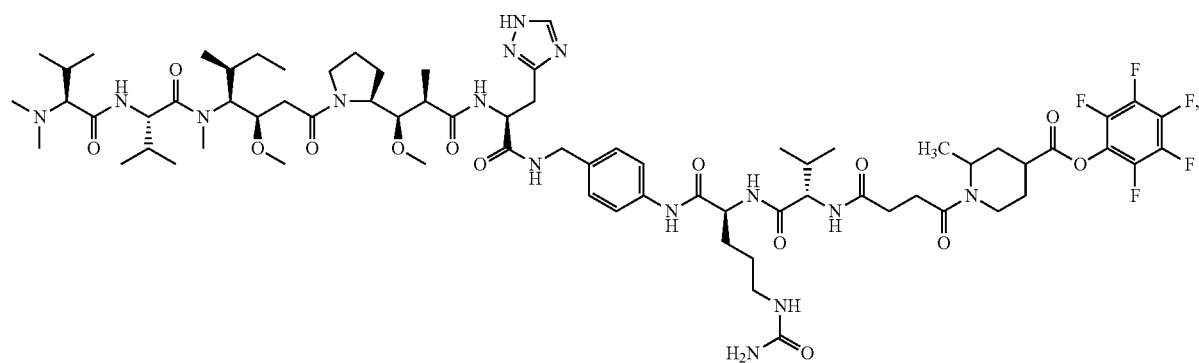
TL019
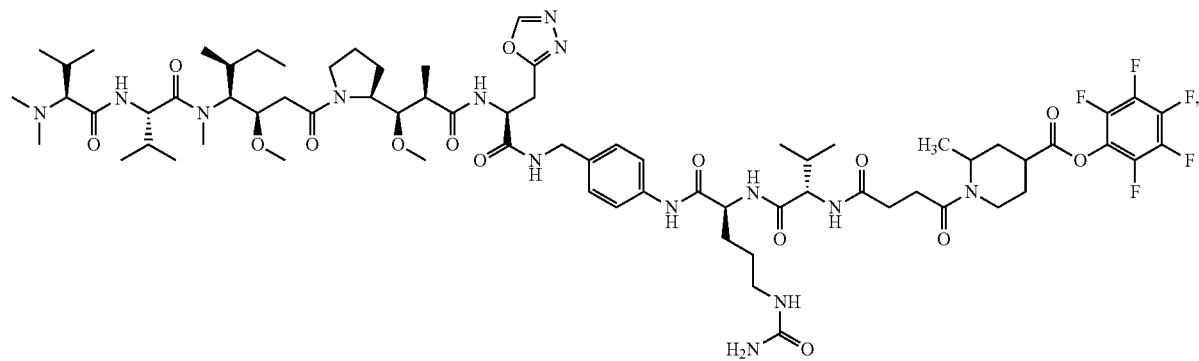
TL020
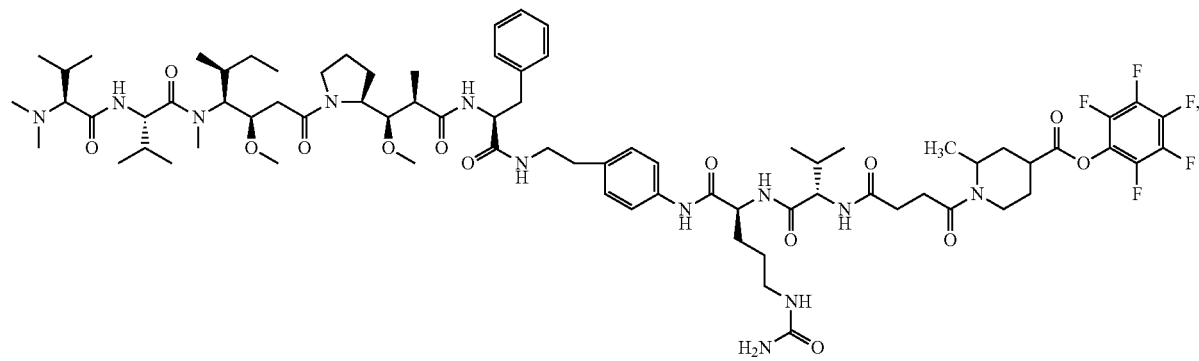

TL021
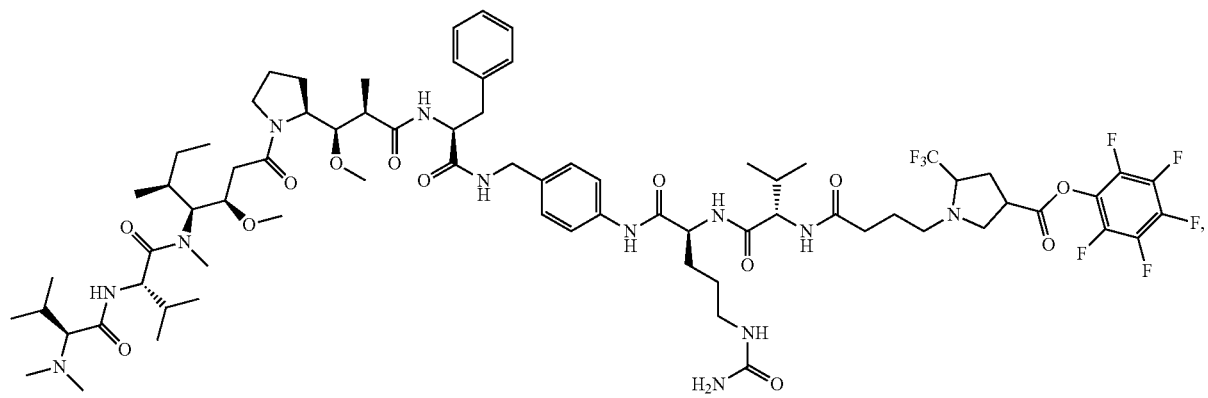
TL022
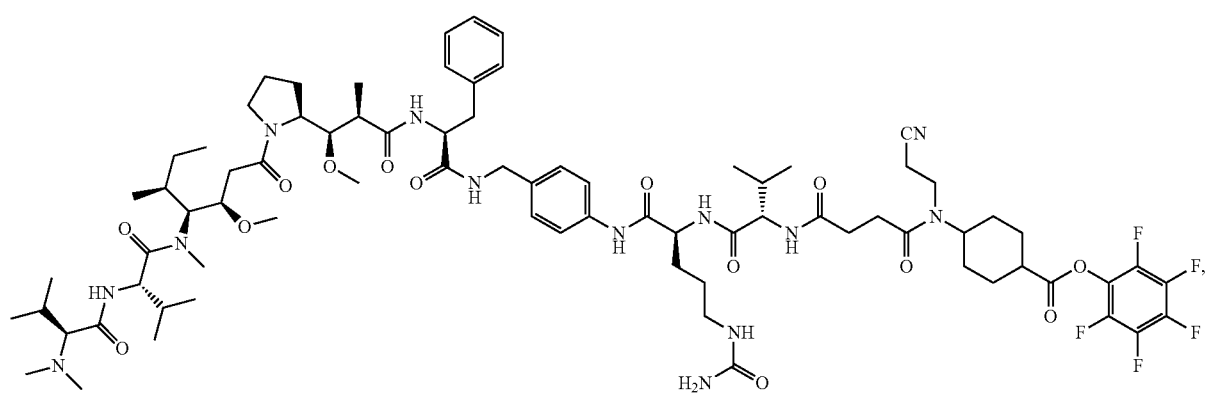
TL023
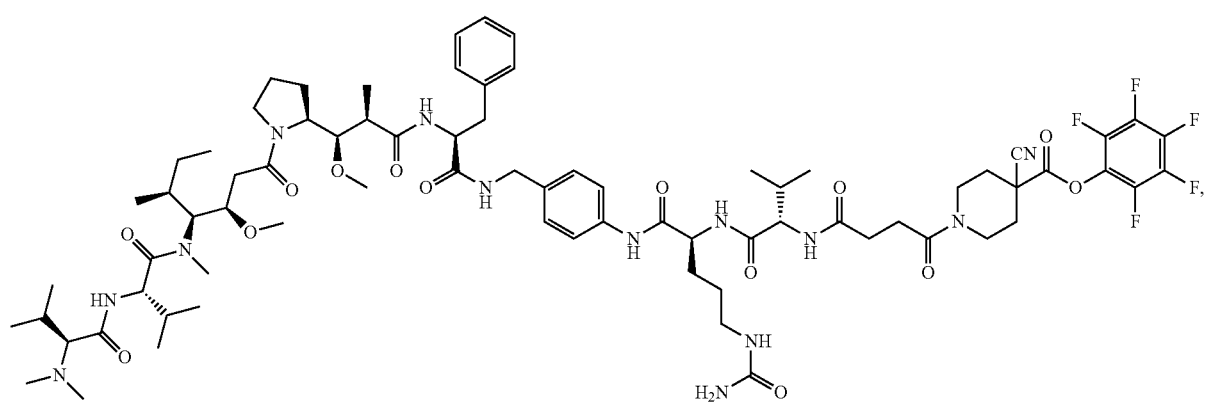
TL024
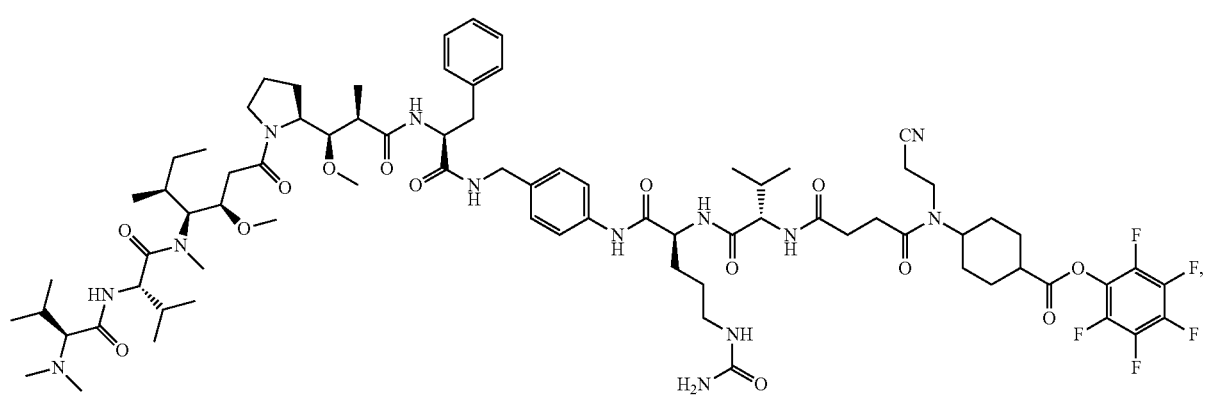

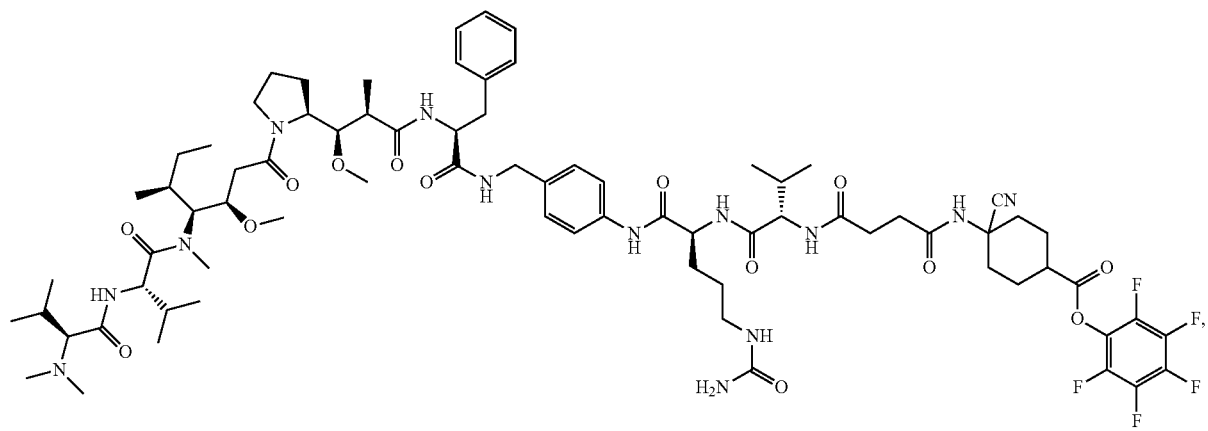
TL025
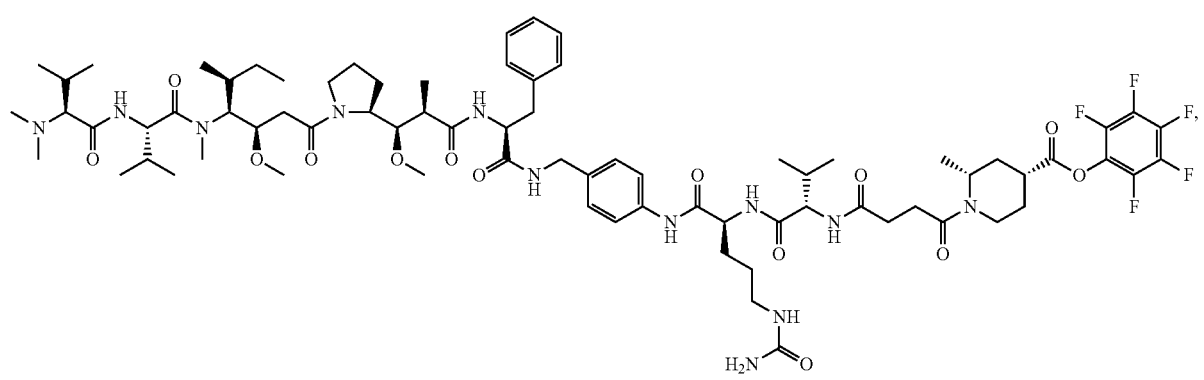
TL030
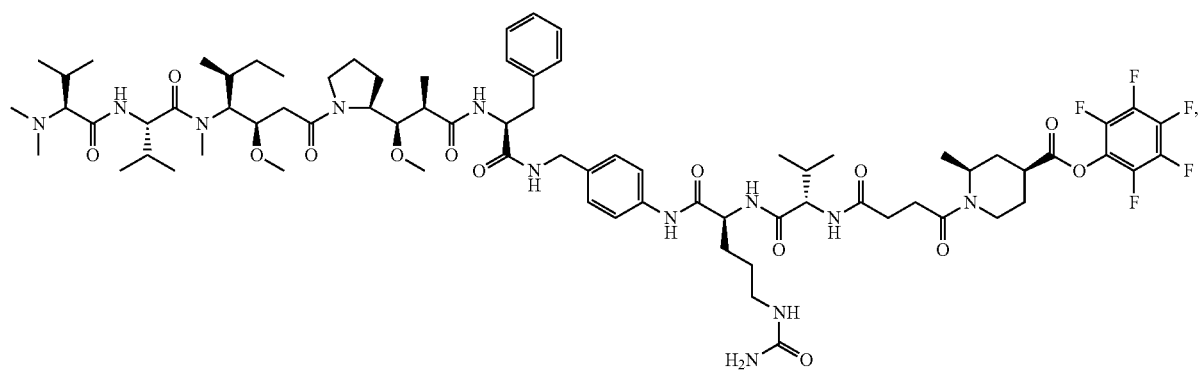
TL031
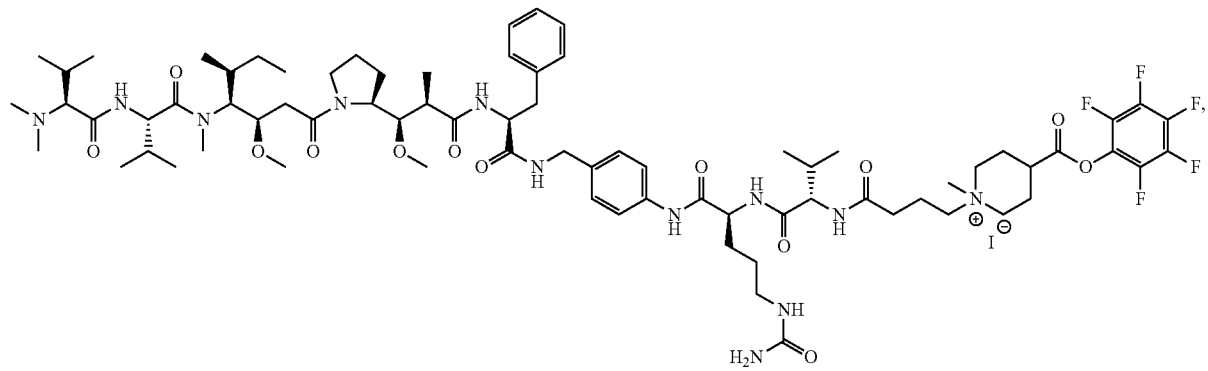
TL033

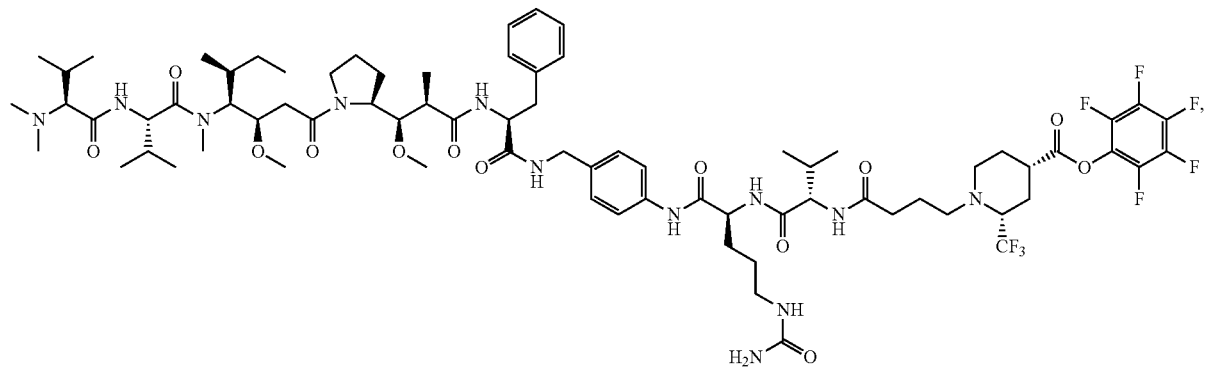
TL034

TL035
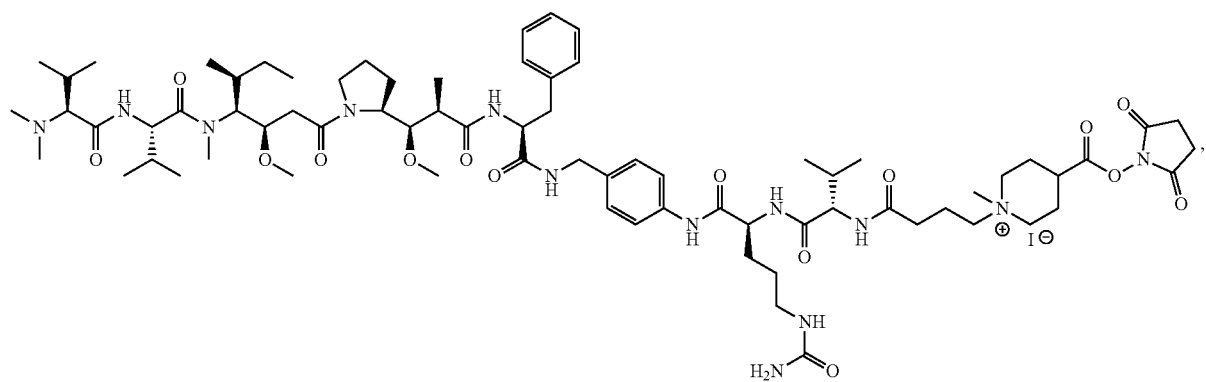
TL036
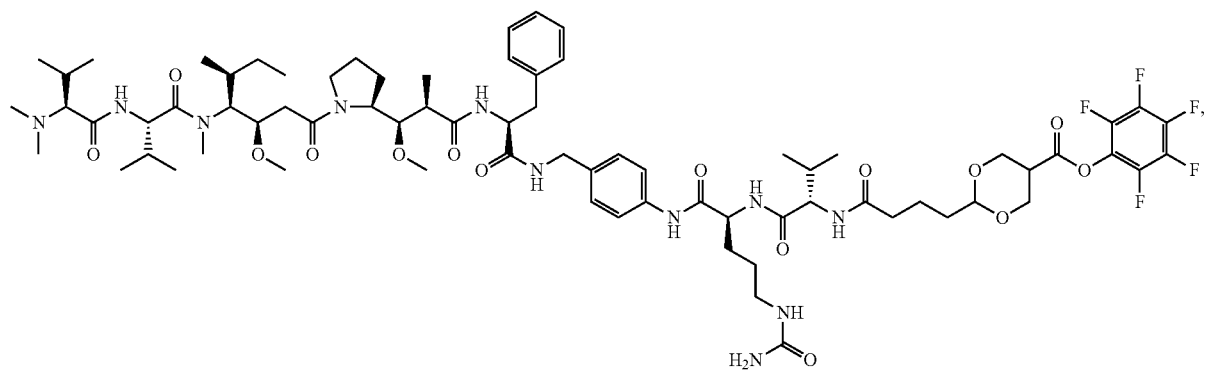
TL037

TL042
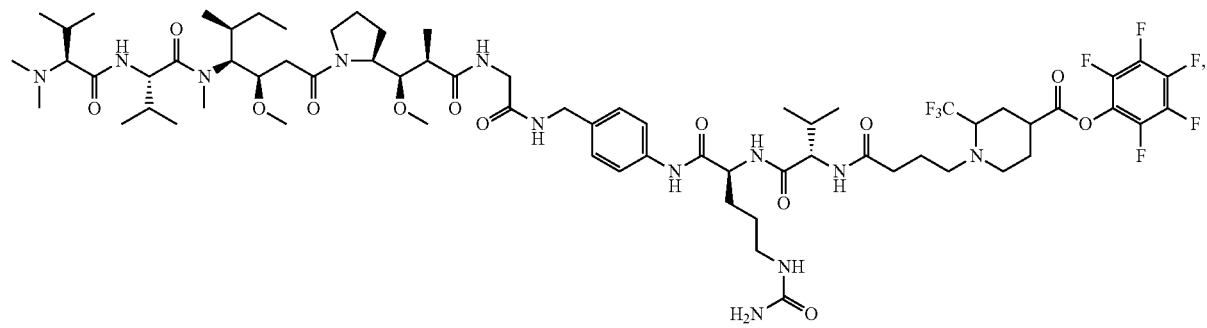
TL059
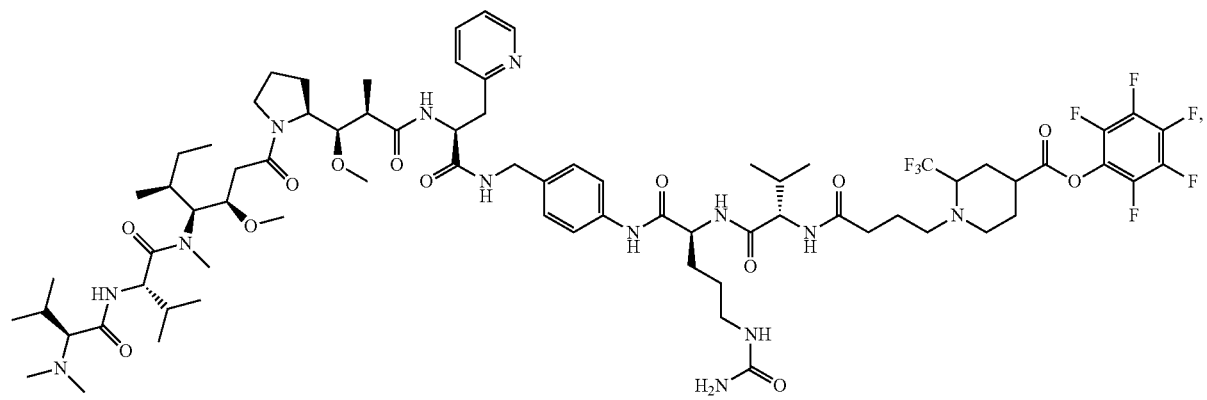
TL060
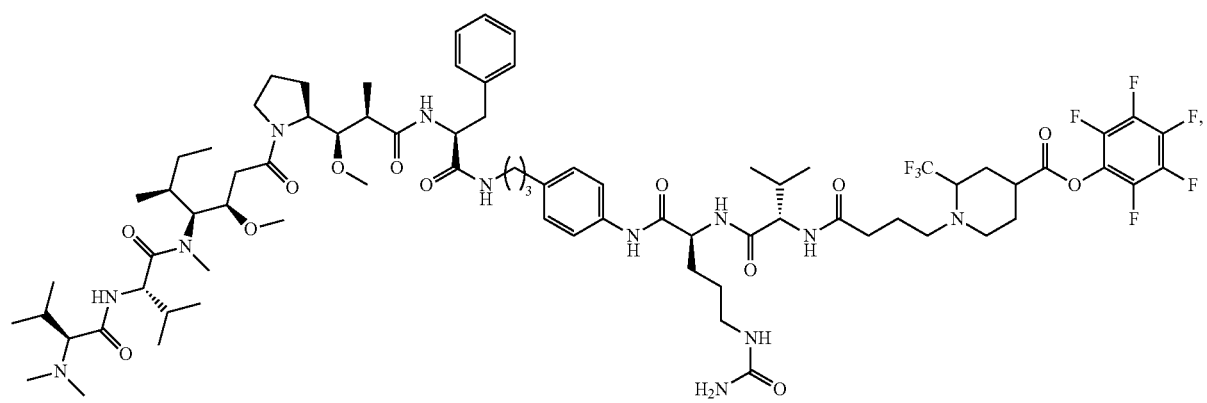
TL061
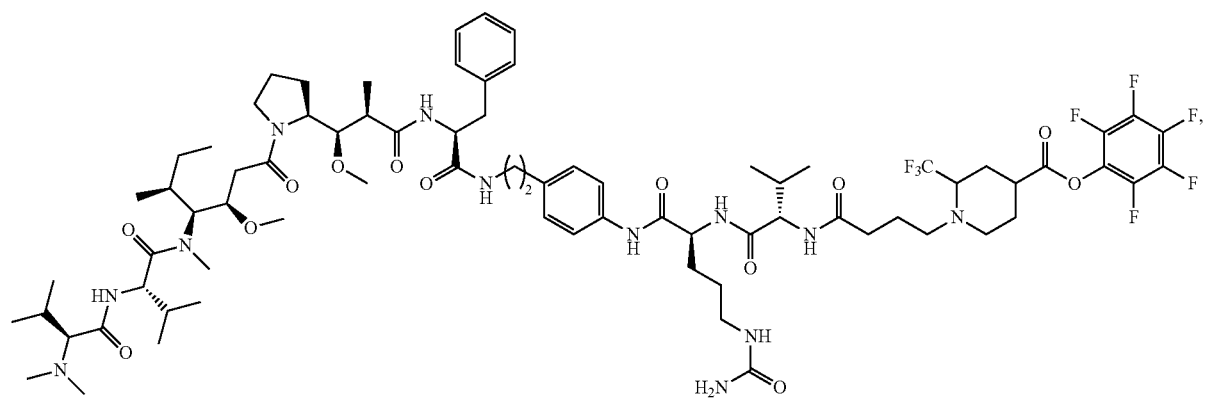

TL065
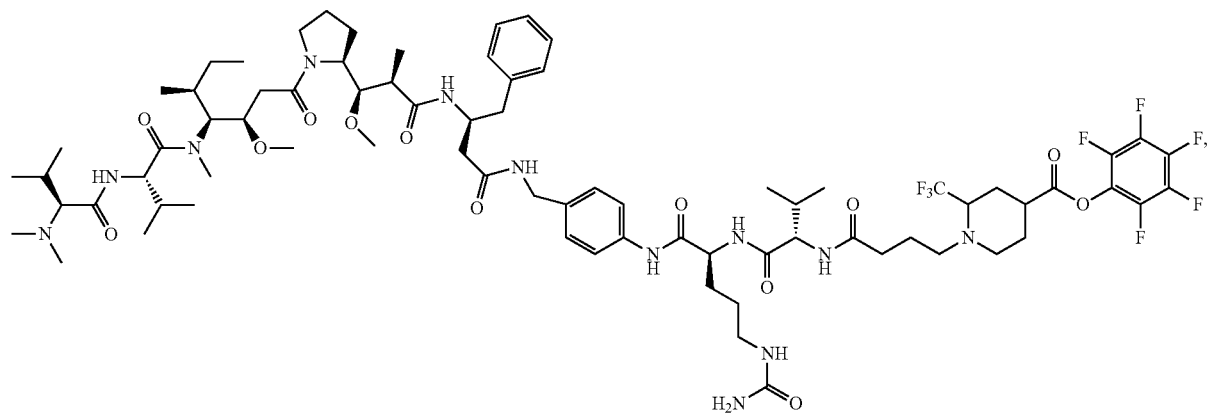
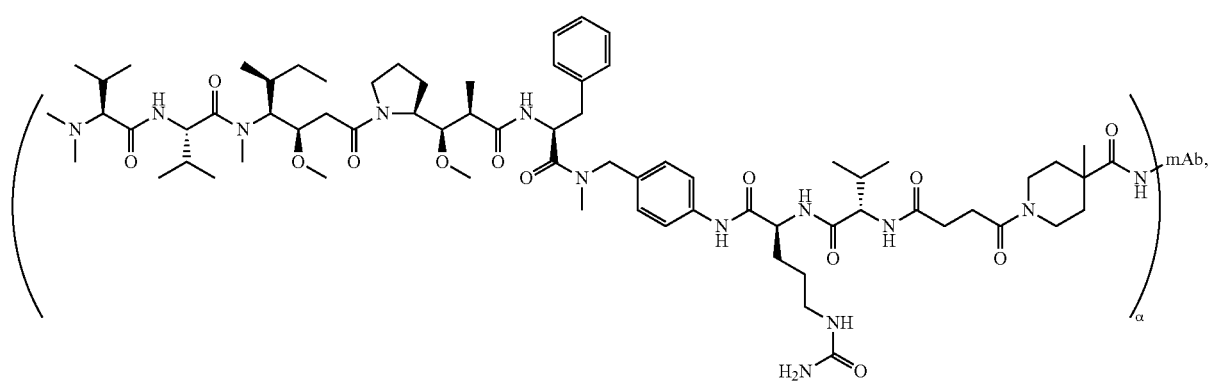
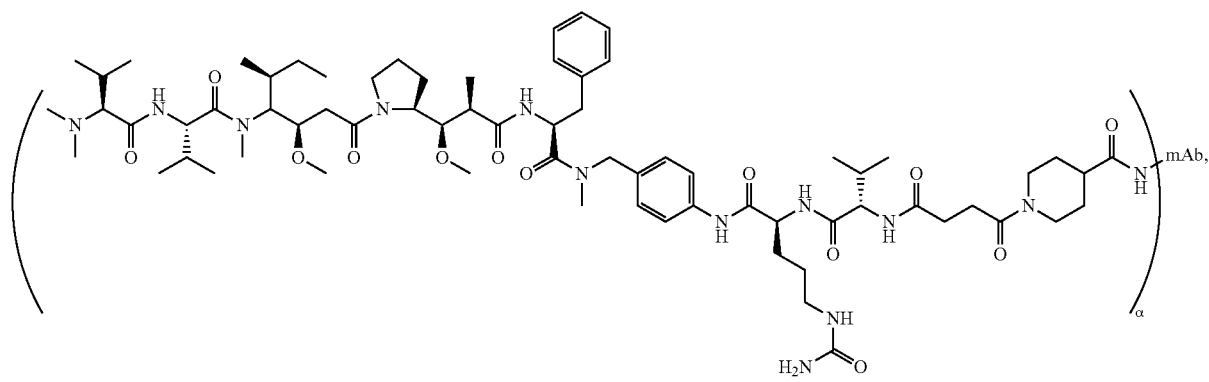
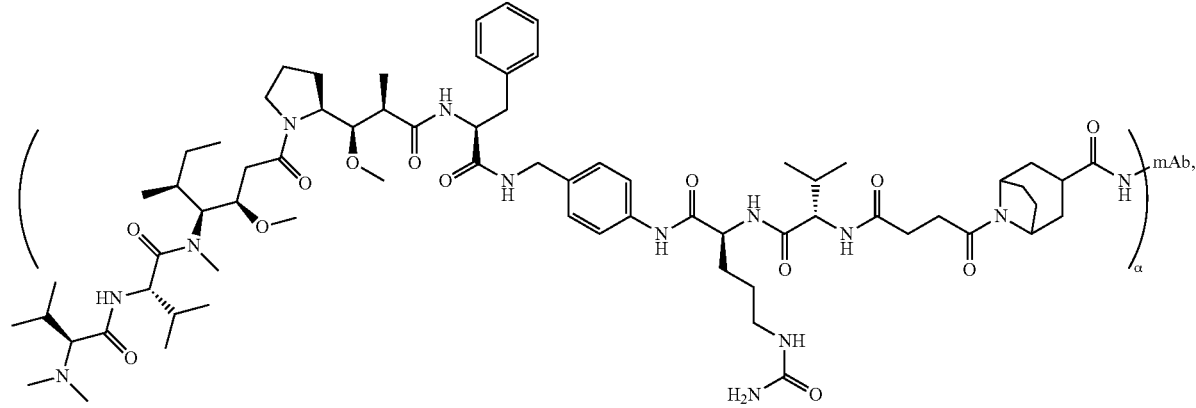

-continued
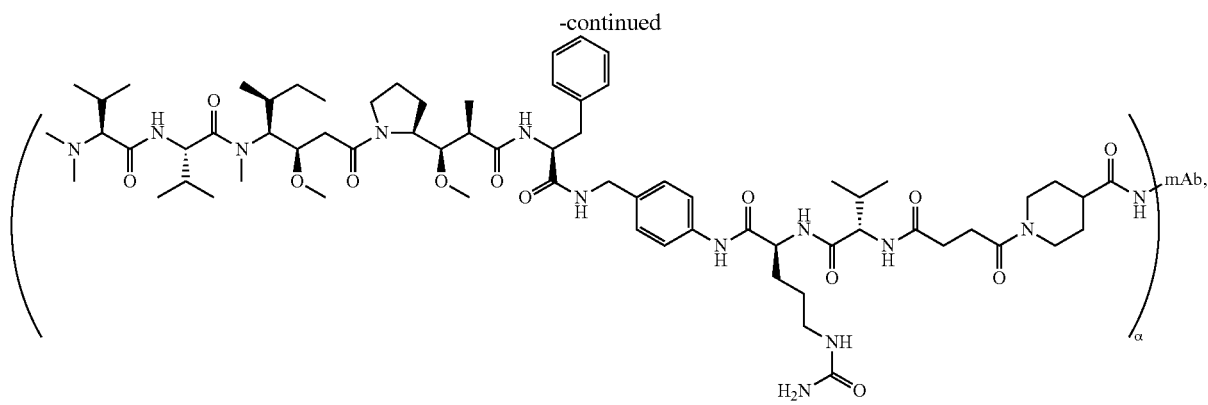
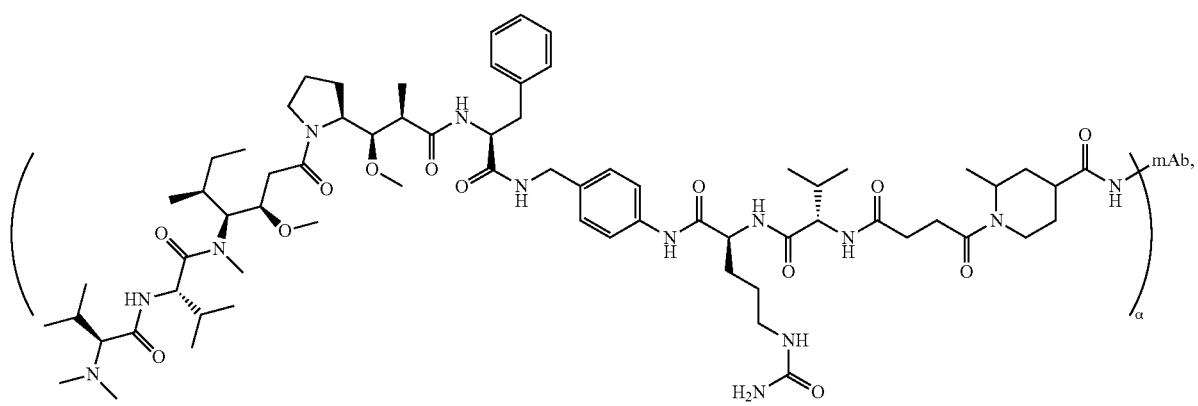
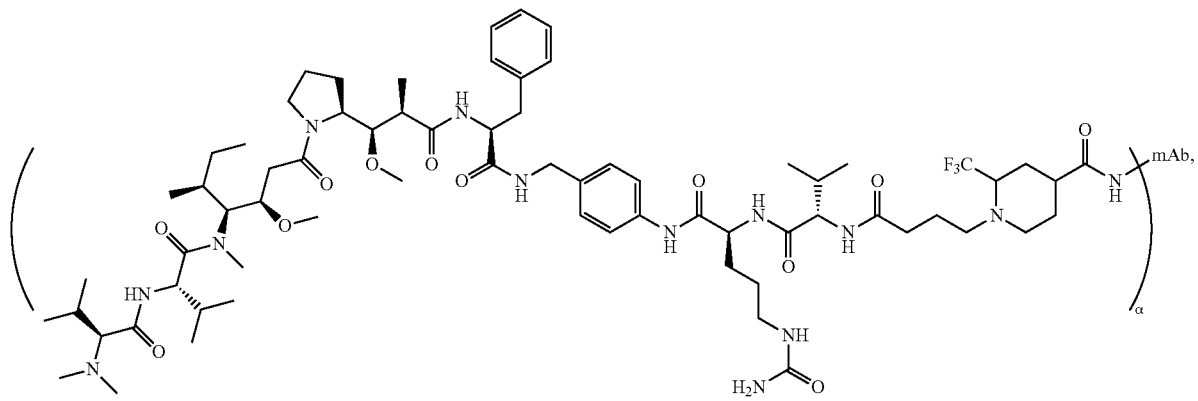
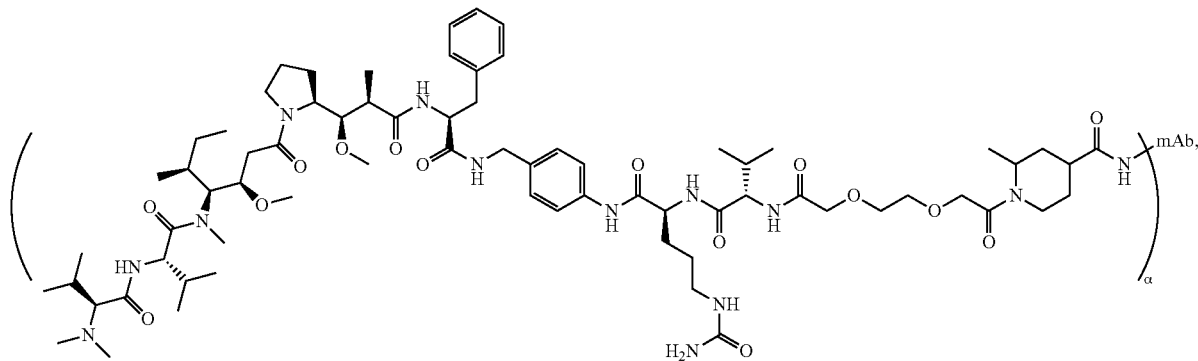

-continued
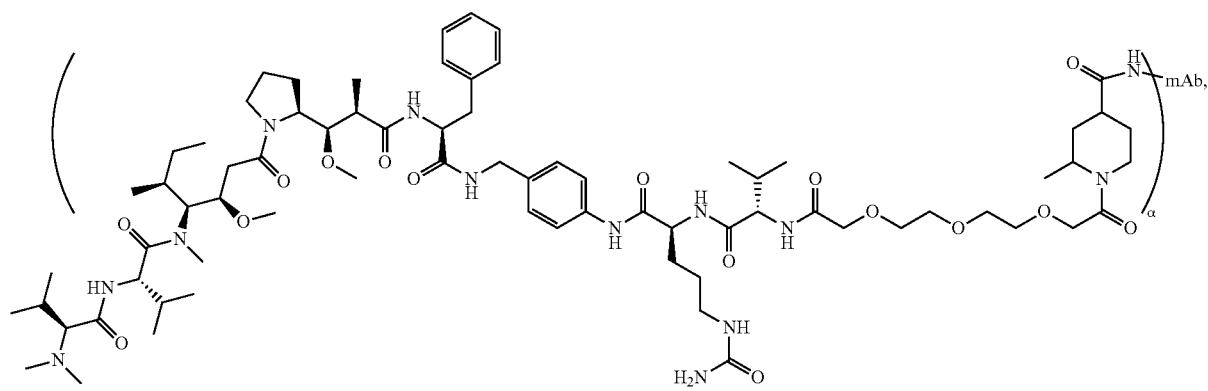
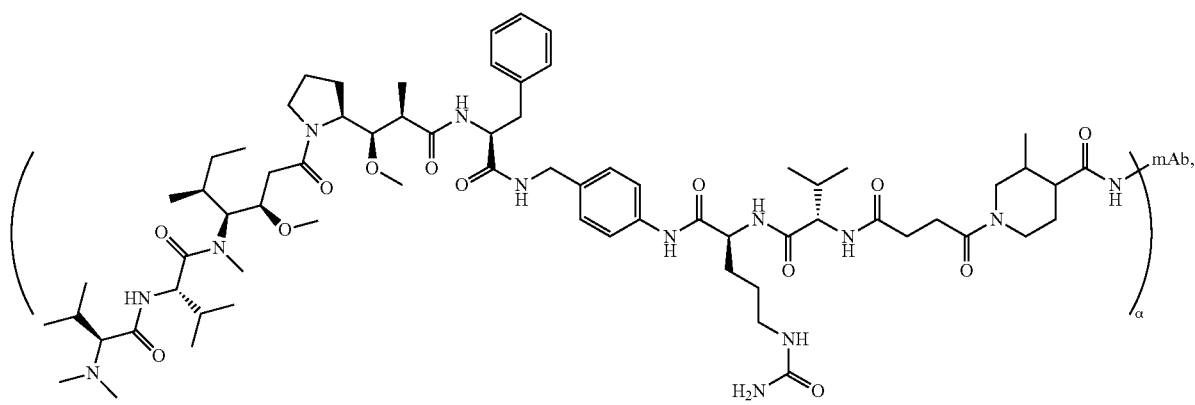
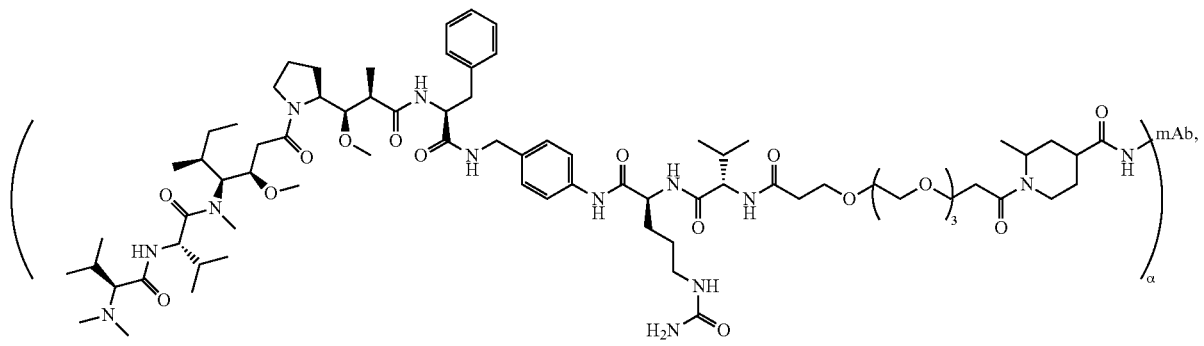
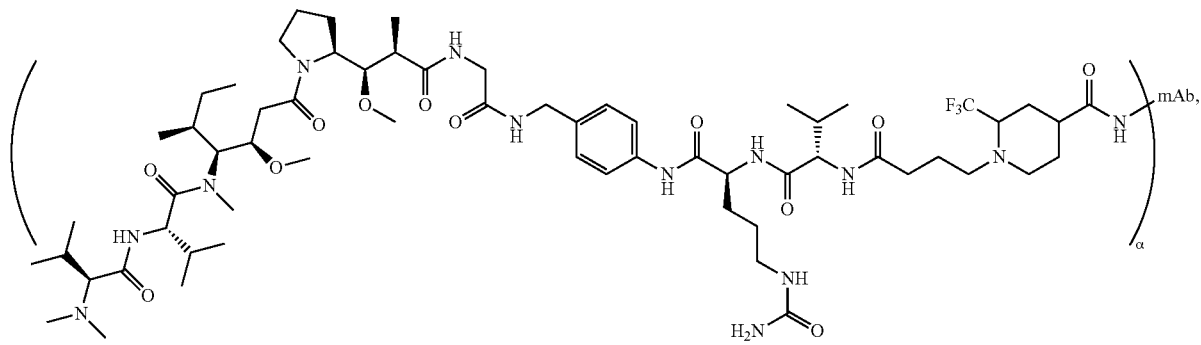

-continued
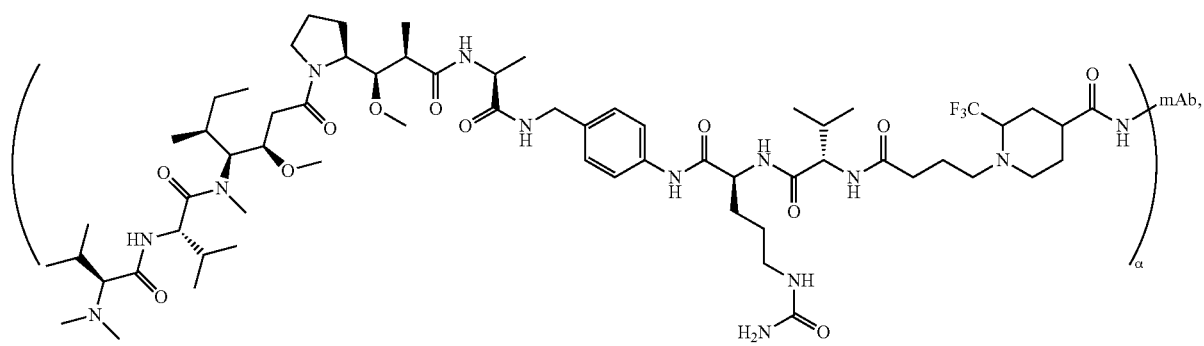
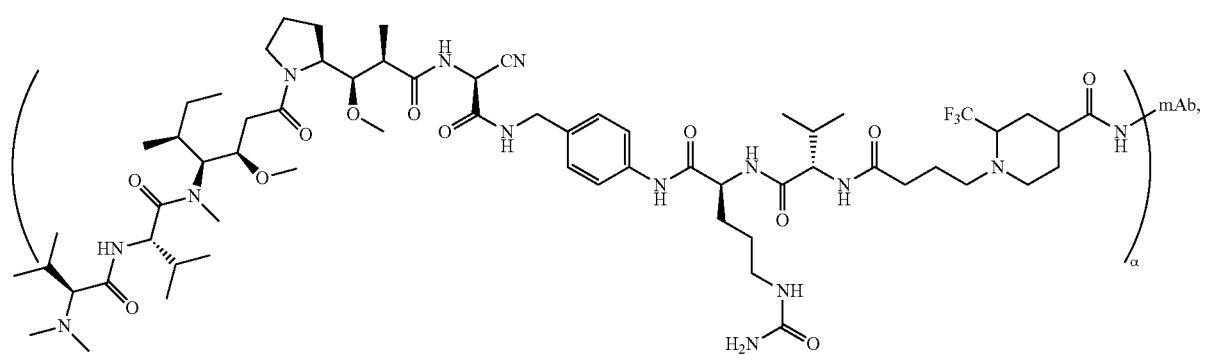
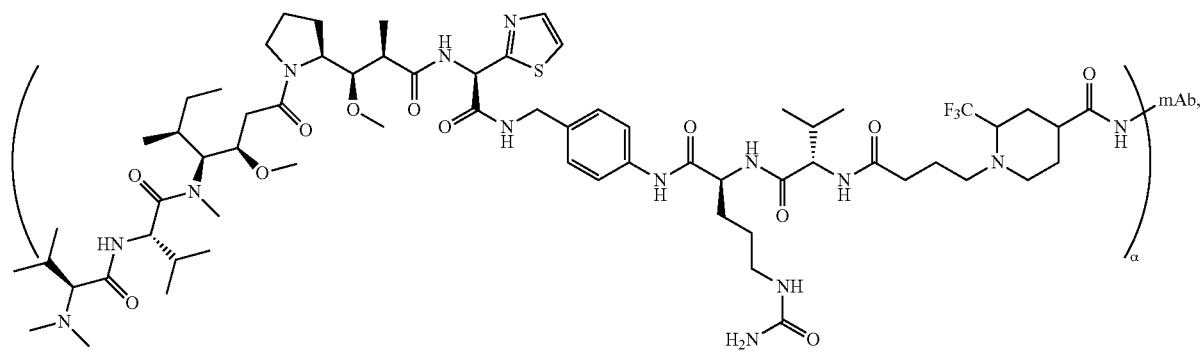
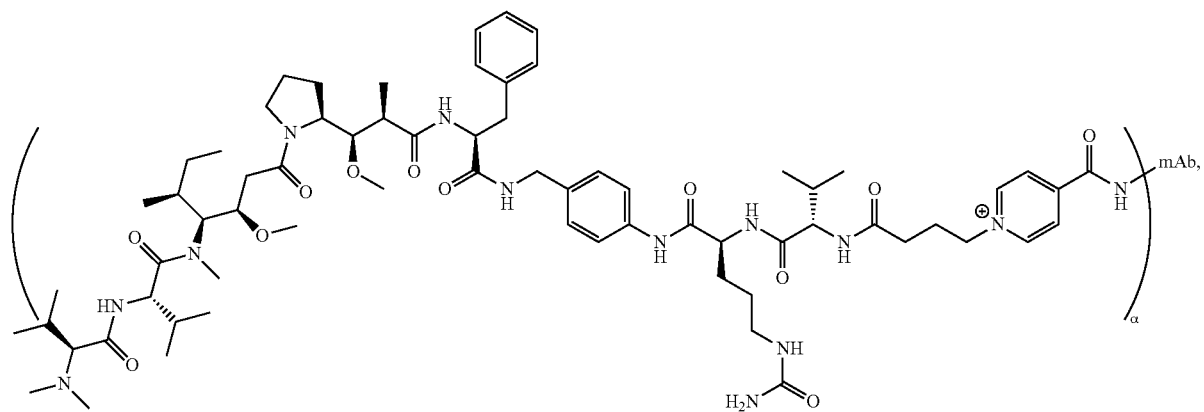

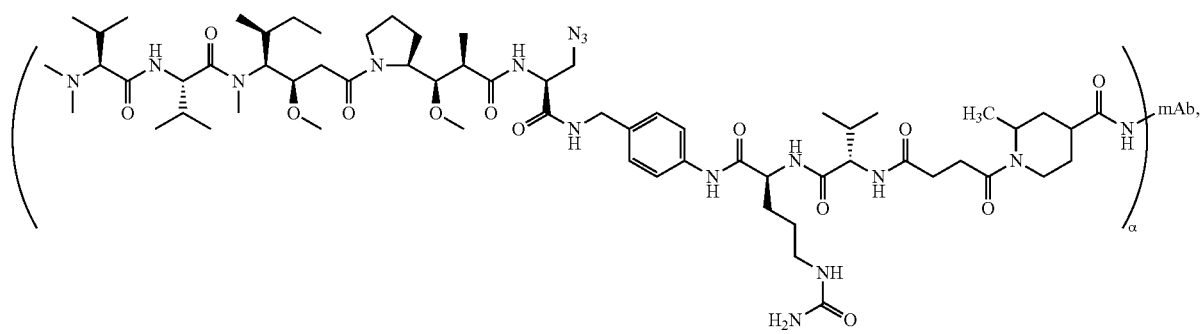
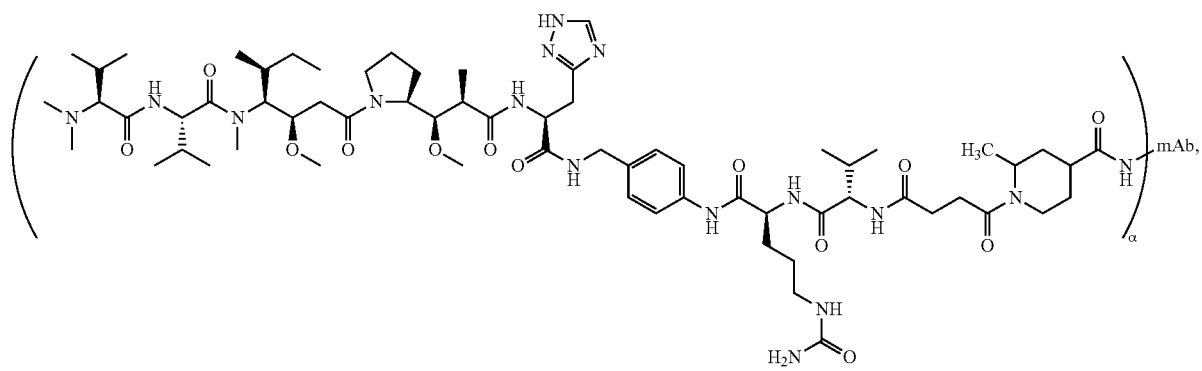
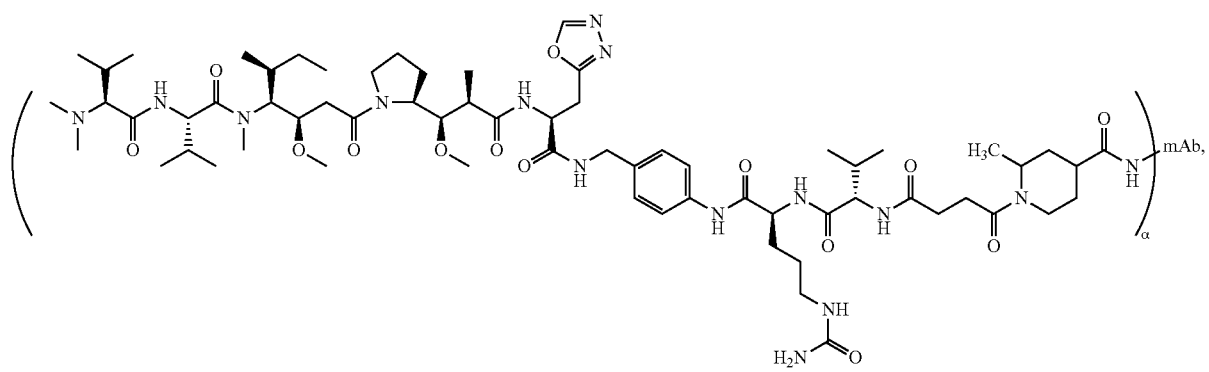
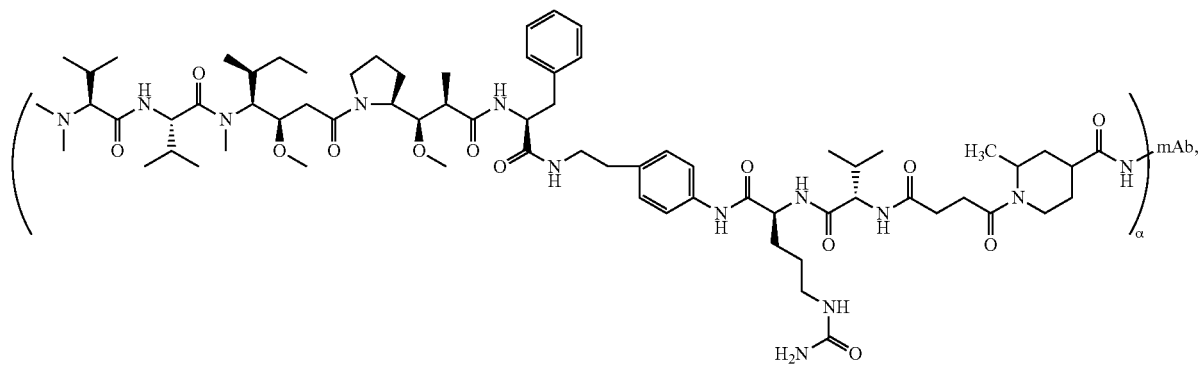

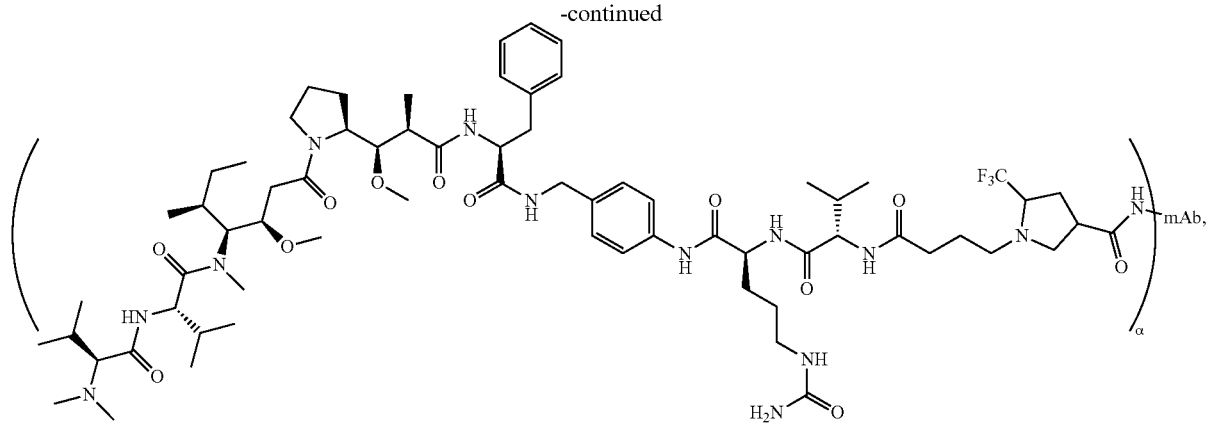
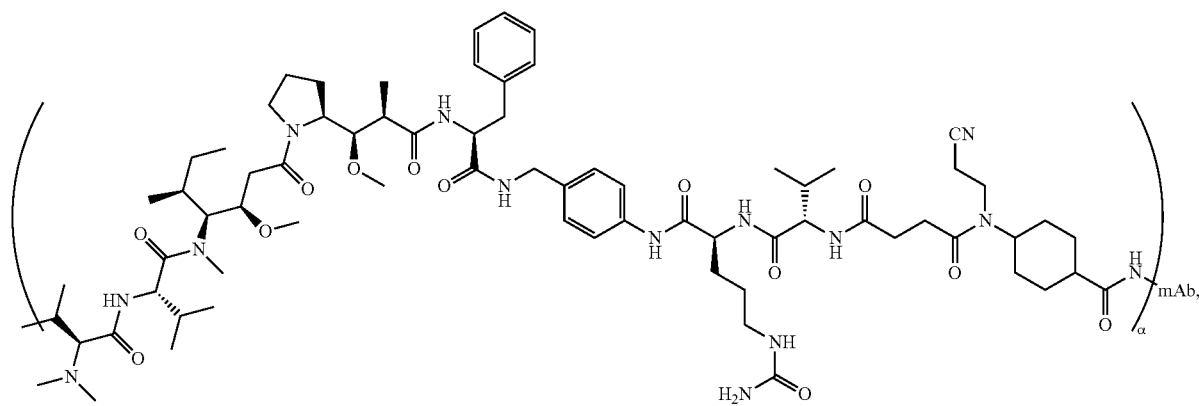
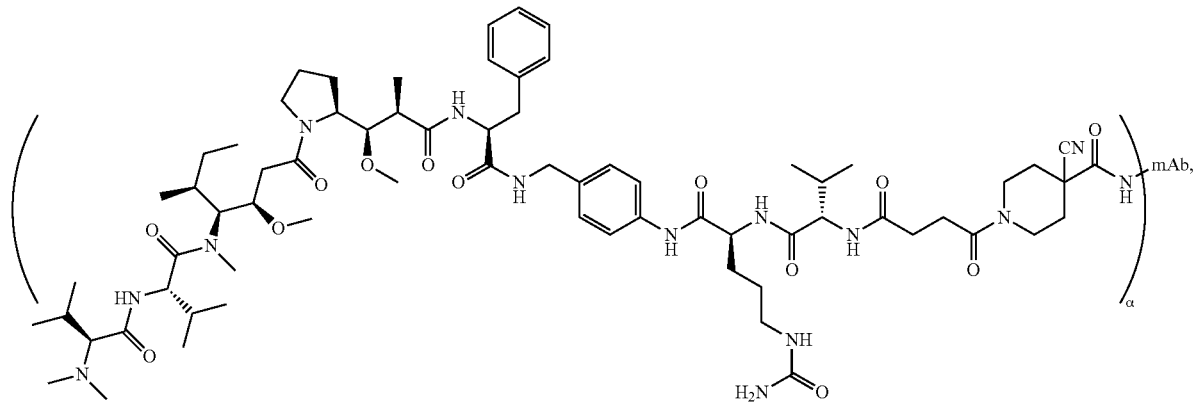
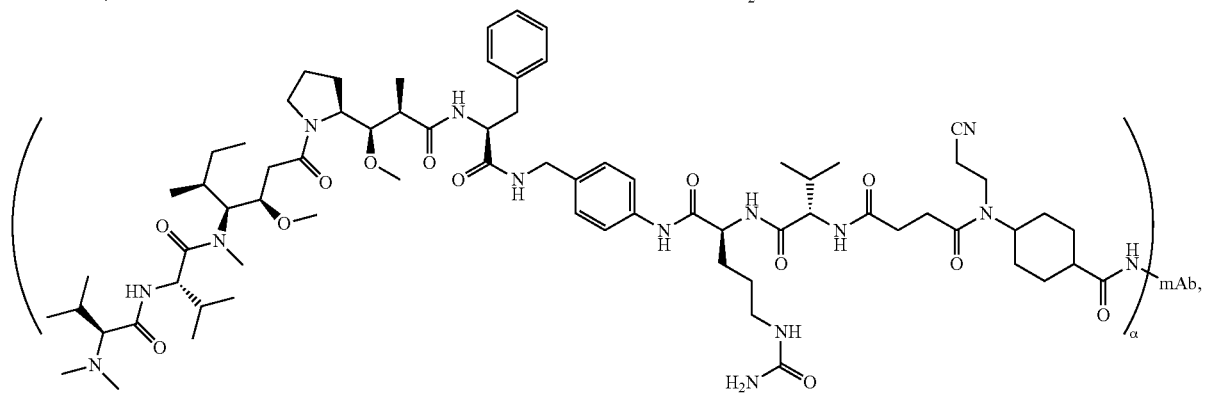

-continued
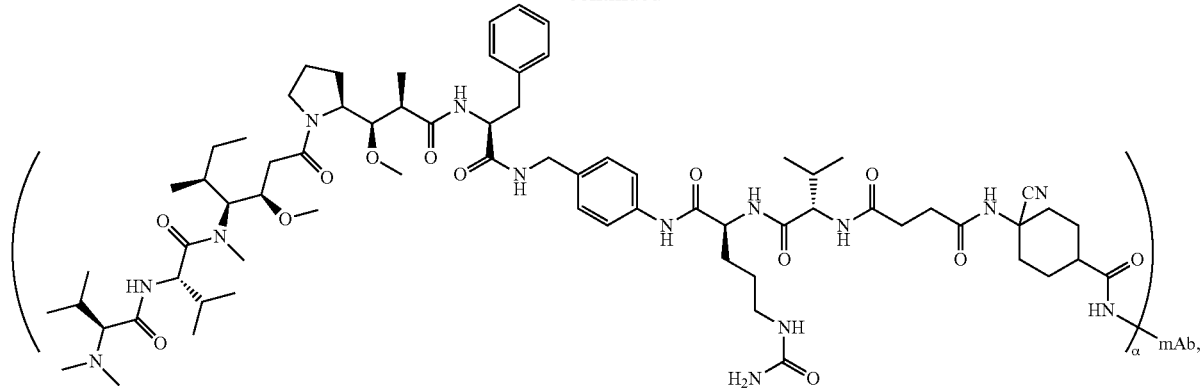
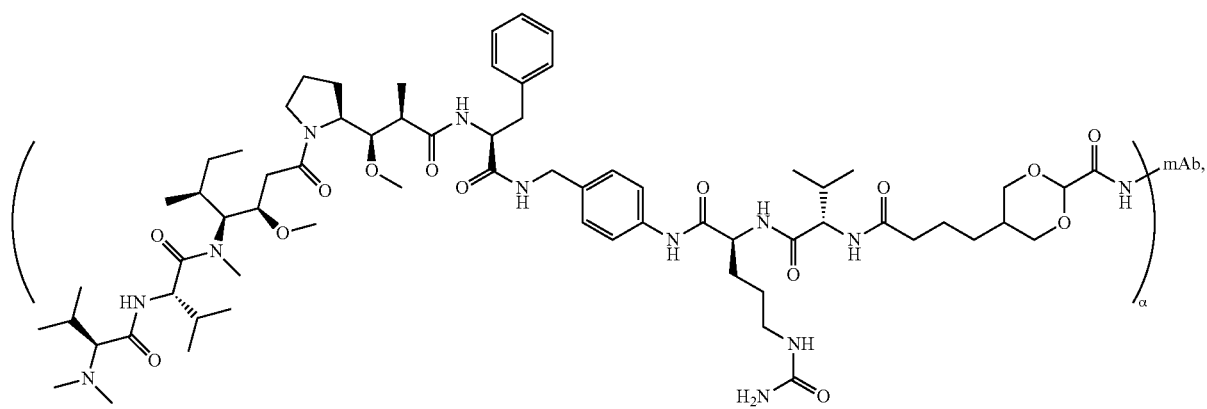
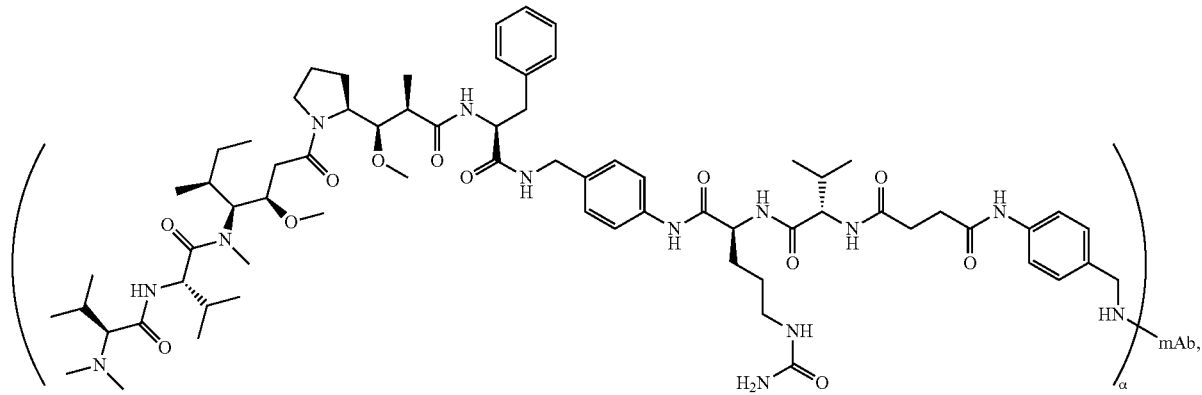
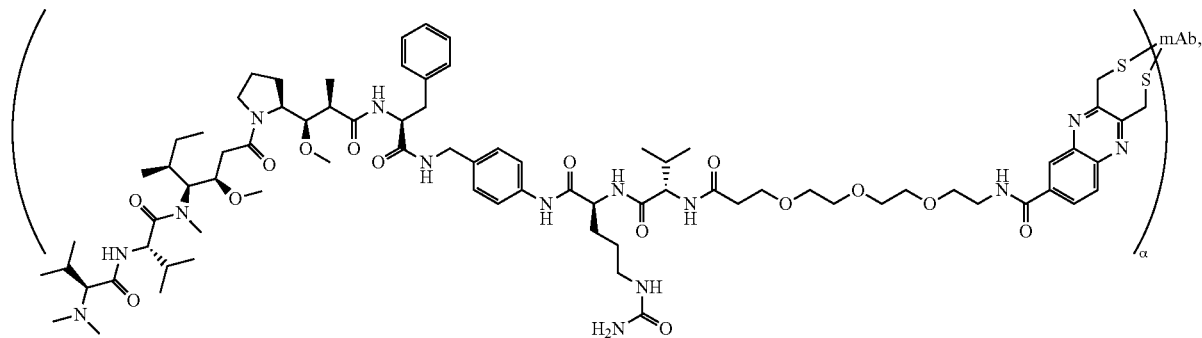

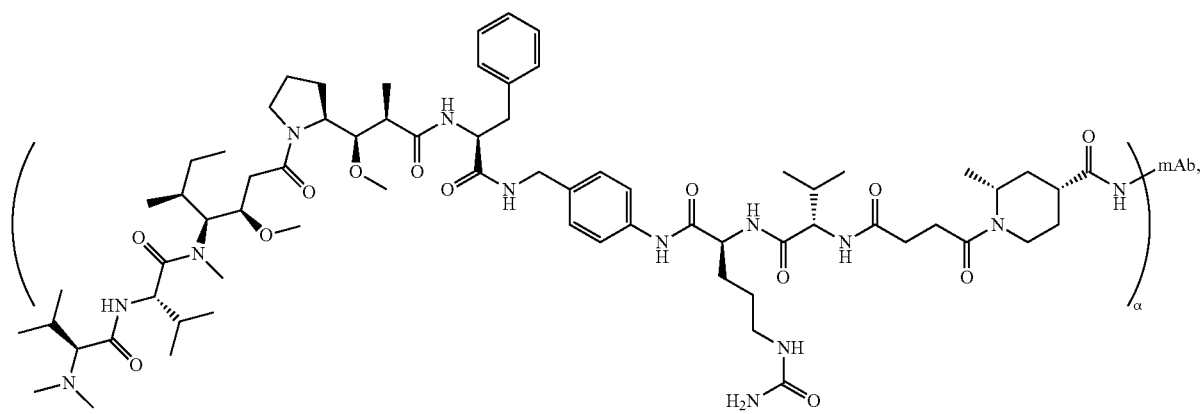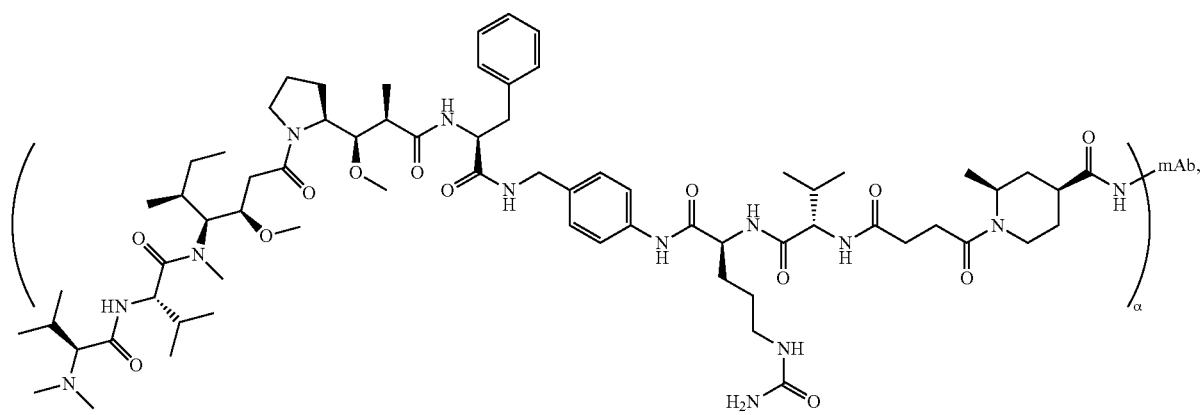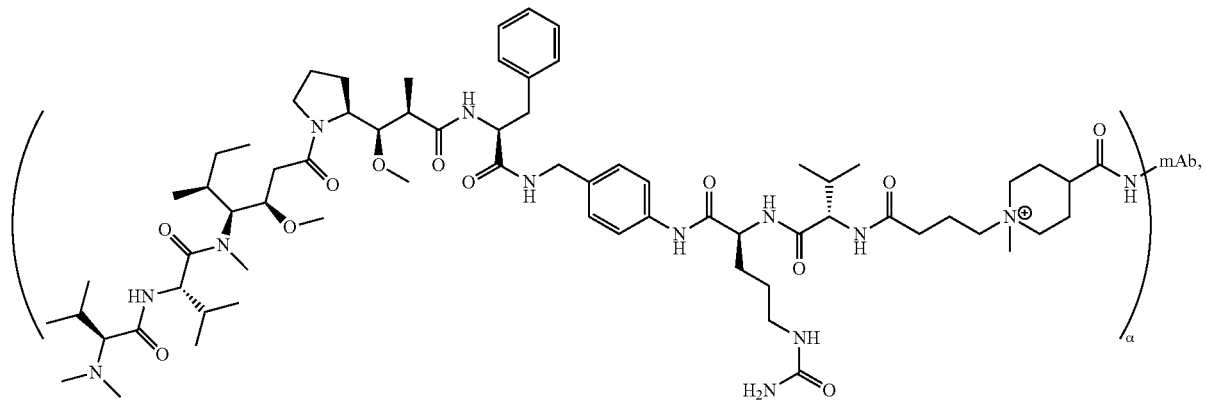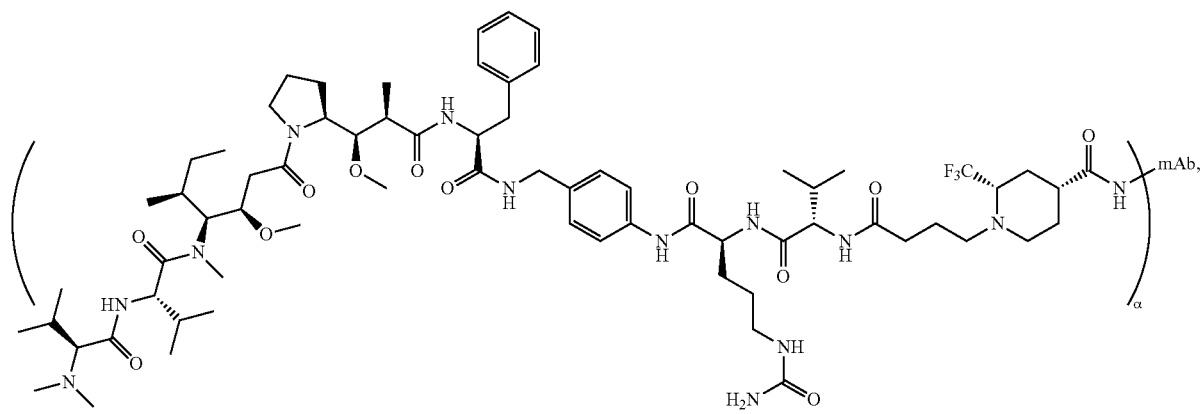

-continued
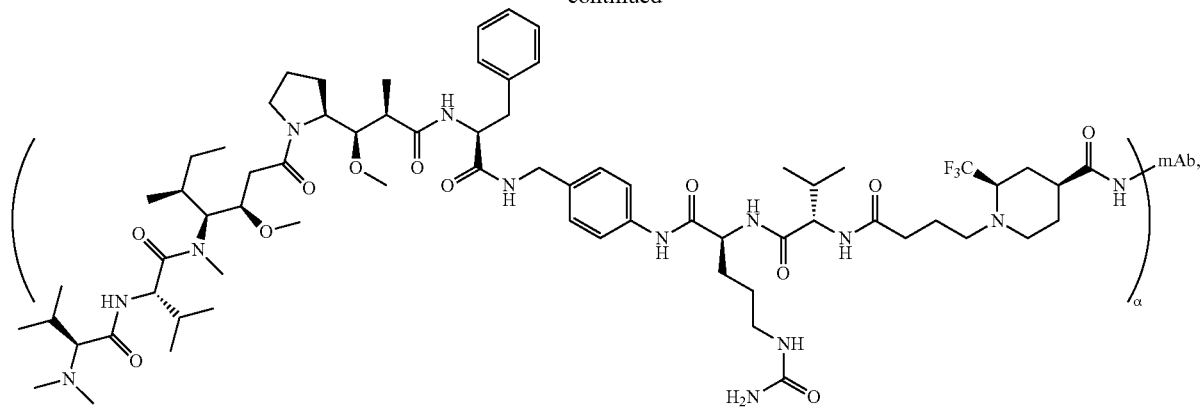
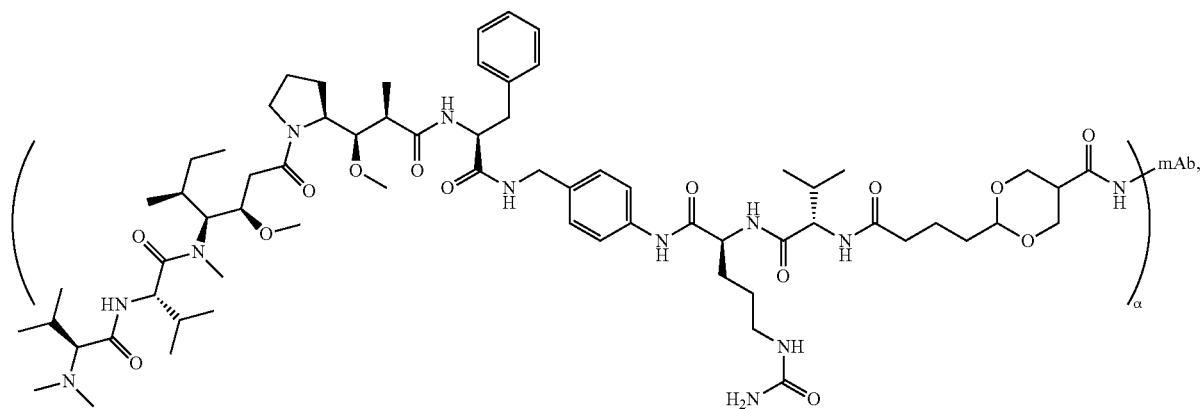
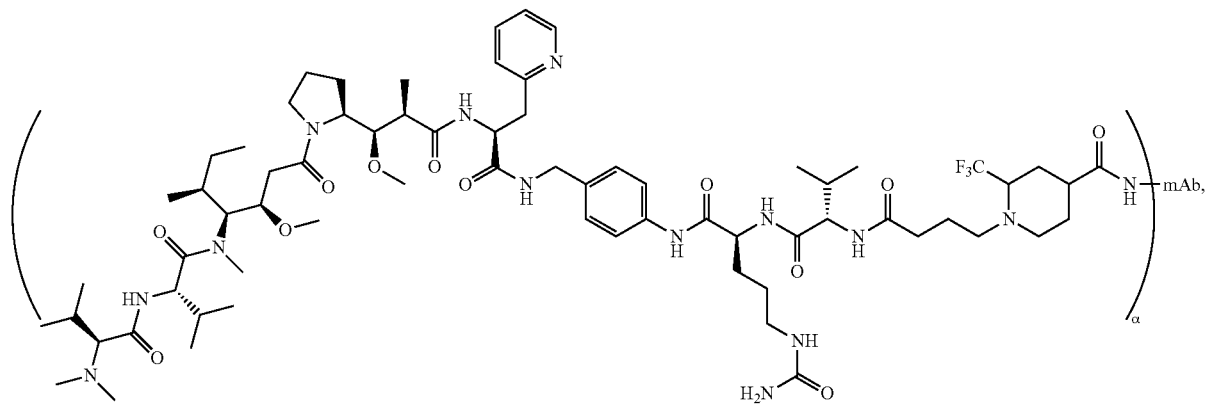
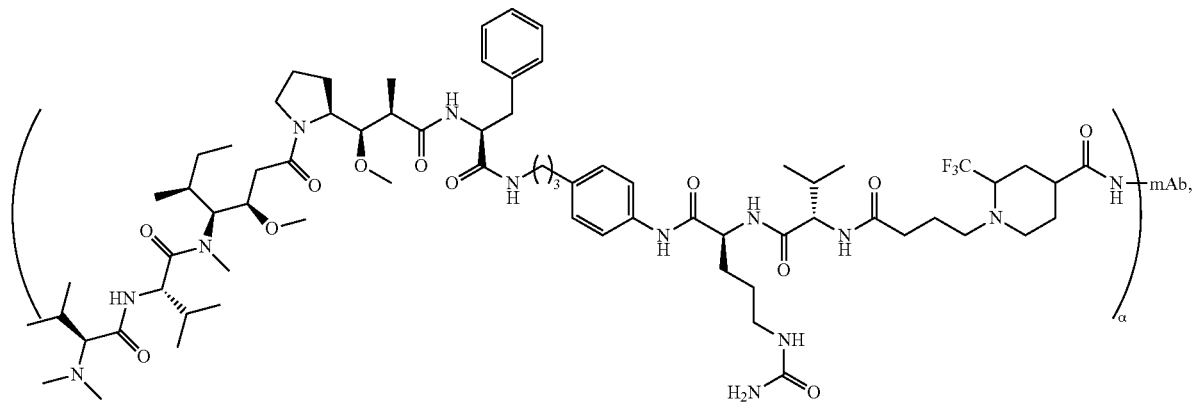

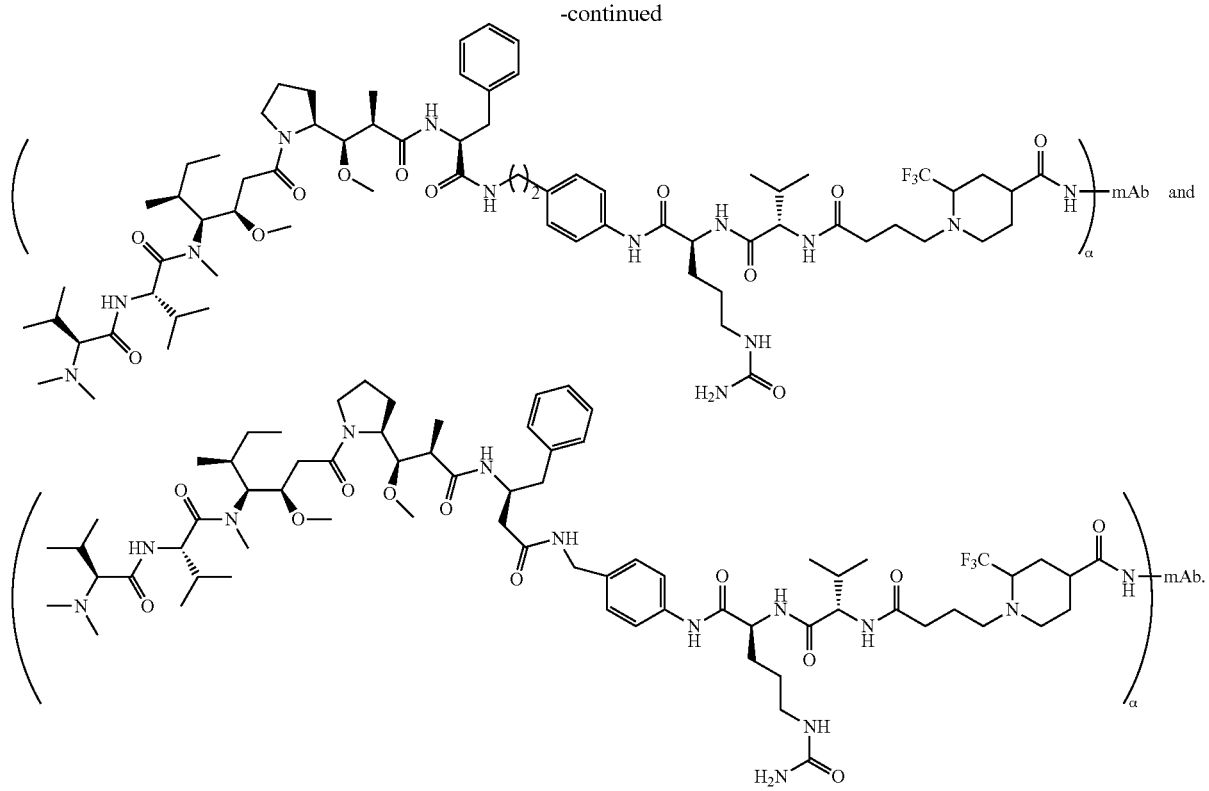

In some embodiments, the drug and mAb in the conjugate are in a coupling ratio (DAR) which is an integer or a decimal between 1-10; the mAb is trastuzumab or sacituzumab.

In some embodiments, the coupling ratio (DAR) of the drug to mAb in the conjugate is an integer or a decimal between 1-10; the mAb is trastuzumab or sacituzumab, or, the mAb is pertuzumab.

In the above embodiments, the coupling ratio (DAR) is represented by a in the structural formula of the conjugate, the trastuzumab, sacituzumab or pertuzumab can be understood to be a group obtained after removing α amino groups from trastuzumab, sacituzumab or pertuzumab.

In some embodiments, DAR is an integer or a decimal between 1-4 (for example, 1, 2, 3, 4).

In some embodiments, the coupling ratio of drug to mAb (DAR) in the conjugate is 1, 2 or 3; the mAb is trastuzumab or sacituzumab.

In some embodiments, the coupling ratio of drug to mAb (DAR) in the conjugate is 1, 2 or 3a the mAb is a group obtained after removing 1, 2 or 3 amino groups from trastuzumab, sacituzumab or pertuzumab.

In some embodiments, DAR is 1, and mAb is a group obtained after removing 1 amino group from trastuzumab.

In some embodiments, DAR is 1, and mAb is a group obtained after removing 1 amino group from pertuzumab.

In some embodiments, DAR is 1, and mAb is a group obtained after removing 1 amino group from sacituzumab.

In some embodiments, DAR is 2, and mAb is a group obtained after removing 2 amino groups from trastuzumab.

In some embodiments, DAR is 2, and mAb is a group obtained after removing 2 amino groups from pertuzumab.

In some embodiments, DAR is 2, and mAb is a group obtained after removing 2 amino groups from sacituzumab.

In some embodiments, the conjugate is selected from:

BT001003

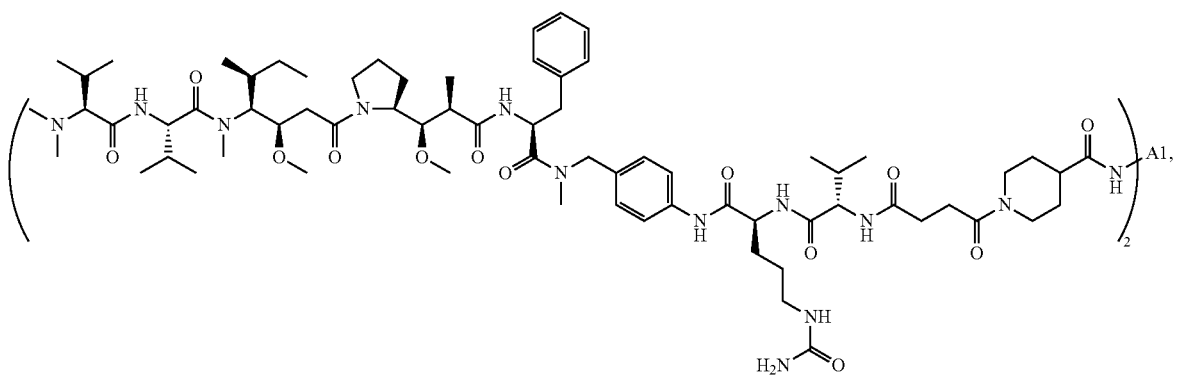

-continued
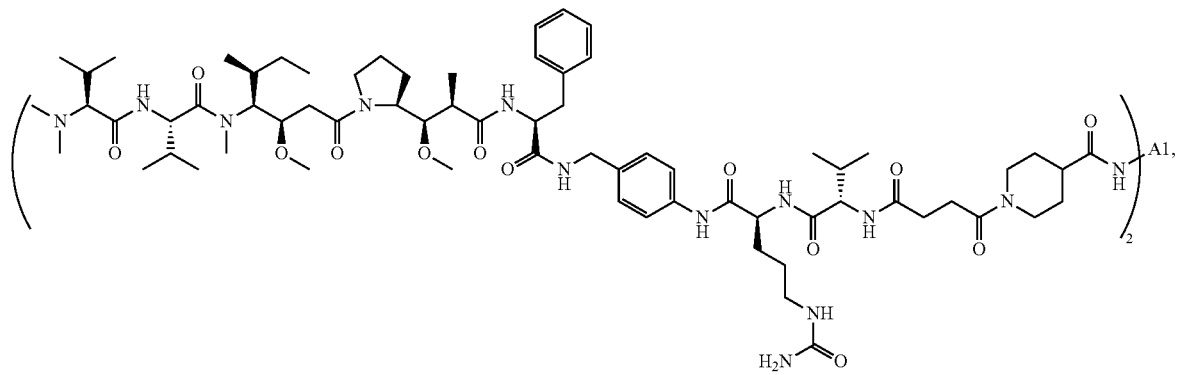
BT001005
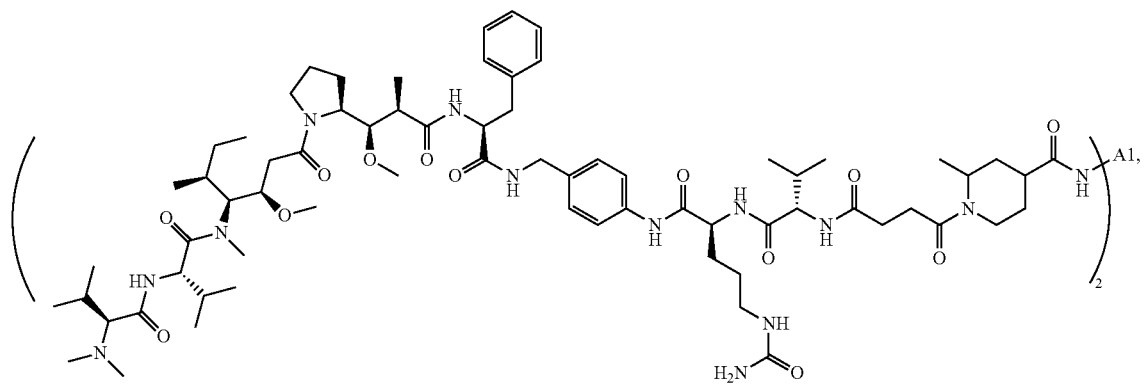
BT001006

BT001007
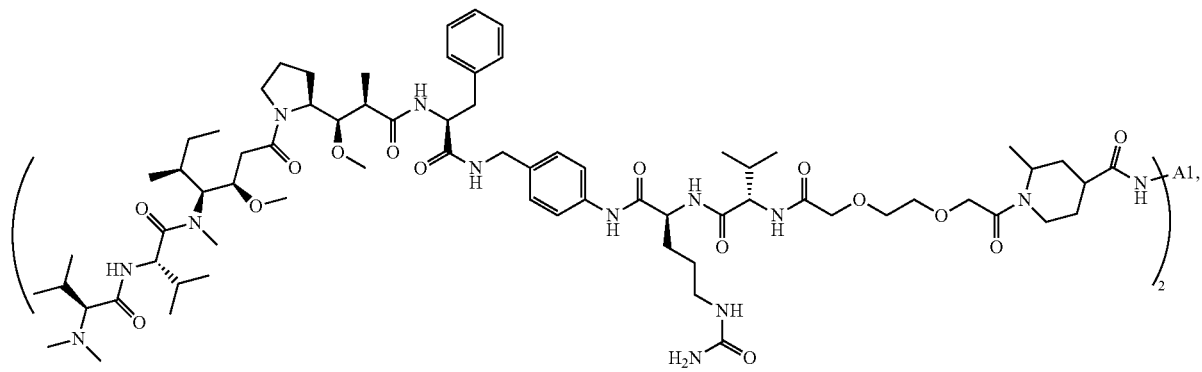
BT001008

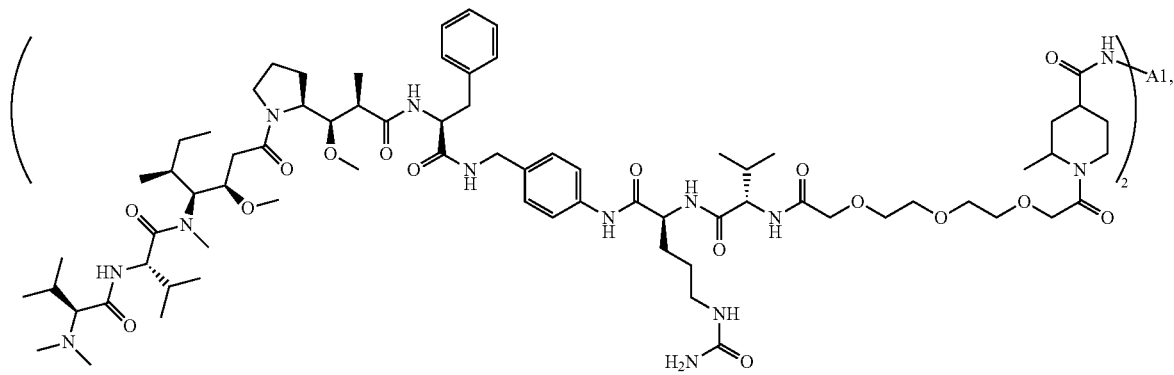
BT001009
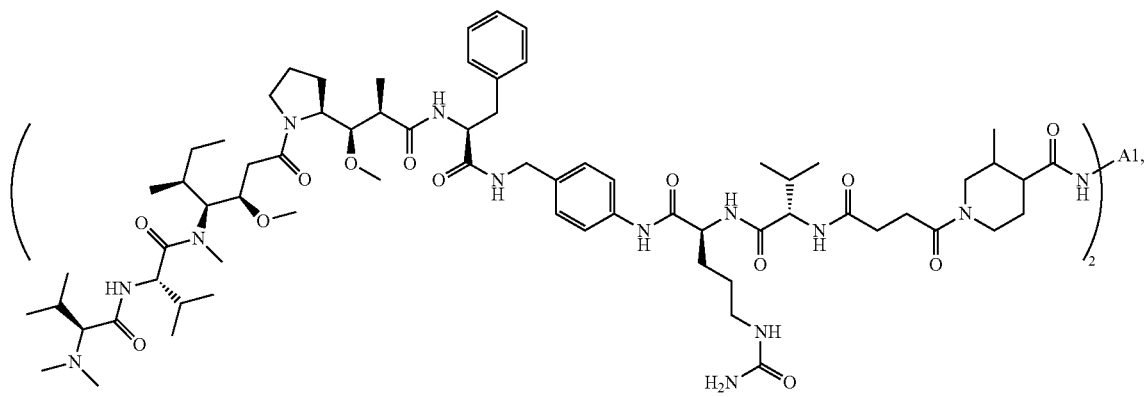
BT001010
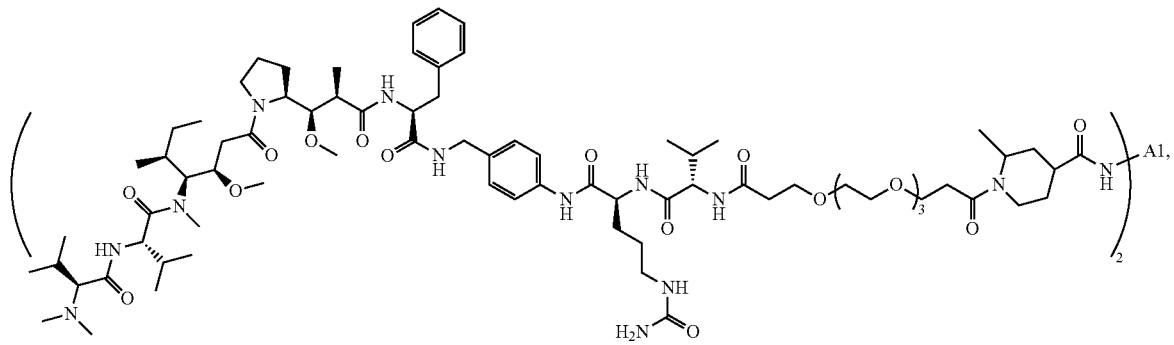
BT001011
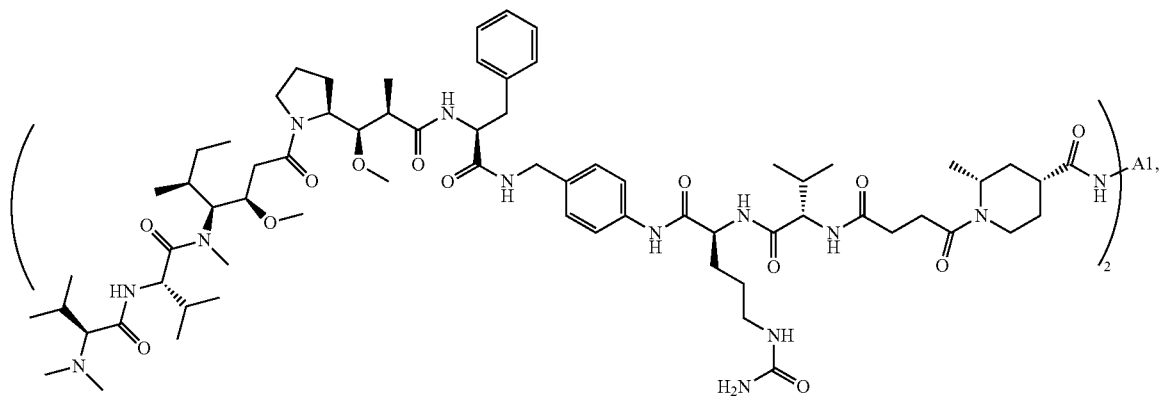
BT001012

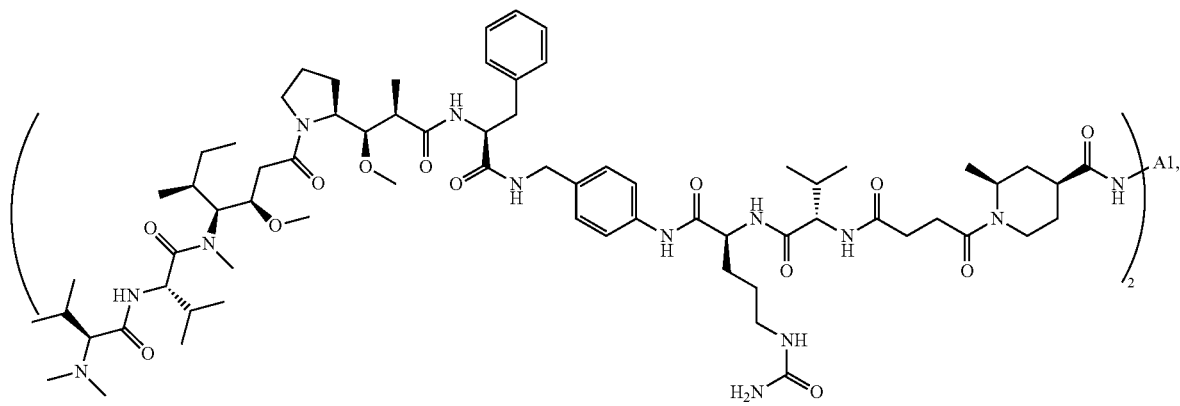
BT001013
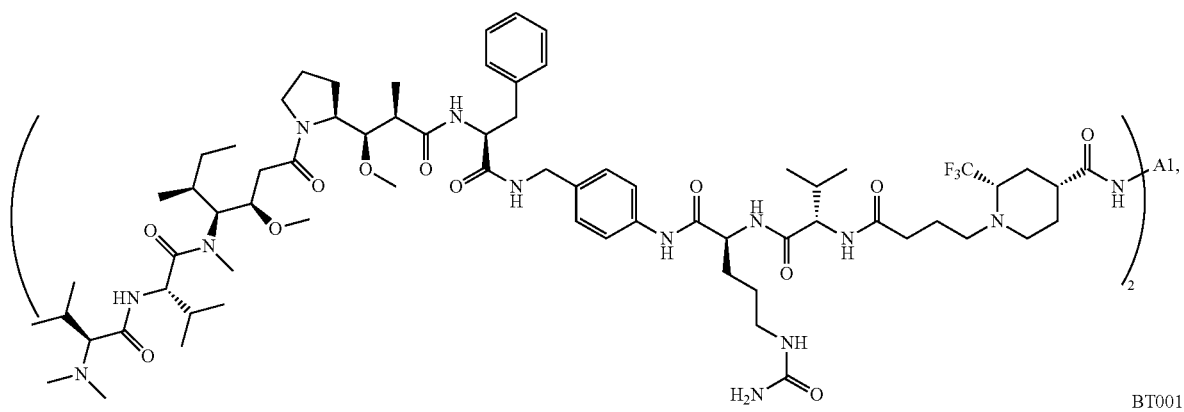
BT001016
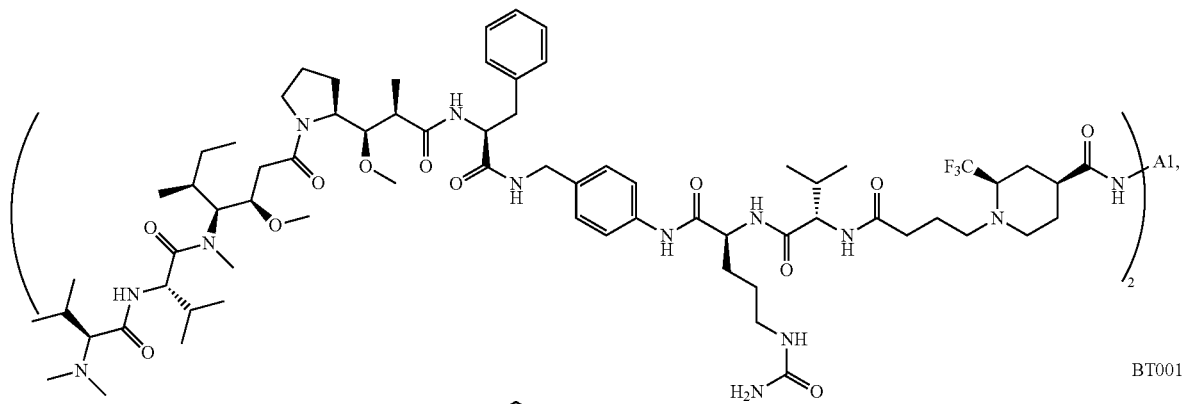
BT001017
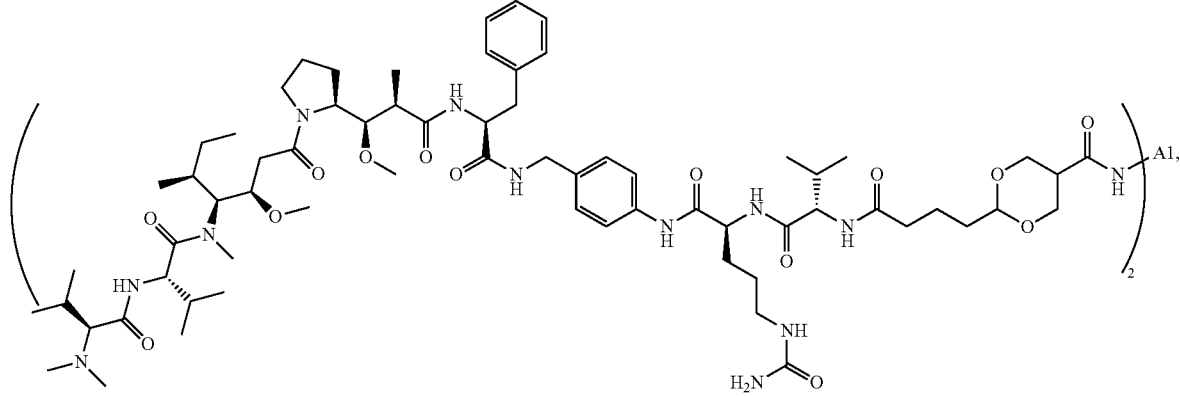
BT001018

-continued
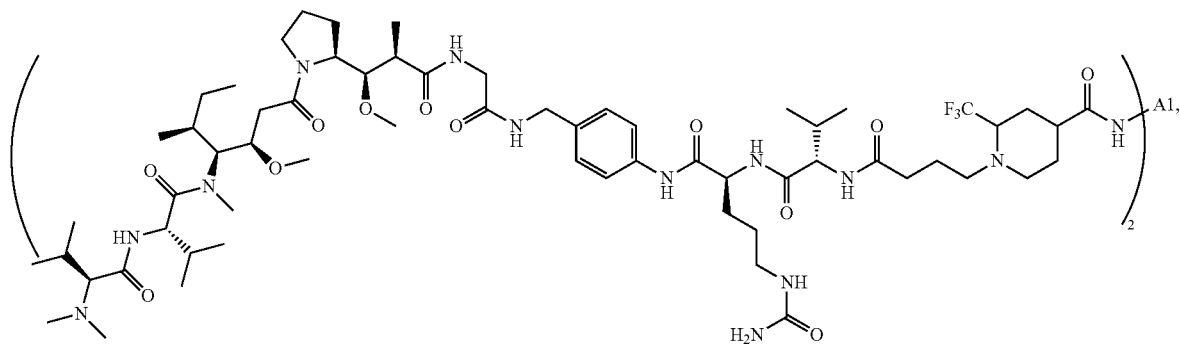
BT001019
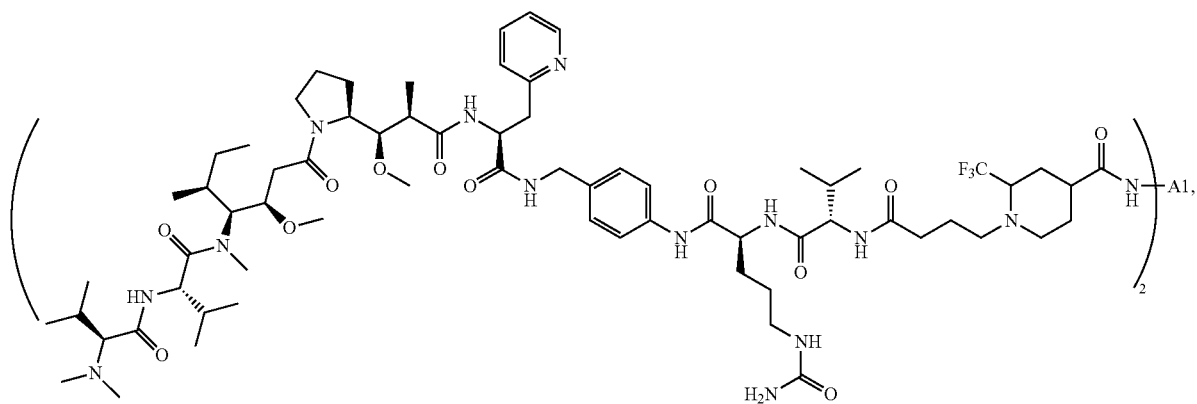
BT001021
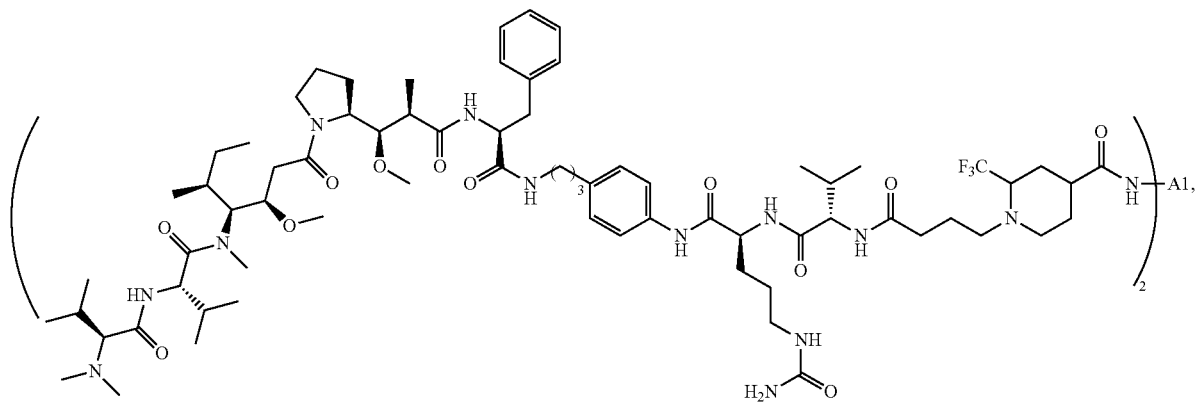
BT001022
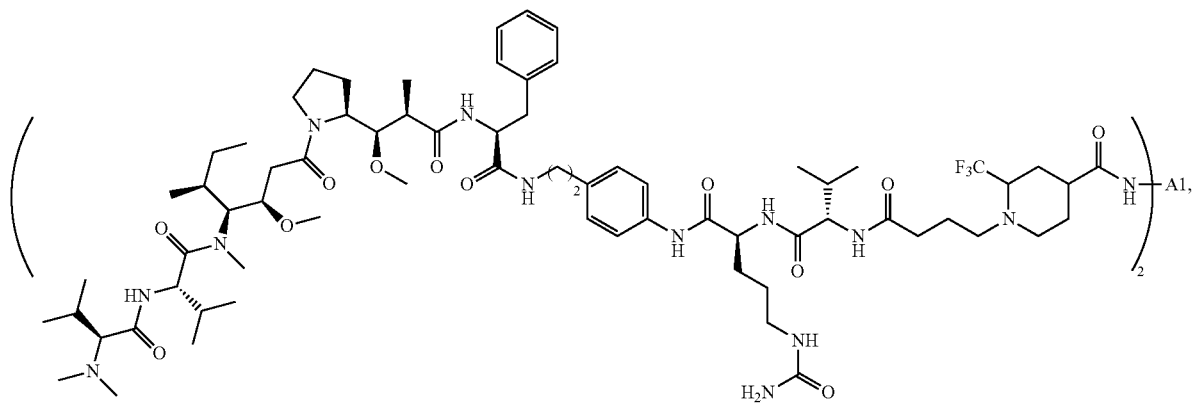
BT001023

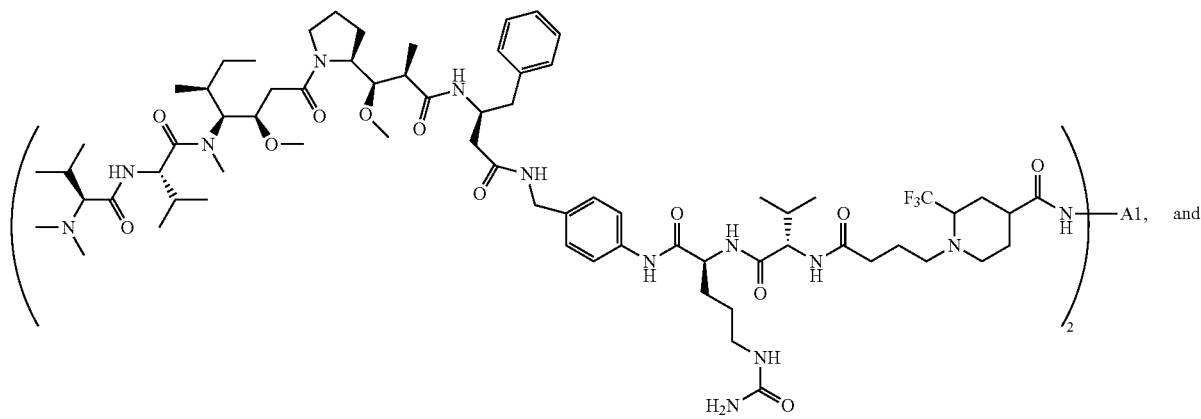
BT001024
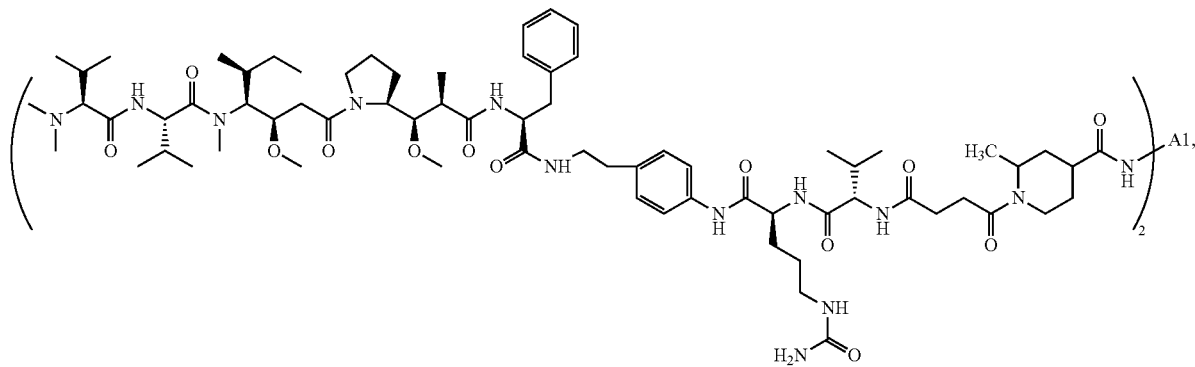
BT001025
Wherein A1 is a group obtained after removing 2 amino groups from trastuzumab.
In some embodiments, the conjugate is selected from:
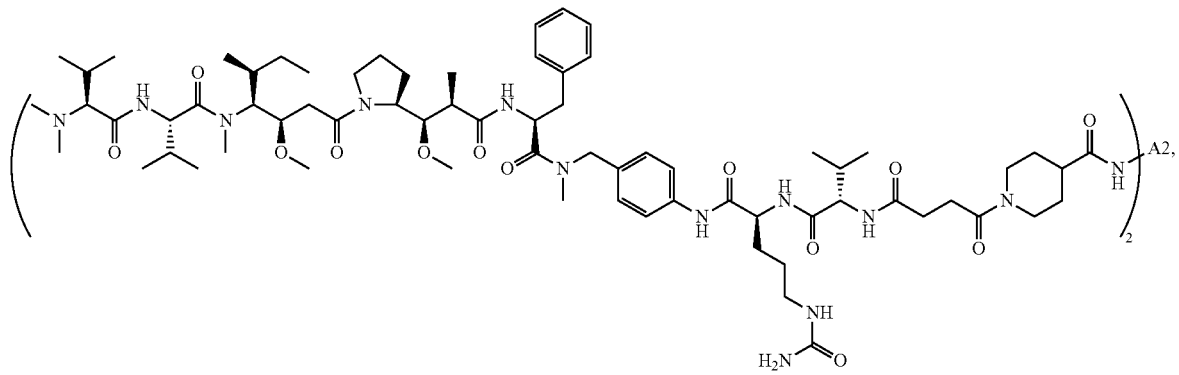
BT001026

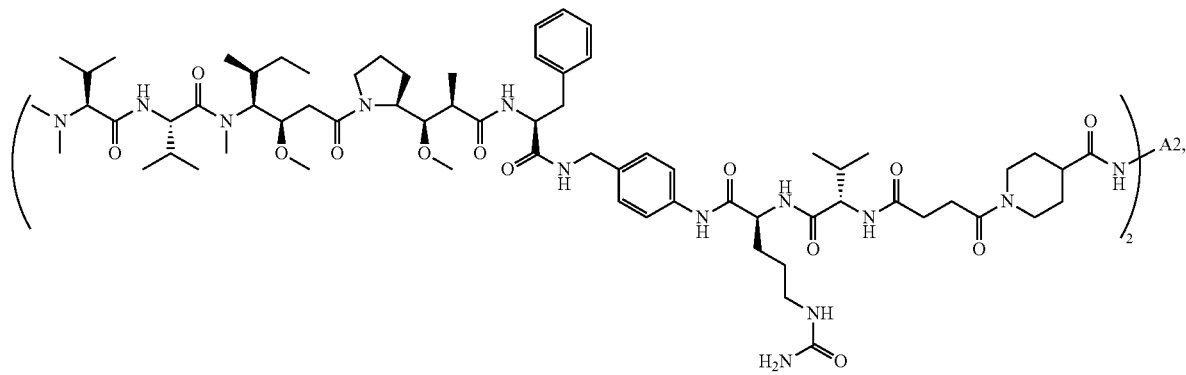
BT001027
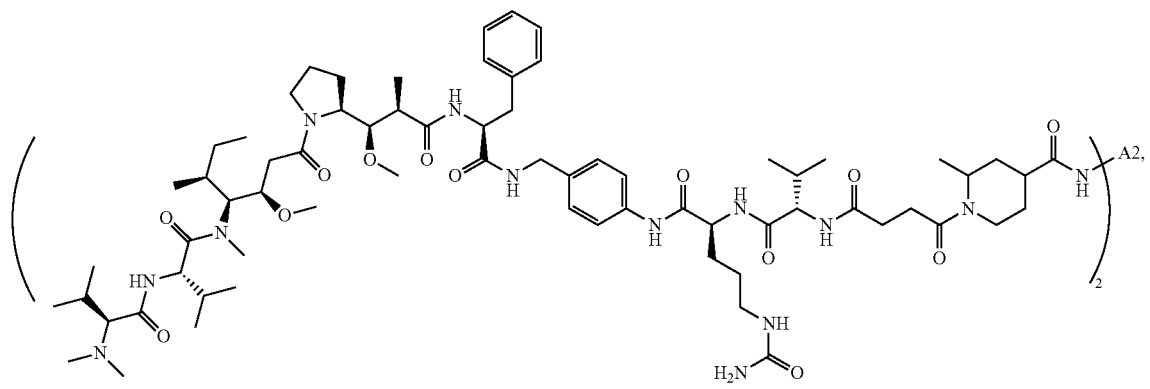
BT001028
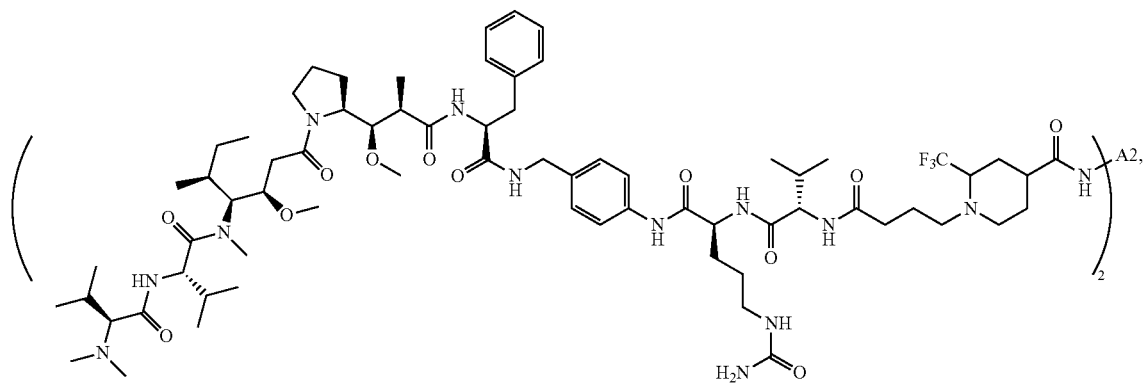
BT001029
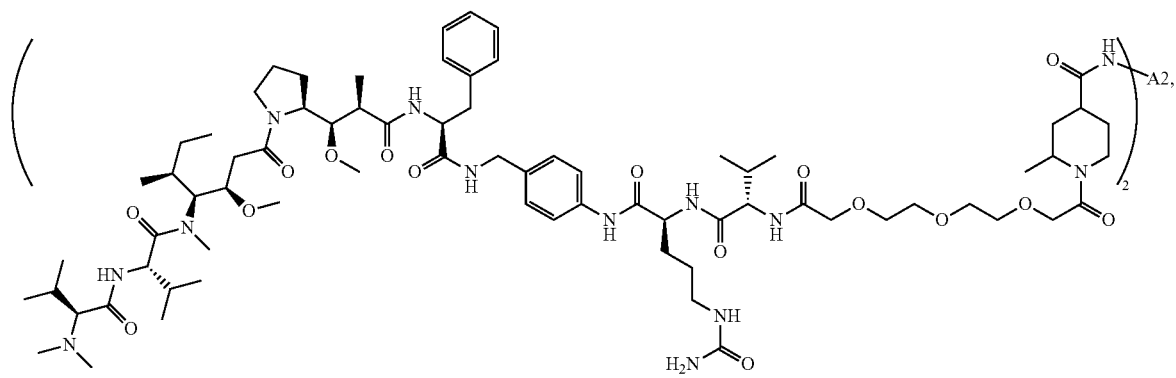
BT001030

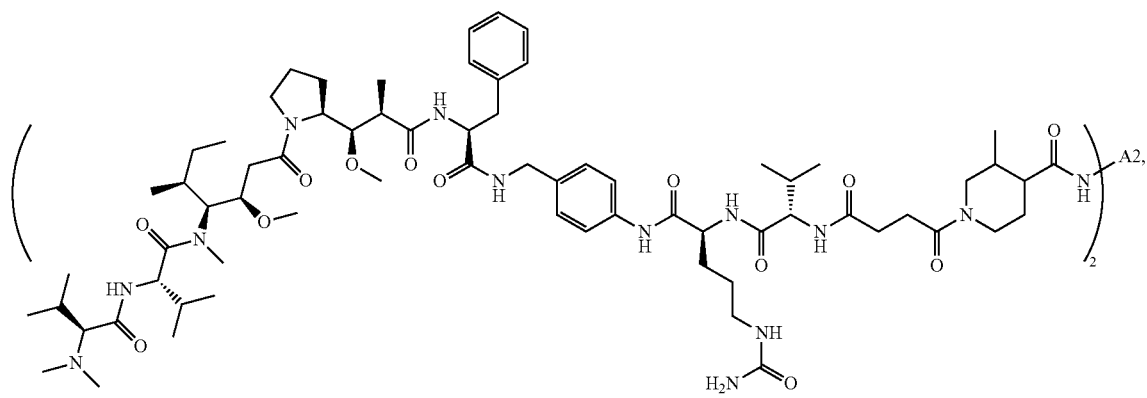
BT001031
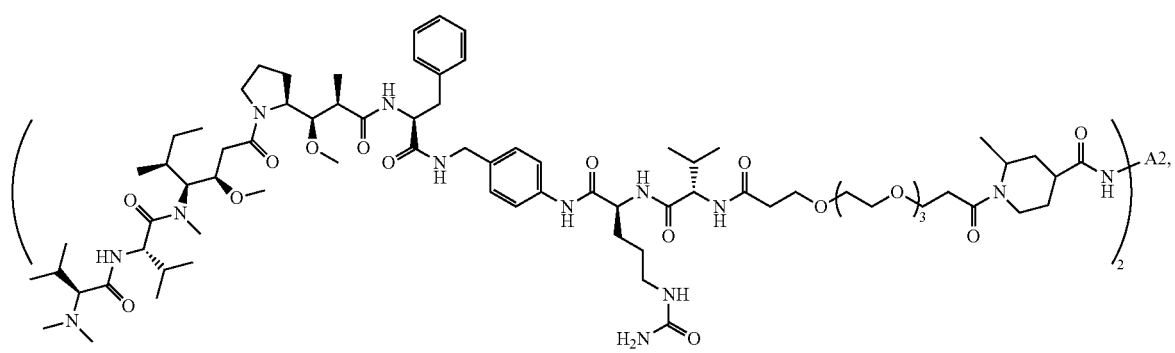
BT001032
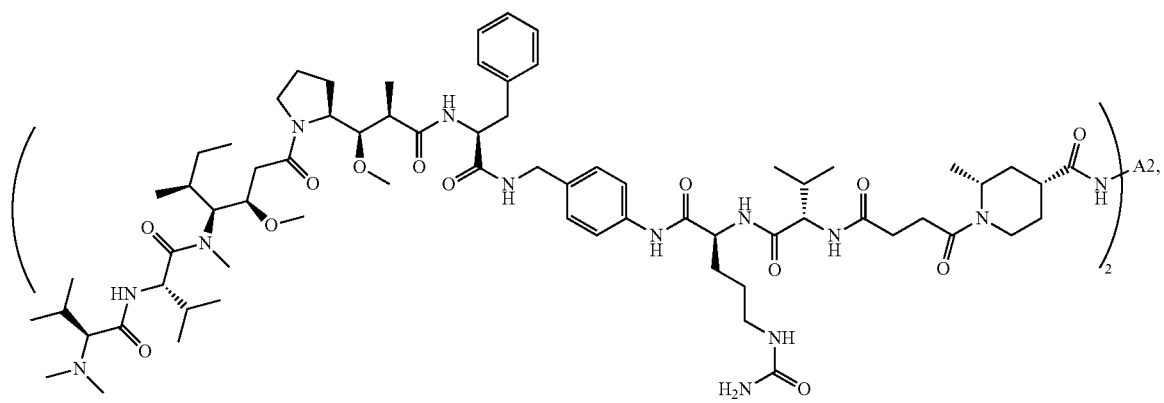
BT001033
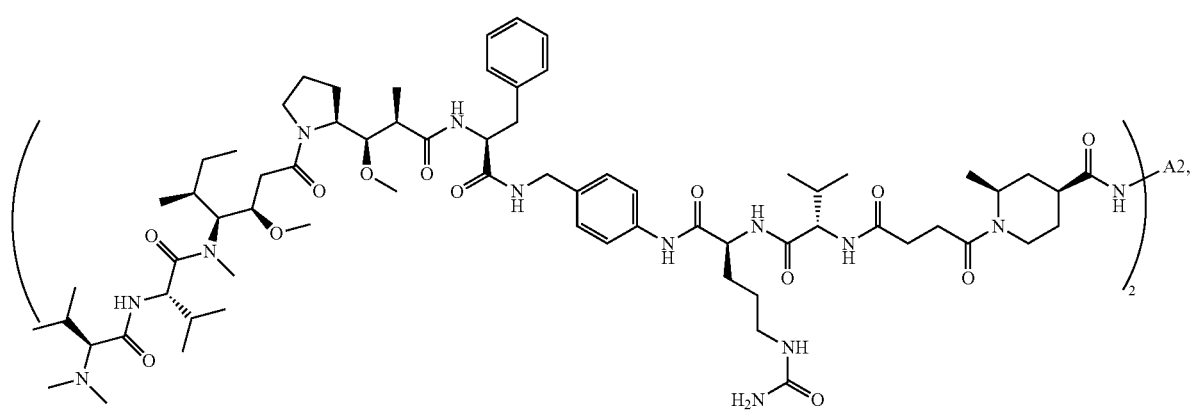
BT001034

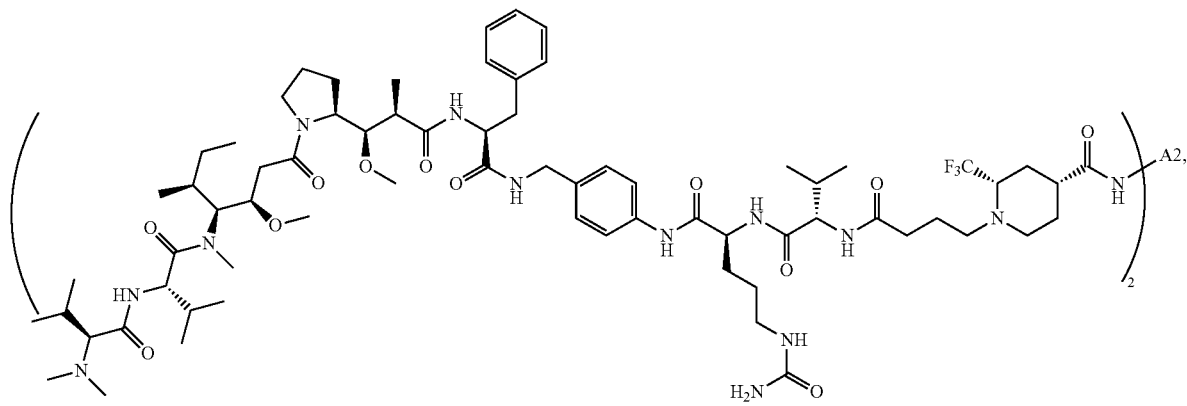
BT001035
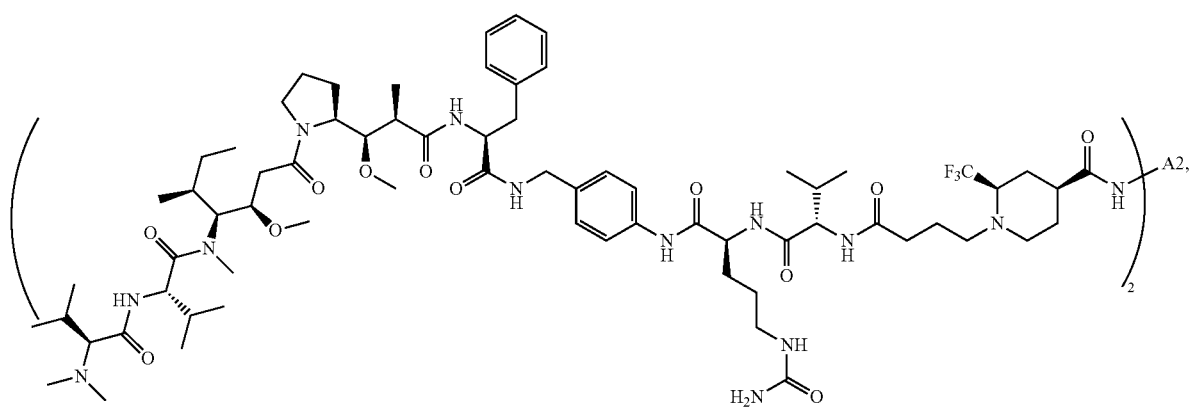
BT001036
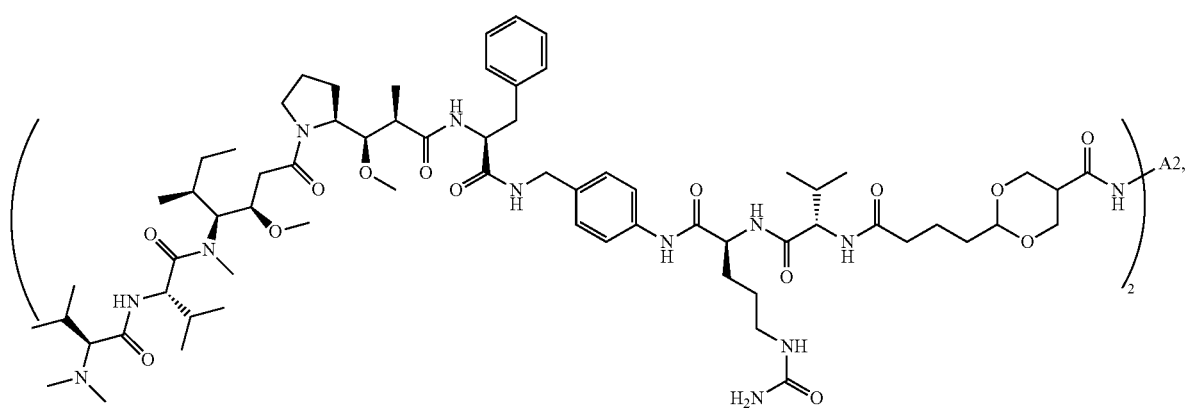
BT001037
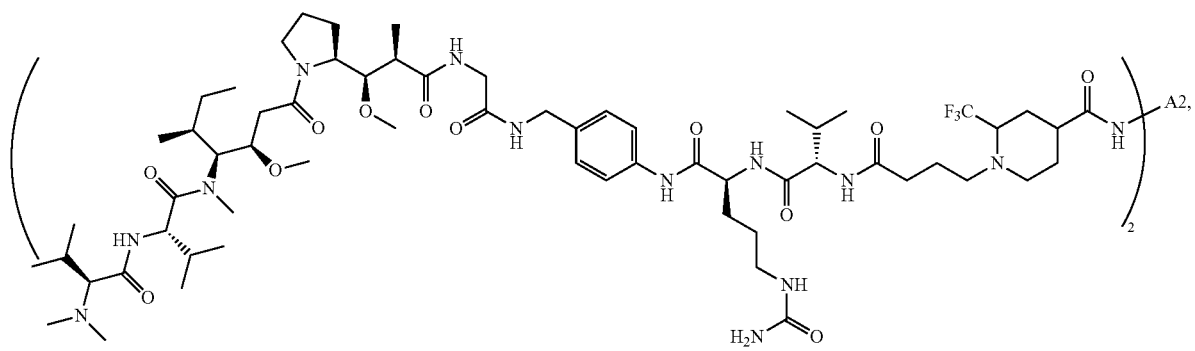
BT001038

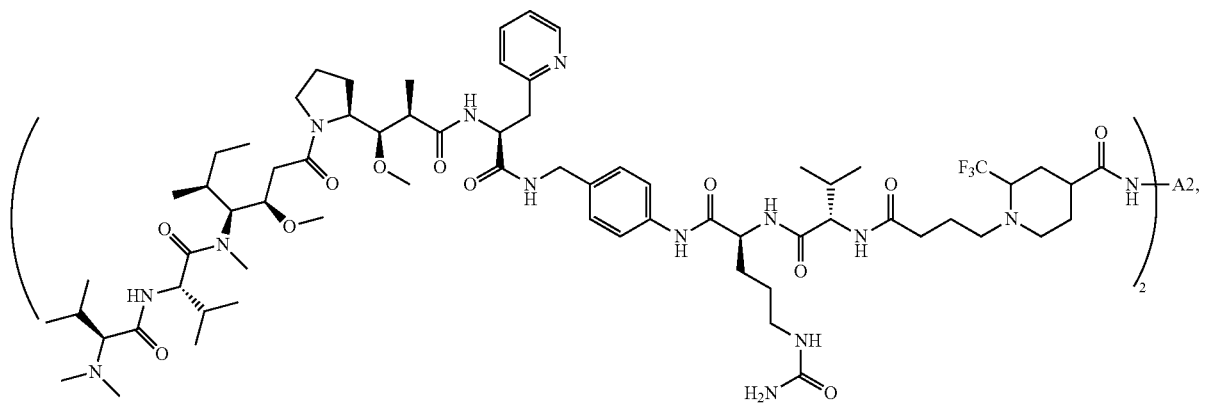
BT001039
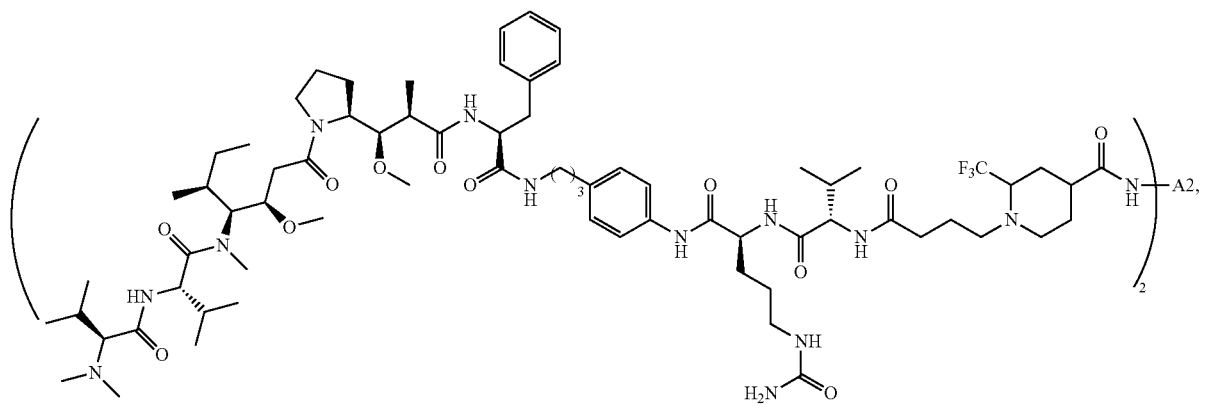
BT001040
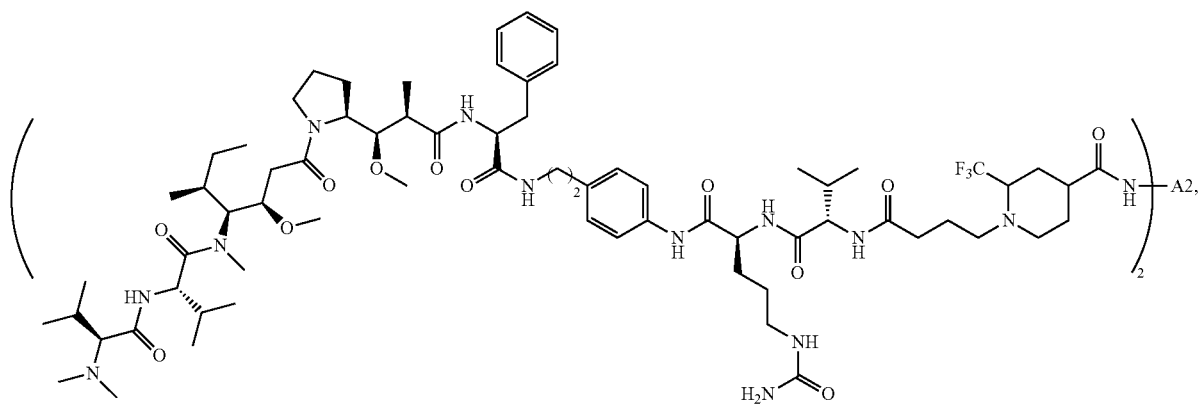
BT001041

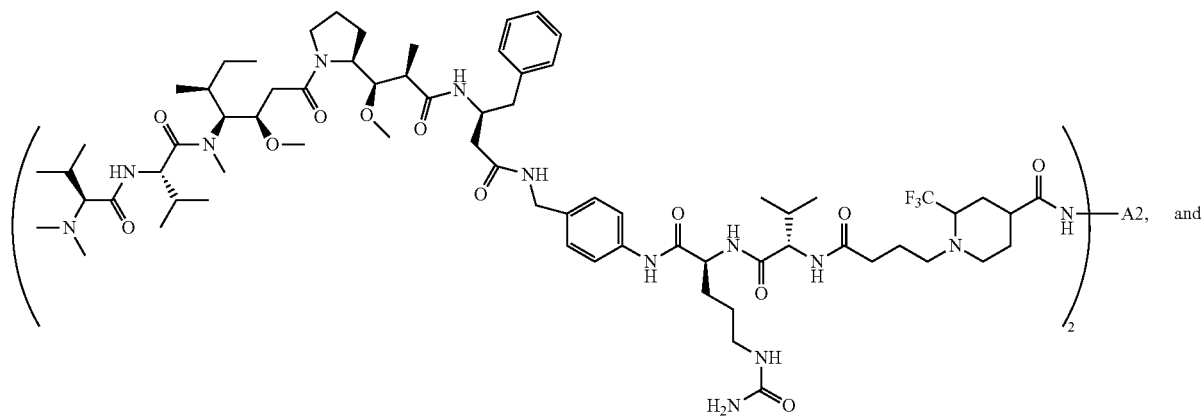
BT001042
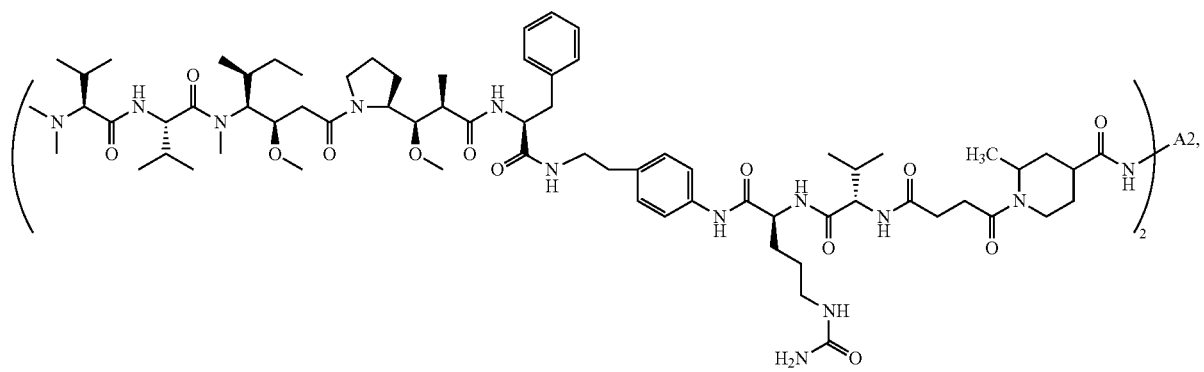
BT001043
wherein A2 is a group obtained after removing 2 amino groups from pertuzumab.
In some embodiments, the conjugate is selected from:
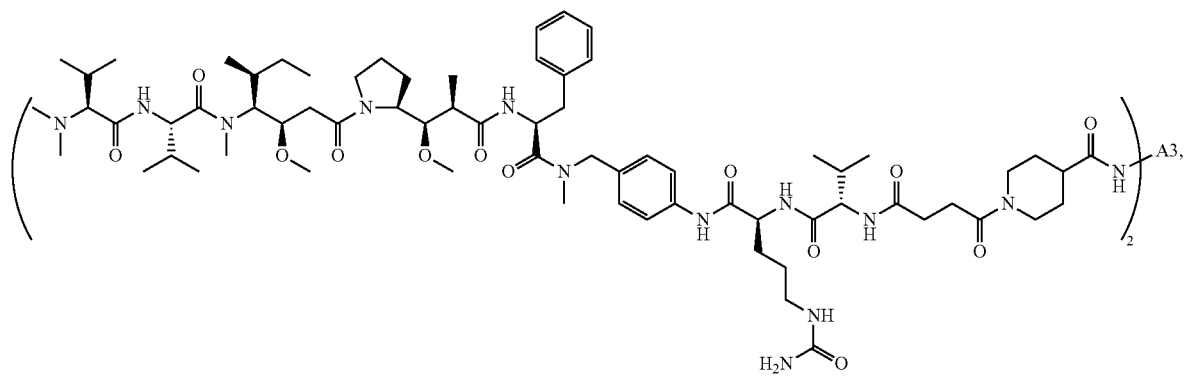
BT001044

-continued
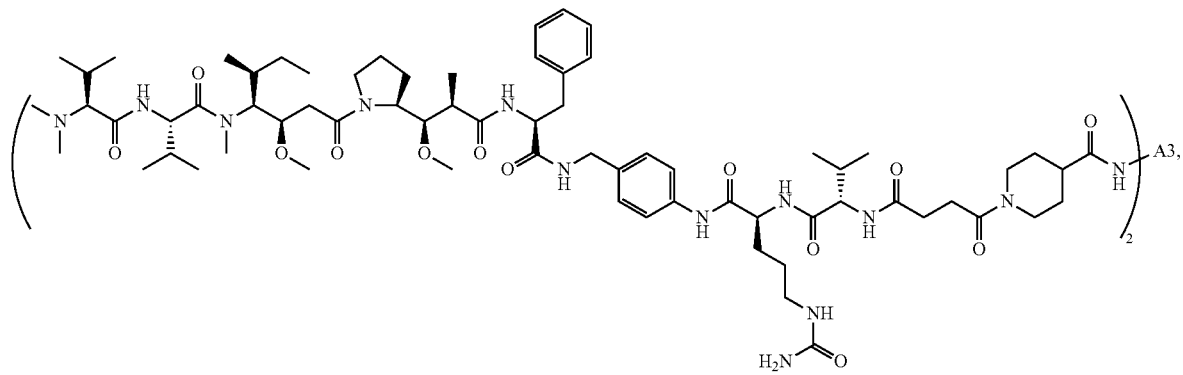
BT001045
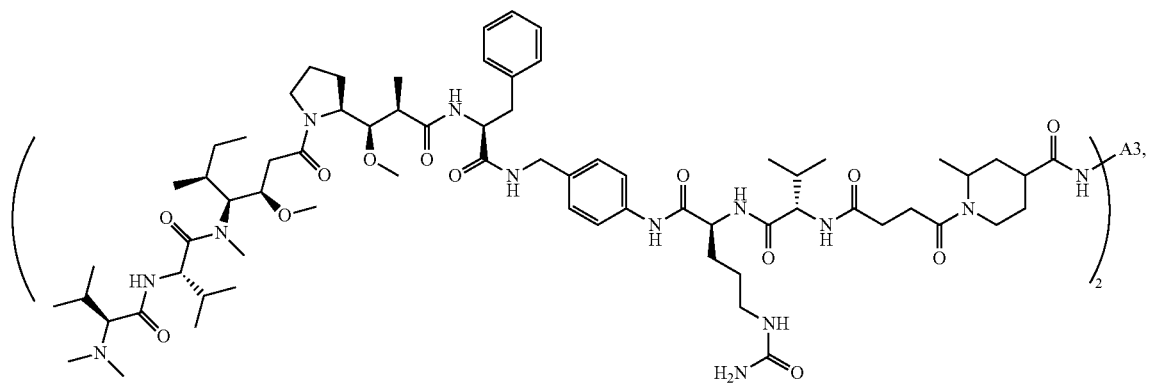
BT001014
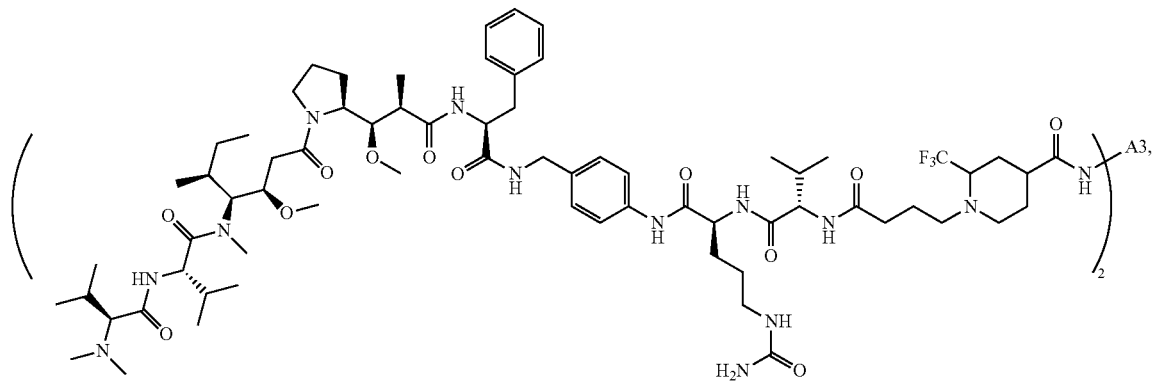
BT001015
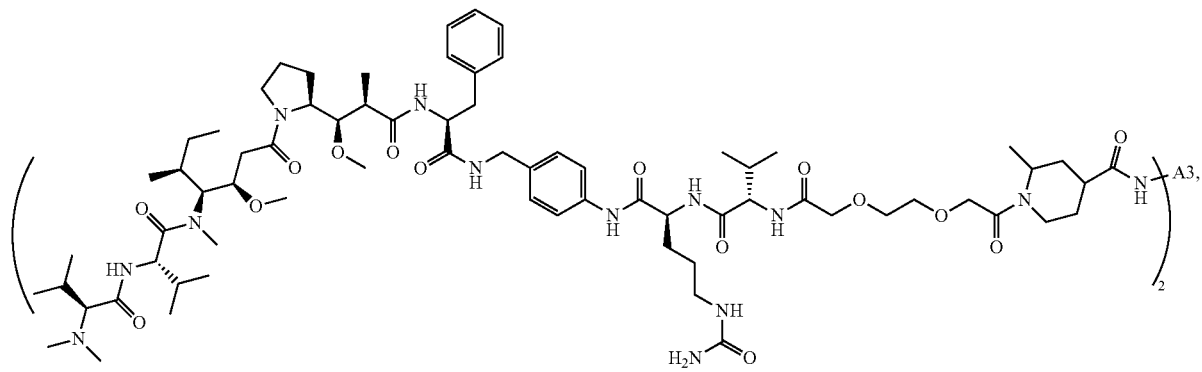
BT001046

-continued
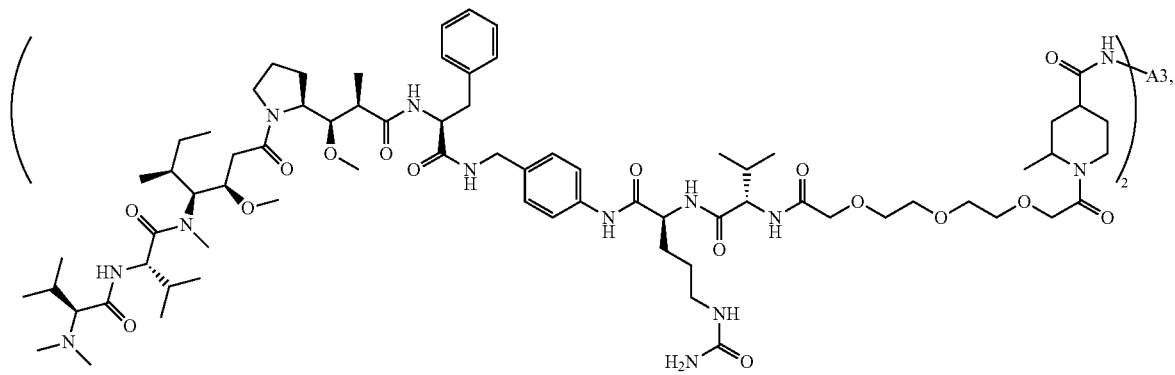
BT001047
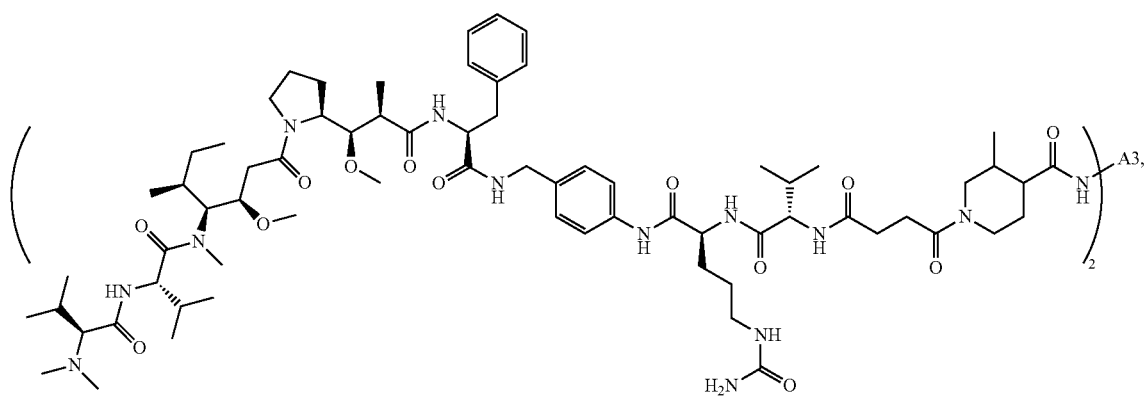
BT001048
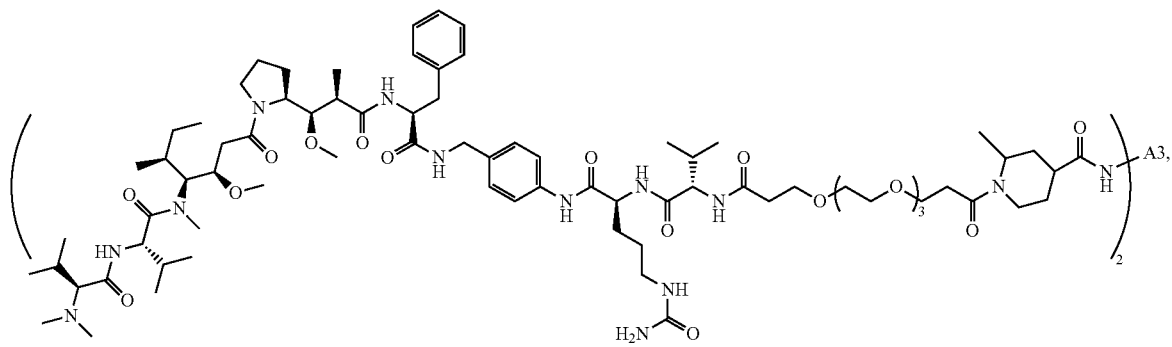
BT001049
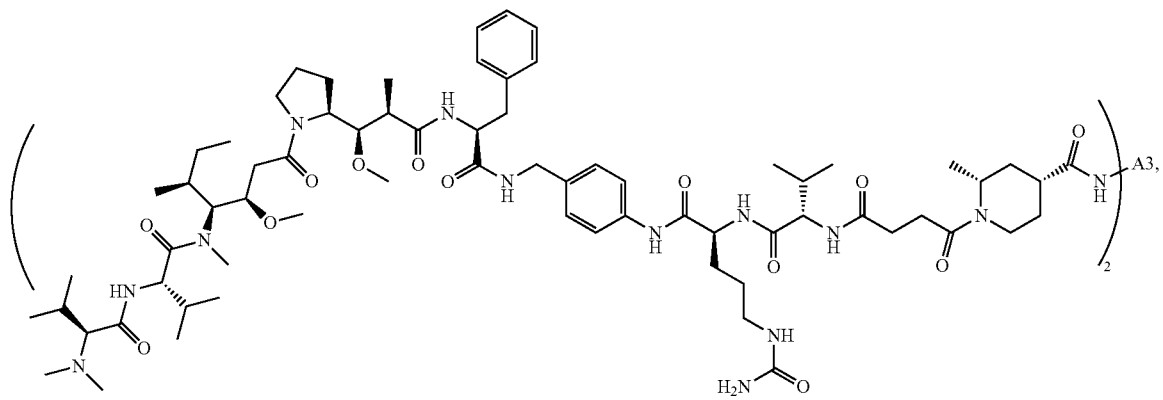
BT001050

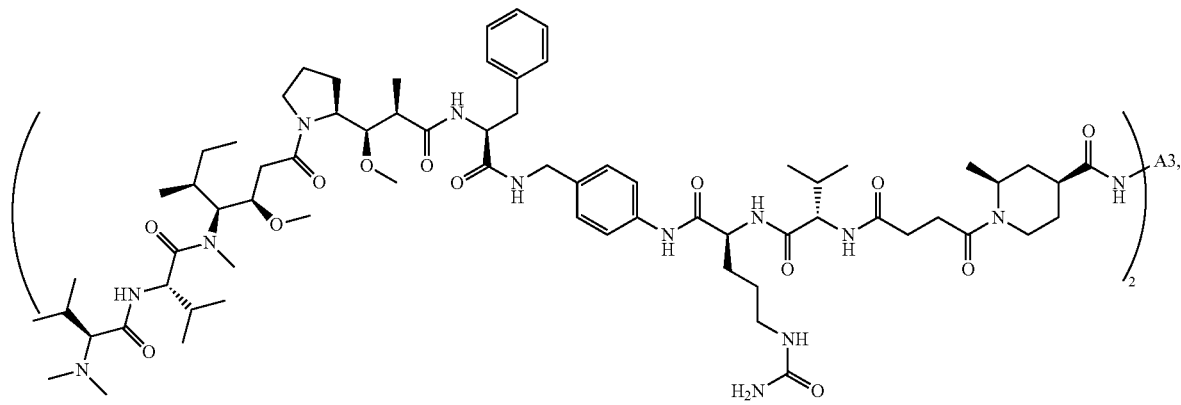
BT001051
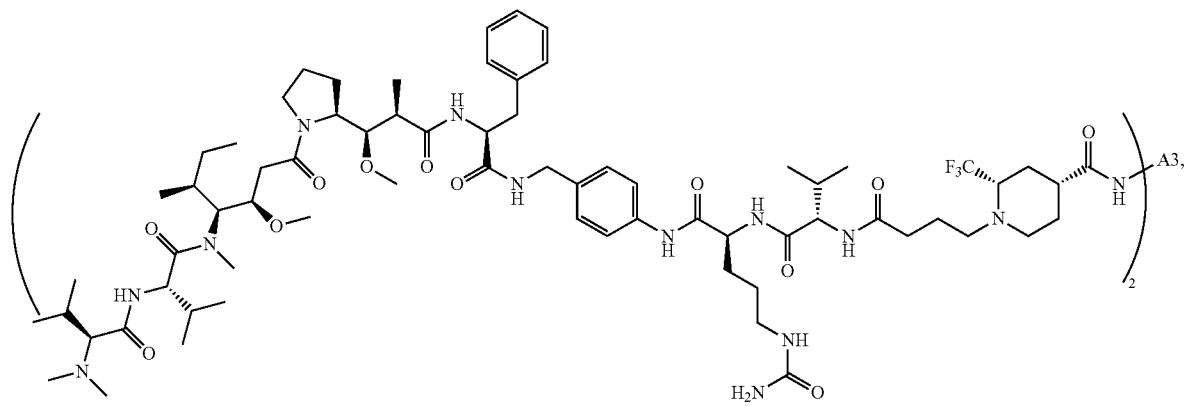
BT001052
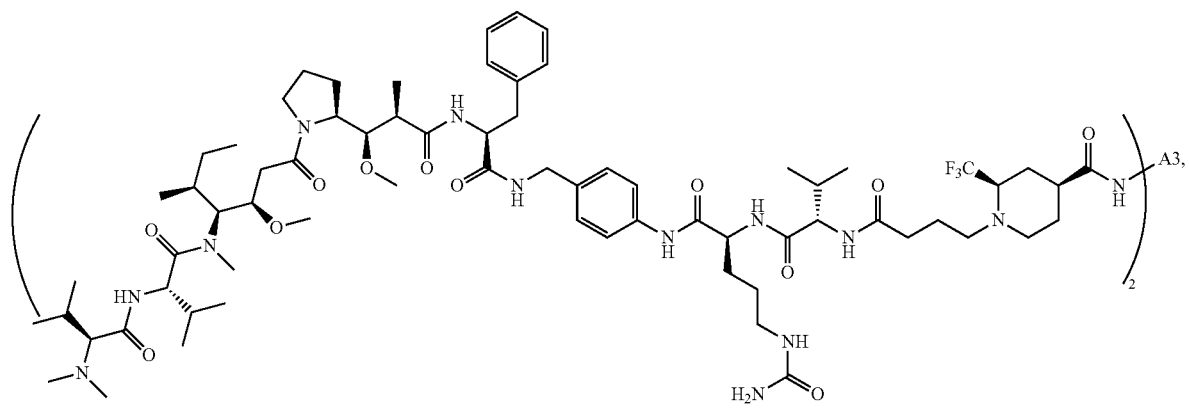
BT001053

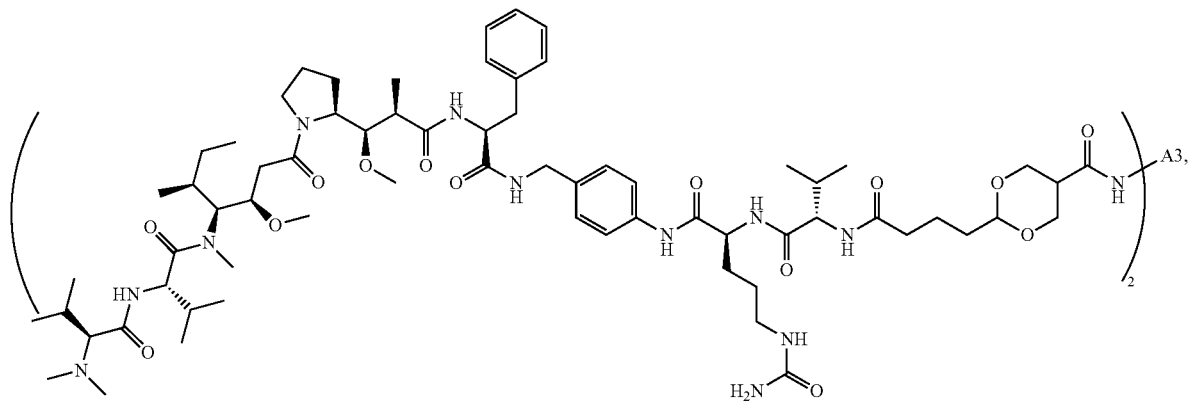
BT001054
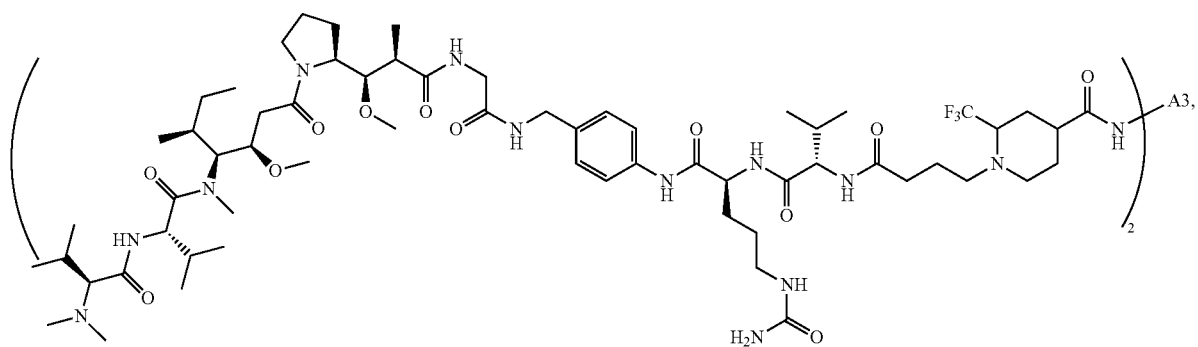
BT001055
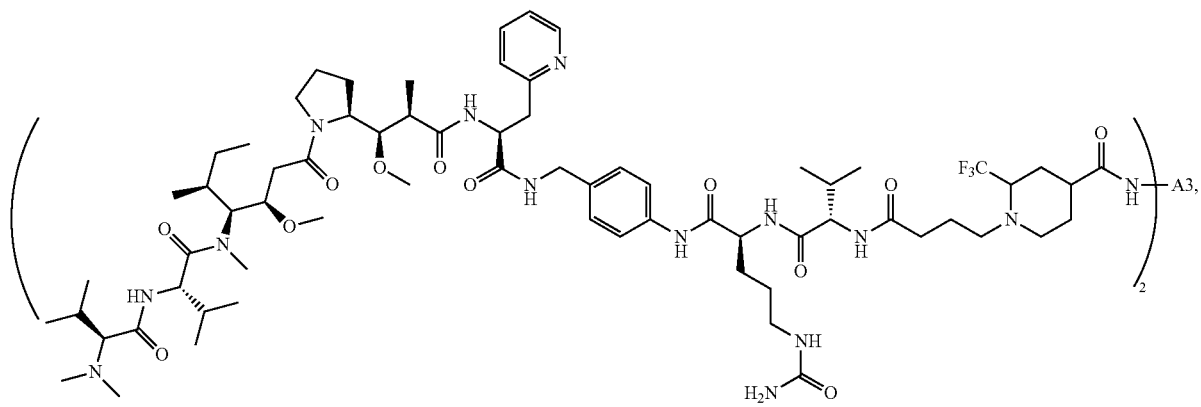
BT001056
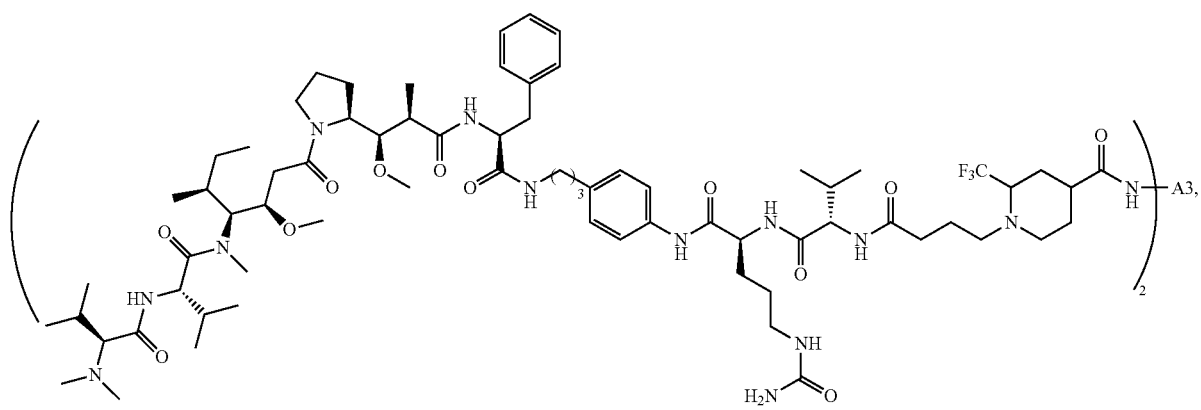
BT001057

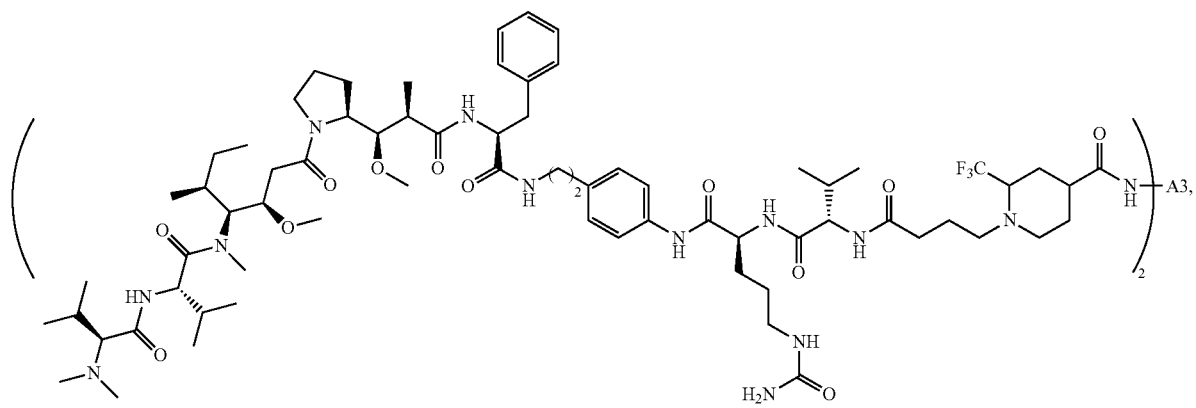
BT001058
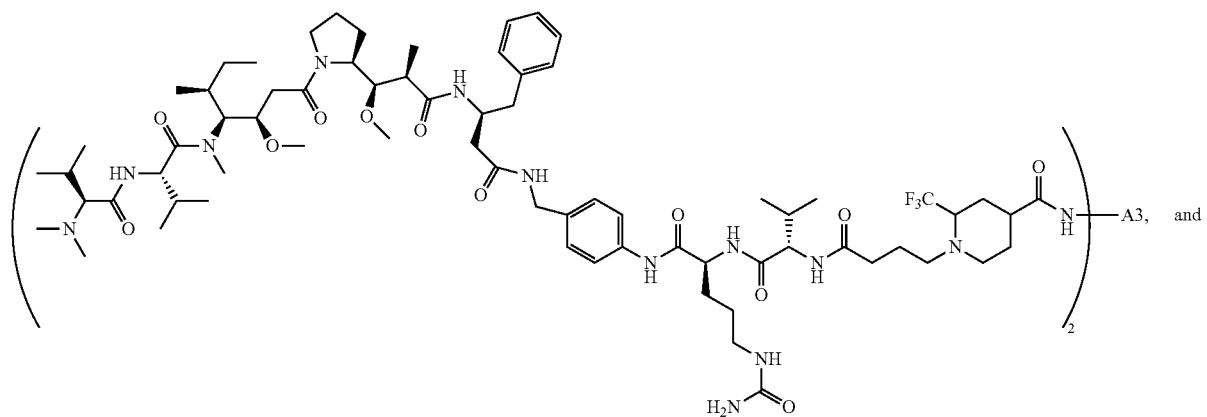
BT001059
and
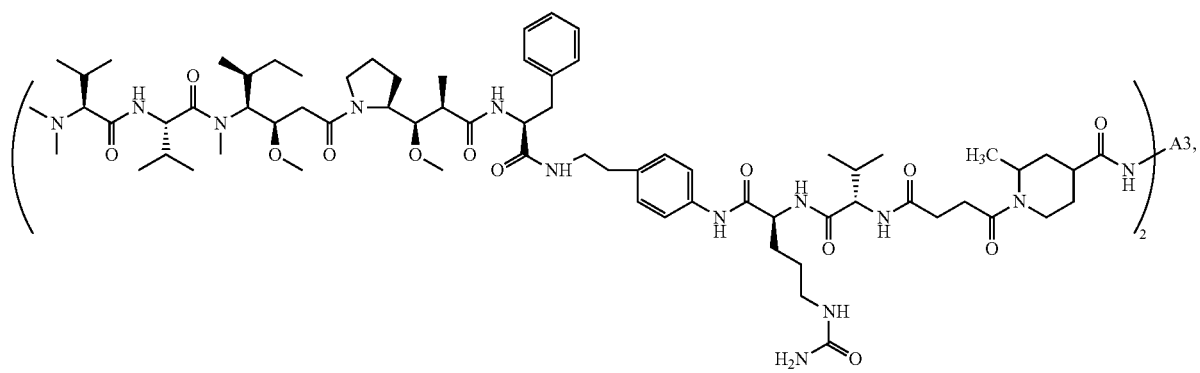
BT001060
wherein A3 is a group obtained after removing 2 amino groups from sacituzumab.

In some embodiments, the conjugate is selected from:
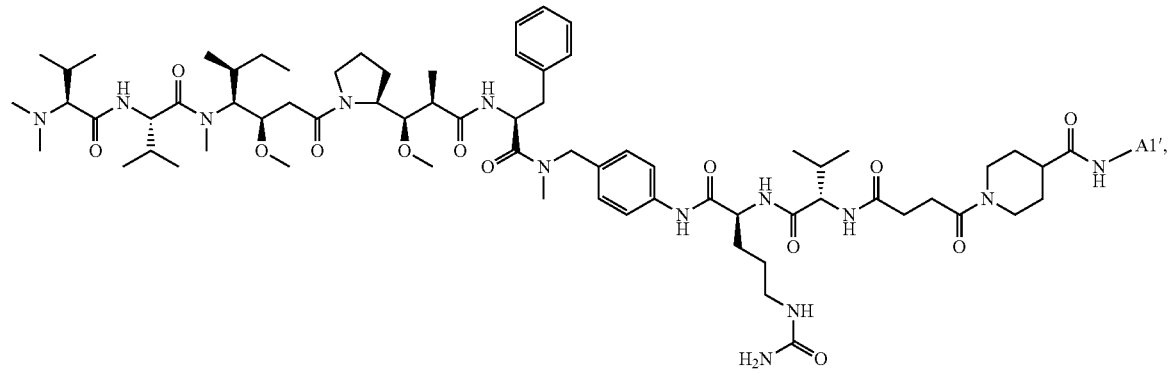
BT001061
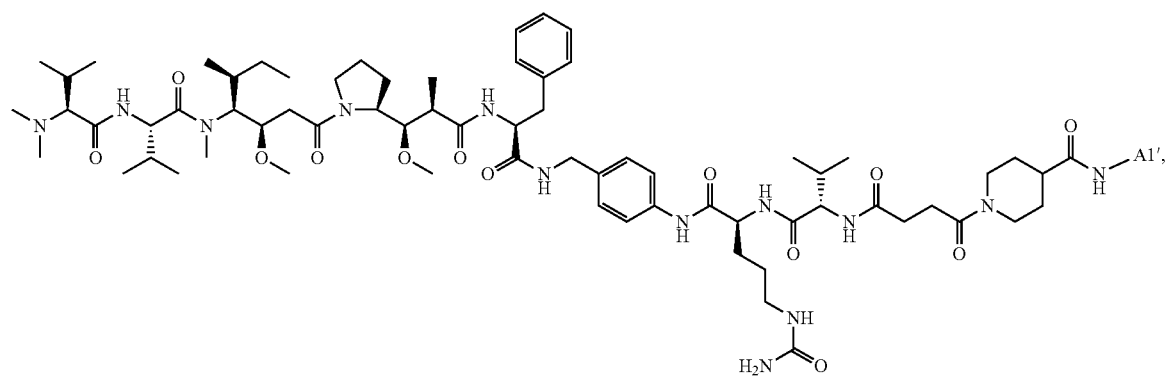
BT001062
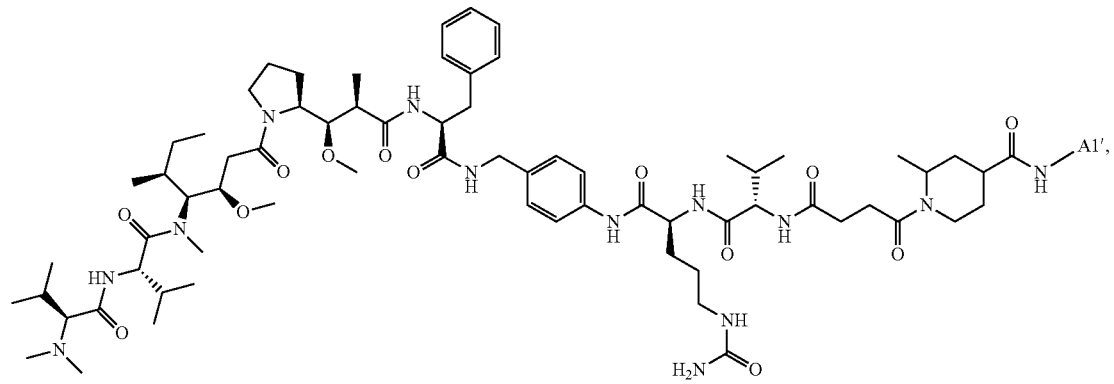
BT001063
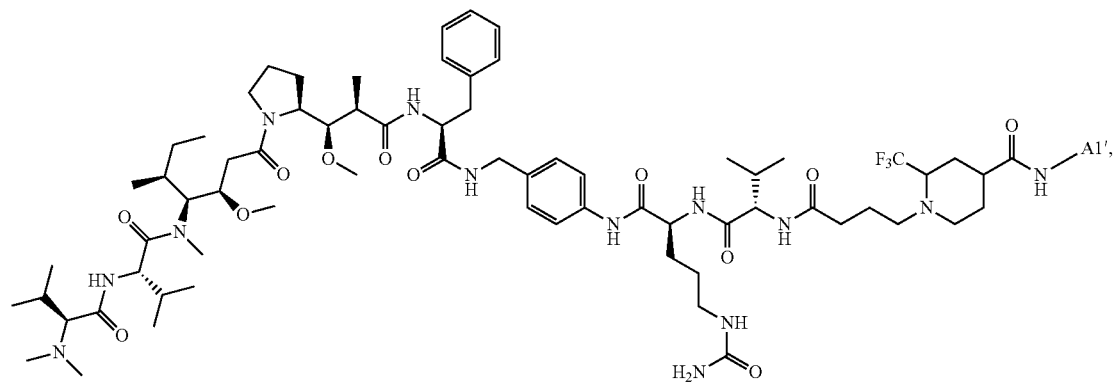
BT001064

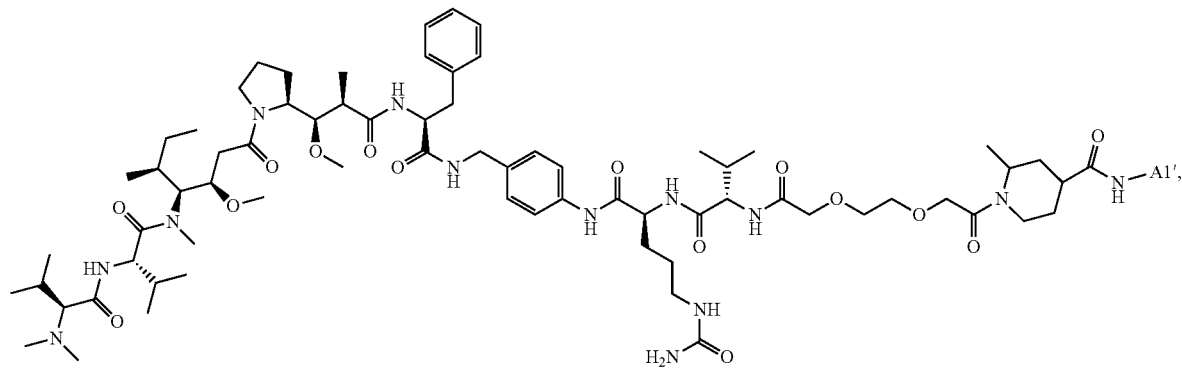
BT001065
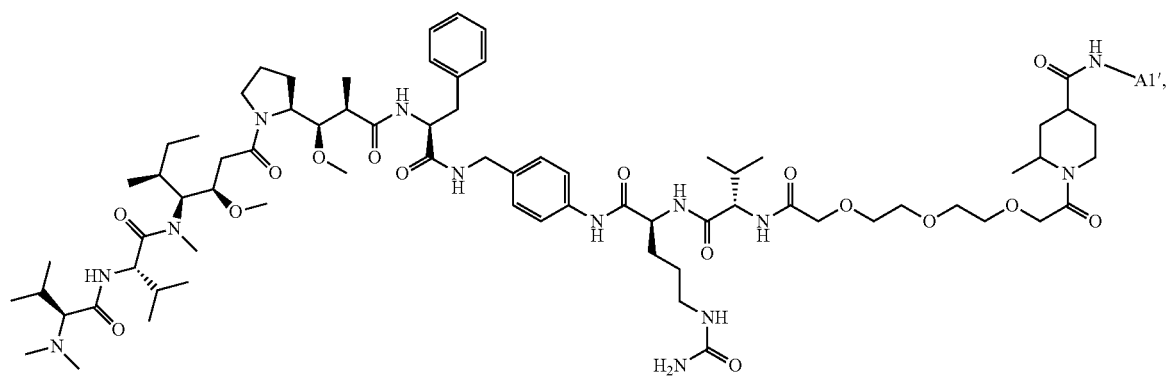
BT001066
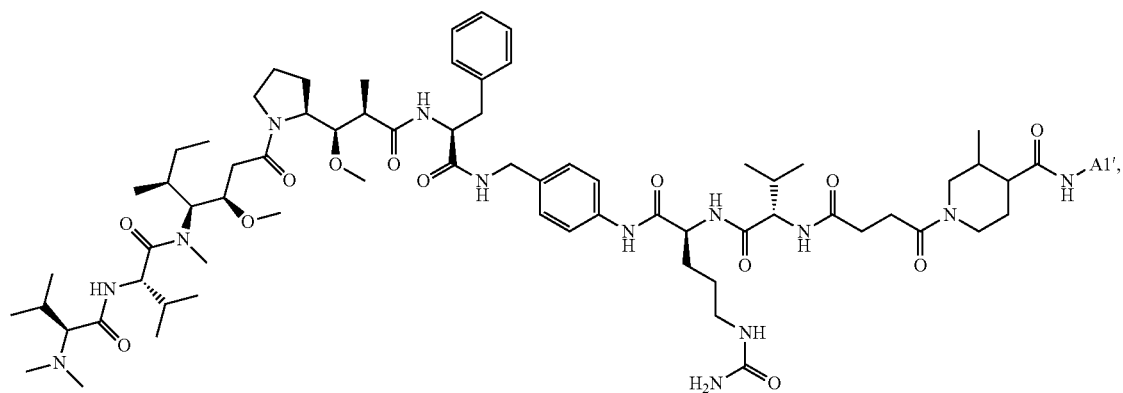
BT001067
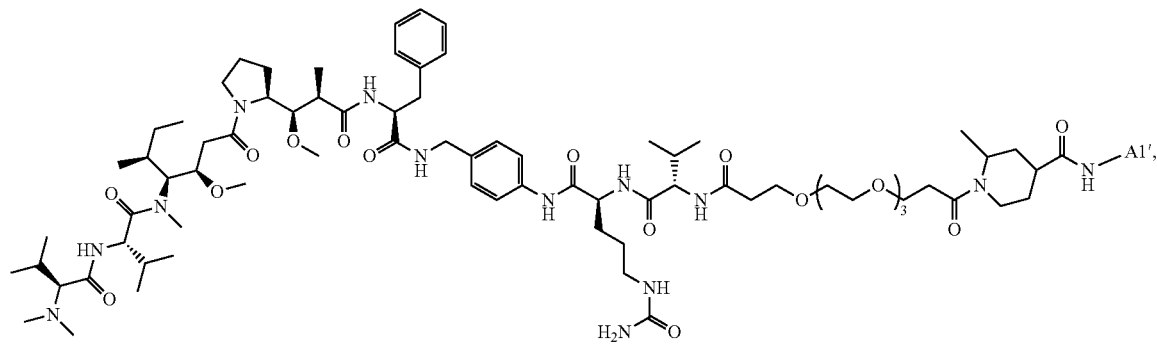
BT001068

-continued
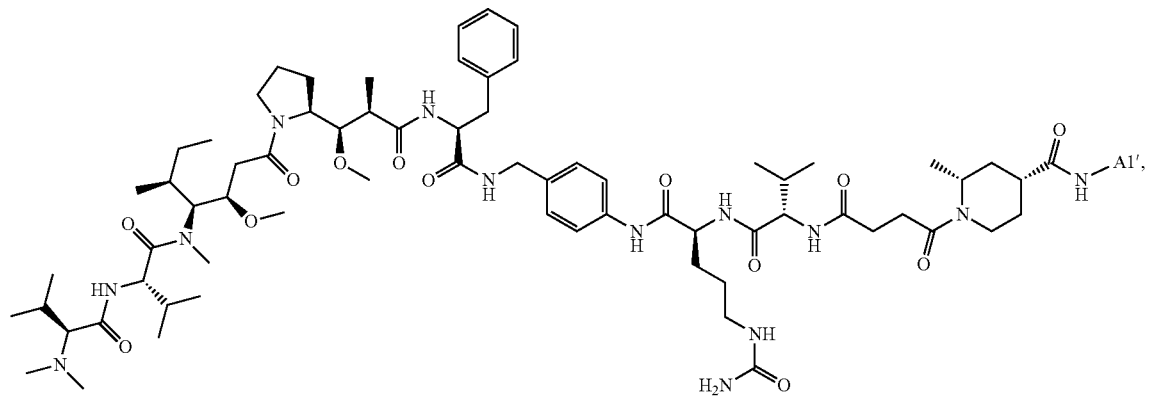
BT001072
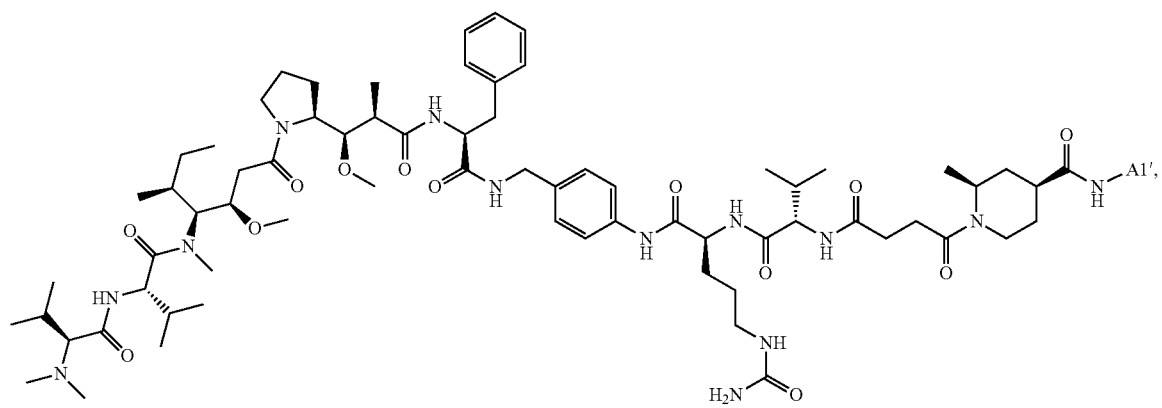
BT001073
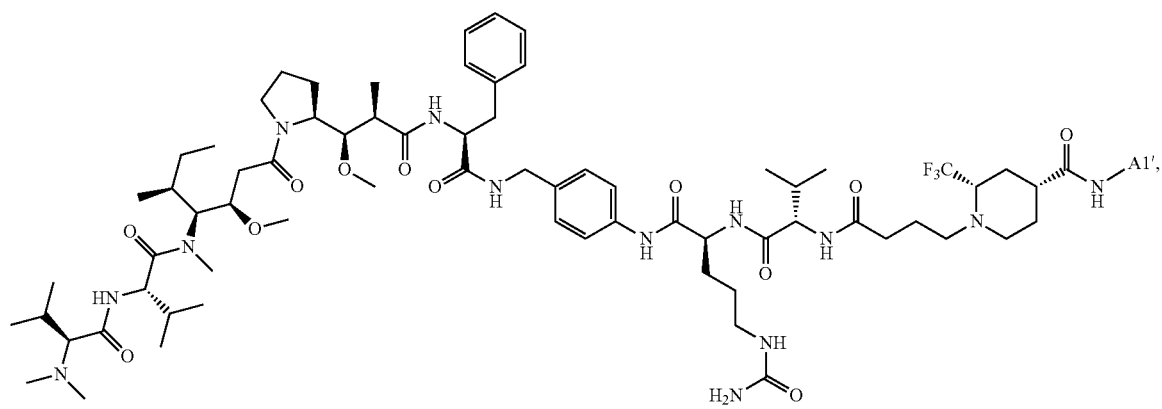
BT001074

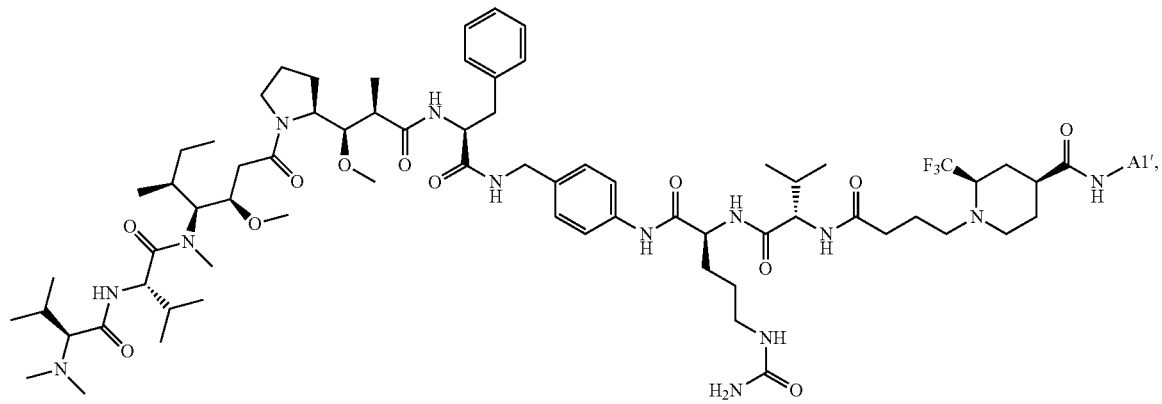
BT001075
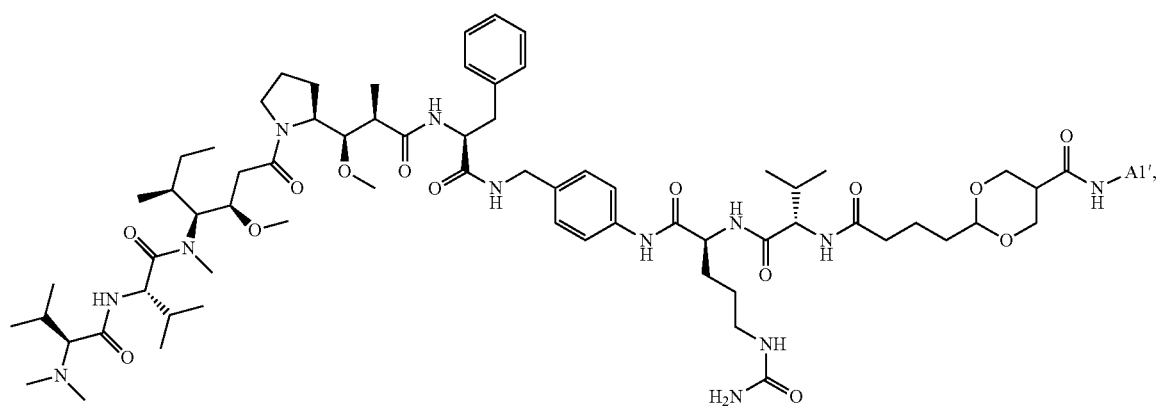
BT001076
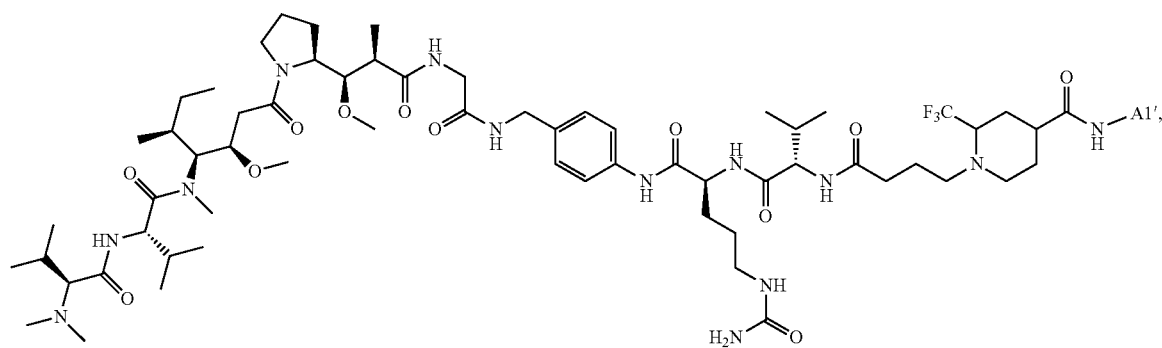
BT001077
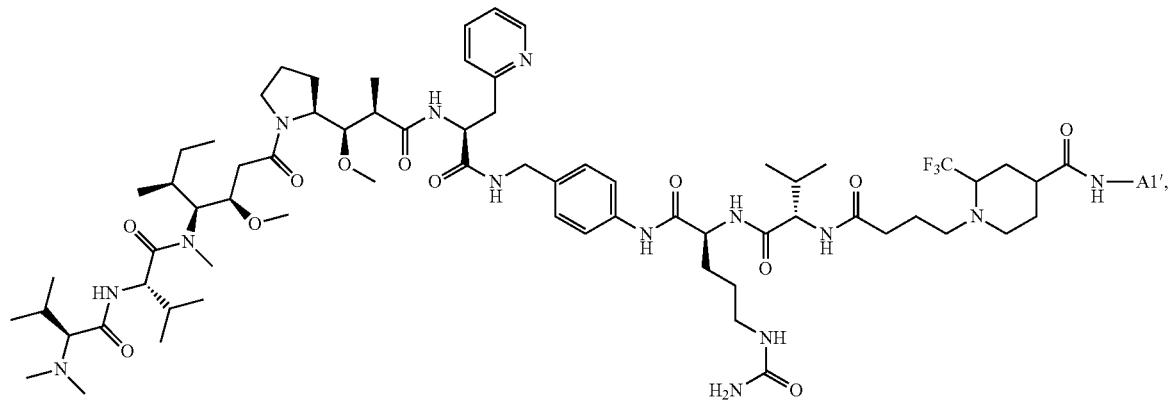
BT001078

-continued
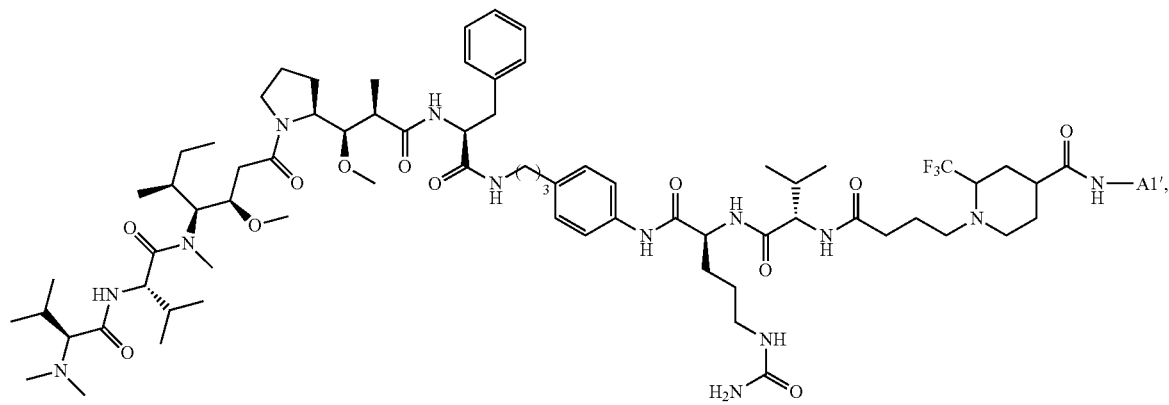
BT001079
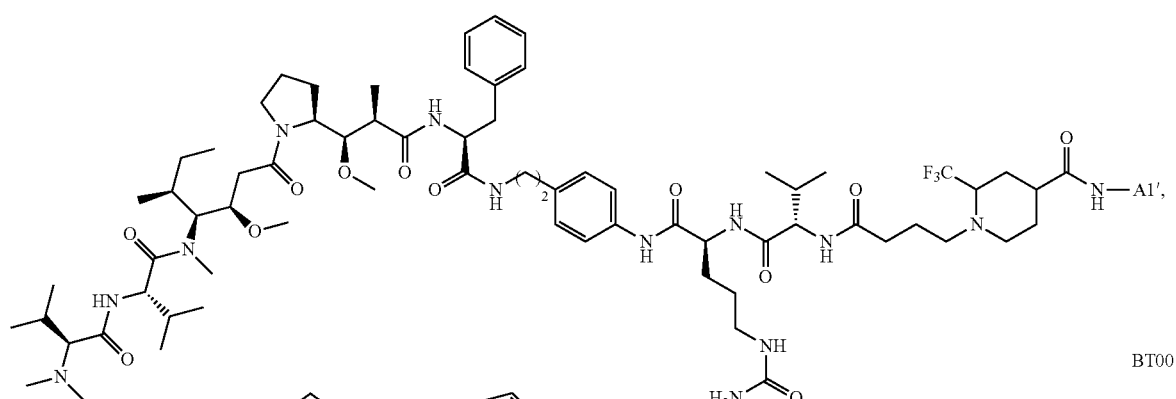
BT001080
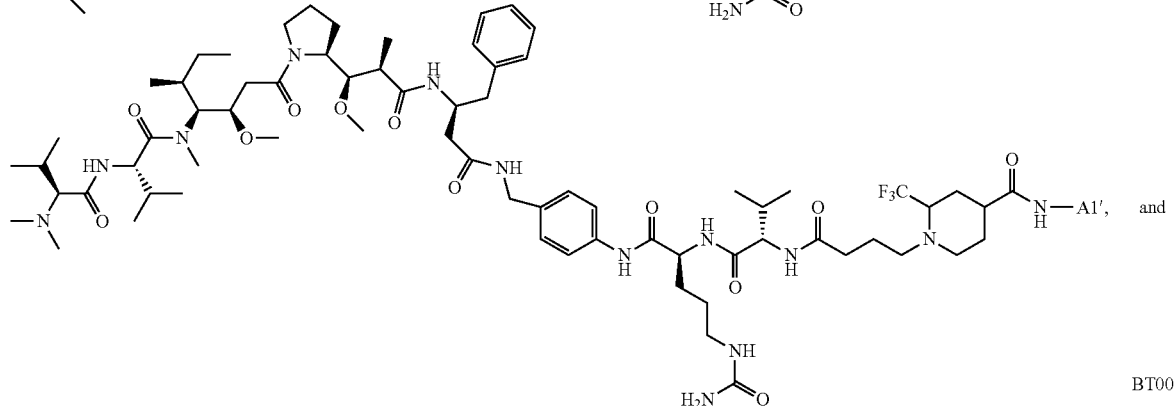
BT001092
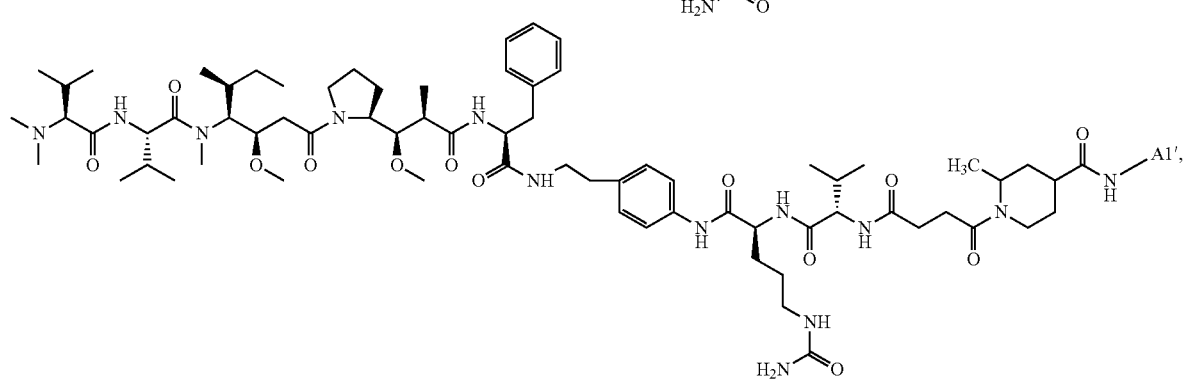
BT001093
and
BT001093
wherein A1' is a group obtained after removing 1 amino group from trastuzumab.

In some embodiments, the conjugate is selected from:
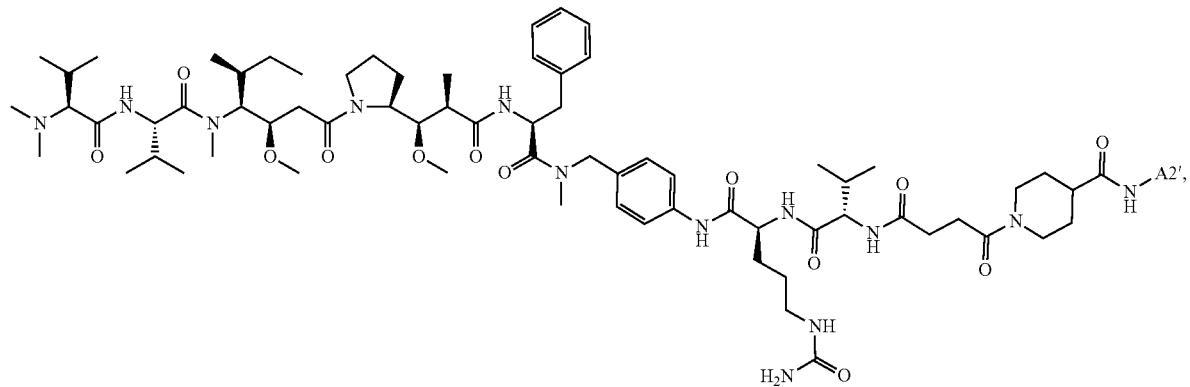
BT001094
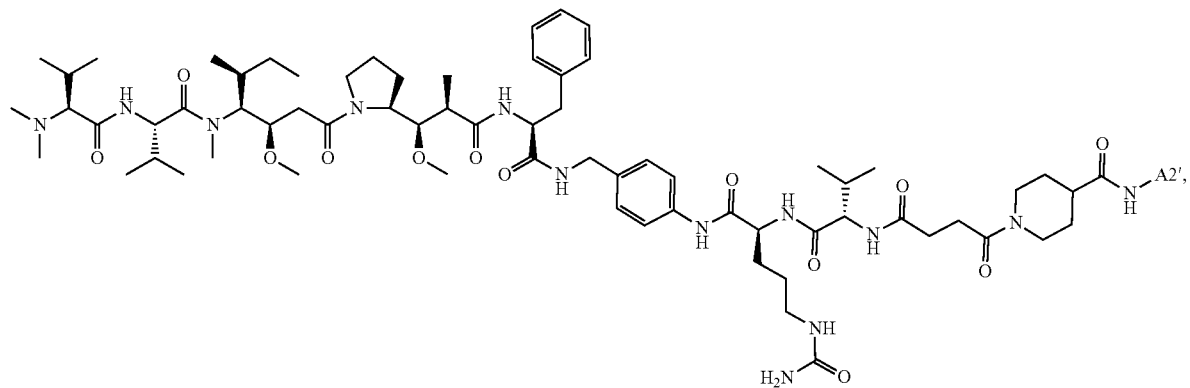
BT001095
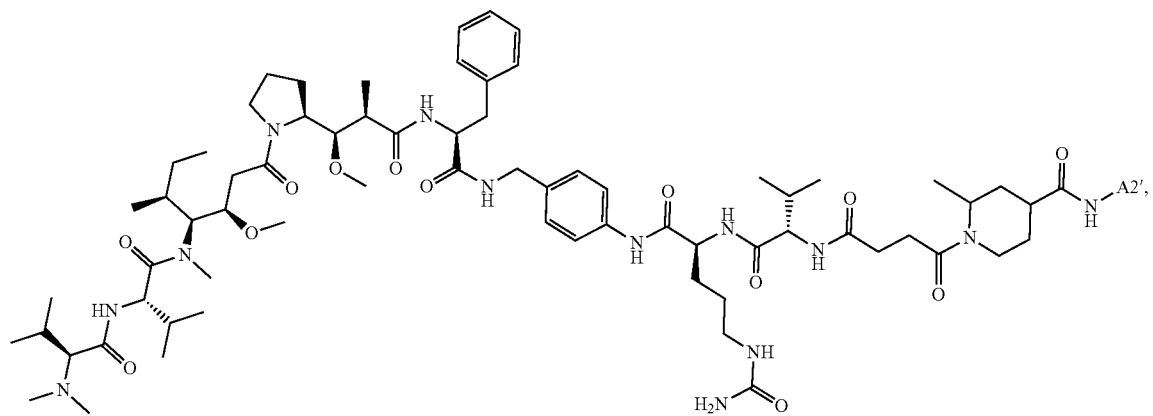
BT001096

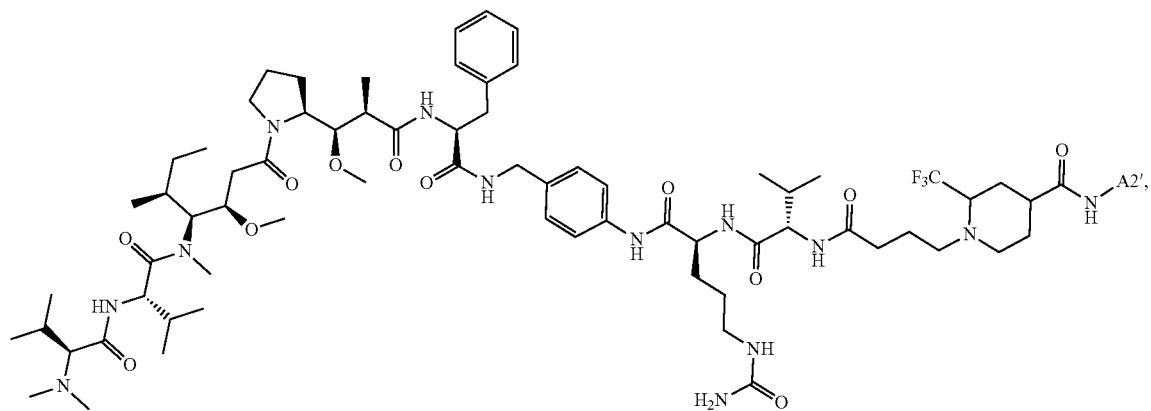
BT001097
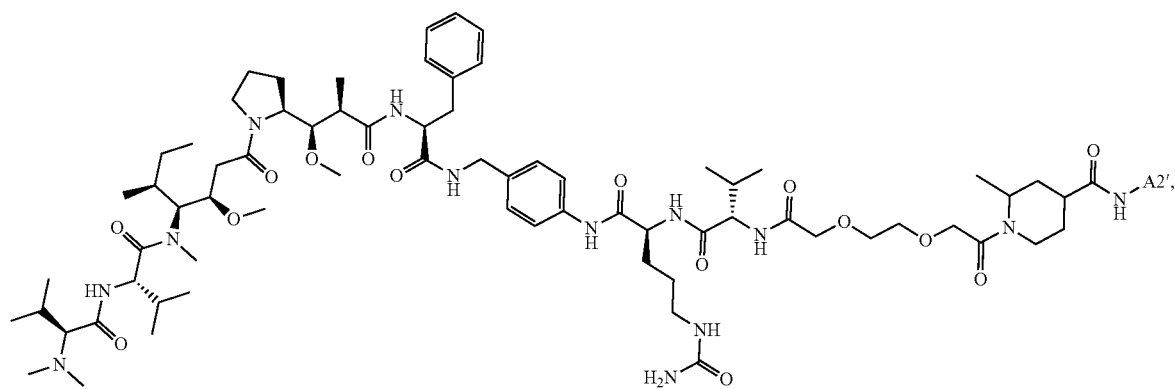
BT001098
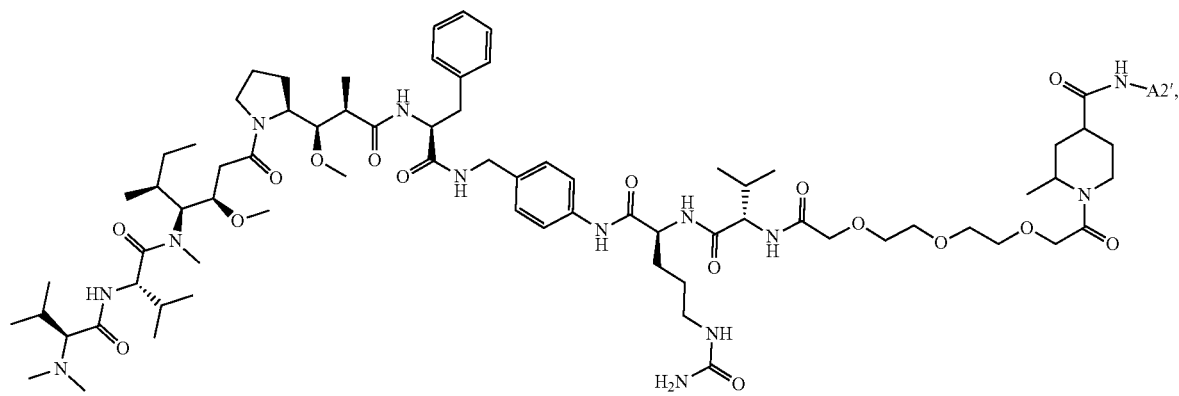
BT001099

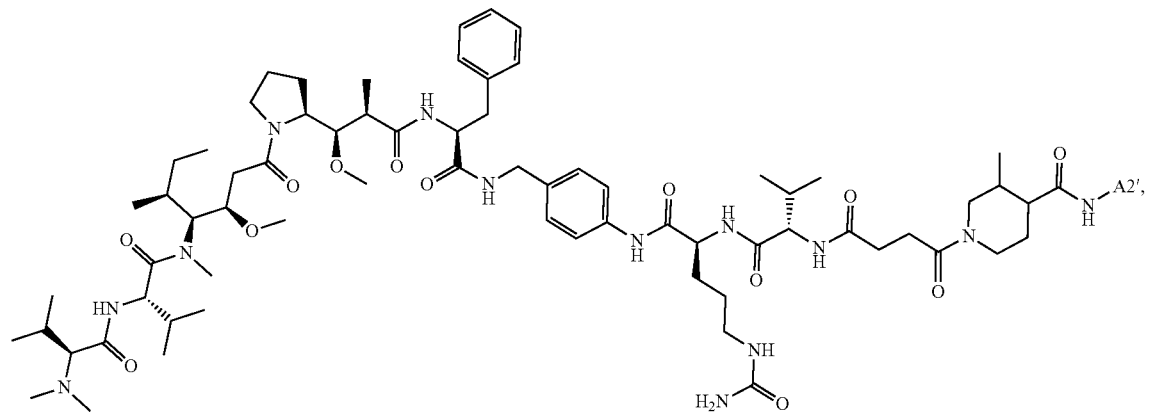
BT001100
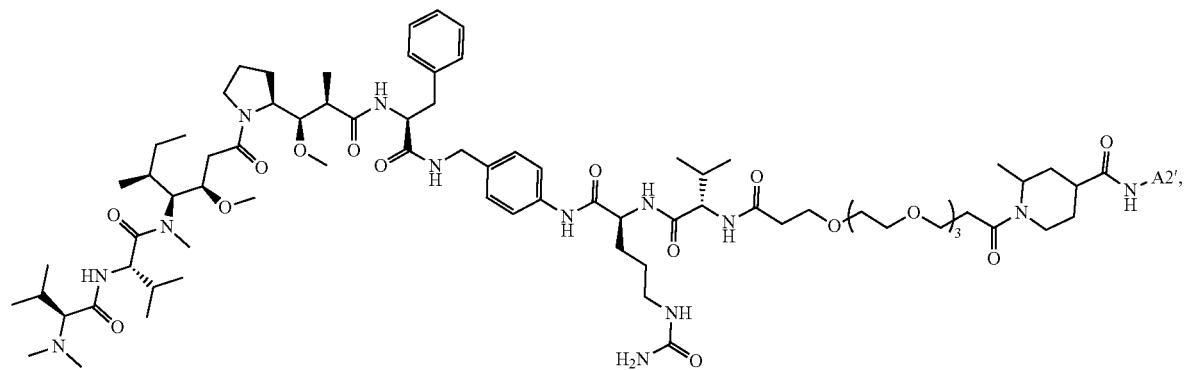
BT001101
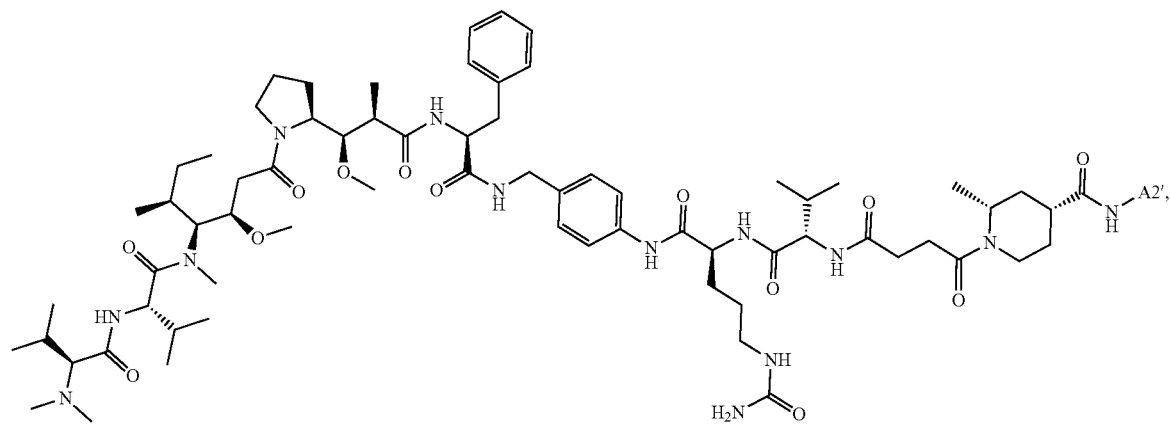
BT001102

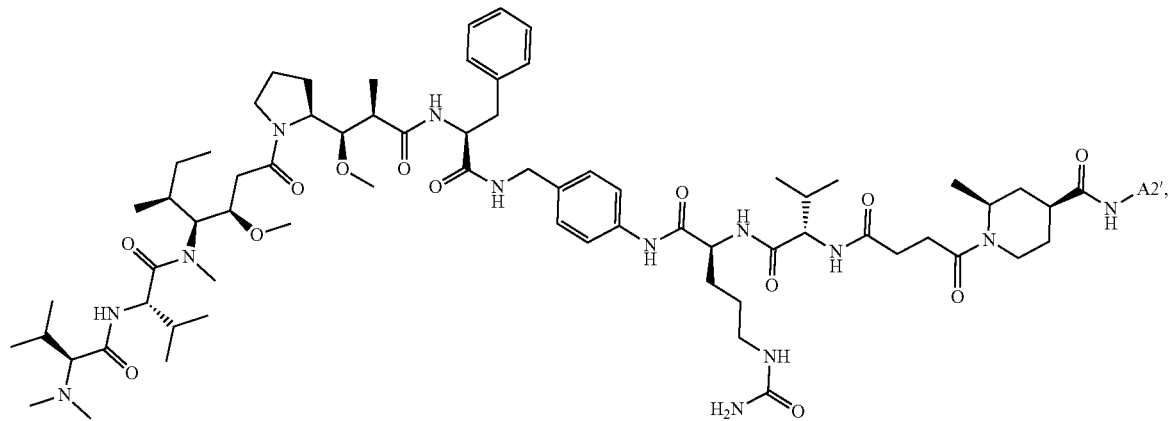
BT001103
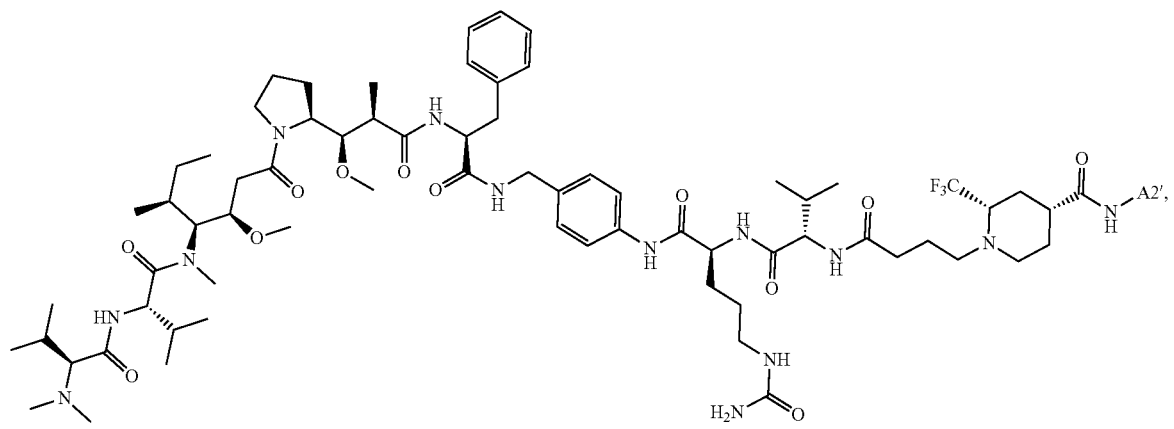
BT001104
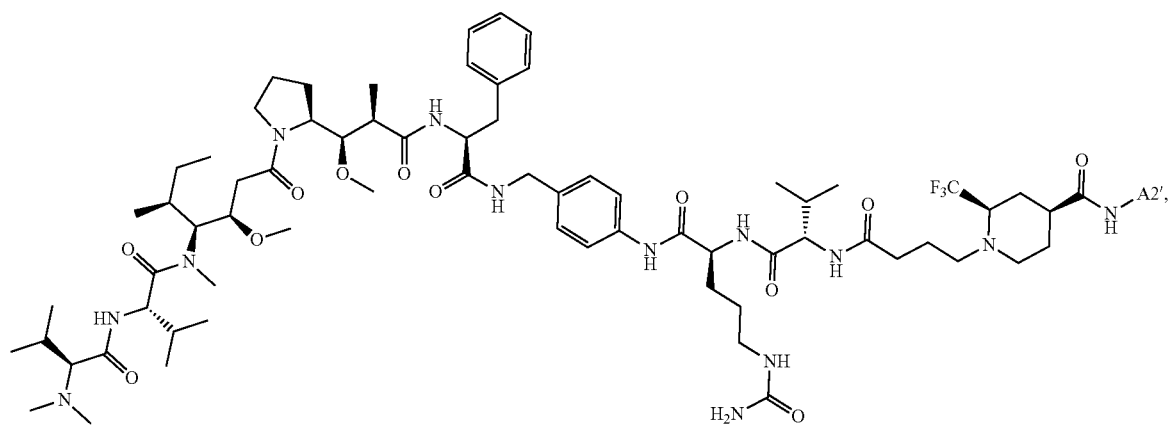
BT001105

-continued
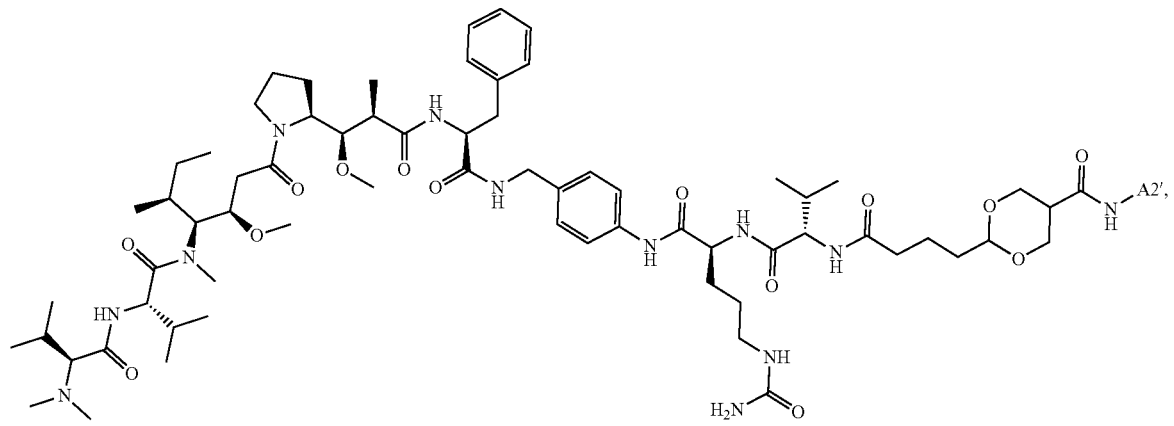
BT001106
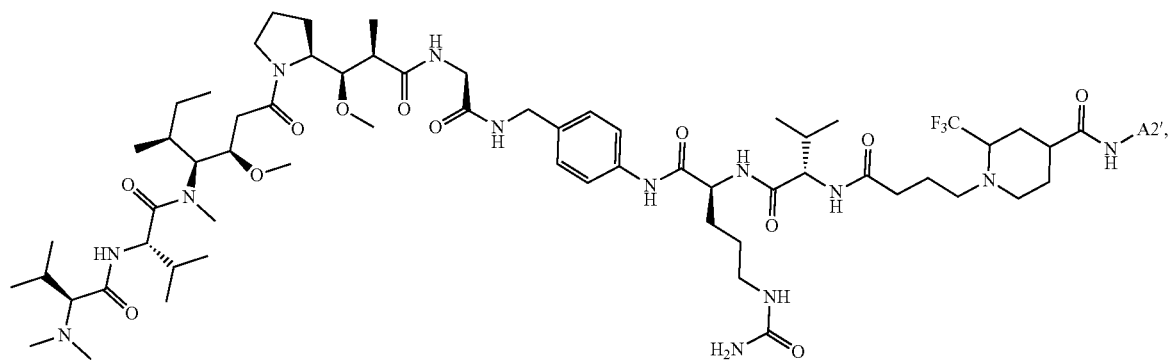
BT001107
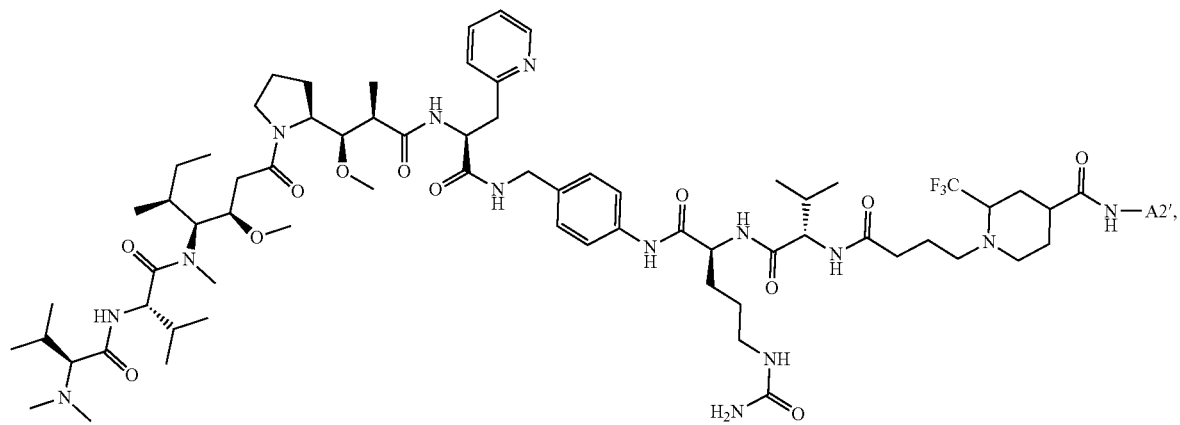
BT001108

-continued
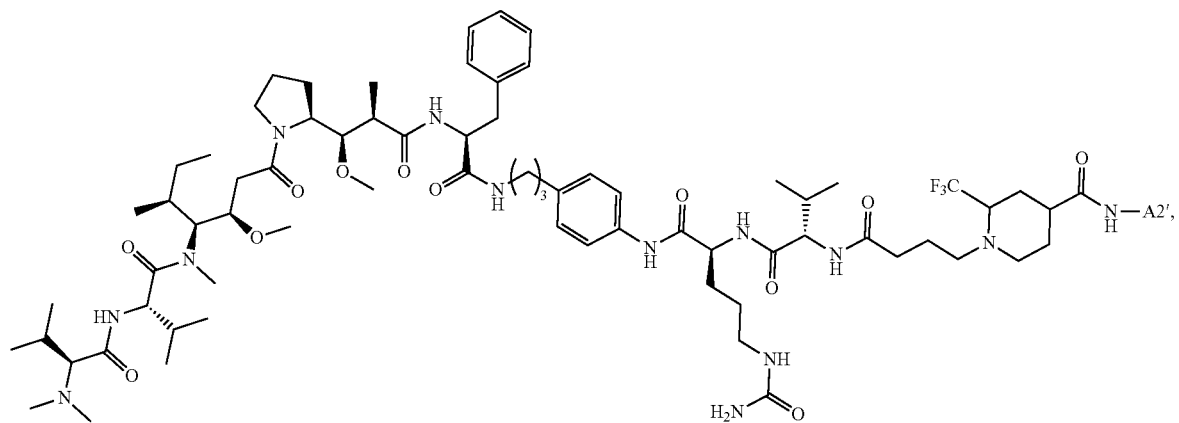
BT001109
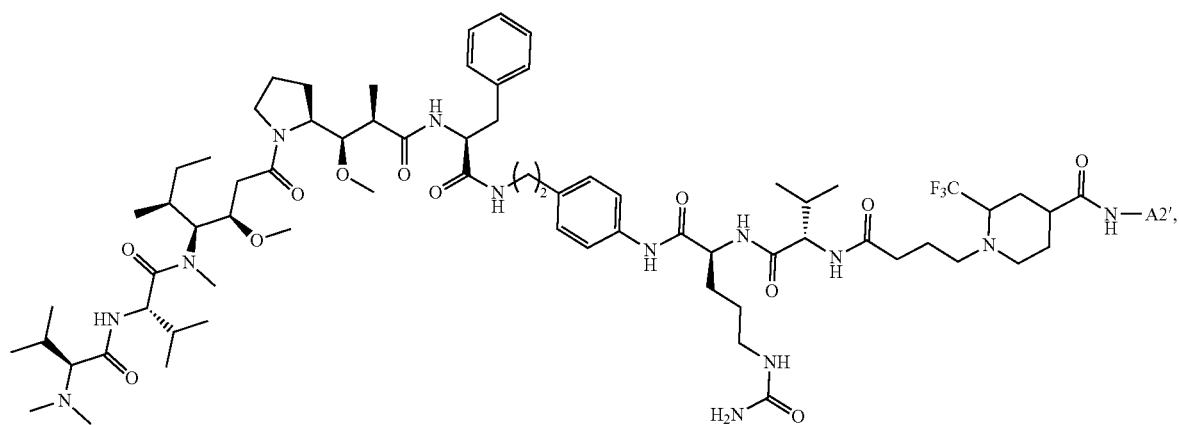
BT001110
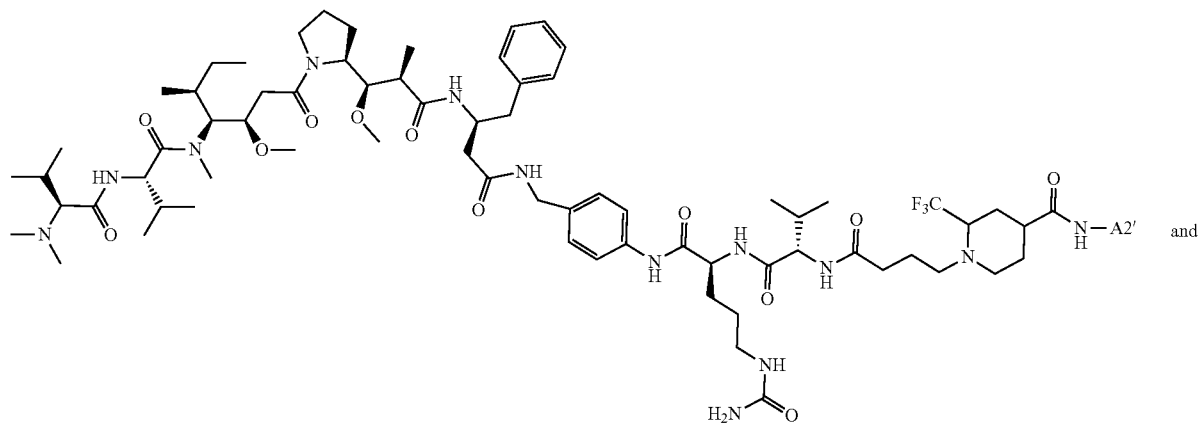
BT001111
and

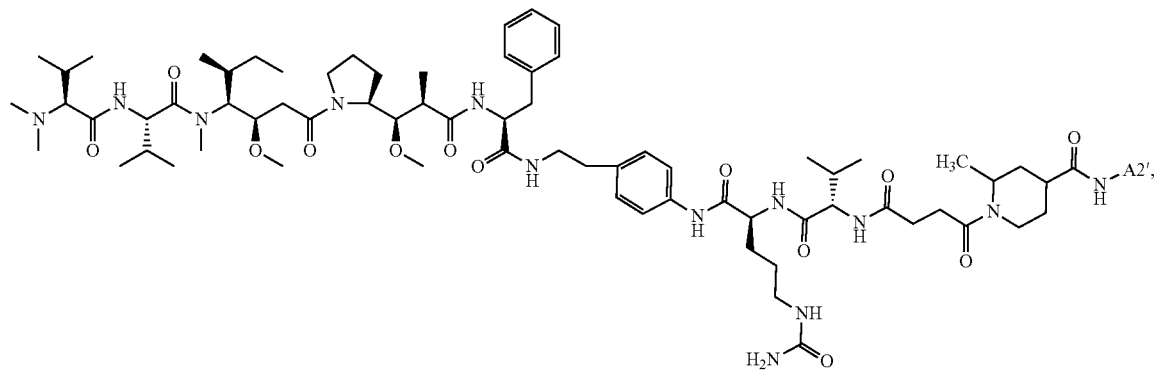
wherein A2' is a group obtained after removing 1 amino group from pertuzumab.
In some embodiments, the conjugate is selected from:
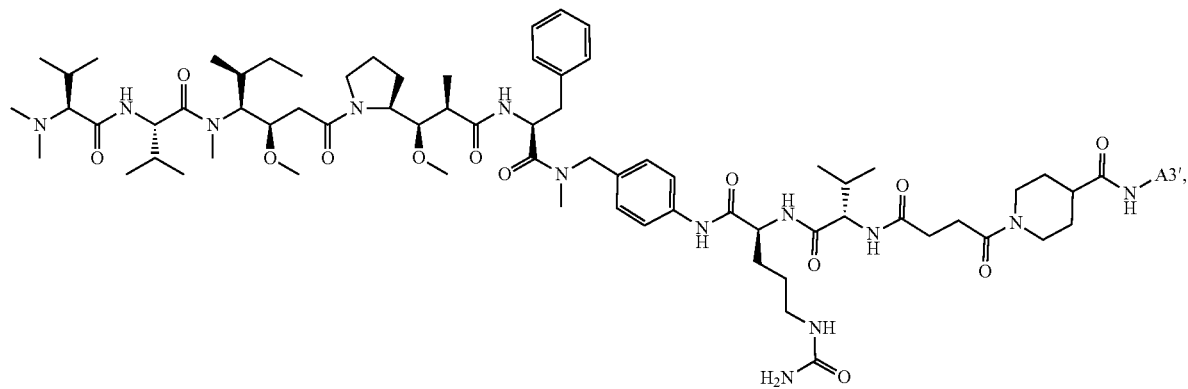
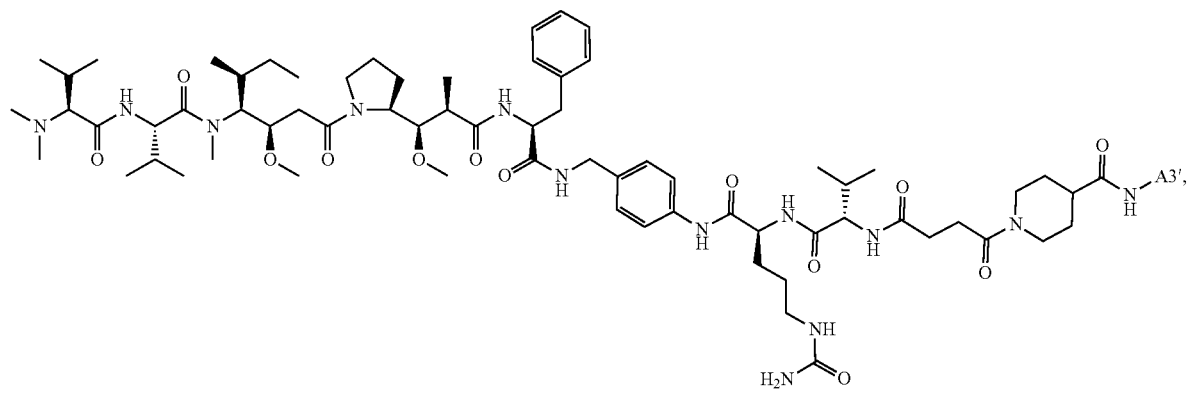

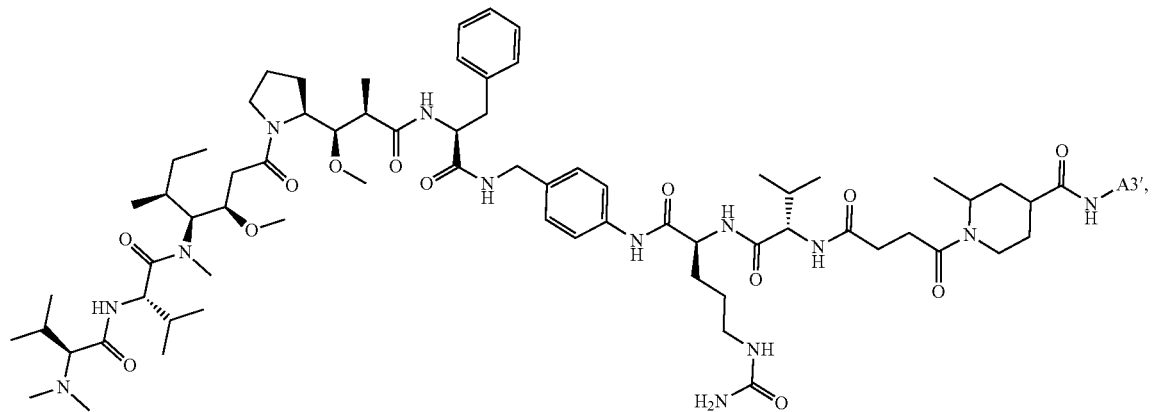
BT001069
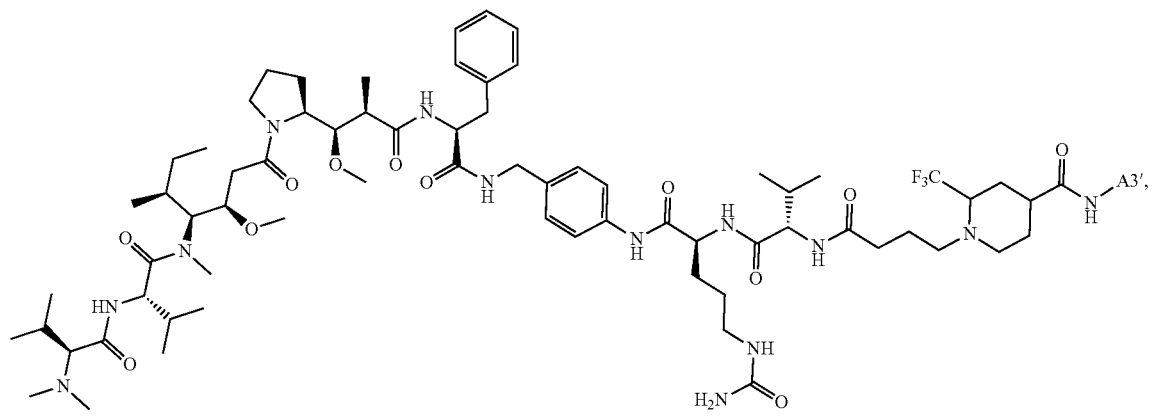
BT001070
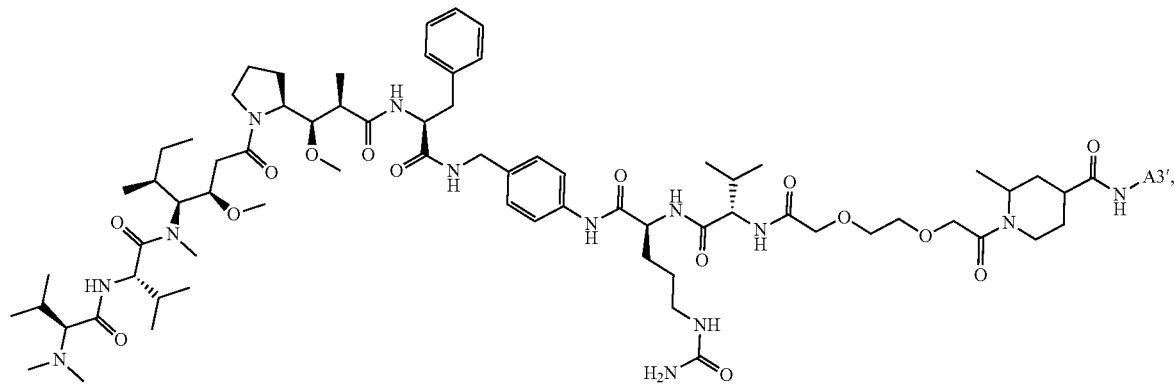
BT001115

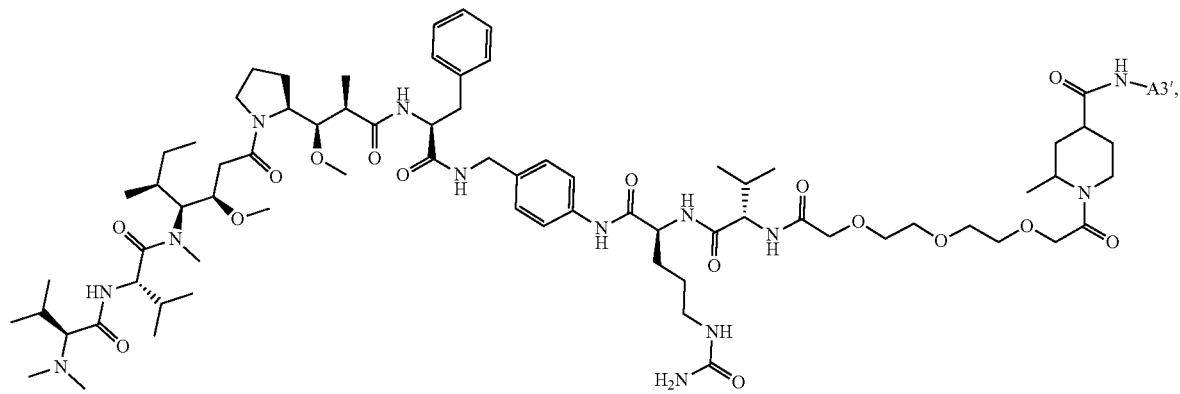
BT001116
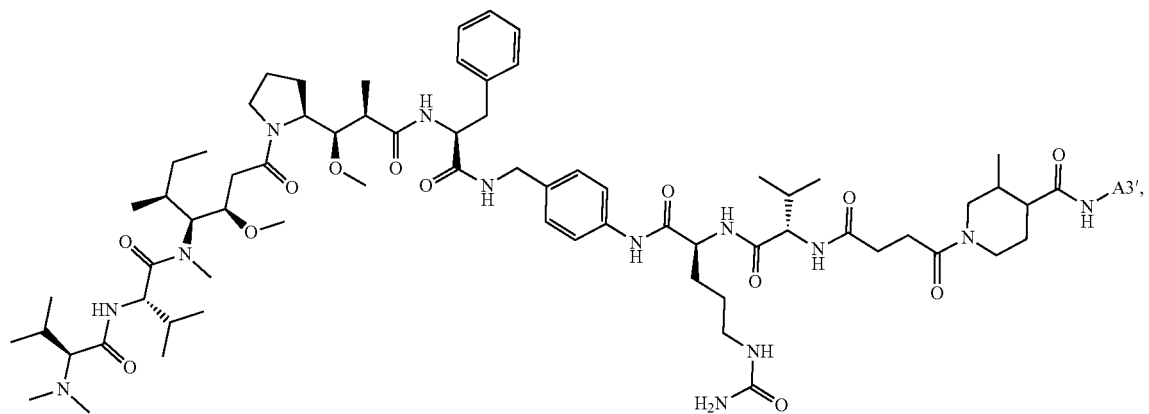
BT001117
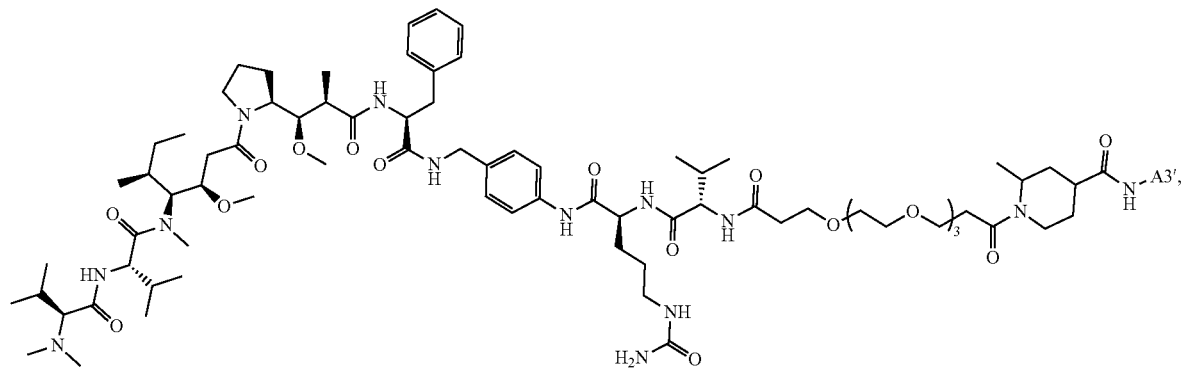
BT001118

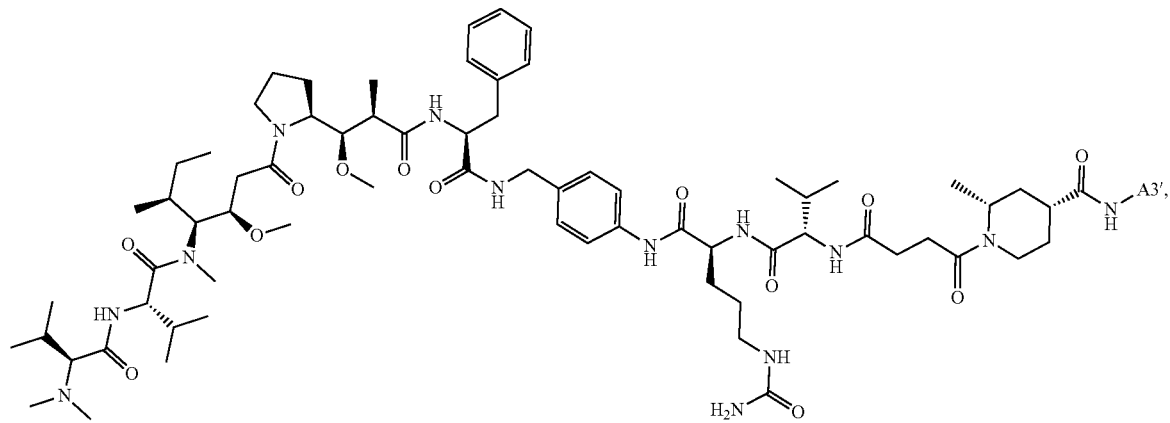
BT001119
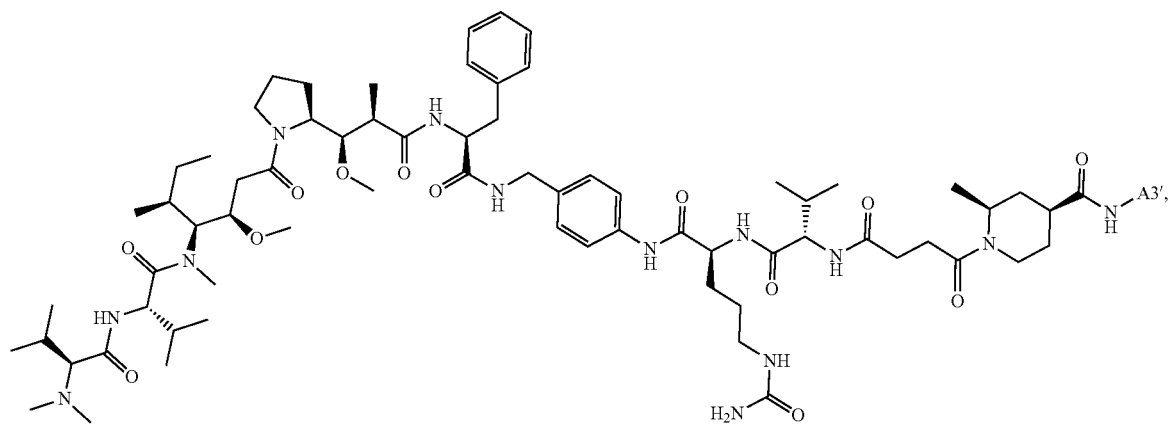
BT001120
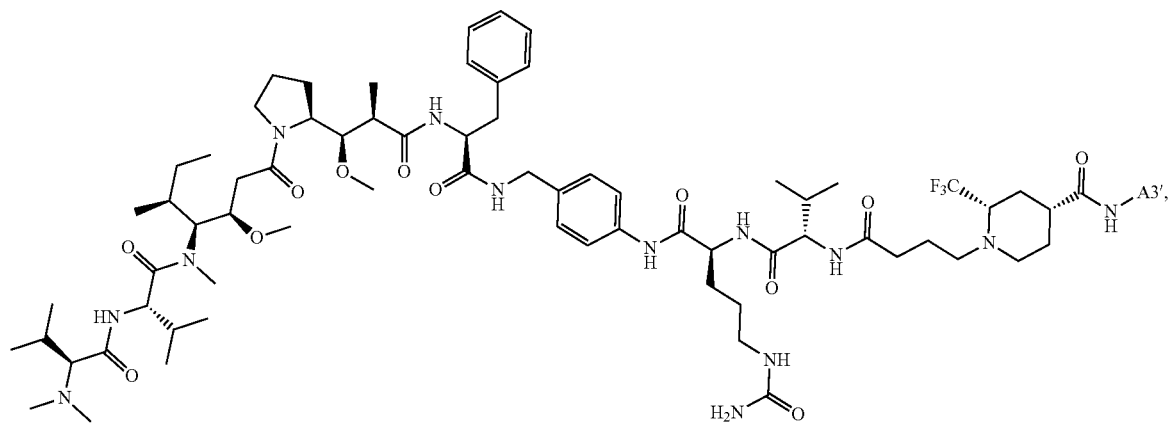
BT001121

-continued
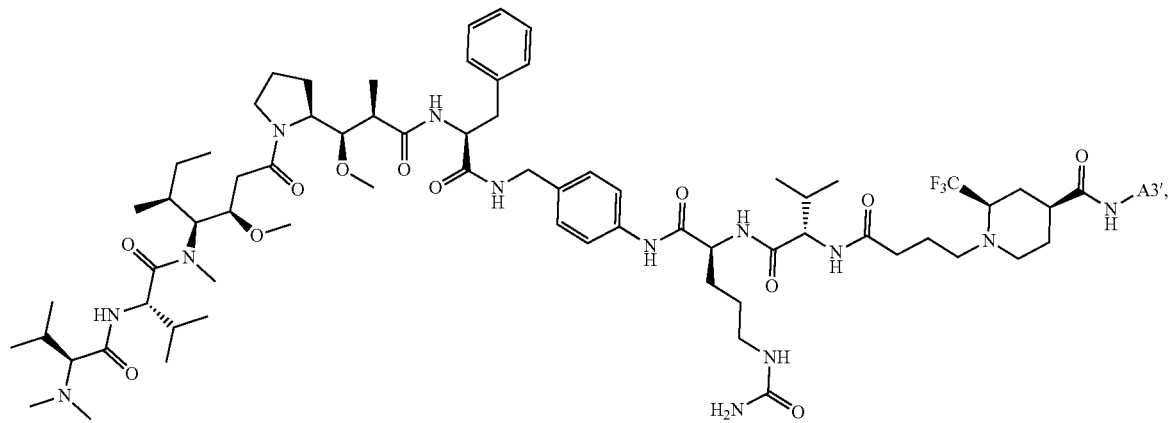
BT001122
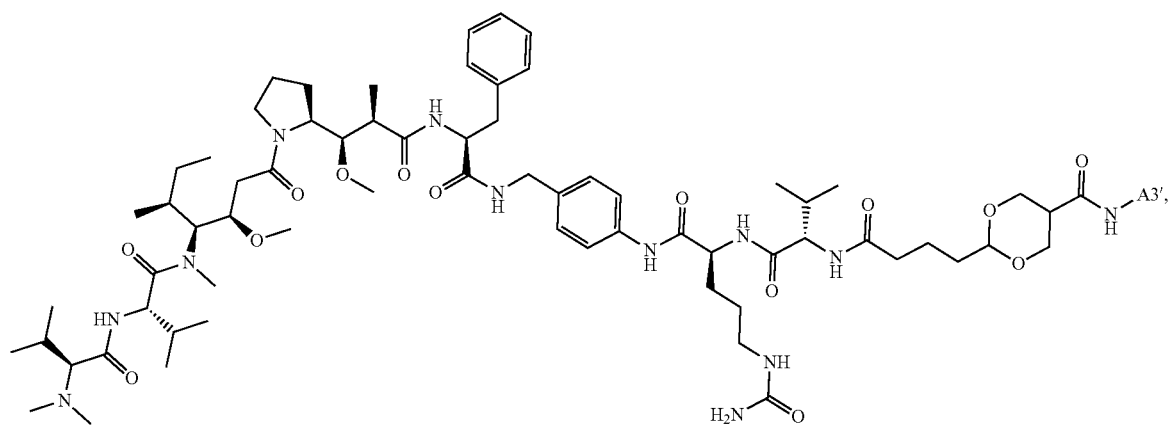
BT001123
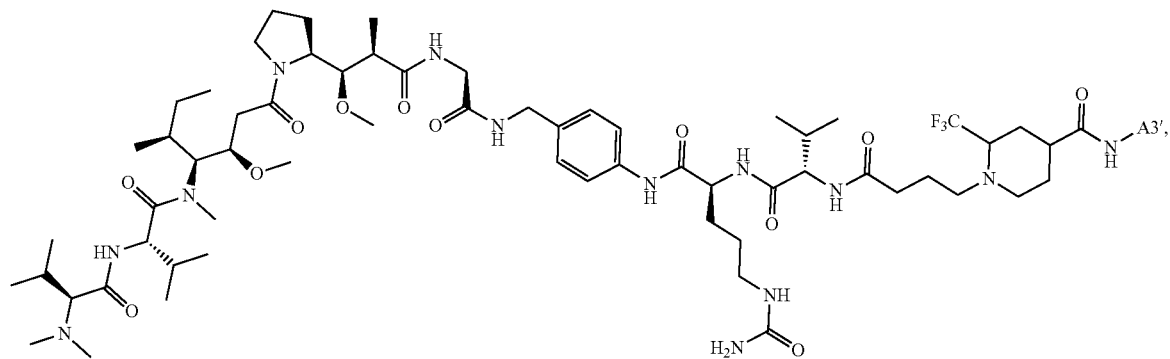
BT001124

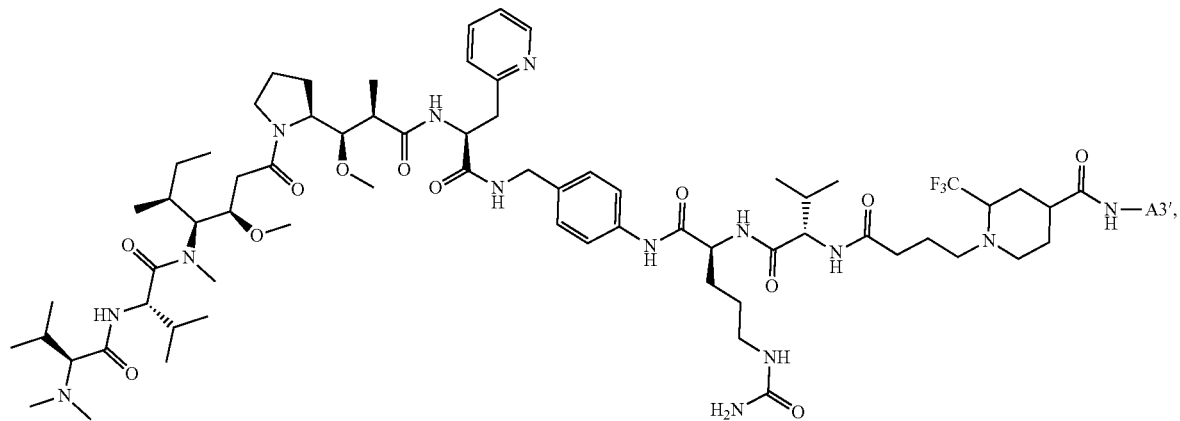
BT001125
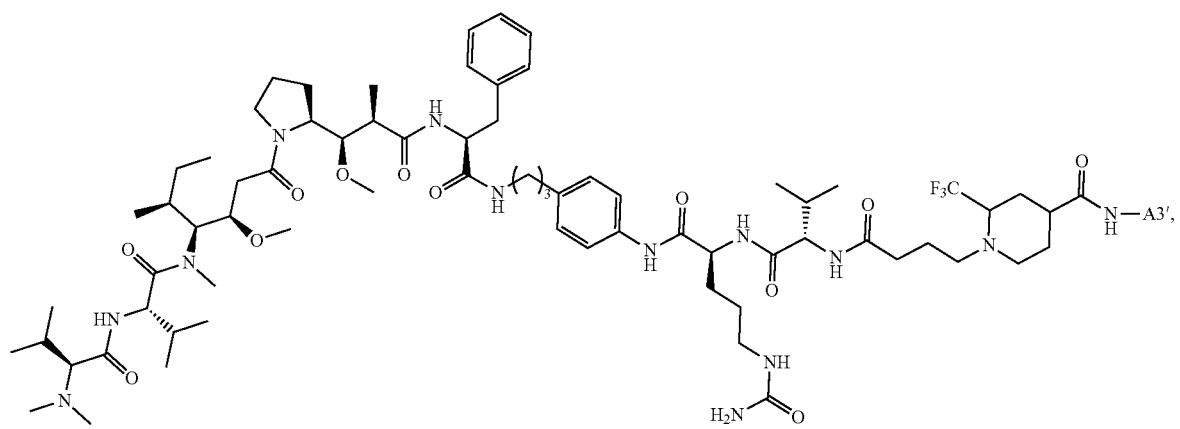
BT001126
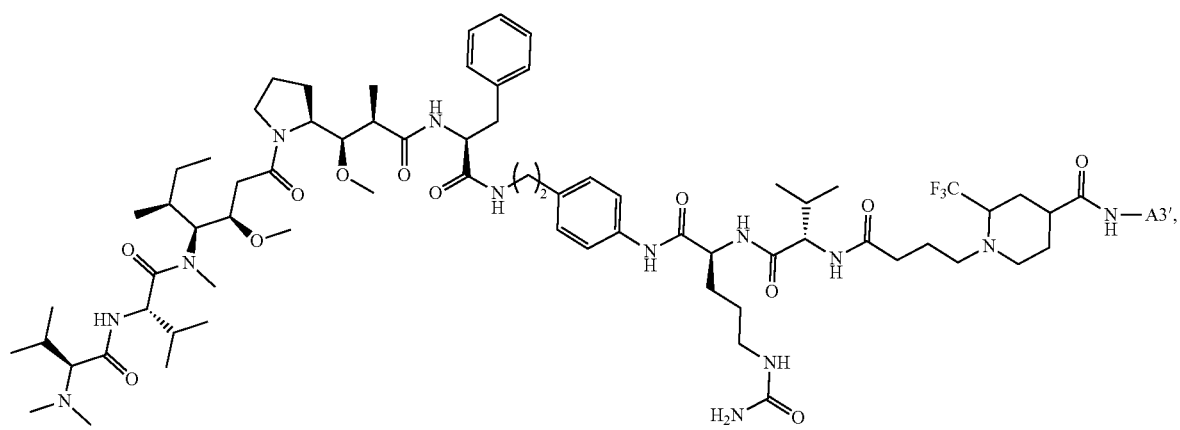
BT001127

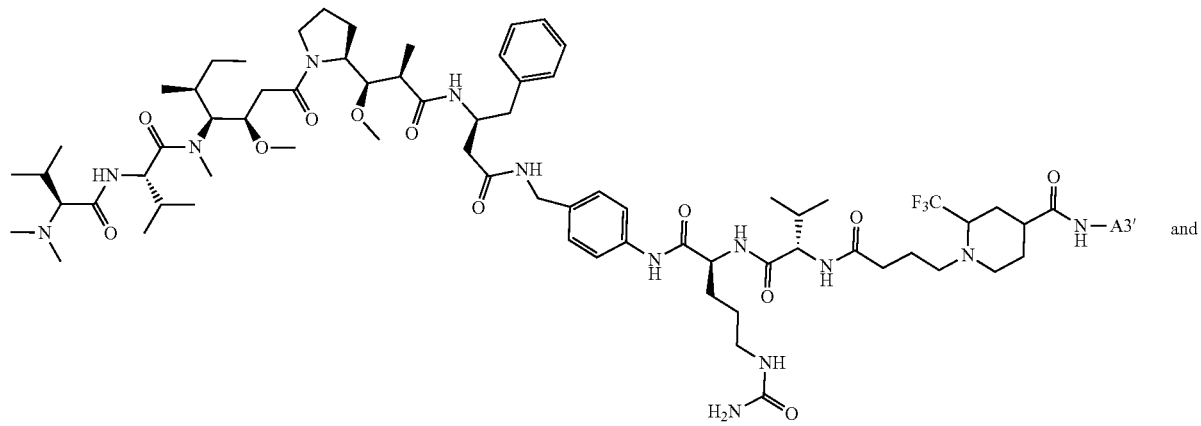
BT001128
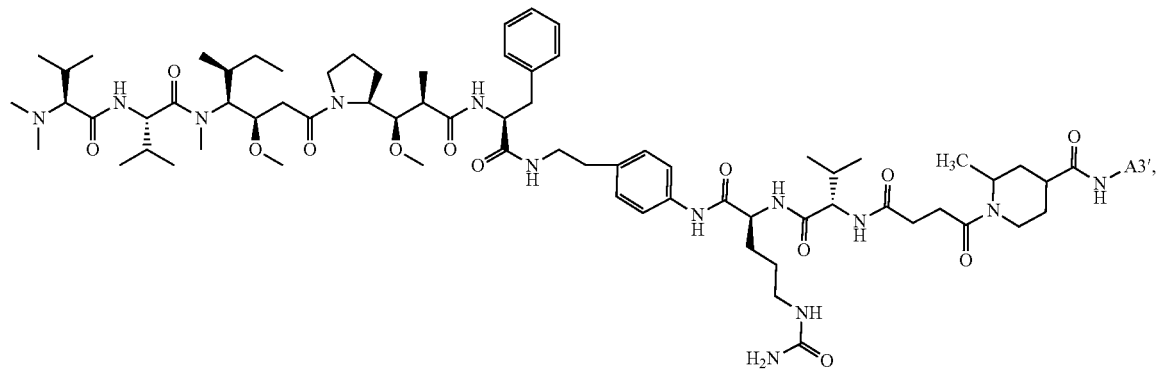
BT001129
Wherein A3' is a group obtained after removing 1 amino group from sacituzumab.
In some embodiments, the conjugate is selected from:
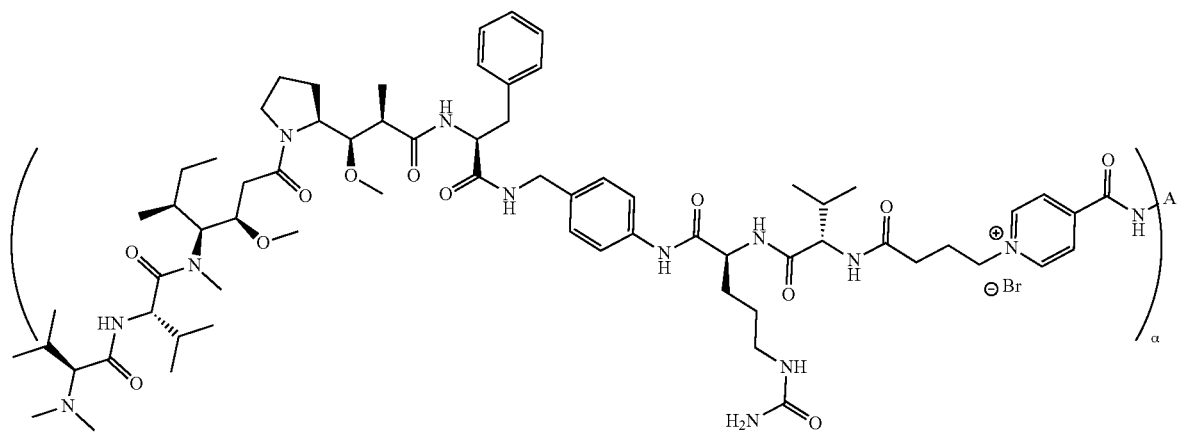

-continued
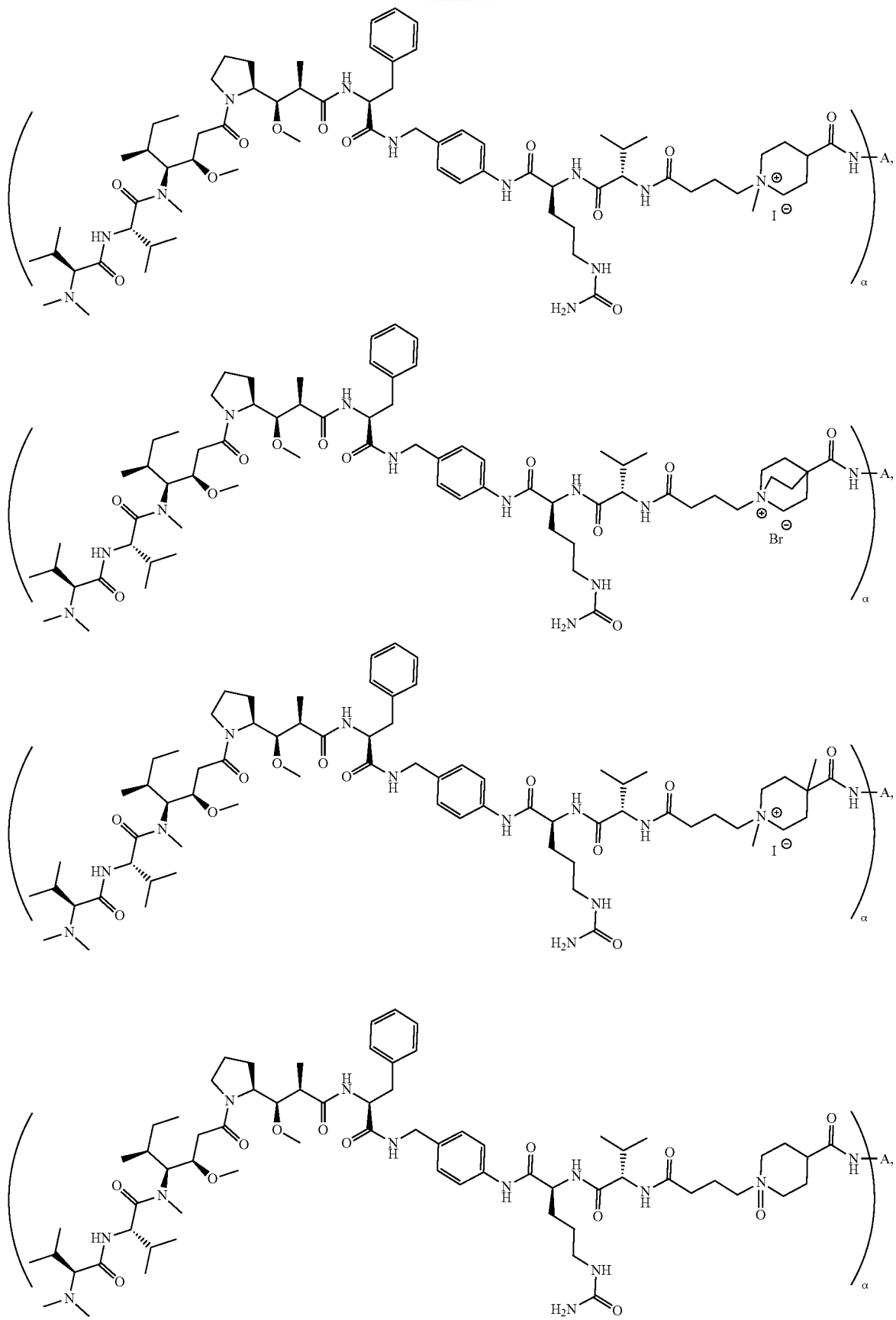

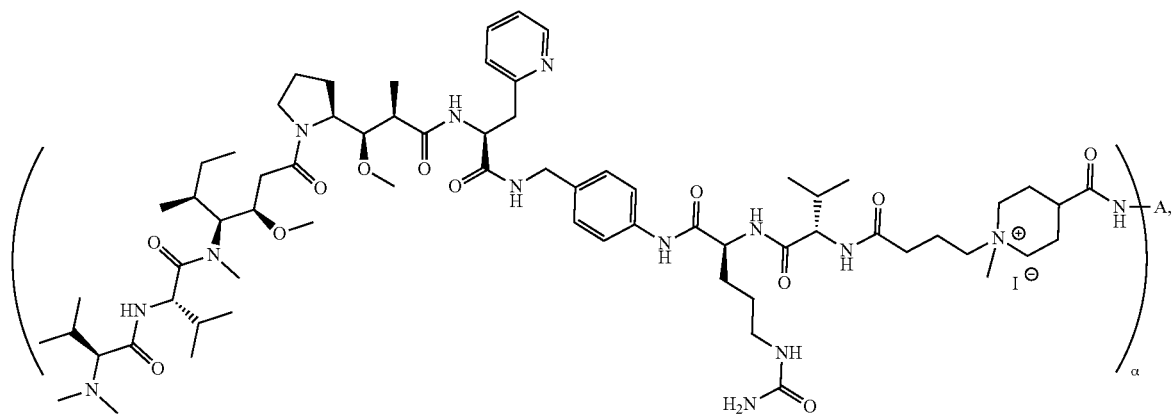
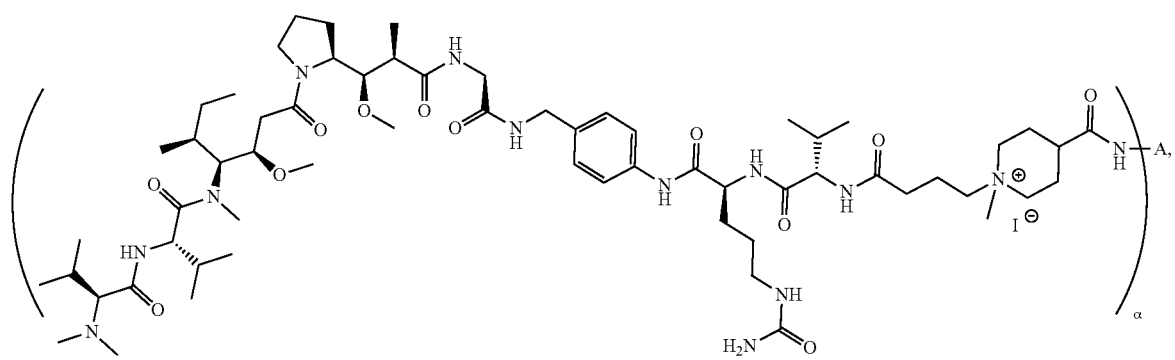
wherein, α is an integer of 1, 2, 3 or 4; and A is a group obtained after removing ca amino groups from trastuzumab, pertuzumab or sacituzumab.
In some embodiments, the conjugate is selected from:
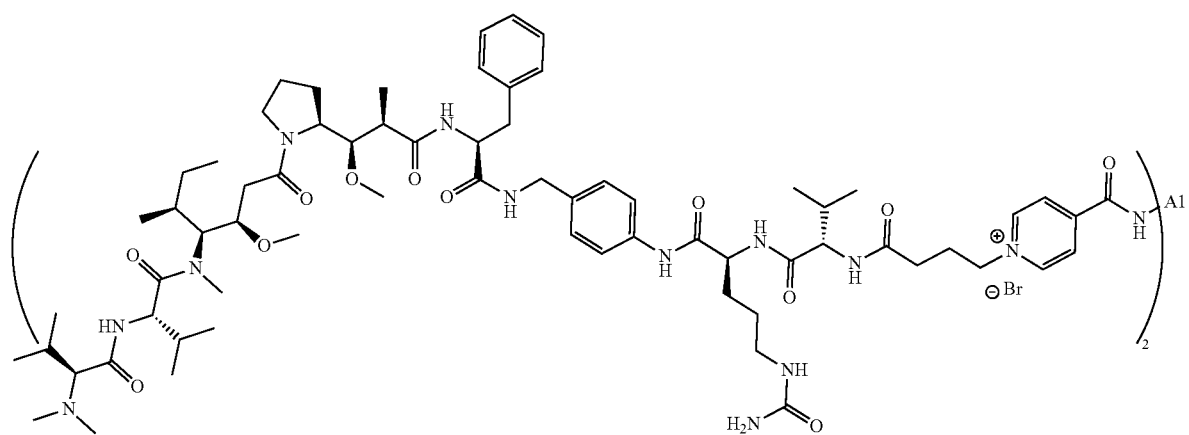
BT001130

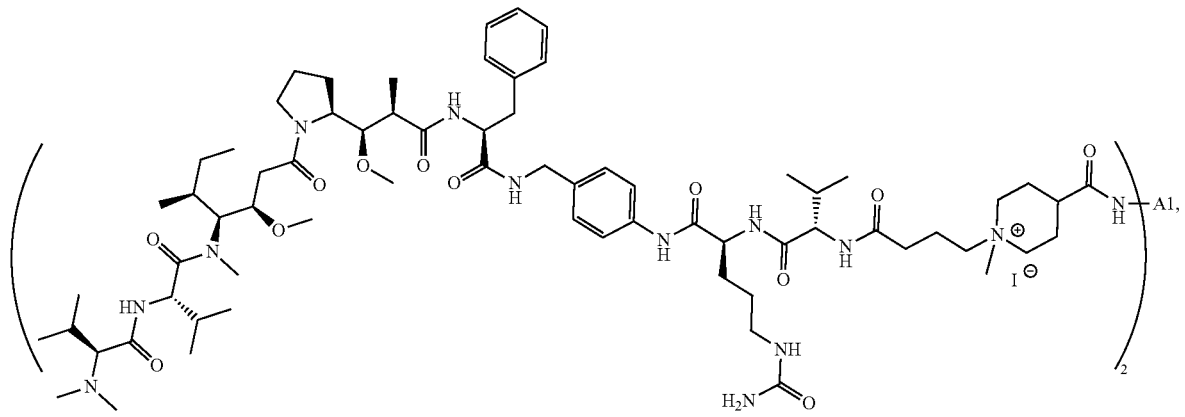
BT001020
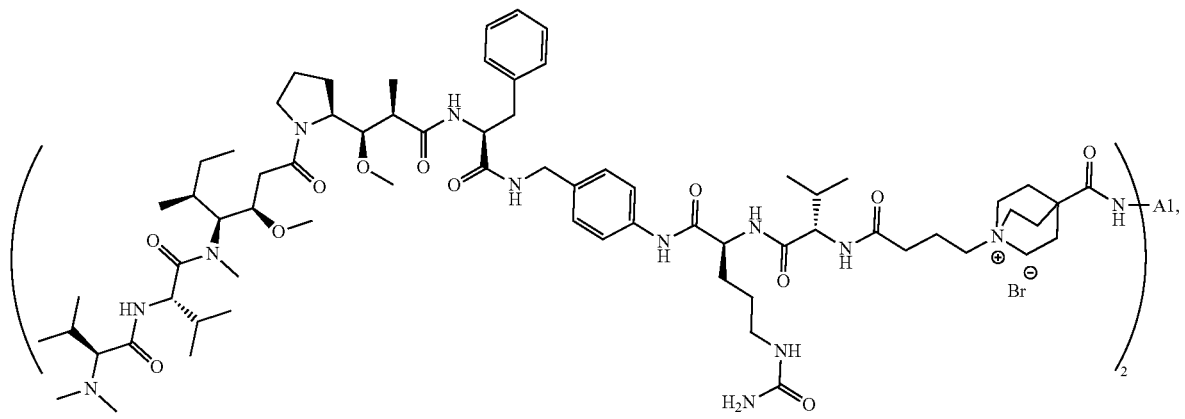
BT001131

BT001132

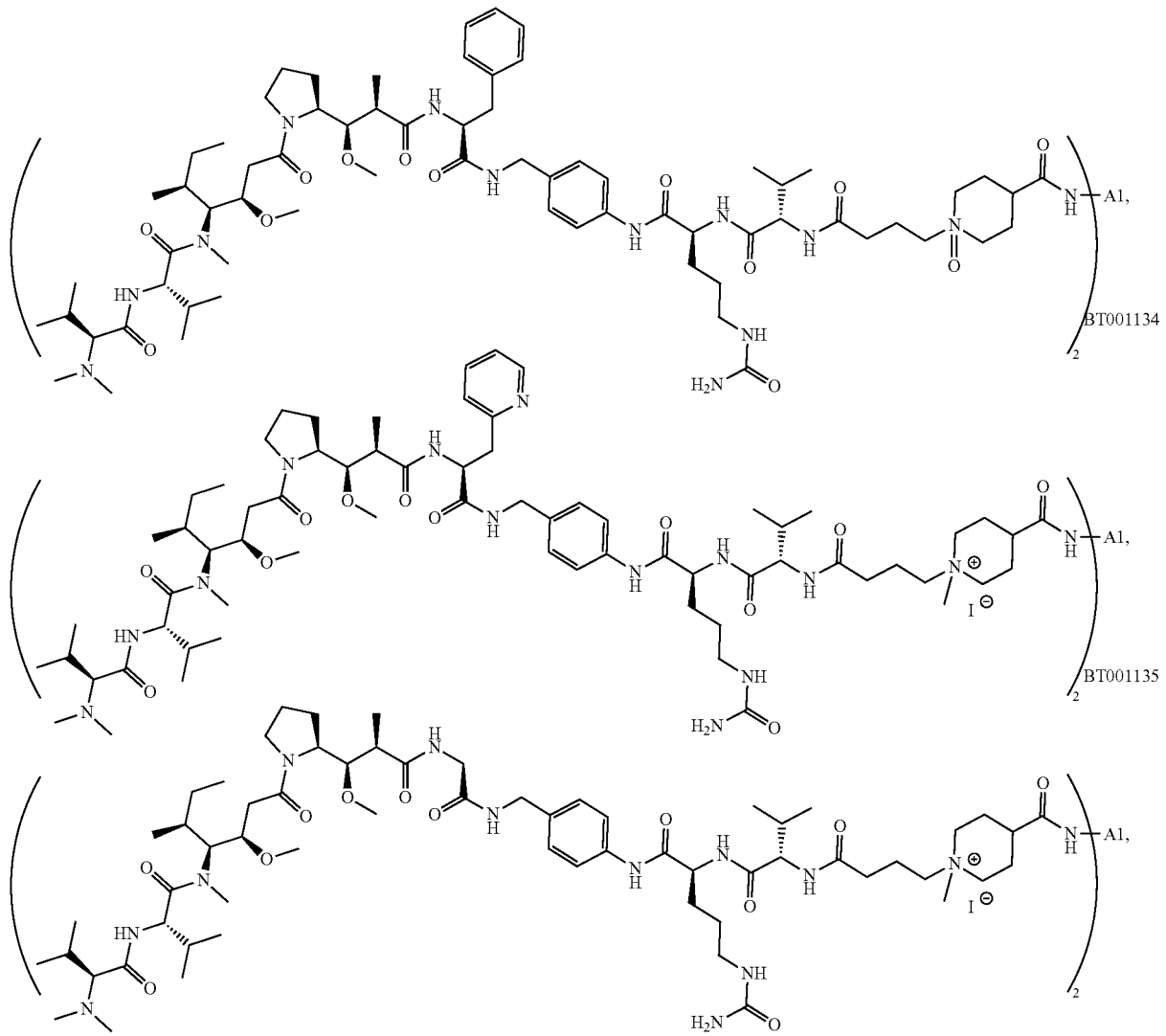
wherein, A1 is a group obtained after removing 2 amino group from trastuzumab.
In some embodiments, the conjugate is selected from:
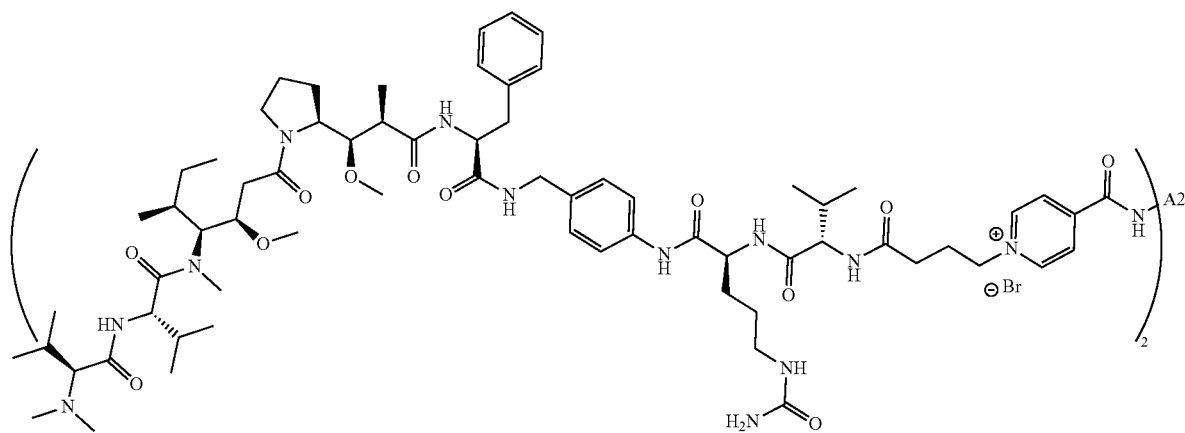

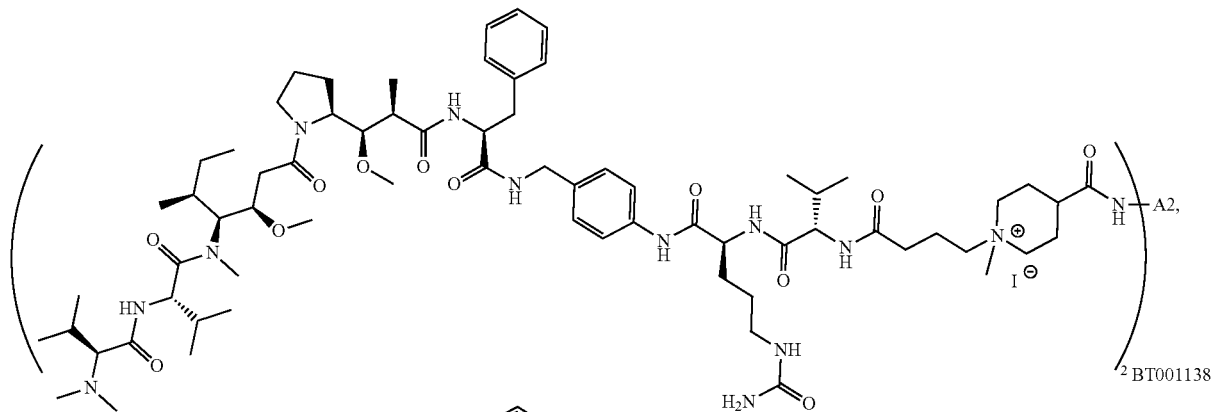
BT001137
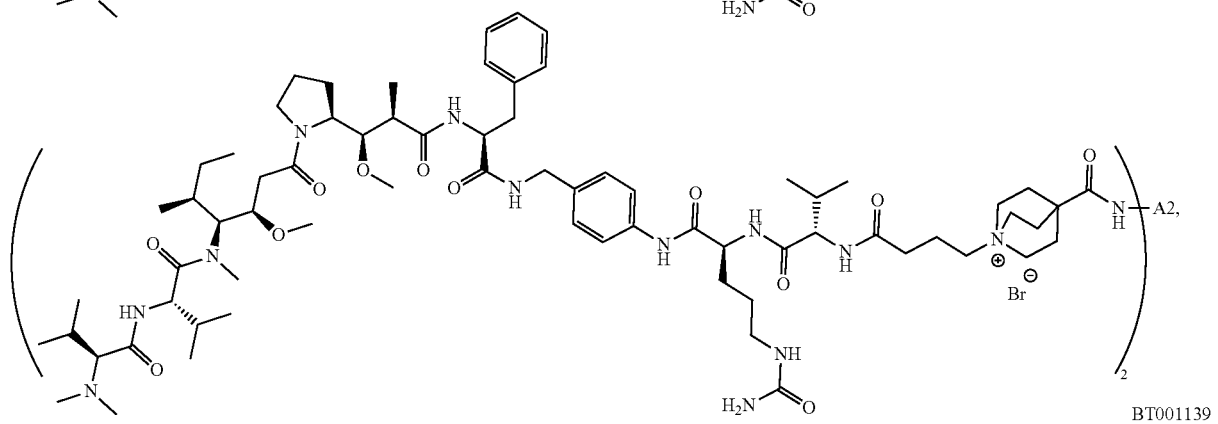
BT001138

BT001139
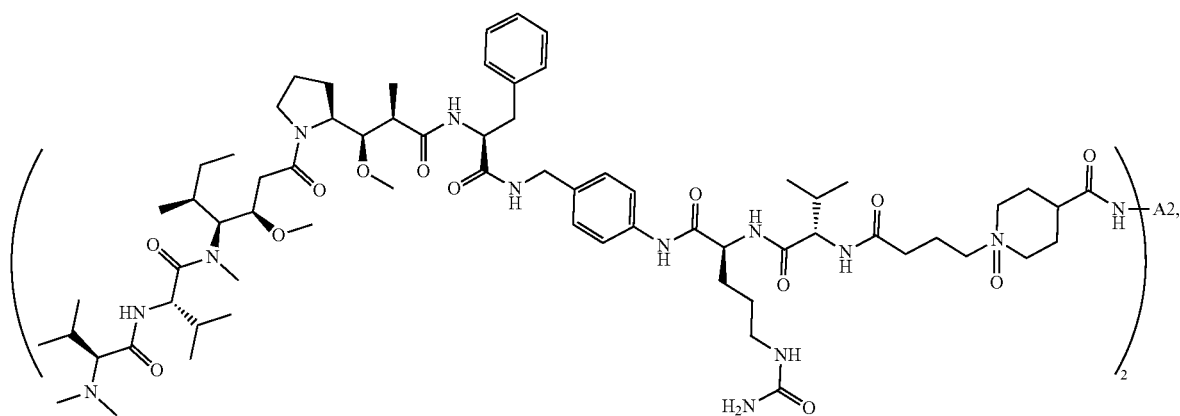
BT001140

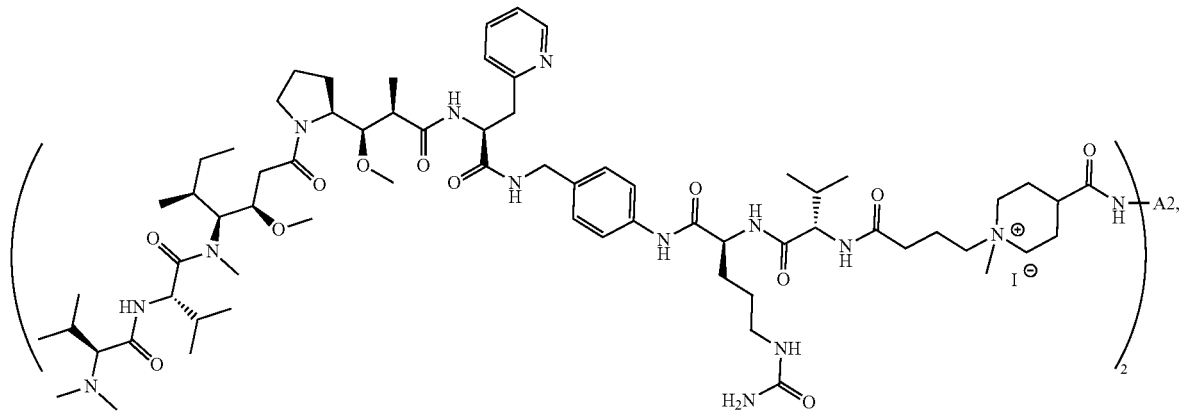
BT001141
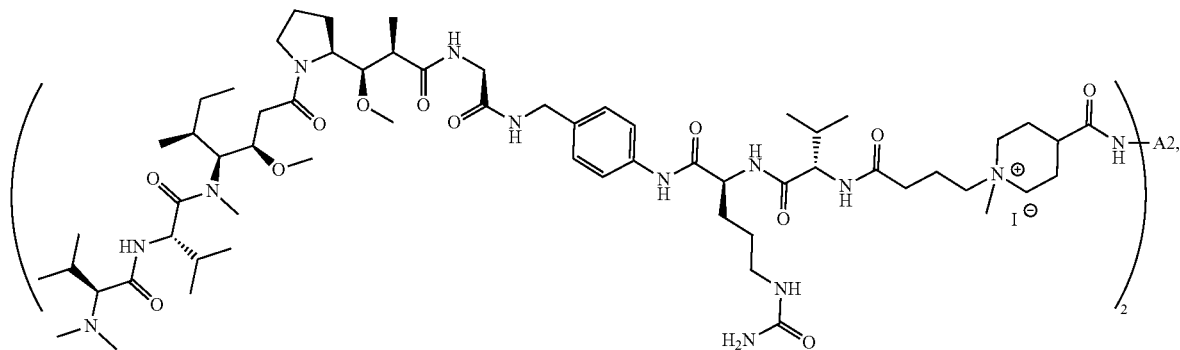
BT001142
wherein, A2 is a group obtained after removing 2 amino groups from pertuzumab.
In some embodiments, the conjugate is selected from:
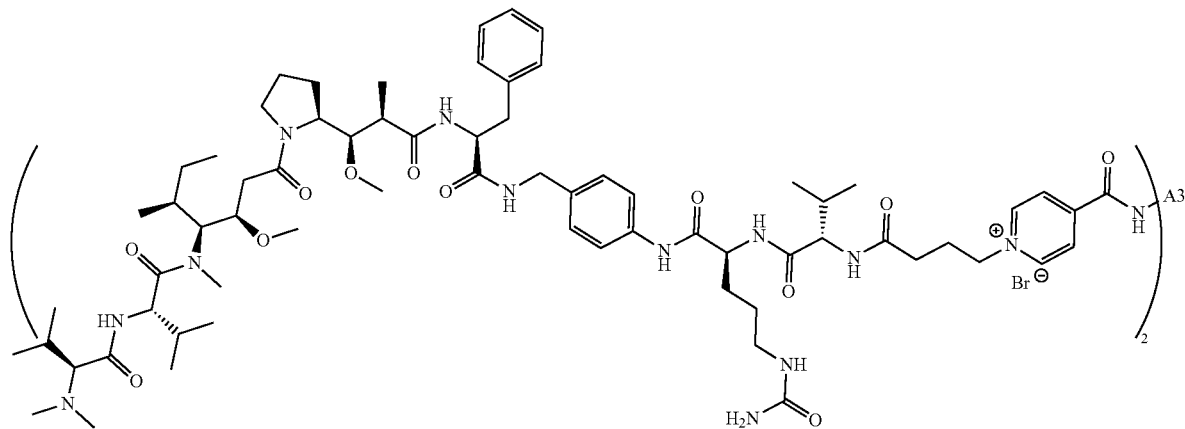
BT001143

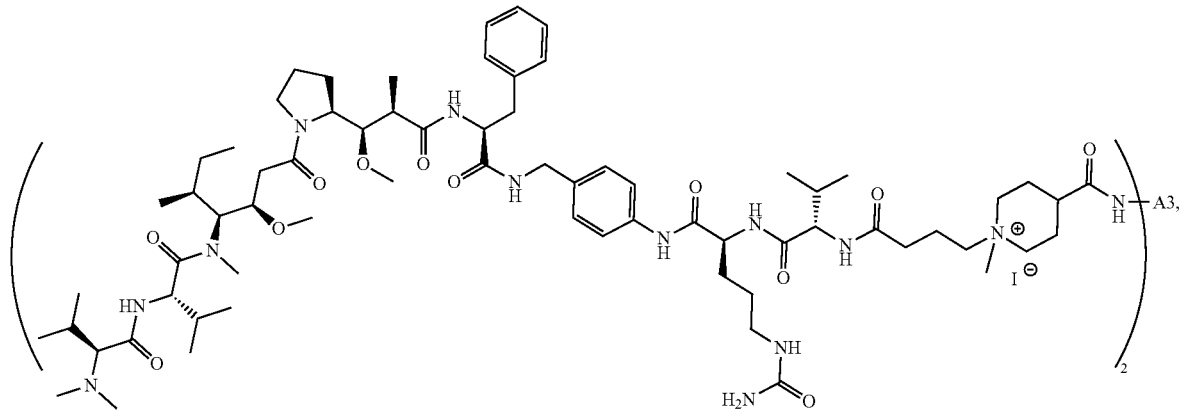
BT001144
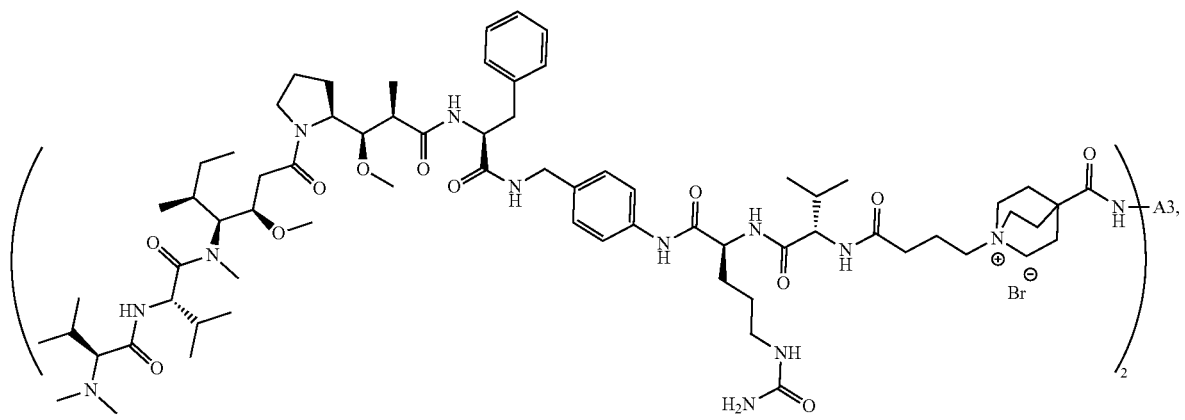
BT001145
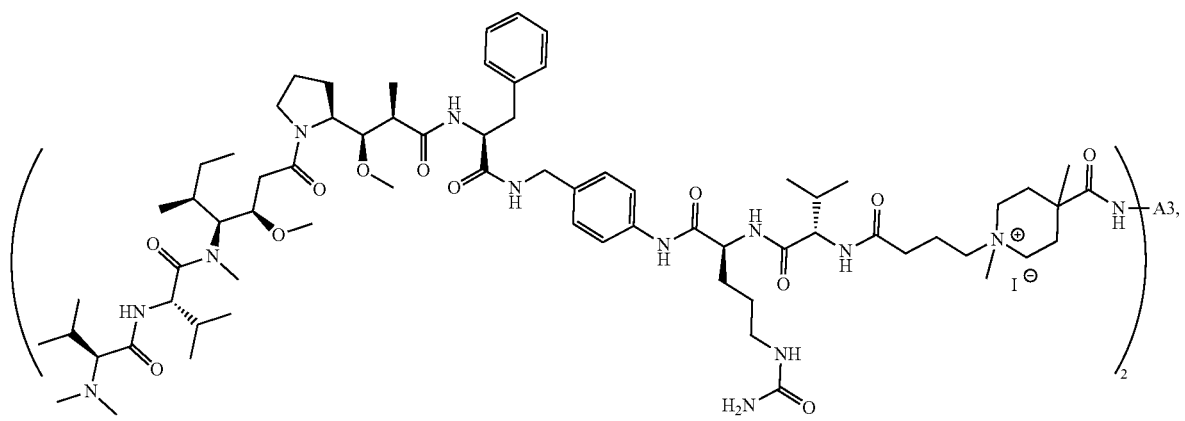
BT001146

-continued
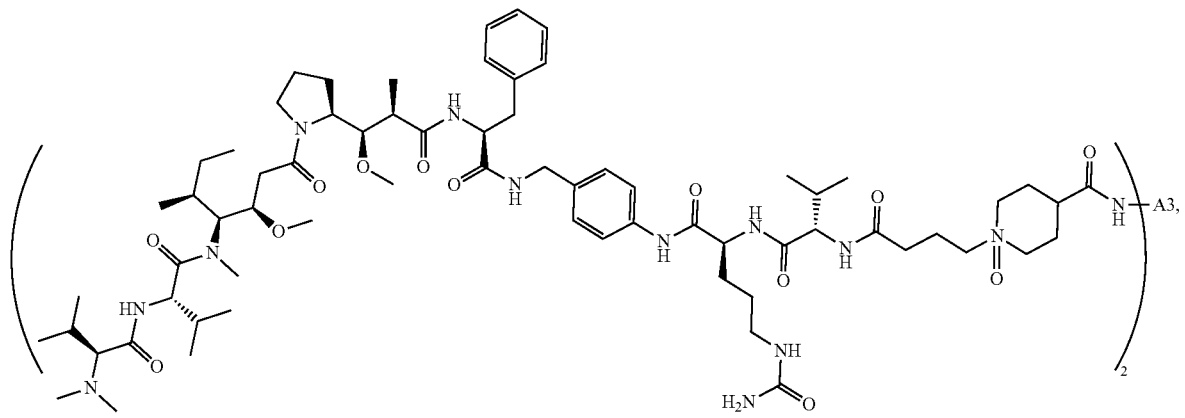
BT001147
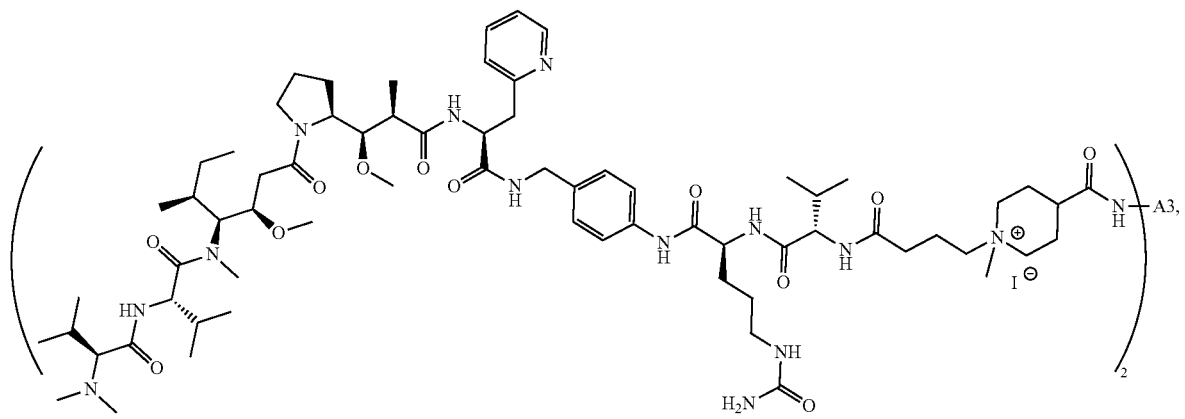
BT001148
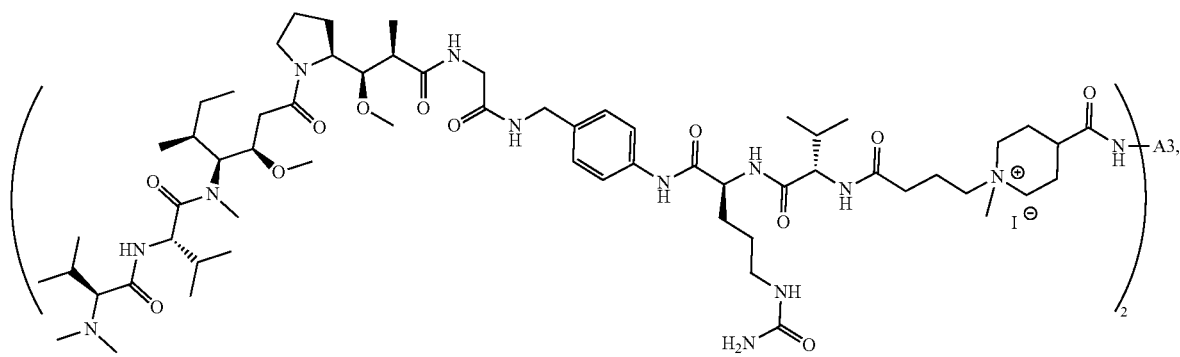
BT001149
wherein, A3 is a group obtained after removing 2 amino groups from sacituzumab.

In some embodiments, the conjugate is selected from:
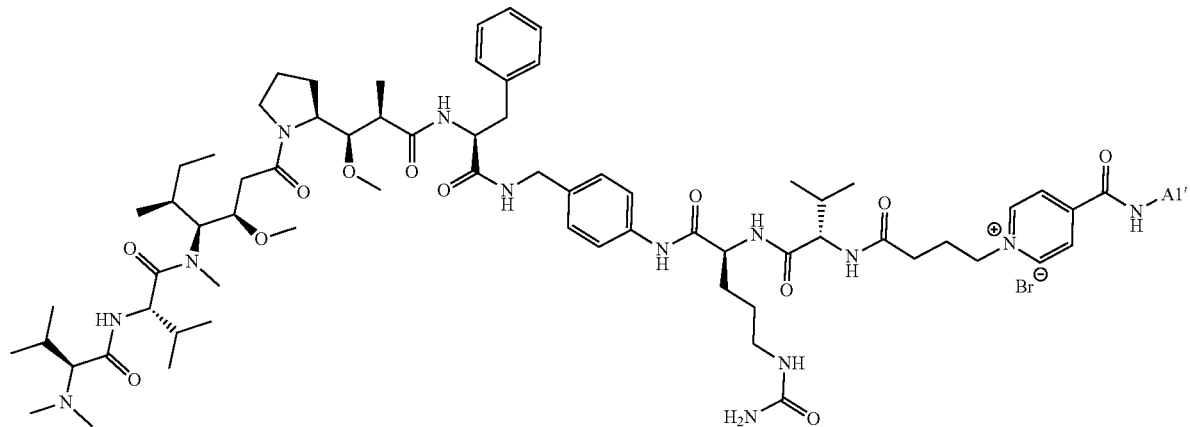
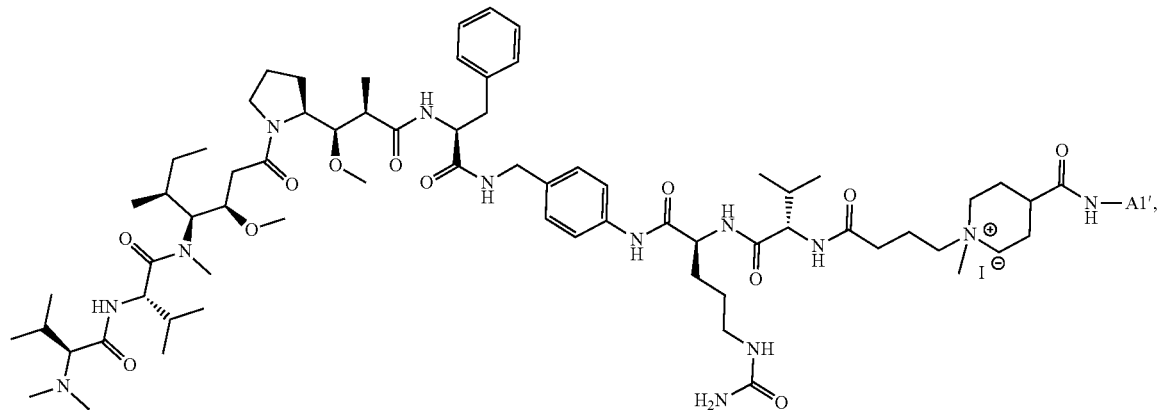
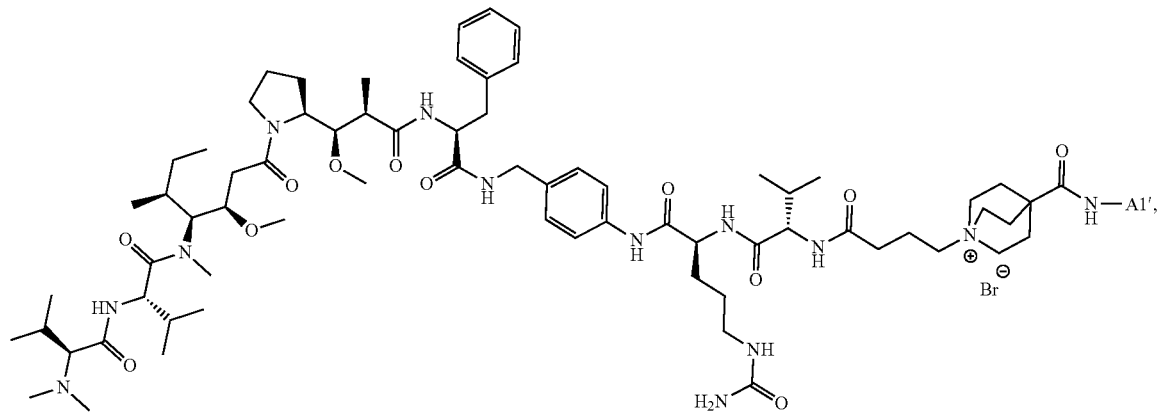

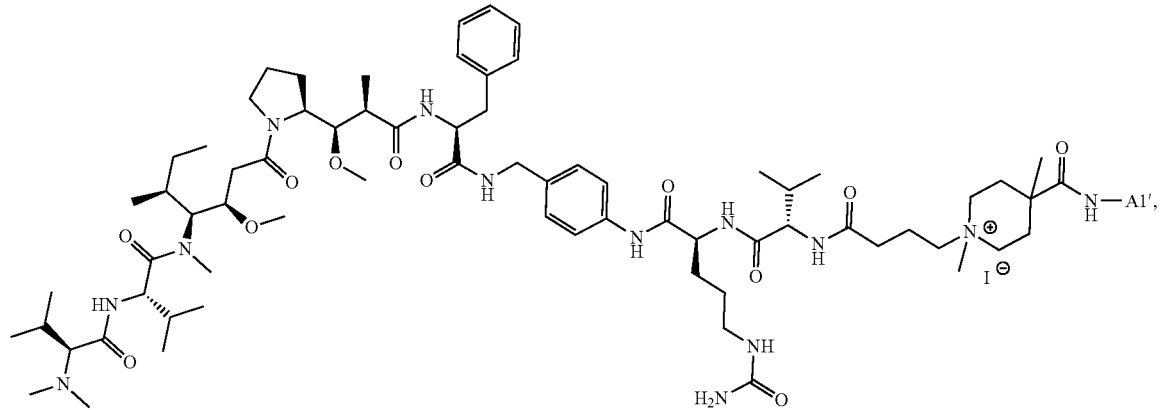
BT001152
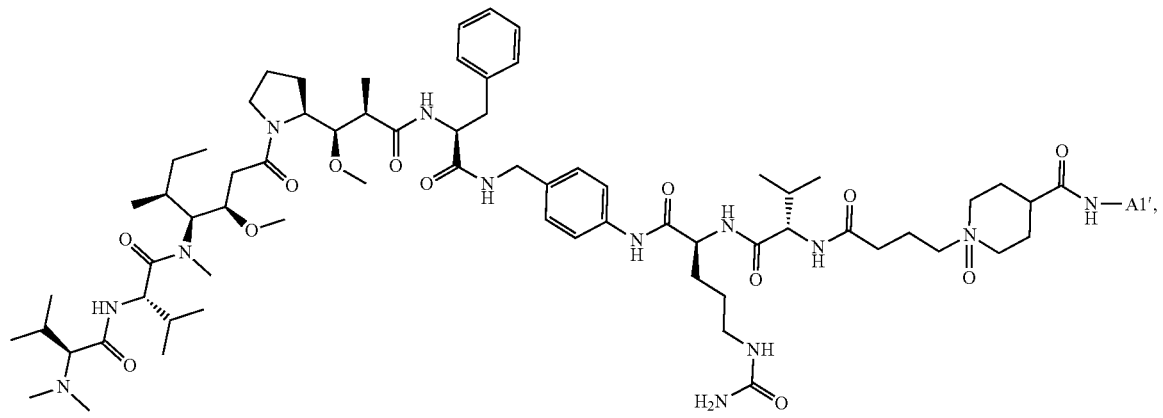
BT001153

BT001154

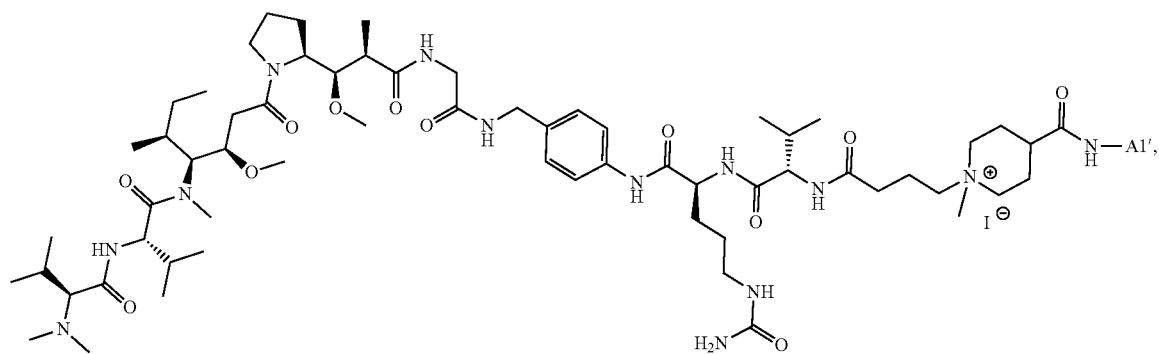
wherein, A1' is a group obtained after removing 1 amino group from trastuzumab.
In some embodiments, the conjugate is selected from
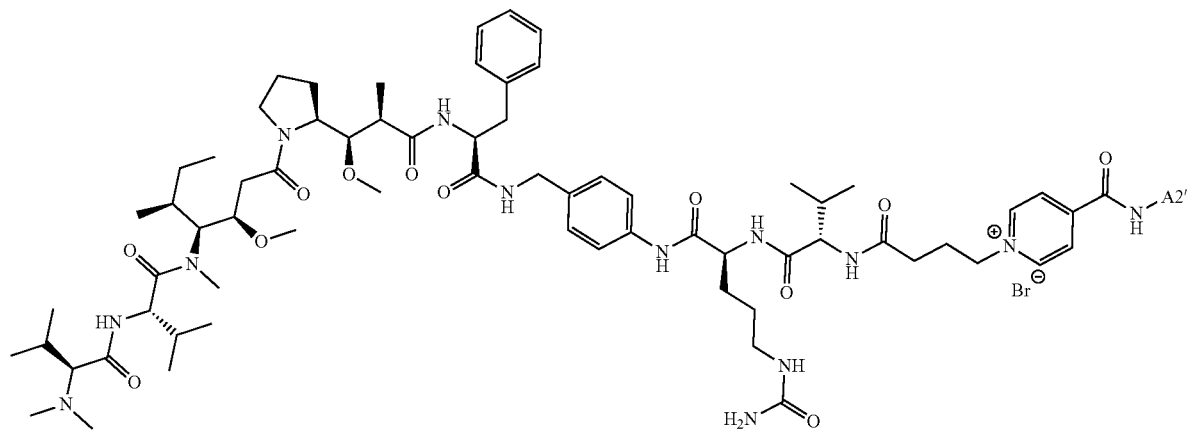
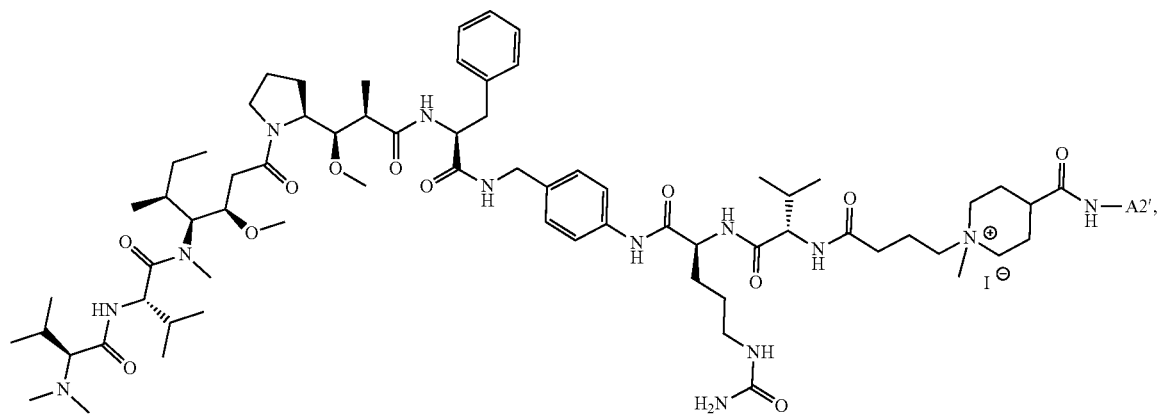

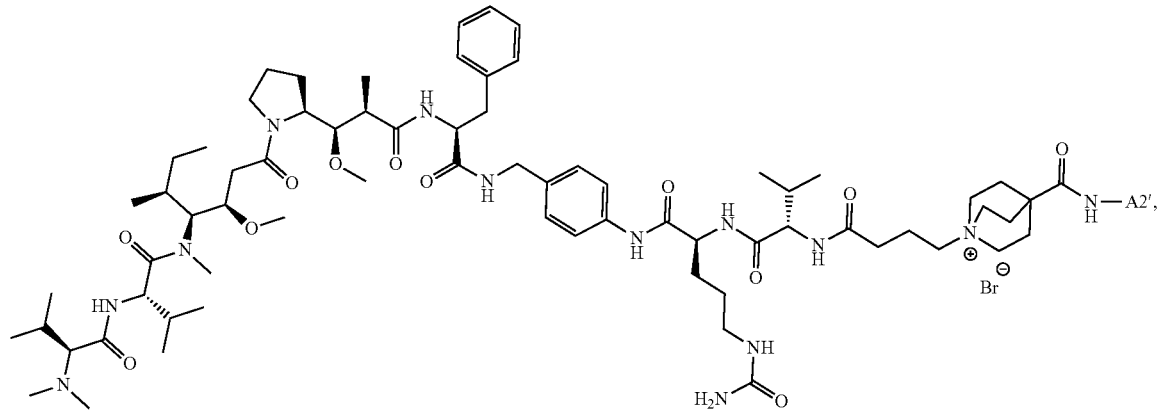
BT001158
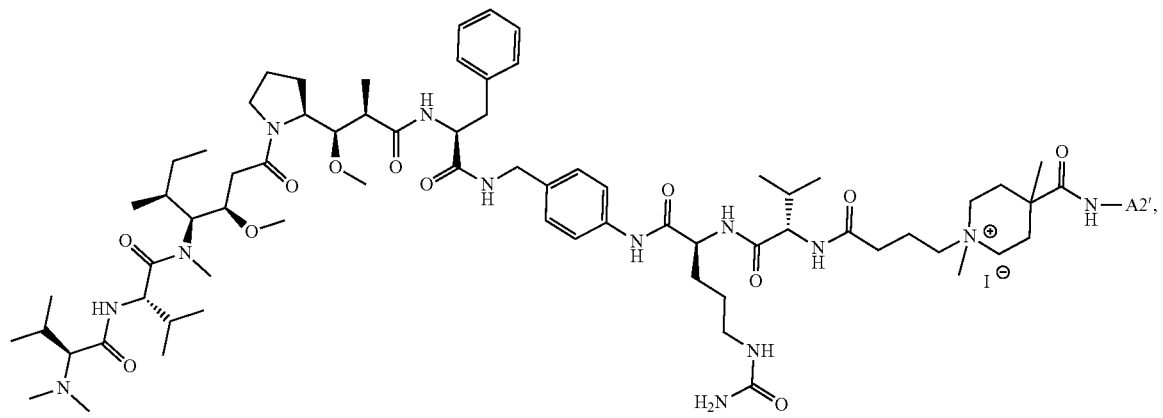
BT001159
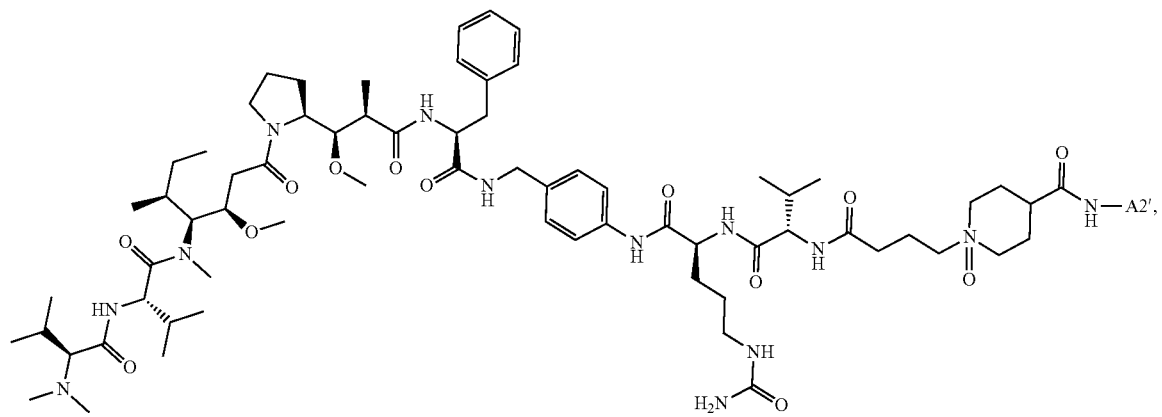
BT001160

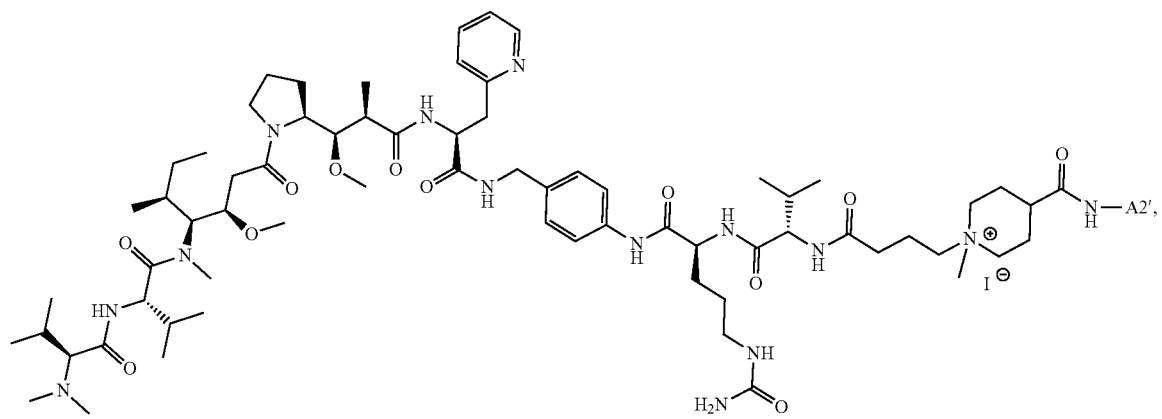
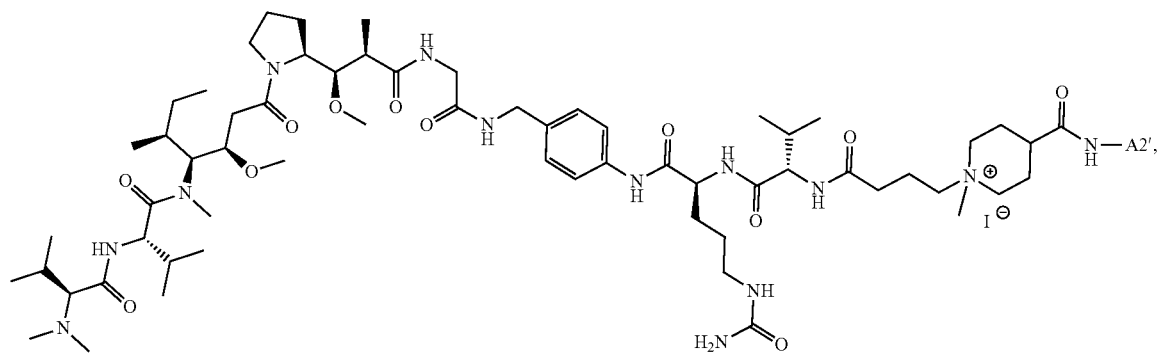
wherein, A2' is a group obtained after removing 1 amino group from pertuzumab.
In some embodiments, the conjugate is selected from:
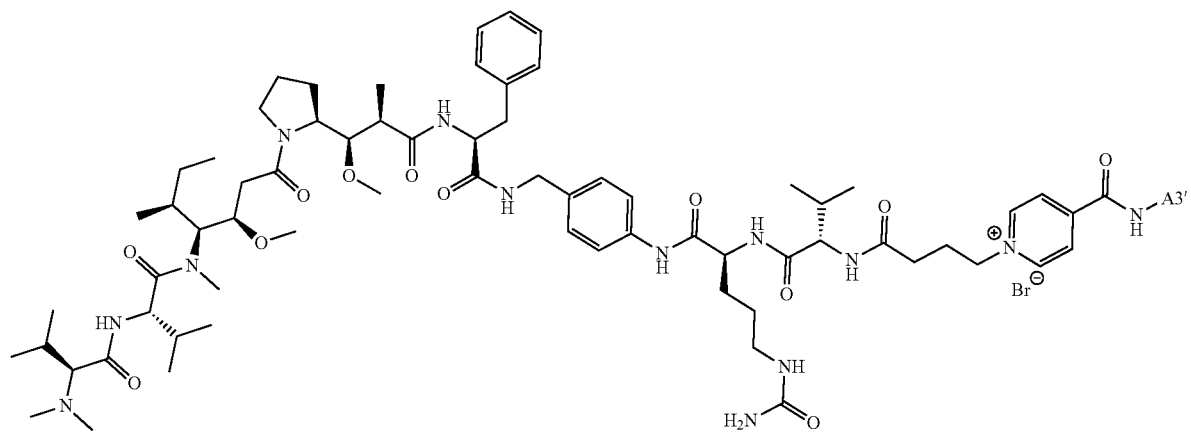

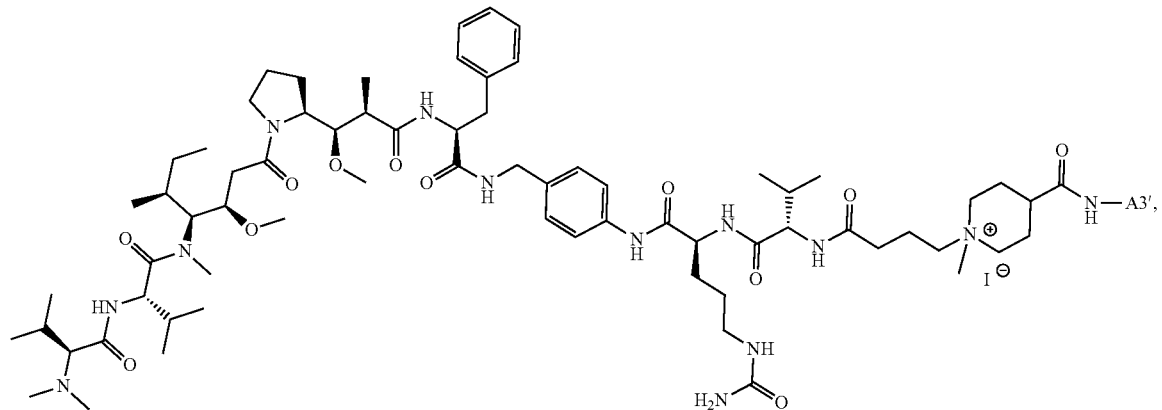
BT001164
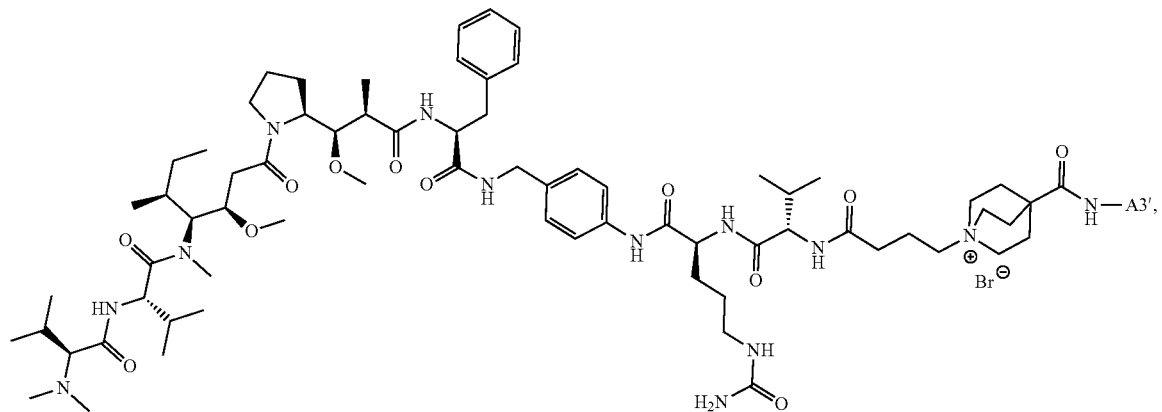
BT001165
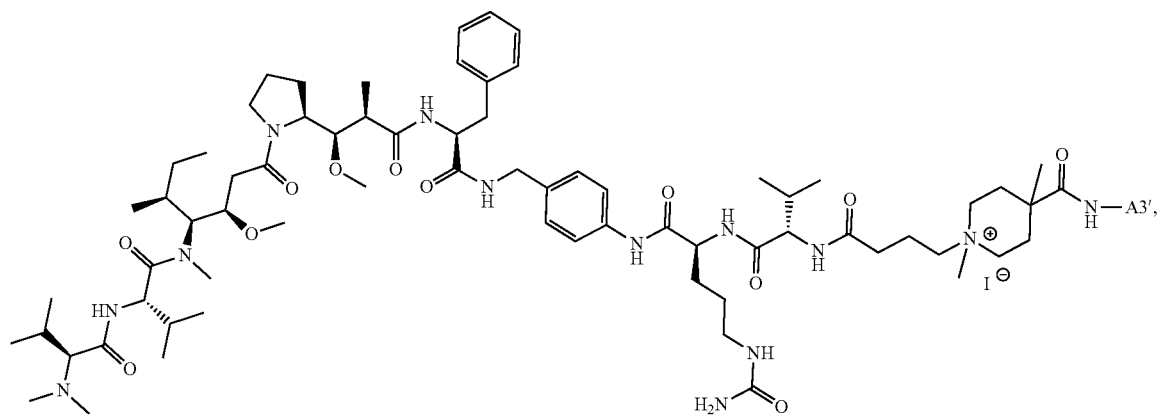
BT001166

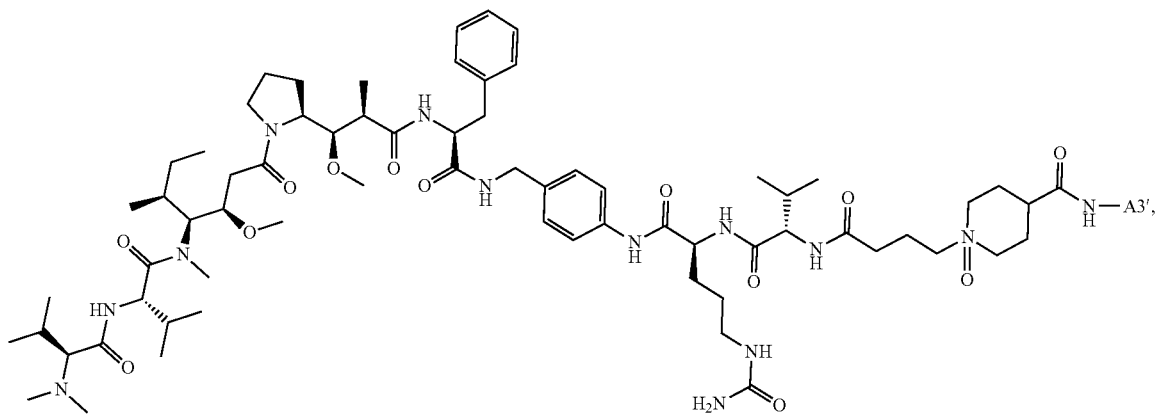

BT001167

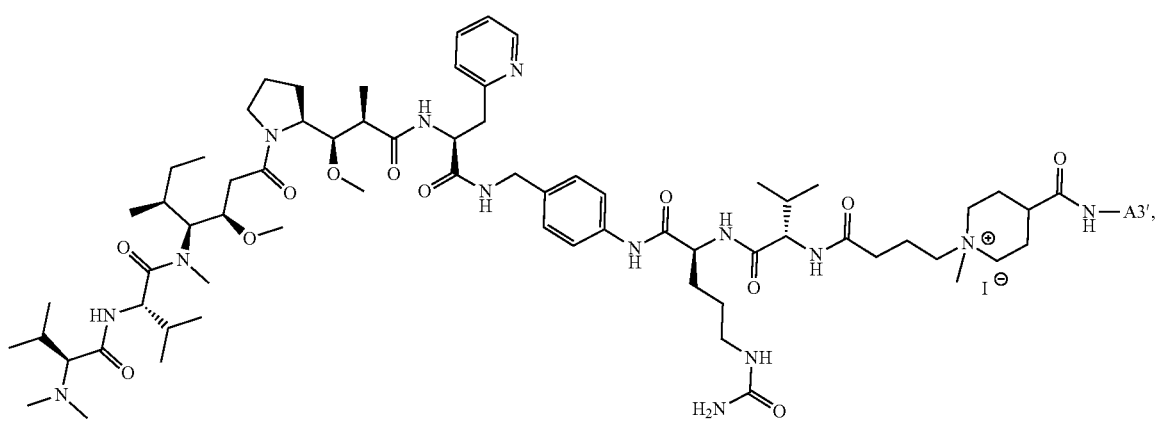

BT001168

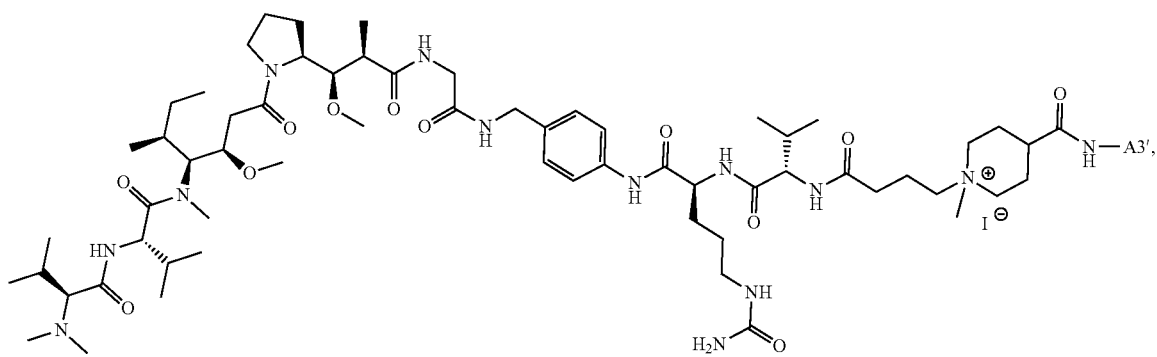

BT001169 wherein, A3' is a group obtained after removing 1 amino group from sacituzumab.

In the structure of the compound involved in the present invention, the groups

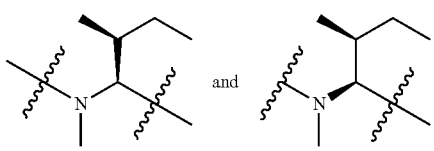

are interchangeable, and the corresponding examples (for example, compound or a pharmaceutically acceptable salt, solvate, hydrate, isomer, crystalline form, racemate, or conjugate comprising the compound or a pharmaceutically acceptable salt, solvate, hydrate, isomer, crystalline form or racemate thereof) are all encompassed within the scope of the present invention.

The present invention also provides a pharmaceutical composition comprising a compound as described above or a pharmaceutically acceptable salt, solvate, hydrate, isomer thereof, or any crystalline form or racemate thereof, or a conjugate as described above, and comprising one or more medicinal excipients.

The present invention also provides use of a compound as described above, or a pharmaceutically acceptable salt, solvate, hydrate, isomer thereof, or any crystalline form or racemate thereof, or a conjugate as described above in inhibiting tumor cell proliferation.

In some embodiments, the tumor cell is selected from esophageal cancer cell (for example, esophageal adenocarcinoma and esophageal squamous cell carcinoma cell), brain tumor cell, lung cancer cell (for example, small cell lung cancer cell and non-small cell lung cancer cell), squamous cell carcinoma cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, non-Hodgkin's lymphoma cell, central nervous system tumor cell (for example, neuroglioma cell, glioblastoma multiforme cell, glioma cell or sarcoma cell), prostate cancer cell and thyroid cancer cell.

In some embodiments, the conjugate comprises a targeting moiety (E); the targeting moiety (E) is a monoclonal antibody against Her 2, for example, trastuzumab, pertuzumab, or the targeting moiety (E) is a monoclonal antibody against Trop-2, for example, sacituzumab; the tumor cell is selected from breast cancer cell, ovarian cancer cell, gastric cancer cell, endometrial cancer cell, salivary gland cancer cell, lung cancer cell, kidney cancer cell, colon cancer cell, thyroid cancer cell, pancreatic cancer cell, bladder cancer cell, liver cancer cell, colorectal cancer cell, prostate cancer cell, cervical cancer cell.

In some embodiments, the targeting moiety (E) is a monoclonal antibody against Her 2, for example, trastuzumab, pertuzumab; the tumor cell is selected from breast cancer cell, ovarian cancer cell, gastric cancer cell, endometrial cancer cell, salivary gland cancer cell, lung cancer cell, kidney cancer cell, colon cancer cell, thyroid cancer cell, pancreatic cancer cell, bladder cancer cell or liver cancer cell.

In some embodiments, the targeting moiety (E) is a monoclonal antibody against Trop-2, for example, sacituzumab, the tumor cell is selected from breast cancer cell, colorectal cancer cell, lung cancer cell, pancreatic cancer cell, ovarian cancer cell, prostate cancer cell, cervical cancer cell.

In some embodiments, the compound as described above or a pharmaceutically acceptable salt, solvate, hydrate, isomer thereof, or any crystalline form or racemate thereof, or a conjugate as described above, is applied to in a vitro cell or cell in a subject, for example, applied to the body of a subject (for example, mammals, such as bovine, equine, goat, porcine, canine, feline, rodent, primate, such as human), to inhibit the proliferation of a tumor cell in a subject; or, applied to an in vitro tumor cell (for example, a cell line or cell from a subject) to inhibit proliferation of an in vitro tumor cell.

The present invention also provides use of a compound as described above, or a pharmaceutically acceptable salt, solvate, hydrate, isomer thereof, or any crystalline form or racemate thereof, or a conjugate as described above, in the manufacture of a medicament for treating a cancer disease.

In some embodiments, the cancer disease is selected from esophageal cancer (for example, esophageal adenocarcinoma and esophageal squamous cell carcinoma), brain tumor, lung cancer (for example, small cell lung cancer and non-small cell lung cancer), squamous epithelium cell carcinoma, bladder cancer, gastric cancer, ovarian cancer, peritoneal cancer, pancreatic cancer, breast cancer, head and neck cancer, cervical cancer, endometrial cancer, colorectal cancer, liver cancer, kidney cancer, solid tumor, non-Hodgkin's lymphoma, central nervous system tumor (for example, neuroglioma, glioblastoma multiforme, glioma or sarcoma), prostate cancer and thyroid cancer.

In some embodiments, the conjugate comprises a targeting moiety (E); the targeting moiety (E) is a monoclonal antibody against Her 2, for example, trastuzumab, pertuzumab, or the targeting moiety (E) is a monoclonal antibody against Trop-2, for example, sacituzumab; the cancer disease is selected from breast cancer, ovarian cancer, gastric cancer, endometrial cancer, salivary gland cancer, lung cancer, kidney cancer, colon cancer, thyroid cancer, pancreatic cancer, bladder cancer, liver cancer, colorectal cancer, prostate cancer, cervical cancer.

In some embodiments, the targeting moiety (E) is a monoclonal antibody against Her 2, for example, trastuzumab, pertuzumab; the cancer disease is selected from breast cancer, ovarian cancer, gastric cancer, endometrial cancer, salivary gland cancer, lung cancer, kidney cancer, colon cancer, thyroid cancer, pancreatic cancer, bladder cancer or liver cancer.

In some embodiments, the targeting moiety (E) is a monoclonal antibody against Trop-2, for example, sacituzumab, the cancer disease is selected from breast cancer, colorectal cancer, lung cancer, pancreatic cancer, ovarian cancer, prostate cancer, cervical cancer.

The present invention also provides a method for preparation of a compound as described above, or a pharmaceutically acceptable salt, solvate, hydrate, isomer thereof, or any crystalline form or racemate thereof, wherein the method is illustrated by the following scheme:

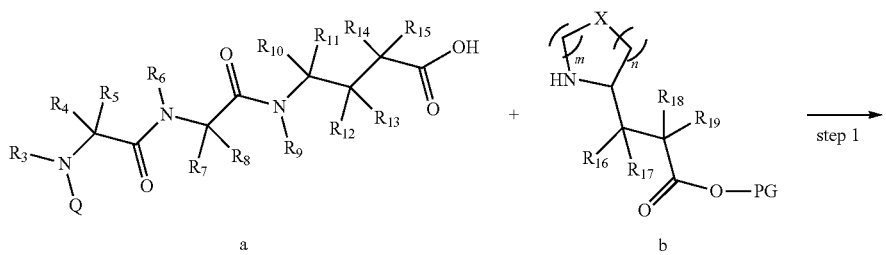

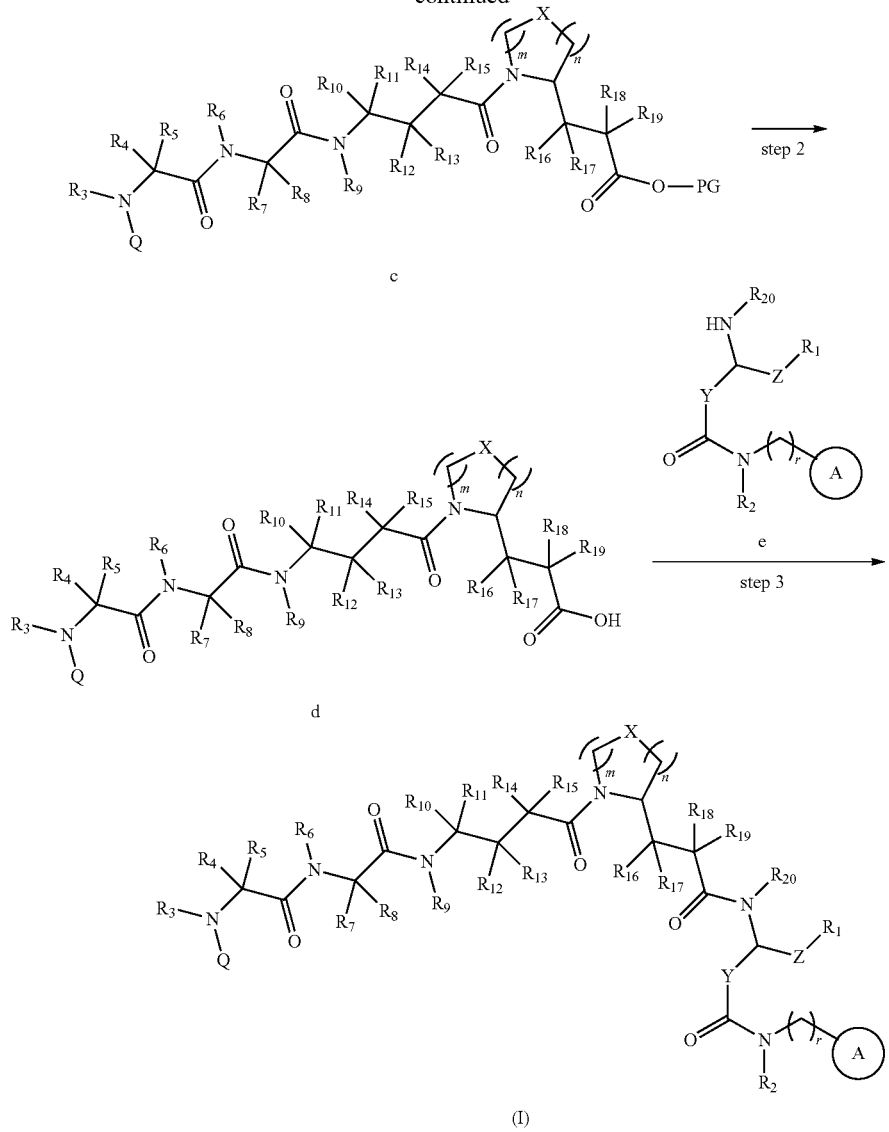

wherein, $R_1$-$R_{20}$, Q, X, Y, A, m, n are as defined in any of the above items, PG is a protecting group, for example, benzyl, substituted benzyl or t-butyl.

The method comprises the following steps:

Step 1: reacting compound a with compound b in the presence of a base and/or a condensation reagent to obtain compound c; Step 2: removing PG from compound c in the presence of hydrogen gas and a catalyst, to obtain compound d;

Step 3: reacting compound d with compound e in the presence of a base and/or a condensation reagent to obtain a compound of formula (I).

In some embodiments, the base is an organic base or an inorganic base.

In some embodiments, the organic base is selected from triethylamine, DIPEA, pyridine, NMM or DMAP.

In some embodiments, the inorganic base is selected from NaH, NaOH, $Na_2CO_3$ or $K_2CO_3$.

In some embodiments, the condensation reagent is selected from HATU, HBTU, EEDQ, DEPC, DCC, DIC, EDC, BOP, PyAOP or PyBOP.

In some embodiments, the step 1 is carried out at a temperature of −10° C. to 60° C. (preferably −5° C. to 25° C.).

In some embodiments, in the step 1, the molar ratio of the compound a to the compound b is 1:(0.5-2), preferably 1:(0.8-2), more preferably 1:(1-1.5).

In some embodiments, in the step 1, the molar ratio of the compound a, the compound b and the base is 1:(0.5-2):(0.5-4), preferably 1:(0.8-2):(0.8-3), more preferably 1:(1-1.5):(1-2).

In some embodiments, in the step 1, the molar ratio of the compound a to the condensation reagent is 1:(1-3), preferably 1:(1.2-2.0).

In some embodiments, in the step 2, the pressure of the hydrogen gas is 1-4 atm, preferably 1-2 atm.

In some embodiments, the catalyst is selected from Pd/C, $Pt_2O$, $Pd(OH)_2$.

In some embodiments, the mass ratio of the compound c to the catalyst is 1:(0.05-2), preferably 1:0.1.

In some embodiments, the step 2 is carried out at a temperature of from 0° C. to 100° C. (preferably from 10° C. to 25° C.).

In some embodiments, the step 3 is carried out at a temperature of −10° C. to 60° C. (preferably −5° C. to 25° C.).

In some embodiments, in the step 3, the molar ratio of the compound d to the compound e is 1:(0.5-2), preferably 1:(0.8-2), more preferably 1:(1-1.5).

In some embodiments, in the step 3, the molar ratio of the compound d, the compound e and the base is 1:(0.5-2):(0.5-4), preferably 1:(0.8-2):(0.8-3), more preferably 1:(1-1.5):(1-2).

In some embodiments, in the step 3, the molar ratio of the compound d to the condensation reagent is 1:(1-3), preferably 1:(1.2-2.0).

In some embodiments, the step 1, the step 2 and/or the step 3 are carried out in an organic solvent.

In some embodiments, the organic solvent is selected from N,N-dimethylformamide, dimethyl sulfoxide, N-methylpyrrolidone, saturated hydrocarbon (for example, cyclohexane, hexane), halogenated hydrocarbon (for example, dichloromethane, chloroform, 1,2-dichloroethane), ethers (for example, tetrahydrofuran, diethyl ether, dioxane, 1,2-dimethoxy ethane), nitriles (for example, acetonitrile), alcohols (for example, methanol, ethanol) and any combination thereof.

In some embodiments, the method results in a mixture of diastereomers of the compound of formula (I).

In some embodiments, the method further comprises: subjecting the mixture of diastereomers of the compound of formula (I) to a preparative high performance liquid chromatography to obtain a pure isomer.

In some embodiments, the preparative high performance liquid chromatography is conducted under a condition comprising one or more of the following:

(1) cellulose-tris(3,5-dimethylphenyl carbamate)-bonded silica gel is used as a filler;

(2) a temperature of 30° C.-50° C. is used for the chromatographic column;

(3) a flow rate of 5.0-20.0 mL/min is used for the eluent;

(4) a detector is used with a detection wavelength of 200-400 nm;

(5) an organic solvent is used as the mobile phase (for example, n-hexane, isopropanol and/or methanol).

In some embodiments, two mobile phases are used, including mobile phase A (for example, n-hexane) and mobile phase B (for example, methanol or isopropanol).

In some embodiments, the preparative high performance liquid chromatography is conducted with a linear gradient elution under the conditions (1) to (5).

The present invention also provides a method of preparing a conjugate as described above (Method I), wherein the method is illustrated by the following scheme:

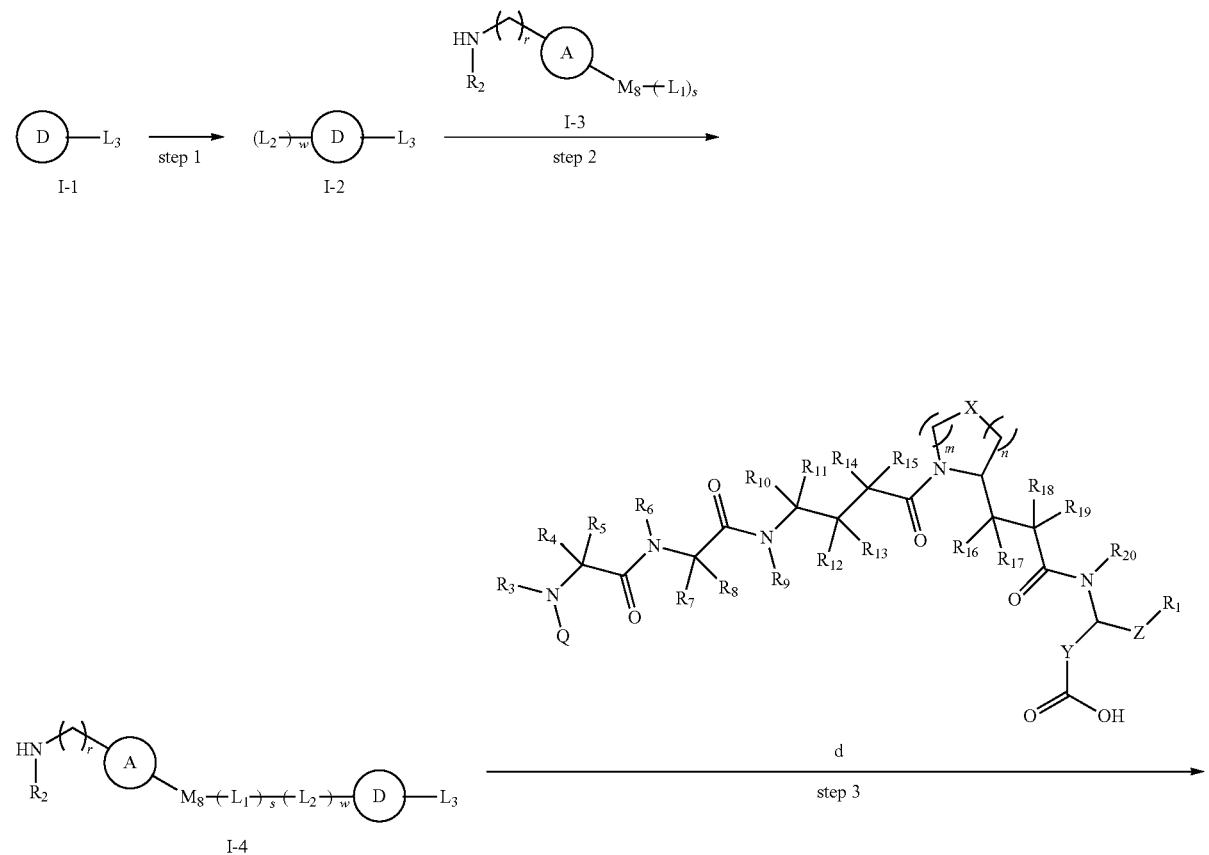

-continued

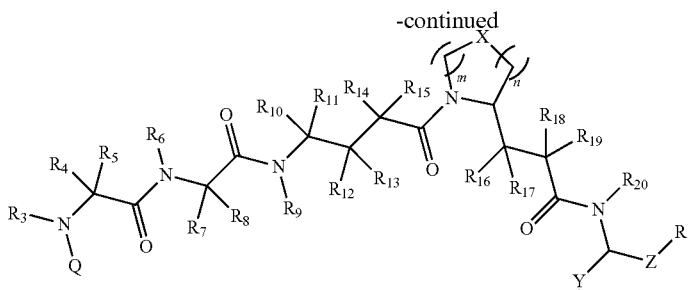

I-5 wherein, $R_1$-$R_{20}$, Q, X, Y, $L_1$, $L_2$, $L_3$, $M_8$, A, D, m, n, r, s, w are as defined in any of the above items.

The method comprises the following steps:

Step 1: reacting compound I-1 with compound $L_2'$ in the presence of a base and/or a condensation reagent to obtain compound I-2, wherein the compound $L_2'$ is $CH_2Br_2$, $CH_2I_2$, $CH_2BrI$, Br—$(CH_2CH_2O)_y$—$(CH_2)_y$—Br, Br—$(CH_2CH_2O)_y$—$(CH_2)_y$—I, I—$(CH_2CH_2O)_y$—$(CH_2)_y$—Br, I—$(CH_2CH_2O)_y$—$(CH_2)_y$—I, or

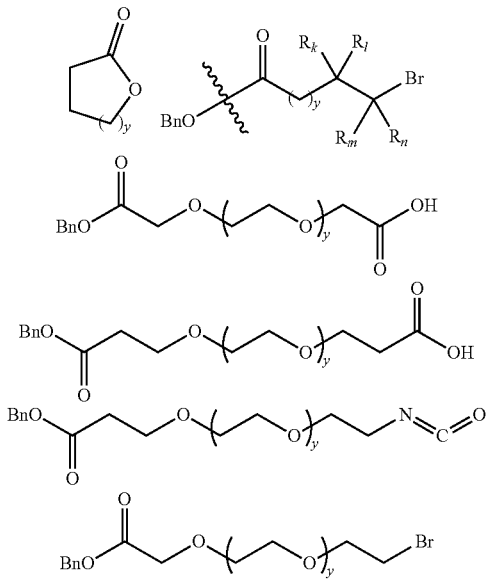

wherein, $R_k$, $R_l$, $R_m$, $R_n$, independently of each other, are selected from H (hydrogen), D (deuterium), halogen, $CF_3$, CN, $CH_2CN$, $C_{1-6}$ alkyl, $C_{1-6}$ alkoxy, $C_{2-10}$ alkynyl, $C_{3-6}$ cycloalkyl;

y, independently of each other, is 0, 1, 2, 3, 4, 5, 6, 7, 8, 9 or 10;

Step 2: reacting compound I-2 with compound I-3 in the presence of a base and/or a condensation reagent to obtain compound I-4;

Step 3: reacting compound I-4 with compound d in the presence of a base and/or a condensation reagent to obtain compound I-5.

In some embodiments, the base is an inorganic base or an organic base.

In some embodiments, the organic base is selected from triethylamine, DIPEA, pyridine, NMM or DMAP.

In some embodiments, the inorganic base is selected from NaH, NaOH, $Na_2CO_3$, $NaHCO_3$, $K_2CO_3$.

In some embodiments, the condensation reagent is selected from HATU, HBTU, EEDQ, DEPC, DCC, DIC, EDC, BOP, PyAOP or PyBOP.

In some embodiments, the step 1 is carried out at a temperature of −20° C.-150° C. (preferably −5° C.-130° C.).

In some embodiments, in the step 1, the molar ratio of the compound I-1 to the compound $L_2'$ is 1:(0.5-5), preferably 1:(0.8-3), more preferably 1:(1-2.5).

In some embodiments, in the step 1, the molar ratio of the compound I-1, the compound $L_2'$ and the base is 1:(0.5-2):(0.5-20), preferably 1:(0.8-2):(0.8-3), more preferably 1:(1-1.5):(1-2).

In some embodiments, in the step 1, the molar ratio of the compound I-1 to the condensation reagent is 1:(1-3), preferably 1:(1.2-2).

In some embodiments, the step 2 is carried out at a temperature of −10° C. to 60° C. (preferably −5° C. to 25° C.).

In some embodiments, in the step 2, the molar ratio of the compound I-2 to the compound I-3 is 1:(0.5-2), preferably 1:(0.8-2), more preferably 1:(1-1.5).

In some embodiments, in the step 2, the molar ratio of the compound I-2, the compound I-3 and the base is 1:(0.5-2):(0.5-4), preferably 1:(0.8-2):(0.8-3), more preferably 1:(1-1.5):(1-2).

In some embodiments, in the step 2, the molar ratio of the compound I-2 to the condensation reagent is 1:(1-3), preferably 1:(1.2-2.0).

In some embodiments, the step 3 is carried out at a temperature of −10° C. to 60° C. (preferably −5° C. to 25° C.).

In some embodiments, in the step 3, the molar ratio of the compound I-4 to the compound d is 1:(0.5-2), preferably 1:(0.8-2), more preferably 1:(1-1.5).

In some embodiments, in the step 3, the molar ratio of the compound I-4, the compound d and the base is 1:(0.5-2):(0.5-4), preferably 1:(0.8-2):(0.8-3), more preferably 1:(1-1.5):(1-2).

In some embodiments, in the step 3, the molar ratio of the compound I-4 to the condensation reagent is 1:(1-3), preferably 1:(1.2-2.0).

In some embodiments, the method further comprises step 4: coupling the compound I-5 with a targeting moiety (E).

In some embodiments, the targeting moiety (E) is a monoclonal antibody against Her 2 (for example, trastuzumab, pertuzumab) or a monoclonal antibody against Trop-2 (for example, sacituzumab), or an active fragment or variant thereof.

In some embodiments, the step 4 comprises: mixing a targeting moiety (E) with the compound I-5.

In some embodiments, the molar ratio of the targeting moiety (E) to the compound I-5 is 1:(1-20).

In some embodiments, the step 4 comprises: mixing a solution comprising a targeting moiety (E) with the compound I-5.

In some embodiments, the step 1, the step 2, the step 3 and/or the step 4 are carried out in water or an organic solvent.

In some embodiments, the organic solvent is selected from N,N-dimethylformamide, dimethyl sulfoxide, N-methylpyrrolidone, saturated hydrocarbons (for example, cyclohexane, hexane), halogenated hydrocarbons (for example, dichloromethane, chloroform, 1,2-dichloroethane), ethers (for example, tetrahydrofuran, diethyl ether, dioxane, 1,2-dimethoxy ethane), nitriles (for example, acetonitrile), alcohols (for example, methanol, ethanol) and any combination thereof.

In some embodiments, the method further comprises step 5, wherein the step 5 comprises: purifying the product of the step 4 by chromatography (for example, one or more of ion exchange chromatography, hydrophobic chromatography, reversed phase chromatography and affinity chromatography).

The present invention also provides a method of preparing a conjugate as described above (Method II), wherein the method is illustrated by the following scheme:

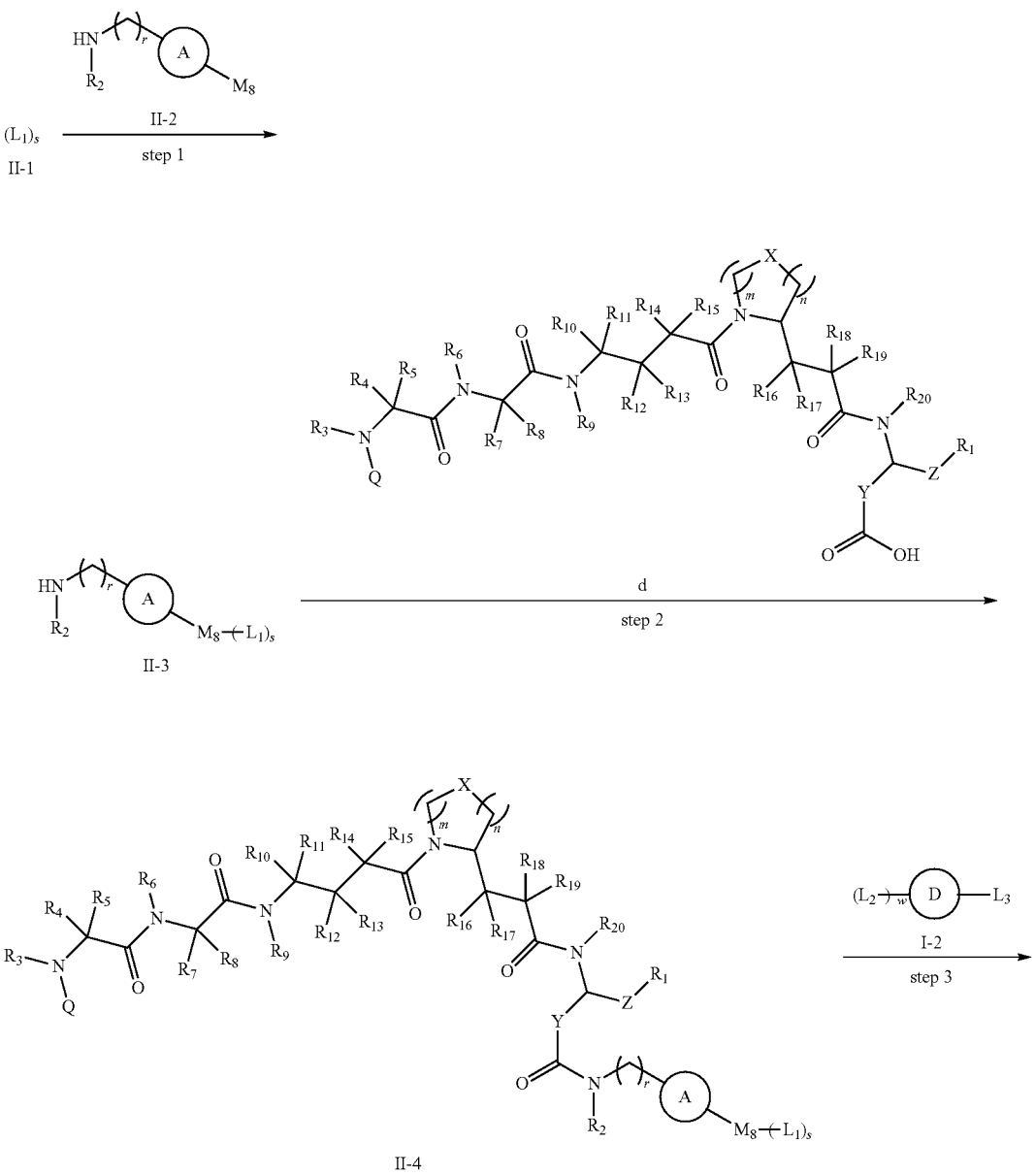

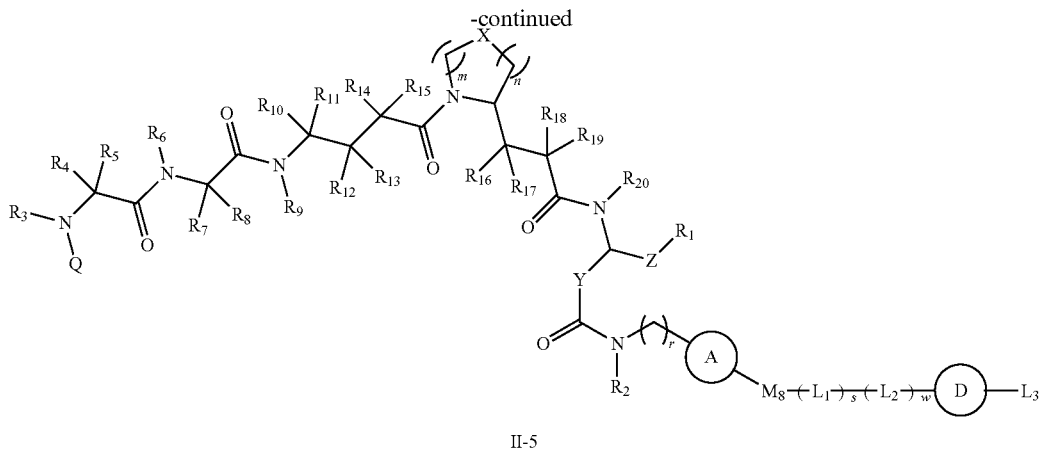

II-5 wherein, $R_1$-$R_{20}$, Q, X, Y, $L_1$, $L_2$, $L_3$, $M_8$, A, D, m, n, r, s, w are as defined in any of the above items;

The method comprises the following steps:

Step 1: reacting compound II-1 with compound II-2 in the presence of a base and/or a condensation reagent to obtain compound II-3;

Step 2: reacting compound II-3 with compound d in the presence of a base and/or a condensation reagent to obtain compound II-4;

Step 3: reacting compound II-4 with compound I-2 in the presence of a base and/or a condensation reagent to obtain compound II-5;

In some embodiments, the base is an organic base or an inorganic base.

In some embodiments, the organic base is selected from triethylamine, DIPEA, pyridine, NMM or DMAP.

In some embodiments, the inorganic base is selected from NaH, NaOH, $Na_2CO_3$, $NaHCO_3$ or $K_2CO_3$.

In some embodiments, the condensation reagent is selected from HATU, HBTU, EEDQ, DEPC, DCC, DIC, EDC, BOP, PyAOP or PyBOP.

In some embodiments, the step 1 is carried out at a temperature of from 20° C. to 120° C. (preferably from 30° C. to 80° C.).

In some embodiments, in the step 1, the molar ratio of the compound II-1 to the compound II-2 is 1:(0.5-5), preferably 1:(0.8-3), more preferably 1:(1-2.5).

In some embodiments, in the step 1, the molar ratio of the compound II-1, the compound II-2 and the base is 1:(0.5-2):(0.5-20), preferably 1:(0.8-2):(0.8-3), more preferably 1:(1-1.5):(1-2).

In some embodiments, in the step 1, the molar ratio of the compound II-1 to the condensation reagent is 1:(1-3), preferably 1:(1.2-2.0).

In some embodiments, the step 2 is carried out at a temperature of −20° C. to 50° C. (preferably −5° C. to 25° C.).

In some embodiments, in the step 2, the molar ratio of the compound II-3 to the compound d is 1:(0.5-5), preferably 1:(0.8-3), more preferably 1:(1-2.5).

In some embodiments, in the step 2, the molar ratio of the compound II-3, the compound d and the base is 1:(0.5-2):(0.5-20), preferably 1:(0.8-2):(0.8-3), more preferably 1:(1-1.5):(1-2).

In some embodiments, in the step 2, the molar ratio of the compound II-3 to the condensation reagent is 1:(1-3), preferably 1:(1.2-2.0).

In some embodiments, the step 3 is carried out at a temperature of −20° C. to 50° C. (preferably −5° C. to 25° C.).

In some embodiments, in the step 3, the molar ratio of the compound II-4 to the compound I-2 is 1:(0.5-5), preferably 1:(0.8-3), more preferably 1:(1-2.5).

In some embodiments, in the step 3, the molar ratio of the compound II-4, the compound I-2 and the base is 1:(0.5-2):(0.5-20), preferably 1:(0.8-2):(0.8-3), more preferably 1:(1-1.5):(1-2).

In some embodiments, in the step 3, the molar ratio of the compound II-4 to the condensation reagent is 1:(1-3), preferably 1:(1.2-2.0).

In some embodiments, the method further comprises step 4: coupling the compound II-5 with a targeting moiety (E).

In some embodiments, the targeting moiety (E) is a monoclonal antibody against Her 2 (for example, trastuzumab, pertuzumab) or a monoclonal antibody against Trop-2 (for example, sacituzumab), or an active fragment or variant thereof.

In some embodiments, the step 4 comprises: mixing a targeting moiety (E) with the compound II-5.

In some embodiments, the molar ratio of the targeting moiety (E) to the compound II-5 is 1:(1-20).

In some embodiments, the step 4 comprises: mixing a solution comprising a targeting moiety (E) with the compound II-5.

In some embodiments, the step 1, the step 2, the step 3 and/or the step 4 are carried out in water or an organic solvent.

In some embodiments, the organic solvent is selected from N,N-dimethylformamide, dimethyl sulfoxide, N-methylpyrrolidone, saturated hydrocarbons (for example, cyclohexane, hexane), halogenated hydrocarbons (for example, dichloromethane, chloroform, 1,2-dichloroethane), ethers (for example, tetrahydrofuran, diethyl ether, dioxane, 1,2-dimethoxy ethane), nitriles (for example, acetonitrile), alcohols (for example, methanol, ethanol) and any combination thereof.

In some embodiments, the method further comprises step 5, wherein the step 5 comprises: purifying the product of the step 4 by chromatography (for example, one or more of ion exchange chromatography, hydrophobic chromatography, reversed phase chromatography and affinity chromatography).

Beneficial Effect

The toxin molecule of the present invention has obvious in vitro cytotoxic activity, good stability, and simple preparation method, and can be efficiently coupled with an antibody by different coupling methods. The linker of the present invention can efficiently couple the toxin molecule with an antibody, and the coupling map shows that the coupling efficiency is high and the remaining antibody is little. The drug-antibody conjugate of the present invention can smoothly release the toxin molecule in a cell, has strong inhibitory ability to tumor cell, and is expected to have excellent anti-tumor effect.

SEQUENCE INFORMATION

Figure 1:
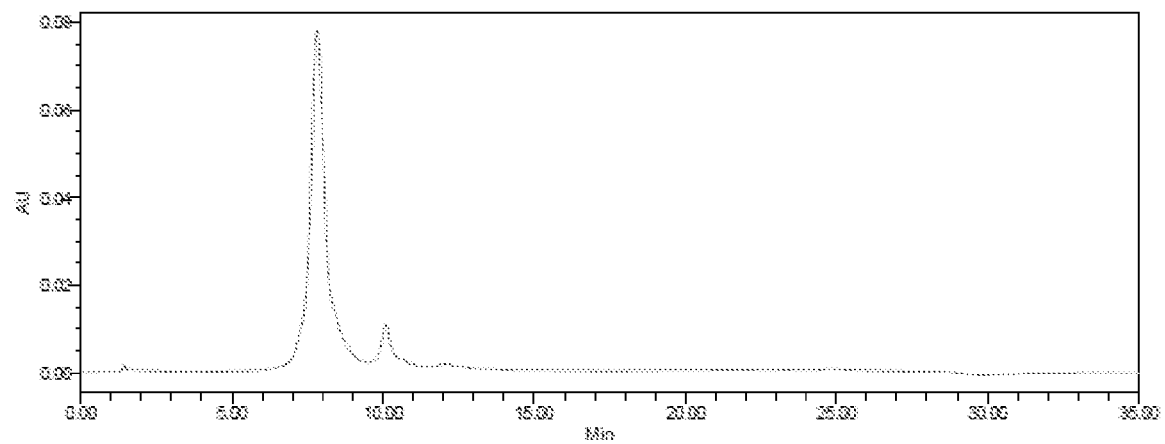
FIG. 1 is HIC map of naked antibody (M141105Y).
Figure 2:
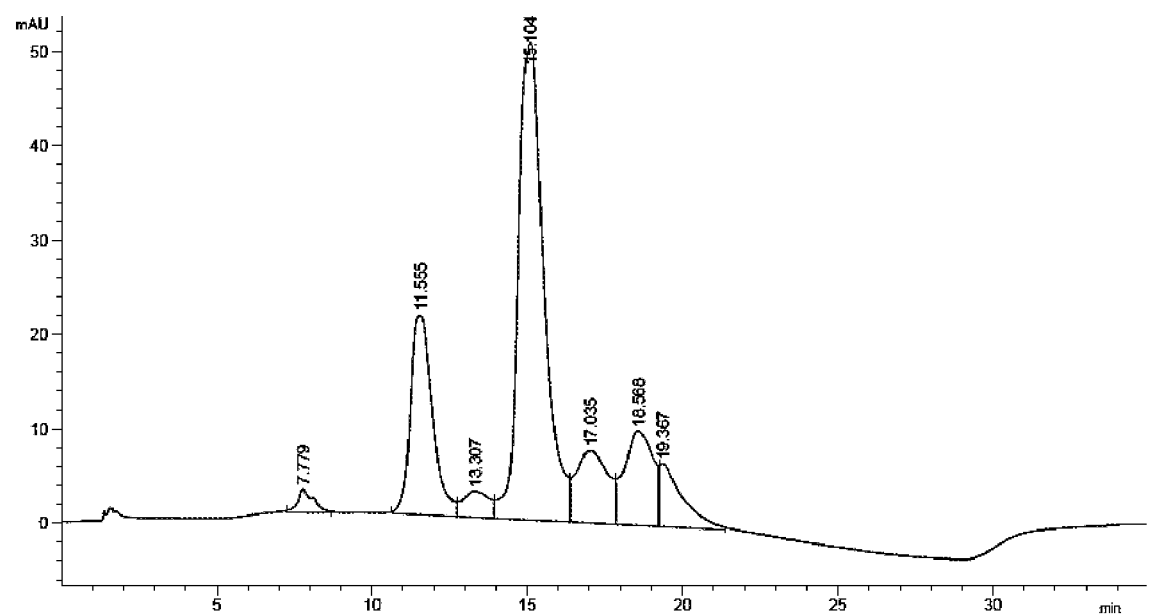
FIG. 2 is HIC map of TL004-T-ADC.
Figure 3:
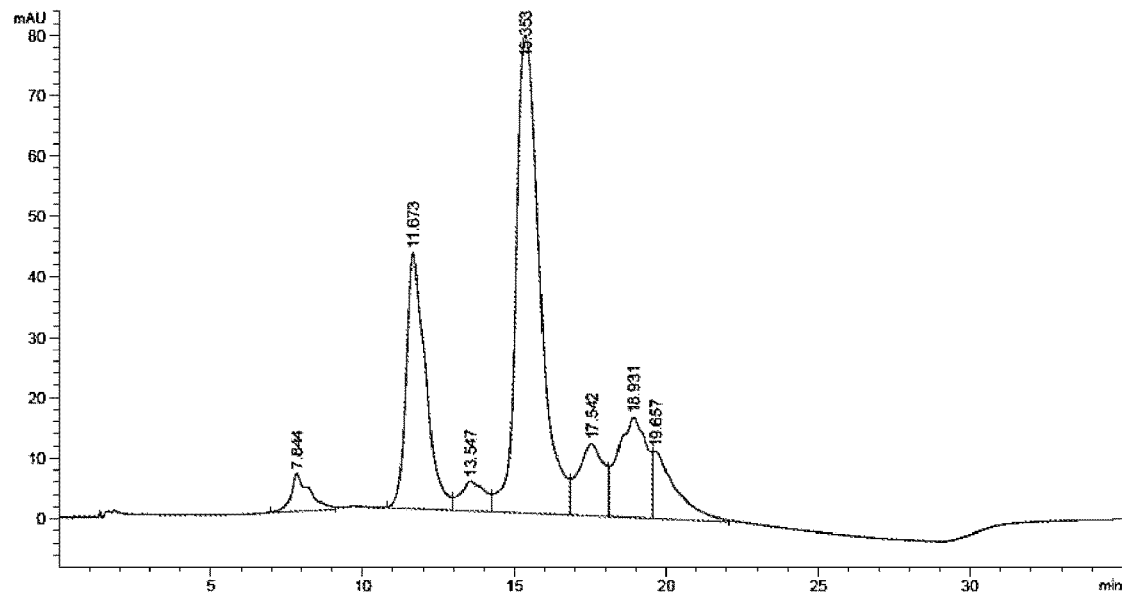
FIG. 3 is HIC map of TL006-T-ADC.
Figure 4:
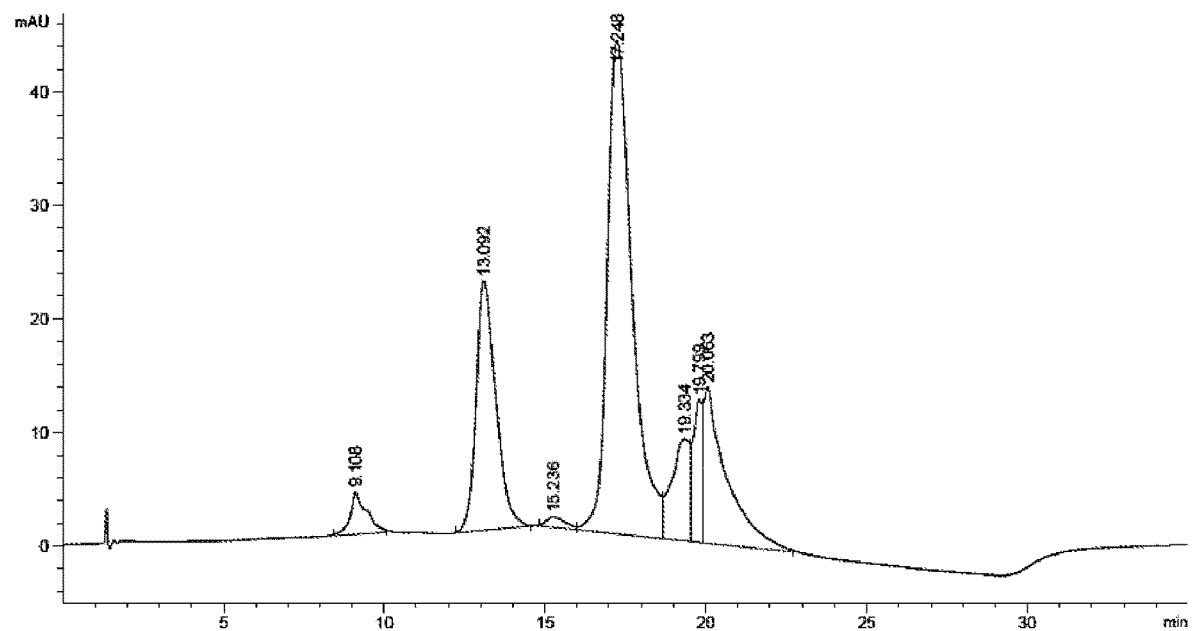
FIG. 4 is HIC map of TL007-T-ADC.
Figure 5:
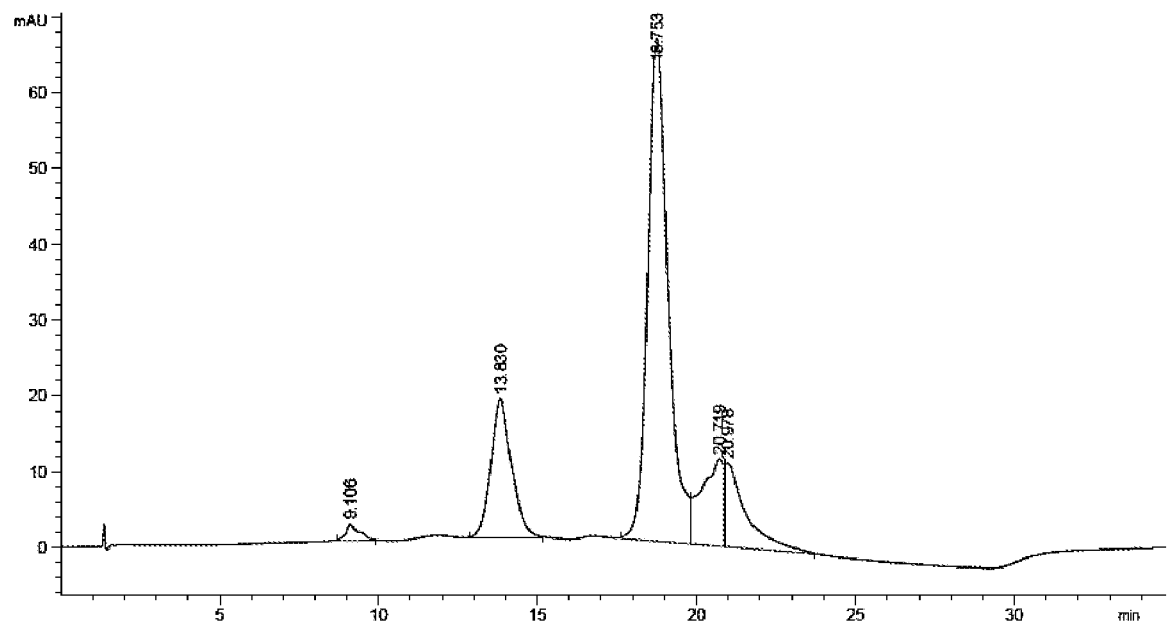
FIG. 5 is HIC map of TL008-T-ADC.
Figure 6:
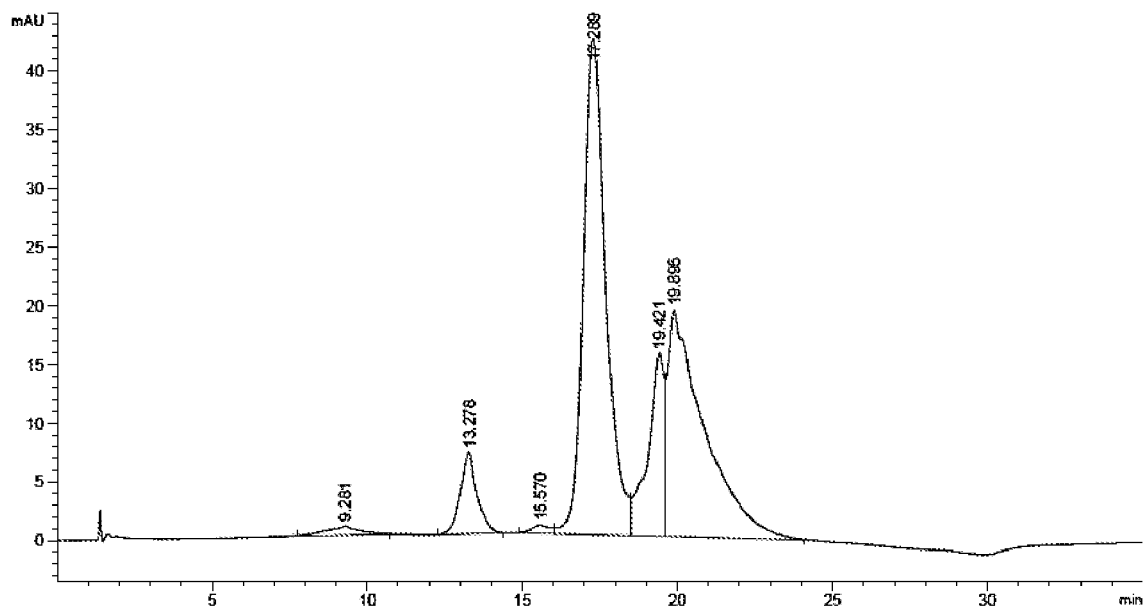
FIG. 6 is HIC map of TL009-T-ADC.
Figure 7:
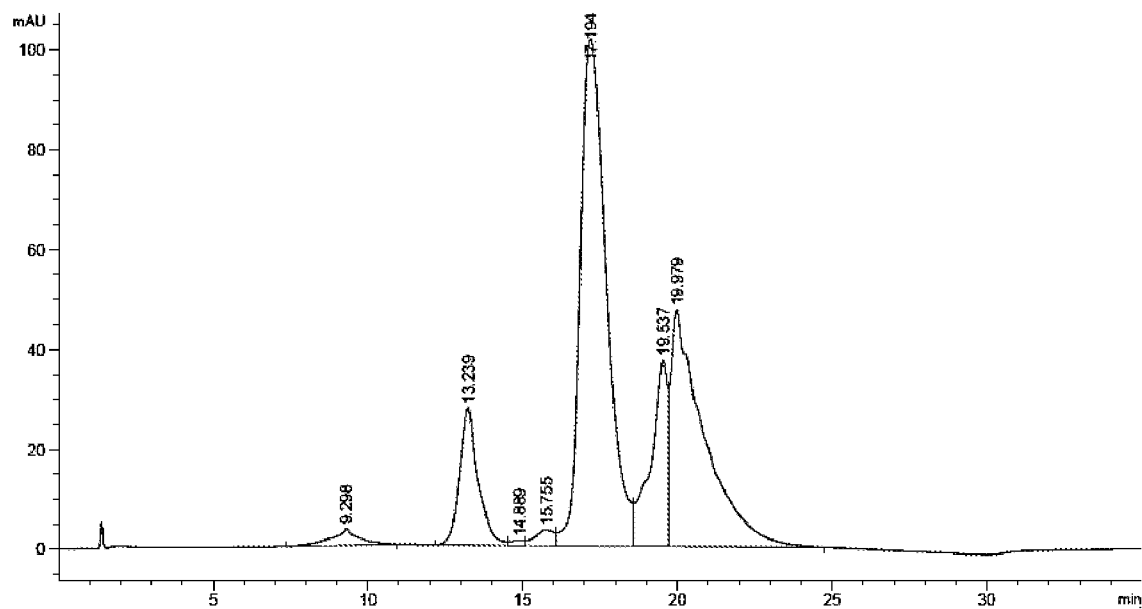
FIG. 7 is HIC map of TL010-T-ADC.
Figure 8:
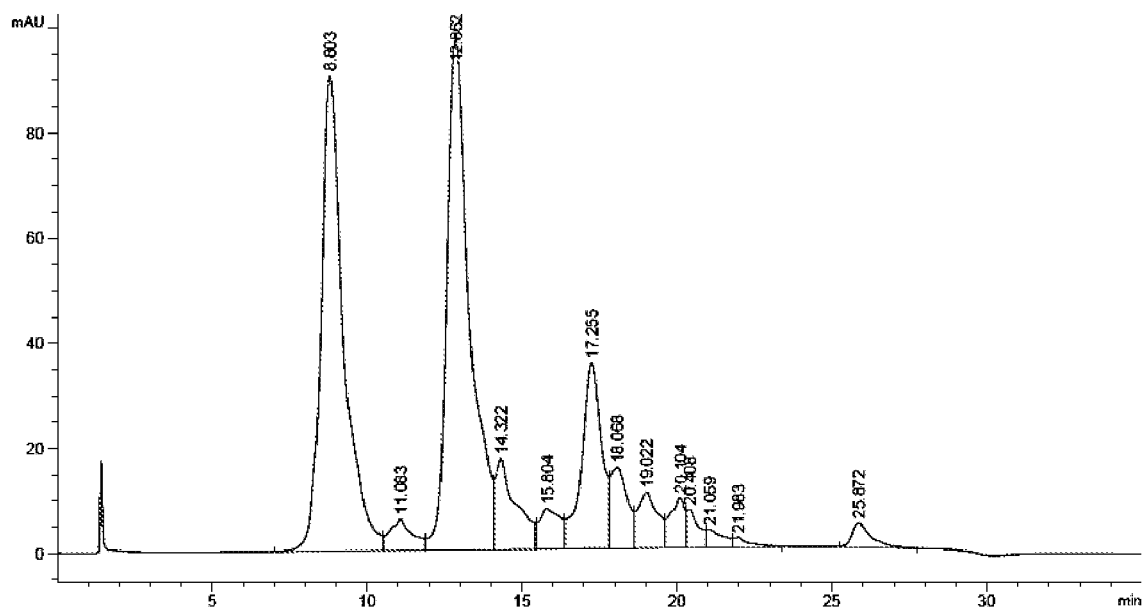
FIG. 8 is HIC map of TL011-T-ADC.
Figure 9:
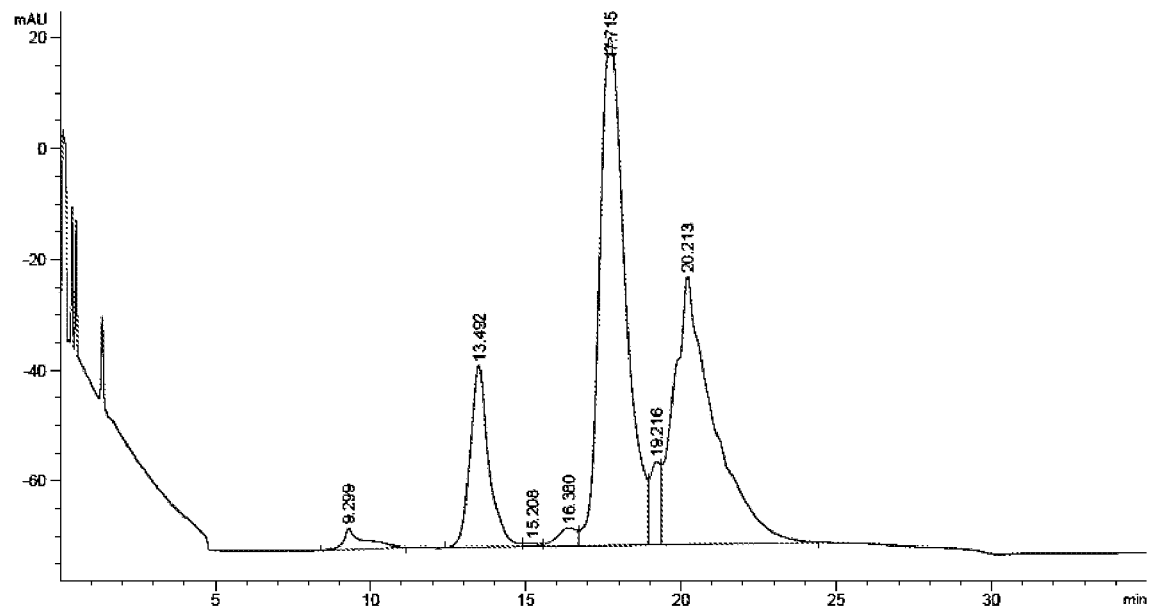
FIG. 9 is HIC map of TL012-T-ADC.
Figure 10:
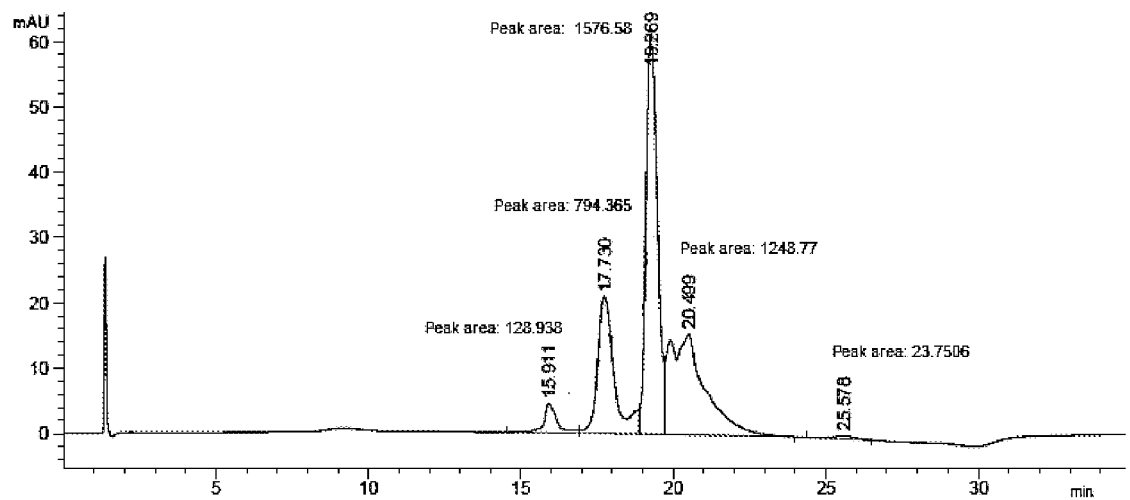
FIG. 10 is HIC map of TL007-S-ADC.
Figure 11:
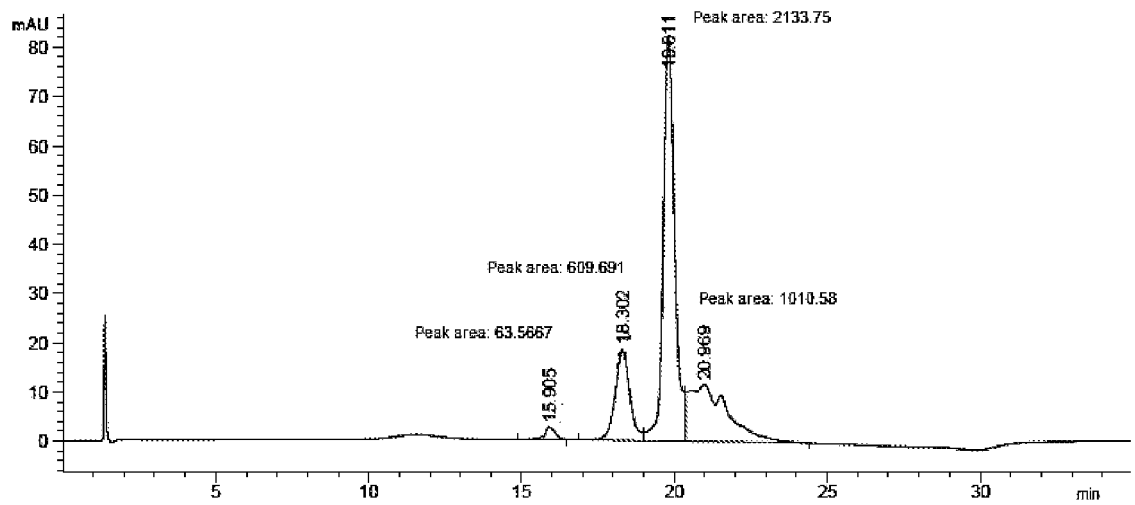
FIG. 11 is HIC map of TL008-S-ADC.

The information of sequences involved in the present invention is provided in the following table.

| Sequence No. (SEQ ID NO:) | Description |
| --- | --- |
| 1 | Heavy chain sequence of trastuzumab |
| 2 | Light chain sequence of trastuzumab |

SEQ ID NO: 1
EVQLVESGGGLVQPGGSLRLSCAASGFNIKDTYIHWVRQAPGKGLEWVAR
TYPTNGYTRYADSVKGRFTISADTSKNTAYLQMNSLRAEDTAVYYCSRWG
GDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 2
DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Mode of Carrying Out the Invention

The present invention is further illustrated by the following description of specific embodiments, but this is not a limitation to the present invention. Various modifications or improvements can be made by those skilled in the art in accordance with the teachings of the present invention without departing from the basic idea and scope of the present invention.

Preparation Scheme

The above contents of the present invention are further described in detail by the specific embodiments of the following examples. However, the scope of the present invention is not limited to the following examples. All technologies that are carried out on the basis of the above contents of the present invention belong to the scope of the present invention.

The structures of the compounds described in the following examples are determined by nuclear magnetic resonance ($^1$H NMR) or mass spectrometry (MS).

The nuclear magnetic resonance ($^1$H NMR) measuring is conducted with Bruker 400 MHz NMR instrument; the solvent is deuterated methanol (CD$_3$OD), deuterated chloroform (CDCl$_3$) or hexadeuterated dimethyl sulfoxide (DMSO-d$_6$); the internal standard is tetramethyl silane (TMS).

The abbreviations for nuclear magnetic resonance (NMR) spectrum used in the examples are given below.

s: singlet, d: doublet, t: triplet, q: quartet, dd: double doublet, qd: quadruple doublet, ddd: double double doublet, ddt: double double triplet, dddd: double double double doublet, m: multiplet, br: broad, J: coupling constant, Hz: hertz, DMSO-d$_6$: deuterated dimethyl sulfoxide.

All δ values are expressed in ppm.

The mass spectrometry (MS) measuring is conducted with Agilent (ESI) mass spectrometer, model: Agilent 6120B.

I. Synthesis of Cytotoxic Agents

Example 1 Synthesis of (2S)—N-((3R,4S,5 S)-1-((2S)-2-((1R,2R)-3-((1-((4-aminobenzyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide (T001)

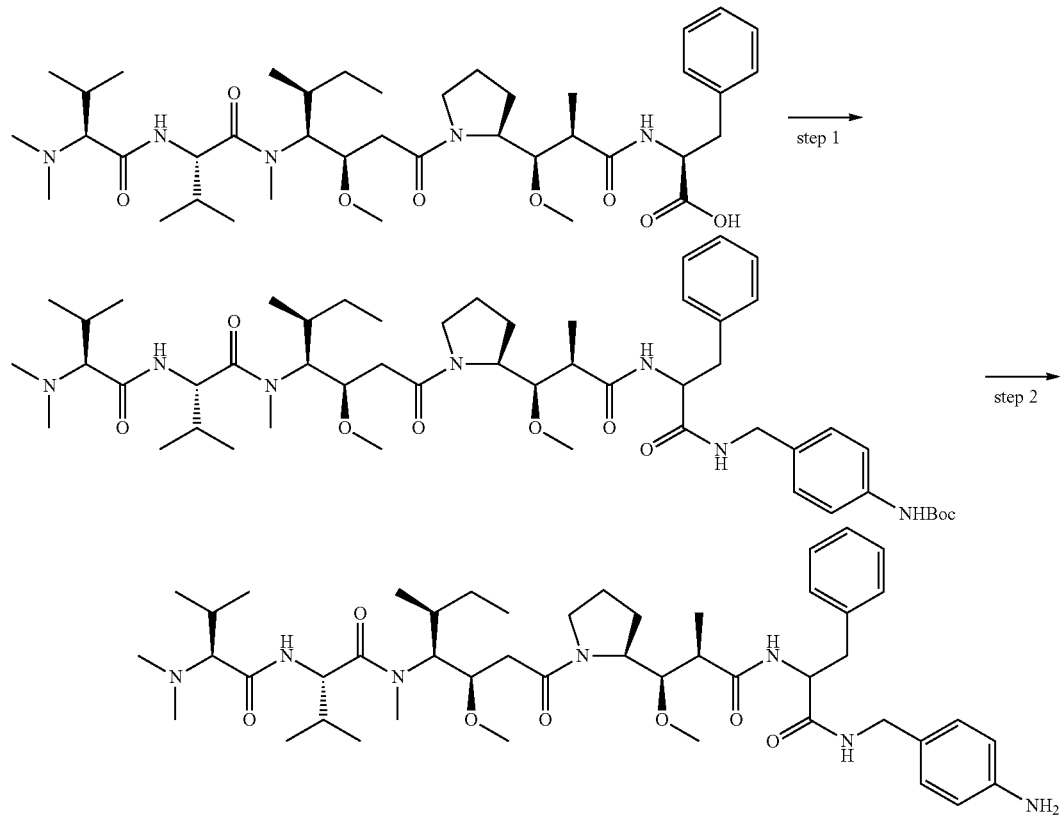

Step 1

Synthesis of tert-butyl (4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl) carbamate At room temperature, 1-hydroxybenzotriazole (2.0 mg, 14.74 μmol) was dissolved in N,N-dimethylformamide (4 mL), cooled down to 0° C., to which were added in sequence tert-butyl (4-methylaminobenzyl)-carbamate (4.0 mg, 16.1 μmol), DIEA (8.5 mg, 66.8 μmol), and ((2R,3R)-3-((S)-1-((3R,4 S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-L-phenylalanine (10.0 mg, 13.5 μmol, purchased), stirred for 5 min, and then benzotriazole-1-yl-oxytripyrrolidinophosphonium hexafluorophosphate (10.0 mg, 20.1 μmol) was added, followed by reaction at 0° C. with stirring for 1 h. A complete reaction of raw materials was monitored by high performance liquid chromatography-mass spectrometry, and the reaction solution was purified by preparative liquid chromatography to give the title compound, a white solid, 9.0 mg. ESI-MS (m/z): 950.5 [M+H]$^+$.

Step 2

Synthesis of (2S)—N-((3R,4S,5S)-1-((2S)-2-((1R,2R)-3-((1-((4-aminobenzyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide At room temperature, tert-butyl (4-((2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)carbamate (9.0 mg, 0.02 mmol) was dissolved in 1,4-dioxane (0.5 mL), cooled down to 0° C., and then HCl-dioxane solution (1 mL, 4.0 M) was added, followed by reaction with stirring at room temperature for 3 h. A complete reaction of raw materials was monitored by high performance liquid chromatography-mass spectrometry, the solvent was removed by vacuum distillation, and the crude product was purified by preparative liquid chromatography, to give the title compound, a white solid, 5.0 mg. ESI-MS (m/z): 850.5 [M+H]$^+$.

Example 2 Synthesis of (S)—N-((3R,4 S,5 S)-1-((S)-2-((1R,2R)-3-(((R)-1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide
(T002)

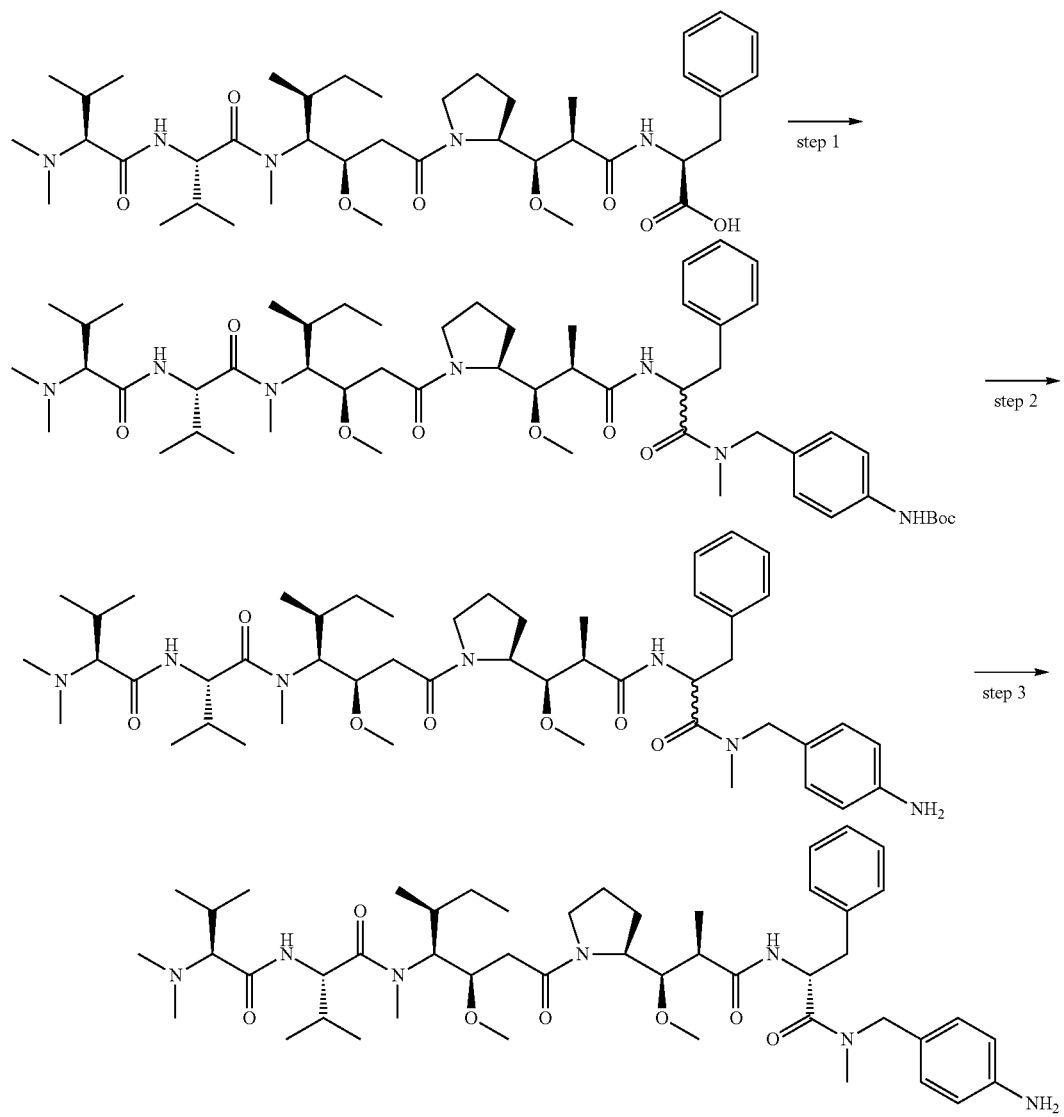

Step 1

Synthesis of tert-butyl (4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)carbamate At room temperature, 1-hydroxybenzotriazole (2.0 mg, 14.74 μmol) was dissolved in N,N-dimethylformamide (2 mL), cooled down to 0° C., to which were added in sequence tert-butyl (4-methylaminobenzyl)-carbamate (2.0 mg, 8.04 μmol), DIEA (4.3 mg, 33.5 μmol), and ((2R,3R)-3-((S)-1-((3R,4 S,5 S)-4-((S)-2-((S)-2-(dimethylamino)-3-methylbutyramido)-N,3-dimethylbutyramido)-3-methoxy-5-methyl-heptanoyl)pyrrolidin-2-yl)-3-methoxy-2-methylpropionyl)-L-phenylalanine (5.0 mg, 6.7 μmol, purchased), stirred for 5 min, and then benzotriazole-1-yl-oxytripyrrolidinophosphonium hexafluorophosphate (5.0 mg, 10.05 μmol) was added, followed by reaction at 0° C. with stirring for 1 h. A complete reaction of raw materials was monitored by high performance liquid chromatography-mass spectrometry, and the reaction solution was purified by preparative liquid chromatography to give the title compound, a white solid, 4.0 mg. ESI-MS (m/z): 964.5 [M+H]+.

Step 2

Synthesis of (2S)—N-((3R,4S,5S)-1-((2R,4S)-2-((1R,2R)-3-((1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide At room temperature, tert-butyl (4-((2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)carbamate (20 mg, 0.02 mmol) was dissolved in 1,4-dioxane (1 mL), cooled down to 0° C., and then HCl-dioxane solution (1 mL, 4.0 M) was added, followed by reaction with stirring at room temperature for 3 h. A complete reaction of raw materials was monitored by high performance liquid chromatography-mass spectrometry, the solvent was removed by vacuum distillation, and the crude product was purified by preparative liquid chromatography to give the title compound, a white solid, 10 mg. ESI-MS (m/z): 864.5 [M+H]⁺.

| Column type | CHIRALCEL OD-H |
|---|---|
| Column specification | 0.46 cm I.D. × 15 cm L |
| Flow phase | Hexane/IPA/MeOH = 85/10/5 (V/V/V) |
| Flow rate | 1.0 ml/min |
| Detection wavelength | UV 240 nm |
| Temperature | 35° C. | to give the title compound, a white solid, 3.6 mg. ee %=95.9%, R$_t$=4.355 min, ESI-MS (m/z): 864.5 [M+H]⁺.

Example 3 Synthesis of (S)—N-((3R,4S,5 S)-1-((S)-2-((1R,2R)-3-(((S)-1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide
(T003)

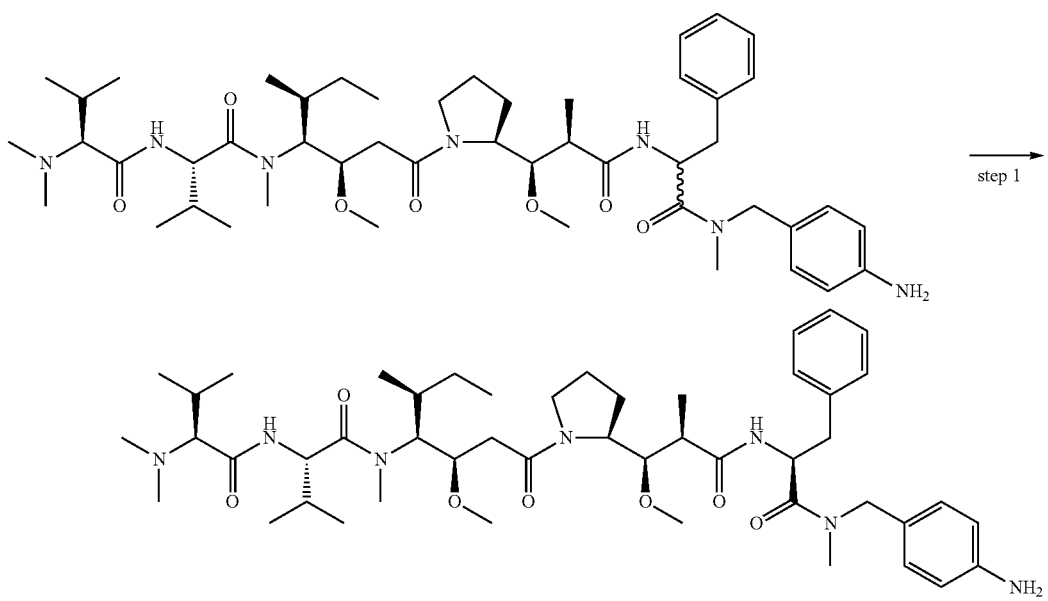

Step 1

Synthesis of (S)—N-((3R,4S,5S)-1-((S)-2-((1R,2R)-3-(((S)-1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide (2S)—N-((3R,4S,5 S)-1-((2S)-2-((1R,2R)-3-((1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide was subjected to chiral separation (under the same conditions as those in Example 2, Step 3), to give the title compound, a white solid, 5.2 mg. ee %=97.8%, Rt=5.554 min, ESI-MS (m/z): 864.5 [M+H]⁺.

Step 3

Synthesis of (S)—N-((3R,4 S,5 S)-1-((S)-2-((1R,2R)-3-(((R)-1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide (2S)—N-((3R,4S,5 S)-1-((2S)-2-((1R,2R)-3-((1-((4-aminobenzyl)(methyl)amino)-1-oxo-3-phenylprop-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyramido)-N,3-dimethylbutyramide was subjected to chiral separation, under the following conditions:

Example 4 Synthesis of (S)—N-((3R,4S,5 S)-1-((S)-2-((1R,2R)-3-((S)-1-((4-aminobenzyl)amino)-1-oxo-3-phenylprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T011)
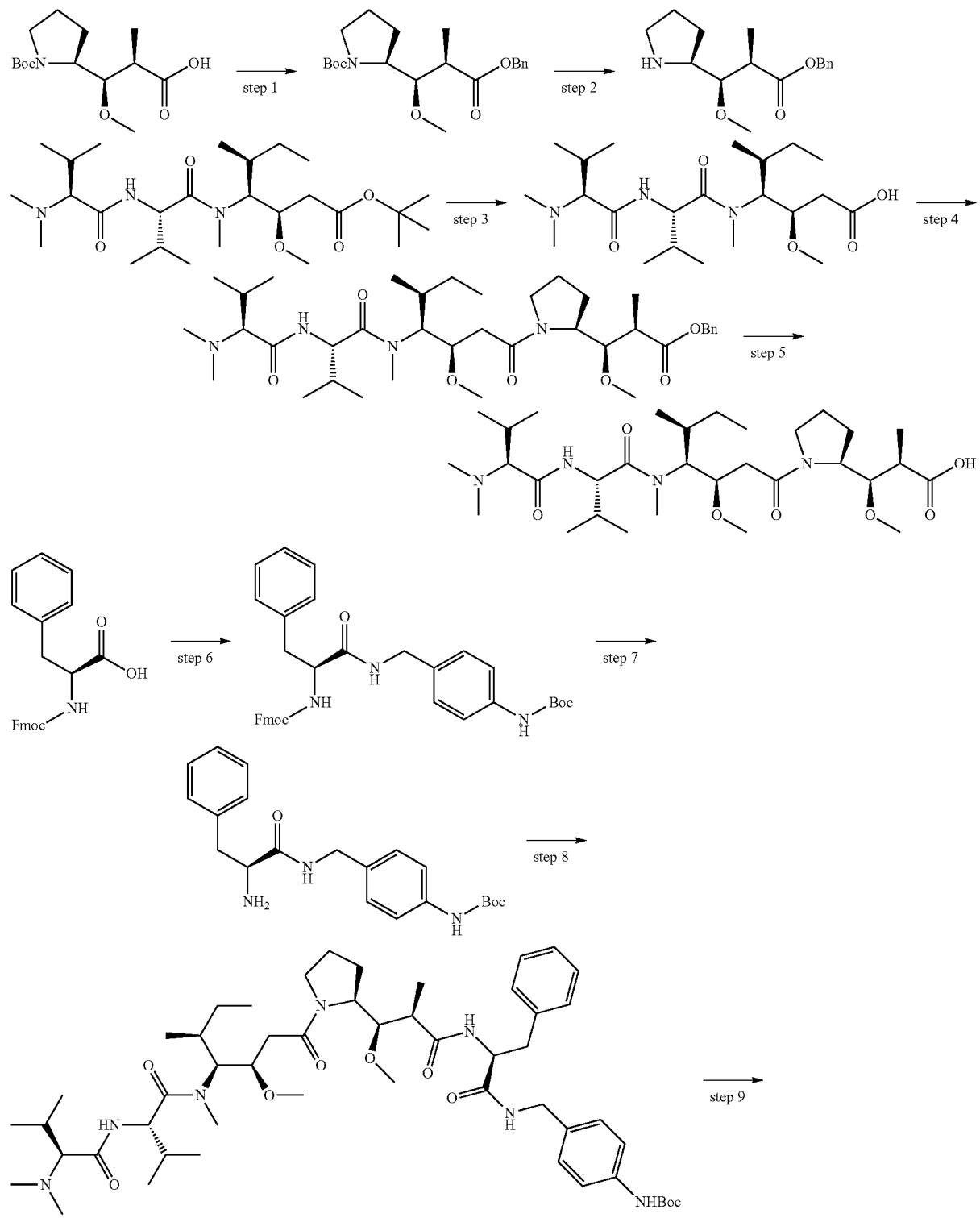

-continued

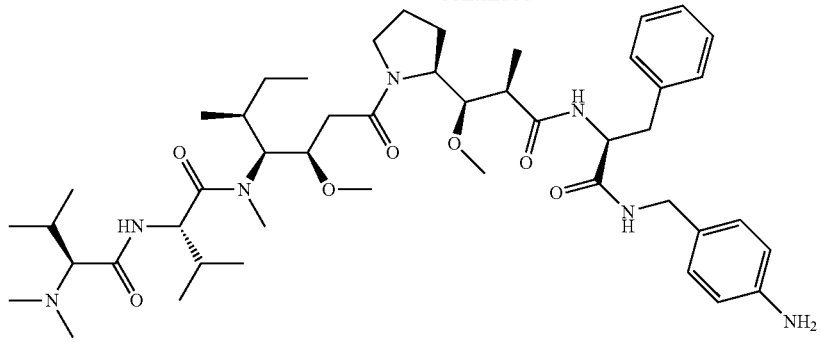

Step 1

Synthesis of tert-butyl (S)-2-((1R,2R)-3-(benzyloxy)-1-methoxy-2-methyl-3-oxopropyl)pyrrolidine-1-formate Cesium carbonate (2.5 g, 7.5 mmol), (2R,3R)-3-((S)-1-(tert-butoxycarbonyl)pyrrolidin-2-yl)-3-methoxy-2-methyl-propionic acid (1.8 g, 6.3 mmol) were added in a solution of N,N-dimethylformamide (25 mL), stirred at room temperature for 0.5 h, then benzyl bromide (1.6 g, 9.3 mmol) was added, and stirred at room temperature overnight. Water (150 mL) was added in the reaction solution, followed by extraction with ethyl acetate (50 mL×3), organic phases were combined, washed with saturated salt solution (50 mL×3), and dried with anhydrous sodium sulfate. The desiccant was removed by filtration, the solvent was removed by vacuum distillation, and purified by silica gel column, to give the title compound, a colorless oily substance, 2.3 g. ESI-MS (m/z): 322.1 [M−56+H]$^+$.

Step 2

Synthesis of benzyl (2R,3R)-3-methoxy-2-methyl-3-((S)-pyrrolidin-2-yl)-propionate Tert-butyl (S)-2-((1R,2R)-3-(benzyloxy)-1-methoxy-2-methyl-3-oxopropyl)pyrrolidine-1-formate (2.3 g, 6.1 mmol) was dissolved in a solution of trifluoroacetic acid (8 mL) in dichloromethane (24 mL), and reacted at room temperature for 4 h. The solvent was removed by vacuum distillation, to give trifluoroacetate of the title compound 2.4 g. Without purification, the product was directly used in the next step of reaction. ESI-MS (m/z): 278.2 [M+H]$^+$.

Step 3

Synthesis of (3R,4S,5S)-4-((S)-2-((S)-2-(dimethylamino)-3-methylbutyramide)-N,3-dimethylbutyramide)-3-methoxy-5-methylheptanoic acid Tert-butyl (3R,4S,5 S)-4-((S)-2-((S)-2-(dimethylamino)-3-methylbutylamino)-N,3-dimethylbutyramide)-3-methoxy-5-methylheptanoate (2.4 g, 4.9 mmol) was dissolved in a solution of trifluoroacetic acid (10 mL) in dichloromethane (30 mL), and reacted at room temperature for 3.5 h. The solvent was removed by vacuum distillation, to give the title compound 2.5 g. Without purification, the product was directly used in the next step of reaction.

ESI-MS (m/z): 430.3[M+H]$^+$.

Step 4

Synthesis of benzyl (2R,3R)-3-((S)-1-((3R,4S,5 S)-4-((S)-2-((S)-2-(dimethylamino)-3-methylbutyramide)-N,3-dimethylbutyramide)-3-methoxy-5-methylheptanoyl)pyrrolidin-2-yl)-3-methoxy-2-methylpropionate Benzyl (2R,3R)-3-methoxy-2-methyl-3-((S)-pyrrolidin-2-yl)-propionate (2.2 g, 4.4 mmol) and (3R,4S,5 S)-4-((S)-2-((S)-2-(dimethylamino)-3-methylbutyramide)-N,3-dimethylbutyramide)-3-methoxy-5-methylheptanoic acid (2.1 g, 4.4 mmol) were dissolved in N,N-dimethylformamide (30 mL), to which were added in sequence diisopropylethylamine (1.14 g, 8.8 mmol), and 2-(7-oxobenzotriazole)-N,N,N',N'-tetramethyluronium hexafluophosphate (2.5 g, 6.6 mmol), and reacted at room temperature overnight. Water (150 mL) was added in quench the reaction, followed by extraction with ethyl acetate (50 mL×4), organic phases were combined, washed with saturated salt solution (30 mL×4), and dried with anhydrous sodium sulfate. The desiccant was removed by filtration, the solvent was removed by vacuum distillation, and the residue was purified by preparative liquid chromatography, to give the title compound, a colorless oily substance, 2.3 g. ESI-MS (m/z): 689.4[M+H]$^+$.

Step 5

Synthesis of (2R,3R)-3-((S)-1-((3R,4S,5S)-4-((S)-2-((S)-2-(dimethylamino)-3-methylbutyramide)-N,3-dimethylbutyramide)-3-methoxy-5-methylheptanoyl)pyrrolidin-2-yl)-3-methoxy-2-methylpropionic acid Benzyl (2R,3R)-3-((S)-1-((3R,4S,5 S)-4-((S)-2-((S)-2-(dimethylamino)-3-methylbutyramide)-N,3-dimethylbutyramide)-3-methoxy-5-methylheptanoyl)pyrrolidin-2-yl)-3-methoxy-2-methylpropionate (2.0 g, 3.0 mmol) was dissolved in a mixed solution of methanol (100 mL) and dichloromethane (5 mL), then Pd—C (200 mg) was added in the reaction solution, and reacted in a hydrogen atmosphere for 2 h. Insolubles were removed by filtration, the filter cake was washed with methanol (30 mL×3), and the solvent was removed by vacuum distillation, to give the title compound, a white-like solid, 1.8 g. ESI-MS (m/z): 599.4 [M+H]$^+$.

Step 6

Synthesis of tert-butyl (S)-(4-((2-(((((9H-fluoren-9-yl) methoxy)carbonyl)amino)-3-phenylpropionamido)methyl)phenyl)carbamate At 0° C., 4-aminobenzylamine (222 mg, 1.0 mmol) and N-methylmorpholine (306 mg, 1.5 mmol) were added in a solution of (S)-2-((((9H-fluoren-9-yl) methoxy)carbonyl)amino)-3-phenylpropionic acid (387 mg, 1.0 mmol) in N,N-dimethylformamide (5 mL), to which were added in sequence HOBT (203 mg, 1.5 mmol), and EDCI (288 mg, 1.5 mmol), followed by reaction at 0° C. overnight. As detected by LCMS, the raw materials disappeared. The reaction solution was poured into water (50 mL), to precipitate out a white solid, and filtered, the filter cake was washed with water (20 mL×3), and the solid was purified by silica gel column, to give the title compound, a white solid, 380 mg. ESI-MS (m/z): 592.3 [M+H]$^+$.

Step 7

Synthesis of tert-butyl (S)-(4-((2-amino-3-phenylpropionamido)methyl)phenyl)carbamate Lithium hydroxide monohydrate (21 mg, 0.51 mmol) was dissolved in water (1 mL), and added in a solution of tert-butyl (S)-(4-((2-(((((9H-fluoren-9-yl) methoxy)carbonyl)amino)-3-phenylpropionamido)methyl)phenyl)carbamate (102 mg, 0.17 mmol) in tetrahydrofuran (2 mL), and reacted at room temperature for 2 h. As detected by LCMS, the raw materials disappeared. Water (20 mL) was added in the reaction solution, followed by extraction with ethyl acetate (30 mL×4). Organic phases were combined, washed with saturated salt solution (30 mL×2), and dried with anhydrous sodium sulfate. The desiccant was removed by filtration, the solvent was removed by vacuum distillation, and the residue was purified by preparative liquid chromatography, to give the title compound, a white solid, 65 mg. ESI-MS (m/z): 370.2 [M+H]$^+$.

Step 8

Synthesis of (4-((S)-2-((2R,3R)-3-((S)-1-((3R,4S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamate At 0° C., tert-butyl (S)-(4-((2-amino-3-phenylpropionamido)methyl)phenyl)carbamate (15 mg, 0.04 mmol) and N-methylmorpholine (12 mg, 0.12 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (24 mg, 0.04 mmol) in N,N-dimethylformamide (2 mL), to which were added in sequence HOBT (8 mg, 0.06 mmol), and EDCI (12 mg, 0.06 mmol), and reacted at 0° C. overnight. As detected by LCMS, the raw materials disappeared. The reaction solution was purified by preparative liquid chromatography, to give the title compound, a white solid, 24 mg. ESI-MS (m/z): 950.6 [M+H]$^+$.

Step 9

Synthesis of (S)—N-((3R,4S,5 S)-1-((S)-2-((1R, 2R)-3-((S)-1-((4-aminobenzyl)amino)-1-oxo-3-phenylprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of (4-((S)-2-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl) phenyl)carbamate (14.0 mg, 0.015 mmol) in dichloromethane (1.5 mL), and reacted at room temperature for 1 h. As detected by LCMS, the raw materials disappeared completely. The solvent was removed by vacuum distillation, and the residue was purified by preparative liquid chromatography, to give trifluoroacetate of the title compound, a white solid, 4.2 mg. ESI-MS (m/z): 850.6 [M+H]$^+$.

Example 5 Synthesis of (S)—N-((3R,4S,5 S)-1-((S)-2-((1R,2R)-3-((R)-1-((4-aminobenzyl)amino)-1-oxo-3-phenylprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T012)

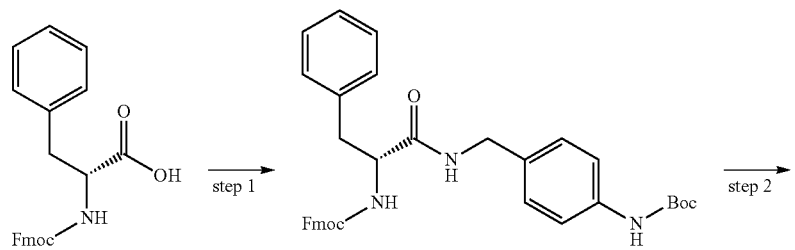

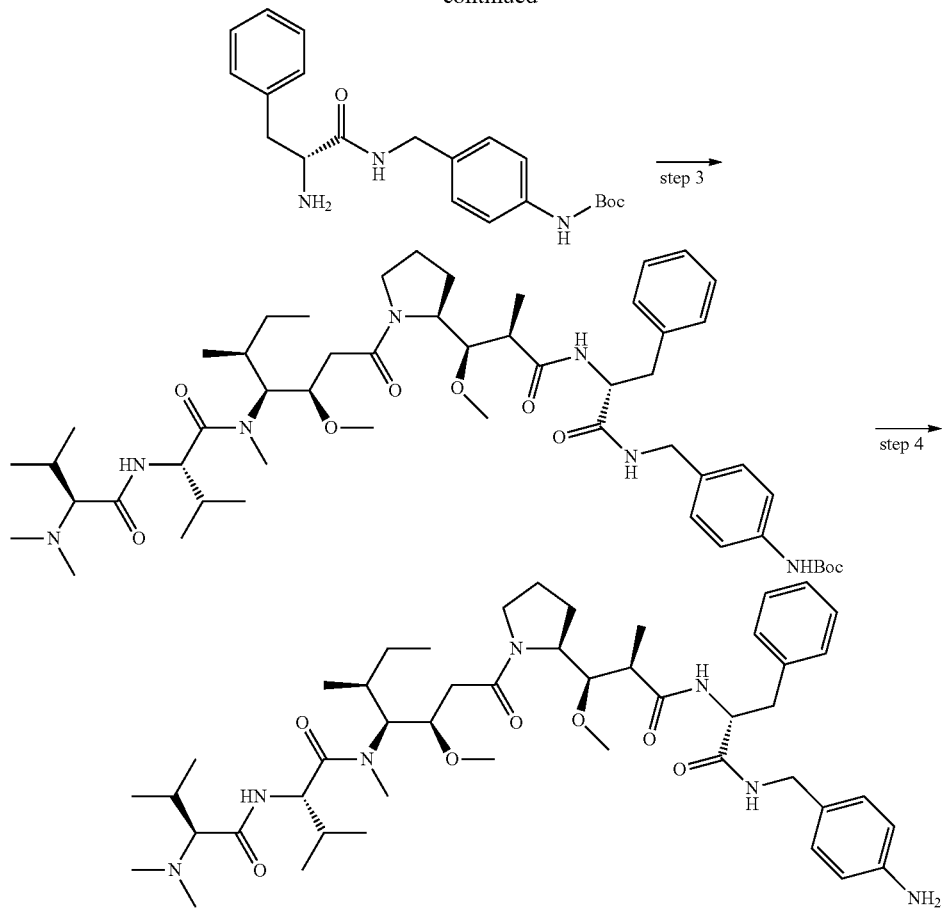

Step 1

Synthesis of tert-butyl (R)-(4-((2-((((9H-fluoren-9-yl) methoxy)carbonyl)amino)-3-phenylpropionamido)methyl)phenyl)carbamate At 0° C., 4-aminobenzylamine (445 mg, 2.0 mmol) and N-methylmorpholine (300 mg, 3.0 mmol) were added in a solution of (R)-2-((((9H-fluoren-9-yl) methoxy)carbonyl) amino)-3-phenylpropionic acid (775 mg, 2.0 mmol) in N,N-dimethylformamide (12 mL), to which were added in sequence HOBT (405 mg, 3.0 mmol), and EDCI (575 mg, 3.0 mmol), and reacted at 0° C. overnight. As detected by LCMS, the raw materials disappeared. The reaction solution was poured into water (50 mL), to precipitate out a white solid, the filter cake was washed with water (20 mL×3), and dried, to give the title compound, a white solid, 880 mg. ESI-MS (m/z): 592.3 [M+H]$^+$.

Step 2

Synthesis of tert-butyl (R)-(4-((2-amino-3-phenylpropionamido)methyl)phenyl)carbamate Lithium hydroxide monohydrate (42 mg, 1.0 mmol) was dissolved in water (2 mL), and added in a solution of tert-butyl (R)-(4-((2-((((9H-fluoren-9-yl)methoxy)carbonyl) amino)-3-phenylpropionamido)methyl)phenyl)carbamate (200 mg, 0.34 mmol) in tetrahydrofuran (3 mL), and reacted at room temperature for 2 h. As detected by LCMS, the raw materials disappeared. Water (20 mL) was added in the reaction solution, which was then extracted with ethyl acetate (30 mL×4). Organic phases were combined, washed with saturated salt solution (30 mL×2), and dried with anhydrous sodium sulfate. The desiccant was removed by filtration, the solvent was removed by vacuum distillation, and the residue was purified by preparative liquid chromatography, to give the title compound, a white solid, 120 mg. ESI-MS (m/z): 370.2 [M+H]$^+$.

Step 3

Synthesis of tert-butyl (4-((R)-2-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido) methyl)phenyl)carbamate At 0° C., tert-butyl (R)-(4-((2-amino-3-phenylpropionamido)methyl)phenyl)carbamate (30 mg, 0.04 mmol) and N-methylmorpholine (24 mg, 0.24 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionic acid (50 mg, 0.08 mmol) in N,N-dimethylformamide (2 mL), to which were added in sequence HOBT (16 mg, 0.12 mmol), and EDCI (23 mg, 0.12 mmol), and reacted at 0° C. overnight. As detected by LCMS, the raw materials disappeared. The reaction solution was purified by preparative liquid chromatography, to give the title compound, a white solid, 32 mg. ESI-MS (m/z): 950.6 [M+H]+.

Step 4

Synthesis of (S)—N-((3R,4S,5S)-1-((S)-2-((1R,2R)-3-((R)-1-((4-aminobenzyl)amino)-1-oxo-3-phenyl-prop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (1 mL) was added in a solution of tert-butyl (4-((R)-2-((2R,3R)-3-((S)-1-((3R,4S,5 S)-4-((S)-3-(methylamino)-3-methylbutyramido)-N,3-dimethylbu-tyramido)-3-methoxy-5-methylheptanoyl)pyrrolidin-2-yl)-3-methoxy-2-methylpropionamido)-3-phenylpropionamido)methyl)phenyl)carbamate (32.0 mg, 0.03 mmol) in dichloromethane (3 mL), and reacted at room temperature for 1 h. As detected by LCMS, the raw materials disappeared completely. The solvent was removed by vacuum distillation, and the residue was purified by preparative liquid chromatography, to give trifluoroacetate of the title compound, a light yellow solid, 13.3 mg. ESI-MS (m/z): 850.6 [M+H]+.

Example 6 Synthesis of (S)—N-((3R,4S,5 S)-1-((S)-2-((1R,2R)-3-(((S)-4-((4-aminobenzyl)amino)-4-oxo-1-phenylbut-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T013)

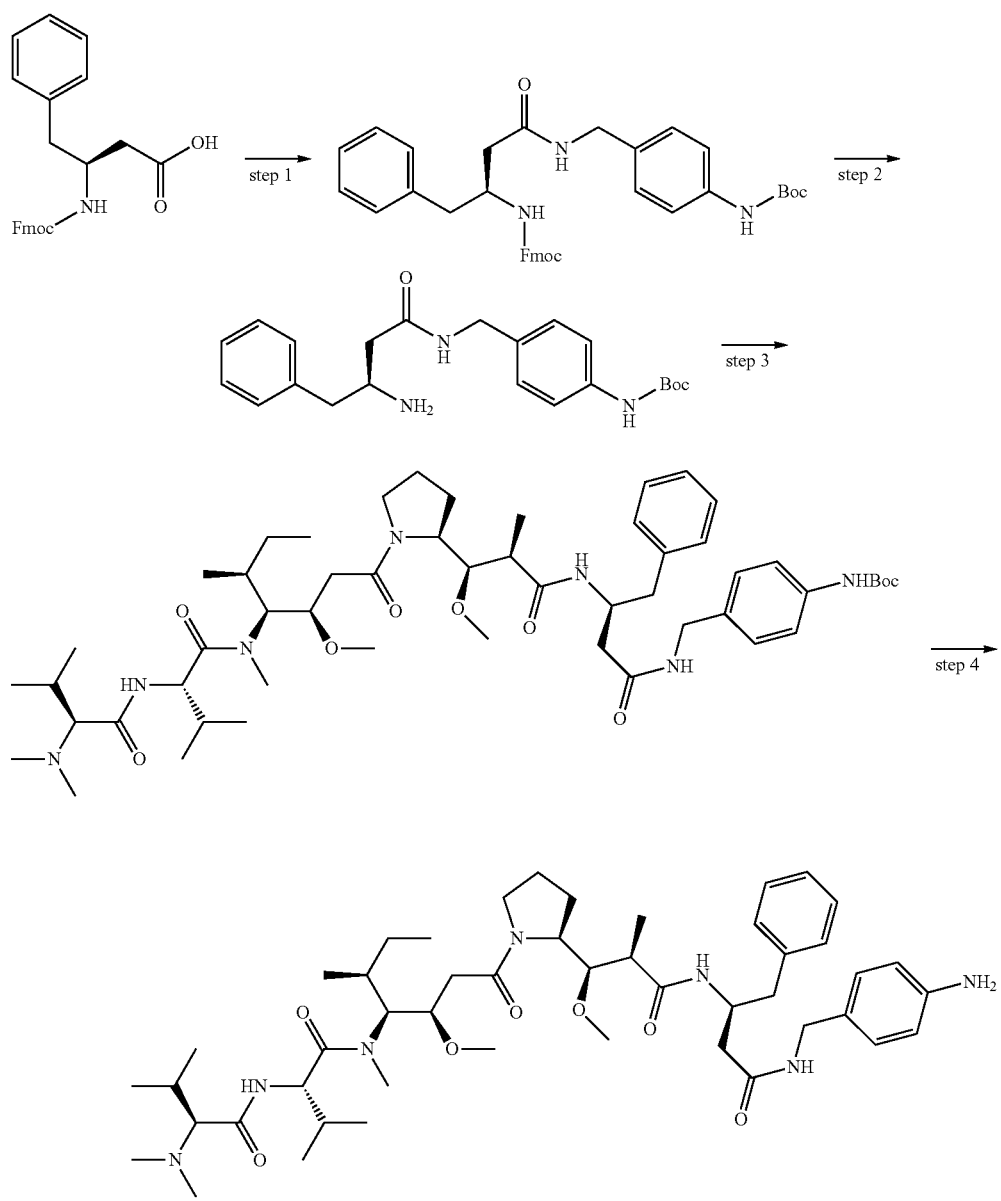

Step 1

Synthesis of tert-butyl (S)-(4-((3-(((((9H-fluoren-9-yl) methoxy)carbonyl)amino)-4-phenylbutyramide) methyl)phenyl)carbamate At 0° C., 4-aminobenzylamine (111 mg, 0.5 mmol) and N-methylmorpholine (150 mg, 1.5 mmol) were added in a solution of (S)-3-((((9H-fluoren-9-yl) methoxy)carbonyl) amino)-4-phenylbutyric acid (200 mg, 0.5 mmol) in N,N-dimethylformamide (5 mL), to which were added in sequence HOBT (101 mg, 0.75 mmol), and EDCI (150 mg, 0.75 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 310 mg. ESI-MS (m/z): 606.3 [M+H]$^+$.

Step 2

Synthesis of tert-butyl (S)-(4-((3-amino-4-phenylbutyramido)methyl)phenyl)carbamate Piperidine (0.5 mL) was added in a solution of a solution of tert-butyl (S)-(4-((3-(((((9H-fluoren-9-yl) methoxy)carbonyl)amino)-4-phenylbutyramido)methyl)phenyl)carbamate (200 mg, 0.66 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and the residue was purified by preparative liquid chromatography, to give the title compound, a white solid, 106 mg. ESI-MS (m/z): 384.2[M+H]$^+$.

Step 3

Synthesis of tert-butyl (4-(((S)-3-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-phenylbutyramido)methyl) phenyl)carbamate At 0° C., tert-butyl (S)-(4-((3-amino-4-phenylbutyramido)methyl)phenyl)carbamate (30 mg, 0.08 mmol) and N-methylmorpholine (24 mg, 0.24 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (50 mg, 0.08 mmol) in N,N-dimethylformamide (2 mL), to which were added in sequence HOBT (16 mg, 0.12 mmol), and EDCI (24 mg, 0.12 mmol), and reacted at 0° C. overnight. As detected by LCMS, the raw materials disappeared. The reaction solution was purified by preparative liquid chromatography, to give the title compound, a white solid, 24 mg. ESI-MS (m/z): 964.6 [M+H]$^+$.

Step 4

Synthesis of (S)—N-((3R,4S,5S)-1-((S)-2-((1R,2R)-3-(((S)-4-((4-aminobenzyl)amino)-4-oxo-1-phenyl-but-2-yl)amino)-1-methoxy-2-methyl-3-oxopropyl) pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of tert-butyl (4-(((S)-3-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-phenylbutyramido) methyl)phenyl)carbamate (24.0 mg, 0.025 mmol) in dichloromethane (1.5 mL), and reacted at room temperature for 1 h. As detected by LCMS, the raw materials disappeared completely. The solvent was removed by vacuum distillation, and the residue was purified by preparative liquid chromatography, to give trifluoroacetate of the title compound, a white solid, 14.0 mg. ESI-MS (m/z): 864.6 [M+H]$^+$.

Example 7 Synthesis of (S)—N-((3R,4S,5 S)-1-((S)-2-((1R,2R)-3-(((R)-4-((4-aminobenzyl)amino)-4-oxo-1-phenylbut-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T014)

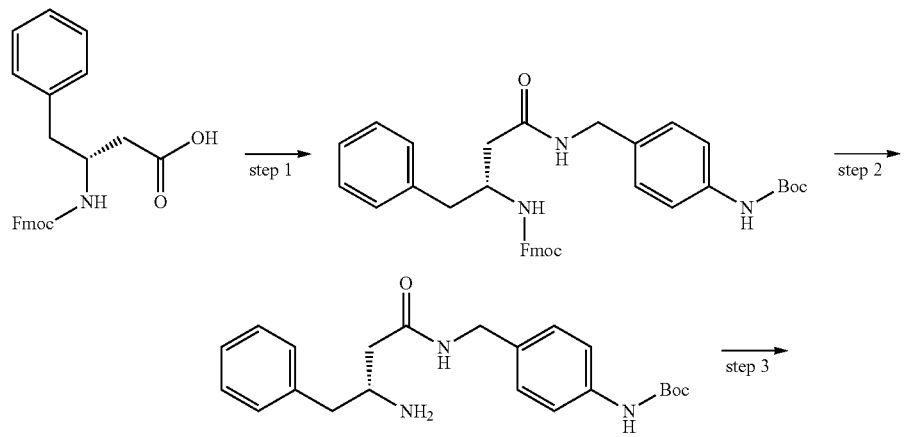

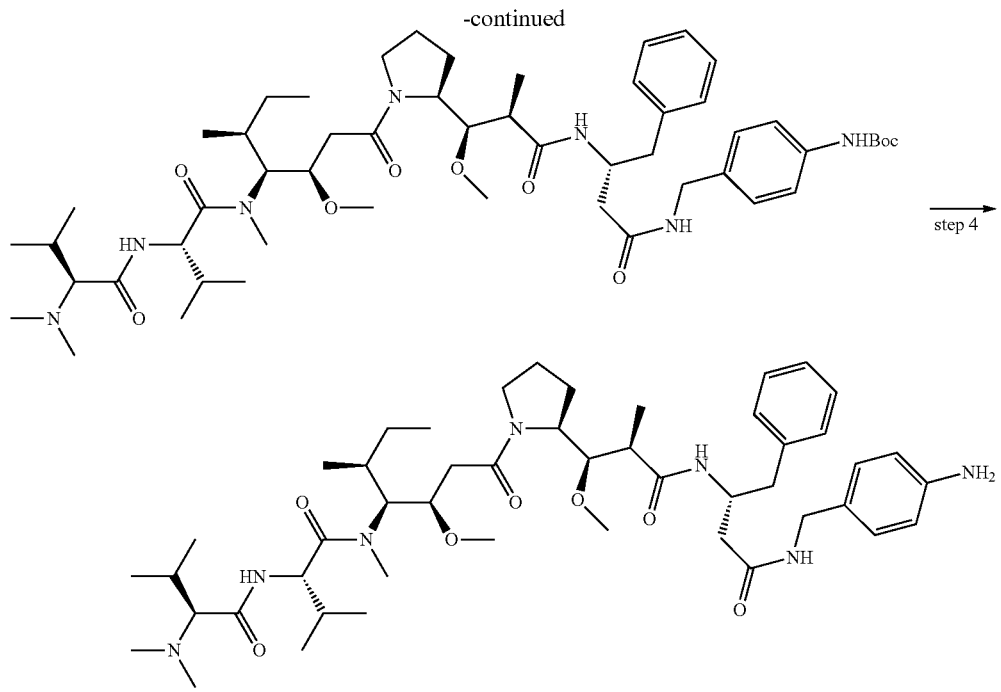

Step 1

Synthesis of tert-butyl (R)-(4-((3-((((9H-fluoren-9-yl) methoxy)carbonyl)amino)-4-phenylbutyramido)methyl)phenyl)carbamate At 0° C., 4-aminobenzylamine (111 mg, 0.5 mmol) and N-methylmorpholine (150 mg, 1.5 mmol) were added in a solution of (R)-3-((((9H-fluoren-9-yl) methoxy)carbonyl)amino)-4-phenylbutyric acid (200 mg, 0.5 mmol) in N,N-dimethylformamide (5 mL), to which were added in sequence HOBT (101 mg, 0.75 mmol), and EDCI (150 mg, 0.75 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 316 mg. ESI-MS (m/z): 606.3 [M+H]$^+$.

Step 2

Synthesis of tert-butyl (R)-(4-((3-amino-4-phenylbutyramido)methyl)phenyl)carbamate Piperidine (0.5 mL) was added in a solution of a solution of tert-butyl (R)-(4-((3-((((9H-fluoren-9-yl) methoxy)carbonyl)amino)-4-phenylbutyramido)methyl)phenyl)carbamate (200 mg, 0.66 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 120 mg. ESI-MS (m/z): 384.2 [M+H]$^+$.

Step 3

Synthesis of tert-butyl (4-((R)-3-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-phenylbutyramido)methyl)phenyl)carbamate At 0° C., tert-butyl (R)-(4-((3-amino-4-phenylbutyramido)methyl)phenyl)carbamate (30 mg, 0.08 mmol) and N-methylmorpholine (24 mg, 0.24 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (50 mg, 0.08 mmol) in N,N-dimethylformamide (2 mL), to which were added in sequence HOBT (16 mg, 0.12 mmol), and EDCI (24 mg, 0.12 mmol), and reacted at 0° C. overnight. As detected by LCMS, the raw materials disappeared. The reaction solution was purified by preparative liquid chromatography, to give the title compound, a white solid, 44 mg. ESI-MS (m/z): 964.6 [M+H]$^+$.

Step 4

Synthesis of (S)—N-((3R,4S,5 S)-1-((S)-2-((1R, 2R)-3-(((R)-4-((4-aminobenzyl)amino)-4-oxo-1-phenylbut-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of tert-butyl (4-((R)-3-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-phenylbutyramido)

methyl)phenyl)carbamate (44.0 mg, 0.045 mmol) in dichloromethane (1.5 mL), and reacted at room temperature for 1 h. As detected by LCMS, the raw materials disappeared completely. The solvent was removed by vacuum distillation, and the residue was purified by preparative liquid chromatography, to give trifluoroacetate of the title compound, a white solid, 24.4 mg. ESI-MS (m/z): 864.6 [M+H]$^+$.

Example 8 Synthesis of (S)—N-((3R,4S,5 S)-1-((S)-2-((1R,2R)-3-((2-((4-aminobenzyl)amino)-2-oxoethyl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T015)

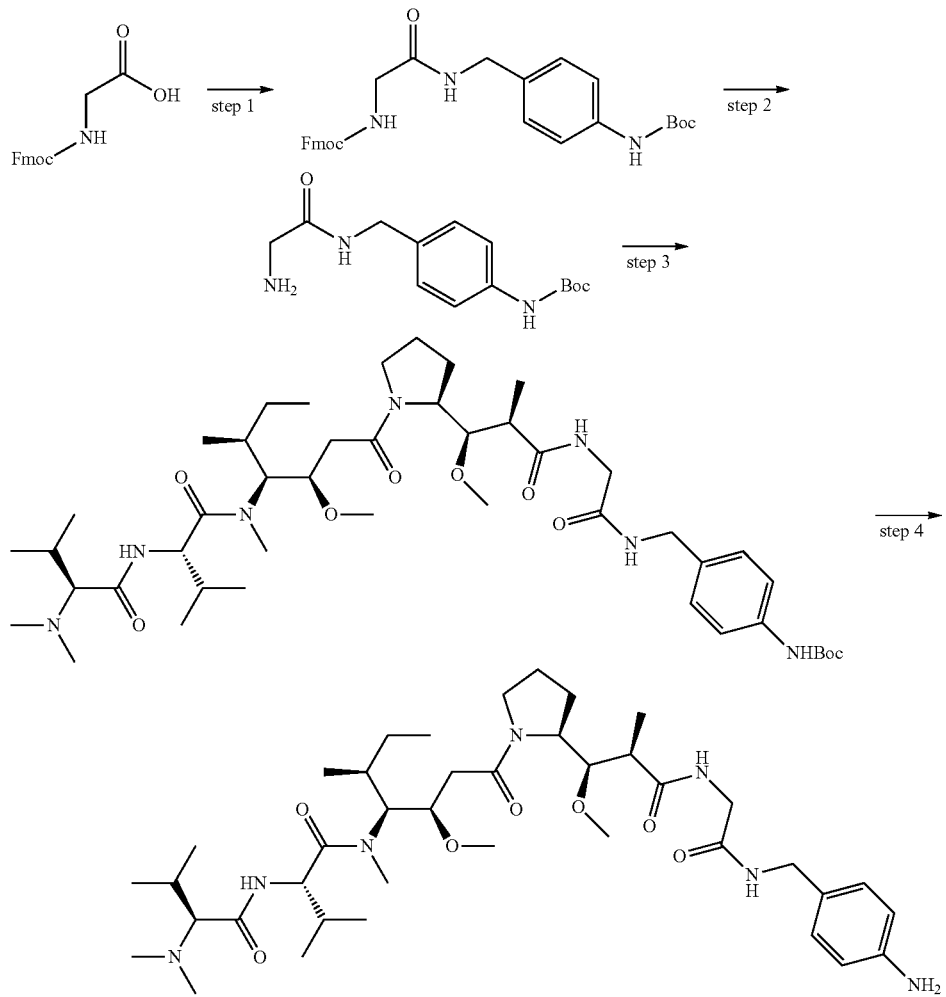

Step 1

Synthesis of tert-butyl (4-((2-((((9H-fluoren-9-yl)methoxy)carbonyl)amino)acetamido)methyl)phenyl)carbamate At 0° C., 4-aminobenzylamine (222 mg, 1.0 mmol) and N-methylmorpholine (306 mg, 1.5 mmol) were added in a solution of 2-((((9H-fluoren-9-yl) methoxy)carbonyl)amino) acetic acid (300 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 498 mg. ESI-MS (m/z): 502.2 [M+H]$^+$.

Step 2

Synthesis of tert-butyl (4-((2-aminoacetamido)methyl)phenyl)carbamate

Piperidine (0.5 mL) was added in a solution of a solution of tert-butyl (4-((2-((((9H-fluoren-9-yl) methoxy)carbonyl) amino)acetamido)methyl)phenyl)carbamate (498 mg, 0.99 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 260 mg. ESI-MS (m/z): 280.2 [M+H]$^+$.

Step 3

Synthesis of tert-butyl (4-((2R,3R)-3-((S)-1-((3R,4S,5 S)-4-((S)-2-((S)-3-(methylamino)-3-methylbutyramido)-N,3-dimethylbutyramido)-3-methoxy-5-methylheptanoyl)pyrrolidin-2-yl)-3-methoxy-2-methylpropionamido)acetamido)methyl)phenyl)carbamate At 0° C., tert-butyl (4-((2-aminoacetamido)methyl)phenyl)carbamate (30 mg, 0.11 mmol) and N-methylmorpholine (30 mg, 0.33 mmol) were added in a solution of (2R,3R)-3-((S)-1-((3R,4S,5 S)-4-((S)-2-((S)-2-(dimethylamino)-3-methylbutyramido)-N-3-trimethylbutyramido)-3-methoxy-5-methylheptanoyl)pyrrolidin-2-yl)-3-methoxy-2-methylpropionic acid (66 mg, 0.11 mmol) in N,N-dimethylformamide (2 ml), to which were added in sequence HOBT (25 mg, 0.17 mmol), and EDCI (30 mg, 0.17 mmol), and reacted at 0° C. overnight. As detected by LCMS, the raw materials disappeared. The reaction solution was purified by preparative liquid chromatography, to give the title compound, a white solid, 62 mg. ESI-MS (m/z): 860.6 [M+H]+.

Step 4

Synthesis of (S)—N-((3R,4S,5 S)-1-((S)-2-((1R,2R)-3-((2-((4-aminobenzyl)amino)-2-oxoethyl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of tert-butyl (4-((2R,3R)-3-((S)-1-((3R,4S,5 S)-4-((S)-2-((S)-3-(methylamino)-3-methylbutyramido)-N,3-dimethylbutyramido)-3-methoxy-5-methylheptanoyl)pyrrolidin-2-yl)-3-methoxy-2-methylpropionamido)acetamido)methyl)phenyl)carbamate (62 mg, 0.072 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 41.0 mg. ESI-MS (m/z): 760.5 [M+H]+.

Example 9 Synthesis of (S)—N-((3R,4S,5 S)-1-((S)-2-((1R,2R)-3-((S)-1-((4-aminobenzyl)amino)-1-oxoprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T016)

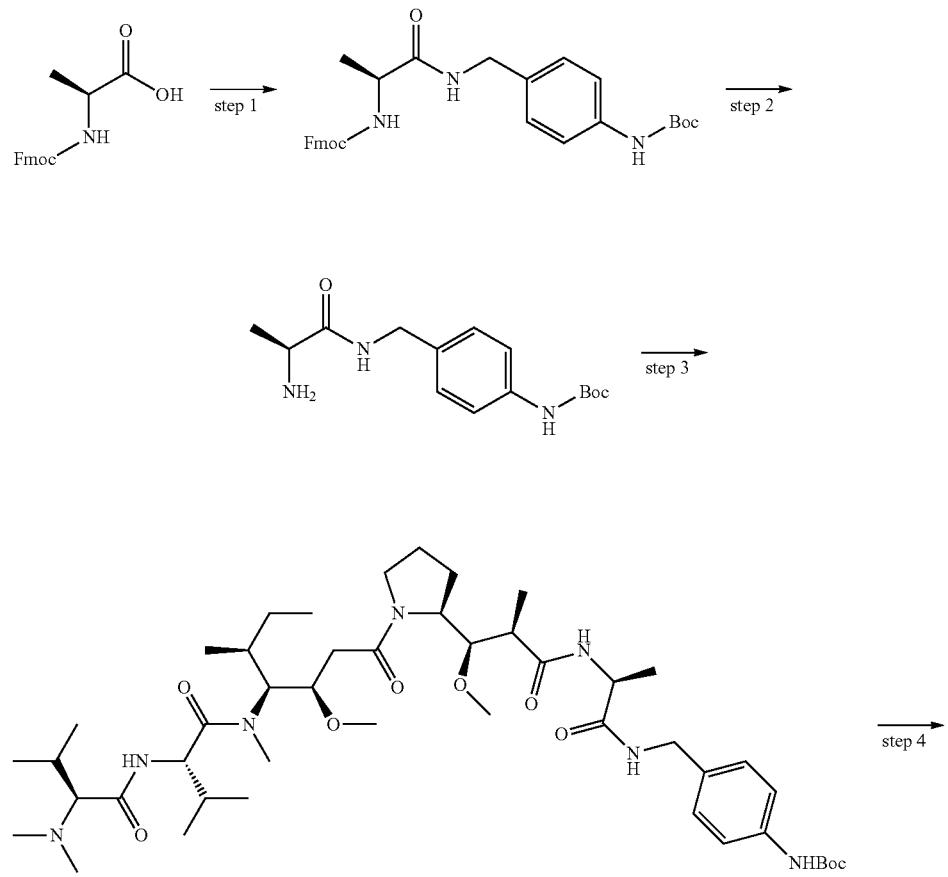

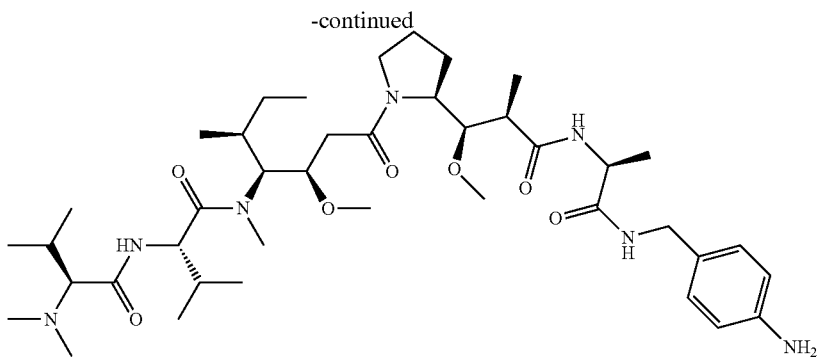

Step 1

Synthesis of tert-butyl (S)-(4-((2-((((9H-fluoren-9-yl) methoxy)carbonyl)amino)propionamido)methyl) phenyl)carbamate At 0° C., 4-aminobenzylamine (222 mg, 1.0 mmol) and N-methylmorpholine (306 mg, 1.5 mmol) were added in a solution of (S)-2-((((9H-fluoren-9-yl) methoxy)carbonyl) amino)propionic acid (311 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 510 mg. ESI-MS (m/z): 516.2 [M+H]⁺.

Step 2

Synthesis of tert-butyl (S)-(4-((2-aminopropionamido)methyl)phenyl)carbamate

Piperidine (0.5 mL) was added in a solution of a solution of tert-butyl (S)-(4-((2-((((9H-fluoren-9-yl) methoxy)carbonyl)amino)propionamido)methyl)phenyl)carbamate (510 mg, 0.99 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 256 mg. ESI-MS (m/z): 294.2 [M+H]⁺.

Step 3

Synthesis of tert-butyl (4-((S)-2-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)propionamido)methyl)phenyl)-carbamate At 0° C., tert-butyl (S)-(4-((2-aminopropionamido) methyl)phenyl)carbamate (30 mg, 0.11 mmol) and N-methylmorpholine (30 mg, 0.33 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (66 mg, 0.11 mmol) in N,N-dimethylformamide (2 mL), to which were added in sequence HOBT (25 mg, 0.17 mmol), and EDCI (30 mg, 0.17 mmol), and reacted at 0° C. overnight. As detected by LCMS, the raw materials disappeared. The reaction solution was purified by preparative liquid chromatography, to give the title compound, a white solid, 58 mg. ESI-MS (m/z): 874.6 [M+H]⁺.

Step 4

Synthesis of (S)—N-((3R,4S,5 S)-1-((S)-2-((1R,2R)-3-((S)-1-((4-aminobenzyl)amino)-1-oxoprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of tert-butyl (4-((S)-2-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)propionamido)methyl) phenyl)-carbamate (58 mg, 0.066 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 49.0 mg. ESI-MS (m/z): 774.5 [M+H]⁺.

Example 10 Synthesis of (S)—N-((3R,4S,5 S)-1-((S)-2-((1R,2R)-3-((S)-1-((4-aminobenzyl)amino)3-cyclopropyl-1-oxoprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide (T029)

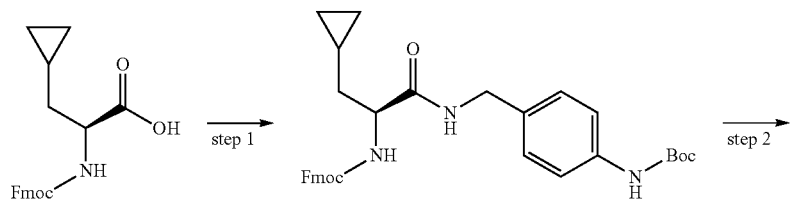

249
250

-continued

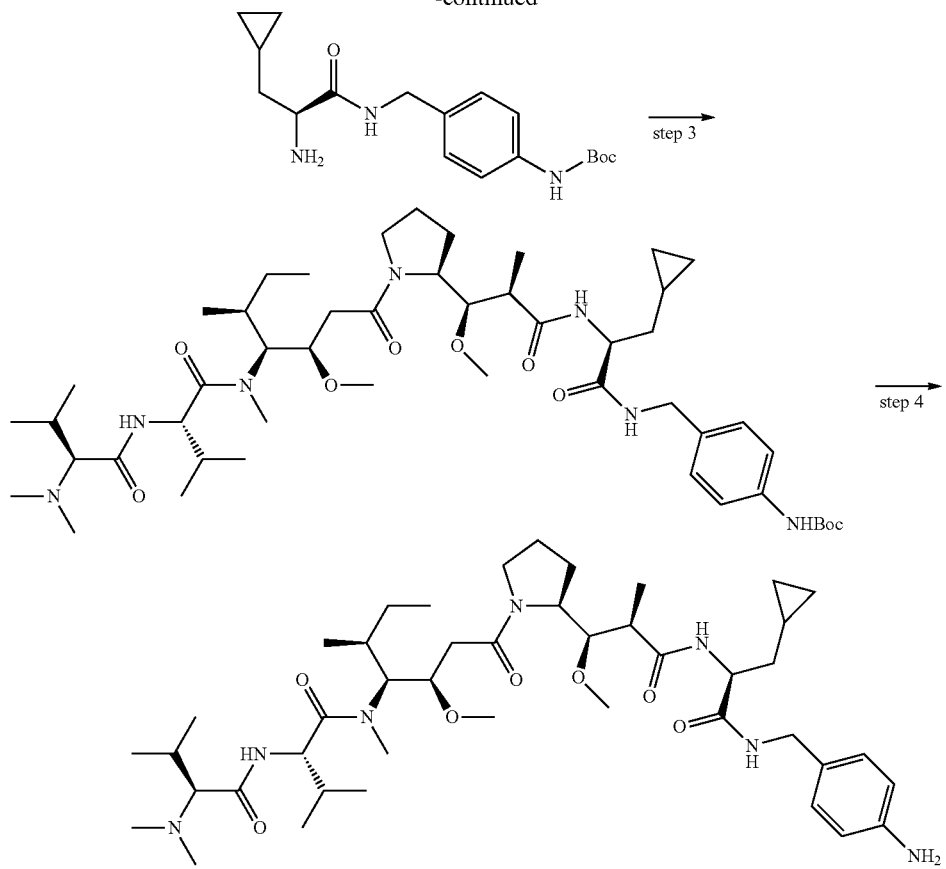

Step 1

Synthesis of tert-butyl (S)-(4-((2-((((9H-fluoren-9-yl) methoxy)carbonyl)amino)-3-cyclopropylpropionamido)methyl)phenyl)carbamate At 0° C., 4-aminobenzylamine (222 mg, 1.0 mmol) and N-methylmorpholine (306 mg, 1.5 mmol) were added in a solution of (S)-2-(((((9H-fluoren-9-yl) methoxy)carbonyl) amino)-3-cyclopropylpropionic acid (351 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 556 mg. ESI-MS (m/z): 556.35 [M+H]$^+$.

Step 2

Synthesis of tert-butyl (S)-(4-((2-amino-3-cyclopropylpropionamido)methyl)phenyl)carbamate Piperidine (0.5 mL) was added in a solution of tert-butyl (S)-(4-((2-(((((9H-fluoren-9-yl) methoxy)carbonyl)amino)-3-cyclopropylpropionamido)methyl)phenyl)carbamate (500 mg, 0.90 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 230 mg. ESI-MS (m/z): 334.2 [M+H]$^+$.

Step 3

Synthesis of tert-butyl (4-(((S)-3-cyclopropyl-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido) propionamido)methyl)phenyl)carbamate At 0° C., tert-butyl (S)-(4-((2-amino-3-cyclopropylpropionamido)methyl)phenyl)carbamate (33 mg, 0.11 mmol) and N-methylmorpholine (30 mg, 0.33 mmol) were added in (2R,3R)-3-((S)-1-((3R,4 S,5 S)-4-((S)-2-((S)-2-(dimethylamino)-3-methylbutyramido)-N, 3-dimethylbutyramido)-3-methoxy-5-methylheptanoyl)pyrrolidin-2-yl-3-methoxy-2-methylpropionic acid (66 mg, 0.11 mmol) in N,N-dimethylformamide (2 mL), to which were added in sequence HOBT (25 mg, 0.17 mmol), and EDCI (30 mg, 0.17 mmol), and reacted at 0° C. overnight. As detected by LCMS, the raw materials disappeared. The reaction solution was purified by preparative liquid chromatography, to give the title compound, a white solid, 70 mg. ESI-MS (m/z): 914.6 [M+H]$^+$.

Step 4

Synthesis of (S)—N-((3R,4S,5 S)-1-((S)-2-((1R,2R)-3-((S)-1-((4-aminobenzyl)amino)3-cyclopropyl-1-oxoprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyramido)-N,3-dimethylbutyramide Trifluoroacetic acid (0.5 mL) was added in a solution of tert-butyl (4-(((S)-3-cyclopropyl-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methyl-heptanoyl)pyrrolidin-2-yl)-3-methoxy-2-methylpropionamido)propionamido)methyl)phenyl)carbamate (70 mg, 0.076 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 45.0 mg. ESI-MS (m/z): 814.6 [M+H]$^+$.

Example 11 Synthesis of (S)—N-((3R,4S,5 S)-1-((S)-2-((1R,2R)-3-((S)-1-((4-aminobenzyl)amino)-3-methyl-1-oxobut-2-yl)amino)-1-methoxy-2-methyl-3-oxopropyl)pyrrolidin-1-yl)-3-methoxy-5-methyl-1-oxoheptyl-4-yl)-2 ((S)-2-(dimethylamino)-3-methylbutyramido)-N,3-dimethylbutyramide (T019)

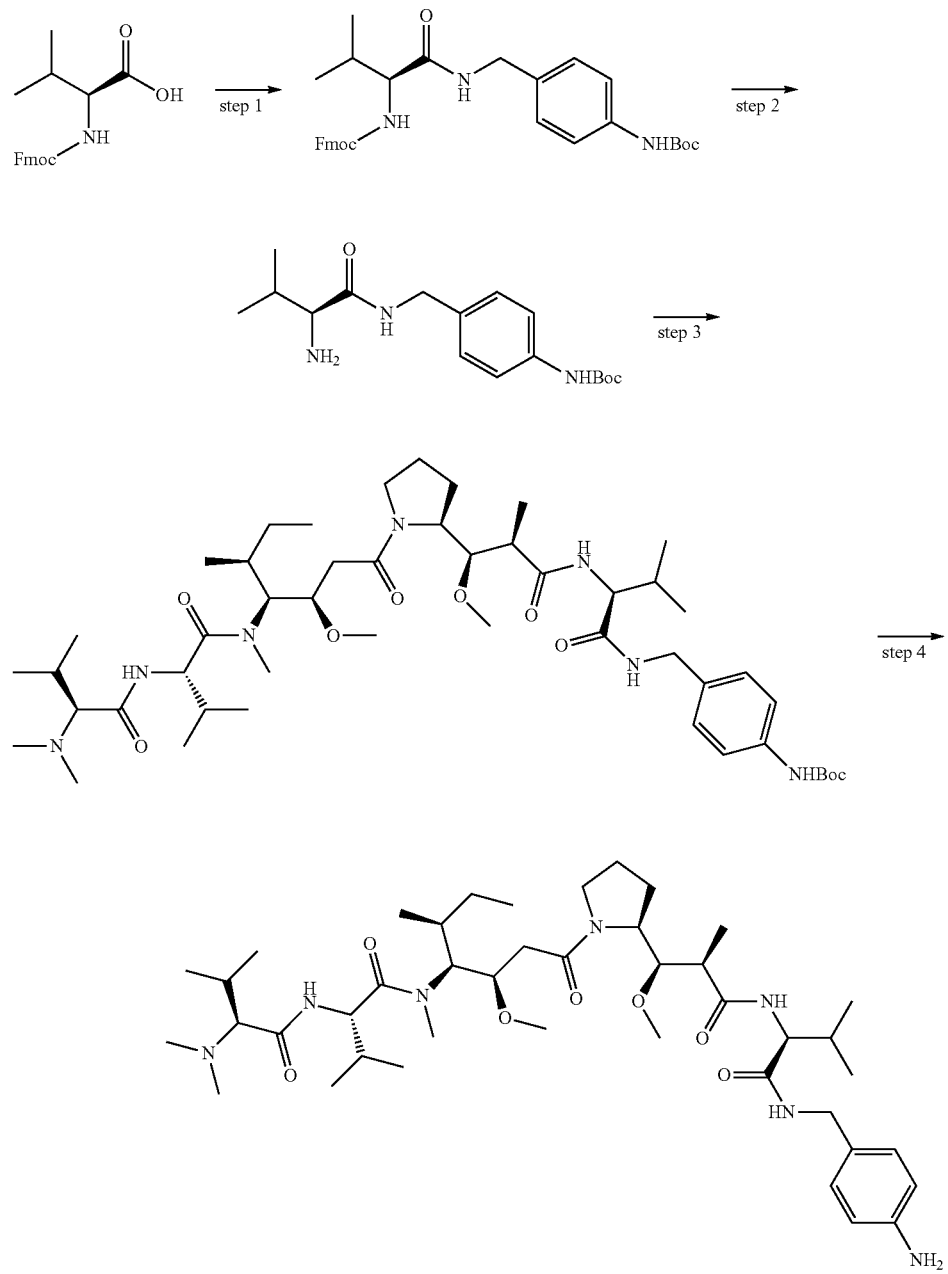

Step 1

Synthesis of tert-butyl (S)-(4-((2-((((9H-fluoren-9-yl) methoxy)carbonyl)amino)-3-methylbutyramido)methyl)phenyl)carbamate At 0° C., 4-aminobenzylamine (222 mg, 1.0 mmol) and N-methylmorpholine (306 mg, 1.5 mmol) were added in a solution of (S)-2-((((9H-fluoren-9-yl) methoxy)carbonyl)amino)-3-methylbutyric acid (340 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 545 mg. ESI-MS (m/z): 544.3 [M+H]$^+$.

Step 2

Synthesis of tert-butyl (S)-(4-((2-amino-3-methyl-butyramido)methyl)phenyl)carbamate Piperidine (0.5 mL) was added in a solution of a solution of tert-butyl (S)-(4-((2-((((9H-fluoren-9-yl) methoxy)carbonyl)amino)-3-methylbutyramido)methyl)phenyl)carbamate (545 mg, 1.0 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 251 mg. ESI-MS (m/z): 322.2 [M+H]$^+$.

Step 3

Synthesis of tert-butyl (4-((S)-2-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-3-methylbutyramido)methyl)phenyl)carbamate At 0° C., tert-butyl (S)-(4-((2-amino-3-methylbutyramido)methyl)phenyl)carbamate (33 mg, 0.11 mmol) and N-methylmorpholine (30 mg, 0.30 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (60 mg, 0.11 mmol) in N,N-dimethylformamide (2 mL), to which were added in sequence HOBT (20 mg, 0.15 mmol), and EDCI (29 mg, 0.15 mmol), and reacted at 0° C. overnight. As detected by LCMS, the raw materials disappeared. The reaction solution was purified by preparative liquid chromatography, to give the title compound, a white solid, 65 mg. ESI-MS (m/z): 902.6 [M+H]$^+$.

Step 4

Synthesis of (S)—N-((3R,4S,5 S)-1-((S)-2-((1R,2R)-3-((S)-1-((4-aminobenzyl)amino)-3-methyl-1-oxobut-2-yl)amino)-1-methoxy-2-methyl-3-oxopropyl)pyrrolidin-1-yl)-3-methoxy-5-methyl-1-oxoheptyl-4-yl)-2 ((S)-2-(dimethylamino)-3-methylbutyramido)-N,3-dimethylbutyramide Trifluoroacetic acid (0.5 mL) was added in a solution of tert-butyl (4-((S)-2-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-3-methylbutyramido)methyl)phenyl)carbamate (65 mg, 0.072 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 17.0 mg. ESI-MS (m/z): 802.6 [M+H]$^+$.

Example 12 Synthesis of (S)—N-(4-aminobenzyl)-2-((2R,3R)-3-((S)-1-((3R,4S,5S)-4-((S)-2-(S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-4-methylvaleramide (T018)

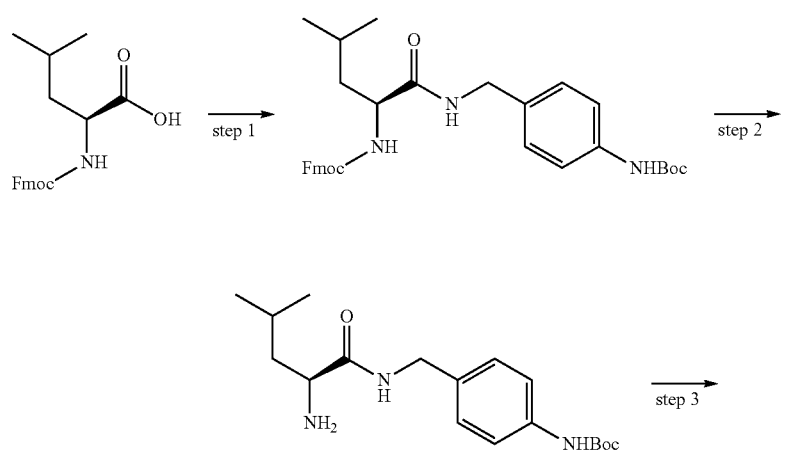

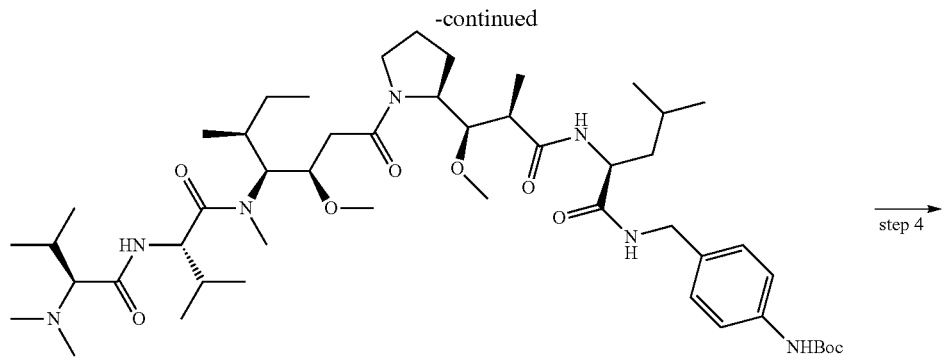

Step 1

Synthesis of tert-butyl (S)-(4-((2-((((9H-fluoren-9-yl) methoxy)carbonyl)amino)-4-methylvaleramido)methyl)phenyl)carbamate At 0° C., 4-aminobenzylamine (222 mg, 1.0 mmol) and N-methylmorpholine (306 mg, 1.5 mmol) were added in a solution of (S)-2-((((9H-fluoren-9-yl) methoxy)carbonyl) amino)-4-methylvaleric acid (352 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20 mL×3), and purified by silica gel column, to give the title compound, a white solid, 562 mg. ESI-MS (m/z): 558.3 [M+H]$^+$.

Step 2

Synthesis of tert-butyl (S)-(4-((2-amino-4-methyl-valeramido)methyl)phenyl)carbamate Piperidine (0.5 mL) was added in a solution of tert-butyl (S)-(4-((2-((((9H-fluoren-9-yl) methoxy)carbonyl)amino)-4-methylvaleramido)methyl)phenyl)carbamate (562 mg, 1.00 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 251 mg. ESI-MS (m/z): 336.2 [M+H]$^+$.

Step 3

Synthesis of tert-butyl (4-((S)-2-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-methylvaleramido)methyl)phenyl)carbamate At 0° C., tert-butyl (S)-(4-((2-amino-4-methyl-valeramido)methyl)phenyl)carbamate (34 mg, 0.11 mmol) and N-methylmorpholine (30 mg, 0.33 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl-3-methoxy-2-methylpropionic acid (60 mg, 0.11 mmol) in N,N-dimethylformamide (2 mL), to which were added in sequence HOBT (25 mg, 0.17 mmol), and EDCI (30 mg, 0.17 mmol), and reacted at 0° C. overnight. As detected by LCMS, the raw materials disappeared. The reaction solution was purified by preparative liquid chromatography, to give the title compound, a white solid, 67 mg. ESI-MS (m/z): 916.6 [M+H]$^+$.

Step 4

Synthesis of (S)—N-(4-aminobenzyl)-2-((2R,3R)-3-((S)-1-((3R,4S,5 S)-4-((S)-2-(S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-4-methylvaleramide Trifluoroacetic acid (0.5 mL) was added in a solution of tert-butyl (4-((S)-2-((2R,3R)-3-((S)-1-((3R,4 S,5 S)-4-((S)-

3-(methylamino)-3-methylbutyramido)-N,3-dimethylbutyramido)-3-methoxy-5-methylheptanoyl)pyrrolidin-2-yl)-3-methoxy-2-methylpropionamido)-4-methylvaleramido)methyl)phenyl)carbamate (62 mg, 0.068 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 51.0 mg. ESI-MS (m/z): 816.6 [M+H]$^+$.

Example 13 Synthesis of (S)—N-((3R,4S,5 S)-1-((S)-2-((1R,2R)-3-(((S)-1-((4-aminobenzyl)amino)-4-(methylsulfonyl)-1-oxo-2-butyl-)amino)-1-methoxy-2-methyl-3-oxopropyl)pyrrolidin-1-yl)-3-methoxy-5-methyl-1-oxo-4-pentyl)-2-((S)-2-(dimethylamino)-3-methylbutyramido)-N,3-dimethylbutyramide (T020)

Step 1

Synthesis of tert-butyl (S)-(4-((2-((((9H-fluoren-9-yl) methoxy)carbonyl)amino)-4-(methylthio)butyramido)methyl)phenyl)carbamate At 0° C., 4-aminobenzylamine (222 mg, 1.0 mmol) and N-methylmorpholine (306 mg, 1.5 mmol) were added in a solution of (S)-2-(((((9H-fluoren-9-yl) methoxy)carbonyl)amino)-4-(methylthio)butyric acid (372 mg, 1.0 mmol) in N,N-dimethylformamide (5 mL), to which were added in sequence HOBT (203 mg, 1.5 mmol), and EDCI (288 mg, 1.5 mmol), and reacted at 0° C. overnight. As detected by LCMS, the raw materials disappeared. The reaction solution was poured into water (50 mL), to precipitate out a white solid, and filtered, the filter cake was washed with water (20

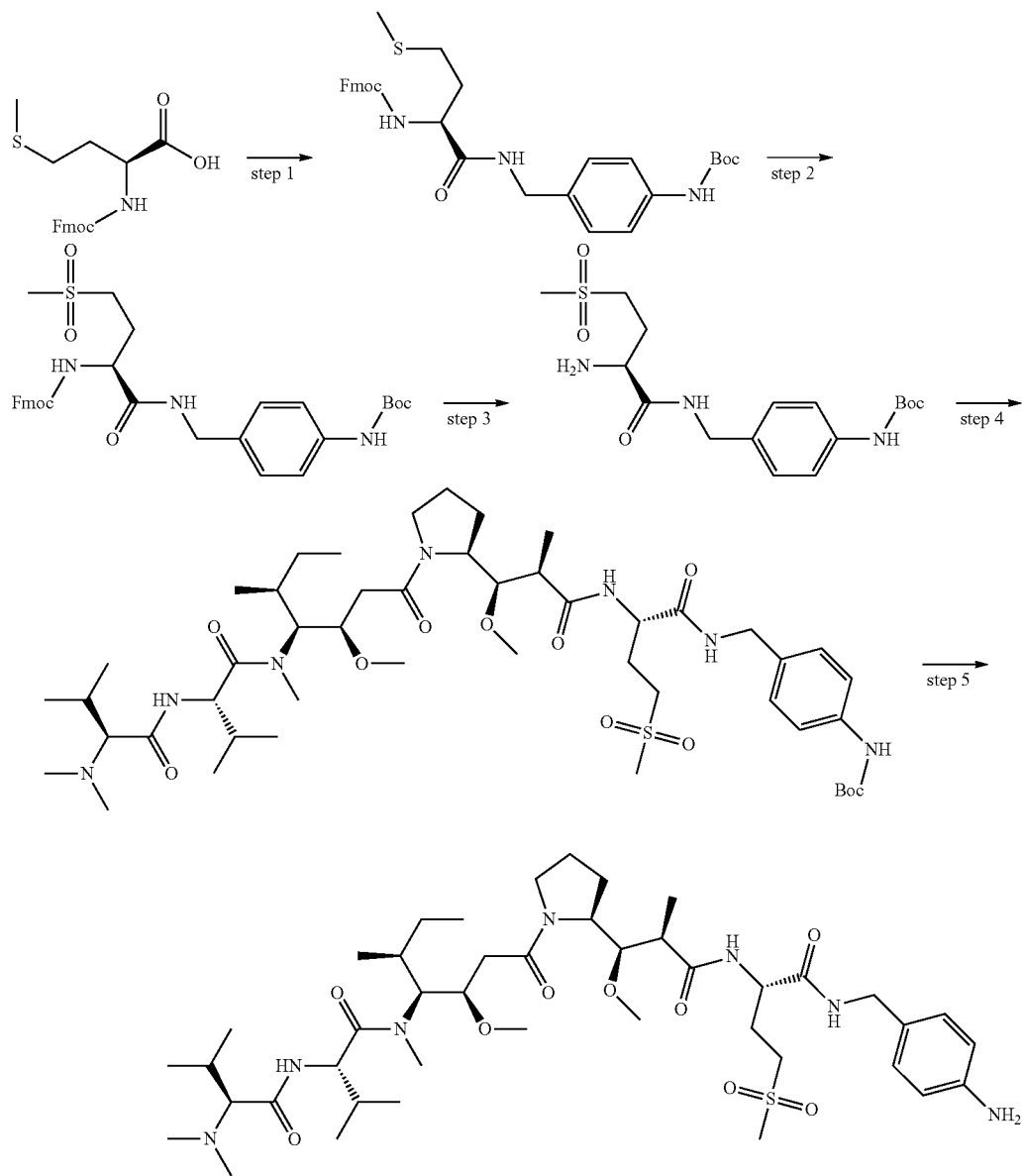

mL×3), and purified by silica gel column, to give the title compound, a white solid, 570 mg. ESI-MS (m/z): 576.2 [M+H]+.

Step 2

Synthesis of tert-butyl (S)-(4-((2-((((9H-fluoren-9-yl) methoxy)carbonyl)amino)-4-(methylsulfonyl) butyramido)methyl)phenyl)carbamate At room temperature, m-chloroperoxybenzoic acid (173 mg, 1.0 mmol) was added in a solution of tert-butyl (S)-(4-((2-((((9H-fluoren-9-yl) methoxy)carbonyl)amino)-4-(methylthio)butyramido)methyl)phenyl)carbamate (288 mg, 0.5 mmol) in dichloromethane (5 mL), and reacted at room temperature overnight. As detected by LCMS, the raw materials disappeared. The reaction solution was washed with 5% Na$_2$SO$_3$ aqueous solution (20 mL×3), and the aqueous phase was extracted with dichloromethane (20 ml×4). The solvent was removed by vacuum distillation, and the residue was purified by silica gel column, to give the title compound, a white solid, 286 mg. ESI-MS (m/z): 608.23 [M+H]+.

Step 3

Synthesis of tert-butyl (S)-(4-((2-amino-4-(methylsulfonyl)butyramido)methyl)phenyl)carbamate Piperidine (0.5 mL) was added in a solution of tert-butyl (S)-(4-((2-((((9H-fluoren-9-yl) methoxy)carbonyl)amino)-4-(methyl sulfonyl)butyramido)methyl)phenyl)carbamate (150 mg, 0.25 mmol) in N,N-dimethylformamide (2.5 mL), and reacted at room temperature overnight. As detected by LCMS, the raw materials disappeared. The solvent was removed by vacuum distillation, to obtain a white solid, the solid was washed with petroleum ether (20 mL×5), and purified by preparative liquid chromatography, to give the title compound, a white solid, 100 mg. ESI-MS (m/z): 386.2 [M+H]+.

Step 4

Synthesis of tert-butyl (4-((S)-2-((2R,3R)-3-((S)-1-((3R,4S,5S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-(methyl sulfonyl) butyramido)methyl)phenyl)carbamate At 0° C., tert-butyl (S)-(4-((2-amino-4-(methylsulfonyl) butyramido)methyl)phenyl)carbamate (39 mg, 0.10 mmol) and N-methylmorpholine (30 mg, 0.30 mmol) were added in a solution of (2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionic acid (60 mg, 0.11 mmol) in N,N-dimethylformamide (2 mL), to which were added in sequence HOBT (20 mg, 0.15 mmol), and EDCI (30 mg, 0.15 mmol), and reacted at 0° C. overnight. As detected by LCMS, the raw materials disappeared. The reaction solution was purified by preparative liquid chromatography, to give the title compound, a white solid, 70 mg. ESI-MS (m/z): 966.63 [M+H]+.

Step 5

Synthesis of (S)—N-((3R,4S,5S)-1-((S)-2-((1R,2R)-3-(((S)-1-((4-aminobenzyl)amino)-4-(methylsulfonyl)-1-oxo-2-butyl-)amino)-1-methoxy-2-methyl-3-oxopropyl)pyrrolidin-1-yl)-3-methoxy-5-methyl-1-oxo-4-pentyl)-2-((S)-2-(dimethylamino)-3-methylbutyramido)-N,3-dimethylbutyramide Trifluoroacetic acid (0.5 mL) was added in a solution of tert-butyl (4-((S)-2-((2R,3R)-3-((S)-1-((3R,4 S,5 S)-4-((S)-3-(methylamino)-3-methylbutyramido)-N,3-dimethylbutyramido)-3-methoxy-5-methylheptanoyl)pyrrolidin-2-yl)-3-methoxy-2-methylpropionamido)-4-(methylsulfonyl) butyramido)methyl)phenyl)carbamate (70 mg, 0.072 mmol) in dichloromethane (1.5 mL), and reacted at room temperature for 1 h. As detected by LCMS, the raw materials disappeared completely. The solvent was removed by vacuum distillation, and purified by preparative liquid chromatography, to give trifluoroacetate of the title compound, a white solid, 40.8 mg. ESI-MS (m/z): 866.6 [M+H]+.

Example 14 Synthesis of (S)—N-((3R,4S,5 S)-1-((S)-2-((1R,2R)-3-(((S)-1-((4-phenylamino)amino)-1-oxo-3-(pyrid-2-yl)prop-2-ylamino)-1-methoxy-2-methyl-3-propionyl)pyrrol-1-yl)-3-methoxy-5-methyl-1-heptano-4-yl)-2-((S)-2-(dimethylamino)-3-methylbutyryl)-N,3-dimethylbutyramide (T025)

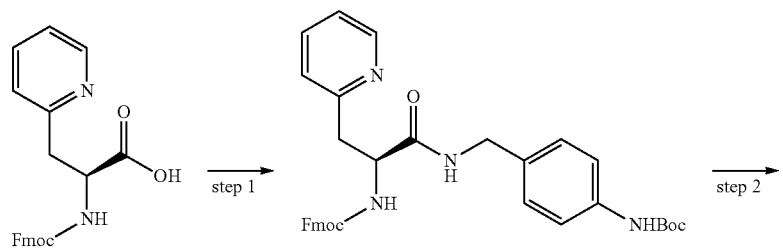

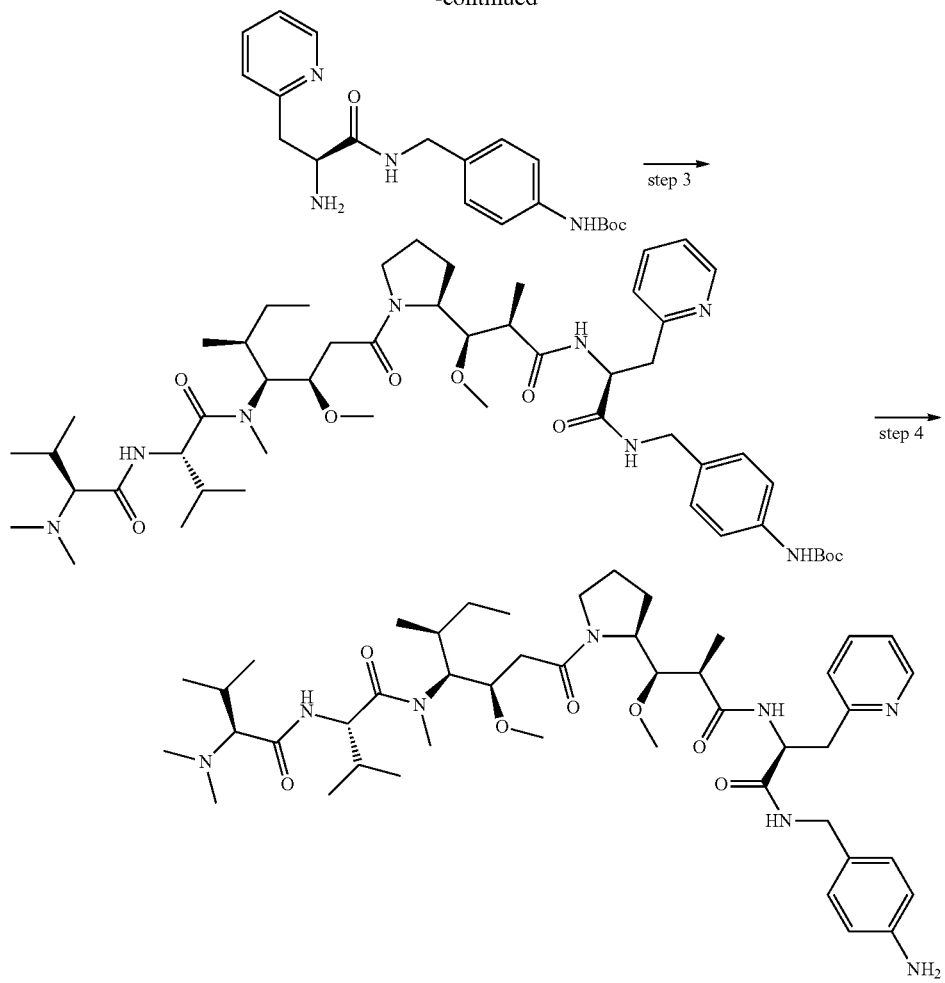

Step 1

Synthesis of (9H-fluoren-9-yl)methyl (S)-1-((4-((tert-butoxycarbonyl)amino)phenyl)amino)-1-oxo-3-(pyrid-2-yl)prop-2-yl) carbamate (S)-2-((((9H-fluoren-9-yl) methoxy)carbonyl)amino)-3-(pyrid-2-yl)propionic acid (200 mg, 0.505 mmol) was dissolved in N,N-dimethylformamide (3 mL), cooled down to 0° C. to which were added in sequence t-butyl (4-(methylamino)phenyl)carbamate (116 mg, 0.505 mmol) and N-methylmorpholine (0.08 mL, 0.758 mmol). Then, 1-hydroxybenzotriazole (103 mg, 0.758 mmol) and 1-(3-dimethylaminopropyl)-3-ethylcarbodiimide HCl salt (147 mg, 0.758 mmol) were added in sequence, and reacted at 0° C. for 3 h. The reaction was stopped once the completion of the reaction was detected by LC-MS. The reaction was added dropwise to water (30 mL), to precipitate out a grey solid, followed by vacuum filtration, to give the title compound, a violet compound: 1.5 g. ESI-MS (m/z): 593.3 [M+H]$^+$.

Step 2

Synthesis of t-butyl (S)-(4-((2-amino-3-(pyrid-2-yl)propionamido)methyl)phenyl)carbamate The crude product (9H-fluoren-9-yl)methyl (S)-1-((4-((tert-butoxycarbonyl) amino)phenyl)amino)-1-oxo-3-(pyrid-2-yl)prop-2-yl) carbamate (1.5 g) obtained in Step 1 of Example 4 was dissolved in N,N-dimethylformamide (3 mL), to which was added piperidine (0.46 mL, 5.05 mmol), and reacted with stirring at room temperature for 3 h. The reaction was stopped once the completion of the reaction was detected by LC-MS. The reaction solution was purified by preparative liquid chromatography, to give the title compound, a light yellow solid: 60 mg. ESI-MS (m/z): 371.2 [M+H]$^+$.

Step 3

Synthesis of t-butyl (4-(((S)-2-((2R,3R)-3-((S)-1-((3R,4S,5 S)-4-((S)-2-((S)-2-(dimethylamino)-3-methylbutyryl)-N,3-dimethylbutyryl)-3-methoxy-5-methylheptanoyl)pyrrol-2-yl)-3-methoxy-2-methylpropionyl)-3-(pyrid-2-yl)propionamido)methyl)phenyl)carbamate T-butyl (S)-(4-((2-amino-3-(pyrid-2-yl)propionamido)methyl)phenyl)carbamate (60 mg, 0.162 mmol) was dissolved in N,N-dimethylformamide (4 mL), to which were added N-methylmorpholine (0.05 mL, 0.486 mmol) and (2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrol-2-yl)-3-methoxy-2- methylpropionic acid (90 mg, 0.162 mmol), and cooled down to 0° C. Then, 1-hydroxybenzotriazole (34 mg, 0.243 mmol) and 1-(3-dimethylaminopropyl)-3-ethylcarbodiimide HCl salt (47 mg, 0.243 mmol) were added in sequence, and reacted at 0° C. for 22 h. The reaction was stopped once the completion of the reaction was detected by LC-MS. The reaction solution was purified by preparative liquid chromatography, to give the title compound, a white solid, 110 mg. ESI-MS (m/z): 951.6 [M+H]$^+$.

Step 4

Synthesis of (S)—N-((3R,4S,5S)-1-((S)-2-((1R,2R)-3-(((S)-1-((4-phenylamino)amino)-1-oxo-3-(pyrid-2-yl)prop-2-ylamino)-1-methoxy-2-methyl-3-propionyl)pyrrol-1-yl)-3-methoxy-5-methyl-1-heptano-4-yl)-2-((S)-2-(dimethylamino)-3-methylbutyryl)-N,3-dimethylbutyramide T-butyl (4-(((S)-2-((2R,3R)-3-((S)-1-((3R,4S,5 S)-4-((S)-2-((S)-2-(dimethylamino)-3-methylbutyryl)-N,3-dimethylbutyryl)-3-methoxy-5-methylheptanoyl)pyrrol-2-yl)-3-methoxy-2-methylpropionyl)-3-(pyrid-2-yl)propionamido)

methyl)phenyl)carbamate (110 mg, 0.116 mmol) was dissolved in dichloromethane (3 mL), to which was added trifluoroacetic acid (1.0 mL) with stirring at room temperature, followed by reaction at room temperature for 1 h. The reaction was stopped once the completion of the reaction was detected by LC-MS. The reaction solution was purified by preparative liquid chromatography, to give trifluoroacetate of the title compound, a white solid, 90 mg. ESI-MS (m/z): 851.6 [M+H]+.

II. Synthesis of Conjugate Comprising Cytotoxin and Linker

Example 15 Synthesis of pentafluorophenol 1-(4-(((S)-1-(((S)-1-((4-(((S)-2-((2R,3R)-3-((S)-1-((3R, 4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate (TL001)

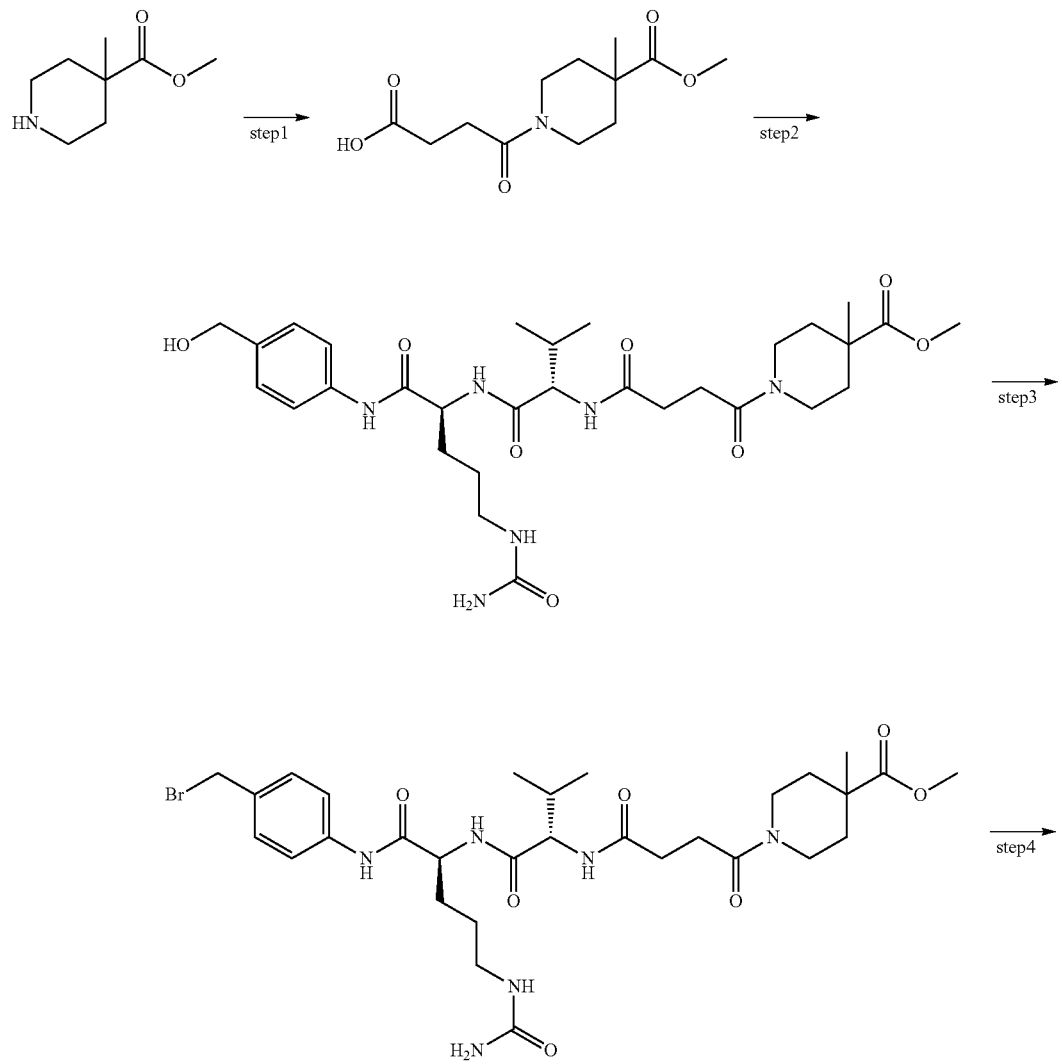

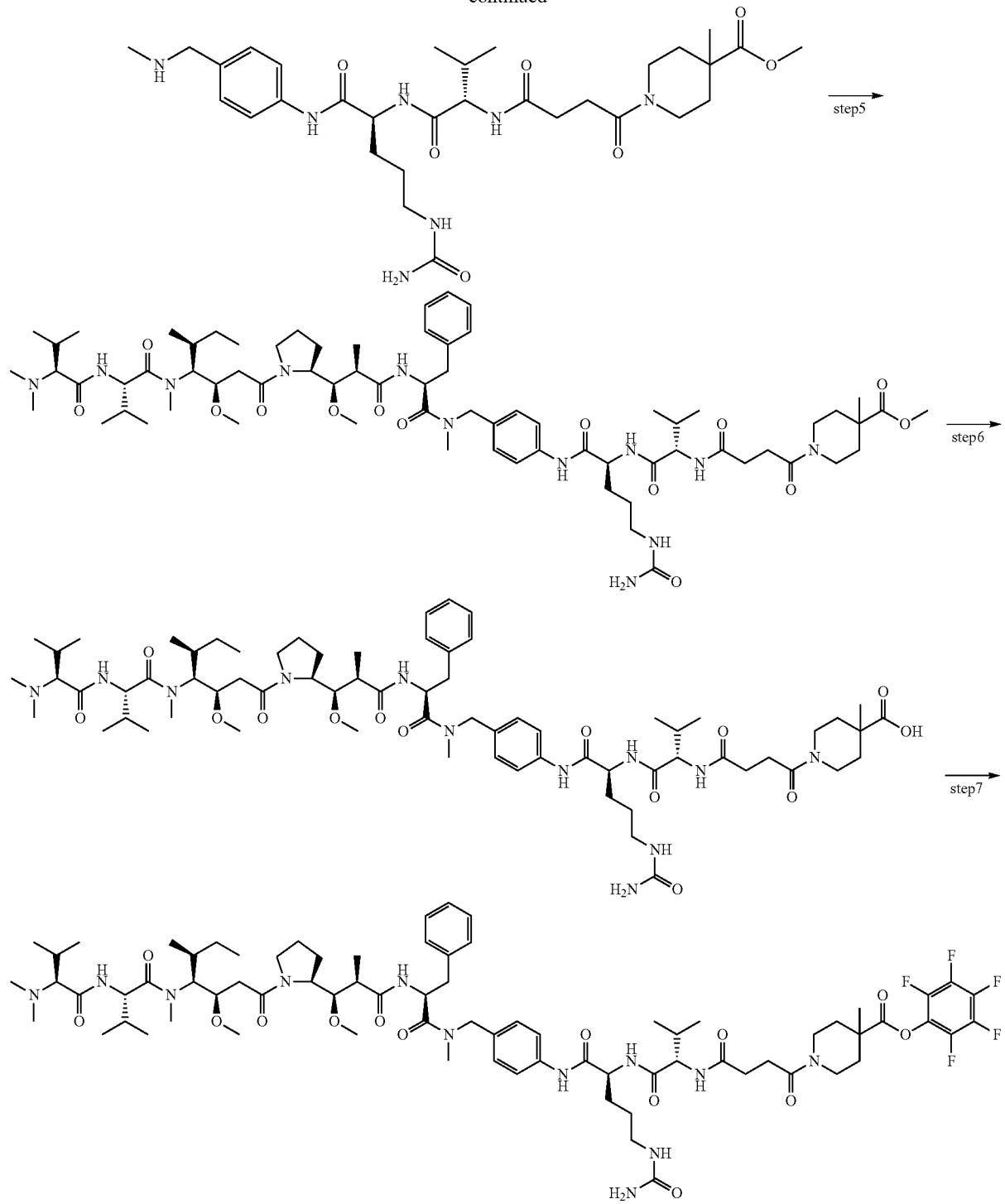

Step 1

Synthesis of 4-(4-methyl-4-methoxycarbonyl-piperidinyl-1-yl)-4-oxobutyric acid

At room temperature, methyl 4-methyl-4-piperidine formate (0.7 g, 4.46 mmol), succinic anhydride (0.45 g, 4.46 mmol), acetonitrile (20 ml) were added in a three-necked bottle, sodium bicarbonate (0.38 g, 4.46 mmol) was added with stirring at room temperature, nitrogen gas was charged to replace air three times, followed by heating up to 50° C., and reacting at this temperature for 4.0 h. The completion of the reaction was detected by LC-MS. Insolubles were removed by filtration, and the solvent was removed by vacuum distillation to give the title compound, a light yellow oily substance, 1.12 g. ESI-MS (m/z): 258.1 [M+H]$^+$.

Step 2

Synthesis of methyl 1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)piperidinyl-4-methyl-4-formate (S)-2-((S)-2-amino-3-methylbutyramide)-N-(4-(hydroxymethyl)phenyl)-5-ureidovaleramide (0.5 g, 1.32 mmol), 4-(4-methyl-4-methoxycarbonyl-piperidinyl-1-yl)-4-oxobutyric acid (0.34 g, 1.32 mmol) was dissolved in N,N-dimethylformamide (10 mL), cooled down to 0° C., to which was added N,N-diisopropylethylamine (0.34 g, 2.64 mmol), and added batchwise benzotriazole-1-yl-oxyltripyrrolidinylphosphonium hexafluorophosphate (1.03 g, 1.98 mmol) within 15 min, followed by naturally heating to room temperature, and reacting for 2.0 h. The reaction was stopped once the completion of the reaction was detected by LC-MS, and then the reaction solution was concentrated to obtain a crude product, which was purified by preparative liquid chromatography, to give the title compound, a white solid, 0.52 g. ESI-MS (m/z): 619.3 $[M+H]^+$.

Step 3

Synthesis of methyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-methyl-4-formate At room temperature, methyl 1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)piperidinyl-4-methyl-4-formate (507 mg, 0.82 mmol) was dissolved in dichloromethane (40 mL), to which was added dropwise 33% HBr in HOAc (2.5 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give a crude product of the title compound, a white solid, 0.58 g. ESI-MS (m/z): 681.1 $[M+H]^+$.

Step 4

Synthesis of methyl 1-(4-(((S)-1-(((S)-1-((4-(methylamino)phenyl)amino)-1-oxo-5-ureidopentyl-2-yl)amino)-3-methyl-1-oxobutyl-2-yl)amino)-4-oxobutyryl)piperidinyl-4-methyl-4-formate The crude product of methyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-methyl-4-formate (0.58 g, 0.82 mmol) was dissolved in dichloromethane (10 mL), added dropwise in $CH_3NH_2$ in THF (10 mL, 2 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 347 mg. ESI-MS (m/z): 632.4 $[M+H]^+$.

Step 5

Synthesis of methyl 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-methyl-4-formate (i.e., TL002)

At room temperature, 1-hydroxybenzotriazole (68 mg, 0.50 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (215 mg, 0.25 mmol), methyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-methyl-4-formate (155 mg, 0.25 mmol), N,N-diisopropylethylamine (162 mg, 1.25 mmol), cooled down to 0° C., stirred for 10 min, then benzotriazole-1-yl-oxyl-tripyrrolidinylphosphonium hexafluorophosphate (195 mg, 0.38 mmol) was added dropwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 209 mg. ESI-MS (m/z): 1359.8 $[M+H]^+$.

Step 6

Synthesis of 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-methyl-4-formic acid Methyl 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-methyl-4-formate (50 mg, 0.037 mmol) was dissolved in a mixed solvent of THF (5 mL) and water (5 mL), to which was added lithium hydroxide (50 mg, 1.20 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1345.8 [M+H]⁺.

Step 7

Synthesis of pentafluorophenol 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)

piperidinyl-4-formic acid (50 mg, 0.037 mmol) was dissolved in N,N-dimethylformamide (5 mL), to which were added in sequence pentafluorophenol (34 mg, 0.185 mmol), 1-ethyl-(3-dimethylaminopropyl)carbodiimide HCl salt (36 mg, 0.185 mmol), and 4-dimethylaminopyridine (14 mg, 0.111 mmol), followed by heating up to 50° C., and reacting overnight. The reaction was stopped once the completion of the reaction was detected by LC-MS. The reaction solution was purified by preparative liquid chromatography, to give the title compound, a white solid, 10.3 mg. ESI-MS (m/z): 1511.8 [M+H]⁺.

Example 16 Synthesis of pentafluorophenol 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate (TL004)

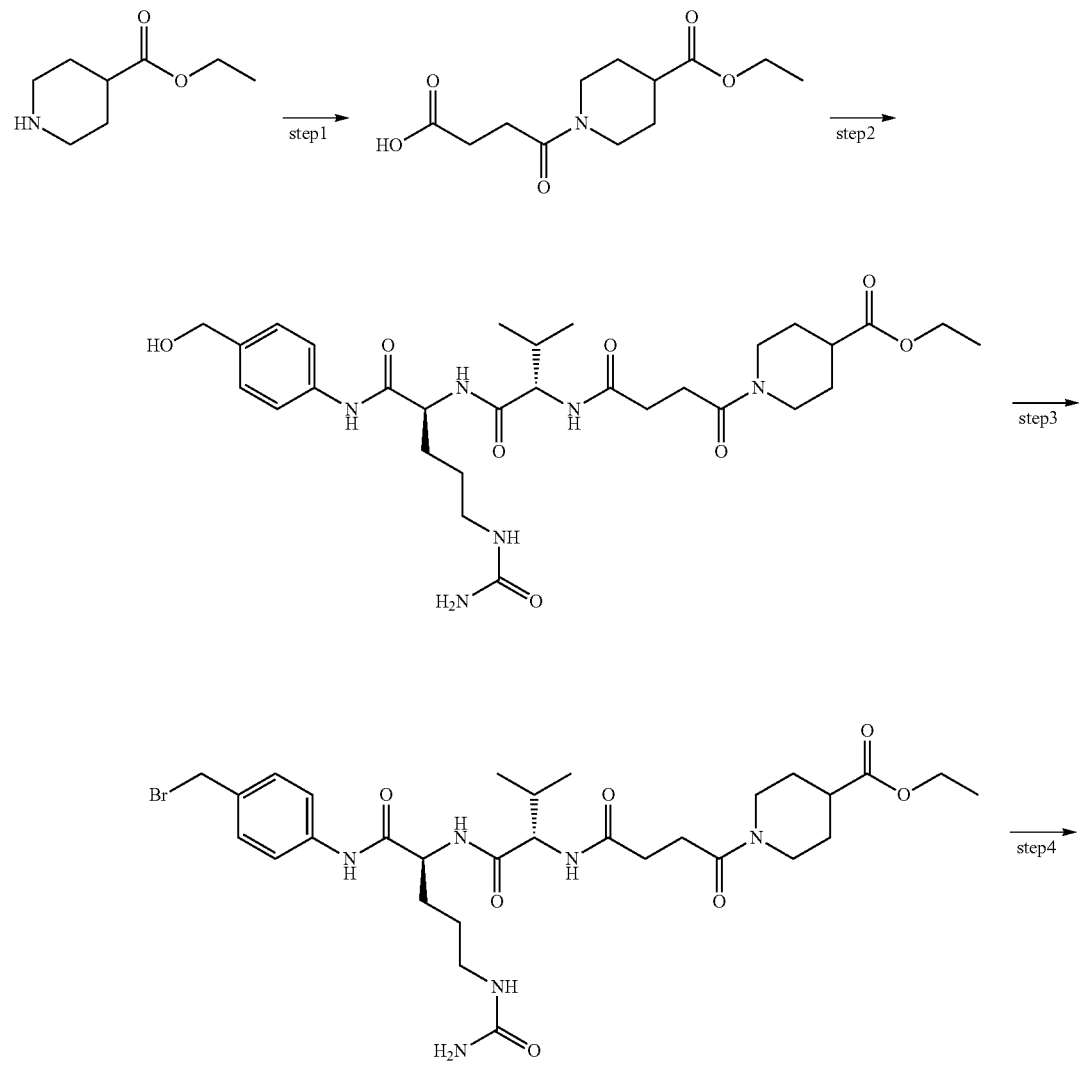

-continued

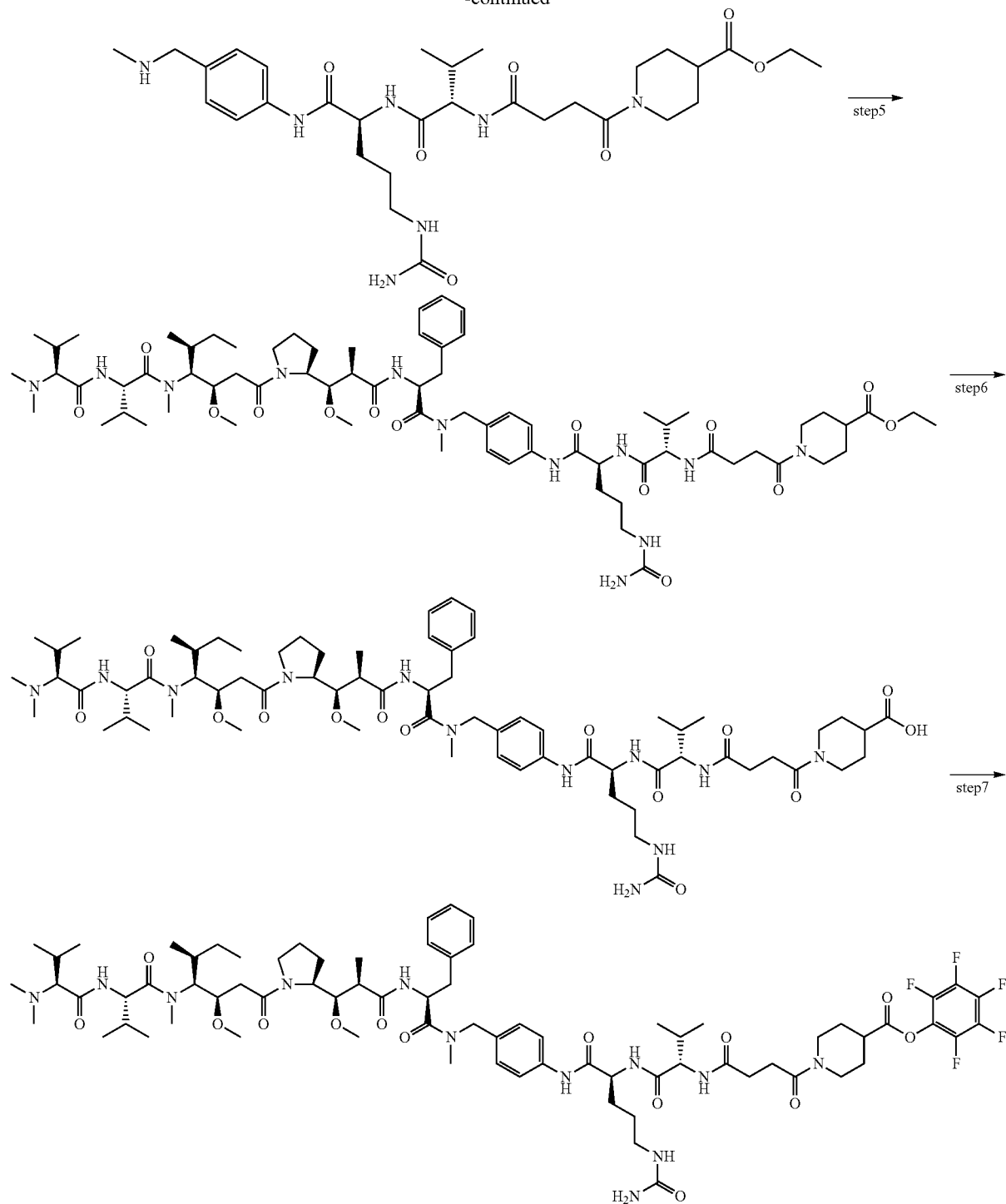

Step 1

Synthesis of 4-(4-(ethoxycarbonyl)piperidinyl-1-yl)-4-oxobutyric acid

At room temperature, ethyl 4-piperidine formate (7.0 g, 44.6 mmol), succinic anhydride (4.46 g, 44.6 mmol), acetonitrile (100 ml) were added in a three-necked bottle, then sodium bicarbonate (3.76 g, 44.6 mmol) was added with stirring at room temperature, nitrogen gas was charged to replace air three times, followed by heating up to 50° C., and reacting at this temperature for 4.0 h. The completion of the reaction was detected by LC-MS. After cooling down to room temperature, the solvent was removed by vacuum distillation, water (50 mL) was added, washed with ethyl acetate (30 mL×3), washed with saturated salt water (20 mL), and dried with anhydrous sodium sulfate. The desiccant was removed by filtration, and the solvent was removed by vacuum distillation to give the title compound, a light yellow oily substance, 11.36 g. ESI-MS (m/z): 258.1 [M+H]$^+$.

Step 2

Synthesis of ethyl 1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)piperidinyl-4-formate (S)-2-((S)-2-amino-3-methylbutyramide)-N-(4-(hydroxymethyl)phenyl)-5-ureidovaleramide (2.0 g, 5.27 mmol), 4-(4-(ethoxycarbonyl)piperidinyl-1-yl)-4-oxobutyric acid (1.35 g, 5.27 mmol) were dissolved in N,N-dimethylformamide (40 mL), cooled down to 0° C., N,N-diisopropylethylamine (1.36 g, 10.54 mmol) was added, and then benzotriazole-1-yl-oxyltripyrrolidinylphosphonium hexafluorophosphate (4.11 g, 7.91 mmol) was added batchwise within 15 min, followed by naturally heating to room temperature, and reacting for 2.0 h. The reaction was stopped once the completion of the reaction was detected by LC-MS, and then the reaction solution was concentrated to obtain a crude product, which was purified by preparative liquid chromatography, to give the title compound, a white solid, 2.1 g. ESI-MS (m/z): 619.3 [M+H]$^+$.

Step 3

Synthesis of ethyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-formate At room temperature, ethyl 1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)piperidinyl-4-formate (507 mg, 0.82 mmol) was dissolved in dichloromethane (40 mL), to which was added dropwise 33% HBr in HOAc (2.5 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give the title compound, a solid crude product 585 mg. ESI-MS (m/z): 681.1 [M+H]$^+$.

Step 4

Synthesis of ethyl 1-(4-(((S)-3-methyl-(((S)-1-((4-(aminomethyl)phenyl)amino)-1-oxo-5-ureidopentyl-2-yl)amino)-1-oxobutyl-2-yl)amino)-4-oxobutyryl)piperidinyl-4-formate The crude product of ethyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-formate (585 mg, 0.82 mmol) was dissolved in dichloromethane (10 mL), added dropwise in CH$_3$NH$_2$ in THF (10 mL, 2 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 163 mg. ESI-MS (m/z): 632.4 [M+H]$^+$.

Step 5

Synthesis of ethyl 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate At room temperature, 1-hydroxybenzotriazole (68 mg, 0.50 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (215 mg, 0.25 mmol), ethyl 1-(4-(((S)-3-methyl-(((S)-1-((4-(aminomethyl)phenyl)amino)-1-oxo-5-ureidopentyl-2-yl)amino)-1-oxobutyl-2-yl)amino)-4-oxobutyryl)piperidinyl-4-formate (163 mg, 0.25 mmol), and N,N-diisopropylethylamine (162 mg, 1.25 mmol), cooled down to 0° C., stirred for 10 min, then benzotriazole-1-yl-oxyltripyrrolidinylphosphonium hexafluorophosphate (195 mg, 0.38 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 259 mg. ESI-MS (m/z): 1359.8 [M+H]$^+$.

Step 6

Synthesis of 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formic acid Ethyl 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate (50 mg, 0.037 mmol) was dissolved in a mixed solvent of THF (5 mL) and water (5 mL), to which was added lithium hydroxide (50 mg, 1.20 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1331.8 [M+H]⁺.

Step 7

Synthesis of pentafluorophenol 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-N-methyl-3-phenylpropionamido)methyl)phenyl)amino)-1-oxo-5-ureidopentyl-2-yl)amino)-3-methyl-1-oxobutyl-2-yl)amino)-4-oxobutyramido)

piperidinyl-4-formic acid (50 mg, 0.037 mmol) was dissolved in N,N-dimethylformamide (5 mL), to which were added in sequence pentafluorophenol (34 mg, 0.185 mmol), 1-ethyl-(3-dimethylaminopropyl)carbodiimide HCl salt (36 mg, 0.185 mmol), and 4-dimethylaminopyridine (14 mg, 0.111 mmol), followed by heating up to 50° C., and reacting overnight. The reaction was stopped once the completion of the reaction was detected by LC-MS. The reaction solution was purified by preparative liquid chromatography, to give the title compound, a white solid, 4.2 mg. ESI-MS (m/z): 1497.8 [M+H]⁺.

Example 17 Synthesis of pentafluorophenol 8-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formate (TL005)

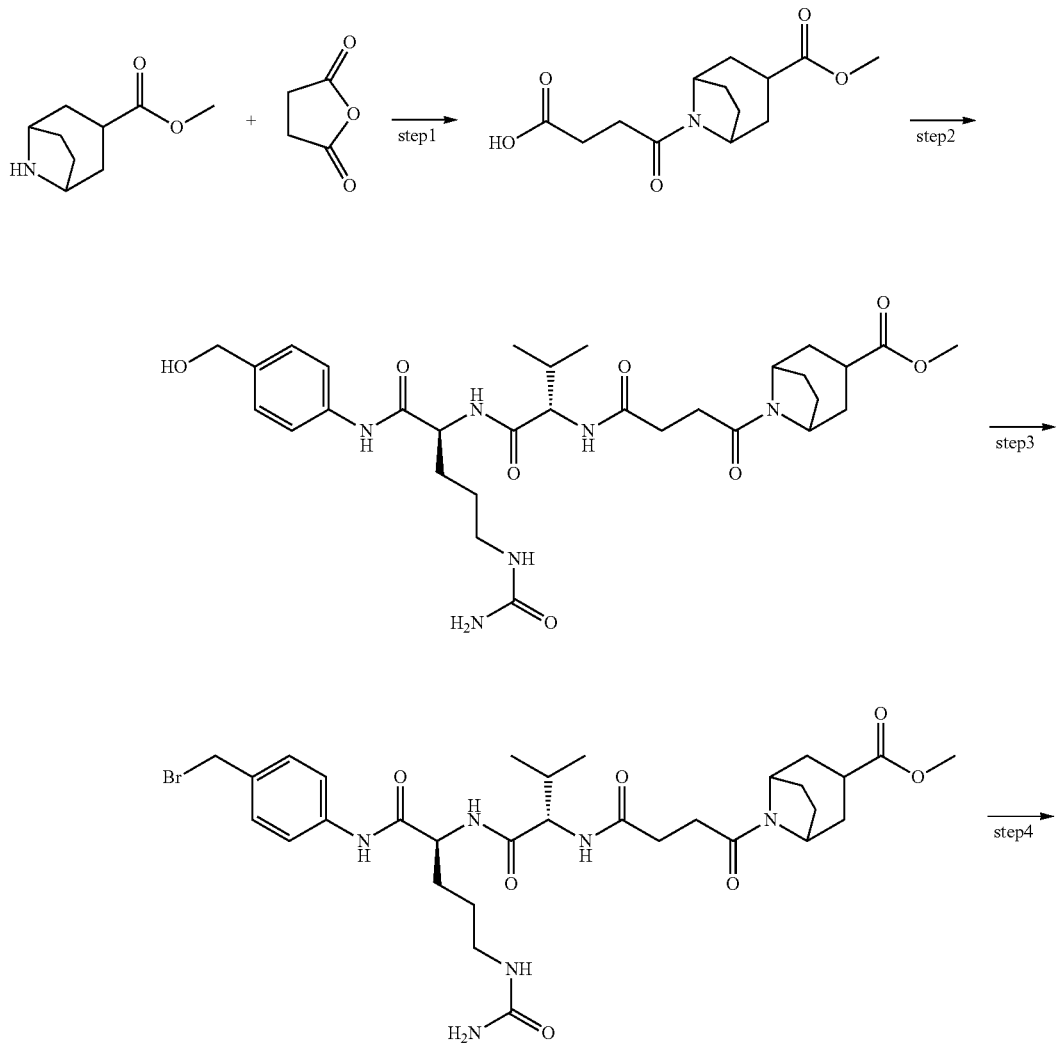

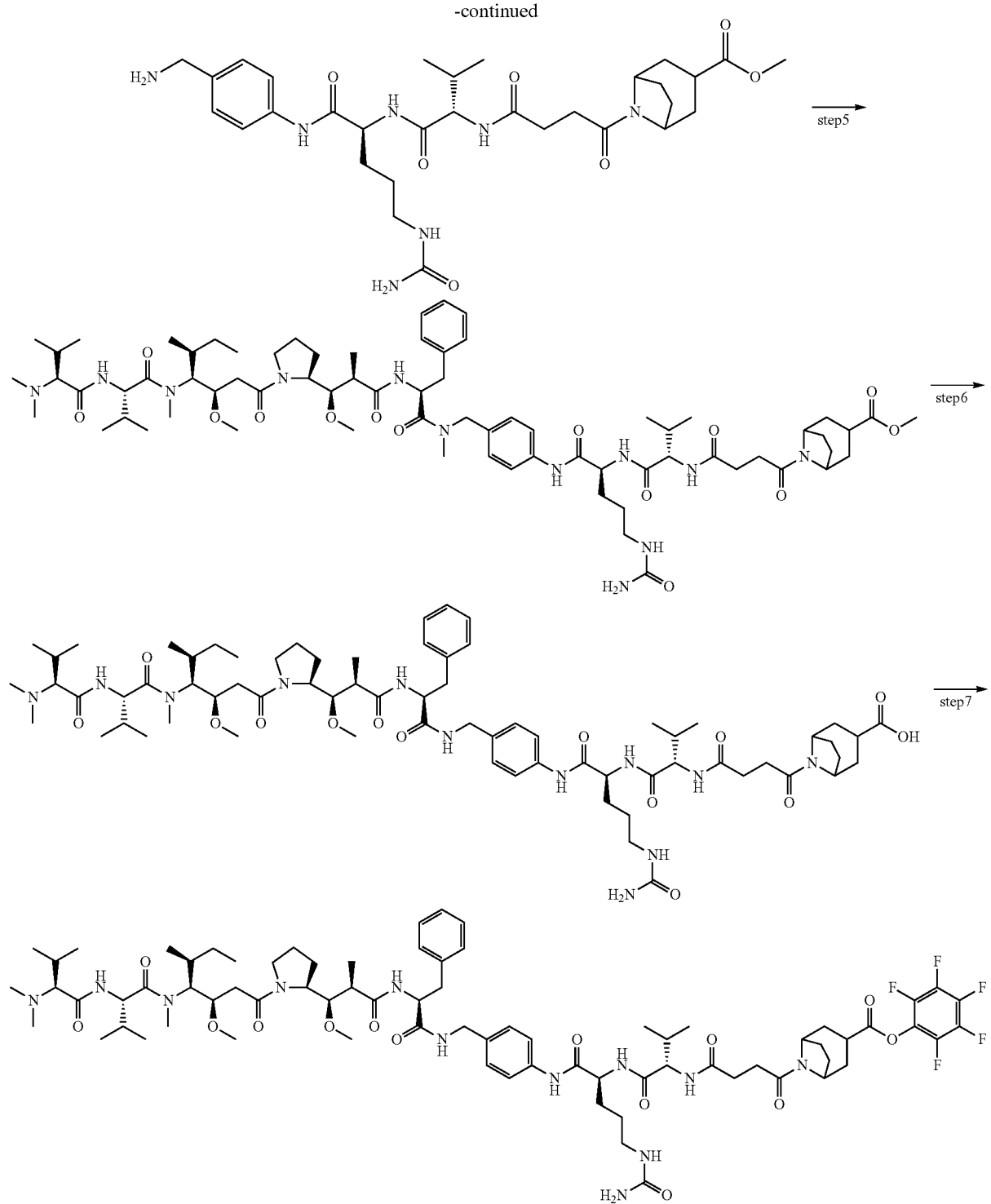

Step 1

Synthesis of 4-(3-methoxycarbonyl-8-azabicyclo[3.2.1]octan-8-yl)-4-oxobutyric acid At room temperature, methyl 8-azabicyclo[3.2.1]octan-3-formate (0.75 g, 4.46 mmol), succinic anhydride (0.45 g, 4.46 mmol), and acetonitrile (20 ml) were added in a three-necked bottle, then sodium bicarbonate (0.38 g, 4.46 mmol) was added with stirring at room temperature, nitrogen gas was charged to replace air three times, followed by heating up to 50° C., and reacting at this temperature for 4.0 h. The completion of the reaction was detected by LC-MS. Insolubles were removed by filtration, and the solvent was removed by vacuum distillation to give the title compound, a light yellow oily substance, 1.18 g. ESI-MS (m/z): 270.1 [M+H]$^+$.

Step 2

Synthesis of methyl 8-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)-8-azabicyclo[3.2.1]octan-3-formate (S)-2-((S)-2-amino-3-methylbutyramide)-N-(4-(hydroxymethyl)phenyl)-5-ureidovaleramide (0.5 g, 1.32 mmol), 4-(4-methyl-4-methoxycarbonyl-piperidinyl-1-yl)-4-oxobutyric acid (0.36 g, 1.32 mmol) was dissolved in N,N-dimethylformamide (10 mL), cooled down to 0° C., N,N-diisopropylethylamine (0.34 g, 2.64 mmol) was added, and benzotriazole-1-yl-oxyltripyrrolidinylphosphonium hexafluorophosphate (1.03 g, 1.98 mmol) was added batchwise within 15 min, followed by naturally heating to room temperature, and reacting for 2.0 h. The reaction was stopped once the completion of the reaction was detected by LC-MS, and then the reaction solution was concentrated to obtain a crude product, which was purified by preparative liquid chromatography, to give the title compound, a white solid, 0.51 g. ESI-MS (m/z): 631.3 [M+H]$^+$.

Step 3

Synthesis of methyl 8-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)-8-azabicyclo[3.2.1]octan-3-formate At room temperature, methyl 8-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)-8-azabicyclo[3.2.1]octan-3-formate (517 mg, 0.82 mmol) was dissolved in dichloromethane (40 mL), to which was added dropwise 33% HBr in HOAc (2.5 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give a crude product of the title compound, a white solid, 536 mg. ESI-MS (m/z): 693.2 [M+H]$^+$.

Step 4

Synthesis of methyl 8-(4-(((S)-1-(((S)-1-((4-aminophenyl)amino)-1-oxo-5-ureidopentyl-2-yl)amino)-3-methyl-1-oxobutyl-2-yl)amino)-4-oxobutyryl)-8-azabicyclo[3.2.1]octan-3-formate The crude product of methyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-methyl-4-formate (536 mg, 0.77 mmol) was dissolved in dichloromethane (10 mL), added dropwise in NH$_3$ in CH$_3$OH (10 mL, 7 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 407 mg. ESI-MS (m/z): 630.3 [M+H]$^+$.

Step 5

Synthesis of methyl 8-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formate At room temperature, 1-hydroxybenzotriazole (68 mg, 0.50 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (215 mg, 0.25 mmol), methyl 8-(4-(((S)-1-(((S)-1-((4-amino-phenyl)amino)-1-oxo-5-ureidopentyl-2-yl)amino)-3-methyl-1-oxobutyl-2-yl)amino)-4-oxobutyryl)-8-azabicyclo[3.2.1]octan-3-formate (157 mg, 0.25 mmol), and N,N-diisopropylethylamine (162 mg, 1.25 mmol), cooled down to 0° C., stirred for 10 min, then benzotriazole-1-yl-oxyltripyrrolidinylphosphonium hexafluorophosphate (195 mg, 0.38 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 196 mg. ESI-MS (m/z): 1357.8 [M+H]$^+$.

Step 6

Synthesis of 8-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formic acid Methyl 8-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formate (50 mg, 0.037 mmol) was dissolved in a mixed solvent of THF (5 mL) and water (5 mL), to which was added lithium hydroxide (50 mg, 1.20 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1343.8[M+H]$^+$.

Step 7

Synthesis of pentafluorophenol 8-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formate 8-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-8-azabicyclo[3.2.1]octan-3-formic acid (50 mg, 0.037 mmol) was dissolved in N,N-dimethylformamide (5 mL), to which were added in sequence pentafluorophenol (34 mg, 0.185 mmol), 1-ethyl-(3-dimethylaminopropyl)carbodiimide HCl salt (36 mg, 0.185 mmol), and 4-dimethylaminopyridine (14 mg, 0.111 mmol), followed by heating up to 50° C., and reacting overnight. The reaction was stopped once the completion of the reaction was detected by LC-MS. The reaction solution was purified by preparative liquid chromatography, to give the title compound, a white solid, 3.2 mg. ESI-MS (m/z): 1509.8 [M+H]$^+$.

Example 18 Synthesis of pentafluorophenol 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate (TL006)

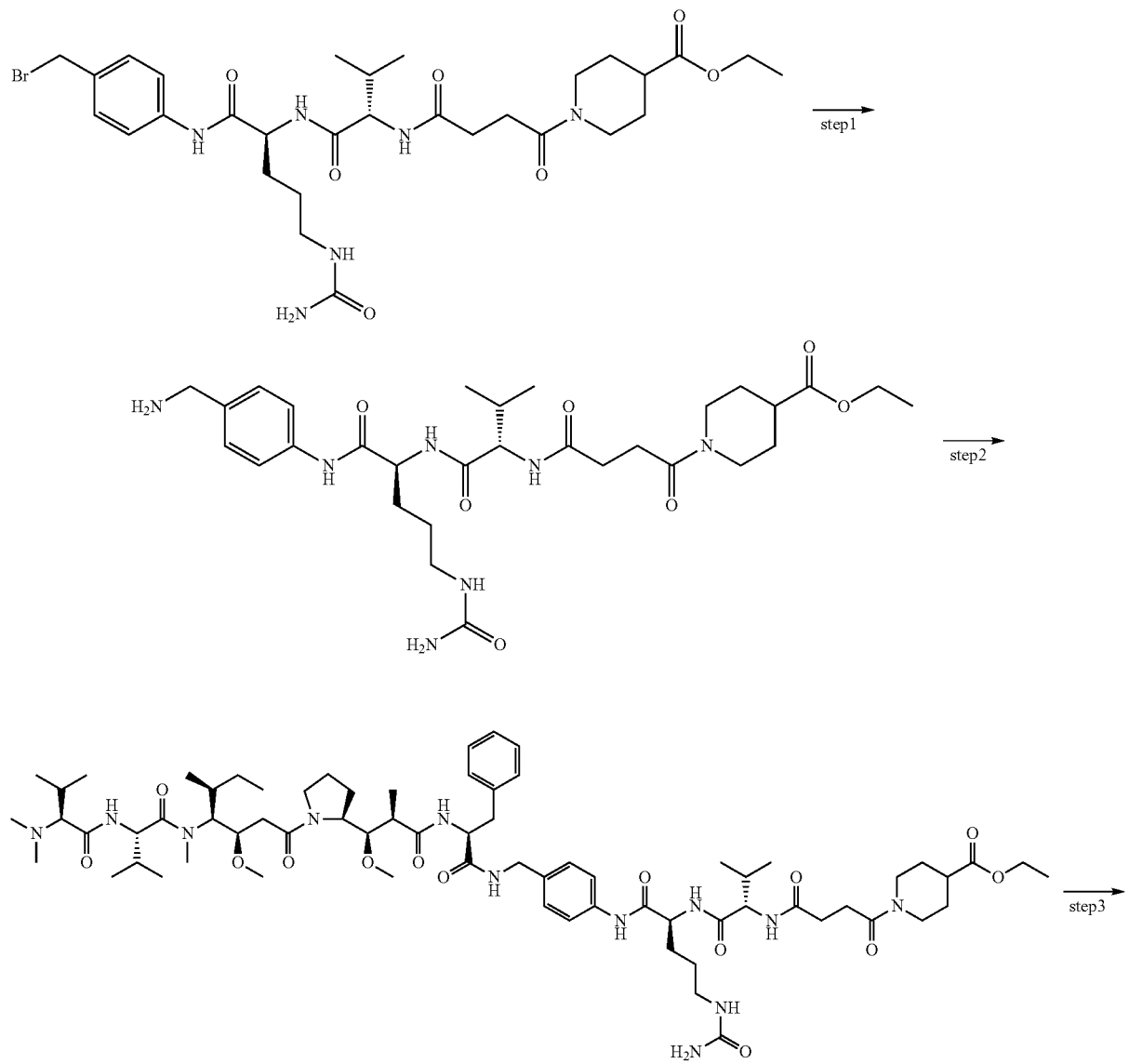

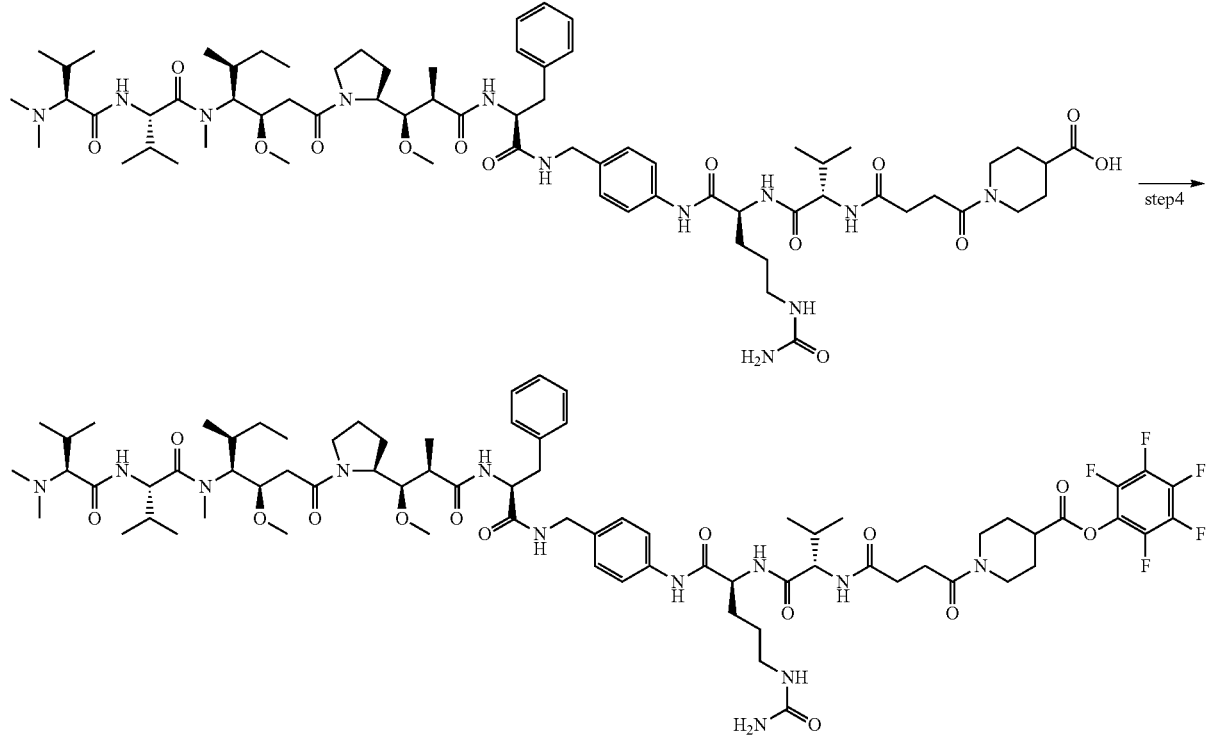

Step 1

Synthesis of ethyl 1-(4-(((S)-1-(((S)-1-((4-(aminomethyl)phenyl)amino)-1-oxo-5-ureidopentyl-2-yl)amino)-3-methyl-1-oxobutyl-2-yl)amino)-4-oxobutyryl)piperidinyl-4-formate The crude product of ethyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-formate (585 mg, 0.82 mmol) was dissolved in dichloromethane (10 mL), added dropwise in NH$_3$ in CH$_3$OH (10 mL, 7 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 158 mg. ESI-MS (m/z): 618.1 [M+H]$^+$.

Step 2

Synthesis of ethyl 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formate At room temperature, 1-hydroxybenzotriazole (68 mg, 0.50 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (215 mg, 0.25 mmol), ethyl 1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-formate (155 mg, 0.25 mmol), and N,N-diisopropylethylamine (162 mg, 1.25 mmol), cooled down to 0° C., stirred for 10 min, then benzotriazole-1-yl-oxyltripyrrolidinylphosphonium hexafluorophosphate (195 mg, 0.38 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 254 mg. ESI-MS (m/z): 1345.6 [M+H]$^+$.

Step 3

Synthesis of 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)piperidinyl-4-formic acid Ethyl 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2- methylpropionamido)-3-phenylpropionamido)methyl) phenyl)amino)-1-oxo-5-ureidopentyl-2-yl)amino)-3-methyl-1-oxobutyl-2-yl)amino)-4-oxobutyramido) piperidinyl-4-formate (50 mg, 0.037 mmol) was dissolved in a mixed solvent of THF (5 mL) and water (5 mL), to which was added lithium hydroxide (50 mg, 1.20 mmol), followed by reaction with stirring at room temperature for 2.0 h. The reaction was stopped once the completion of the reaction was detected by LC-MS. HCl solution (0.5 mol/L) was added to adjust pH=3-4, and a part of the solvent was removed by vacuum distillation, followed by freeze drying to give a crude product, ready for the next step of reaction. ESI-MS (m/z): 1317.8 [M+H]$^+$.

Step 4

Synthesis of pentafluorophenol 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido) methyl)phenyl)amino)-1-oxo-5-ureidopentyl-2-yl) amino)-3-methyl-1-oxobutyl-2-yl)amino)-4-oxobutyramido)piperidinyl-4-formate 1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl) phenyl)amino)-1-oxo-5-ureidopentyl-2-yl)amino)-3-methyl-1-oxobutyl-2-yl)amino)-4-oxobutyramido) piperidinyl-4-formic acid (50 mg, 0.037 mmol) was dissolved in N,N-dimethylformamide (5 mL), to which were added in sequence pentafluorophenol (34 mg, 0.185 mmol), 1-ethyl-(3-dimethylaminopropyl)carbodiimide HCl salt (36 mg, 0.185 mmol), and 4-dimethylaminopyridine (14 mg, 0.111 mmol), followed by heating up to 50° C., and reacting overnight. The reaction was stopped once the completion of the reaction was detected by LC-MS. The reaction solution was purified by preparative liquid chromatography, to give the title compound, a white solid, 14 mg. ESI-MS (m/z): 1482.8 [M+H]$^+$.

Example 19 Synthesis of pentafluorophenol cis-1-(4-(((S)-1-(((S)-1-((4-(((S)-2-((2R,3R)-3-((S)-1-((3R,4 S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate (TL007)

Step 1

Synthesis of cis-4-(4-(methoxy carbonyl)-2-methylpiperidinyl-1-yl)-4-oxobutyric acid At room temperature, methyl cis-2-methylpiperidinyl-4-formate HCl salt (200 mg, 1.04 mmol), succinic anhydride (104 mg, 1.04 mmol), and acetonitrile (5 ml) were added in a three-necked bottle, then sodium bicarbonate was added with stirring at room temperature (87.4 mg, 1.04 mmol), nitrogen gas was charged to replace air three times, followed by heating up to 50° C., and reacting at this temperature for 4.0 h. The completion of the reaction was detected by LC-MS. After cooling down to room temperature, the solvent was removed by vacuum distillation, were added in water (10 mL), washed with ethyl acetate (30 mL×3), washed with saturated salt solution (30 mL×2), and dried with anhydrous sodium sulfate. The desiccant was removed by filtration, and the solvent was removed by vacuum distillation to give the target compound, a light yellow oily substance, 250 mg. ESI-MS (m/z): 258.1 [M+H]$^+$.

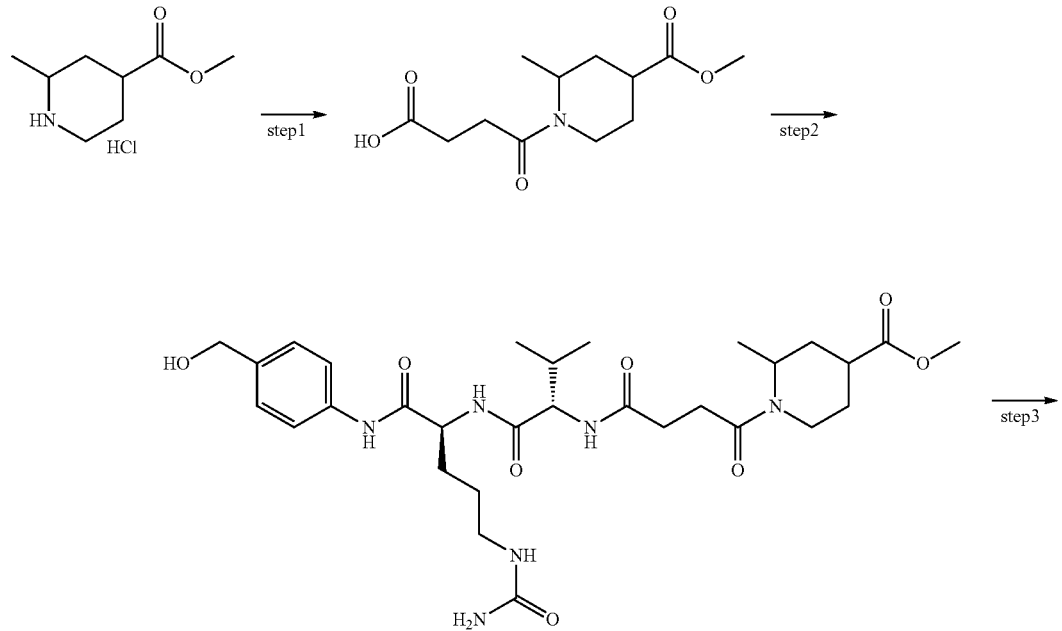

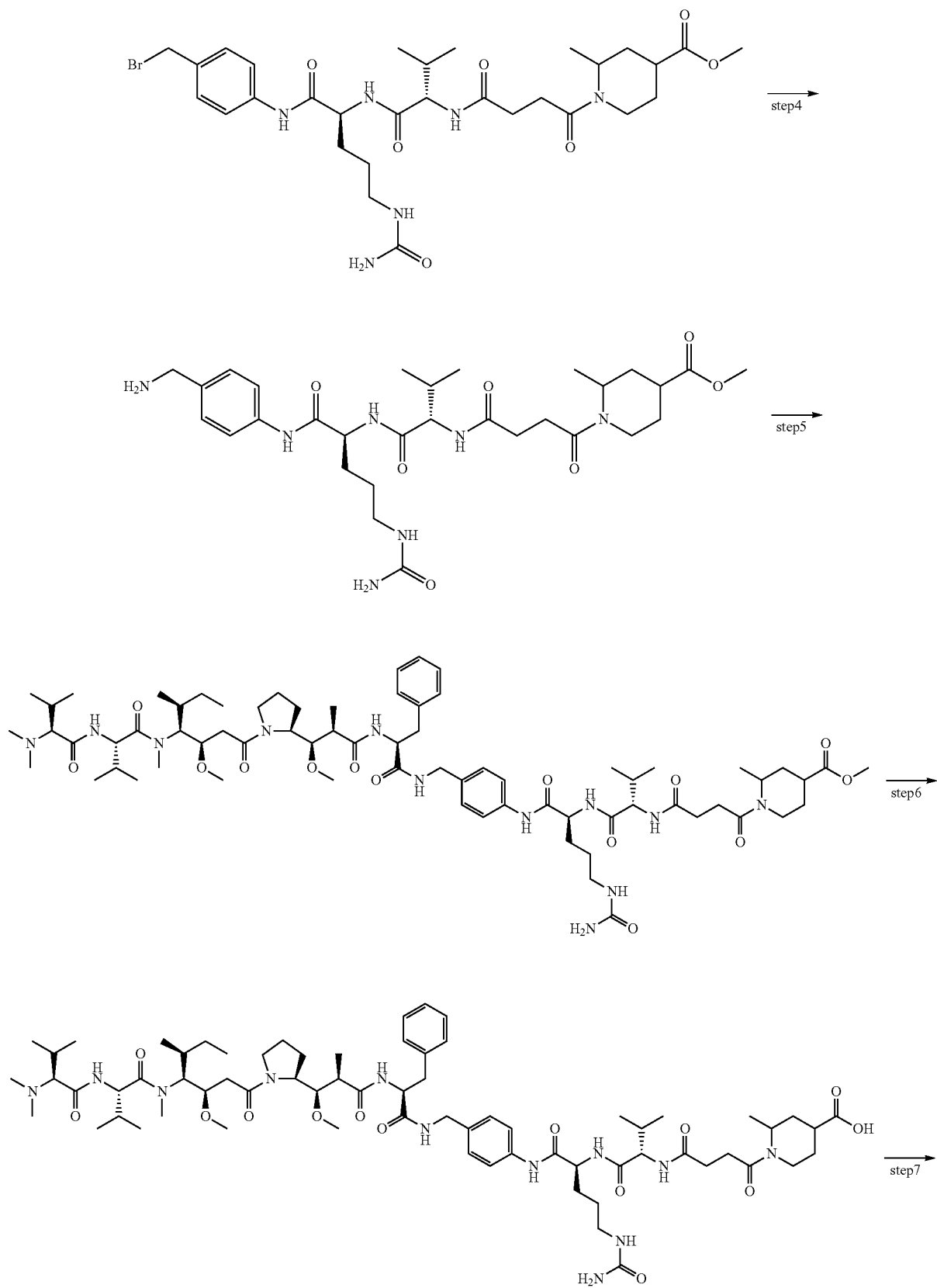

-continued

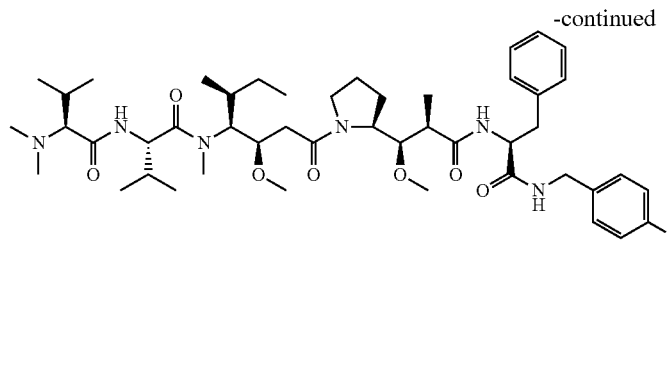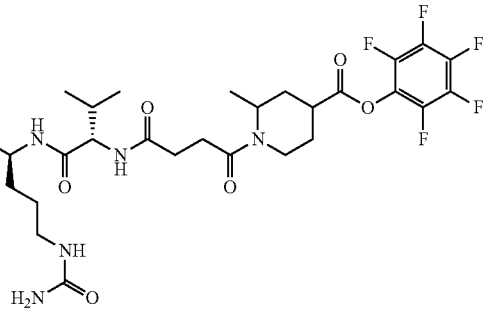

Step 2

Synthesis of methyl cis-1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)-2-methylPiperidine-4-formate (S)-2-((S)-2-amino-3-methylbutyramide)-N-(4-(hydroxymethyl)phenyl)-5-ureidovaleramide (370 mg, 0.97 mmol), and cis-4-(4-(methoxy carbonyl)-2-methylpiperidinyl-1-yl)-4-oxobutyric acid (250 mg, 0.97 mmol) were dissolved in N,N-dimethylformamide (5 mL), cooled down to 0° C., N,N-diisopropylethylamine (375 mg, 2.91 mmol) was added, benzotriazole-1-yl-oxyltripyrrolidinylphosphonium hexafluorophosphate (757 mg, 1.46 mmol) was added batchwise within 15 min, followed by naturally heating to room temperature, and reacting for 2.0 h. The reaction was stopped once the completion of the reaction was detected by LC-MS, and then the reaction solution was concentrated to obtain a crude product, which was purified by preparative liquid chromatography, to give the target compound, a white solid, 360 mg. ESI-MS (m/z): 619.3 [M+H]$^+$.

Step 3

Synthesis of methyl cis-1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)-2-methylpiperidinyl-4-formate At room temperature, methyl cis-1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)piperidinyl-4-formate (200 mg, 0.32 mmol) was dissolved in dichloromethane (5 mL), to which was added dropwise 33% HBr in HOAc (2.5 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, extracted with dichloromethane (30 mL×3), washed with saturated salt solution (30 mL×2), and dried with anhydrous sodium sulfate. The desiccant was removed by filtration, and the solvent was removed by vacuum distillation to give the title compound, a solid crude product 220 mg. ESI-MS (m/z): 681.3 [M+H]$^+$.

Step 4

Synthesis of methyl cis-1-(4-(((S)-1-(((S)-1-((4-(aminomethyl)phenyl)amino)-1-oxo-5-ureidopentyl-2-yl)amino)-3-methyl-1-oxobutyl-2-yl)amino)-4-oxobutyryl)-2methylpiperidinyl-4-formate The crude product of methyl cis-1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)piperidinyl-4-formate (220 mg, 0.32 mmol) was dissolved in dichloromethane (5 mL), added dropwise in NH$_3$ in CH$_3$OH (10 ml, 7 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the target compound, a white solid, 110 mg. ESI-MS (m/z): 618.3 [M+H]$^+$.

Step 5

Synthesis of methyl cis-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate At room temperature, 1-hydroxybenzotriazole (44 mg, 0.32 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (138 mg, 0.16 mmol), methyl cis-1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)-2-methylpiperidinyl-4-formate (100 mg, 0.16 mmol), and N,N-diisopropylethylamine (103 mg, 0.8 mmol), cooled down to 0° C., stirred for 10 min, and then benzotriazole-1-yl-oxyltripyrrolidinylphosphonium hexafluorophosphate (125 mg, 0.24 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the target compound, a white solid, 167 mg. ESI-MS (m/z): 1345.8 [M+H]+.

Step 6

Synthesis of cis-1-(4-(((S)-1-(((S)-1-((4-(((S)-2-((2R,3R)-3-((S)-1-((3R,4S,5S)-4-((S)-2-((S)-2-(dimethyl amino)-3-methylbutyramido)-N,3-dimethylbutyramido)-3-methoxy-5-methylheptanoyl) pyrrolidinyl-2-yl)-3-methoxy-2-methylpropionamido)-3-phenylpropionamido) methyl)phenyl)amino)-1-oxo-5-ureidopentyl-2-yl) amino)-3-methyl-1-oxobutyl-2-yl)amino)-4-oxobutyramido)-2-methylpiperidinyl-4-formic acid Methyl cis-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl) phenyl)amino)-1-oxo-5-ureidopentyl-2-yl)amino)-3-methyl-1-oxobutyl-2-yl)amino)-4-oxobutyramido)-2-methylpiperidinyl-4-formate (50 mg, 0.037 mmol) was dissolved in a mixed solvent of THF (2 mL) and water (4 mL), to which was added lithium hydroxide (15 mg, 0.37 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1331.8 [M+H]+.

Step 7

Synthesis of pentafluorophenol cis-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido) methyl)phenyl)amino)-1-oxo-5-ureidopentyl-2-yl) amino)-3-methyl-1-oxobutyl-2-yl)amino)-4-oxobutyramido)-2-methylpiperidinyl-4-formate Cis 1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl) phenyl)amino)-1-oxo-5-ureidopentyl-2-yl)amino)-3-methyl-1-oxobutyl-2-yl)amino)-4-oxobutyramido)-2-methylpiperidinyl-4-formic acid (50 mg, 0.037 mmol) was dissolved in N,N-dimethylformamide (2 mL), cooled down to 0° C., to which were added in sequence 1-ethyl-(3-dimethylaminopropyl)carbodiimide HCl salt (11 mg, 0.056 mmol), and 4-dimethylaminopyridine (14 mg, 0.111 mmol), stirred at this temperature for 5 min, and then pentafluorophenol (68 mg, 0.37 mmol) was added, followed by reaction for 6 h. The reaction was stopped once the completion of the reaction was detected by LC-MS. The reaction solution was purified by preparative liquid chromatography, to give the target compound, a white solid, 30 mg. ESI-MS (m/z): 1497.8 [M+H]+.

Example 20 Synthesis of pentafluorophenol cis-1-(4-(((2S)-1-(((2S)-1-((4-((2-((2R,3R)-3-((S)-1-((3R, 4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl) phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate (TL008)

Step 1

Synthesis of methyl cis-(E)-1-(4-(benzyloxy)-4-oxobut-2-en-1-yl)-2-trifluoromethyl-piperidinyl-4-formate At room temperature, methyl cis-2-trifluoromethyl-piperidinyl-4-formate (100 mg, 0.47 mmol), 4-benzyl bromocrotonate (242 mg, 0.94 mmol), and potassium carbonate (130 mg, 0.94 mmol) were added in a 20 mL one-necked bottle, and stirred until well mixed, followed by heating up to 100° C. and reacting for 6 h. A complete reaction of raw materials was monitored by high performance liquid chromatography-mass spectrometry, and rapidly purified by silica gel column to give the title compound, a light yellow oily liquid 80 mg. ESI-MS (m/z): 386.1 [M+H]+.

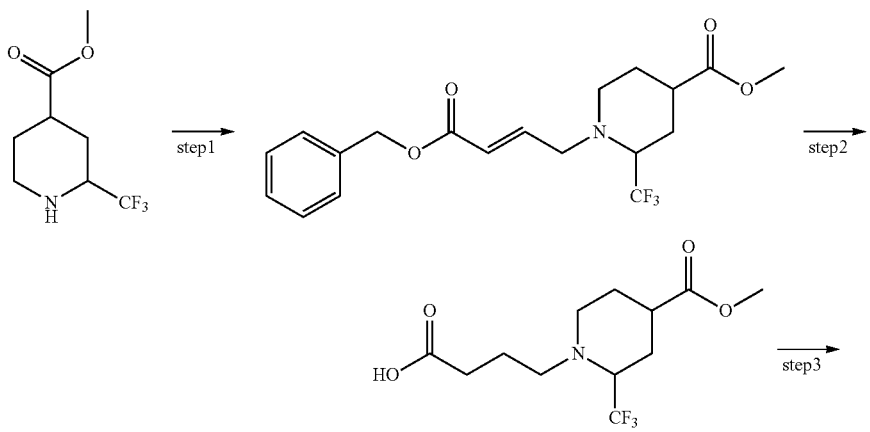

293 294
-continued
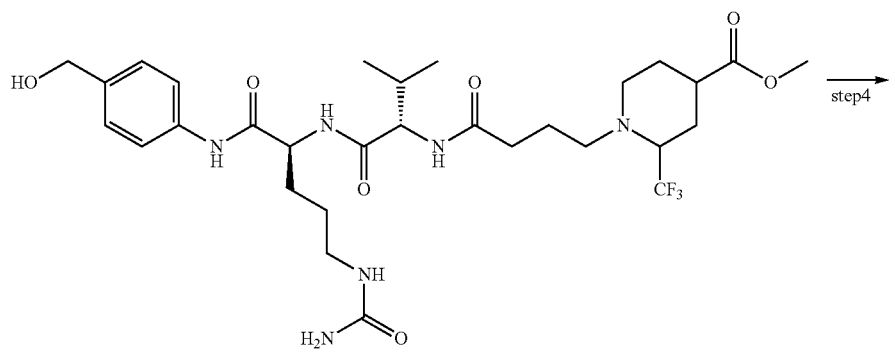
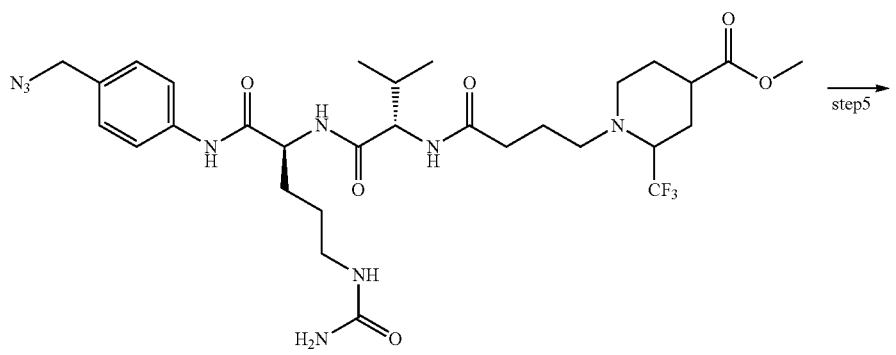
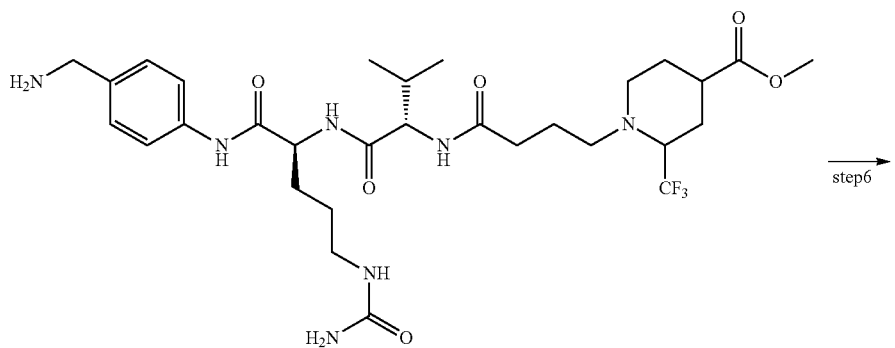
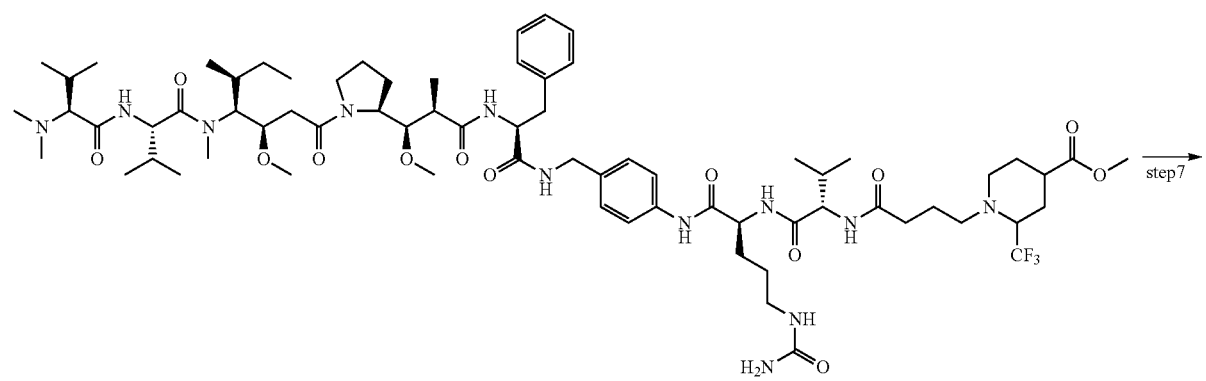

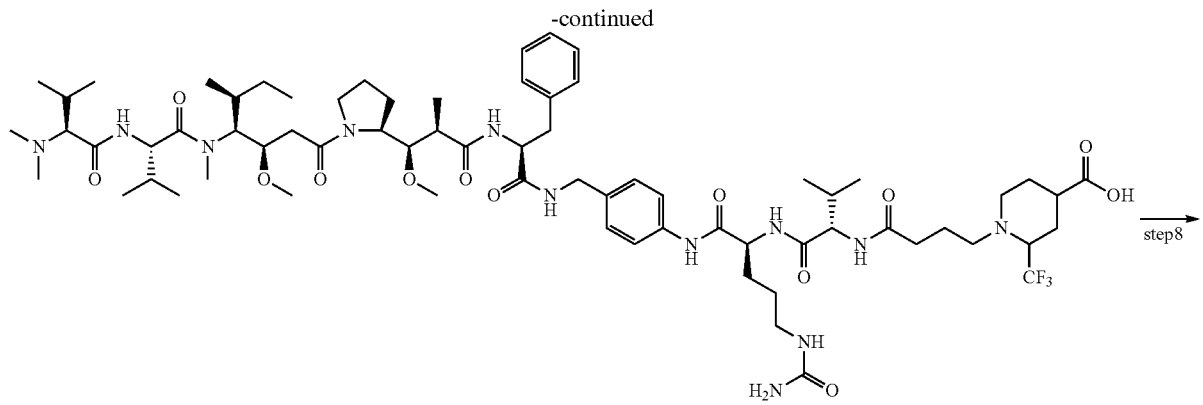

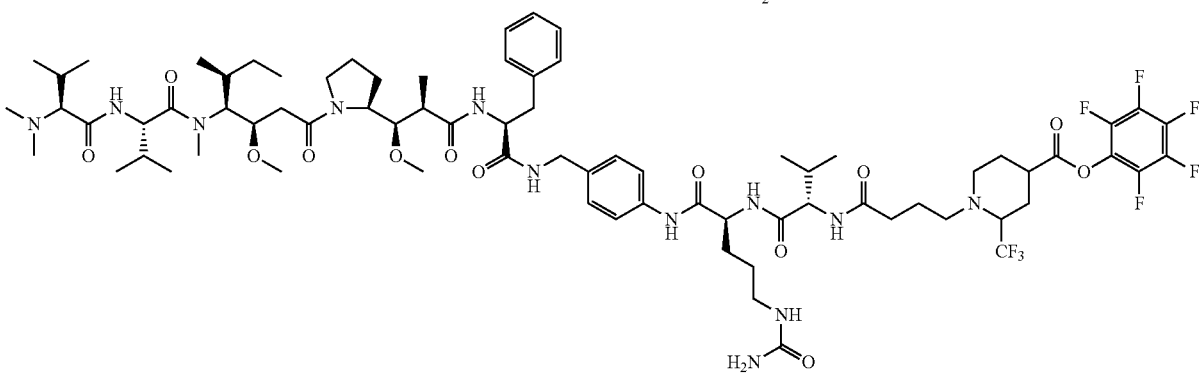

Step 2

Synthesis of cis-4-(4-(methoxycarbonyl)-2-(trifluoromethyl)piperidinyl-1-yl)-butyric acid At room temperature, methyl cis-(E)-1-(4-(benzyloxy)-4-oxobut-2-en-1-yl)-2-trifluoromethyl-piperidinyl-4-formate (20 mg, 0.05 mmol) was dissolved in ethanol (4 mL), platinum dioxide (5 mg) was added under protection of nitrogen gas, and hydrogen gas was charged to replace the nitrogen gas three times, followed by reaction at room temperature in hydrogen atmosphere for 20 min. A complete reaction of raw materials was monitored by high performance liquid chromatography-mass spectrometry, Insolubles were removed by filtration, the filtrate was concentrated under reduced pressure to give the title compound, a colorless oily liquid 15 mg. ESI-MS (m/z): 298.1 [M+H]$^+$.

Step 3

Synthesis of methyl cis-1-(4-(((S)-1-(((S)-1-((4-(hydroxymethyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate (S)-2-((S)-2-amino-3-methylbutyramido)-N-(4-(hydroxymethyl)phenyl)-5-ureidovaleramide (50 mg, 0.13 mmol), and cis-4-(4-(methoxycarbonyl)-2-(trifluoromethyl)piperidinyl-1-yl)butyric acid (39 mg, 0.13 mmol) were dissolved in N,N-dimethylformamide (2 mL), cooled down to 0° C., to which were added in sequence N,N-diisopropylethylamine (34 mg, 0.26 mmol), and benzotriazole-1-yl-oxytripyrrolidinophosphonium hexafluorophosphate (101 mg, 0.195 mmol), followed by reaction with stirring at room temperature for 2 h. A complete reaction of raw materials was monitored by high performance liquid chromatography-mass spectrometry, and the reaction solution was purified by preparative liquid chromatography to give the title compound, a white solid, 20 mg. ESI-MS (m/z): 659.3 [M+H]$^+$.

Step 4

Synthesis of methyl cis-1-(4-(((S)-1-(((S)-1-((4-(benzylazido)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate Methyl cis-1-(4-(((S)-1-(((S)-1-((4-(hydroxymethyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate (20 mg, 0.03 mmol) was dissolved in THF (2 mL), to which were added in sequence 1,8-diazabicyclo[5.4.0]undec-7-ene (15 mg, 0.09 mmol), and diphenylphosphoryl azide (42 mg, 0.15 mmol), followed by reaction with stirring at room temperature for 4 h. A complete reaction of raw materials was monitored by high performance liquid chromatography-mass spectrometry, and the reaction solution was purified by preparative liquid chromatography to give the title compound, a white solid, 15 mg. ESI-MS (m/z): 684.3 [M+H]$^+$.

Step 5

Synthesis of methyl cis-1-(4-(((S)-1-(((S)-1-((4-(aminomethyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate Methyl cis-1-(4-(((S)-1-(((S)-1-((4-(benzylazido)phenyl)amino)-1-oxo-5-uranoylpentyl-2-yl)amino)-3-methyl-1- oxobutyl-2-yl)amino)-4-oxobutyl)-2-(trifluoromethyl)piperidinyl-4-carboxylate (100 mg, 0.15 mmol) was dissolved in a mixed solvent of THF and water (v:v=10:1 5.5 mL), and triphenylphosphine (77 mg, 0.29 mmol) was added with stirring, followed by reaction with stirring at room temperature for 4 h. A complete reaction of raw materials was monitored by high performance liquid chromatography-mass spectrometry, and the reaction solution was purified by preparative liquid chromatography to give the title compound, a white solid, 80 mg. ESI-MS (m/z): 658.3 [M+H]$^+$.

Step 6

Synthesis of methyl cis-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl) pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl) piperidinyl-4-carboxylate At room temperature, 1-hydroxybenzotriazole (27 mg, 0.20 mmol) was dissolved in N,N-dimethylformamide (2 mL), cooled down to 0° C., to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylalanine (68 mg, 0.09 mmol), DIEA (59 mg, 0.46 mmol), and methyl cis-1-(4-(((S)-1-(((S)-1-((4-(aminomethyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate (60 mg, 0.09 mmol), stirred for 5 min, and then benzotriazole-1-yl-oxytripyrrolidinophosphonium hexafluorophosphate (71 mg, 0.14 mmol) was added, followed by reaction with stirring at room temperature for 2 h. A complete reaction of raw materials was monitored by high performance liquid chromatography-mass spectrometry, and the reaction solution was purified by preparative liquid chromatography to give the title compound, a white solid, 80 mg. ESI-MS (m/z): 693.4 [M/2+H]$^+$.

Step 7

Synthesis of cis-1-(4-(((S)-1-(((S)-1-((4-(((S)-2-((2R,3R)-3-((S)-1-((3R,4S,5S)-4-((S)-2-((S)-2-(dimethyl amino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl) piperidinyl-4-carboxylic acid Methyl cis-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl) amino)-1-oxo-5-uranoylpentyl-2-yl)amino)-3-methyl-1-oxobutyl-2-yl)amino)-4-oxobutyl)-2-(trifluoromethyl) piperidinyl-4-carboxylate (80 mg, 0.06 mmol) was dissolved in THF (2 mL), and water (4 mL), lithium hydroxide monohydrate (25 mg, 0.06 mmol) was added with stirring, followed by reaction with stirring at room temperature for 2 h. A complete reaction of raw materials was monitored by high performance liquid chromatography-mass spectrometry, the reaction solution was adjusted with diluted HCl (1N) to pH=3-4, followed by freeze drying to give the title compound, a white solid, 80 mg. ESI-MS (m/z): 686.5 [M/2+H]$^+$.

Step 8

Synthesis of pentafluorophenol cis-1-(4-(((2S)-1-(((2S)-1-((4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl) phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate At room temperature, cis-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl) amino)-1-oxo-5-uranoylpentyl-2-yl)amino)-3-methyl-1-oxobutyl-2-yl)amino)-4-oxobutyl)-2-(trifluoromethyl) piperidinyl-4-carboxylic acid (70 mg, 0.05 mmol) was dissolved in N,N-dimethylformamide (4 mL), cooled down to 0° C., to which were added in sequence 1-(3-dimethylaminopropyl)-3-ethylcarbodiimide HCl salt (15 mg, 0.08 mmol), and 4-dimethylaminopyridine (19 mg, 0.15 mmol), and then pentafluorophenol (94 mg, 0.51 mmol) was added all at once, followed by reaction with stirring at room temperature for 3 h. A complete reaction of raw materials was monitored by high performance liquid chromatography-mass spectrometry, and the reaction solution was directly purified by preparative liquid chromatography to give the title compound, a white solid, 60 mg. ESI-MS (m/z): 1537.6 [M+H]$^+$.

Example 21 Synthesis of pentafluorophenol cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino) carbamoyl)-9-isopropyl-1,8,11-trioxo-13, 16-dioxo-2,7,10-triazaoctadecyl-18-yl)-2-methylpiperidinyl-4-formate (TL009)

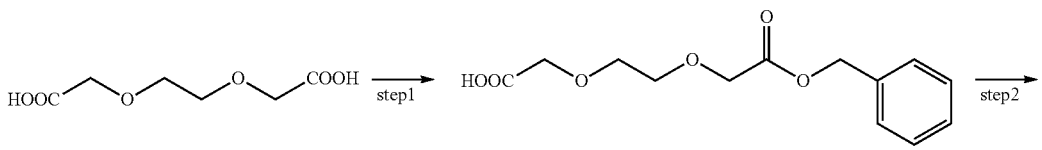

-continued
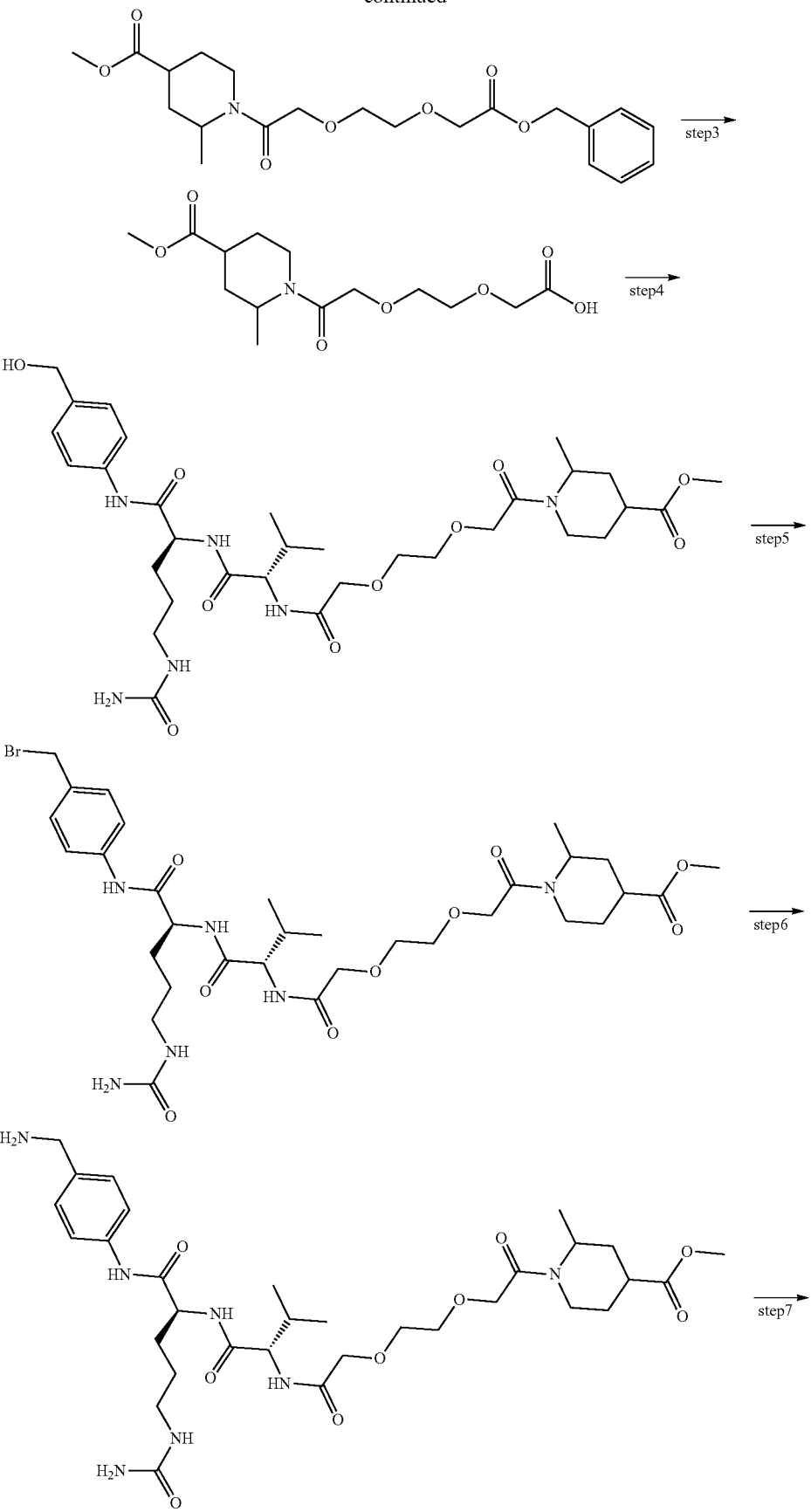

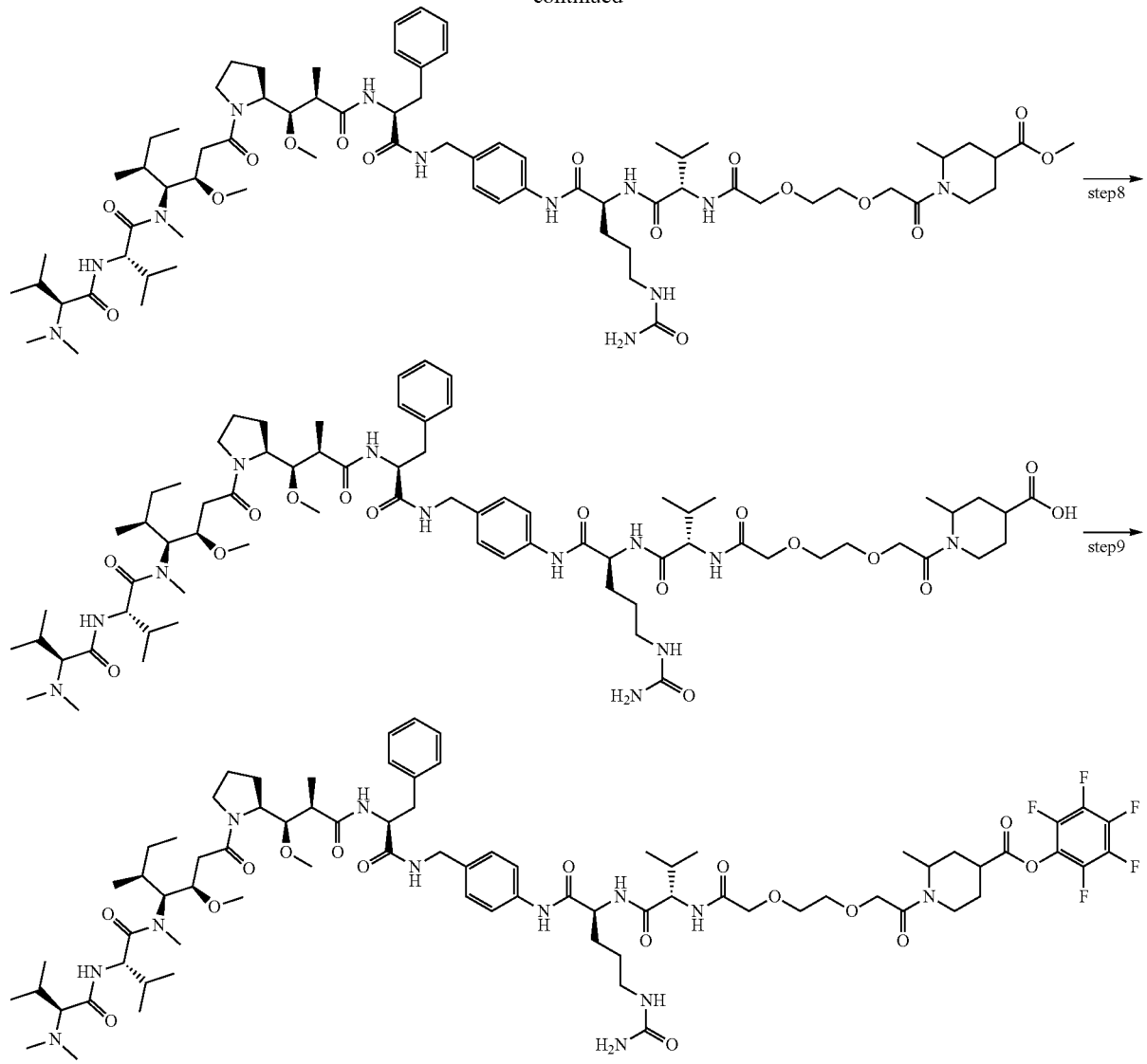

Step 1

Synthesis of 2-(2-(2-(benzyloxy)-2-oxoethoxy)ethoxy)acetic acid

At room temperature, 2,2'-(ethane-1,2-diylbis(oxy))-diacetic acid (3.0 g, 16.8 mmol), and triethylamine (3.0 g, 29.7 mmol) were added in N,N-dimethylformamide (150 mL), cooled down to 0° C., benzyl bromide was added dropwise slowly, and stirred at 0° C. for 4 h, followed by heating up to room temperature and reacting for 15 h. The completion of the reaction was detected by LC-MS. The reaction solution was poured into 1N HCl saturated with NaCl, and extracted with ethyl acetate (100 mL×6), the ethyl acetate phases were combined, and dried with anhydrous sodium sulfate. The desiccant was removed by filtration, the solvent was removed by vacuum distillation to give a crude product. The crude product was purified by silica gel column (petroleum ether:ethyl acetate=1:1) to give the title compound, a colorless oily substance, 680 mg. ESI-MS (m/z): 269.1 [M+H]$^+$.

Step 2

Synthesis of methyl cis-1-(2-(2-(2-(benzyloxy)-2-oxoethoxy)ethoxy)acetyl)-2-methylpiperidinyl-4-carboxylate Methyl 2-(2-(2-(benzyloxy)-2-oxoethoxy)ethoxy)acetic acid (660 mg, 2.5 mmol), cis-2-methylpiperidinyl-4-carboxylate HCl salt (400 mg, 2.0 mmol), 2-(7-azabenzotriazolyl)-N,N,N',N'-tetramethyluronium hexafluophosphate (1.6 g, 4.2 mmol), and N,N-diisopropylethylamine (588 mg, 4.6 mmol) were added in N,N-dimethylformamide (60 mL), followed by reaction with stirring at room temperature for 2 h. The completion of the reaction was detected by LC-MS. The reaction solution was poured into water, and extracted with ethyl acetate (100 mL×2), the ethyl acetate phases were combined, washed with saturated salt solution (100 mL×3) and dried with anhydrous sodium sulfate. The desiccant was removed by filtration, and the solvent was removed by vacuum distillation to give the title compound, a colorless oily substance, 600 mg. ESI-MS (m/z): 408.2 [M+H]$^+$.

Step 3

Synthesis of 2-(2-(2-((cis-(-4-(methoxy carbonyl)-2-methylpiperidinyl-1-yl)-2-oxoethoxy)ethoxy)acetic acid At room temperature, methyl cis-1-(2-(2-(2-(benzyloxy)-2-oxoethoxy)ethoxy)acetyl)-2-methylpiperidinyl-4-carboxylate (600 mg, 1.4 mmol) was added in methanol (6 mL), to which was added Pd—C (60 mg, 10%), hydrogen gas was charged to replace air three times, followed by reaction in hydrogen atmosphere with stirring at room temperature for 16 h. The completion of the reaction was detected by LC-MS. The reaction solution was filtered with diatomite, and the mother liquor was concentrated to dryness under reduced pressure, to give the title compound, a colorless oily substance, 460 mg. ESI-MS (m/z): 318.2 [M+H]$^+$.

Step 4

Synthesis of ethyl cis-1-((6S,9S)-1-amino-6-((4-(hydroxymethyl)phenyl)carbamoyl)-9-isopropyl-1,8,11-trioxo-13, 16-dioxa-2,7,10-triazaoctadecyl-18-yl)-2-methylpiperidinyl-4-carboxylate 2-(2-(2-((cis-(-4-(methoxy carbonyl)-2-methylpiperidinyl-1-yl)-2-oxoethoxy)ethoxy)acetic acid (320 mg, 1.0 mmol), (S)-2-((S)-2-amino-3-methylbutyramido)-N-(4-(hydroxymethyl)phenyl)-5-ureidovaleramide (382 mg, 1.0 mmol), and N,N-diisopropylethylamine (260 mg, 2.5 mmol) were added in N,N-dimethylformamide (4 mL), cooled down to 0° C., then benzotriazole-1-yl-oxyltripyrrolidinylphosphonium hexafluorophosphate (787 mg, 1.5 mmol) was added batchwise within 5 min, followed by reaction with stirring at room temperature for 3 h. The completion of the reaction was detected by LC-MS, and the reaction solution was directly purified by preparative liquid chromatography, to give the title compound, a white solid, 500 mg. ESI-MS (m/z): 679.4 [M+H]$^+$.

Step 5

Synthesis of ethyl cis-1-((6S,9S)-1-amino-6-((4-(bromomethyl)phenyl)carbamoyl)-9-isopropyl-1,8,11-trioxo-13, 16-dioxa-2,7,10-triazaoctadecyl-18-yl)-2-methylpiperidinyl-4-carboxylate At room temperature, ethyl cis-1-((6S,9S)-1-amino-6-((4-(hydroxymethyl)phenyl)carbamoyl)-9-isopropyl-1,8,11-trioxo-13, 16-dioxa-2,7,10-triazaoctadecyl-18-yl)-2-methylpiperidinyl-4-carboxylate (300 mg, 0.44 mmol) was dissolved in dichloromethane (6 mL), to which was added dropwise a solution of 33% HBr in HOAc (1.5 mL) in dichloromethane (6 mL) within 10 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give the title compound, a solid crude product 380 mg. ESI-MS (m/z): 741.2 [M+H]$^+$.

Step 6

Synthesis of ethyl cis-1-(6S,9S)-1-amino-6-((4-(aminomethyl)phenyl)carbamoyl)-9-isopropyl-1,8,11-trioxo-13, 16-dioxa-2,7,10-triazaoctadecyl-18-yl)-2-methylpiperidinyl-4-carboxylate The crude product of ethyl cis-1-((6S,9S)-1-amino-6-((4-(bromomethyl)phenyl)carbamoyl)-9-isopropyl-1,8,11-trioxo-13, 16-dioxa-2,7,10-triazaoctadecyl-18-yl)-2-methylpiperidinyl-4-carboxylate (380 mg, 0.51 mmol) was dissolved in dichloromethane (10 mL), and added dropwise in NH$_3$ in CH$_3$OH (25 mL, 7 mol/L) within 10 min, followed by reaction at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 150 mg. ESI-MS (m/z): 678.3 [M+H]$^+$.

Step 7

Synthesis of ethyl cis-methyl-1-((6S,9S)-1-amino-6-((4-(((S)-2-((2R,3R)-3-((S) ((3R,4S,5 S)-4-((S)-2-((S)-2-(dimethylamino)-3-methylbutyramido)-N,3-dimethylbutyramido)-3-methoxy-5-methylheptanoyl)-2-yl)-3-methoxy-2-methylpropionamido)-3-phenylpropionamido) methyl)phenyl)carbamoyl)-9-isopropyl-1,8,11-trioxo-13, 16-dioxo-2,7,10-triazaoctadecyl-18-yl)-2-methylpiperidinyl-4-carboxylate At room temperature, 1-hydroxybenzotriazole (30 mg, 0.22 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (95 mg, 0.11 mmol), methyl cis-1-((6S,9S)-1-amino-6-((4-(aminomethyl)phenyl)carbamoyl)-9-isopropyl-1,8,11-trioxo-13,16,19-trioxa-2,7,10-triazaheneicosane-21-acyl)-2-methylpiperidinyl-4-formate (80 mg, 0.11 mmol), and N,N-diisopropylethylamine (71 mg, 55 mmol), cooled down to 0° C., stirred for 10 min, and then benzotriazole-1-yl-oxyl-tripyrrolidinylphosphonium hexafluorophosphate (88 mg, 0.17 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 125 mg. ESI-MS (m/z): 703.4 [M/2+H]$^+$.

Step 8

Synthesis of cis-1-((6S,9S)-1-amino-6-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl) carbamoyl)-9-isopropyl-1,8,11-trioxo-13, 16-dioxa-2,7,10-triazaoctadecene-18-acyl)-2-methylpiperidinyl-4-formic acid Ethyl cis-methyl-1-((6S,9S)-1-amino-6-((4-(((S)-2-((2R,3R)-3-((S) ((3R,4S,5S)-4-((S)-2-((S)-2-(dimethyl amino)-3- methylbutyramido)-N,3-dimethylbutyramido)-3-methoxy-5-methylheptanoyl)-2-yl)-3-methoxy-2-methylpropionamido)-3-phenylpropionamido)methyl)phenyl)carbamoyl)-9-isopropyl-1,8,11-trioxo-13, 16-dioxo-2,7,10-triazaoctadecyl-18-yl)-2-methylpiperidinyl-4-carboxylate (50 mg, 0.035 mmol) was dissolved in a mixed solvent of THF (1 mL) and water (2 mL), to which was added lithium hydroxide (46 mg, 1.11 mmol), followed by reaction with stirring at room temperature for 1.0 h. The reaction was stopped once the completion of the reaction was detected by LC-MS. Diluted HCl (0.5 mol/L) was added to adjust pH=3-4, followed by freeze drying to give a crude product 50 mg, ready for the next step of reaction. 696.4 [M/2+H]$^+$.

Step 9

Synthesis of pentafluorophenol cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)carbamoyl)-9-isopropyl-1,8,11-trioxo-13, 16-dioxo-2,7,10-triazaoctadecyl-18-yl)-2-methylpiperidinyl-4-formate The crude product of cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl) carbamoyl)-9-isopropyl-1,8,11-trioxo-13, 16-dioxa-2,7,10-triazaoctadecyl-18-yl)-2-methylpiperidinyl-4-formic acid (50 mg, 0.035 mmol) was dissolved in N,N-dimethylformamide (6 mL), to which were added in sequence 1-(3-dimethylaminopropyl)-3-ethylcarbodiimide HCl salt (10 mg, 0.053 mmol), and 4-dimethylaminopyridine (13 mg, 0.101 mmol), cooled down to 0° C., and then pentafluorophenol (65 mg, 0.350 mmol) was added, followed by naturally heating up to room temperature, and reacting overnight. The reaction was stopped once the completion of the reaction was detected by LC-MS. The reaction solution was purified by preparative liquid chromatography, to give the title compound, a white solid, 29 mg. ESI-MS (m/z): 779.6 [M/2+H]$^+$.

Example 22 Synthesis of pentafluorophenol cis-1-((6S,9S)-1-amino-6-((4-(((S)-2-((2R,3R)-3-((S)-1-((3R,4 S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)carbamoyl)-9-isopropyl-1,8,11-trioxo-13,16,19-trioxa-2,7,10-triazaheneicosane-21-acyl)-2-methylpiperidinyl-4-formate (TL010)

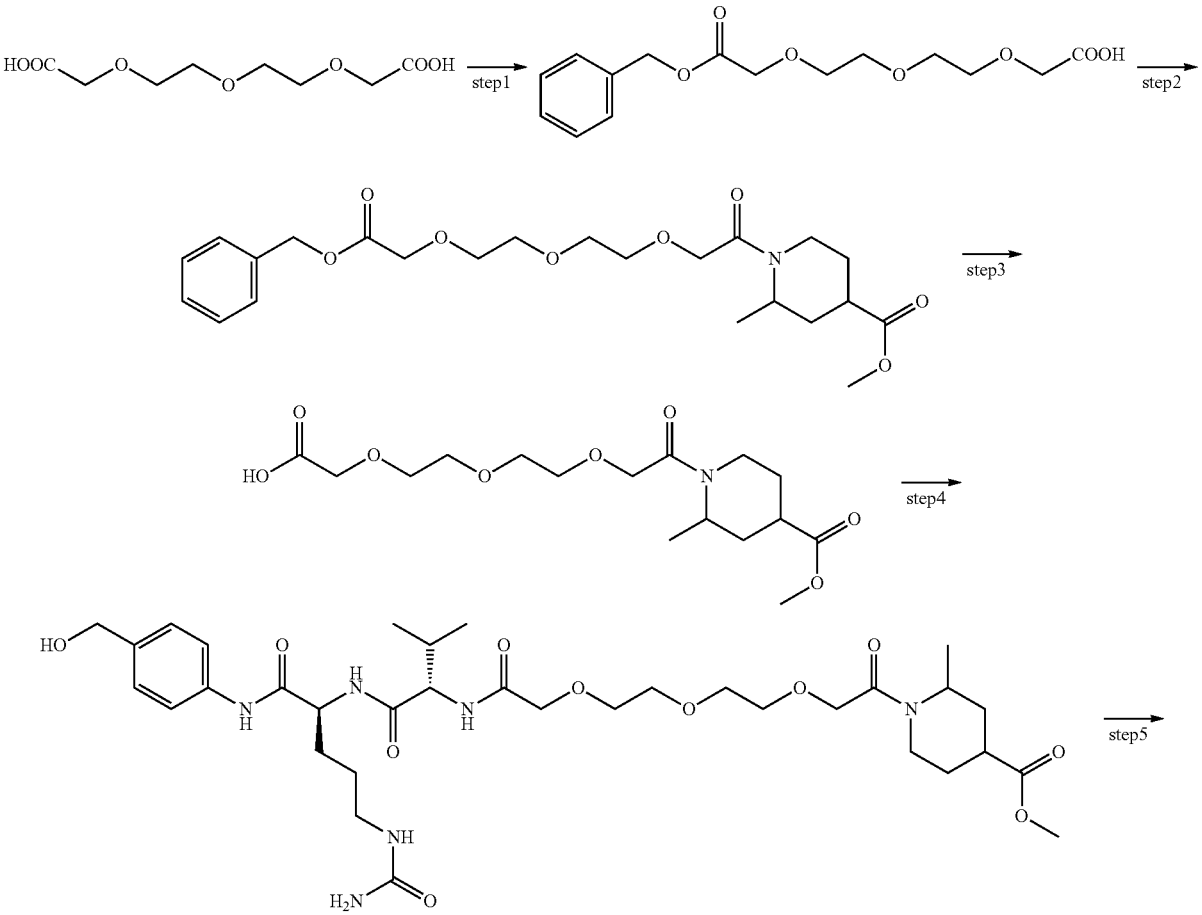

307 308
-continued
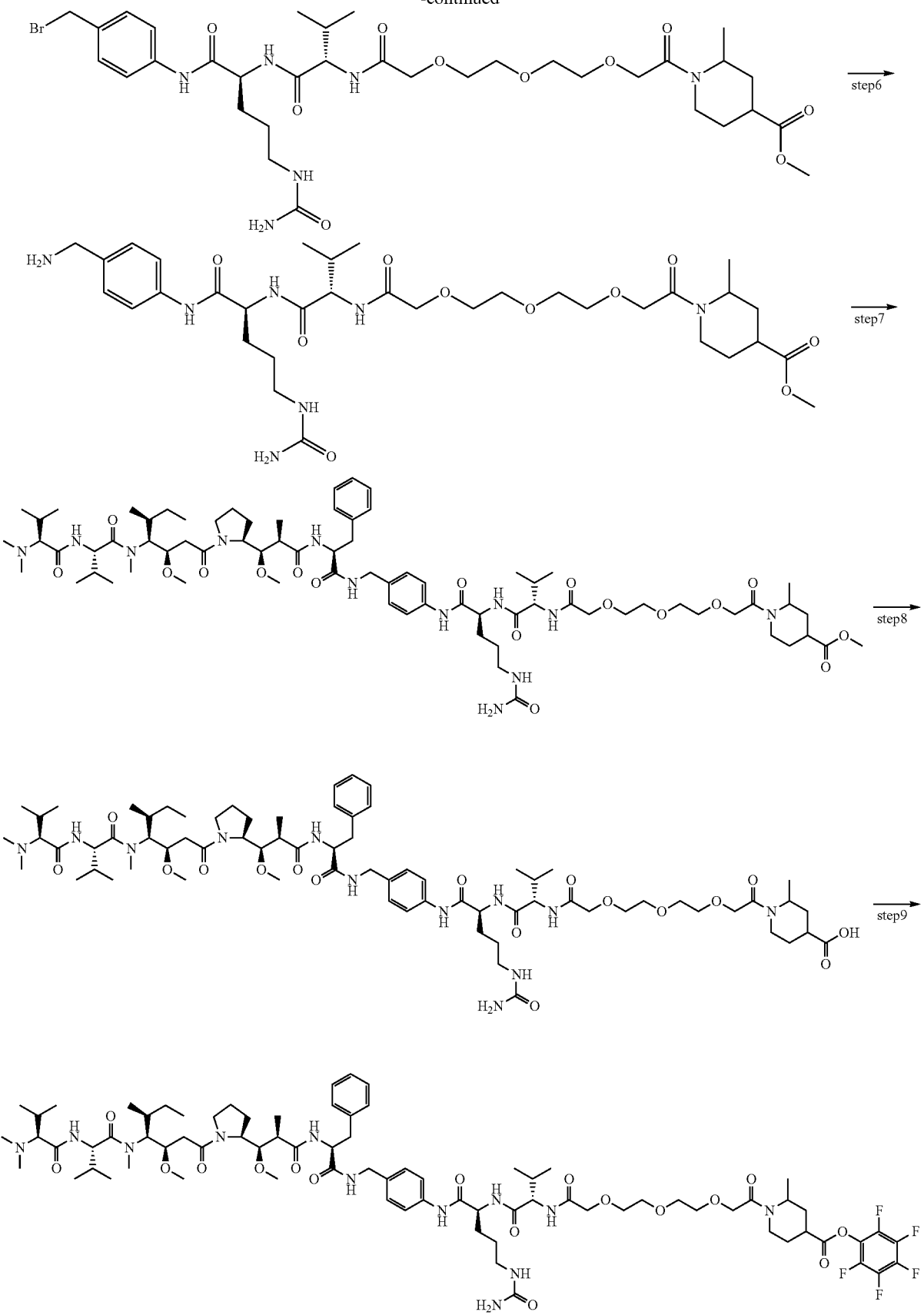

Step 1

Synthesis of 3-oxo-1-phenyl-2,5,8,11-tetraoxatridecane-13-carboxylic acid 3,6,9-trioxaundecanedioic acid (5.0 g, 22.50 mmol) was dissolved in N,N-dimethylformamide (250 mL), cooled down to −2° C., to which was added dropwise a solution of benzyl bromide (3.16 g, 18.49 mmol) in N,N-dimethylformamide (250 mL) within 2.5 h, followed by heating up to 0° C., and reacting at this temperature for 4.0 h, and then naturally heating up to room temperature, and stirring overnight. The completion of the reaction was detected by LC-MS. The reaction solution was poured into HCl (1 mol/L) saturated with NaCl, and washed with ethyl acetate (50 mL×6), organic phases were combined, and the solvent was removed by vacuum distillation, followed by rapid purification by column chromatography to give the title compound, a light yellow oily substance, 800 mg. ESI-MS (m/z): 313.1 $[M+H]^+$.

Step 2

Synthesis of methyl cis-2-methyl-1-(3-oxo-1-phenyl-2,5,8,11-tetraoxatridecane-13-acyl)piperidinyl-4-formate 3-Oxo-1-phenyl-2,5,8,11-tetraoxatridecane-13-carboxylic acid (710 mg, 2.28 mmol), methyl cis-2-methylpiperidinyl-4-formate HCl salt (400 mg, 2.07 mmol), 2-(7-azabenzotriazolyl)-N,N,N',N'-tetramethyluronium hexafluophosphate (1.573 g, 4.14 mmol), and N,N-diisopropylethylamine (587 mg, 4.55 mmol) were dissolved in N,N-dimethylformamide (10 mL), and reacted at room temperature for 1.0 h. The reaction was stopped once the completion of the reaction was detected by LC-MS. Water (30 mL) was added in the reaction solution, which was then extracted with ethyl acetate (20 mL×3), the organic phases were combined, washed with water (20 mL×2), washed with saturated sodium bicarbonate (20 mL) once, washed with saturated salt water (20 mL), and dried with anhydrous sodium sulfate. The desiccant was removed by filtration, and the solvent was removed by distillation, to give the title compound, a colorless oily substance, 882 mg. ESI-MS (m/z): 452.2 $[M+H]^+$.

Step 3

Synthesis of 2-(2-(2-(2-(cis-4-(methoxycarbonyl)-2-methylpiperidinyl-1-yl)-2-formyl methoxy)ethoxy)ethoxy)acetic acid At room temperature, methyl cis-2-methyl-1-(3-oxo-1-phenyl-2,5,8,11-tetraoxatridecane-13-acyl)piperidinyl-4-formate (220 mg, 0.49 mmol) was dissolved in anhydrous methanol (6 mL), to which was added Pd—C (40 mg, 10%), and hydrogen gas was charged to replace air three times, followed by reaction with stirring at room temperature for 1.0 h. The reaction was stopped once the completion of the reaction was detected by LC-MS. Insolubles were removed by filtration, Pd—C was washed multiple times with anhydrous methanol, and the solvent was removed by vacuum distillation, to give a crude product of the title compound 181 mg, which was directly used in the next step of reaction. ESI-MS (m/z): 362.2 $[M+H]^+$.

Step 4

Synthesis of methyl cis-1-((6S,9S)-1-amino-6-((4-(hydroxymethyl)phenyl)carbamoyl)-9-isopropyl-1,8,11-trioxo-13,16,19-trioxa-2,7,10-triazaheneicosane-21-acyl)-2-methylpiperidinyl-4-formate (S)-2-((S)-2-amino-3-methylbutyramide)-N-(4-(hydroxymethyl)phenyl)-5-ureidovaleramide (186 mg, 0.49 mmol), and 2-(2-(2-(2-(cis-4-(methoxycarbonyl)-2-methylpiperidinyl-1-yl)-2-formyl methoxy)ethoxy)ethoxy)acetic acid (177 mg, 0.49 mmol) were dissolved in N,N-dimethylformamide (5 mL), cooled down to 0° C., N,N-diisopropylethylamine (127 mg, 0.98 mmol) was added, benzotriazole-1-yl-oxyltripyrrolidinylphosphonium hexafluorophosphate (382 mg, 0.74 mmol) was added batchwise within 5 min, followed by naturally heating to room temperature, and reacting for 1.0 h. The reaction was stopped once the completion of the reaction was detected by LC-MS, and then the reaction solution was concentrated to obtain a crude product, which was purified by preparative liquid chromatography, to give the title compound, a white solid, 230 mg. ESI-MS (m/z): 723.3 $[M+H]^+$.

Step 5

Synthesis of methyl cis-1-((6S,9S)-1-amino-6-((4-(bromomethyl)phenyl)carbamoyl)-9-isopropyl-1,8,11-trioxo-13,16,19-trioxa-2,7,10-triazaheneicosane-21-acyl)-2-methylpiperidinyl-4-formate At room temperature, methyl cis-1-((6S,9S)-1-amino-6-((4-(hydroxymethyl)phenyl)carbamoyl)-9-isopropyl-1,8,11-trioxo-13,16,19-trioxa-2,7,10-triazaheneicosane-21-acyl)-2-methylpiperidinyl-4-formate (200 mg, 0.28 mmol) was dissolved in dichloromethane (6 mL), to which was added dropwise a solution of 33% HBr in HOAc (1.0 mL) in dichloromethane (6 mL) within 10 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give the title compound, a solid crude product 230 mg. ESI-MS (m/z): 785.2 $[M+H]^+$.

Step 6

Synthesis of methyl cis-1-((6S,9S)-1-amino-6-((4-(aminomethyl)phenyl)carbamoyl)-9-isopropyl-1,8,11-trioxo-13,16,19-trioxa-2,7,10-triazaheneicosane-21-acyl)-2-methylpiperidinyl-4-formate The crude product of methyl cis-1-((6S,9S)-1-amino-6-((4-(bromomethyl)phenyl)carbamoyl)-9-isopropyl-1,8,11-trioxo-13,16,19-trioxa-2,7,10-triazaheneicosane-21-acyl)-2-methylpiperidinyl-4-formate (230 mg, 0.28 mmol) was dissolved in dichloromethane (10 mL), and added dropwise in $NH_3$ in $CH_3OH$ (25 ml, 7 mol/L) within 10 min, followed by reaction at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 80 mg. ESI-MS (m/z): 722.3 [M+H]⁺.

Step 7

Synthesis of methyl cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido) methyl)phenyl) carbamoyl)-9-isopropyl-1,8,11-trioxo-13,16,19-trioxa-2,7,10-triazaheneicosane-21-acyl)-2-methylpiperidinyl-4-formate At room temperature, 1-hydroxybenzotriazole (30 mg, 0.22 mmol) was dissolved in N,N-dimethylformamide (6 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (95 mg, 0.11 mmol), methyl cis-1-((6S,9S)-1-amino-6-((4-(aminomethyl) phenyl)carbamoyl)-9-isopropyl-1,8,11-trioxo-13,16,19-trioxa-2,7,10-triazaheneicosane-21-acyl)-2-methylpiperidinyl-4-formate (80 mg, 0.11 mmol), and N,N-diisopropylethylamine (71 mg, 55 mmol), cooled down to 0° C., stirred for 10 min, and then benzotriazole-1-yl-oxyl-tripyrrolidinylphosphonium hexafluorophosphate (88 mg, 0.17 mmol) was added batchwise within 10 min, followed by reaction at this temperature for 1.0 h. The reaction was stopped once the completion of the reaction was detected by LC-MS, and then the reaction solution was concentrated to obtain a crude product, which was purified by preparative liquid chromatography, to give the title compound, a white solid, 125 mg. ESI-MS (m/z): 725.5 [M/2+H]⁺.

Step 8

Synthesis of cis-1-((6S,9S)-1-amino-6-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl) carbamoyl)-9-isopropyl-1,8,11-trioxo-13,16,19-trioxa-2,7,10-triazaheneicosane-21-acyl)-2-methylpiperidinyl-4-formic acid Methyl cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl) phenyl) carbamoyl)-9-isopropyl-1,8,11-trioxo-13,16,19-trioxa-2,7,10-triazaheneicosane-21-acyl)-2-methylpiperidinyl-4-formate (50 mg, 0.034 mmol) was dissolved in a mixed solvent of THF (1 mL) and water (2 mL), to which was added lithium hydroxide (46 mg, 1.11 mmol), followed by reaction with stirring at room temperature for 1.0 h. The reaction was stopped once the completion of the reaction was detected by LC-MS. HCl solution (0.5 mol/L) was added to adjust pH=3-4, followed by freeze drying to give a crude product 50 mg, ready for the next step of reaction. 718.5 [M/2+H]⁺.

Step 9

Synthesis of pentafluorophenol cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido) methyl)phenyl)amino)carbamoyl)-9-isopropyl-1,8, 11-trioxo-13,16,19-trioxa-2,7,10-triazaheneicosane-21-acyl)-2-methylpiperidinyl-4-formate The crude product of cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl) phenyl) carbamoyl)-9-isopropyl-1,8,11-trioxo-13,16,19-trioxa-2,7,10-triazaheneicosane-21-acyl)-2-methylpiperidinyl-4-formic acid (50 mg, 0.034 mmol) was dissolved in N,N-dimethylformamide (6 mL), to which were added in sequence 1-(3-dimethylaminopropyl)-3-ethylcarbodiimide HCl salt (10 mg, 0.053 mmol), and 4-dimethylaminopyridine (13 mg, 0.101 mmol), cooled down to 0° C., and then pentafluorophenol (65 mg, 0.350 mmol) was added, followed by naturally heating up to room temperature, and reacting overnight. The reaction was stopped once the completion of the reaction was detected by LC-MS. The reaction solution was purified by preparative liquid chromatography, to give the title compound, a white solid, 25 mg. ESI-MS (m/z): 801.5 [M/2+H]⁺.

Example 23 Synthesis of pentafluorophenol (3R, 4R)-1-(4-(((2S)-1-(((2S)-1-(4-((2-((2R,3R)-3-((S)-1-((3R,4 S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formate (TL011)

Step 1

Synthesis of methyl cis-1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)-3-methylpiperidinyl-4-formate At room temperature, (S)-2-((S)-2-amino-3-methylbutyramido)-N-(4-(hydroxymethyl)phenyl)-5-ureidopropionamide (300 mg, 0.79 mmol) and 4-(cis-4-(methoxycarbonyl)-3-methylpiperidinyl-1-yl)-4-oxobutyric acid (207 mg, 0.79 mmol) were dissolved in N,N-dimethylformamide (4 mL), cooled down to 0° C., to which were added in sequence N,N-diisopropylethylamine (204 mg, 1.58 mmol) and benzotriazole-1-yl-oxytripyrrolidinophosphonium hexafluorophosphate (616 mg, 1.19 mmol), followed by stirring the reaction system at room temperature for 3 h. The reaction solution was purified by preparative liquid chromatography, to give the title compound 300 mg, a white solid. ESI-MS (m/z): 619.2 [M+H]⁺.

313 314
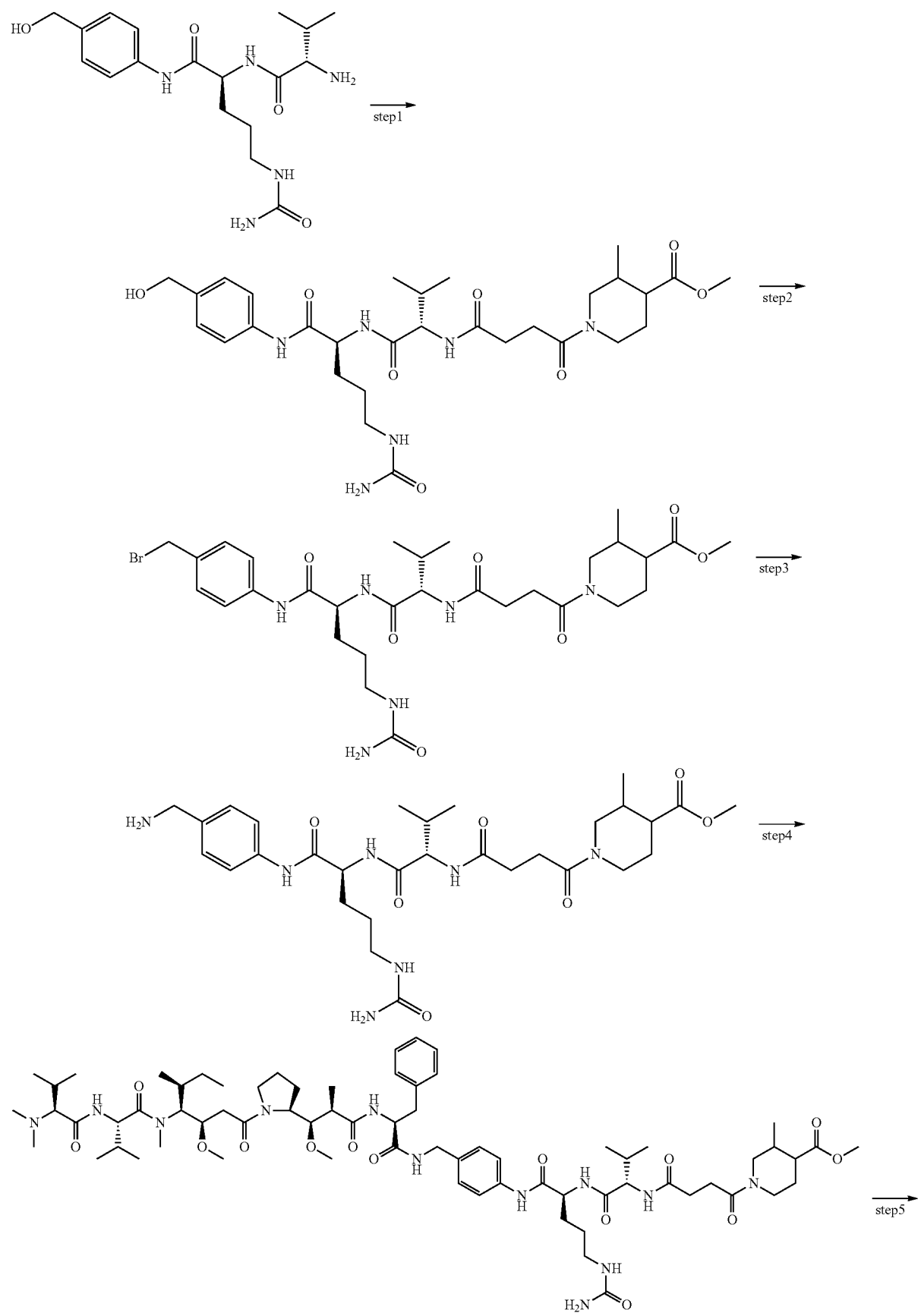

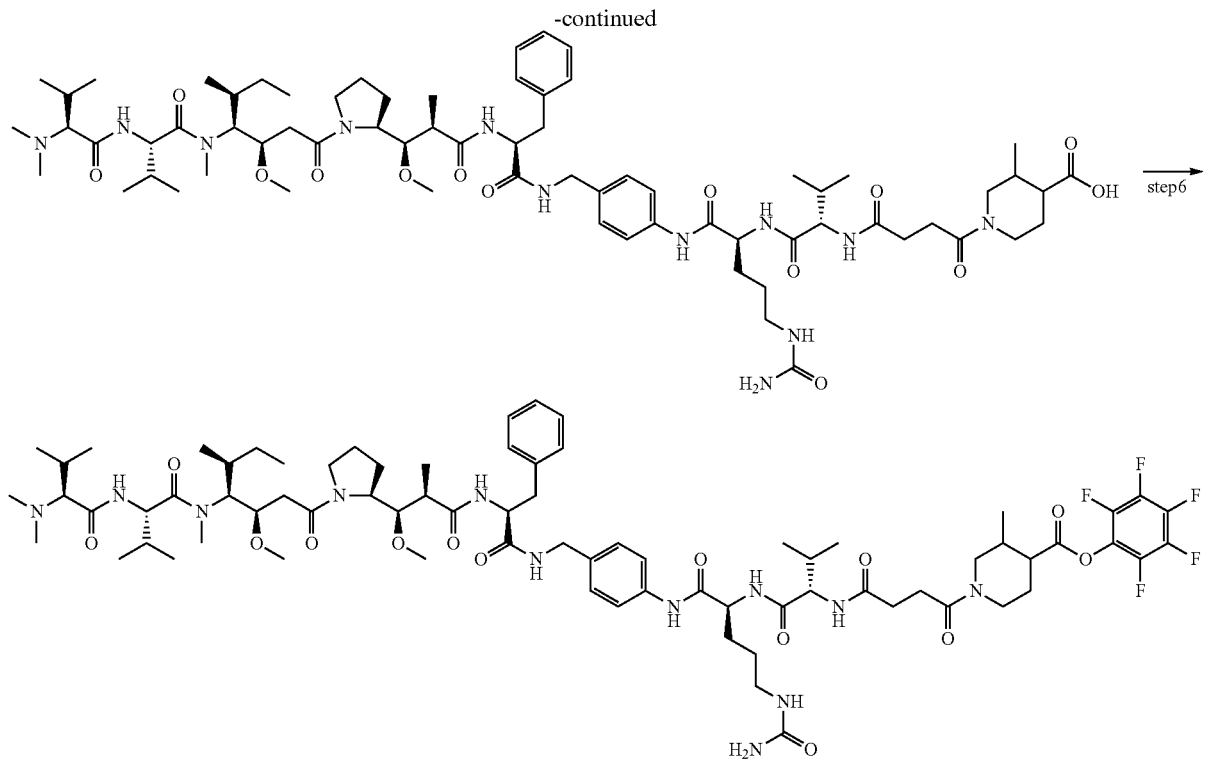

Step 2

Synthesis of methyl cis-1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)-3-methylpiperidinyl-4-formate At room temperature, ethyl cis-1-(4-(((S)-1-(((S)-1-((4-(hydroxymethyl)phenyl)amino)-1-oxo-5-ureidopentyl-2-yl)amino)-3-methyl-1-oxobutyl-2-yl)amino)-4-oxobutyryl)-3-methylpiperidinyl-4-formate (200 mg, 0.32 mmol) was dissolved in dichloromethane (20 mL), to which was added dropwise a solution of 33% HBr in HOAc (0.7 mL) in dichloromethane (6 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give a crude product of the title compound, a white solid, 220 mg. ESI-MS (m/z): 681.1 [M+H]$^+$.

Step 3

Synthesis of methyl cis-1-(4-(((S)-1-(((S)-1-((4-(aminomethyl)phenyl)amino)-1-oxo-5-ureidopentyl-2-yl)amino)-3-methyl-1-oxobutyl-2-yl)amino)-4-oxobutyryl)-3-methylpiperidinyl-4-formate Methyl cis-1-(4-(((S)-1-(((S)-1-((4-(bromomethyl)phenyl)amino)-1-oxo-5-ureidopentyl-2-yl)amino)-3-methyl-1-oxobutyl-2-yl)amino)-4-oxobutyryl)-3-methylpiperidinyl-4-formate (220 mg, 0.32 mmol) was dissolved in dichloromethane (10 mL), added dropwise in NH$_3$ in CH$_3$OH (10 ml, 7 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 70 mg. ESI-MS (m/z): 618.1 [M+H]$^+$.

Step 4

Synthesis of methyl cis-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formate At room temperature, 1-hydroxybenzotriazole (22 mg, 0.162 mmol) was dissolved in N,N-dimethylformamide (1 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (70 mg, 0.081 mmol), methyl cis-1-(4-(((S)-1-(((S)-1-((4-(aminomethyl)phenyl)amino)-1-oxo-5-ureidopentyl-2-yl)amino)-3-methyl-1-oxobutyl-2-yl)amino)-4-oxobutyryl)-3-methylpiperidinyl-4-formate (50 mg, 0.081 mmol), and N,N-diisopropylethylamine (52 mg, 0.405 mmol), cooled down to 0° C., stirred for 10 min, then benzotriazole-1-yl-oxyl-tripyrrolidinylphosphonium hexafluorophosphate (63 mg, 0.12 mmol) was added batchwise within 10 min, followed by reaction at this temperature for 1.0 h. The reaction was stopped once the completion of the reaction was detected by LC-MS. The reaction solution was purified by preparative liquid chromatography, to give the title compound, a white solid, 88 mg. ESI-MS (m/z): 1345.6 [M+H]$^+$.

Step 5

Synthesis of cis-1-(4-(((2S)-1-(((2S)-1-((4-((2-((2R,3R)-3-((S)-1-((3R,4S,5S)-4-((S)-2-((S)-2-(dimethyl-amino)-3-methylbutyramido)-N,3-dimethylbu-tyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formic acid Methyl cis-1-(4-(((2S)-1-(((2S)-1-((4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formate (50 mg, 0.037 mmol) was dissolved in a mixed solvent of THF (5 mL) and water (5 mL), to which was added lithium hydroxide (50 mg, 1.20 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1331.8 [M+H]$^+$.

Step 6

Synthesis of pentafluorophenol cis-1-(4-(((2S)-1-(((2S)-1-((4-((2-((2R,3R)-3-((S)-1-((3R,4S,5 S)-4-((S)-2-((S)-2-(dimethylamino)-3-methylbu-tyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formate Cis-1-(4-(((2S)-1-(((2S)-1-((4-((2-((2R,3R)-3-((S)-1-((3R,4S,5 S)-4-((S)-2-((S)-2-(dimethylamino)-3-methylbu-tyramido)-N,3-dimethylbutyramido)-3-methoxy-5-methyl-heptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-3-methylpiperidinyl-4-formic acid (50 mg, 0.037 mmol) was dissolved in N,N-dimethylformamide (2 mL), to which were added 1-ethyl-(3-dimethylaminopropyl)carbodiimide HCl salt (11 mg, 0.056 mmol), and 4-dimethylaminopyridine (14 mg, 0.113 mmol) under the protection of nitrogen, cooled down to 0° C., and then pentafluorophenol (69 mg, 0.376 mmol) was added, followed by heating up to room temperature, and reacting overnight. The reaction was stopped once the completion of the reaction was detected by LC-MS. The reaction solution was purified by preparative liquid chromatography, to give the title compound 34 mg, a white solid. ESI-MS (m/z): 1497.8 [M+H]$^+$.

Example 24 Synthesis of pentafluorophenol cis-1-((6S,9S)-1-amino-6-((4-(((S)-2-((2R,3R)-3-((S)-1-((3R,4 S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formate (TL012)

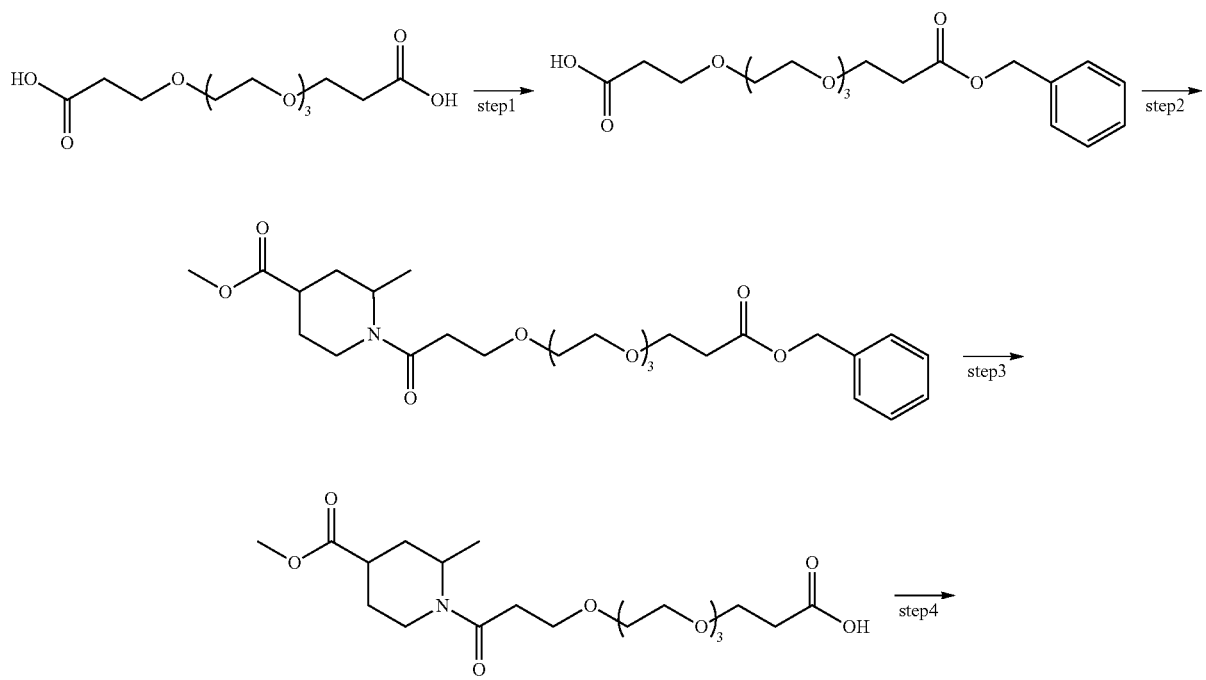

-continued
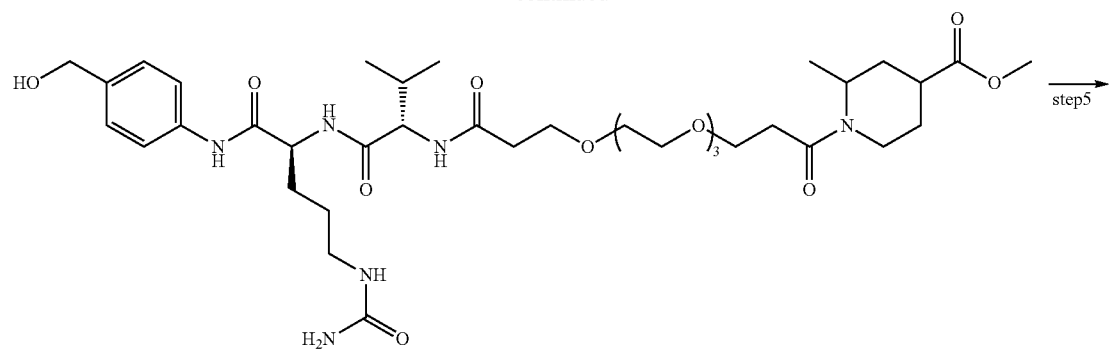
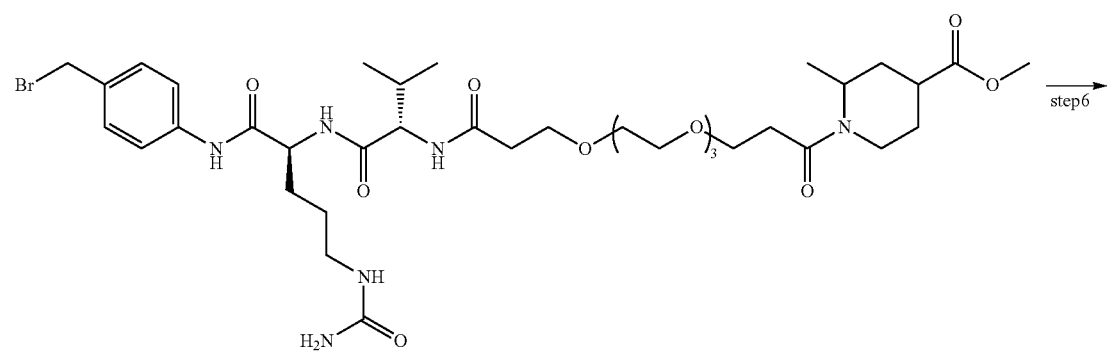
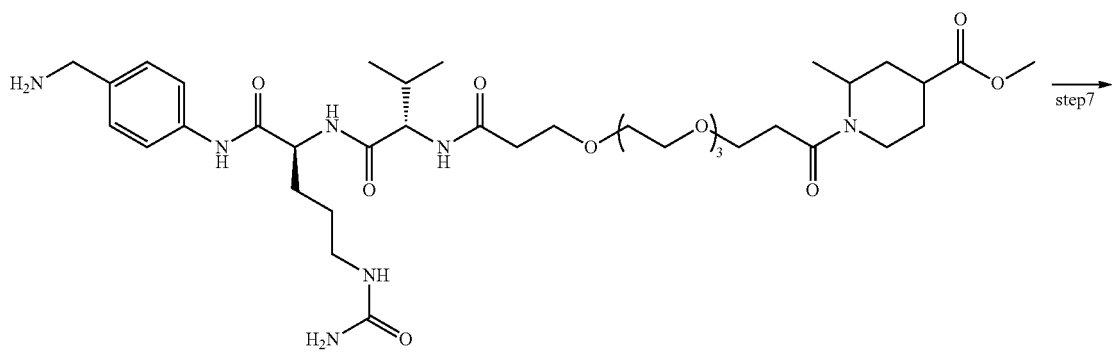
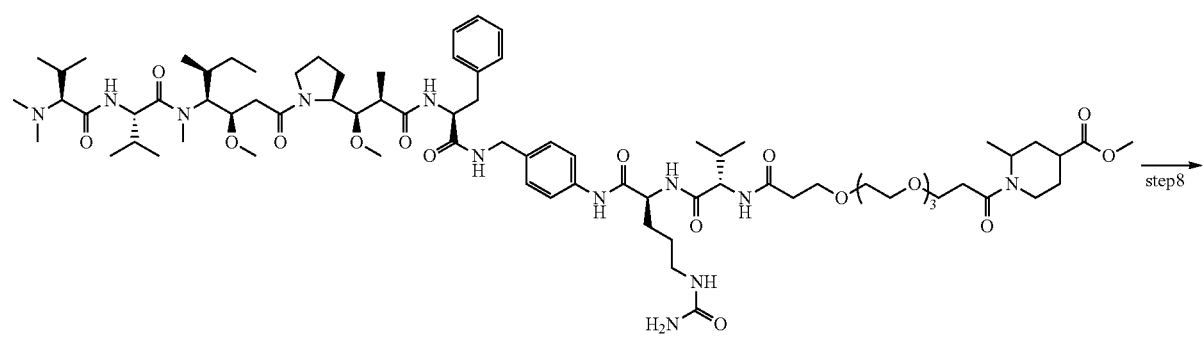
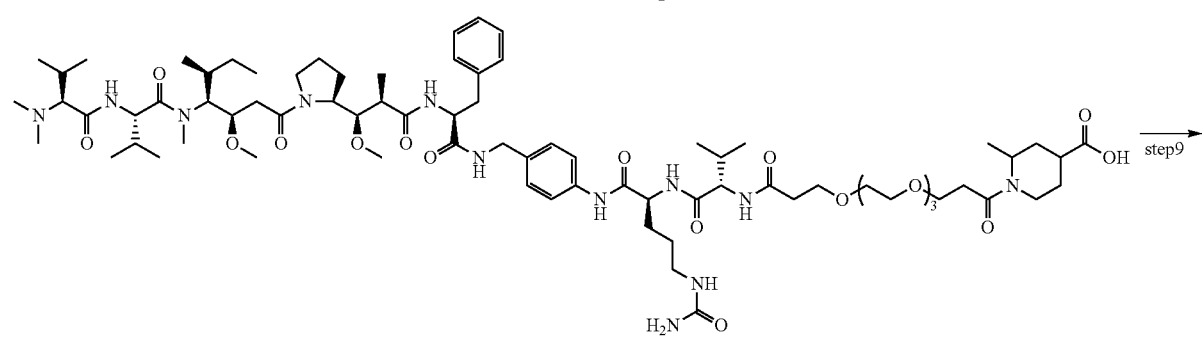

-continued

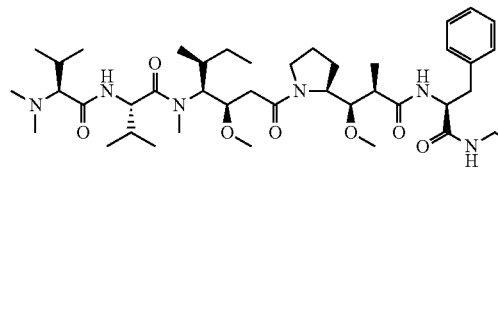

Step 1

Synthesis of 3-oxyl-1-phenyl-2,6,9,12,15-pentaoxaoctadecane-18-carboxylic acid At room temperature, 4,7,10,13-tetraoxahexadecandioic acid (1.0 g, 3.4 mmol) was dissolved in N,N-dimethylformamide (20 mL), to which was added triethylamine (1.3 g, 10.2 mmol). Then, benzyl bromide (580 mg, 0.34 mmol) was added dropwise within 15 min, followed by stirring at room temperature overnight. The reaction solution was purified to give the target compound 356 mg, a colorless oily substance. ESI-MS (m/z): 385.2 [M+H]$^+$.

Step 2

Synthesis of methyl cis-2-methyl-1-(3-oxyl-1-phenyl-2,6,9,12,15-pentaoxaoctadecane-18-yl)piperidinyl-4-formate At room temperature, 3-oxyl-1-phenyl-2,6,9,12,15-pentaoxaoctadecane-18-carboxylic acid (200 mg, 0.52 mmol), methyl cis-2-methylpiperidinyl-4-formate HCl salt (100 mg, 0.52 mmol), O-(7-azabenzotriazol-1-yl)-N,N,N',N'-tetramethyluronium hexafluorophosphate (395 mg, 1.04 mmol), and N,N-diisopropylethylamine (168 mg, 1.3 mmol) were dissolved in N,N-dimethylformamide (3 mL), and stirred at room temperature for 3 h. Water (30 mL) was added in the reaction solution, which was then extracted with ethyl acetate (20 mL×3), washed with saturated salt water (20 mL), and dried with anhydrous sodium sulfate. The desiccant was removed by filtration, and the solvent was removed by vacuum distillation to give the title compound 330 mg, a colorless oily substance. ESI-MS (m/z): 534.1 [M+H]$^+$.

Step 3

Synthesis of 16-(cis-4-(methoxycarbonyl)-2-methylpiperidinyl-1-yl)-16-oxo-4,7,10,13-tetraoxahexadecanoic acid At room temperature, methyl cis-2-methyl-1-(3-oxyl-1-phenyl-2,6,9,12,15-pentaoxaoctadecane-18-yl)piperidinyl-4-formate (330 mg, 0.69 mmol) was dissolved in methanol (5 mL), to which was added Pd—C (10%, 30 mg). Hydrogen gas was charged to replace air, followed by reaction in hydrogen atmosphere with stirring at room temperature for 3 h. Insolubles were removed by filtration, and the solvent was removed by vacuum distillation to give the title compound 270 mg, a colorless oily substance. ESI-MS (m/z): 434.2 [M+H]$^+$.

Step 4

Synthesis of methyl cis-1-((6S,9S)-1-amino-6-((4-(hydroxymethyl)phenyl)carbamoyl)-9-isopropyl-1,8,11-trioxo-14,17,20,23-tetraoxa-2,7,10-triazahexadecane-26-oxyl)-2-methylpiperidinyl-4-formate At room temperature, 16-(cis-4-(methoxycarbonyl)-2-methylpiperidinyl-1-yl)-16-oxo-4,7,10,13-tetraoxahexadecanoic acid (270 mg, 0.69 mmol) and (S)-2-((S)-2-amino-3-methylbutyramido)-N-(4-(hydroxymethyl)phenyl)-5-ureidopropionamide (262 mg, 0.69 mmol) were dissolved in N,N-dimethylformamide (3 mL), cooled down to 0° C., to which were added in sequence N,N-diisopropylethylamine (178 mg, 1.38 mmol) and benzotriazole-1-yl-oxytripyrrolidinophosphonium hexafluorophosphate (540 mg, 1.04 mmol), followed by stirring the reaction system at room temperature for 3 h. The reaction solution was purified by preparative liquid chromatography, to give the title compound, a white solid, 160 mg. ESI-MS (m/z): 795.2 [M+H]$^+$.

Step 5

Synthesis of methyl cis-1-((6S,9S)-1-amino-6-((4-(bromomethyl)phenyl)carbamoyl)-9-isopropyl-1,8,11-trioxo-14,17,20,23-tetraoxa-2,7,10-triazahexadecane-26-oxyl)-2-methylpiperidinyl-4-formate At room temperature, methyl cis-1-((6S,9S)-1-amino-6-((4-(hydroxymethyl)phenyl)carbamoyl)-9-isopropyl-1,8,11-trioxo-14,17,20,23-tetraoxa-2,7,10-triazahexacosan-26-hydroxy)-2-methylpiperidinyl-4-formate (160 mg, 0.2 mmol) was dissolved in dichloromethane (20 mL), to which was added dropwise a solution of 33% HBr in HOAc (0.4 mL) within 15 min, followed by stirring at room temperature for 1.0 h. The reaction was stopped once the completion of the reaction was detected by LC-MS. Water (20 mL) was added in the reaction solution, which was then adjusted with saturated sodium bicarbonate to pH=7-8, washed with dichloromethane (20 mL×3), washed with saturated salt water (20 mL), and dried with anhydrous sodium sulfate. The desiccant was removed by filtration, and the solvent was removed by vacuum distillation to give the title compound, a solid crude product 190 mg. ESI-MS (m/z): 857.2 [M+H]$^+$.

Step 6

Synthesis of methyl cis-1-((6S,9S)-1-amino-6-((4-(aminomethyl)phenyl)carbamoyl)-9-isopropyl-1,8,11-trioxo-14,17,20,23-tetraoxa-2,7,10-triazahexadecane-26-oxyl)-2-methylpiperidinyl-4-formate Methyl cis-1-((6S,9S)-1-amino-6-((4-(bromomethyl)phenyl)carbamoyl)-9-isopropyl-1,8,11-trioxo-14,17,20,23-tetraoxa-2,7,10-triazahexacosan-26-hydroxy)-2-methylpiperidinyl-4-formate (190 mg, 0.22 mmol) was dissolved in dichloromethane (10 mL), added dropwise in NH$_3$ in CH$_3$OH (10 ml, 7 mol/L), and reacted at room temperature for 0.5 h. The reaction was stopped once the completion of the reaction was detected by LC-MS, and then the reaction solution was concentrated to obtain a crude product, which was purified by preparative liquid chromatography, to give the title compound, a white solid, 100 mg. ESI-MS (m/z): 794.2 [M+H]$^+$.

Step 7

Synthesis of methyl cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formate At room temperature, 1-hydroxybenzotriazole (34 mg, 0.252 mmol) was dissolved in N,N-dimethylformamide (3 mL), to which were added in sequence (S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionic acid (108 mg, 0.126 mmol), methyl cis-1-((6S,9S)-1-amino-6-((4-(aminomethyl)phenyl)carbamoyl)-9-isopropyl-1,8,11-trioxo-14,17,20,23-tetraoxa-2,7,10-triazahexadecane-26-oxyl)-2-methylpiperidinyl-4-formate (100 mg, 0.126 mmol), and N,N-diisopropylethylamine (81 mg, 0.63 mmol), cooled down to 0° C., stirred for 10 min, then benzotriazole-1-yl-oxyltripyrrolidinylphosphonium hexafluorophosphate (98 mg, 0.19 mmol) was added batchwise within 10 min, followed by reaction at this temperature for 1.0 h. The reaction was stopped once the completion of the reaction was detected by LC-MS. The reaction solution was purified by preparative liquid chromatography, to give the title compound, a white solid, 148 mg. ESI-MS (m/z): 1522.6 [M+H]$^+$.

Step 8

Synthesis of cis-1-((6S,9S)-1-amino-6-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formic acid Methyl cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formate (60 mg, 0.04 mmol) was dissolved in a mixed solvent of THF (5 mL) and water (5 mL), to which was added lithium hydroxide (60 mg, 1.43 mmol), followed by reaction with stirring at room temperature for 2.0 h. The reaction was stopped once the completion of the reaction was detected by LC-MS. HCl solution (0.5 mol/L) was added to adjust pH=3-4, and the solvent was removed by vacuum distillation, to give a product directly used in the next step of reaction. ESI-MS (m/z): 1508.5 [M+H]$^+$.

Step 9

Synthesis of pentafluorophenol cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formate Cis-1-((6S,9S)-1-amino-6-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)carbamoyl)-9-isopropyl-1,8,11-trioxo-14,17,20,23-tetraoxa-2,7,10-triazahexadecane-26-oxyl)-2-methylpiperidinyl-4-formic acid (58 mg, 0.04 mmol) was dissolved in N,N-dimethylformamide (2 mL), to which were added 1-ethyl-(3-dimethylaminopropyl)carbodiimide HCl salt (11 mg, 0.06 mmol), and 4-dimethylaminopyridine (15 mg, 0.12 mmol) under the protection of nitrogen, cooled down to 0° C., and then pentafluorophenol (74 mg, 0.4 mmol) was added, followed by heating up to room temperature, and reacting overnight. The reaction was stopped once the completion of the reaction was detected by LC-MS. The reaction solution was purified by preparative liquid chromatography, to give the title compound, a white solid, 7 mg. ESI-MS (m/z): 1674.5 [M+H]$^+$.

Example 25 Synthesis of pentafluorophenol (2R, 4R)-1-(4-(((S)-1-(((S)-1-((4-(((S)-2-((2R,3R)-3-((S)-1-((3R,4S,5 S)-4-((S)-2-(S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate (TL030) and (2S,4S)-1-(4-(((S)-1-(((S)-1-((4-(((S)-2-((2R,3R)-3-((S)-1-((3R,4S,5S)-4-((S)-2-(S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate (TL031)

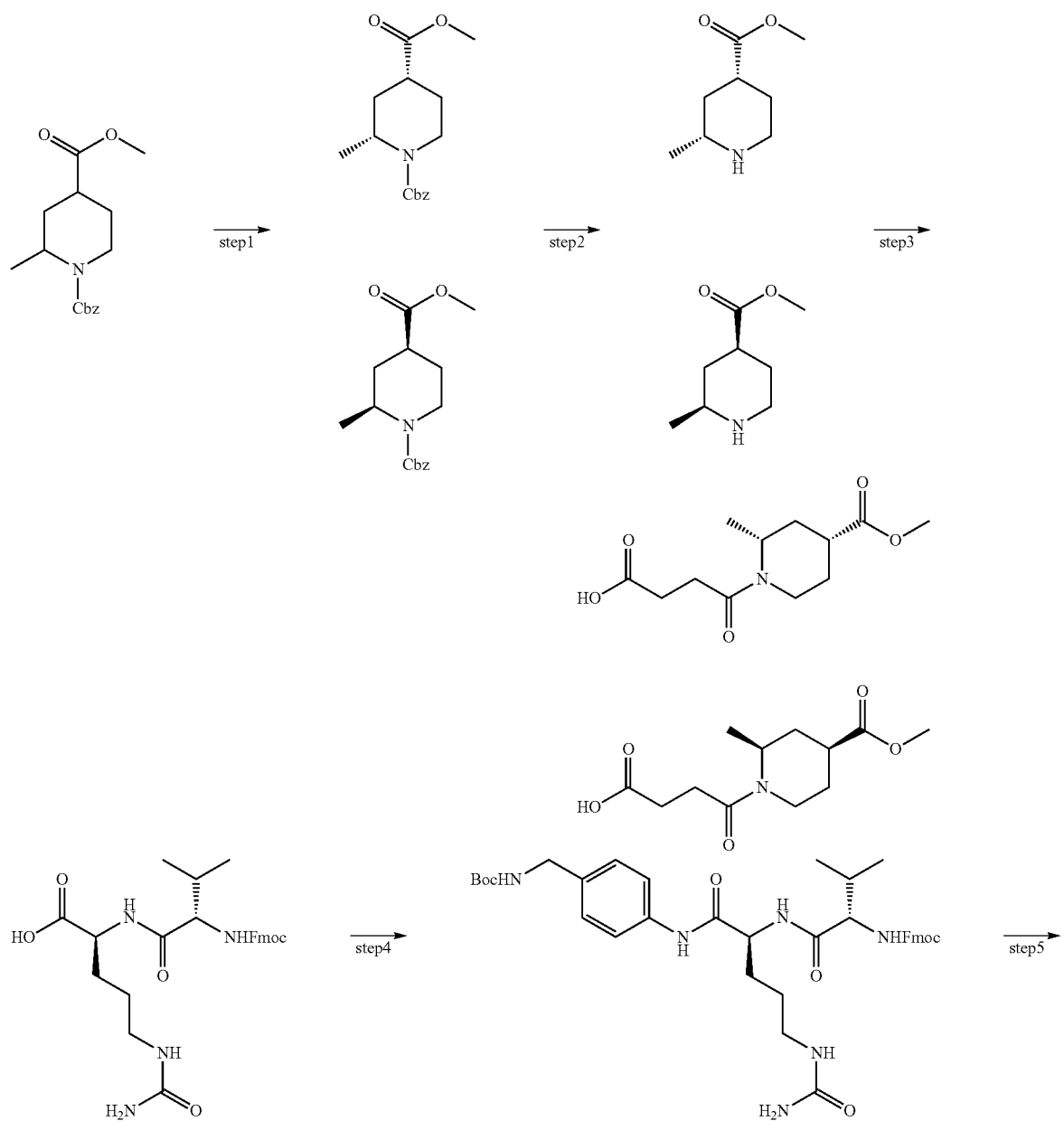

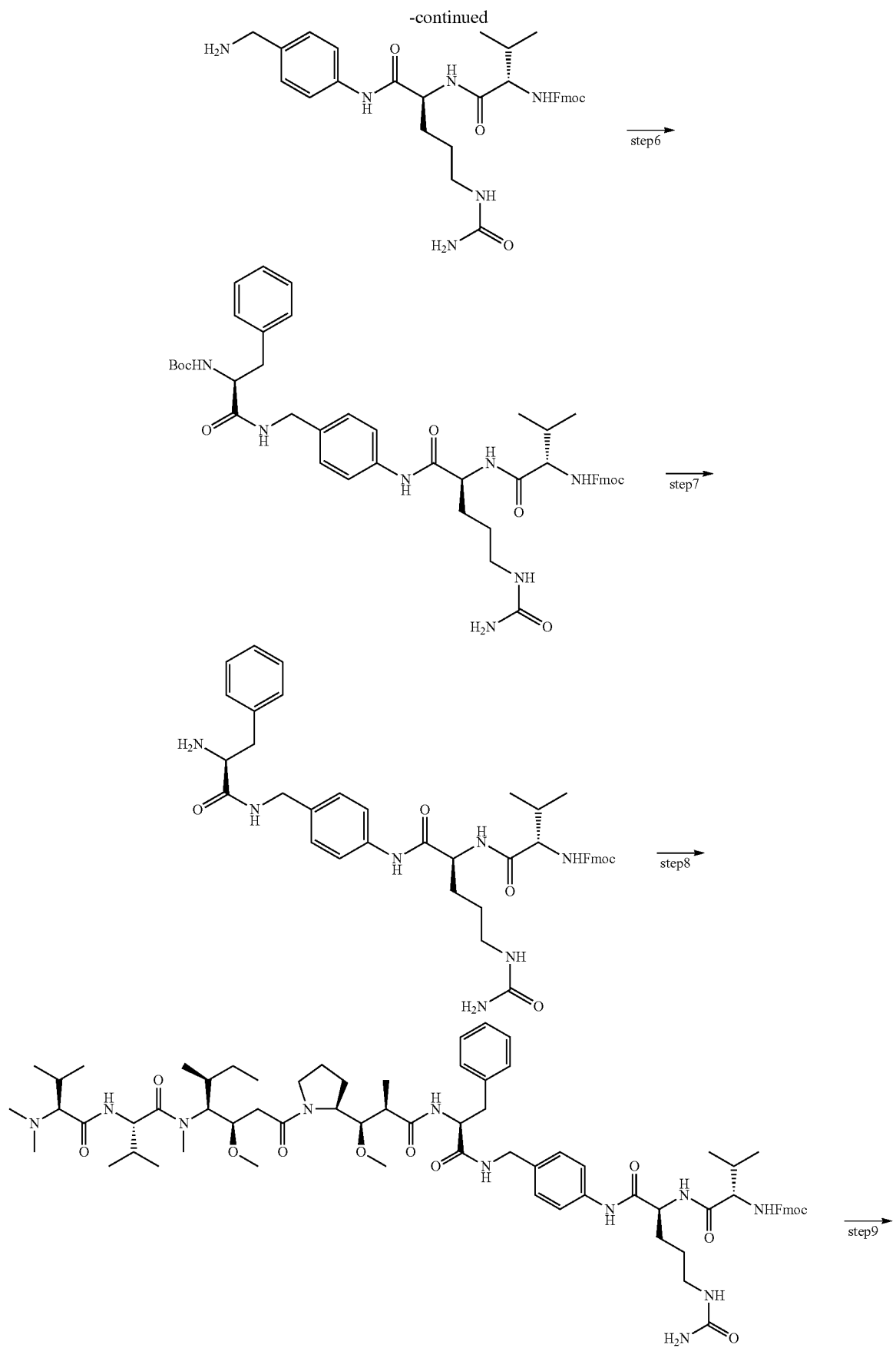

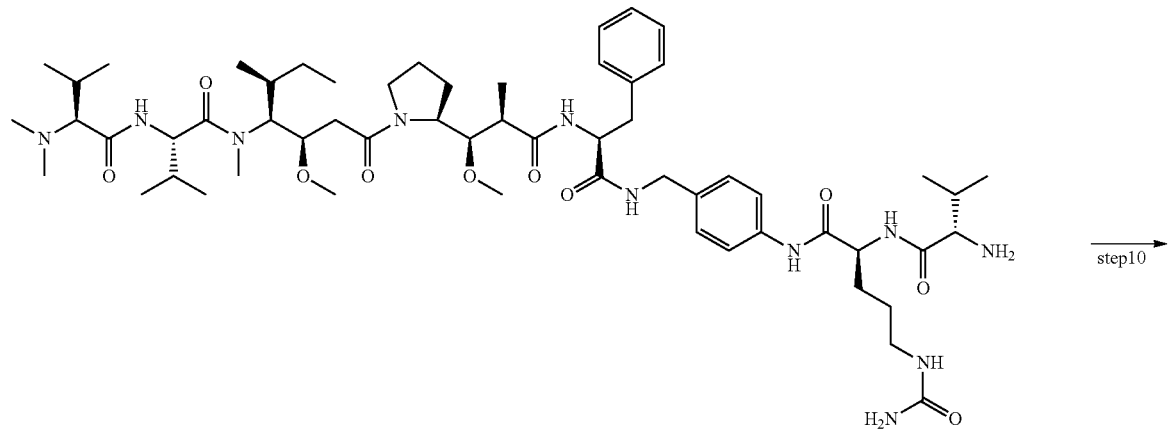
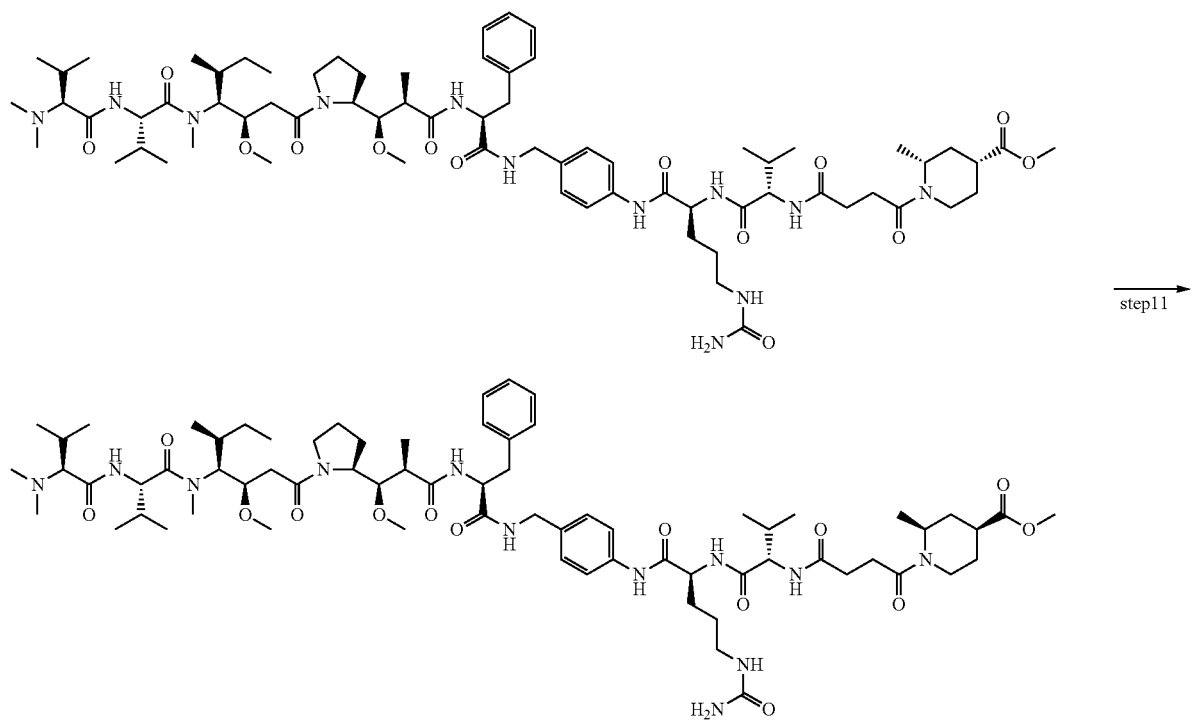

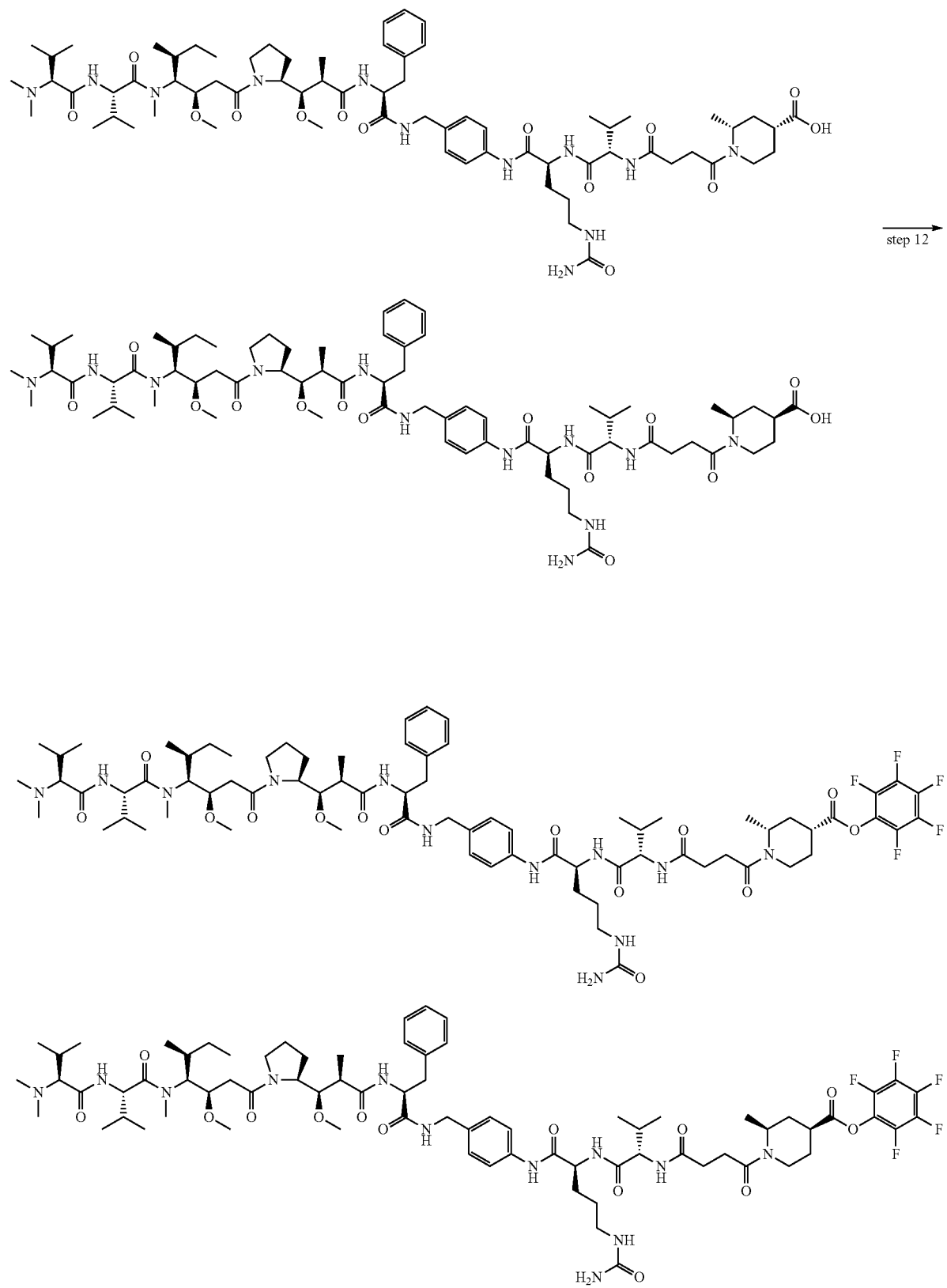

Step 1

Synthesis of methyl (2R,4R)-1-benzyloxycarbonyl-2-methylpiperidinyl-4-carboxylate and methyl (2S,4S)-1-benzyloxycarbonyl-2-methylpiperidinyl-4-carboxylate Methyl cis-1-benzyloxycarbonyl-2-methylpiperidinyl-4-carboxylate (1.88 g) was separated by chiral chromatography under the following conditions:

| Column | CHIRALPAK AY-H |
|---|---|
| Column size | 0.46 cm I.D. × 15 cm L |
| Flow phase | Hexane/IPA = 70/30 (V/V) |
| Flow rate | 1.0 ml/min |
| Wavelength | UV 210 nm |
| Temperature | 35° C. |

The above two title compounds were obtained by separation (i.e., Isomer 30-1a and Isomer 30-1b), Isomer 30-1a, a white solid, 752 mg, ee %=99.4%, Rt=6.018 min. ESI-MS (m/z): 292.2 $[M+H]^+$.

Isomer 30-1b, a white solid, 797 mg, ee %=98.9%, Rt=7.367 min. ESI-MS (m/z): 292.2 $[M+H]^+$.

Step 2

Synthesis of methyl (2R,4R)-2-methylpiperidinyl-4-formate and methyl (2S,4S)-2-methylpiperidinyl-4-formate At room temperature, 30-1a (400 mg, 1.37 mmol), THF (10 mL) were added in a 50 mL one-necked bottle, then Pd—C (150 mg, 10% Pd) was added with stirring at room temperature, nitrogen gas was charged to replace air three times, and hydrogen gas was charged to replace nitrogen gas 3 times, followed by reaction under pressurized hydrogen gas for 1 h. The completion of the reaction was detected by LC-MS. The reaction solution was directly filtered under vacuum, the filter cake was washed with THF (10 mL), and the filtrate was distilled under vacuum to give the target compound (30-2a), a light yellow oily substance, 200 mg. ESI-MS (m/z): 158.1 $[M+H]^+$.

At room temperature, 30-1b (330 mg, 1.1 mmol), THF (10 mL) were added in a 50 mL one-necked bottle, then Pd—C (100 mg, 10% Pd) was added with stirring at room temperature, nitrogen gas was charged to replace air three times, and hydrogen gas was charged to replace nitrogen gas 3 times, followed by reaction under pressurized hydrogen gas for 1 h. The completion of the reaction was detected by LC-MS. The reaction solution was directly filtered under vacuum, the filter cake was washed with THF (10 mL), and the filtrate was distilled under vacuum to give the target compound (30-2b), a light yellow oily substance, 160 mg. ESI-MS (m/z): 158.1 $[M+H]^+$.

Step 3

Synthesis of 4-((2R,4R)-4-(methoxy carbonyl)-2-methylpiperidinyl-1-yl)-4-oxobutyric acid and 4-((2S,4S)-4-(methoxy carbonyl)-2-methylpiperidinyl-1-yl)-4-oxobutyric acid At room temperature, 30-2a (200 mg, 1.27 mmol), succinic anhydride (127 mg, 1.27 mmol), and acetonitrile (10 ml) were added in a three-necked bottle, then sodium bicarbonate (160 mg, 1.91 mmol) was added with stirring at room temperature, and nitrogen gas was charged to replace air three times, followed by heating up to 50° C., and reacting at this temperature for 4.0 h. The completion of the reaction was detected by LC-MS. After cooling down to room temperature, the solvent was removed by vacuum distillation, water (30 mL) was added, then the reaction solution was extracted with ethyl acetate (30 mL×3), the organic phase was washed with saturated salt solution (30 mL×2), and dried with anhydrous sodium sulfate. The desiccant was removed by filtration, and the solvent was removed by vacuum distillation to give the target compound (30-3a), a light yellow oily substance, 260 mg. ESI-MS (m/z): 258.1 $[M+H]^+$.

At room temperature, 30-2b (160 mg, 1.0 mmol), succinic anhydride (100 mg, 1.0 mmol), and acetonitrile (10 ml) were added in a three-necked bottle, then sodium bicarbonate (126 mg, 1.5 mmol) was added with stirring at room temperature, and nitrogen gas was charged to replace air three times, followed by heating up to 50° C., and reacting at this temperature for 4.0 h. The completion of the reaction was detected by LC-MS. After cooling down to room temperature, the solvent was removed by vacuum distillation, water (30 mL) was added, then the reaction solution was extracted with ethyl acetate (30 mL×3), the organic phase was washed with saturated salt solution (30 mL×2), and dried with anhydrous sodium sulfate. The desiccant was removed by filtration, and the solvent was removed by vacuum distillation to give the target compound (30-3b), a light yellow oily substance, 250 mg. ESI-MS (m/z): 258.1 $[M+H]^+$.

Step 4

Synthesis of (9H-fluoren-9-yl)-methyl-((S)-1-(((S)-1-((4-(((tert-butoxycarbonyl)amino)methyl)phenyl)amino)-1-oxo-5-ureidopentyl-2-yl)amino)-3-methyl-1-oxobutyl-2-yl)-carbamate At room temperature, 4-(N-Boc-aminomethyl)-aniline (6.0 g, 27 mmol), (S)-2-((S)-2-((((9H-fluoren-9-yl)-methoxy)carbonyl)amino)-3-methylbutyramido)-5-ureidovaleric acid (3.35 g, 6.75 mmol), and 2-ethoxy-1-ethoxycarbonyl-1,2-dihydroquinoline (3.34 g, 13.5 mmol) were dissolved in a mixed solvent of dichloromethane (140 mL) and methanol (70 mL), heated up to 45° C., and stirred at this temperature for 8.0 h. The reaction was stopped once the completion of the reaction was detected by LC-MS. The reaction solution was cooled down to room temperature, to precipitate out a large amount of solid, followed by vacuum filtration to give the title compound, a white-like solid, 3.65 g. ESI-MS (m/z): 701.4 $[M+H]^+$.

Step 5

Synthesis of (9H-fluoren-9-yl)-methyl-((S)-1-(((S)-1-((4-(aminomethyl)phenyl)amino)-1-oxo-5-ureidopentyl-2-yl)amino)-3-methyl-1-oxobutyl-2-yl)-carbamate At room temperature, trifluoroacetic acid (15 mL) was added in (9H-fluoren-9-yl)-methyl-((S)-1-(((S)-1-((4-(((tert-butoxycarbonyl)amino)methyl)phenyl)amino)-1-oxo-5-ureidopentyl-2-yl)amino)-3-methyl-1-oxobutyl-2-yl)-carbamate (3.0 g, 4.29 mmol), followed by stirring at room temperature for 1.0 h. The reaction was stopped once the completion of the reaction was detected by LC-MS. The solvent was removed by vacuum distillation to obtain a yellow oily substance, and then anhydrous ethyl ether (20 mL) was added, to precipitate out a large amount of solid, followed by stirring vigorously for 0.5 h, and vacuum filtration, to give trifluoroacetate of the title compound, a white-like solid, 3.06 g. ESI-MS (m/z): 601.3 [M+H]$^+$.

Step 6

Synthesis of (9H-fluoren-9-yl)-methyl-((S)-1-(((S)-1-((4-(((R)-2-((tert-butoxycarbonyl)amino)-3-phenylpropionamido)methyl)phenyl)amino-1-oxo-5-ureidopentyl-2-yl)amino)-3-methyl-1-oxobutyl-2-yl)-carbamate At room temperature, Boc-D-phenylalanine (1.1 g, 4.2 mmol), (9H-fluoren-9-yl)-methyl-((S)-1-(((S)-1-((4-(aminomethyl)phenyl)amino)-1-oxo-5-ureidopentyl-2-yl)amino)-3-methyl-1-oxobutyl-2-yl)-carbamate trifluoroacetate (3.0 g, 4.2 mmol) were dissolved in N,N-dimethylformamide (40 mL), cooled down to 0° C., to which were added in sequence 1-(3-dimethylaminopropyl)-3-ethylcarbodiimide HCl salt (1.2 g, 6.3 mmol), 1-hydroxybenzotriazole (0.9 g, 6.3 mmol), and N-methylmorpholine (1.7 g, 16.8 mmol), and stirred at this temperature for 1.0 h. The reaction was stopped once the completion of the reaction was detected by LC-MS. The reaction solution was added dropwise in an ice-water bath (400 mL), and stirred vigorously for 0.5 h, to precipitate out a large amount of solid, followed by vacuum filtration, to give the title compound, a yellow solid, 3.3 g. ESI-MS (m/z): 848.4 [M+H]$^+$.

Step 7

Synthesis of (9H-fluoren-9-yl)-methyl-((S)-1-(((S)-1-((4-(((R)-2-amino-3-phenylpropionamido)methyl)phenyl)amino)-1-oxo-5-ureidopentyl-2-yl)amino)-3-methyl-1-oxobutyl-2-yl)-carbamate At room temperature, (9H-fluoren-9-yl)-methyl-((S)-1-(((S)-1-((4-(((R)-2-((tert-butoxycarbonyl)amino)-3-phenylpropionamido)methyl)phenyl)amino-1-oxo-5-ureidopentyl-2-yl)amino)-3-methyl-1-oxobutyl-2-yl)-carbamate (3.0 g, 3.3 mmol) was dissolved in trifluoroacetic acid (30 mL), followed by reaction with stirring at room temperature for 1.0 h. The reaction was stopped once the completion of the reaction was detected by LC-MS. The solvent was removed by vacuum distillation to obtain a yellow oily substance, anhydrous ethyl ether (100 mL) was added, and stirred vigorously for 0.5 h, to precipitate out a large amount of solid, followed by vacuum filtration, to give trifluoroacetate of the title compound, a light yellow solid, 2.1 g. ESI-MS (m/z): 748.4 [M+H]$^+$.

Step 8: Synthesis of ((S)-1-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino-(9H-fluorenyl)-methyl-formate At room temperature, (2R,3R)-3-((S)-1-((3R,4S,5S)-4-((S)-2-((S)-(dimethylamino)-3-butyramido)-N,3-dimethylbutyramido)-3-methoxy-5-methylheptanoyl)pyrrol-2-yl)-3-methoxy-2-methylpropionic acid (1.3 g, 2.17 mmol) and ((S)-1-(((S)-1-((4-(((S)-2-amino-3-phenylpropionamido)methyl)phenyl)amino)-1-oxo-5-pentylureido-2-yl)amino)-3-methyl-1-oxobut-2-yl)amino-(9H-fluorenyl)methyl-formate trifluoroacetate (1.8 g, 2.17 mmol) were dissolved in N,N-dimethylformamide (20 mL), cooled down to 0° C., to which were added in sequence 1-hydroxybenzotriazole (440 mg, 3.26 mmol) and N-methylmorpholine (658 mg, 6.51 mmol), and finally added 1-(3-dimethylaminopropyl)-3-ethylcarbodiimide HCl salt (624 mg, 1.38 mmol), and then the reaction solution was stirred at 0° C. for 5 h, followed by purification by preparative liquid chromatography, to give the title compound 1.8 g, a white solid. ESI-MS (m/z): 1329.2 [M+H]$^+$.

Step 9

Synthesis of (S)-2-((S)-2-amino-3-butyramido)-N-(4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)-5-ureidovaleramide At room temperature, ((S)-1-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino-(9H-fluorenyl)methyl-formate (500 mg, 0.38 mmol) was dissolved in N,N-dimethylformamide (5 mL), to which was added piperidine (324 mg, 3.8 mmol), and then the reaction solution was stirred at room temperature for 3 h, followed by purification to give the target compound, a white solid, 350 mg. ESI-MS (m/z): 1107.2 [M+H]$^+$.

Step 10

Synthesis of methyl (2R,4R)-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate and methyl (2S,4S)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate At room temperature, 30-3a (14 mg, 0.054), and (S)-2-((S)-2-amino-3-butyramido)-N-(4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)-5-ureidovaleramide (60 mg, 0.054 mmol) were dissolved in N,N-dimethylformamide (3 mL), to which was added N,N-diisopropylethylamine (21 mg, 0.16 mmol), cooled down to 0° C., stirred for 10 min, and then benzotriazole-1-yl-oxyltripyrrolidinylphosphonium hexafluorophosphate (42 mg, 0.08) was added batchwise, followed by slowly heating up to room temperature and reacting for 2.0 h. The completion of the reaction was detected by LC-MS. The reaction solution was directly purified by preparative liquid chromatography, to give the target compound (30-4a), a white solid, 50 mg. ESI-MS (m/z): 1345.8 [M+H]$^+$.

At room temperature, 30-3b (12 mg, 0.045), and (2S)-2-((S)-2-amino-3-methylbutyramido)-N-(4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)-5-ureidovaleramide (50 mg, 0.045 mmol) were dissolved in N,N-dimethylformamide (2 mL), to which was added N,N-diisopropylethylamine (18 mg, 0.14 mmol), cooled down to 0° C., stirred for 10 min, and then benzotriazole-1-yl-oxyltripyrrolidinylphosphonium hexafluorophosphate (36 mg, 0.07) was added batchwise, followed by slowly heating up to room temperature and reacting for 2.0 h. The completion of the reaction was detected by LC-MS. The reaction solution was directly purified by preparative liquid chromatography, to give the target compound (30-4b), a white solid, 45 mg. ESI-MS (m/z): 1345.8 [M+H]$^+$.

Step 11

Synthesis of (2R,4R)-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formic acid and ((2S,4S)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidinyl-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formic acid 30-4a (30 mg, 0.022 mmol) was dissolved in a mixed solvent of THF (1 mL) and water (2 mL), to which was added lithium hydroxide monohydrate (10 mg, 0.24 mmol), followed by reaction with stirring at room temperature for 4.0 h. The reaction was stopped once the completion of the reaction was detected by LC-MS. HCl solution (0.5 mol/L) was added to adjust pH=3-4, and a part of the solvent was removed by vacuum distillation, followed by freeze drying to give a crude product (30-5a), ready for the next step of reaction. ESI-MS (m/z): 1331.8 [M+H]$^+$.

30-4b (30 mg, 0.022 mmol) was dissolved in a mixed solvent of THF (1 mL) and water (2 mL), to which was added lithium hydroxide monohydrate (10 mg, 0.24 mmol), followed by reaction with stirring at room temperature for 4.0 h. The reaction was stopped once the completion of the reaction was detected by LC-MS. HCl solution (0.5 mol/L) was added to adjust pH=3-4, and a part of the solvent was removed by vacuum distillation, followed by freeze drying to give a crude product (30-5b), ready for the next step of reaction. ESI-MS (m/z): 1331.8 [M+H]$^+$.

Step 12

Synthesis of pentafluorophenol (2R,4R)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate and pentafluorophenol (2S,4S)-1-(4-(((2S)-1-(((2S)-1-((4-((2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-ureidopentyl-2-yl)amino)-3-methyl-1-oxobutyl-2-yl)amino)-4-oxobutyramido)-2-methylpiperidinyl-4-formate 30-5a (30 mg, 0.023 mmol) was dissolved in N,N-dimethylformamide (2 mL), cooled down to 0° C., to which were added in sequence 1-ethyl-(3-dimethylaminopropyl)carbodiimide HCl salt (7 mg, 0.034 mmol), and 4-dimethylaminopyridine (8 mg, 0.069 mmol), followed by stirring at 0° C. for 5 min, then pentafluorophenol (42 mg, 0.23 mmol) was added, followed by reacting for 16 h. The reaction was stopped once the completion of the reaction was detected by LC-MS. The reaction solution was purified by preparative liquid chromatography, to give the target compound (30-6a), a white solid, 13 mg. ESI-MS (m/z): 1497.8 [M+H]$^+$.

30-5b (30 mg, 0.023 mmol) was dissolved in N,N-dimethylformamide (2 mL), cooled down to 0 度, to which were added in sequence 1-ethyl-(3-dimethylaminopropyl)carbodiimide HCl salt (7 mg, 0.034 mmol), and 4-dimethylaminopyridine (8 mg, 0.069 mmol), followed by stirring at 0° C. for 5 min, then pentafluorophenol (42 mg, 0.23 mmol) was added, followed by reacting for 16 h. The reaction was stopped once the completion of the reaction was detected by LC-MS. The reaction solution was purified by preparative liquid chromatography, to give the target compound (30-6b), a white solid, 13 mg. ESI-MS (m/z): 1497.8 [M+H]$^+$.

Example 27 Synthesis of 1-(4-(((S)-1-(((S)-1-((4-(((S)-2-((2R,3R)-3-((S)-1-((3R,4S,5 S)-4-((S)-2-(S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-1-methyl-4-((pentafluorophenolato)carbonyl)piperidine iodide (TL033)

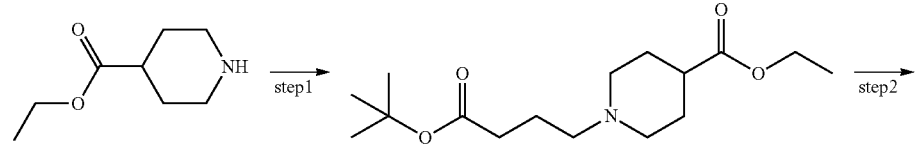

-continued

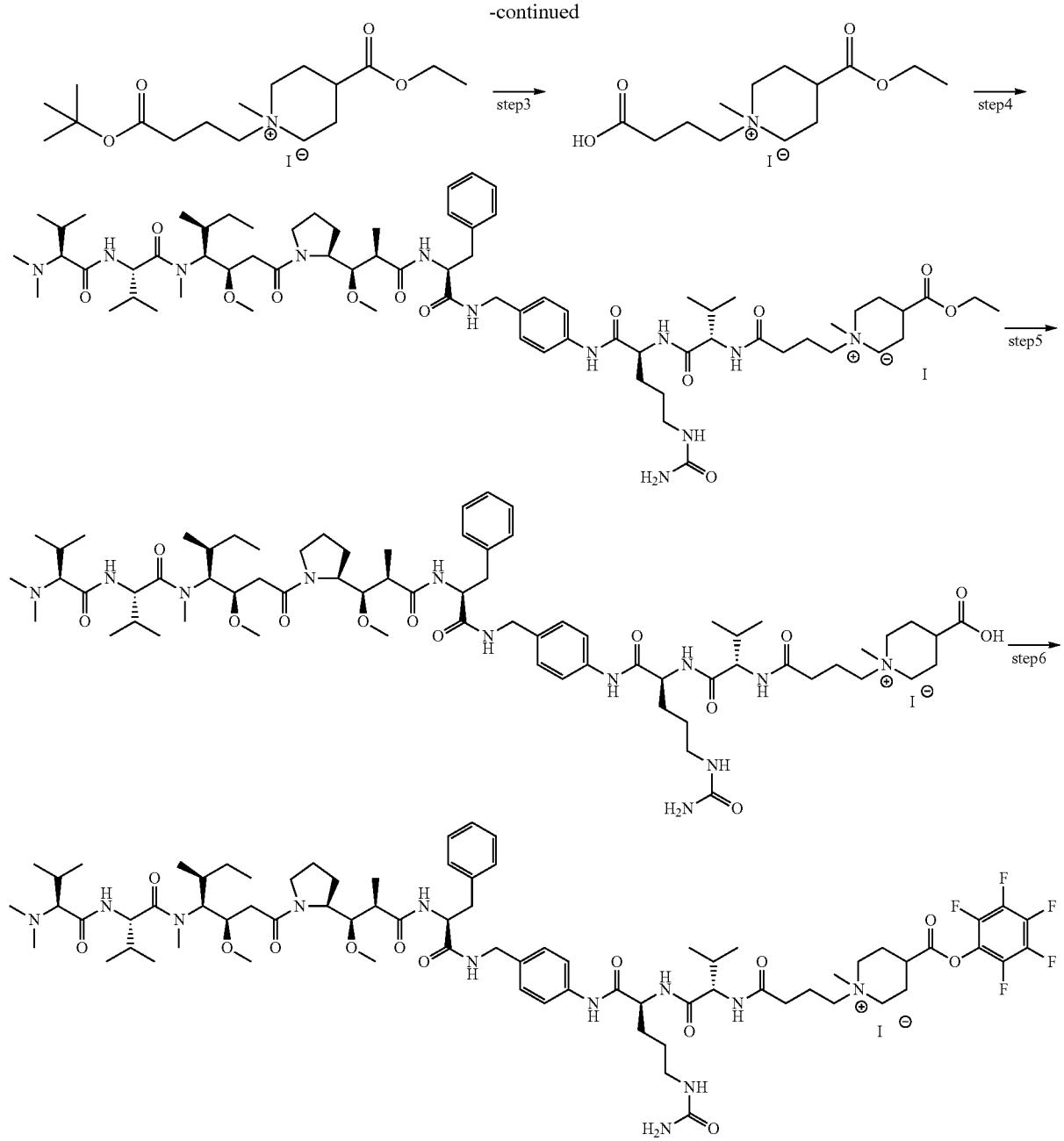

Step 1

Synthesis of ethyl 1-(4-(tert-butoxy)-4-oxobutyl) piperidinyl-4-formate

At room temperature, ethyl 4-piperidine formate (1.0 g, 6.4 mmol) was dissolved in N,N-dimethylformamide (10 mL), to which were added tert-butyl 4-boromobutyrate (1.7 g, 7.6 mmol), potassium carbonate (1.77 g, 12.8 mmol) and potassium iodide (0.53 g, 3.2 mmol), followed by reaction with stirring at room temperature for 5 h. The reaction solution was poured into water, extracted with ethyl acetate (20 mL×3), washed with saturated salt water (20 mL), and dried with anhydrous sodium sulfate, The desiccant was removed by filtration, and the solvent was removed by vacuum distillation, followed by purification by silica gel column (petroleum ether/ethyl acetate=3/2), to give the target compound 1.5 g, a light yellow oily substance. ESI-MS (m/z): 300.2 [M+H]+.

Step 2

Synthesis of 1-(4-(tert-butoxy)-4-oxobutyl)-4-(ethoxycarbonyl)-1-methylpiperidine iodide At room temperature, ethyl 1-(4-(tert-butoxy)-4-oxobutyl)piperidinyl-4-formate (500 mg, 1.7 mmol) and methyl iodide (2413 mg, 17.0 mmol) were dissolved in dichloromethane (10 mL), and stirred at room temperature for 1 h. The solvent was removed by vacuum distillation to give the title compound 530 mg, a light yellow oily substance. ESI-MS (m/z): 314.2 [M]+.

Step 3

Synthesis of 1-(3-carboxypropyl)-4-(ethoxycarbonyl)-1-methylpiperidine iodide

At room temperature, 1-(4-(tert-butoxy)-4-oxobutyl)-4-(ethoxycarbonyl)-1-methylpiperidine iodide (530 mg, 1.7 mmol) was dissolved in dichloromethane (3 mL), to which was added trifluoroacetic acid (5 mL), followed by stirring at room temperature for 2 h. The solvent was removed by vacuum distillation to give the title compound 500 mg, a light yellow oily substance. ESI-MS (m/z): 258.2 [M]$^+$.

Step 4

Synthesis of 1-(4-(((S)-1-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(ethoxycarbonyl)-1-methylpiperidine iodide

At room temperature, (S)-2-((S)-2-amino-3-butyramido)-N-(4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)-5-ureidovaleramide (300 mg, 0.27 mmol) and 1-(3-carboxypropyl)-4-(ethoxycarbonyl)-1-methylpiperidine iodide (127 mg, 0.33 mmol) were dissolved in N,N-dimethylformamide (3 mL), cooled down to 0° C., to which were added in sequence N,N-diisopropylethylamine (105 mg, 0.81 mmol) and benzotriazole-1-yl-oxytripyrrolidinophosphonium hexafluorophosphate (281 mg, 0.54 mmol), followed by stirring the reaction system at room temperature for 3 h. The reaction solution was purified by preparative liquid chromatography, to give the title compound, a white solid, 200 mg. ESI-MS (m/z): 1346.2 [M]$^+$.

Step 5

Synthesis of 1-(4-(((S)-1-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(carboxy)-1-methylpiperidine iodide

1-(4-(((S)-1-(((S)-((4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(ethoxycarbonyl)-1-methylpiperidine iodide (200 mg, 0.15 mmol) was dissolved in a mixed solvent of THF (5 mL) and water (5 mL), to which was added lithium hydroxide (36 mg, 1.5 mmol), followed by reaction with stirring at room temperature for 2.0 h. The reaction was stopped once the completion of the reaction was detected by LC-MS. HCl solution (0.5 mol/L) was added to adjust pH=3-4, and a part of the solvent was removed by vacuum distillation, followed by purification to give the target compound 150 mg, a white solid. ESI-MS (m/z): 1318.2 [M]$^+$.

Step 6

Synthesis of 1-(4-(((S)-1-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-1-methyl-4-((pentafluorophenolato)carbonyl)piperidine iodide

1-(4-(((S)-1-(((S)-((4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(carboxy)-1-methylpiperidine iodide (50 mg, 0.04 mmol) was dissolved in N,N-dimethylformamide (2 mL), to which were added 1-ethyl-(3-dimethylaminopropyl) carbodiimide HCl salt (11 mg, 0.06 mmol), and 4-dimethylaminopyridine (15 mg, 0.12 mmol) under the protection of nitrogen, followed by cooling down to 0° C., and then pentafluorophenol (74 mg, 0.4 mmol) was added, followed by heating up to room temperature, and reacting overnight. The reaction was stopped once the completion of the reaction was detected by LC-MS. The reaction solution was purified, to give the title compound. ESI-MS (m/z): 1484.2 [M]$^+$.

Example 28

Synthesis of pentafluorophenol (2R, 4S)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate (TL034) and pentafluorophenol (2S, 4R)-1-(4-(((S)-1-(((S)-1-((4-(((S)-2-((2R,3R)-3-((S)-1-((3R,4S,5 S)-4-((S')-2-((S)-2-(dim ethyl amino)-3-methylbutyramido)-N.3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate (TL035)

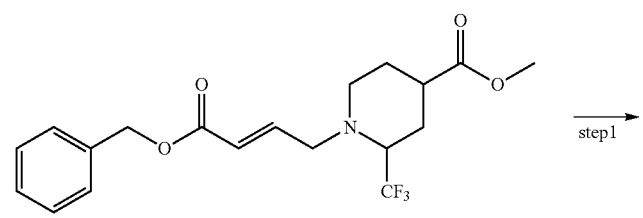

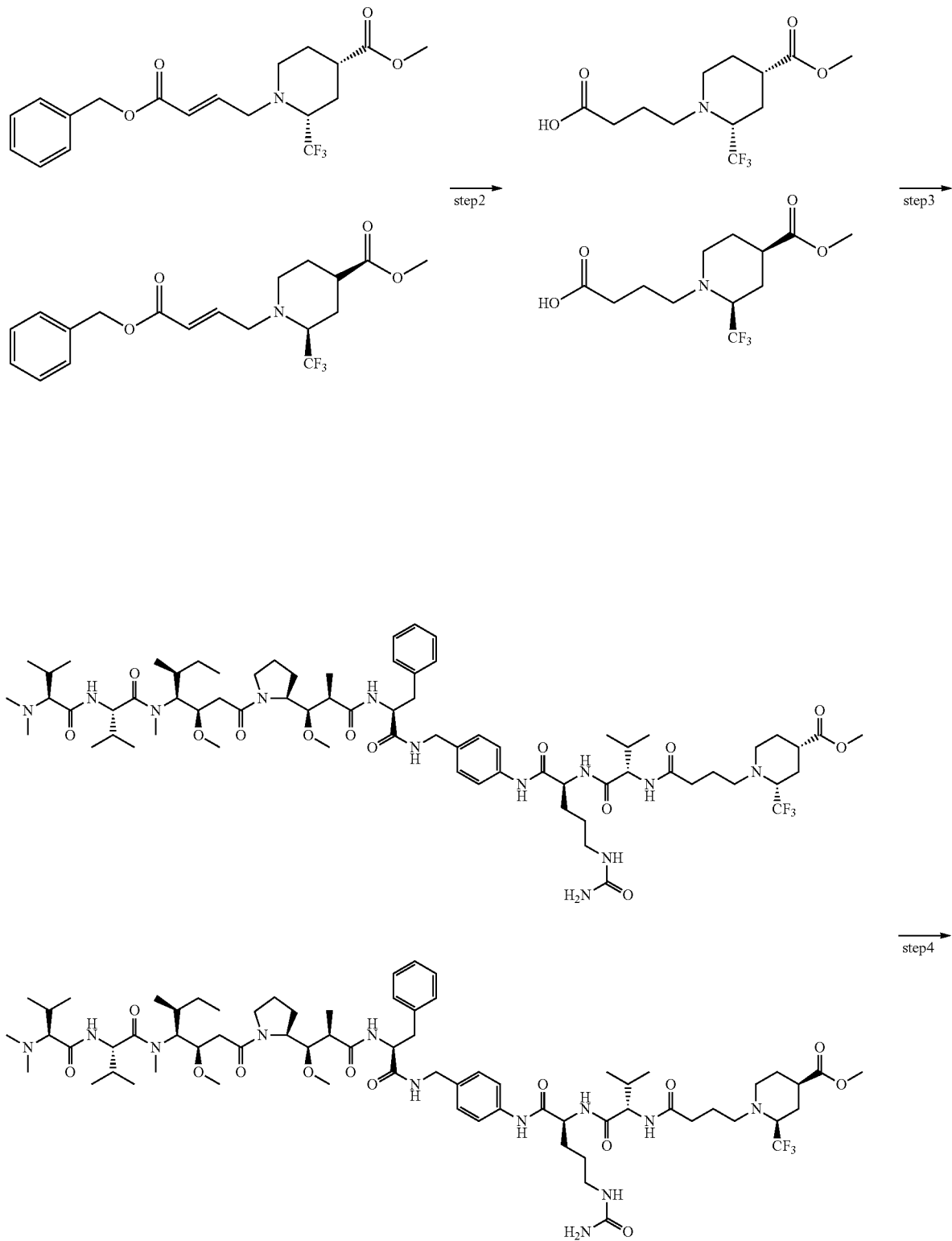

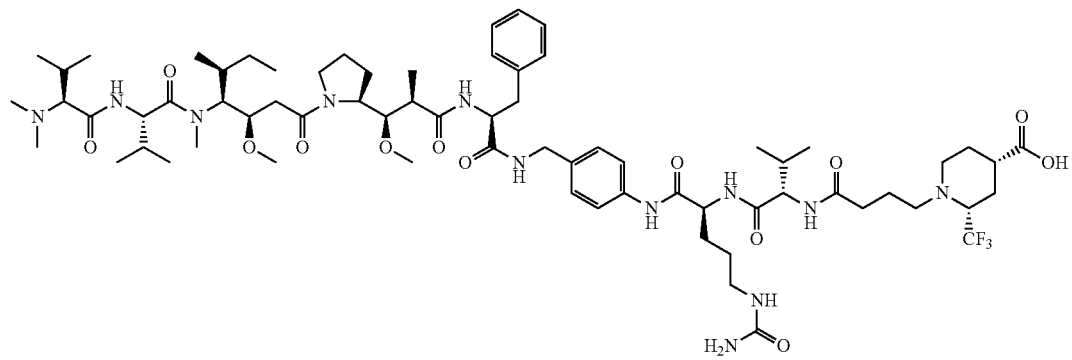
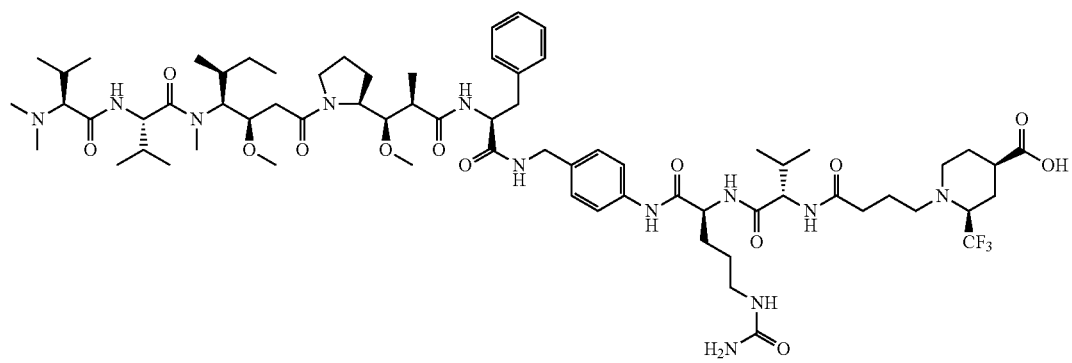
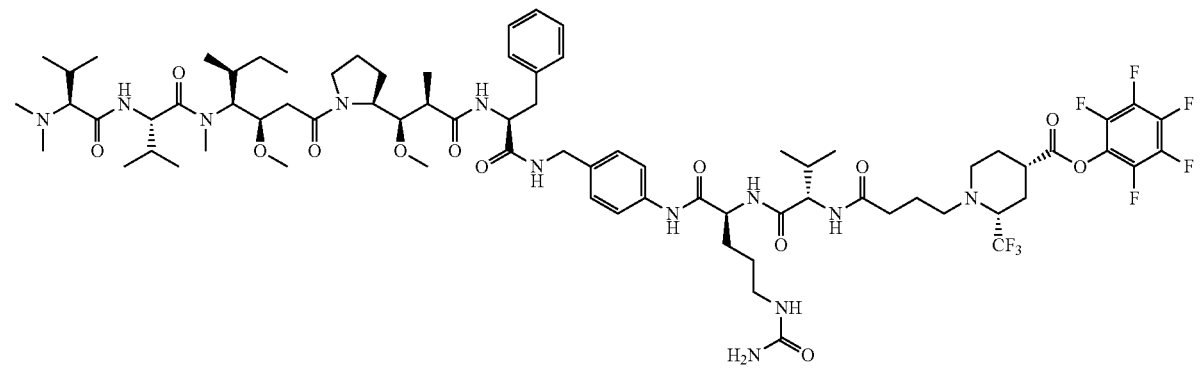
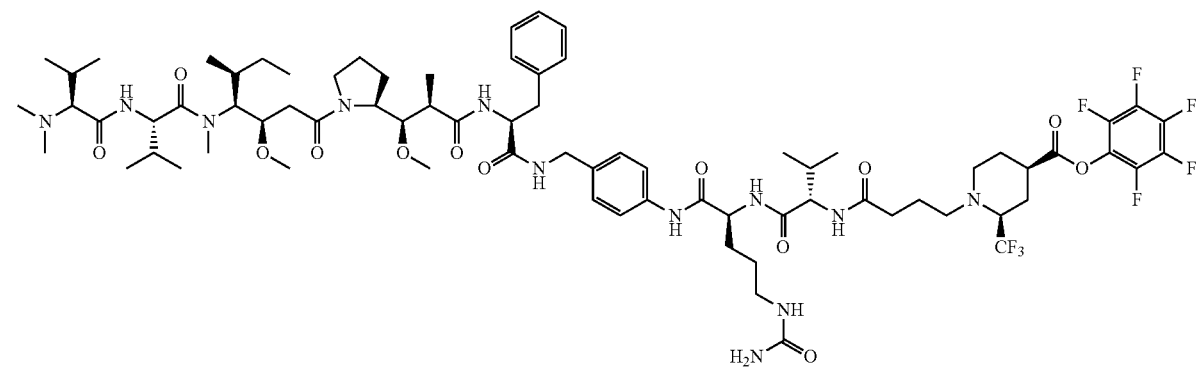

Step 1

Synthesis of methyl (2R, 4S)-1-((E)-4-(benzyloxy)-4-oxobut-2-en-1-yl)-2-(trifluoromethyl)piperidinyl-4-formate and methyl (2S, 4R)-1-((E)-4-(benzyloxy)-4-oxobut-2-en-1-yl)-2-(trifluoromethyl)piperidinyl-4-formate Methyl cis-1-((E)-4-(benzyloxy)-4-oxobut-2-en-1-yl)-2-(trifluoromethyl)piperidinyl-4-formate (950 mg) was separated by chiral chromatography under the following conditions:

| Column | CHIRALCEL OD-H |
| --- | --- |
| Column size | 0.46 cm I.D. × 15 cm L |
| Flow phase | Hexane/IPA = 90/10 (V/V) |
| Flow rate | 1.0 ml/min |
| Wavelength | UV 214 nm |
| Temperature | 35° C. |

The above two title compounds were obtained by separation, which were respectively:

35-1a: a white solid, 428 mg, ee %=99.9%, Rt=7.825 min. ESI-MS (m/z): 386.1 [M+H]$^+$;

35-1b: a white solid, 420 mg, ee %=99.6%, Rt=10.728 min. ESI-MS (m/z): 386.1 [M+H]$^+$.

Step 2

Synthesis of 4-((2R, 4S)-4-(methoxycarbonyl)-2-(trifluoromethyl)piperidinyl-1-yl)butyric acid and 4-((2S, 4R)-4-(methoxycarbonyl)-2-(trifluoromethyl)piperidinyl-1-yl)butyric acid At room temperature, 35-1a (50 mg, 0.13 mmol) was dissolved in ethanol (5 mL), platinum dioxide (5 mg) was added under protection of nitrogen gas, and hydrogen gas was charged to replace the nitrogen gas three times, followed by reaction in hydrogen atmosphere at room temperature for 2 h. A complete reaction of raw materials was monitored by high performance liquid chromatography-mass spectrometry, the reaction solution was filtered, and the filtrate was evaporated to dryness under reduced pressure to give the title compound, a colorless oily liquid 38 mg (35-2a). ESI-MS (m/z): 298.1 [M+H]$^+$.

At room temperature, 35-1b (50 mg, 0.13 mmol) was dissolved in ethanol (5 mL), platinum dioxide (5 mg) was added under protection of nitrogen gas, and hydrogen gas was charged to replace the nitrogen gas three times, followed by reaction in hydrogen atmosphere at room temperature for 2 h. A complete reaction of raw materials was monitored by high performance liquid chromatography-mass spectrometry, the reaction solution was filtered, and the filtrate was evaporated to dryness under reduced pressure to give the title compound, a colorless oily liquid 38 mg (35-2b). ESI-MS (m/z): 298.1 [M+H]$^+$.

Step 3

Synthesis of methyl (2R, 4S)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate and methyl (2S, 4R)-1-(4-(((S)-1-(((S)-1-((4-(((S)-2-((2R,3R)-3-((S)-1-((3R,4S, 5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylate At room temperature, (S)-2-((S)-2-amino-3-methylbutyramido)-N-(4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionyl)methyl)phenyl)-5-ureidovaleramide (30 mg, 0.027 mmol) and 35-2a (10 mg, 0.033 mmol) were dissolved in N,N-dimethylformamide (2 mL), cooled down to 0° C., to which were added in sequence DIEA (10 mg, 0.081 mmol), and benzotriazole-1-yl-oxytripyrrolidinophosphonium hexafluorophosphate (28 mg, 0.054 mmol), followed by reaction with stirring at room temperature for 2 h. A complete reaction of raw materials was monitored by high performance liquid chromatography-mass spectrometry, and the reaction solution was directly purified by preparative liquid chromatography to give the title compound, a white solid (35-3a), 30 mg. ESI-MS (m/z): 693.6 [M/2+H]$^+$.

At room temperature, (S)-2-((S)-2-amino-3-methylbutyramido)-N-(4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionyl)methyl)phenyl)-5-ureidovaleramide (30 mg, 0.027 mmol) and 35-2b (10 mg, 0.033 mmol) were dissolved in N,N-dimethylformamide (2 mL), cooled down to 0° C., to which were added in sequence DIEA (10 mg, 0.081 mmol), and benzotriazole-1-yl-oxytripyrrolidinophosphonium hexafluorophosphate (28 mg, 0.054 mmol), followed by reaction with stirring at room temperature for 2 h. A complete reaction of raw materials was monitored by high performance liquid chromatography-mass spectrometry, and the reaction solution was directly purified by preparative liquid chromatography to give the title compound (35-3b), a white solid, 30 mg. ESI-MS (m/z): 693.6 [M/2+H]$^+$.

Step 4

Synthesis of (2R, 4S)-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylic acid and (2S, 4R)-1-(4-(((S)-1-(((S)-1-((4-(((S)-2-((2R,3R)-3-((S)-1-((3R, 4S,5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-carboxylic acid 35-3a (30 mg, 0.02 mmol) was dissolved in THF (2 mL), water (4 mL), to which was added lithium hydroxide monohydrate (9 mg, 0.2 mmol) with stirring, followed by reaction with stirring at room temperature for 3 h. A complete reaction of raw materials was monitored by high performance liquid chromatography-mass spectrometry, and the reaction solution was adjusted with 1N HCl to pH=3-4, followed by freeze drying to give the title compound, a white solid (35-4a), 40 mg. ESI-MS (m/z): 686.6 [M/2+H]$^+$.

35-3b (30 mg, 0.02 mmol) was dissolved in THF (2 mL), water (4 mL), to which was added lithium hydroxide monohydrate (9 mg, 0.2 mmol) with stirring, followed by reaction with stirring at room temperature for 3 h. A complete reaction of raw materials was monitored by high performance liquid chromatography-mass spectrometry, and the reaction solution was adjusted with 1N HCl to pH=3-4, followed by freeze drying to give the title compound, a white solid (35-4b), 40 mg. ESI-MS (m/z): 686.6 [M/2+H]$^+$.

Step 5

Synthesis of pentafluorophenol (2R, 4S)-1-(4-(((S)-1-(((S)-1-((4-(((S)-2-((2R,3R)-3-((S)-1-((3R,4S,5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate and pentafluorophenol (2S, 4R)-1-(4-(((S)-1-(((S)-1-((4-(((S)-2-((2R,3R)-3-((S)-1-((3R,4S,5S)-4-((S)-2-((S)-2-(dimethylamino)-3-methylbutyramido)-N, 3-dimethylbutyramido)-3-methoxy-5-methylheptanoyl)pyrrolidin-2-yl)-3-methoxy-2-methylpropionyl)-3-phenylpropionamido)methyl)phenyl)amino)-1-oxo-5-uranoylpentyl-2-yl)amino)-3-methyl-1-oxobutyl-2-yl)amino)-4-oxobutyl)-2-(trifluoromethyl)piperidinyl-4-formate At room temperature, 35-4a (30 mg, 0.02 mmol) was dissolved in N,N-dimethylformamide (2 mL), to which were added in sequence 1-(3-dimethylaminopropyl)-3-ethylcarbodiimide HCl salt (6.0 mg, 0.03 mmol), and 4-dimethylaminopyridine (8.0 mg, 0.06 mmol), and then pentafluorophenol (10 mg, 0.2 mmol) was added all at once, followed by reaction with stirring at room temperature overnight. A complete reaction of raw materials was monitored by high performance liquid chromatography-mass spectrometry, and the reaction solution was directly purified by preparative liquid chromatography to give the title compound, a white solid (35-5a), 10 mg. ESI-MS (m/z): 769.6 [M/2+H]$^+$.

At room temperature, 35-4b (30 mg, 0.02 mmol) was dissolved in N,N-dimethylformamide (2 mL), to which were added in sequence 1-(3-dimethylaminopropyl)-3-ethylcarbodiimide HCl salt (6.0 mg, 0.03 mmol), and 4-dimethylaminopyridine (8.0 mg, 0.06 mmol), and then pentafluorophenol (10 mg, 0.2 mmol) was added all at once, followed by reaction with stirring at room temperature overnight. A complete reaction of raw materials was monitored by high performance liquid chromatography-mass spectrometry, and the reaction solution was directly purified by preparative liquid chromatography to give the title compound, a white solid (35-5b), 8.0 mg. ESI-MS (m/z): 769.6 [M/2+H]$^+$.

Example 29

Synthesis of 1-(4-(((S)-1-((4-(((S)-2-((2R,3R)-3-((S)-1-((3R,4S,5 S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(((2,5-dioxopyrrolidin-1-yl)oxyl)carbonyl)-1-methylpiperidine iodide (TL036)

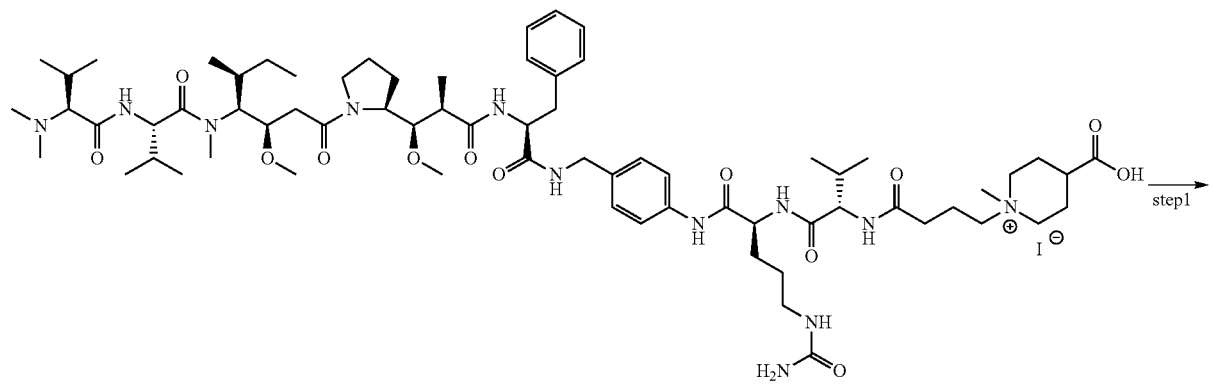

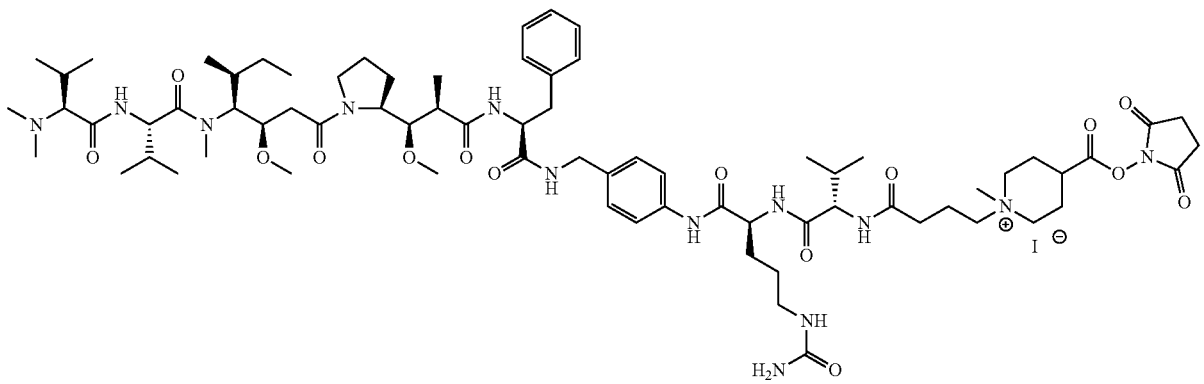

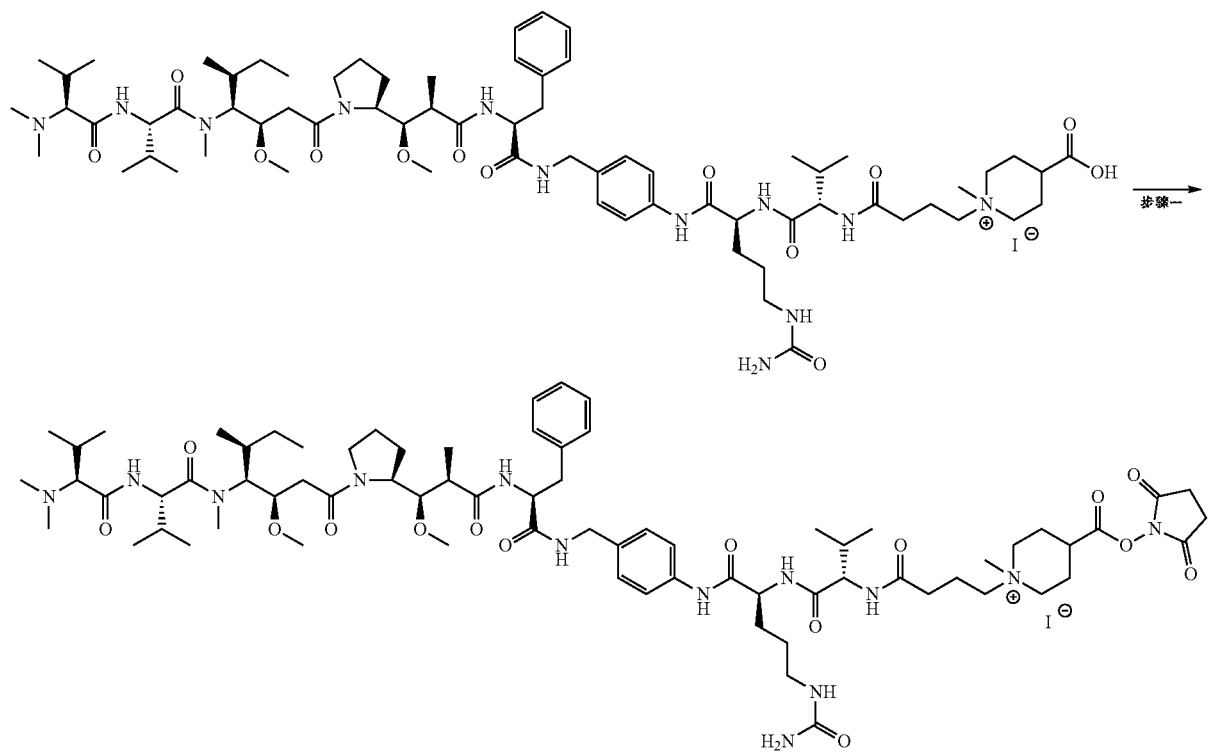

Step 1

Synthesis of 1-(4-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(((2,5-dioxopyrrolidin-1-yl)oxy)carbonyl)-1-methylpiperidine iodide 1-(4-(((S)-1-((4-(((S)-2-((2R,3R)-3-((S)-1-((3R,4S,5S)-4-((S)-2-((S)-2-(dimethylamino)-3-butyramido)-N,3-dimethylbutyramido)-3-methoxy-5-methylheptanoyl)pyrrol-2-yl)-3-methoxy-2-methylpropionamido)-3-phenylpropionamido)methyl)phenyl)amino)-1-oxo-5-pentylureido-2-yl)amino)-3-methyl-1-oxobut-2-yl)amino)-4-oxobutyl)-4-(carboxy)-1-methylpiperidine iodide (50 mg, 0.04 mmol) was dissolved in N,N-dimethylformamide (2 mL), to which were added 1-ethyl-(3-dimethylaminopropyl)carbodiimide HCl salt (11 mg, 0.06 mmol), and 4-dimethylaminopyridine (15 mg, 0.12 mmol) under the protection of nitrogen gas, cooled down to 0° C., and then N-hydroxysuccinimide (46 mg, 0.4 mmol) was added, followed by heating up to room temperature, and reacting overnight. The reaction was stopped once the completion of the reaction was detected by LC-MS. The reaction solution was purified, to give the title compound. ESI-MS (m/z): 1415.2 [M+H]$^+$.

Example 30 Synthesis of pentafluorophenyl 2-(4-((2S)-1-(((2S)-1-((4-(((2S)-2-((2R,3R)-3-(4S, 5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylate (TL037)
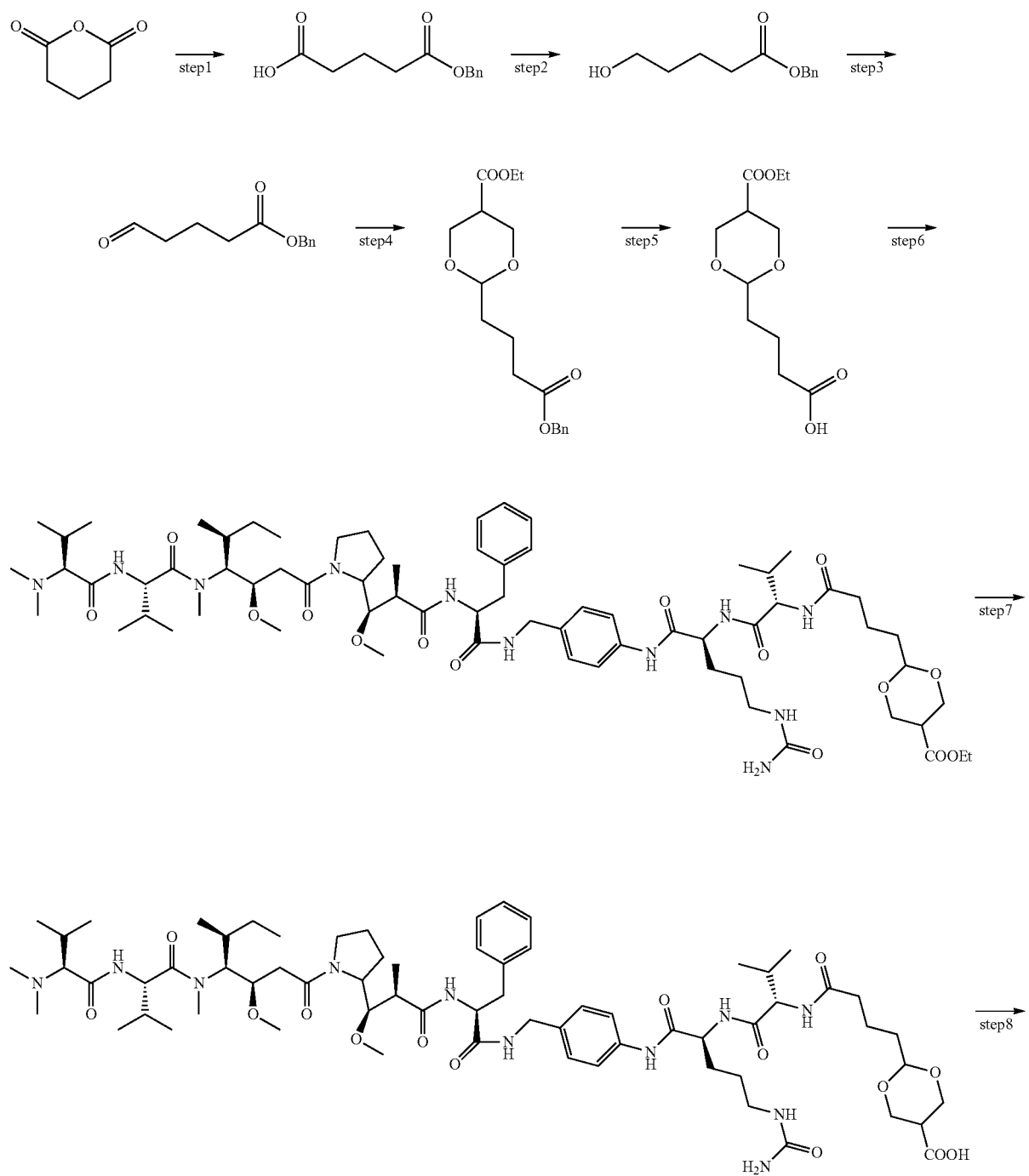

-continued

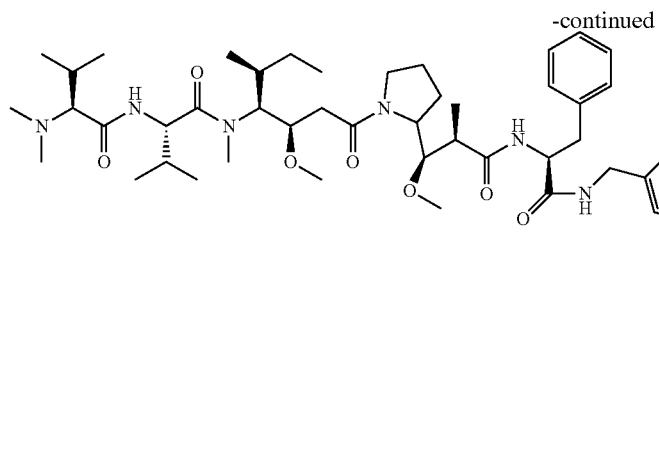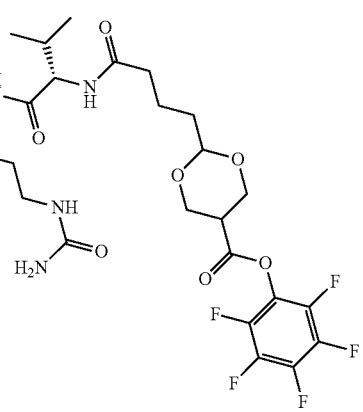

Step 1

Synthesis of 5-(benzyloxy)-5-oxovaleric acid

Glutaric anhydride (5.0 g, 43.8 mmol) was added in N,N-dimethylformamide (20 mL), cooled down to 0° C., to which was added benzyl bromide (4.7 mL, 39.4 mmol), and then added dropwise N,N-diisopropylethylamine (10 mL, 48.2 mmol), followed by stirring at room temperature for 16 h. The completion of the reaction was detected by LC-MS. The reaction solution was concentrated to dryness, dissolved with ethyl acetate (200 mL), and washed with sodium bicarbonate solution (200 mL), the aqueous phase was isolated, adjusted with 2N HCl solution to pH=about 4, and extracted with ethyl acetate (100 mL×3), then the ethyl acetate phases were combined, and dried with anhydrous sodium sulfate. The desiccant was removed by filtration, and the solvent was removed by vacuum distillation to give the title compound, a colorless oily substance, 7.8 g. ESI-MS (m/z): 223.1 [M+H]$^+$.

Step 2

Synthesis of benzyl 5-hydroxyvalerate 5-(benzyloxy)-5-oxovaleric acid (7.8 g, 35.1 mmol) was added in THF (60 mL), cooled down to 0° C., to which was added dropwise borane THF solution (70 mL, 70.2 mmol), followed by reaction with stirring at room temperature for 16 h. The completion of the reaction was detected by LC-MS. cooled down to 0° C., to which was added dropwise water slowly to quench the reaction. The reaction solution was extracted with dichloromethane (100 mL×3), then the organic phases were combined, washed with saturated salt solution (100 mL), and dried with anhydrous sodium sulfate. The desiccant was removed by filtration, and the solvent was removed by vacuum distillation to give a crude product, which was purified by silica gel column to give the title compound, a colorless oily substance, 2.85 g. ESI-MS (m/z): 209.1 [M+H]$^+$.

Step 3

Synthesis of benzyl 5-formylvalerate

At room temperature, benzyl 5-hydroxyvalerate (2.85 g, 13.7 mmol) was added in dichloromethane (80 mL), cooled down to 0° C., to which were added pyridinium dichromate (7.7 g, 20.5 mmol) and sodium acetate (600 mg, 6.85 mmol), followed by stirring at room temperature for 16 h. The completion of the reaction was detected by LC-MS. The reaction solution was filtered with diatomite, the filtrate was concentrated, and the residue was purified by silica gel column to give the title compound, a colorless oily substance, 1.3 g. ESI-MS (m/z): 207.1 [M+H]$^+$.

Step 4

Synthesis of ethyl 2-(4-(benzyloxy)-4-oxobutyl)-1,3-dioxane-5-carboxylate

Benzyl 5-formylvalerate (1.2 g, 5.8 mmol), ethyl 2,2-dimethyl-1,3-dioxane-5-carboxylate (1.32 g, 7.0 mmol), and p-toluenesulfonic acid (1.0 g, 5.8 mmol) were added in n-hexane (25 mL), followed by heating up to 68° C. and stirring for 16 h. The completion of the reaction was detected by LC-MS, the reaction solution was concentrated to dryness, and the residue was purified by preparative liquid chromatography, to give the title compound, a colorless oily substance, 120 mg. ESI-MS (m/z): 337.1 [M+H]$^+$.

Step 5

Synthesis of 4-(5-(ethoxycarbonyl)-1,3-dioxane-2-yl)butyric acid

At room temperature, ethyl 2-(4-(benzyloxy)-4-oxobutyl)-1,3-dioxane-5-carboxylate (120 mg, 0.36 mmol) was added in methanol (3 ml), to which was added Pd—C (12 mg, 10%), hydrogen gas was charged to replace air three times, followed by reaction in hydrogen atmosphere with stirring at room temperature for 16 h. The completion of the reaction was detected by LC-MS. The reaction solution was filtered with diatomite, the filtrate was concentrated to dryness, and the residue was purified by preparative liquid chromatography, to give the title compound, a colorless oily substance, 24 mg. ESI-MS (m/z): 247.1 [M+H]$^+$.

Step 6

Synthesis of ethyl 2-(4-((2S)-1-(((2S)-1-((4-(((2S)-2-((2R,3R)-3-(1-4S, 5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylate At room temperature, (2S)-2-((S)-2-amino-3-methylbutyramido)-N-(4-((2S)-2-((2R,3R)-3-(1, 5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)-5-ureidovaleramide (30 mg, 0.027 mmol) was dissolved in N,N-dimethylformamide (6 mL), to which were added in sequence 4-(5-(ethoxycarbonyl)-1,3-dioxane-2-yl)-butyric acid (8 mg, 0.033 mmol), and N,N-diisopropylethylamine (14 mg, 0.108 mmol), cooled down to 0° C., stirred for 10 min, then benzotriazole-1-yl-oxyltripyrrolidinylphosphonium hexafluorophosphate (28 mg, 0.054 mmol) was added batchwise within 2 min, followed by reaction at this temperature for 1.0 h. The reaction was stopped once the completion of the reaction was detected by LC-MS. The reaction solution was purified by preparative liquid chromatography, to give the title compound, a white solid, 125 mg. ESI-MS (m/z): 668.2 [M/2+H]⁺.

Step 7

Synthesis of 2-(4-((2S)-1-(((2S)-1-((4-(((2S)-2-((2R,3R)-3-(1, 5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylic acid Ethyl 2-(4-((2S)-1-(((2S)-1-((4-(((2S)-2-((2R,3R)-3-(1-4S, 5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylate (18 mg, 0.013 mmol) was dissolved in a mixed solvent of THF (1 mL) and water (2 mL), to which was added lithium hydroxide (46 mg, 1.11 mmol), followed by reaction with stirring at room temperature for 1.0 h. The reaction was stopped once the completion of the reaction was detected by LC-MS. HCl solution (0.5 mol/L) was added to adjust pH=3-4, followed by freeze drying to give the title compound, a white solid, 18 mg. Without purification, the product was directly used in the next step of reaction. ESI-MS (m/z): 653.8 [M/2+H]⁺.

Step 8

Synthesis of pentafluorophenyl 2-(4-((2S)-1-(((2S)-1-((4-(((2S)-2-((2R,3R)-3-(4S, 5S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylate 2-(4-((2S)-1-(((2S)-1-((4-(((2S)-2-((2R,3R)-3-(1, 5 S)-4-((S)-2-((S)-2-(dimethylamino)-3-methylbutyramido)-N,3-dimethylbutyramido)-3-methoxy-5-methylheptanoyl)pyrrolidin-2-yl)-3-methoxy-2-methylpropionamido)-3-phenylpropionamido)methyl)phenyl)amino)-1-oxo-5-acridin-2-yl)amino)-3-methyl-1-oxobut-2-yl)amino)-4-oxobutyl)-1,3-dioxane-5-carboxylic acid (18 mg, 0.013 mmol) was dissolved in N,N-dimethylformamide (3 mL), cooled down to 0° C., to which were added in sequence 1-(3-dimethylaminopropyl)-3-ethylcarbodiimide HCl salt (4 mg, 0.026 mmol), 4-dimethylaminopyridine (5 mg, 0.040 mmol), and pentafluorophenol (25 mg, 0.130 mmol), followed by naturally heating up to room temperature, and reacting overnight. The completion of the reaction was detected by LC-MS. The reaction solution was purified by preparative liquid chromatography, to give the title compound, a white solid, 0.89 mg. ESI-MS (m/z): 737.0 [M/2+H]⁺.

The following compounds can be synthesized with a reference to the synthetic methods in Examples 15-30:

| Name | Structure | ESI-MS (m/z) |
|---|---|---|
| TL042 | 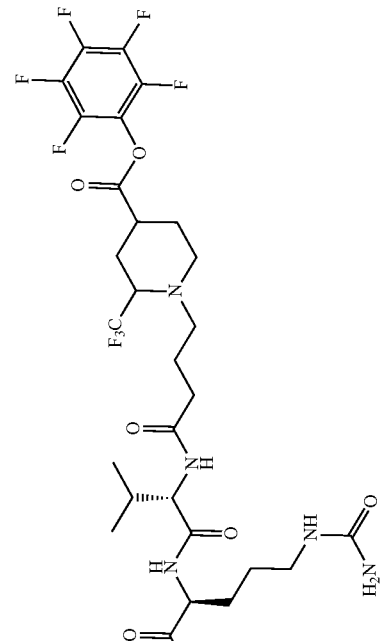 | 1447.7 [M + H]+ |
| TL059 | 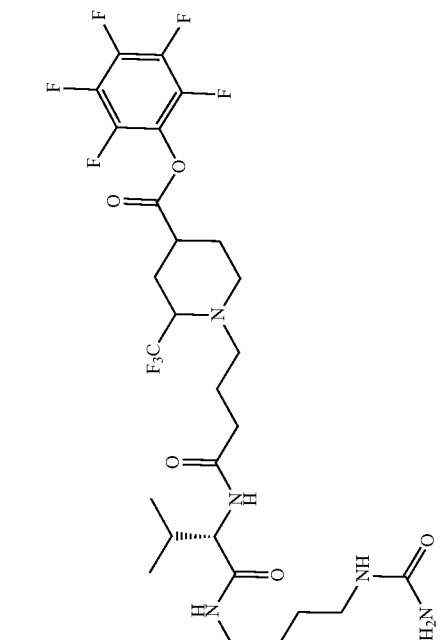 | 1539.6 [M + H]+ |

| Name | Structure | ESI-MS (m/z) |
|---|---|---|
| TL060 | 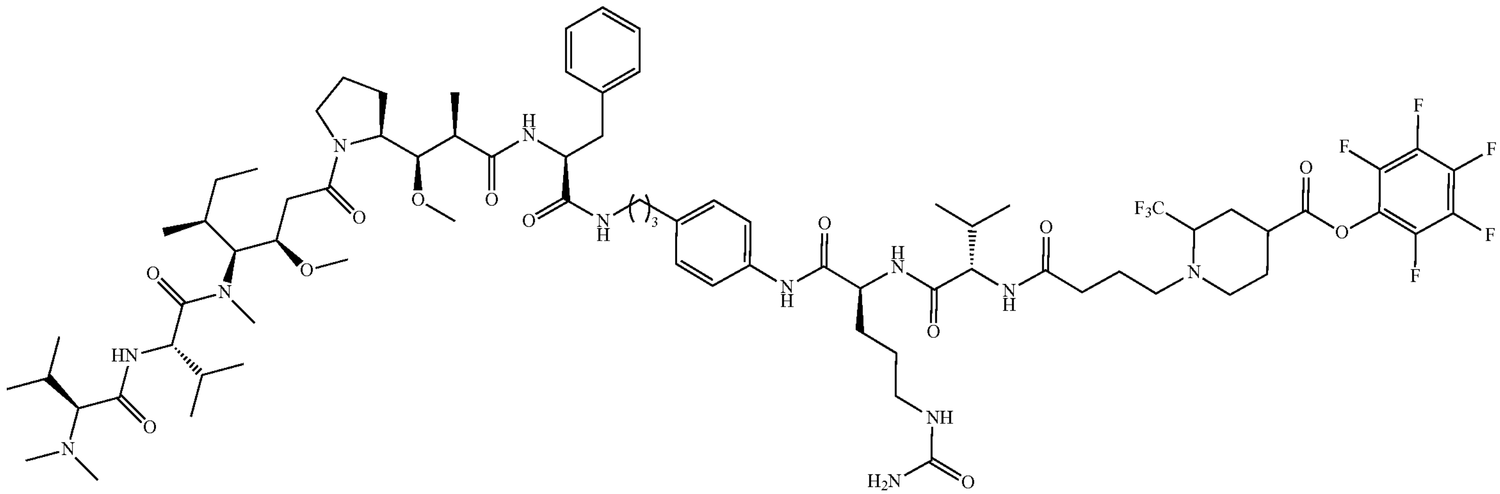 | 783.5 [M/2 + H]+ |
| TL061 | 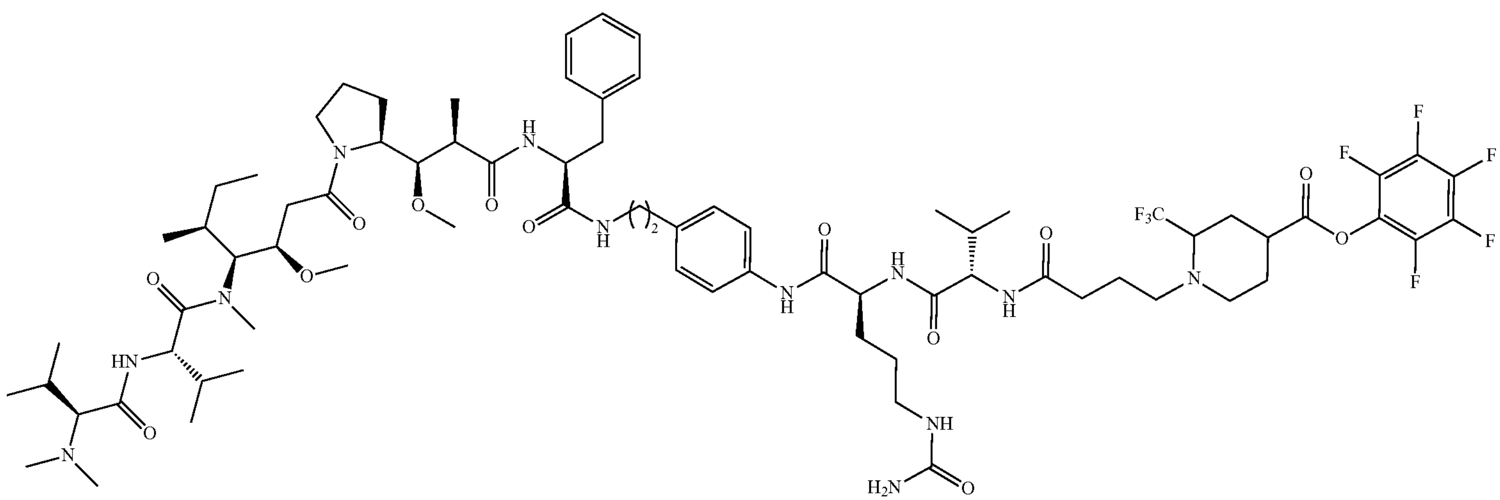 | 1552.6 [M + H]+ |

-continued
| Name | Structure | ESI-MS (m/z) |
|---|---|---|
| TL065 | 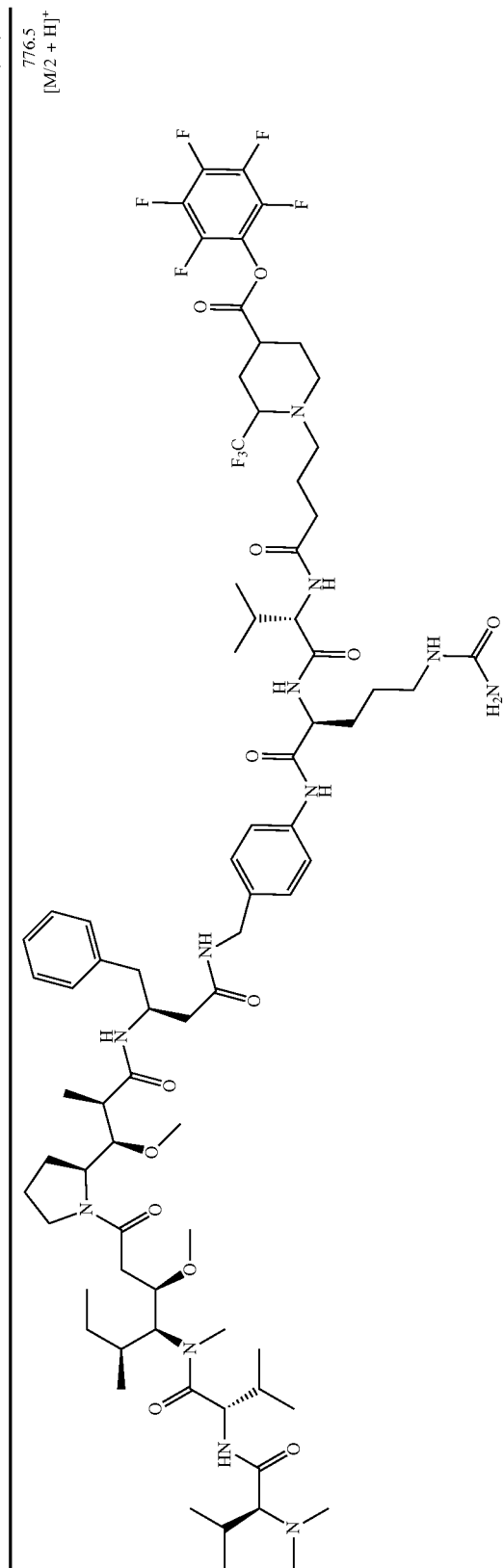 | 776.5 [M/2 + H]+ |

III. Synthesis of Conjugate Comprising Cytotoxin, Linker and Monoclonal Antibody Example 31 Synthesis of TL004-T-ADC To 1 mL of a solution of trastuzumab in a concentration of 10 mg/ml at pH 7.6, a compound TL004 dissolved in DMA was added in a 5-fold amount, and stirred gently for 12 hours at room temperature. The fractions of different retention time in HIC-HPLC were collected, to obtain specific conjugates with DAR values of 1, 2 and 3, which were named BT001061, BT001003, and BT001081, respectively.

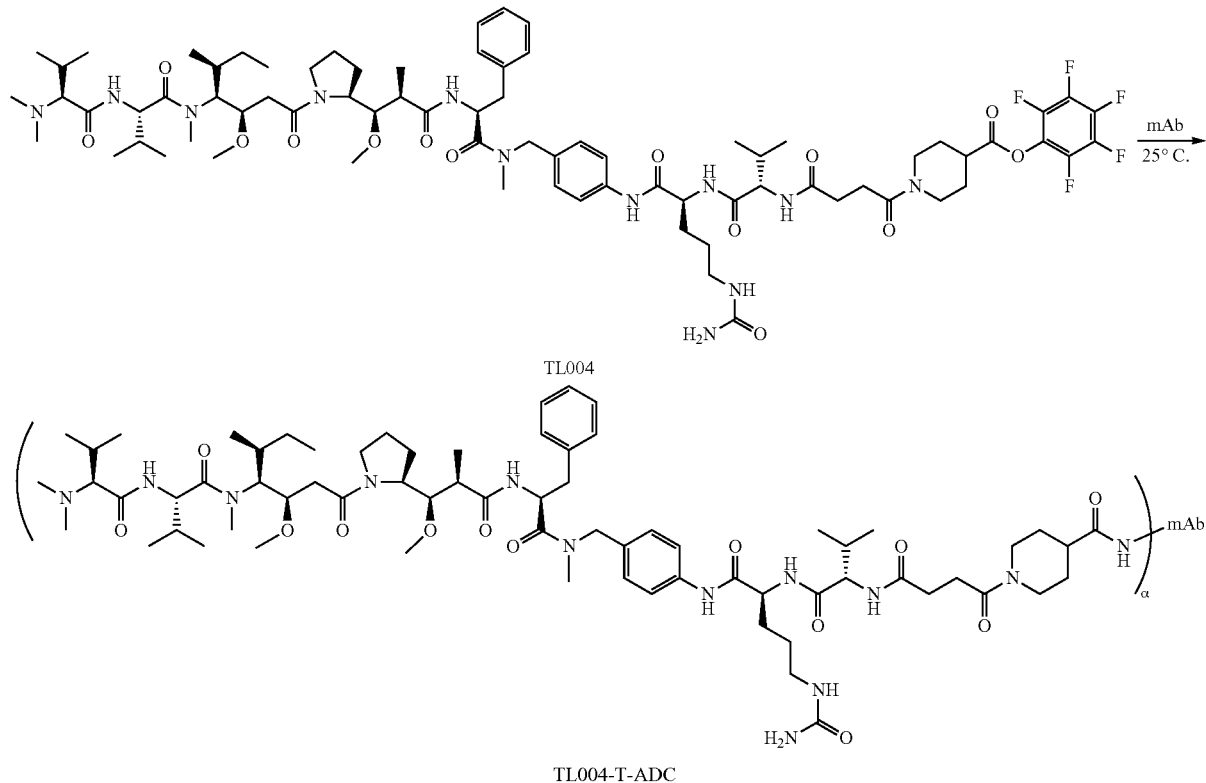

TL004

TL004-T-ADC the specific conjugates are respectively:

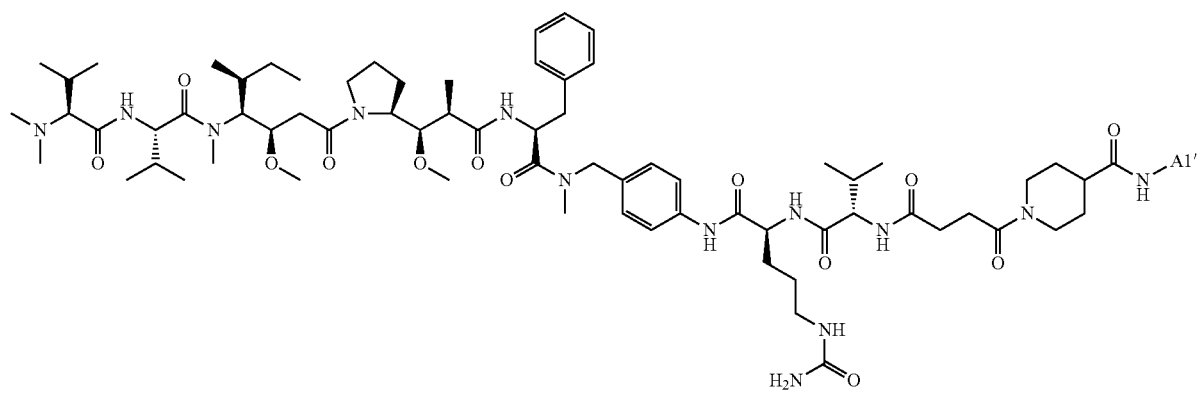

BT001061 wherein A1' is a group obtained after removing two amino groups from trastuzumab;

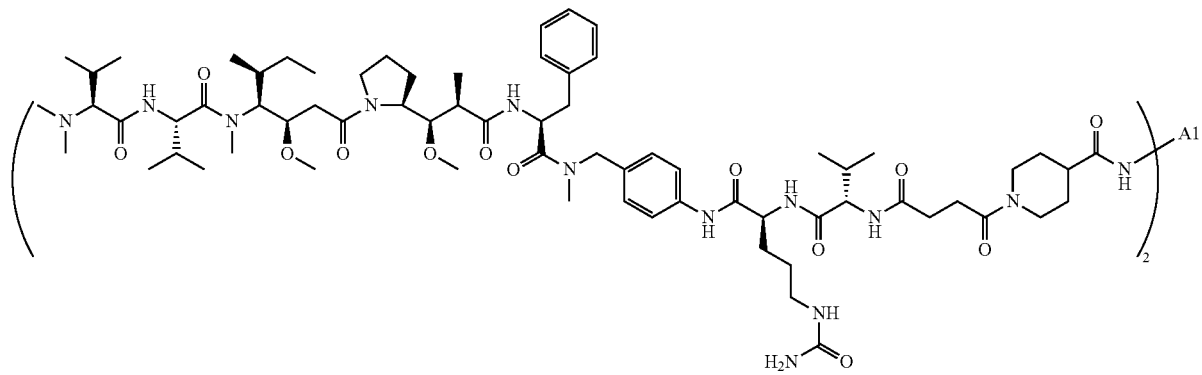

wherein A1 is a group obtained after removing two amino groups from trastuzumab; and

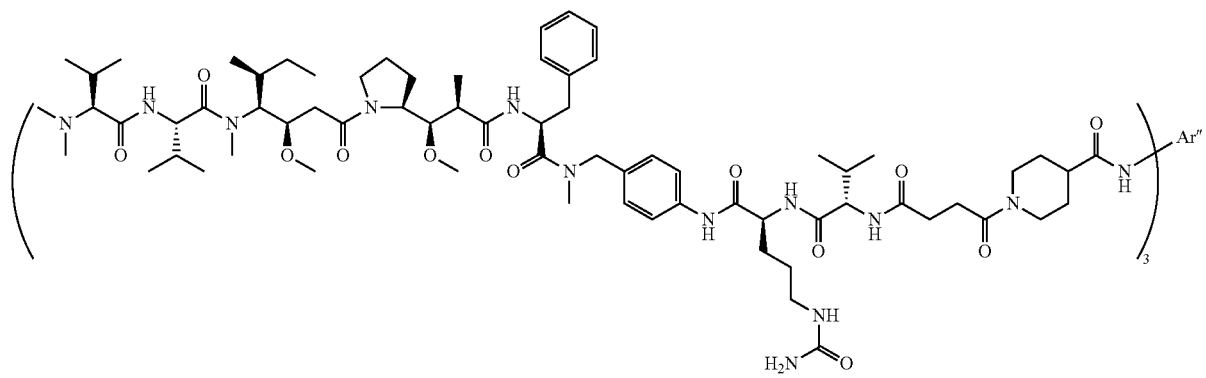

wherein A1″ is a group obtained after removing three amino groups from trastuzumab.

Example 32 Synthesis of TL006-T-ADC

To 1 mL of a solution of trastuzumab in a concentration of 15 mg/ml at pH 7.2, a compound TL006 dissolved in DMA was added in a 10-fold amount, and stirred gently for 12 hours at room temperature. The fractions of different retention time in HIC-HPLC were collected, to obtain specific conjugates with DAR values of 1, 2 and 3, which were named BT001062, BT001005, and BT001082, respectively.

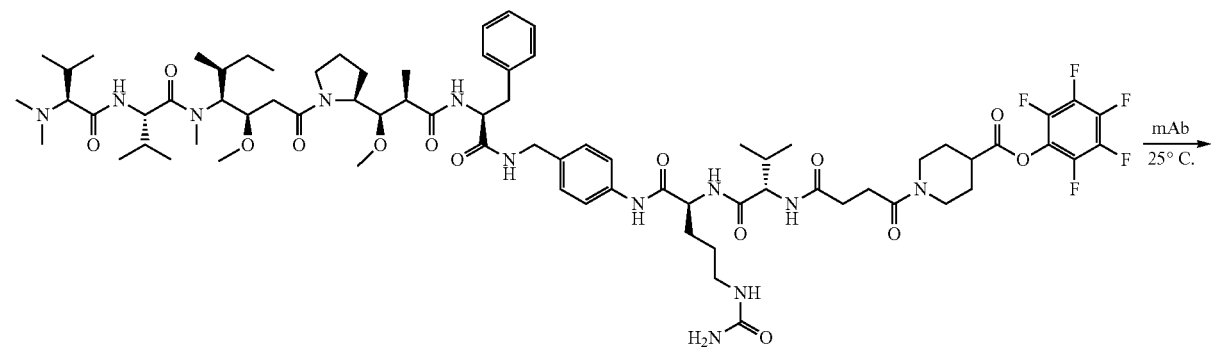

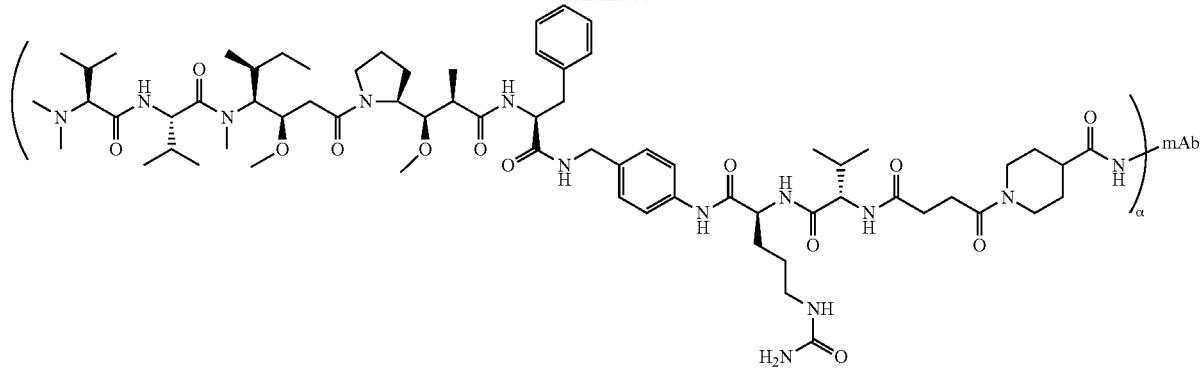
TL006-T-ADC
the specific conjugates are respectively:
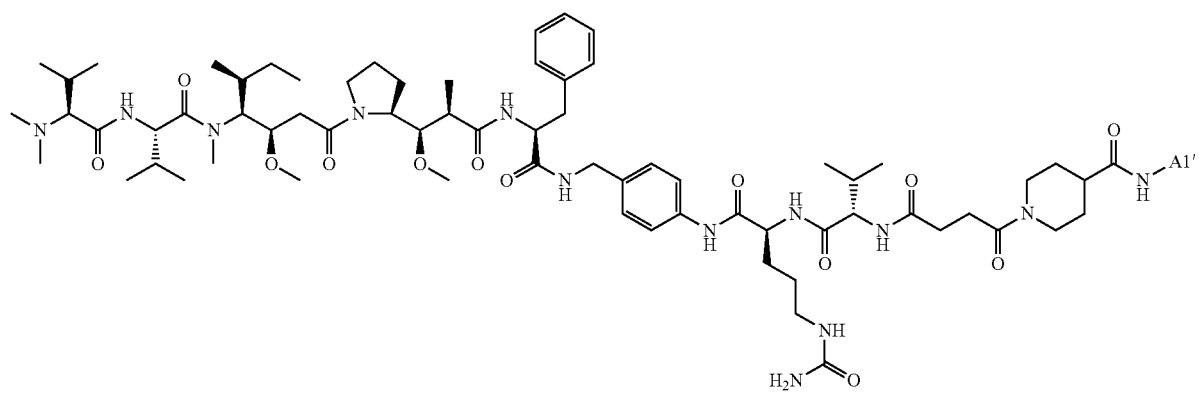
BT001062
wherein A1' is a group obtained after removing one amino group from trastuzumab;
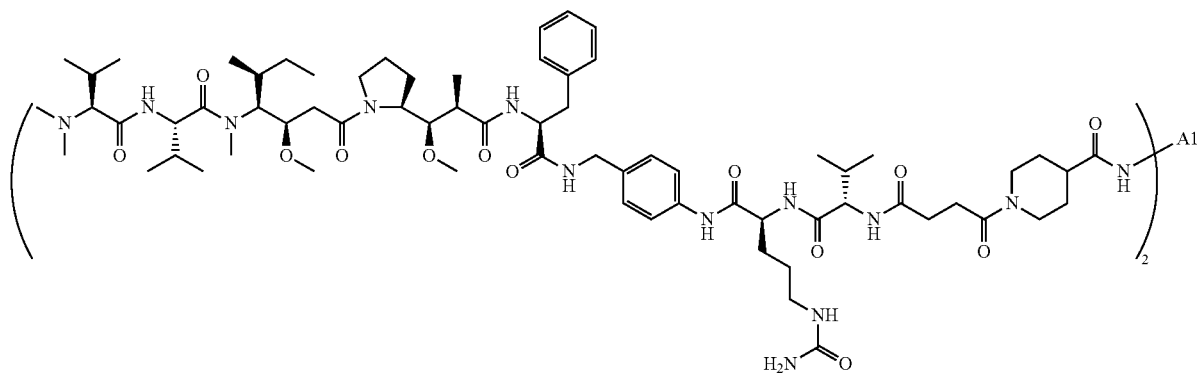
BT001005
wherein A1 is a group obtained after removing two amino groups from trastuzumab; and

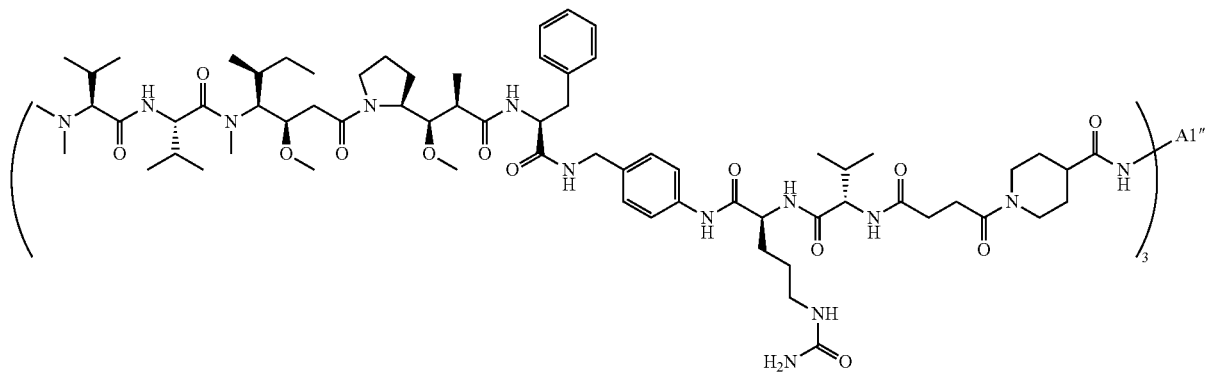

BT001082 wherein A1″ is a group obtained after removing three amino groups from trastuzumab.

Example 33 Synthesis of TL007-T-ADC

To 1 mL of a solution of trastuzumab in a concentration of 20 mg/ml at pH 7.4, a compound TL007 dissolved in DMA was added in a 6-fold amount, and stirred gently for 12 hours at room temperature. The fractions of different retention time in HIC-HPLC were collected, to obtain specific conjugates with DAR values of 1, 2 and 3, which were named BT001063, BT001006, and BT001083, respectively.

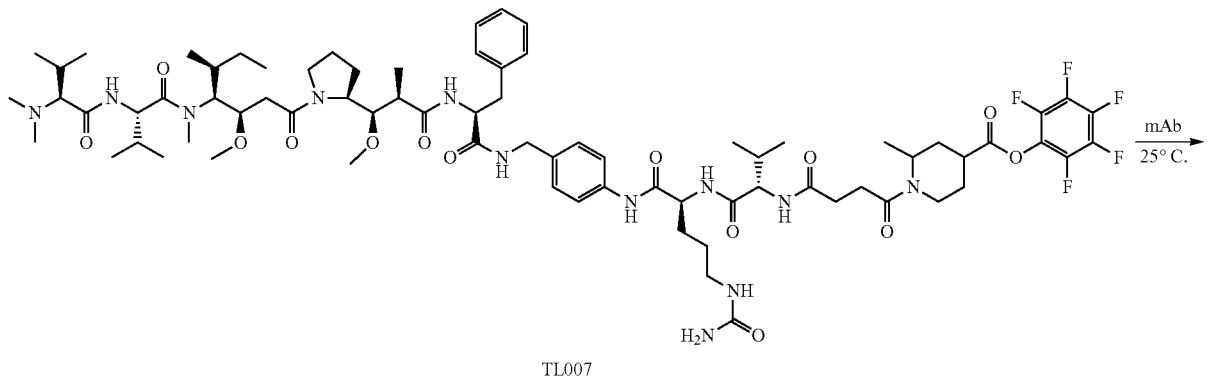

TL007

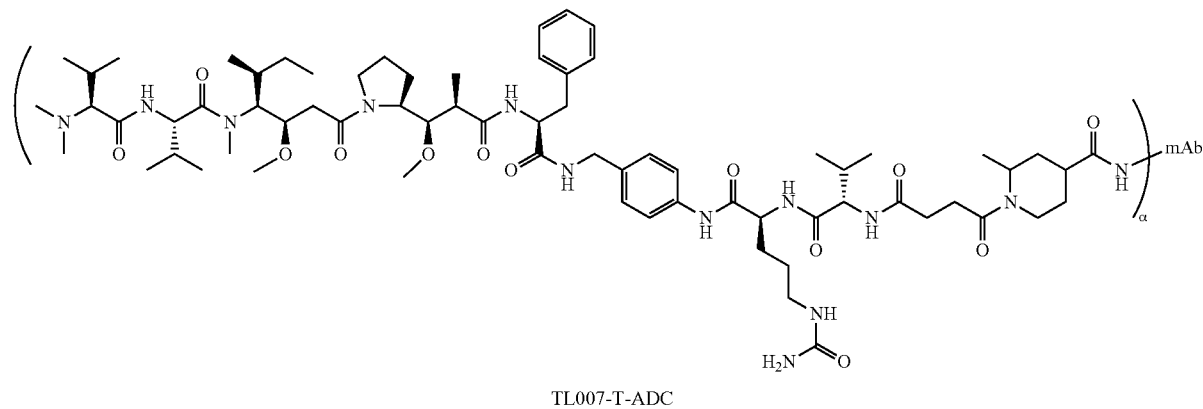

TL007-T-ADC the specific conjugates are respectively:
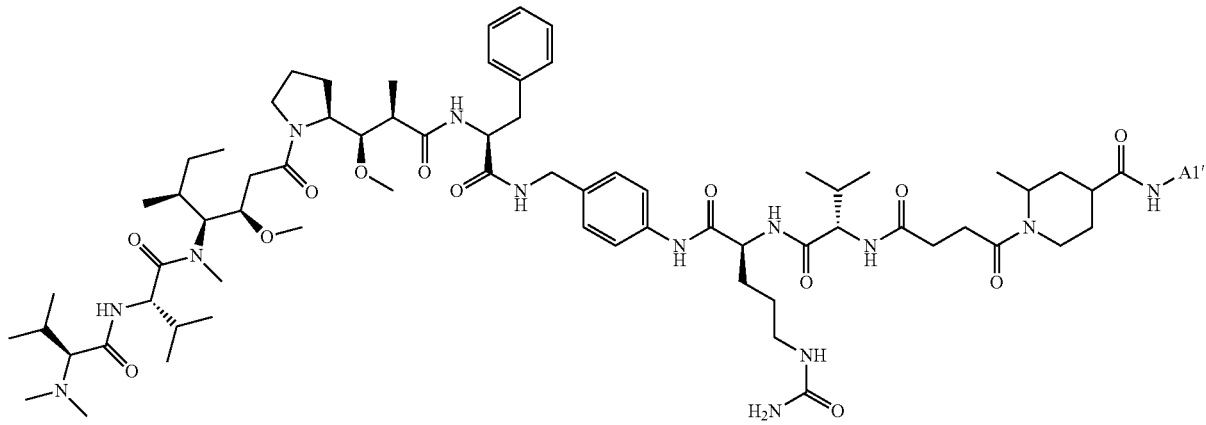
wherein A1' is a group obtained after removing one amino group from trastuzumab;
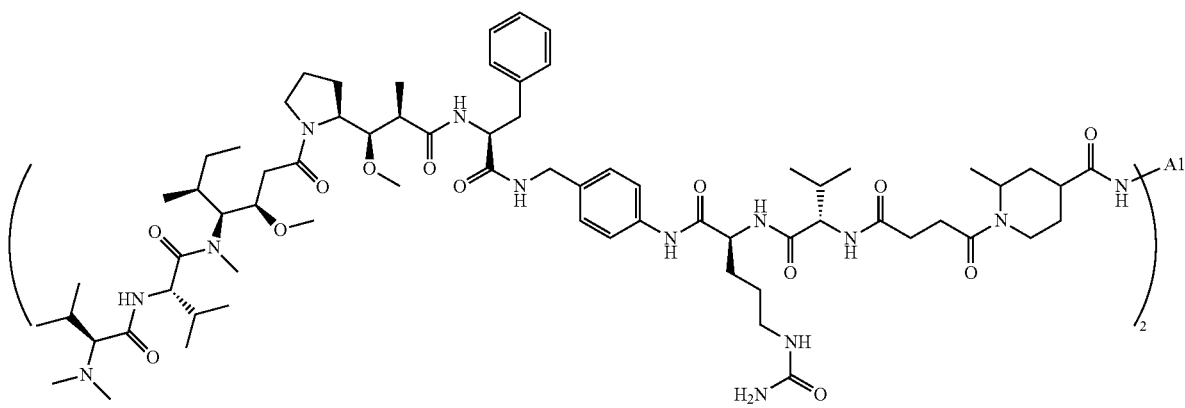
wherein A1 is a group obtained after removing two amino groups from trastuzumab; and
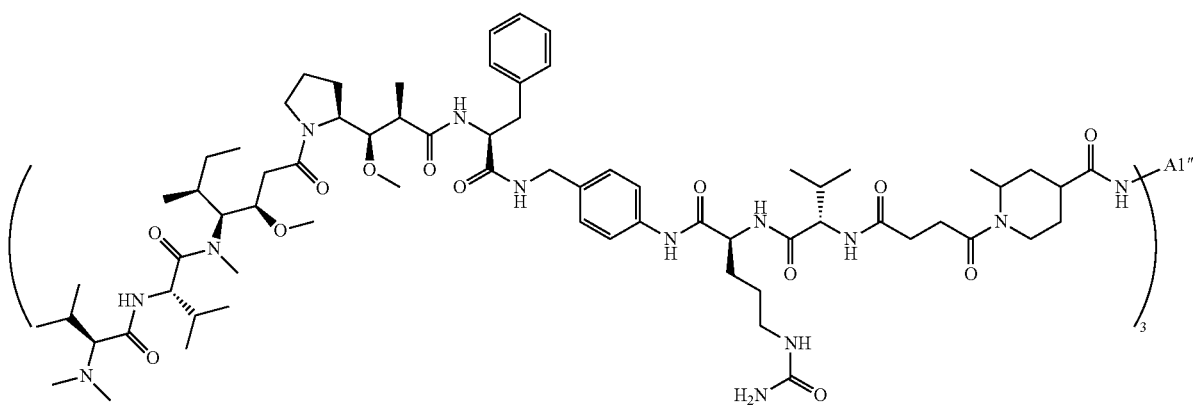
wherein A1" is a group obtained after removing three amino groups from trastuzumab.

Example 34 Synthesis of TL008-T-ADC

To 1 mL of a solution of trastuzumab in a concentration of 20 mg/ml at pH 7.0, a compound TL008 dissolved in DMA was added in a 6-fold amount, and stirred gently for 12 hours at room temperature. The fractions of different retention time in HIC-HPLC were collected, to obtain specific conjugates with DAR values of 1, 2 and 3, which were named BT001064, BT001007, and BT001084, respectively.

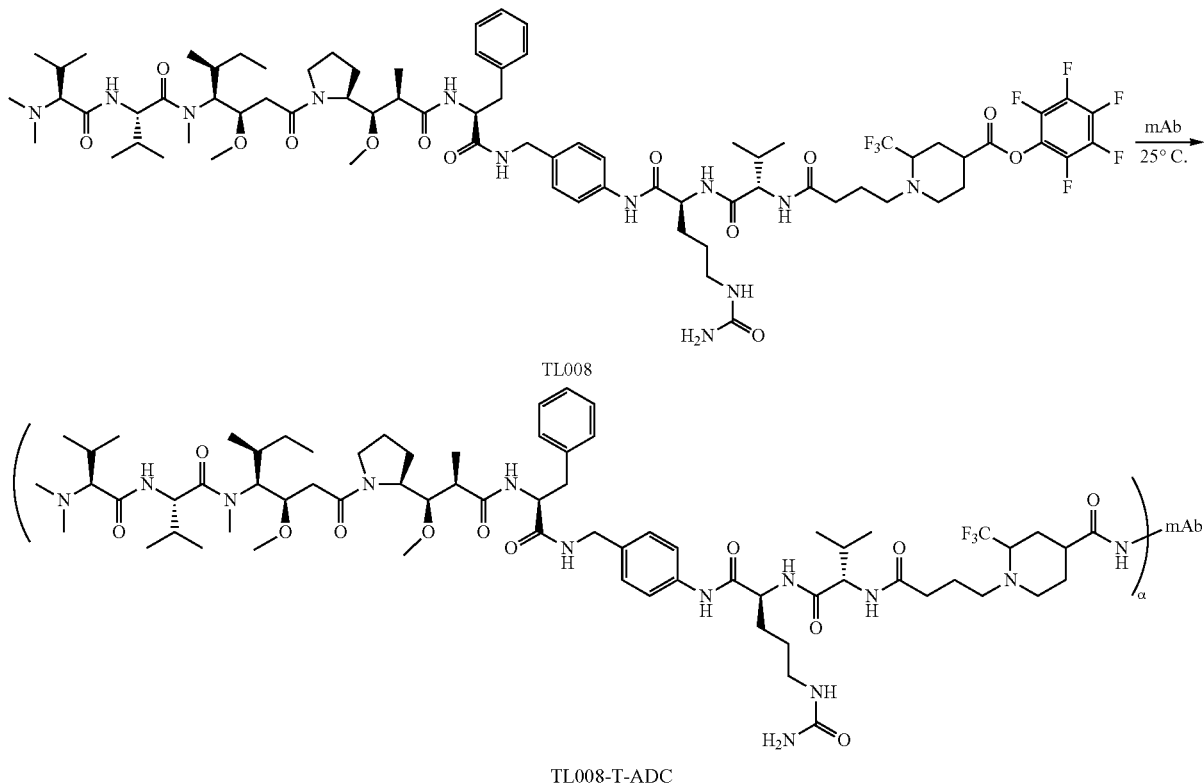

the specific conjugates are respectively:

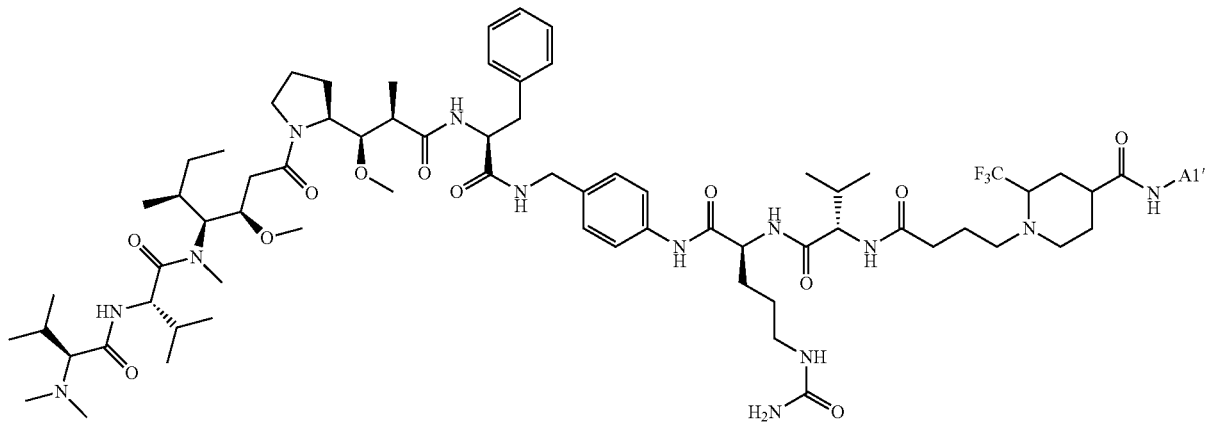

wherein A1' is a group obtained after removing one amino group from trastuzumab;

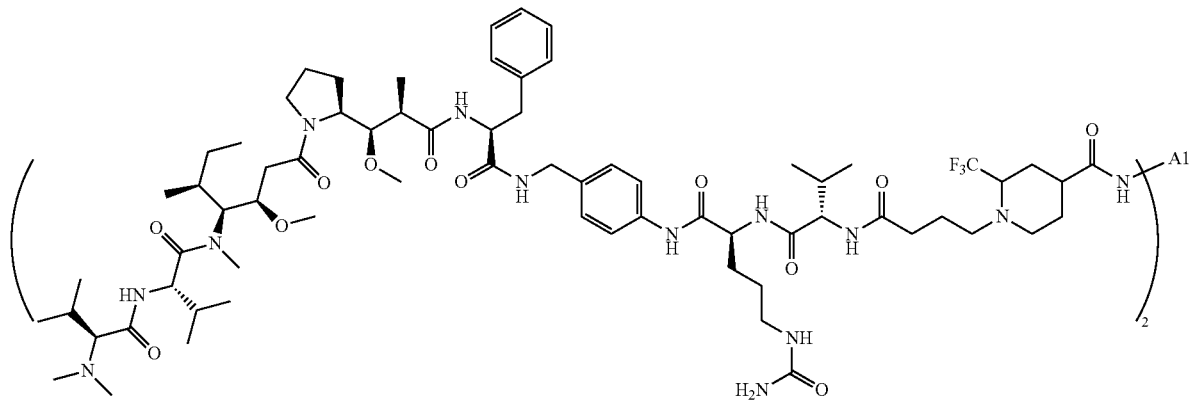

wherein A1 is a group obtained after removing two amino groups from trastuzumab; and

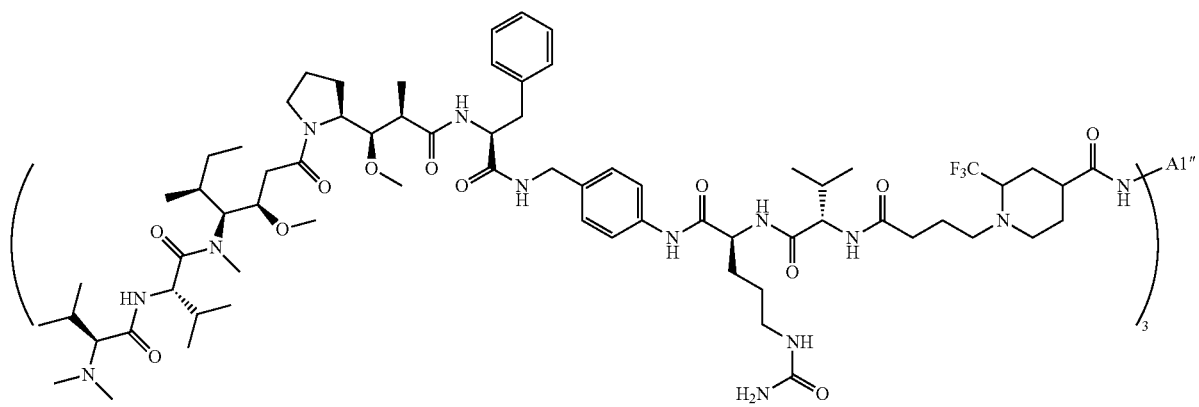

wherein A1″ is a group obtained after removing three amino groups from trastuzumab.

Example 35 Synthesis of TL009-T-ADC

To 1 mL of a solution of trastuzumab in a concentration of 20 mg/ml at pH 7.4, a compound TL009 dissolved in DMA was added in a 8-fold amount, and stirred gently for 12 hours at room temperature. The fractions of different retention time in HIC-HPLC were collected, to obtain specific conjugates with DAR values of 1, 2 and 3, which were named BT001065, BT001008, and BT001085, respectively.

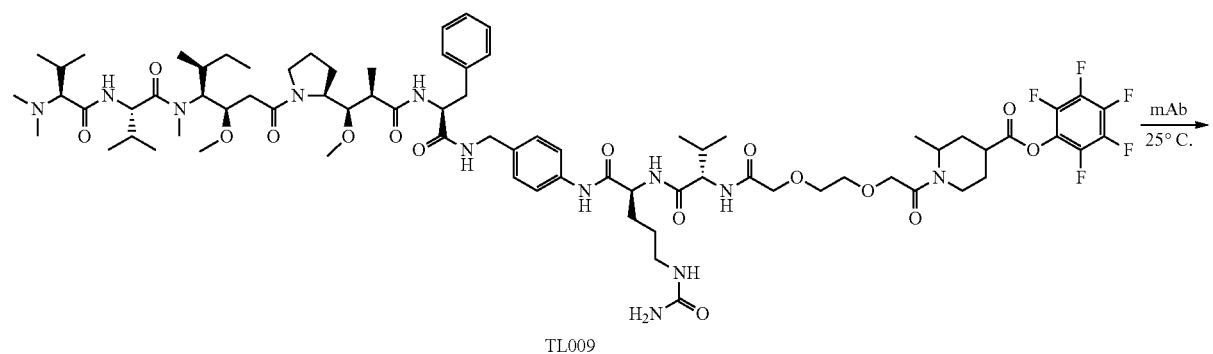

TL009

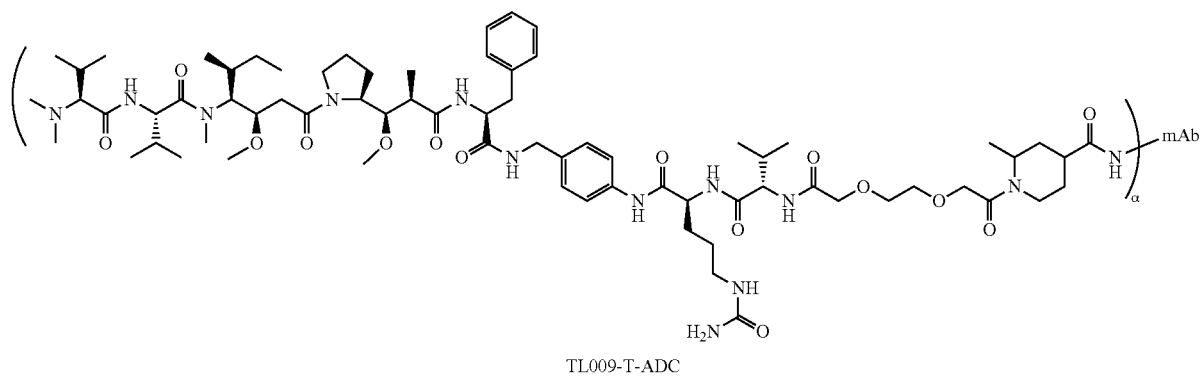
TL009-T-ADC
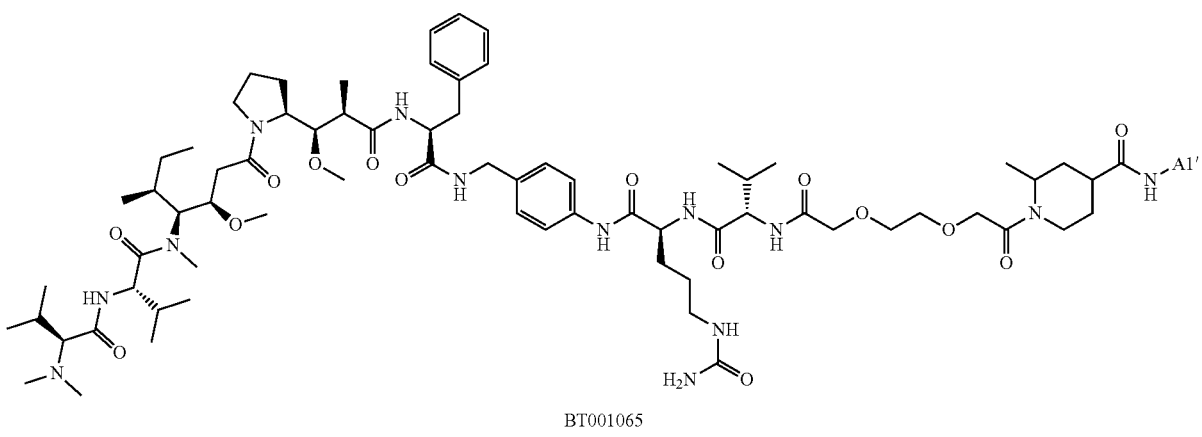
BT001065
wherein A1' is a group obtained after removing one amino group from trastuzumab.
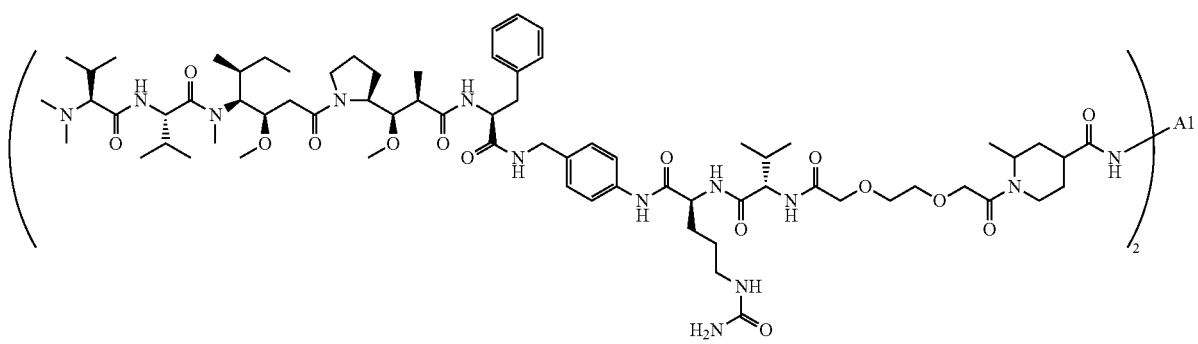
BT001008
wherein A1 is a group obtained after removing two amino groups from trastuzumab; and

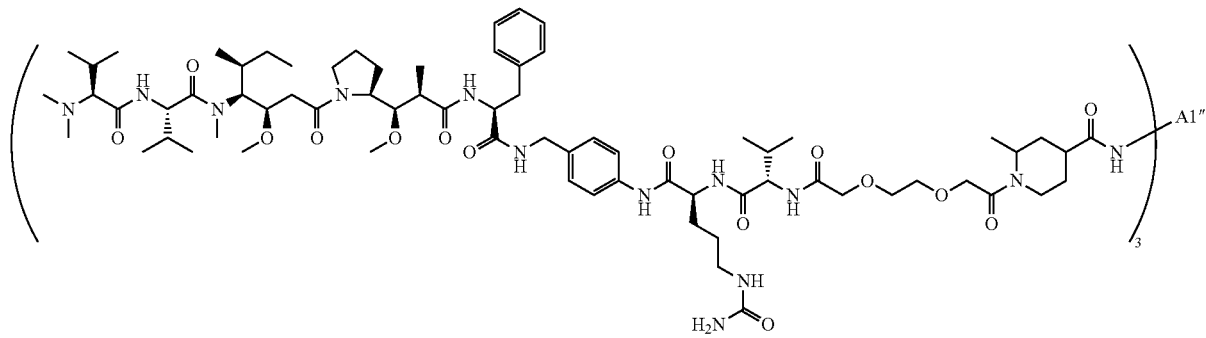

wherein A1″ is a group obtained after removing three amino groups from trastuzumab.

Example 36 Synthesis of TL010-T-ADC

To 1 mL of a solution of trastuzumab in a concentration of 15 mg/ml at pH 7.2, a compound TL010 dissolved in DMA was added in a 8-fold amount, and stirred gently for 12 hours at room temperature. The fractions of different retention time in HIC-HPLC were collected, to obtain specific conjugates with DAR values of 1, 2 and 3, which were named BT001066, BT001009, and BT001086, respectively.

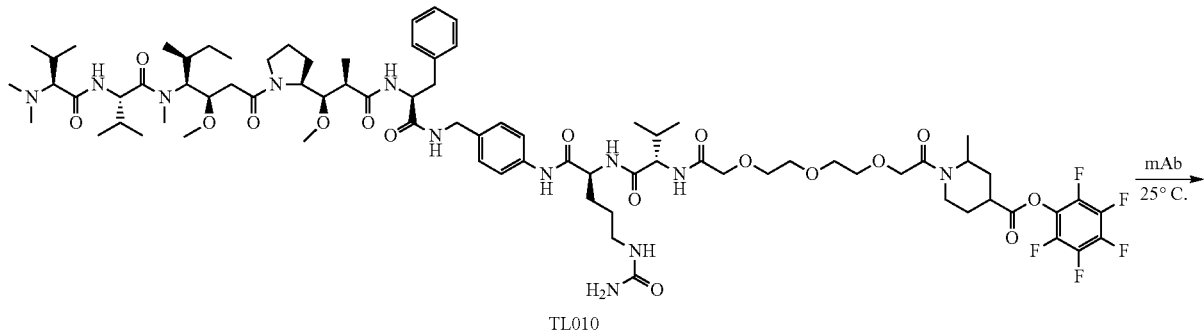

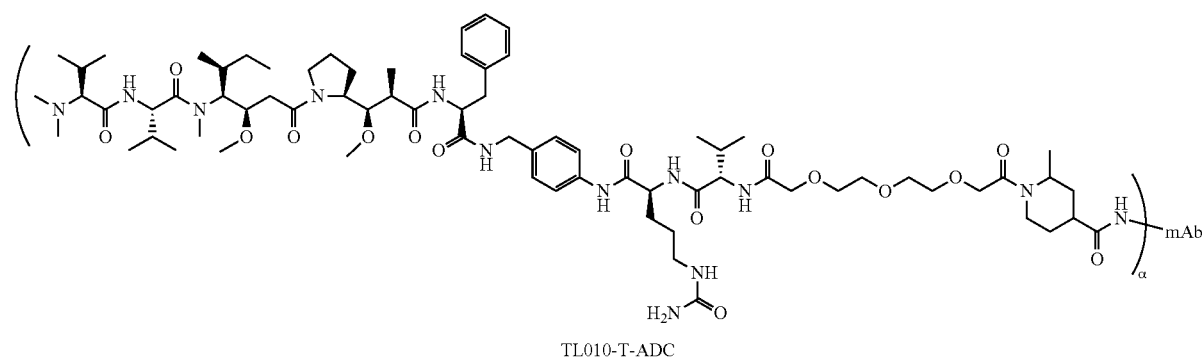

the specific conjugates are respectively:
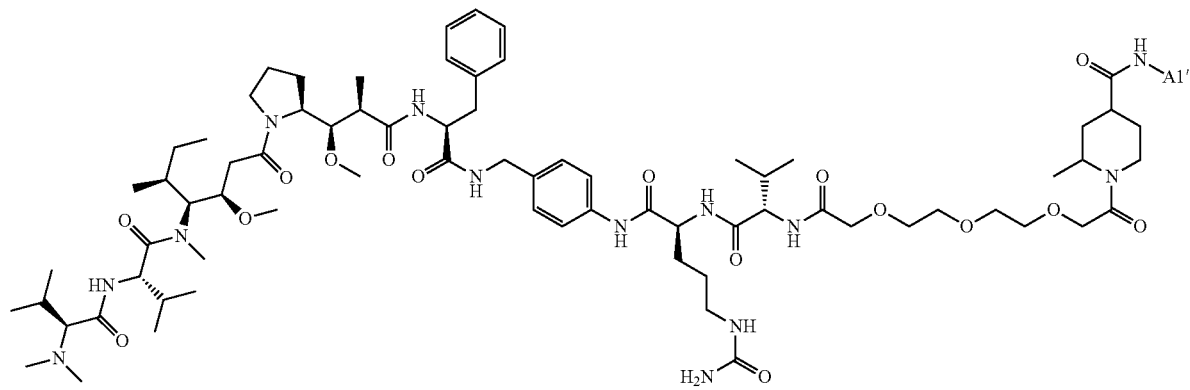
wherein A1' is a group obtained after removing one amino group from trastuzumab;
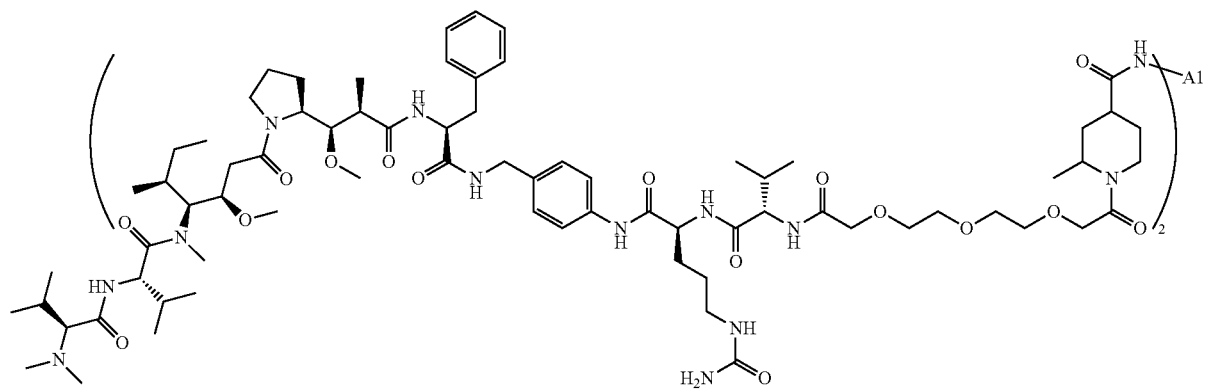
wherein A1 is a group obtained after removing two amino groups from trastuzumab; and
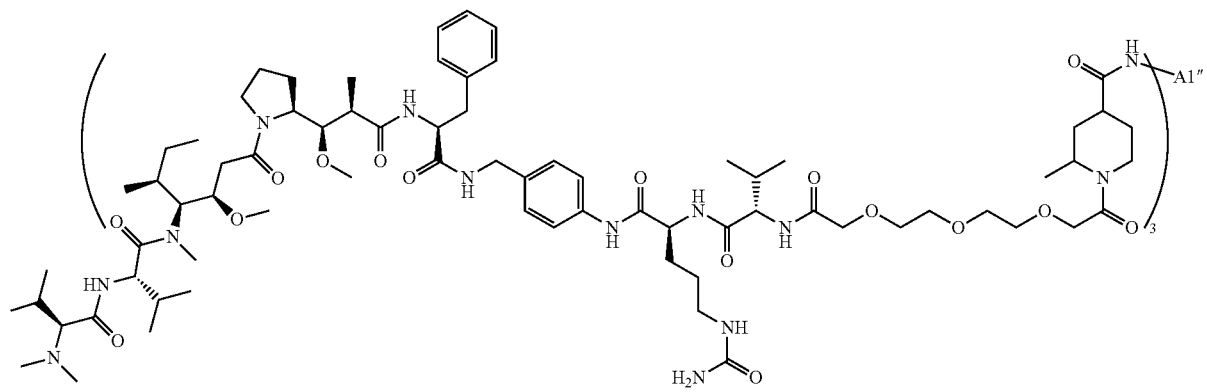
wherein A1" is a group obtained after removing three amino groups from trastuzumab.

Example 37 Synthesis of TL011-T-ADC

To 1 mL of a solution of trastuzumab in a concentration of 18 mg/ml at pH 7.5, a compound TL011 dissolved in DMA was added in a 4-fold amount, and stirred gently for 12 hours at room temperature. The fractions of different retention time in HIC-HPLC were collected, to obtain specific conjugates with DAR values of 1, 2 and 3, which were named BT001067, BT001010, and BT001087, respectively.

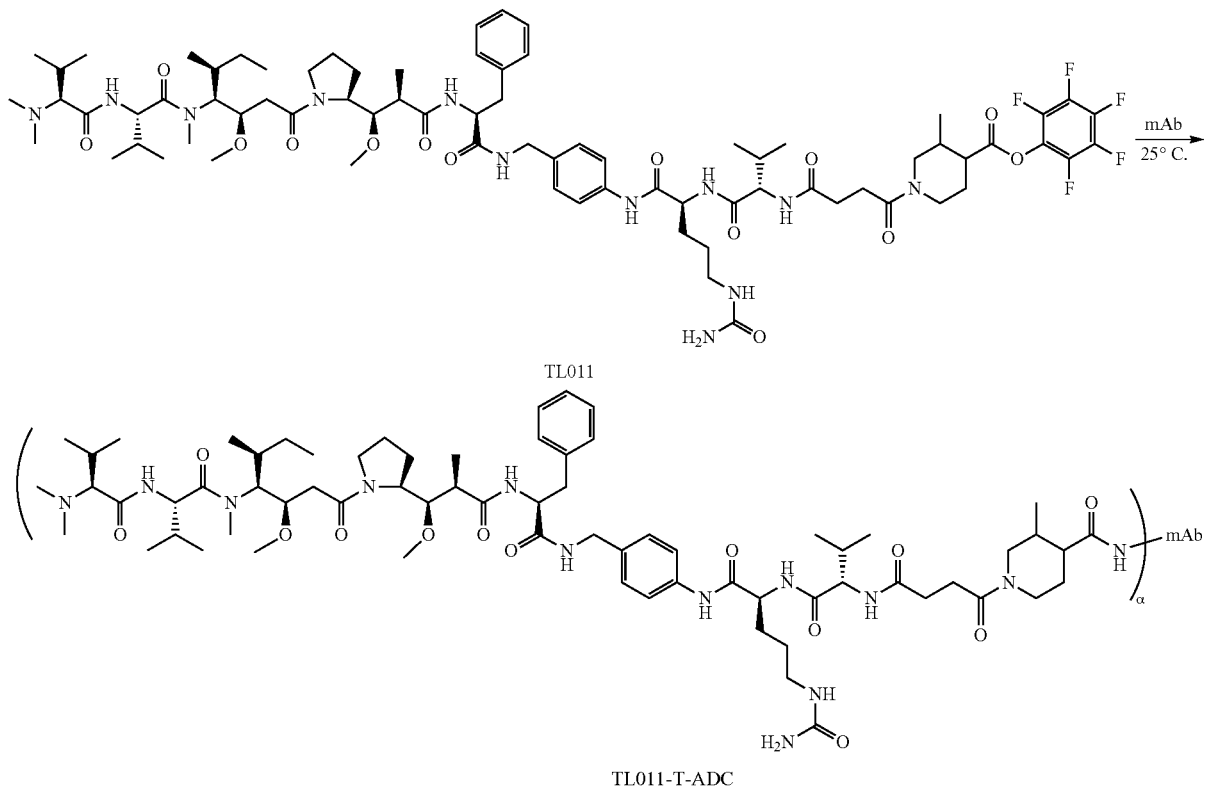

wherein, the specific conjugates are respectively:

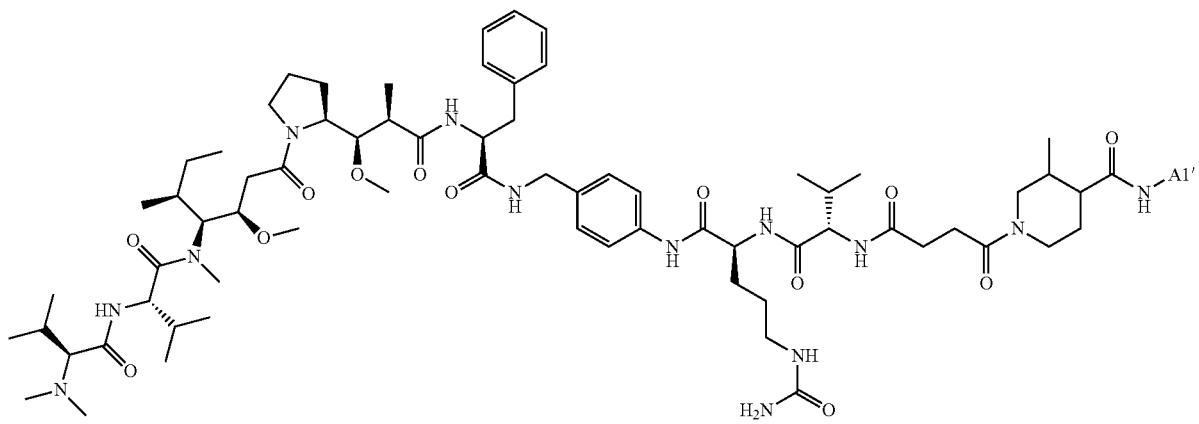

wherein A1' is a group obtained after removing one amino group from trastuzumab;

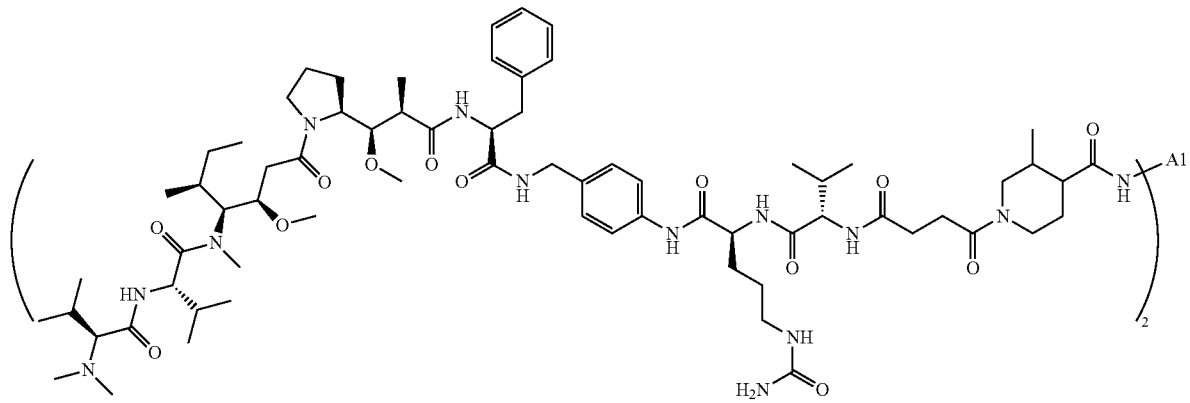

BT001010 wherein A1 is a group obtained after removing two amino groups from trastuzumab; and

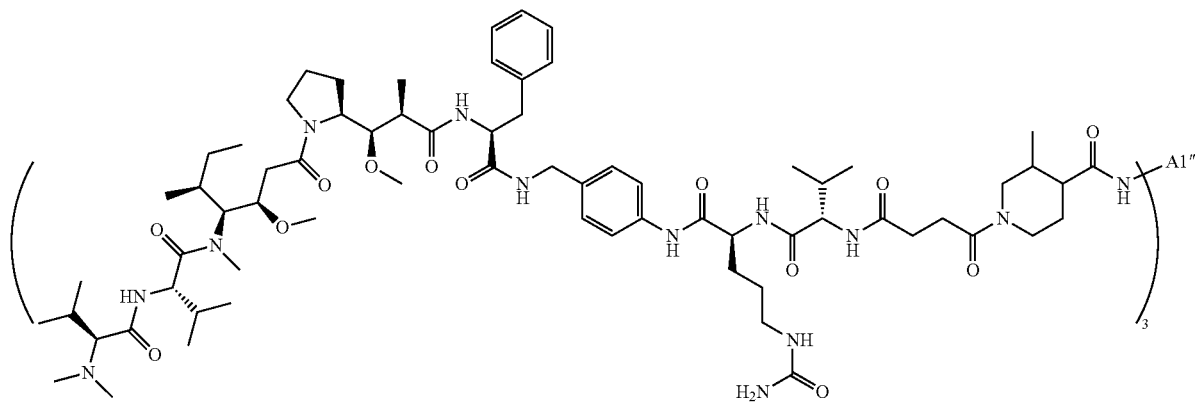

BT001087 wherein A1″ is a group obtained after removing three amino groups from trastuzumab.

Example 38 Synthesis of TL012-T-ADC

To 1 mL of a solution of trastuzumab in a concentration of 18 mg/ml at pH 7.5, a compound TL011 dissolved in DMA was added in a 4-fold amount, and stirred gently for 12 hours at room temperature. The fractions of different retention time in HIC-HPLC were collected, to obtain specific conjugates with DAR values of 1, 2 and 3, which were named BT001067, BT001010, and BT001087, respectively.

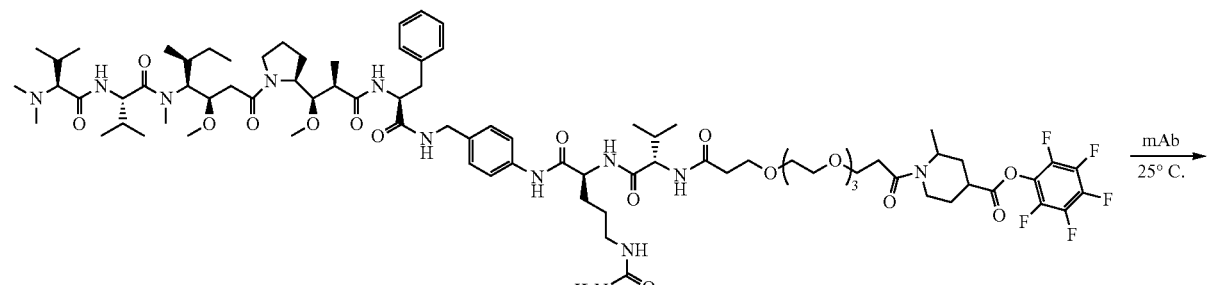

TL012

-continued
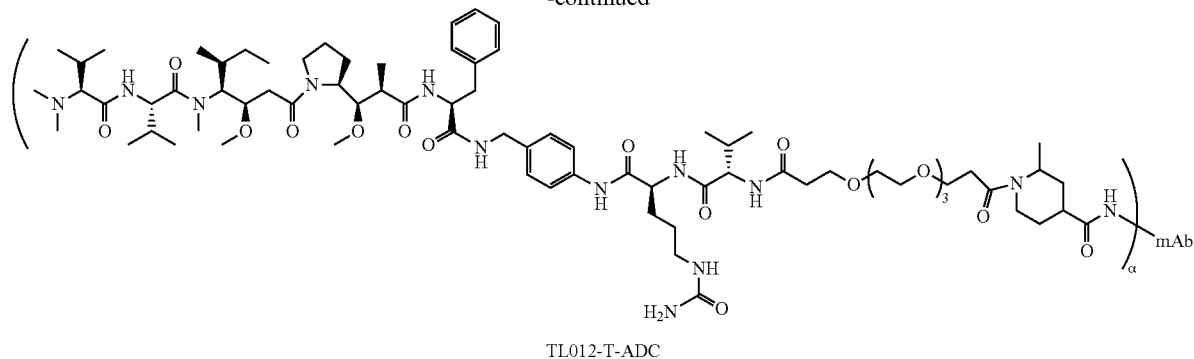
TL012-T-ADC
wherein, the specific conjugates are respectively:
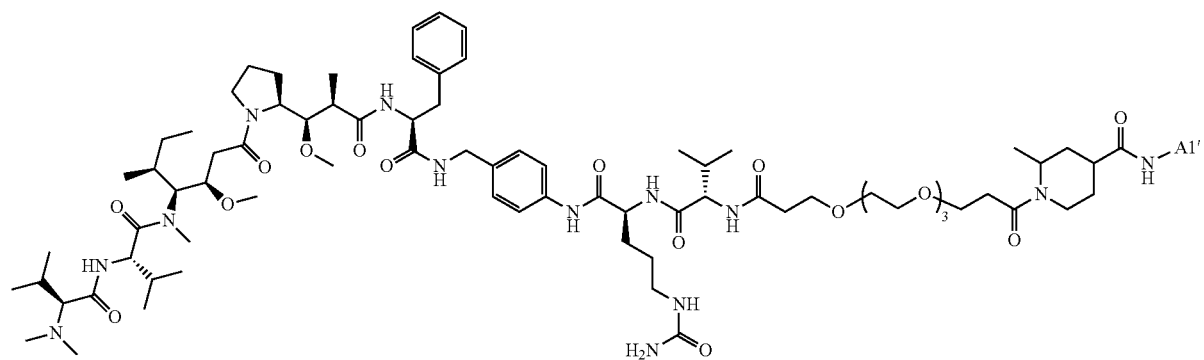
BT001068
wherein A1' is a group obtained after removing one amino group from trastuzumab;

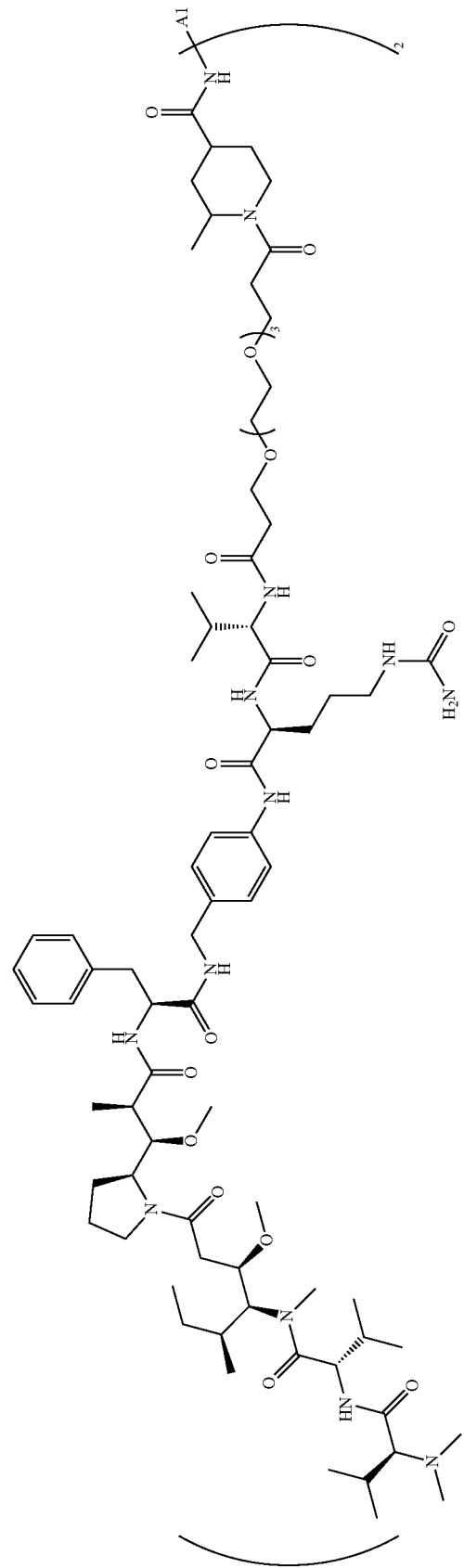

wherein A1 is a group obtained after removing two amino groups from trastuzumab; and

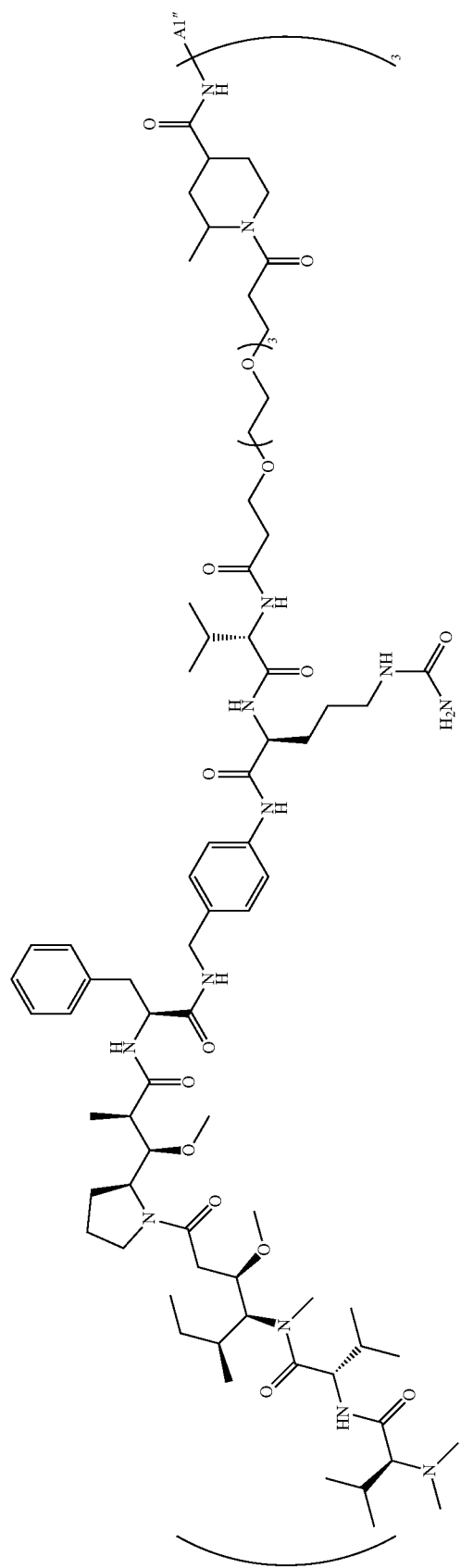

wherein A1″ is a group obtained after removing three amino groups from trastuzumab.

Example 39 Synthesis of TL007-S-ADC

To 0.4 mL of a solution of anti-Trop2 antibody sacituzumab in a concentration of 6.8 mg/ml at pH 7.4, a compound TL007 dissolved in DMA was added in a 6-fold amount, and stirred gently for 12 hours at room temperature. The fractions of different retention time in HIC-HPLC were collected, to obtain specific conjugates with DAR values of 1, 2 and 3, which were named BT001069, BT001014, and BT001089, respectively.

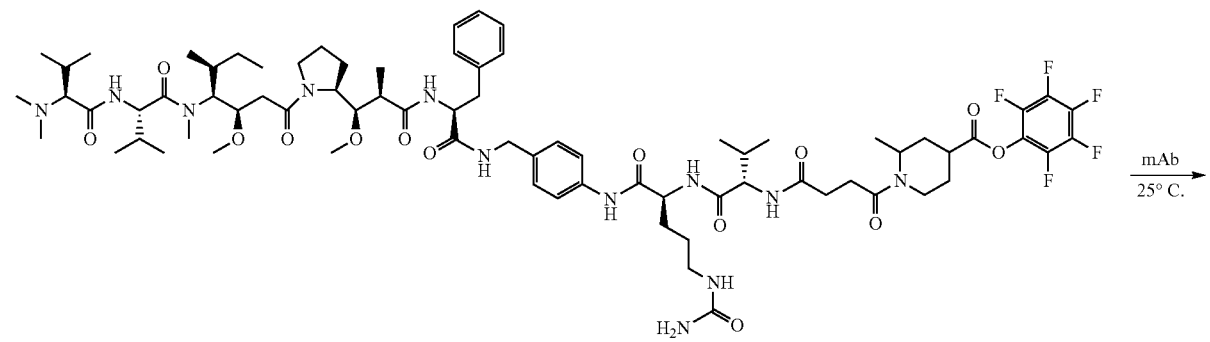
TL007

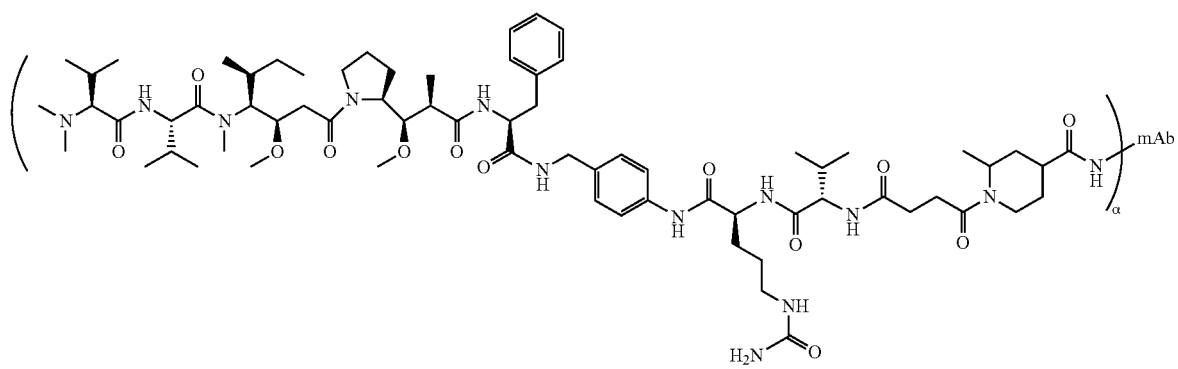
TL007-S-ADC wherein, the specific conjugates are respectively:

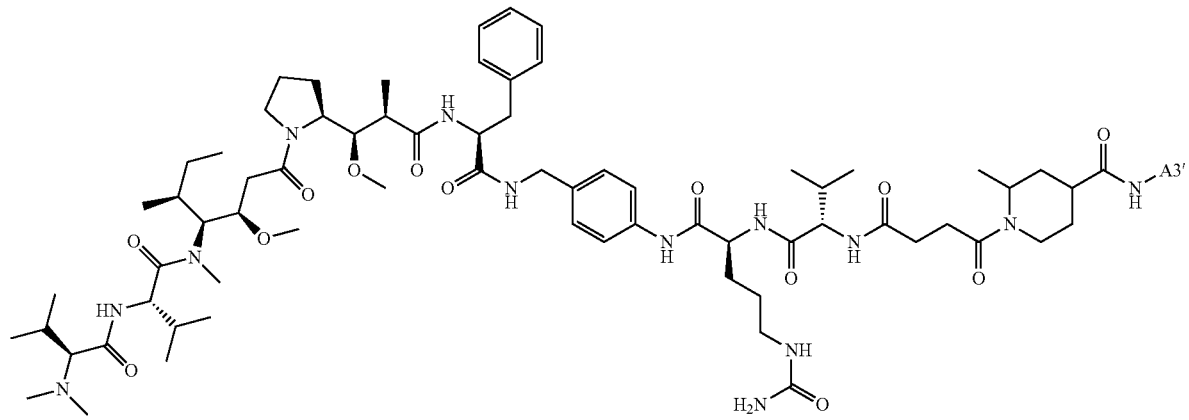
BT001069 wherein A3′ is a group obtained after removing one amino group from sacituzumab;

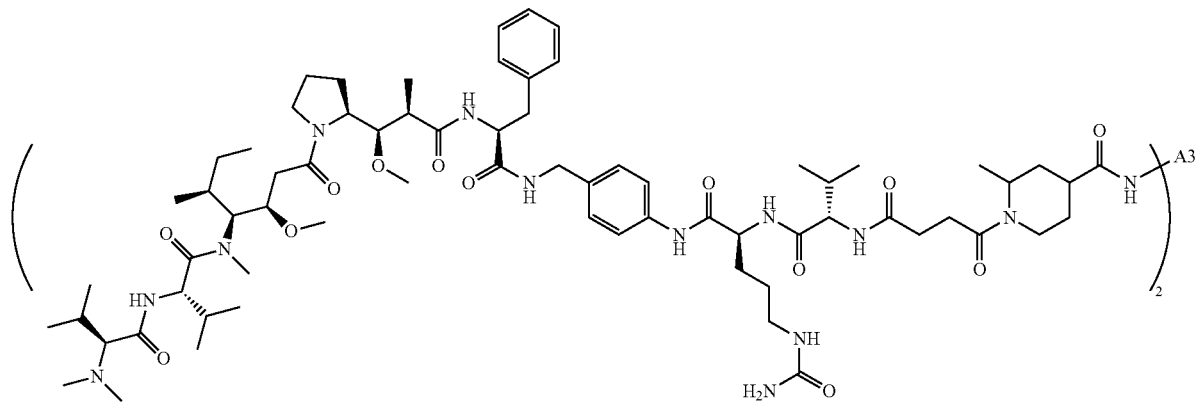

wherein A3 is a group obtained after removing two amino groups from sacituzumab; and

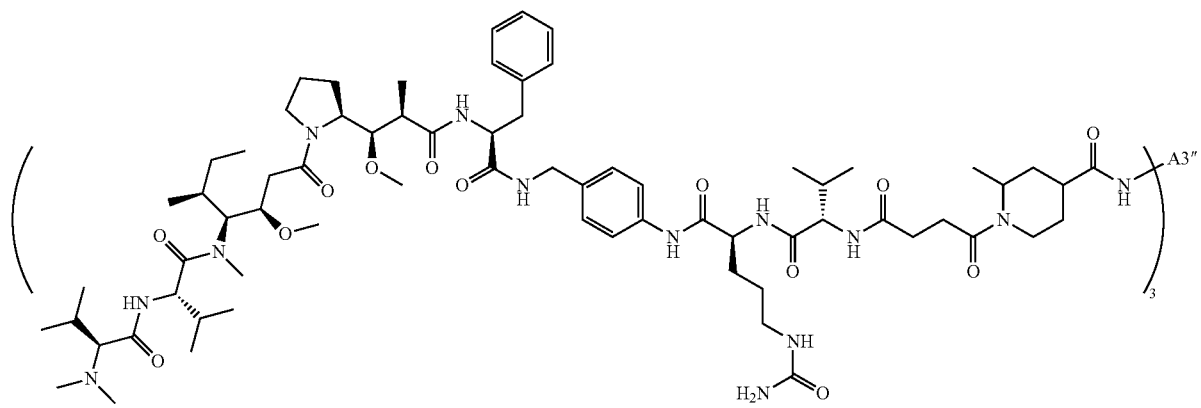

wherein A3″ is a group obtained after removing three amino groups from sacituzumab.

Example 40 Synthesis of TL008-S-ADC

To 0.4 mL of a solution of anti-Trop2 antibody sacituzumab in a concentration of 6.8 mg/ml at pH 7.4, a compound TL008 dissolved in DMA was added in a 6-fold amount, and stirred gently for 12 hours at room temperature. The fractions of different retention time in HIC-HPLC were collected, to obtain specific conjugates with DAR values of 1, 2 and 3, which were named BT001070, BT001015, and BT001090, respectively.

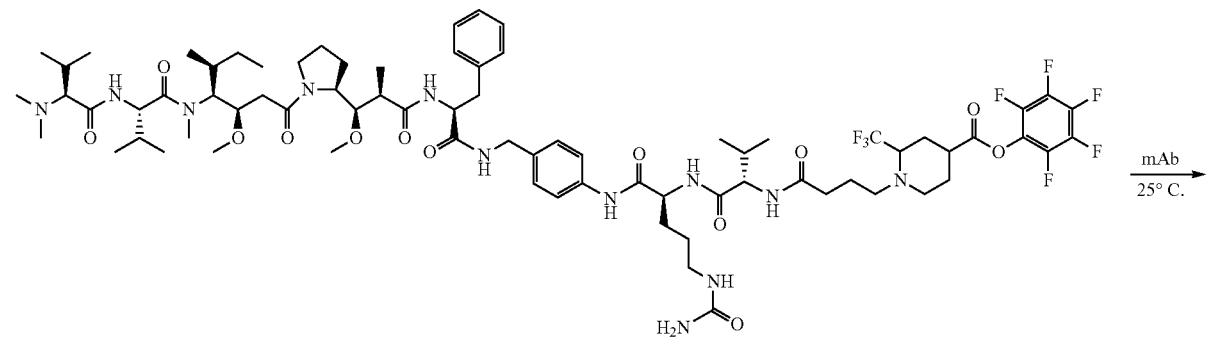

-continued
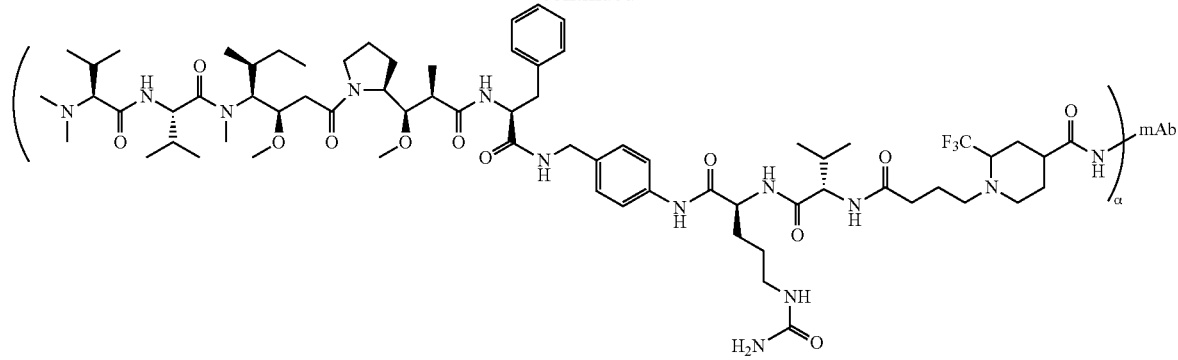
TL008-S-ADC
wherein, the specific conjugates are respectively:
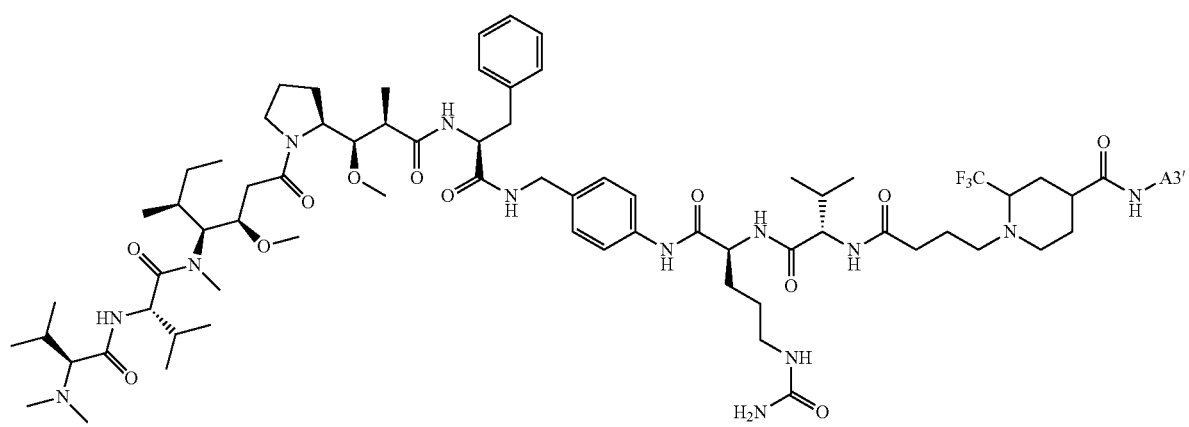
BT001070
wherein A3' is a group obtained after removing one amino group from sacituzumab;
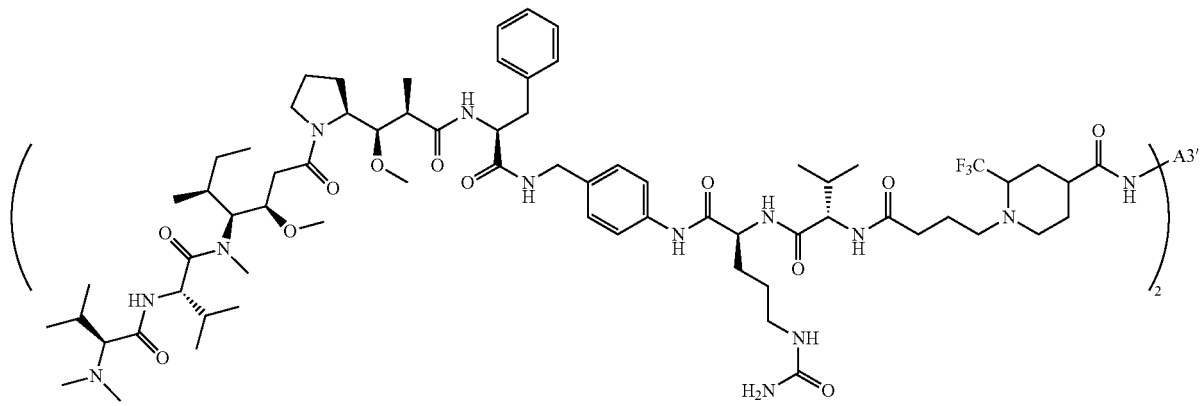
BT001015
wherein A3 is a group obtained after removing two amino groups from sacituzumab; and

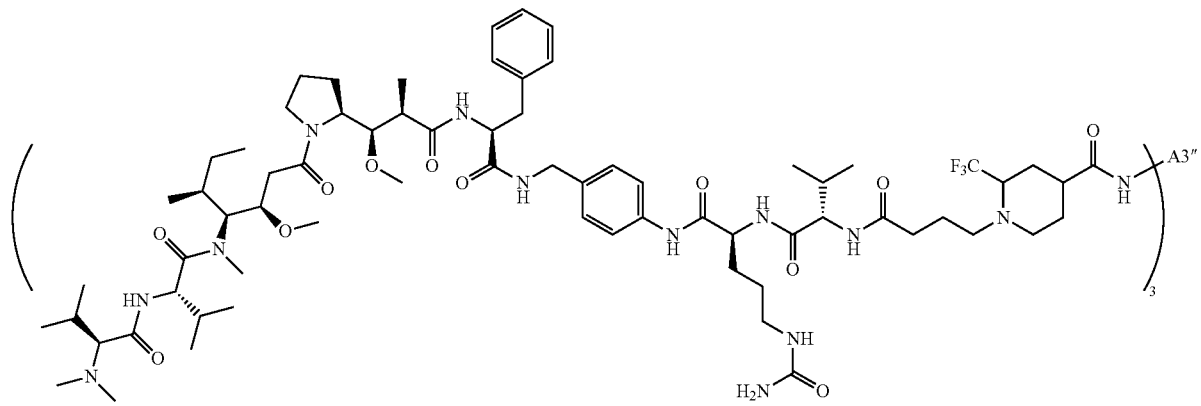

wherein A3" is a group obtained after removing three amino groups from sacituzumab.

Example 41 Synthesis of TL033-T-ADC

To 1 mL of a solution of trastuzumab in a concentration of 18 mg/ml at pH 7.5, a compound TL033 dissolved in DMF was added in a 4-fold amount, and stirred gently for 12 hours at room temperature. The fractions of different retention time in HIC-HPLC were collected, to obtain specific conjugates with DAR values of 1, 2 and 3, which were named BT001071, BT001020, and BT001091, respectively.

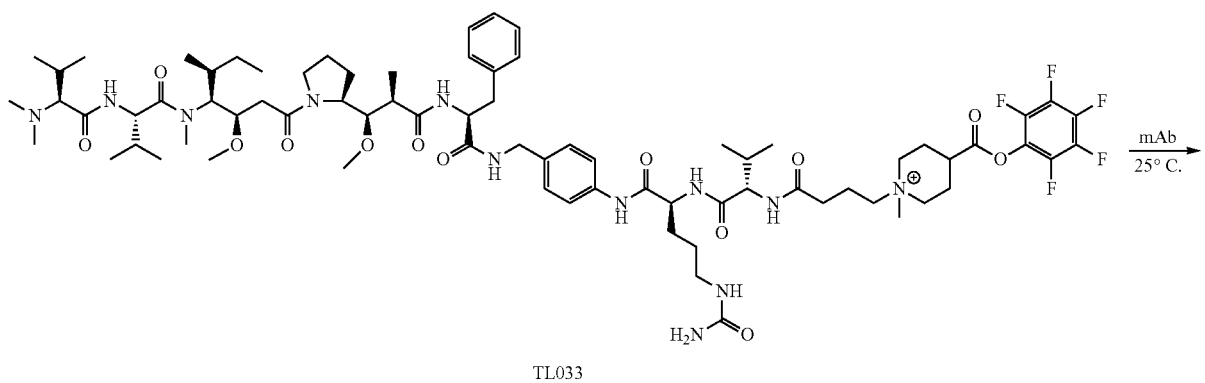

TL033

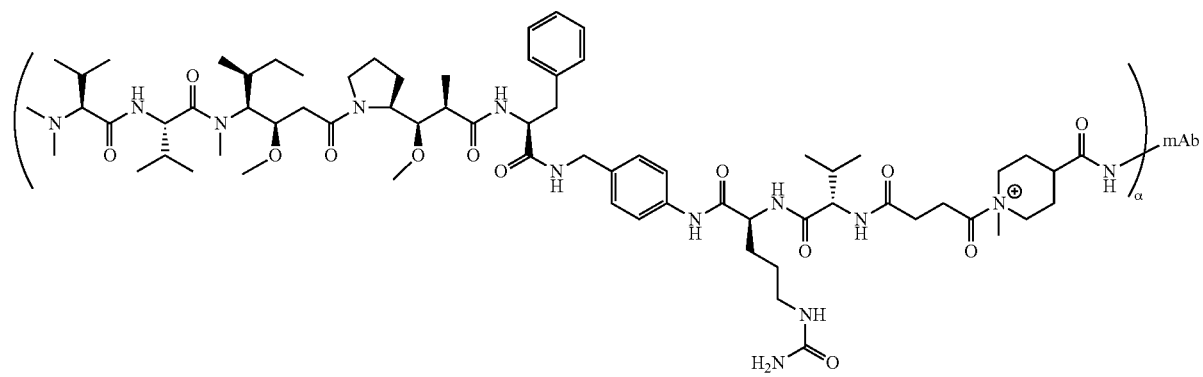

TL033-T-ADC

-continued
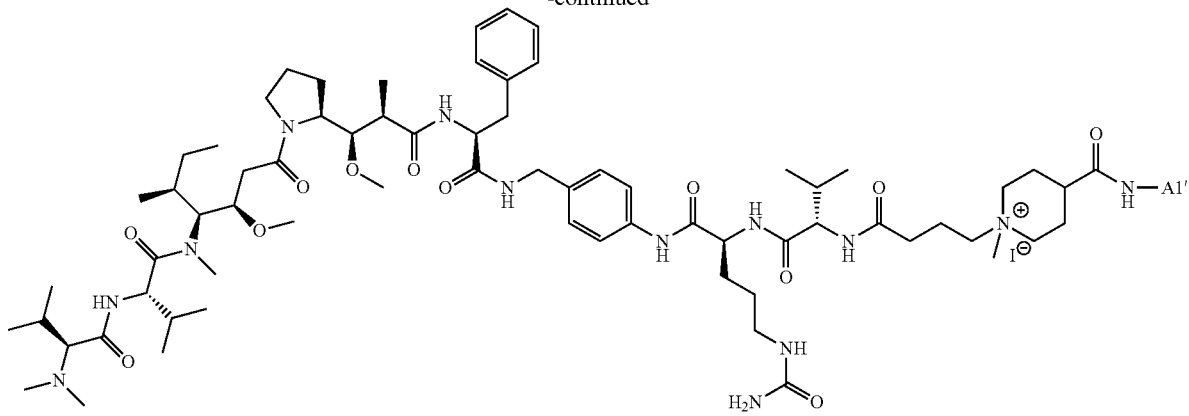
BT001071
wherein A1' is a group obtained after removing one amino groups from trastuzumab;
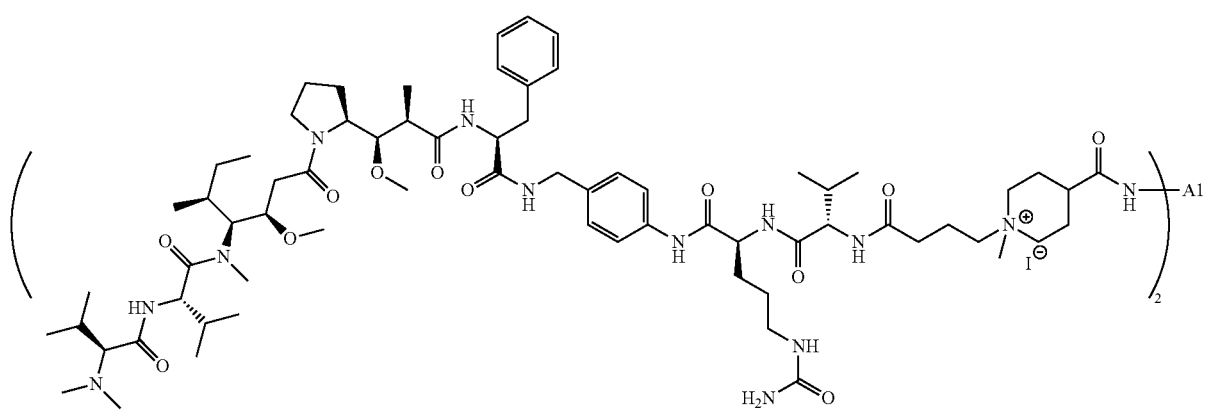
BT001020
wherein A1 is a group obtained after removing two amino groups from trastuzumab; and
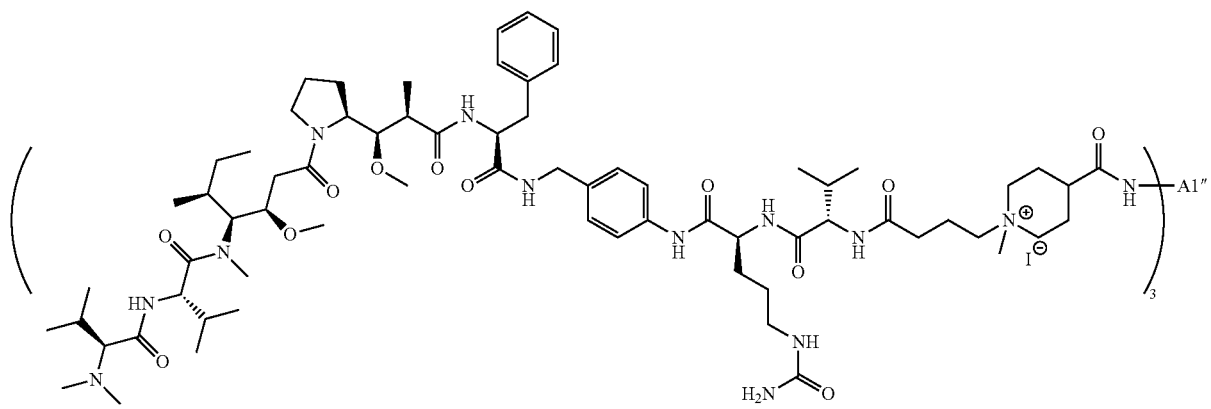
BT001091
wherein A1" is a group obtained after removing three amino groups from trastuzumab.

Example 42 Synthesis of TL030-T-ADC

A method similar to that of Example 31 was performed, except that TL004 was replaced with TL030, to obtain specific conjugates with DAR values of 1 and 2, which were named BT001072, BT001012, respectively.

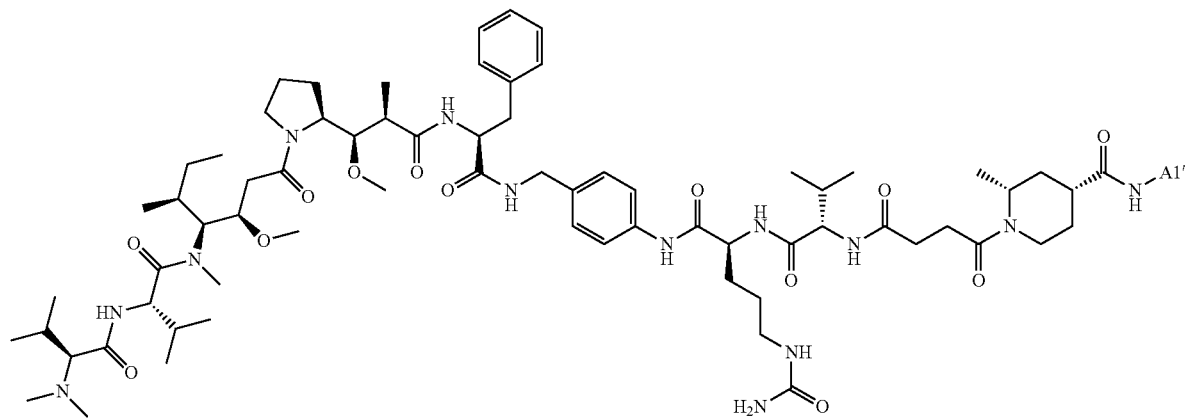
BT001072 wherein A1' is a group obtained after removing one amino group from trastuzumab;

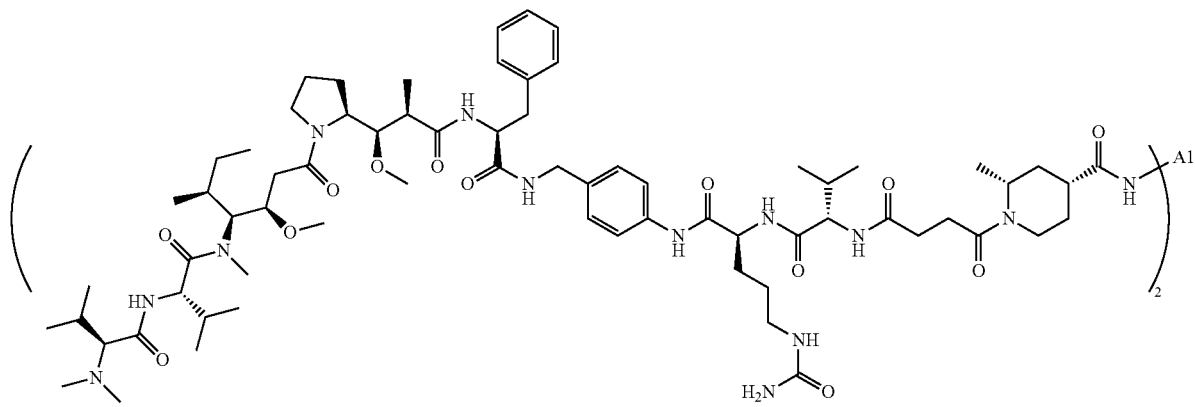
BT001012 wherein A1 is a group obtained after removing two amino groups from trastuzumab.

Example 43 Synthesis of TL031-T-ADC

A method similar to that of Example 31 was performed, except that TL004 was replaced with TL031, to obtain specific conjugates with DAR values of 1 and 2, which were named BT001073, BT001013, respectively.

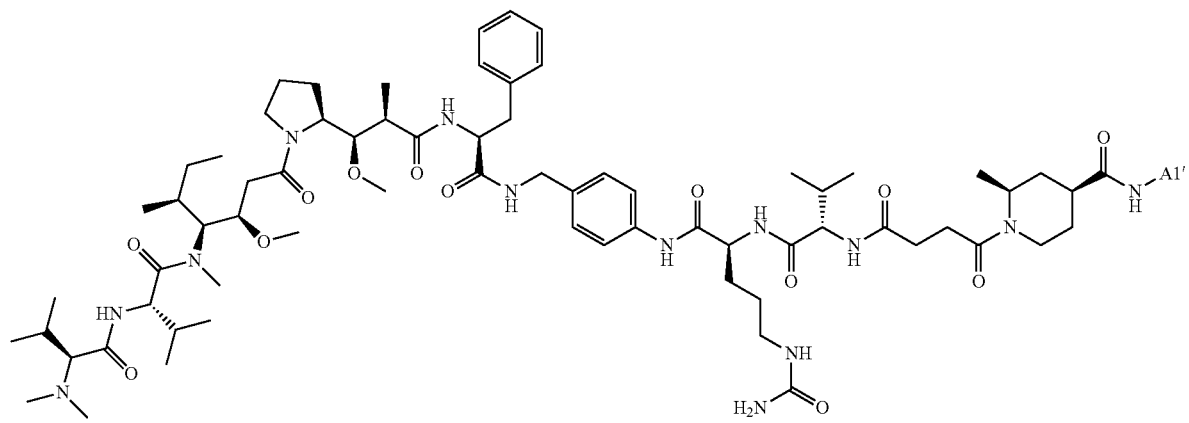

BT001073 wherein A1' is a group obtained after removing one amino group from trastuzumab; and

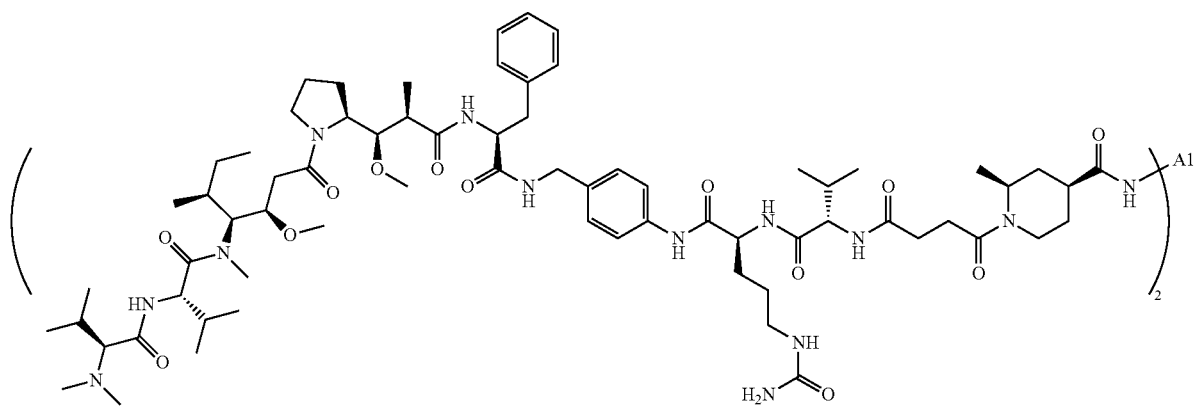

BT001013 wherein A1 is a group obtained after removing two amino groups from trastuzumab.

Example 44 Synthesis of TL034-T-ADC

A method similar to that of Example 31 was performed, except that TL004 was replaced with TL034, to obtain specific conjugates with DAR values of 1 and 2, which were named BT001075, BT001017, respectively.

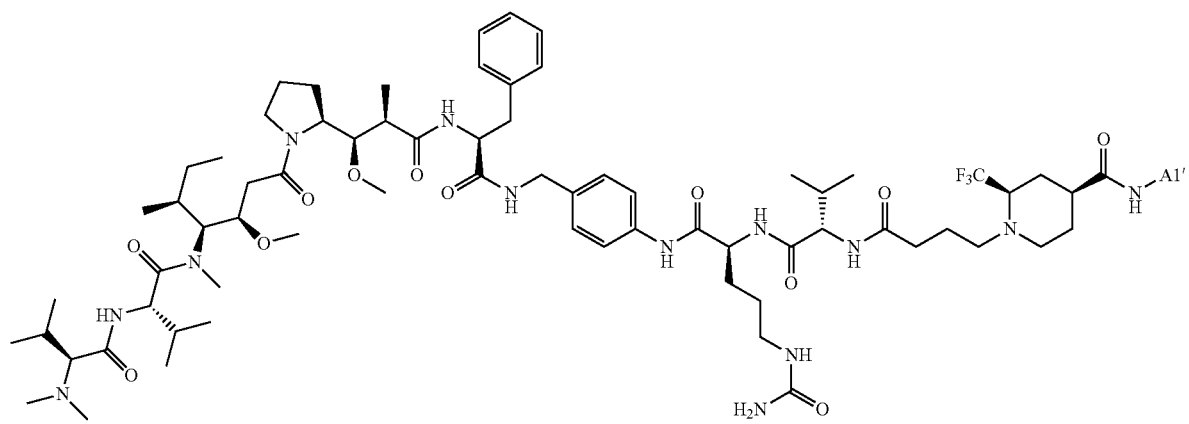

BT001075 wherein A1' is a group obtained after removing one amino group from trastuzumab; and

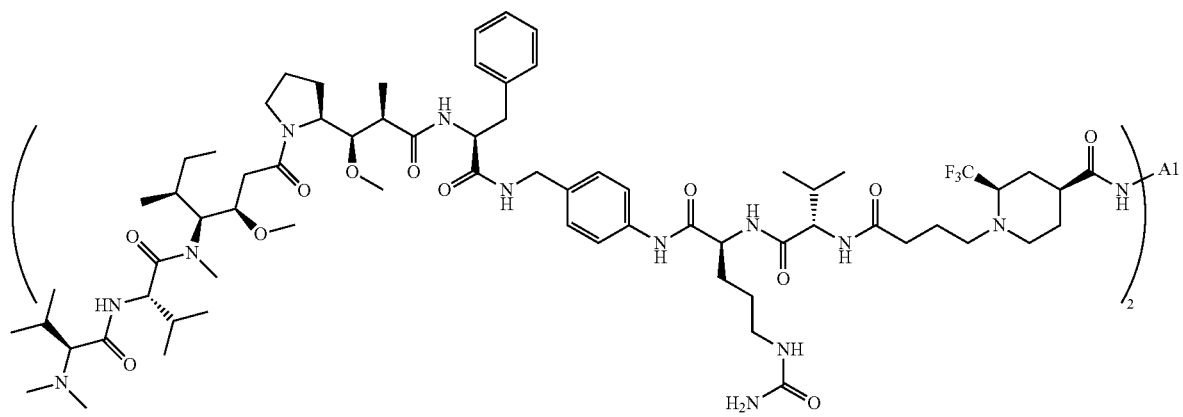

BT001017 wherein A1 is a group obtained after removing two amino groups from trastuzumab;

Example 45 Synthesis of TL035-T-ADC

A method similar to that of Example 31 was performed, except that TL004 was replaced with TL035, to obtain specific conjugates with DAR values of 1 and 2, which were named BT001074, BT001016, respectively.

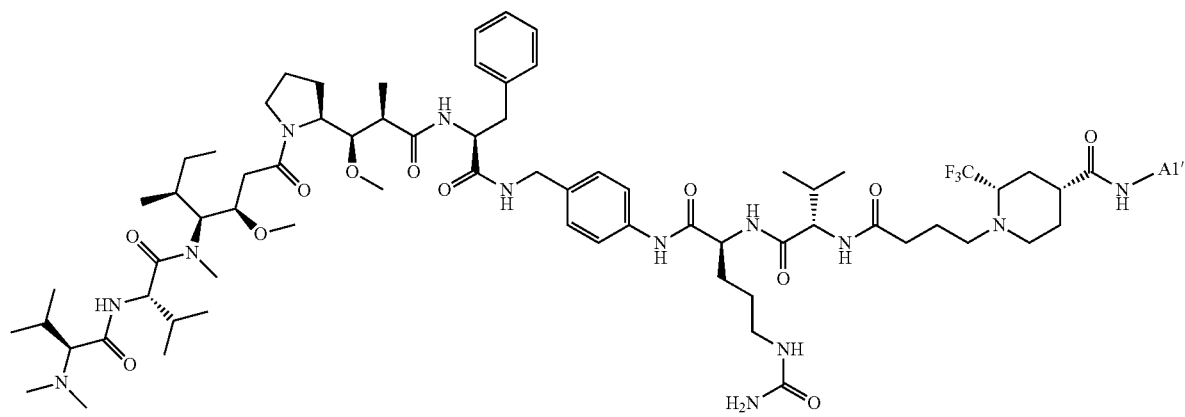

BT001074 wherein A1' is a group obtained after removing one amino group from trastuzumab; and

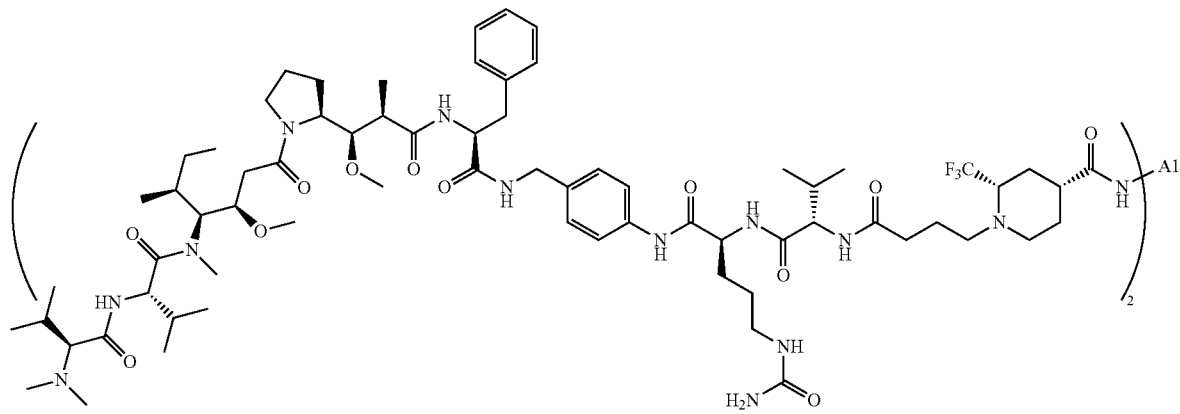

BT001016 wherein A1 is a group obtained after removing two amino groups from trastuzumab.

Example 46 Synthesis of TL042-T-ADC

A method similar to that of Example 31 was performed, except that TL004 was replaced with TL042, to obtain specific conjugates with DAR values of and 2, which were named BT001077, BT001019, respectively.

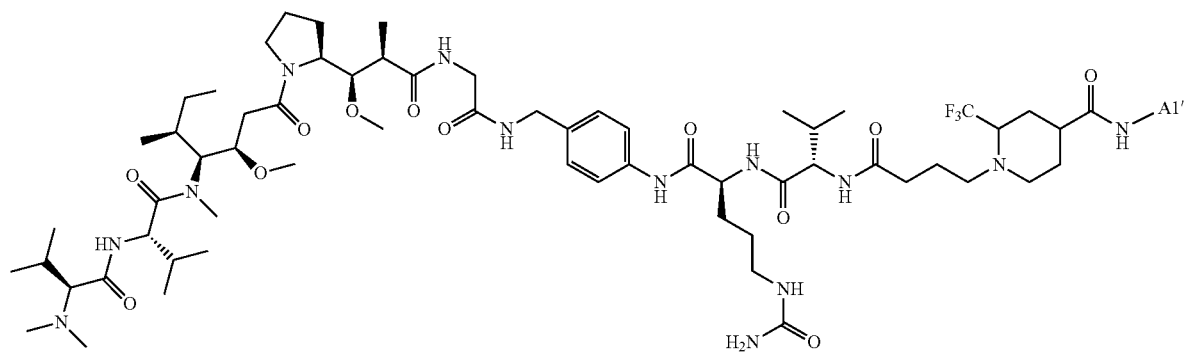

BT001077 wherein A1' is a group obtained after removing one amino group from trastuzumab; and

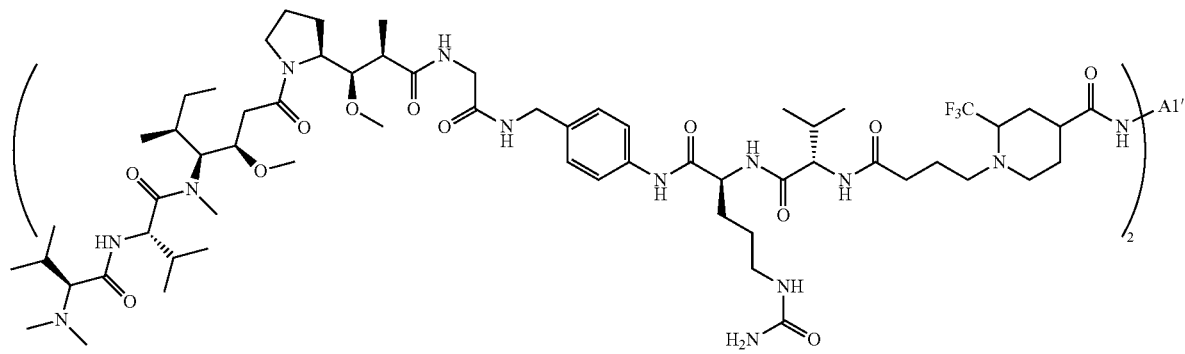

BT001019 wherein A1 is a group obtained after removing two amino groups from trastuzumab.

Example 47 Synthesis of TL059-T-ADC

A method similar to that of Example 31 was performed, except that TL004 was replaced with TL059, to obtain specific conjugates with DAR values of 1 and 2, which were named BT001078, BT001021, respectively.

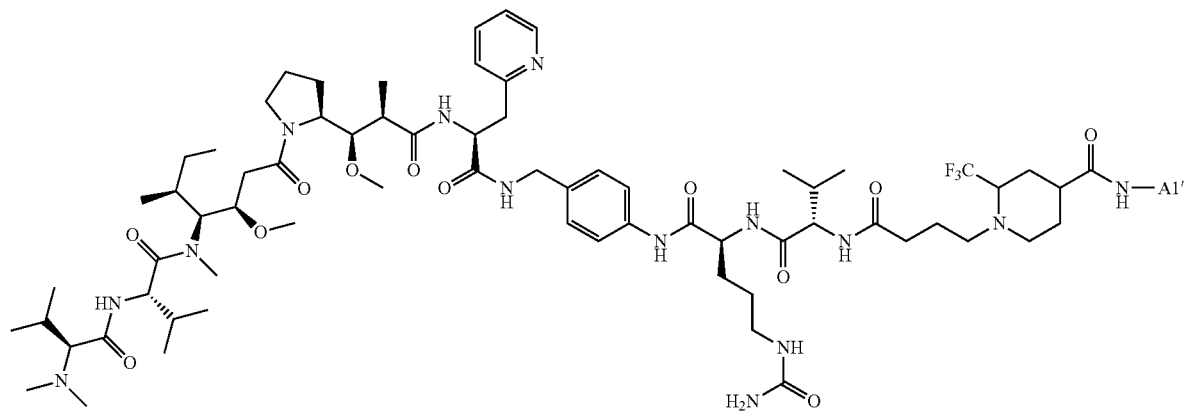

wherein A1' is a group obtained after removing one amino group from trastuzumab;

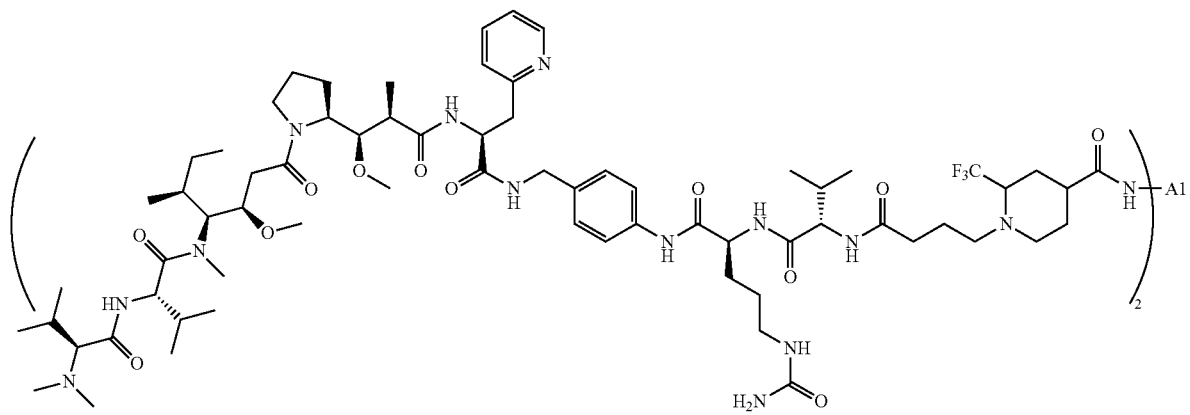

wherein A1 is a group obtained after removing two amino groups from trastuzumab.

Example 48 Characterization of Conjugates by Hydrophobic Chromatograph

The reaction was monitored by HIC-HPLC, and the conjugate was subjected to HIC detection.

HIC conditions:
Liquid chromatography column: TOSOH TSKgel Butyl-NPR, 4.6×100 mm
Mobile phase A: 1.5 M ammonium sulfate
Mobile phase B: 25 mM $Na_2HPO_4$, pH 7.0, 2530 isopropanol
Flow rate: 0.5 ml/min
Detection wavelength: 280 nm
Column temperature 30° C. (volume %)
Sample chamber temperature: 8° C.

Elution conditions:

|  | Time (min) | | | | | |
| --- | --- | --- | --- | --- | --- | --- |
|  | 0 | 3 | 25 | 30 | 30.1 | 35 |
| Mobile phase A (volume %) | 70 | 70 | 55 | 15 | 70 | 70 |
| Mobile phase B (volume %) | 30 | 30 | 45 | 85 | 30 | 30 |

Figure 22:
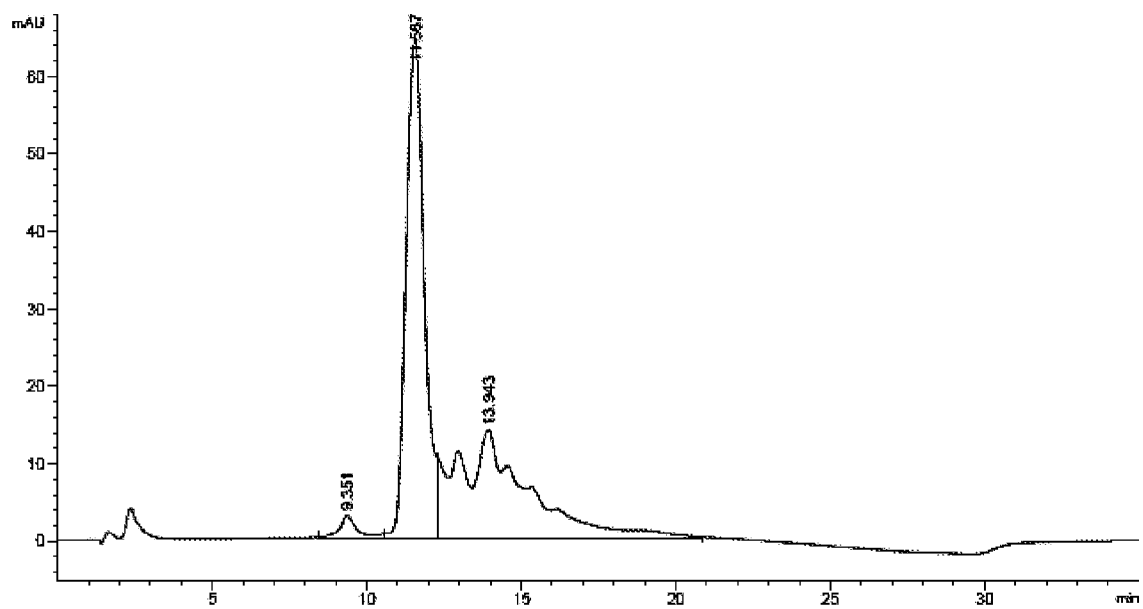
FIG. 22 is HIC map of TL042-T-ADC.

FIG. 1 was the HIC chromatogram of naked antibody (M141105Y). As shown in the figure, the naked antibody had a retention time of about 8.00 min. FIGS. 2 to 11 were HIC chromatograms of TL004-T-ADC, TL006-T-ADC, TL007-T-ADC, TL008-T-ADC, TL009-T-ADC, TL010-T-ADC, TL011-T-ADC, TL012-T-ADC, TL007-S-ADC, TL008-S-ADCHIC, respectively. FIG. 22 was HIC chromatograms of TL042-T-ADC. The overall analysis of FIGS. 2 to 11 and FIG. 22 showed that there was less residual naked antibody in the coupled system, and several conjugate peaks appeared after the naked antibody peak, which proved a high efficient coupling between the small molecule and the antibody. By calculation, the coupling ratio (DAR, i.e., the molar ratio of small molecule to antibody in ADC) was various, and the DAR was between 1-4.

Example 49 Determination of Molecular Weight

Molecular weight was determined after enrichment of the fraction with the highest peak concentration in the HIC map.

Determination Conditions:

Liquid chromatography column: ACQUITU UPLC® Protein BEH C4 1.7 μm 2.1 mm×100 mm

Mobile phase A: 0.1% FA/98% $H_2O$/2% ACN

Mobile phase B: 0.1% FA/2% $H_2O$/98% ACN

Flow rate: 0.25 ml/min

Sample chamber temperature: 8° C.

|  | Time (min) | | | | |
| --- | --- | --- | --- | --- | --- |
|  | 1 | 7 | 8 | 9 | 13 |
| Mobile phase A (V %) | 90 | 20 | 20 | 90 | 90 |
| Mobile phase B (V %) | 10 | 80 | 80 | 10 | 10 |

Mass spectrometry: Triple TOF 5600+

GS1 60; GS2 60; CUR30; TEM600; ISVF5000; DP300; CE10 m/z600-5000

The results were given as follows:

For TL007-T-ADC, the theoretical molecular weight of ADC was calculated based on the molecular weights of the naked antibody and of the toxin-linker as follows:

|  | ADC-DAR1 | |
| --- | --- | --- |
| Glycoform | Theoretical value | Measured value |
| G0F/G0F | 149371.5 | 149373.8 |
| G0F/G1F | 149533.6 | 149532.4 |
| G0F/G2F | 149695.8 | Not detected |

In the table, ADC-DAR1 represents a conjugate comprising one toxin and one antibody, ADC-DAR2 represents a conjugate comprising two toxins and one antibody, and the glycoform represents the oligosaccharides on two heavy chains, G0F: fucosylated without galactose, G1F: fucosylated monogalactose, G2F: fucosylated digalactose.

Figure 12:
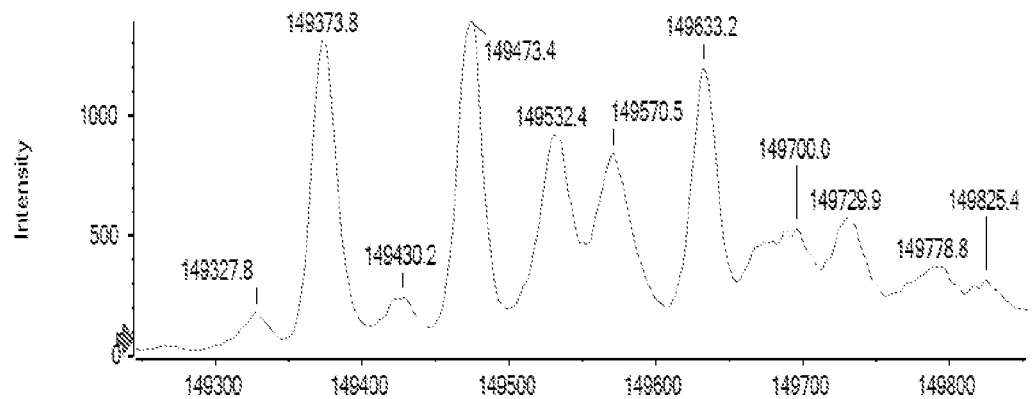
FIG. 12 is mass spectrometry test result of BT001063, which shows the molecular weight of the component corresponding to Peak2 of the HIC map of TL007-T-ADC.

The molecular weight measurement result of the component corresponding to Peak2 (RT13.092) of the HIC chromatogram (FIG. 4) was shown in FIG. 12, and, by comparing with the theoretical molecular weight, it was confirmed that the peak corresponded to BT001063.

For TL008-T-ADC, the theoretical molecular weight of ADC was calculated based on the molecular weights of the naked antibody and of the toxin-linker as follows:

|  | ADC-DAR1 | | ADC-DAR2 | |
| --- | --- | --- | --- | --- |
| Glycoform | Theoretical value | Measured value | Theoretical value | Measured value |
| G0F/G0F | 149411.5 | 149412.8 | 150765.1 | 150767.1 |
| G0F/G1F | 149573.6 | Not detected | 150927.3 | Not detected |
| G0F/G2F | 149735.8 | Not detected | 151089.4 | Not detected |

Figure 13:
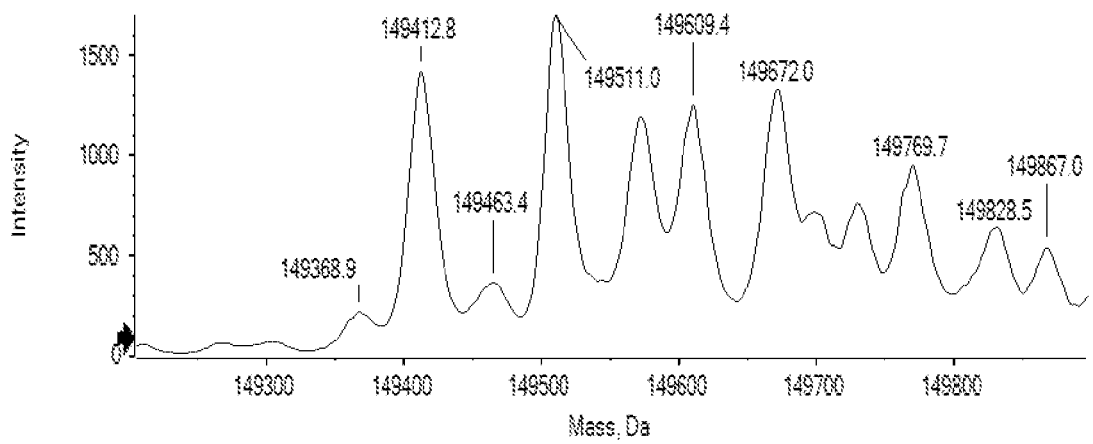
FIG. 13 is mass spectrometry test result of BT001064, which shows the molecular weight of the component corresponding to Peak2 of the HIC map of TL008-T-ADC.

The molecular weight measurement result of the component corresponding to Peak2 (RT13.830) of the HIC chromatogram (FIG. 5) was shown in FIG. 13, and, by comparing with the theoretical molecular weight, it was confirmed that the peak corresponded to ADC-DAR1, i.e., BT001064.

Figure 14:
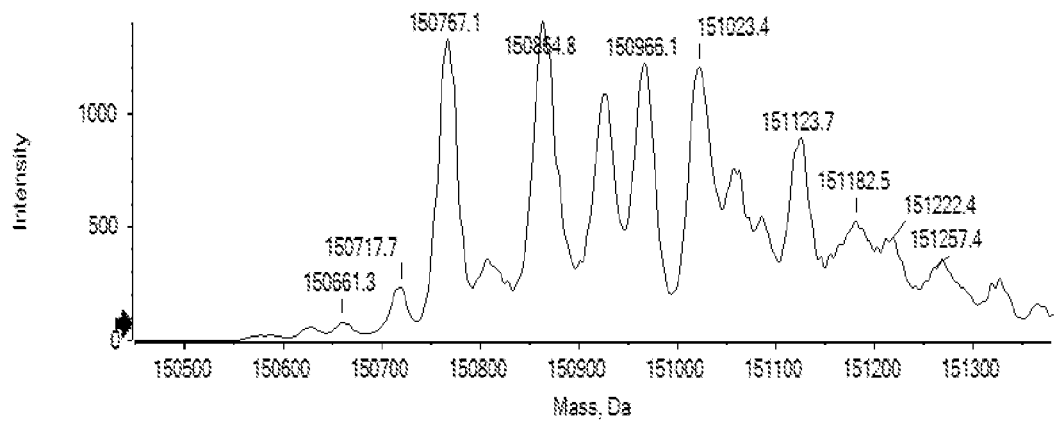
FIG. 14 is mass spectrometry test result of BT001007, which shows the molecular weight of the component corresponding to Peak3 of the HIC map of TL008-T-ADC.

The molecular weight measurement result of the component corresponding to Peak3 (RT18.753) of the HIC chromatogram was shown in FIG. 14, and, by comparing with the theoretical molecular weight, it was confirmed that the peak corresponded to ADC-DAR2, i.e., BT001007.

For TL009-T-ADC, the theoretical molecular weight of ADC was calculated based on the molecular weights of the naked antibody and of the toxin-linker as follows:

|  | ADC-DAR2 | |
| --- | --- | --- |
| Glycoform | Theoretical value | Measured value |
| G0F/G0F | 150805.3 | 150806.7 |
| G0F/G1F | 150967.4 | 150966.7 |
| G0F/G2F | 151129.6 | 151129.4 |

Figure 15:
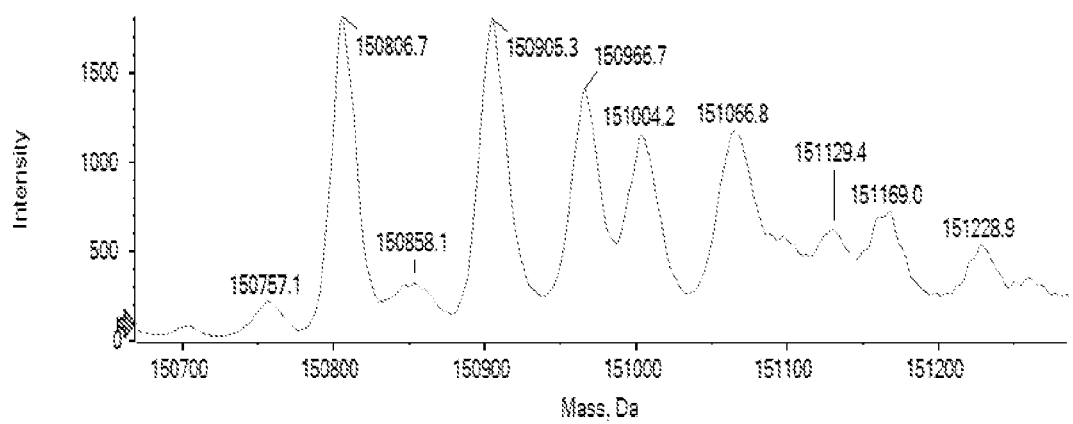
FIG. 15 is mass spectrometry test result of BT001008, which shows the molecular weight of the component corresponding to Peak3 of the HIC map of TL009-T-ADC.

The molecular weight measurement result of the component corresponding to Peak3 (RT17.289) of the HIC chromatogram (FIG. 6) was shown in FIG. 15, and, by comparing with the theoretical molecular weight, it was confirmed that the peak corresponded to ADC-DAR2, i.e., BT001008.

For TL010-T-ADC, the theoretical molecular weight of ADC was calculated based on the molecular weights of the naked antibody and of the toxin-linker as follows:

|  | ADC-DAR2 | | ADC-DAR3 | |
| --- | --- | --- | --- | --- |
| Glycoform | Theoretical value | Measured value | Theoretical value | Measured value |
| G0F/G0F | 150893.4 | 150896.1 | 152311.2 | 152314.0 |
| G0F/G1F | 151055.5 | 151052.7 | 152473.3 | 152473.1 |
| G0F/G2F | 151217.7 | Not detected | 152635.4 | Not detected |

Figure 16:
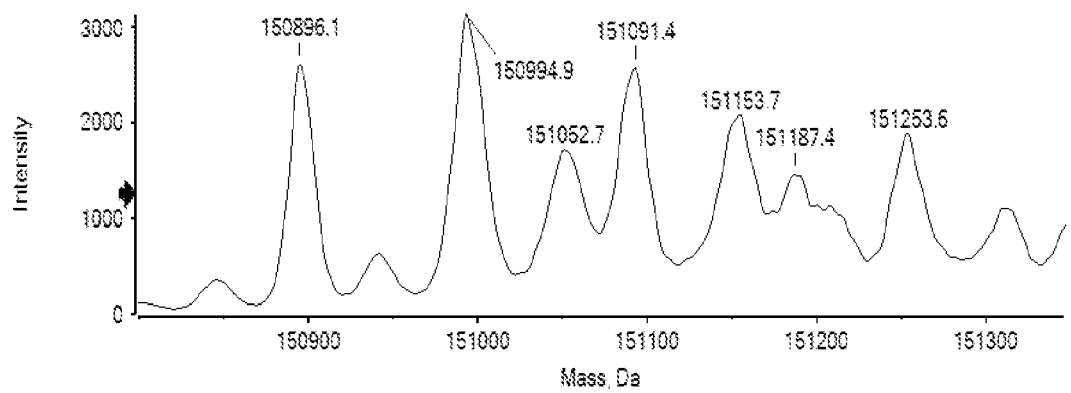
FIG. 16 is mass spectrometry test result of BT001009, which shows the molecular weight of the component corresponding to Peak3 of the HIC map of TL010-T-ADC.

The molecular weight measurement result of the component corresponding to Peak3 (RT17.194) of the HIC chromatogram (FIG. 7) was shown in FIG. 16, and, by comparing with the theoretical molecular weight, it was confirmed that the peak corresponded to ADC-DAR2, i.e., BT001009.

Figure 17:
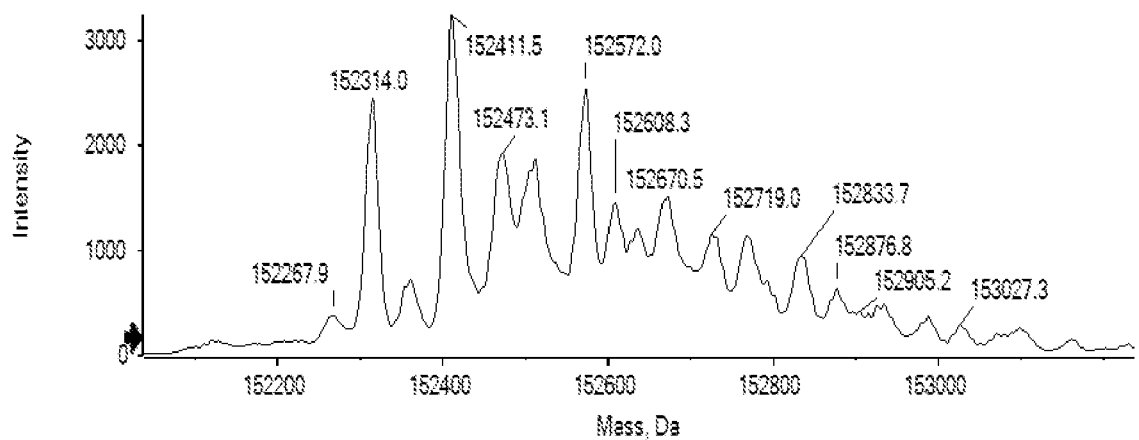
FIG. 17 is mass spectrometry test result of BT001086, which shows the molecular weight of the component corresponding to Peak4 of the HIC map of TL010-T-ADC.

The molecular weight measurement result of the component corresponding to Peak4 (RT19.573 and 19.979) of the HIC chromatogram was shown in FIG. 17, and, by comparing with the theoretical molecular weight, it was confirmed that the peak corresponded to ADC-DAR3, i.e., BT001086.

For TL033-T-ADC, the theoretical molecular weights of ADC-DAR1, ADC-DAR2 after coupling calculated based on the molecular weights of the naked antibody and of the toxin-linker and the measured molecular weights were as follows:

|  | Naked antibody | ADC-DAR1 | | ADC-DAR2 | |
|---|---|---|---|---|---|
| Glycoform | Theoretical value (Da) | Theoretical value (Da) | Measured value (Da) | Theoretical value (Da) | Measured value (Da) |
| G0F/G0F | 148057.8 | 149358.6 | 149359.5 | 150661.1 | 150658.5 |
| G0F/G1F | 148220.0 | 149520.7 | 149518.8 | 150823.3 | 150821.6 |
| G0F/G2F | 148382.1 | 149682.8 | 149680.9 | 150985.4 | 150984.2 |

Figure 18:
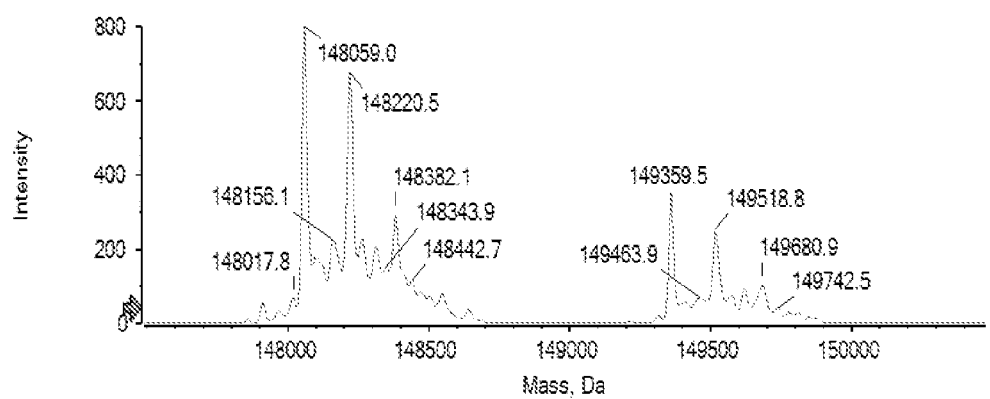
FIG. 18 is mass spectrometry test result of BT001071.
Figure 21:
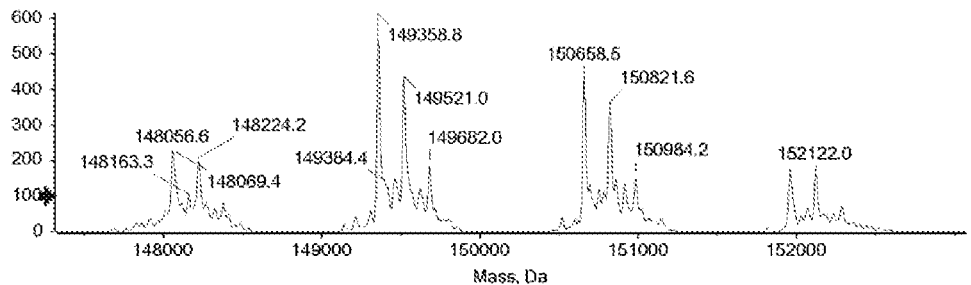
FIG. 21 is mass spectrometry test result of BT001020.

According to mass spectrometry, the measured values matched the theoretical values (as shown in FIGS. 18 and 21), indicating successful coupling, wherein ADC-DAR1 was BT001071, ADC-DAR2 was BT001020.

For TL042-T-ADC, the theoretical molecular weight of ADC was calculated based on the molecular weights of the naked antibody and of the toxin-linker as follows:

|  | ADC-DAR1 | | ADC-DAR2 | |
|---|---|---|---|---|
| Glycoform | Theoretical value | Measured value | Theoretical value | Measured value |
| G0F/G0F | 149321.4 | Not detected | 150584.9 | 150584.9 |
| G0F/G1F | 149485.5 | Not detected | 150747.0 | 150748.2 |
| G0F/G2F | 149645.7 | Not detected | 150909.2 | 150908.8 |

Figure 23:
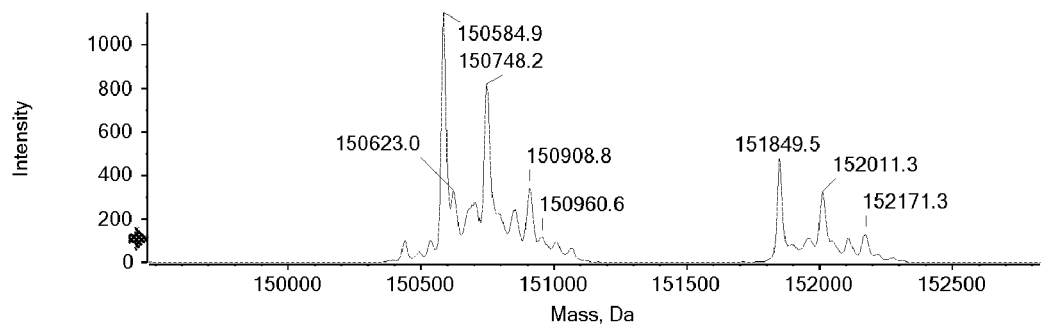
FIG. 23 is mass spectrometry test result of BT001019.

The molecular weight measurement result of the component corresponding to Peak1 (RT11.567) of the HIC chromatogram (FIG. 22) was shown in FIG. 23, and, by comparing with the theoretical molecular weight, it was confirmed that the peak corresponded to ADC-DAR2, i.e., BT001019.

For TL007-S-ADC, the theoretical molecular weight of ADC was calculated based on the molecular weights of the naked antibody and of the toxin-linker as follows:

|  | ADC-DAR1 | | ADC-DAR2 | |
|---|---|---|---|---|
| Glycoform | Theoretical value | Measured value | Theoretical value | Measured value |
| G0F/G0F | 149443.7 | Not detected | 150757.3 | 150762.0 |
| G0F/G1F | 149605.8 | Not detected | 150919.5 | 150923.5 |
| G0F/G2F | 149768.0 | Not detected | 151081.6 | Not detected |

Figure 24:
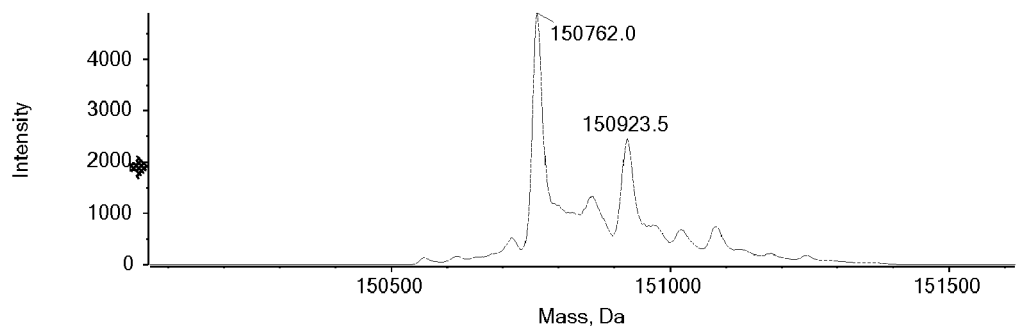
FIG. 24 is mass spectrometry test result of BT001014.

The molecular weight measurement result of the component corresponding to Peak3 (RT19.269) of the HIC chromatogram (FIG. 10) was shown in FIG. 24, and, by comparing with the theoretical molecular weight, it was confirmed that the peak corresponded to ADC-DAR2, i.e., BT001014.

For TL008-S-ADC, the theoretical molecular weight of ADC was calculated based on the molecular weights of the naked antibody and of the toxin-linker as follows:

|  | ADC-DAR1 | | ADC-DAR2 | |
|---|---|---|---|---|
| Glycoform | Theoretical value | Measured value | Theoretical value | Measured value |
| G0F/G0F | 149483.7 | Not detected | 150837.3 | 150840.4 |
| G0F/G1F | 149645.8 | Not detected | 150999.5 | 151001.7 |
| G0F/G2F | 149807.9 | Not detected | 151161.6 | Not detected |

Figure 25:
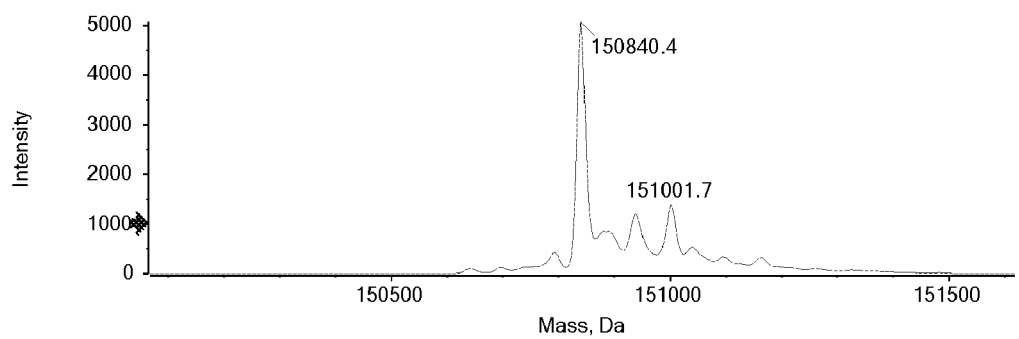
FIG. 25 is mass spectrometry test result of BT001015.

The molecular weight measurement result of the component corresponding to Peak3 (RT19.811) of the HIC chromatogram (FIG. 11) was shown in FIG. 25, and, by comparing with the theoretical molecular weight, it was confirmed that the peak corresponded to ADC-DAR2, i.e., BT001015.

Using the analytical method similar to that of TL007-T-ADC, the following results were obtained:

For TL011-T-ADC, BT001067 was an ADC molecule with DAR value equal to 1, BT001010 was an ADC molecule with DAR value equal to 2.

For TL012-T-ADC, BT001068 was an ADC molecule with DAR value equal to 1, BT001011 was an ADC molecule with DAR value equal to 2.

For TL030-T-ADC, BT001072 was an ADC molecule with DAR value equal to 1, BT001012 was an ADC molecule with DAR value equal to 2.

For TL031-T-ADC, BT001073 was an ADC molecule with DAR value equal to 1, BT001013 was an ADC molecule with DAR value equal to 2.

For TL035-T-ADC, BT001074 was an ADC molecule with DAR value equal to 1, BT001016 was an ADC molecule with DAR value equal to 2.

For TL034-T-ADC, BT001075 was an ADC molecule with DAR value equal to 1, BT001017 was an ADC molecule with DAR value equal to 2.

For TL059-T-ADC, BT001078 was an ADC molecule with DAR value equal to 1, BT001021 was an ADC molecule with DAR value equal to 2.

Example 50 Detection of Release of Small Molecule Toxins

In this example, the release of small molecule toxin in the conjugate was verified by cleavage of TL002 with protease in lysosome in vitro Experimental procedure: An appropriate amount of TL002 was co-incubated with cathepsin B at 37° C.; a blank with no enzyme was provided under the same conditions; and RP-HPLC-MS analysis was performed after a certain time. The detection found that two new peaks (TM1, TM2) appeared in the TIC analysis compared to the blank, the retention time of TM1 was 5.9 min, and the retention time of TM2 was 7.9 min. As detected by mass spectrometry, the TIC peak of TM1 was a fragment with a molecular weight of 513.28; the TIC peak of TM2 was a fragment with a molecular weight of 863.59.

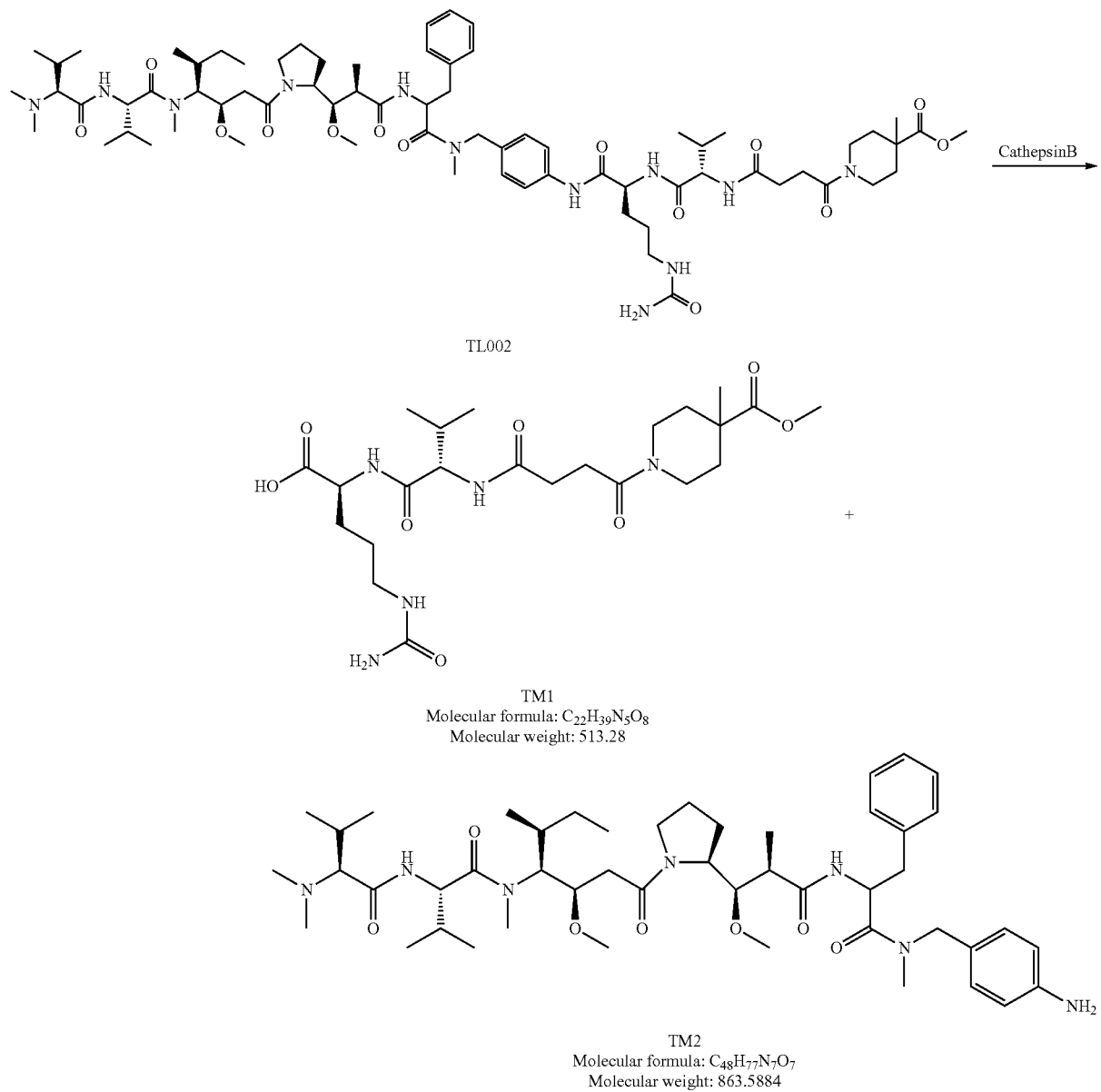

The experiment showed that, under the action of proteases in lysosome, the conjugate of the present invention could release small molecule toxins smoothly, thereby producing biological effects Example 51 Test of the Inhibitory Effect of Small Molecule Toxins on Cell Activity In Vitro First, tumor cells MDA-MB-468 and NCI-H322M were cultured; the small molecule toxins of the present invention, maytansin derivative (DM1, Nanjing Lianning), monomethyl auristatin F (MMAF, Nanjing Lianning) were co-cultured respectively with the tumor cells. Then, CCK8 reagent (Dongren Chemical Technology Co., Ltd.) was added, followed by detection with the microplate reader (manufacturer: Molecular Devices, model: SpectraMax M2) (wavelength: 450 nm). The activity of dehydrogenase in mitochondria was detected, to evaluate the inhibitory effect of small molecule toxins on cell proliferation.

Specific steps were as follows:

Tumor cell culture: the source of tumor cells and the corresponding medium components were listed in Table 1.

TABLE 1

| Cell name | Tumor type | Source | Medium components |
|---|---|---|---|
| MDA-MB-468 | Breast cancer | Concortis | DMEM/F12 + 10% FBS |
| NCI-H322M | Non-small cell lung cancer | Concortis | RPMI1640 + 10% FBS |

Test of cell activity in vitro: toxins were diluted (10 concentration gradients) with the corresponding test medium (containing 2% FBS). Tumor cells were trypsinized by a conventional method using trypsin, and cells were collected by tube and resuspended in the corresponding test medium (containing 2% FBS). The diluted toxins were added to a 96-well plate, to which were added the cells.

Thereafter, 20 μL of CCK8 reagent was added to each well, and reaction was carried out for 4 hours, followed by detection with the microplate reader (wavelength: 450 nm). The experimental conditions and test results were listed in Tables 2 and 3.

TABLE 2

| Cell name | Small molecule toxin | Concentration gradient | $EC_{50}$(nM) |
|---|---|---|---|
| NCI-H322M (5000 cells/well, 3 days) | maytansin derivative (DM1) | starting at 20000 nM, 5-fold dilution | 38.84 |
|  | monomethyl auristatin F (MMAF) | starting at 20000 nM, 5-fold dilution | 117.6 |
|  | T001 | starting at 20000 nM, 5-fold dilution | 2.003 |
| MDA-MB-468 (7500 cells/well, 4 days) | maytansin derivative (DM1) | starting at 10000 nM, 3-fold dilution | 7.611 |
|  | monomethyl auristatin F (MMAF) | starting at 10000 nM, 3-fold dilution | 98.44 |
|  | T001 | starting at 500 nM, 3-fold dilution | 0.538 |

TABLE 3

| Cell name | Toxin name | Concentration gradient | $EC_{50}$(nM) |
|---|---|---|---|
| MDA-MB-468 (7500 cells/well, 4 days) | T001 | starting at 10 nM, 2-fold dilution | 1.126 |
|  | T002 |  | >10 |
|  | T003 |  | 3.2 |
|  | T011 |  | 0.211 |
|  | T012 |  | 1.621 |
|  | T013 |  | 0.414 |
|  | T014 |  | 1.240 |
|  | T015 |  | 7.428 |
|  | T016 |  | 5.714 |
|  | T017 |  | 1.302 |
|  | T018 |  | 2.351 |
|  | T019 |  | 1.155 |

Example 52 Test of the Inhibitory Effect of Antibody-Drug Conjugates on Cell Activity In Vitro First, tumor cell HCC1954 was cultured in the medium RPMI1640+10% FBS. HCC1954 was a Her2-positive cell that had endocytosis to a conjugate (e.g., an anti-Her2 antibody trastuzumab drug conjugate). The conjugate was diluted with the corresponding test medium (containing 2% FBS) (starting at 1 μg/mL, 2-fold dilution, 10 concentration gradients), and the tumor cells were trypsinized by a conventional method using trypsin, and cells were collected by tube and resuspended in the corresponding test medium (containing 2% FBS). The diluted conjugate was added to a 96-well plate, and the resuspended cells were added to the corresponding wells containing the conjugate (10000 cells/well) and co-cultured for 3 days. Then, 20 μL of CCK8 reagent (Dongren Chemical Technology Co., Ltd.) was added to each well, and reaction was carried out for 1.5 hours, followed by detection with the microplate reader (manufacturer: Molecular Devices, model: SpectraMax M2) (wavelength: 450 nm). The activity of dehydrogenase in mitochondria was detected, to evaluate the inhibitory effect of antibody-drug conjugates on cell proliferation. According to WO2016123412, a conjugate T-ADC-19 was prepared by conjugating compound 19 therein with trastuzumab, and its activity was detected as a control.

The experimental results were shown in Table 4. According to the literature, T-DM1 (Kadcyla, a trastuzumab-DM1 conjugate, a marketed product) had an $EC_{50}$ of 43 ng/mL (Howard A. Burris III et al, Clinical Breast Cancer, Vol. 11, No. 5, 275-82), T-ADC-19 had an $EC_{50}$ of 20.5 ng/mL, while all the conjugates of the present invention were more potent in inhibiting cell proliferation than the above control.

TABLE 4

| ADC | $EC_{50}$(ng/mL) |
|---|---|
| T-ADC-19 | 20.5 |
| BT001005 | 10.7 |
| BT001006 | 10.8 |
| BT001007 | 14.5 |
| BT001008 | 7.4 |
| BT001009 | 7.8 |
| BT001010 | 6.3 |
| BT001011 | 8.9 |
| BT001020 | 13.5 |

The BT001014, BT001015 prepared in the present invention were co-cultured with the tumor cell BxPC-3 (ATCC, pancreatic cancer, medium: RPMI1640+10% FBS). Then, CCK8 reagent (Dongren Chemical Technology Co., Ltd.) was added, followed by detection with the microplate reader (manufacturer: Molecular Devices, model: SpectraMax M2) (wavelength: 450 nm). The activity of dehydrogenase in mitochondria was detected, to evaluate the inhibitory effect of antibodies on cell proliferation.

Specific steps were as follows:

The conjugates of the invention were diluted with the corresponding test medium (containing 2% FBS) (starting at 10 ug/mL, 3-fold dilution, 12 concentration gradients). The above tumor cells were trypsinized by a conventional method using trypsin, and cells were collected by tube and resuspended in the corresponding test medium (containing 2% FBS). The diluted conjugate was added to a 96-well plate, and the resuspended cells were added to the corresponding wells containing the conjugate (5000 cells/well) and co-cultured for 3 days. Then, 20 μL of CCK8 reagent was added to each well, and reaction was carried out for 4 hours, followed by detection with the microplate reader (wavelength: 450 nm). According to WO2016123412, a conjugate S-ADC-19 was prepared by conjugating compound 19 therein with Anti-Trop2 antibody sacituzumab, and its activity was detected as a control.

Experimental Results:

| Name | $EC_{50}$(ng/mL) |
|---|---|
| BT001014 | 5.7 |
| BT001015 | 10.4 |
| S-ADC-19 | 16.0 |

Figure 19:
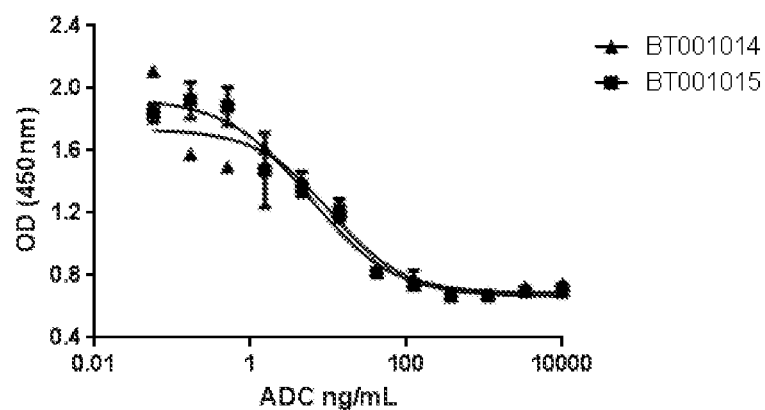
FIG. 19 is an inhibition curve of BT001014, BT001015 against tumor cell BxPC-3.

Inhibition curves of BT001014 and BT001015 against tumor cell BxPC-3 were shown in FIG. 19. As could be seen from the figure, the conjugates of the present invention had inhibitory activity against pancreatic cancer cells, and there was a good dose-effect relationship. The toxin and linker of the present invention had tumor inhibitory activity superior to those of the prior art.

Example 53 Activity Test In Vivo

In the present example, the inhibitory effect of the conjugate of the present invention on tumor proliferation of a mouse subcutaneously transplanted with human tumor cells was evaluated, and the safety of the conjugate of the present invention when used in vivo was evaluated. Specifically, in the present example, the conjugate was administered to a mouse subcutaneously transplanted human breast cancer cell line JIMT-1 by a single tail vein injection, and the tumor volume was detected to characterize the efficacy (anti-tumor effect) of the conjugate on the tumor-bearing mouse.

Experiment Procedure:

Construction of a JIMT-1 Tumor-Bearing Mouse Model

Each of the mice was inoculated subcutaneously in the right scapula with $5\times10^6$ JIMT-1 tumor cells (suspended in 0.1 ml PBS). Mice with too small (less than 100 mm$^3$) or too large (greater than 200 mm$^3$) tumor volume were excluded when the tumor growth range was 100-200 mm$^3$ after 7-10 days of inoculation.

Efficacy Test In Vivo

An appropriate amount of the conjugates of the present invention (BT001006, BT001007, BT001009) was weighed, formulated into a stock solution of a certain concentration with sterile ultrapure water, gently shaken, and then dispensed and stored at −80° C. At the time of use, it was diluted with physiological saline according to the dose to obtain a treatment solution, and the same concentration of physiological saline was used as a solvent control.

The tumor-bearing mice with a tumor volume of 100-200 mm$^3$ were randomly grouped, 7/group (the number of groups was determined according to the number of samples). The dose was 3 mg/kg. The route of administration was a single tail vein injection. Observed for 4 weeks after the administration, the tumor diameter was measured with a vernier caliper every 4 days, and the tumor volume was calculated according to the following formula: $V=0.5\,a^2\times b$, wherein a and b represent the long and short diameters of the tumor, respectively. Animal deaths were recorded daily.

Figure 20:
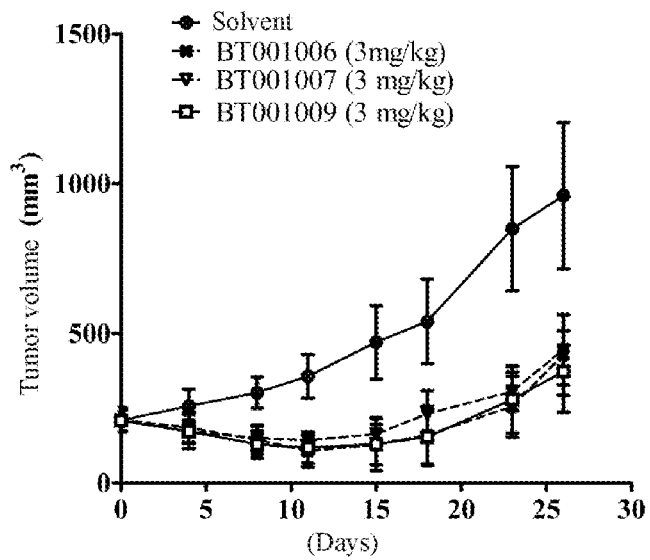
FIG. 20 is a curve of tumor volume over time in Example 53.

Curves of tumor volume over time was shown in FIG. 20. As could be seen from FIG. 20, the conjugates BT001006, BT001007 and BT001009 of the present invention had significant inhibitory activity against breast cancer during the evaluation period. During the evaluation period, in the administered group (3 mg/kg), the anti-tumor effect was significant, the body weight of the animals tended to increase, no death occurred, and the tolerance was good during the administration. After a single administration, the anti-tumor effect could last up to 23 days, indicating that the conjugates of the invention were relatively stable in the peripheral blood circulation of the animals.

Although the specific embodiments of the present invention have been described in detail, those skilled in the art will understand that various modifications and changes to the details can be made according to all the instructions already disclosed, and that these changes are all within the scope of protection of the present invention. The entire scope of the present invention is given by the appended claims and any equivalents thereof.

The invention claimed is:
1. A compound, or a pharmaceutically acceptable salt, solvate, hydrate, isomer thereof, or crystalline form or racemate thereof, wherein the compound has the structure of formula (II):

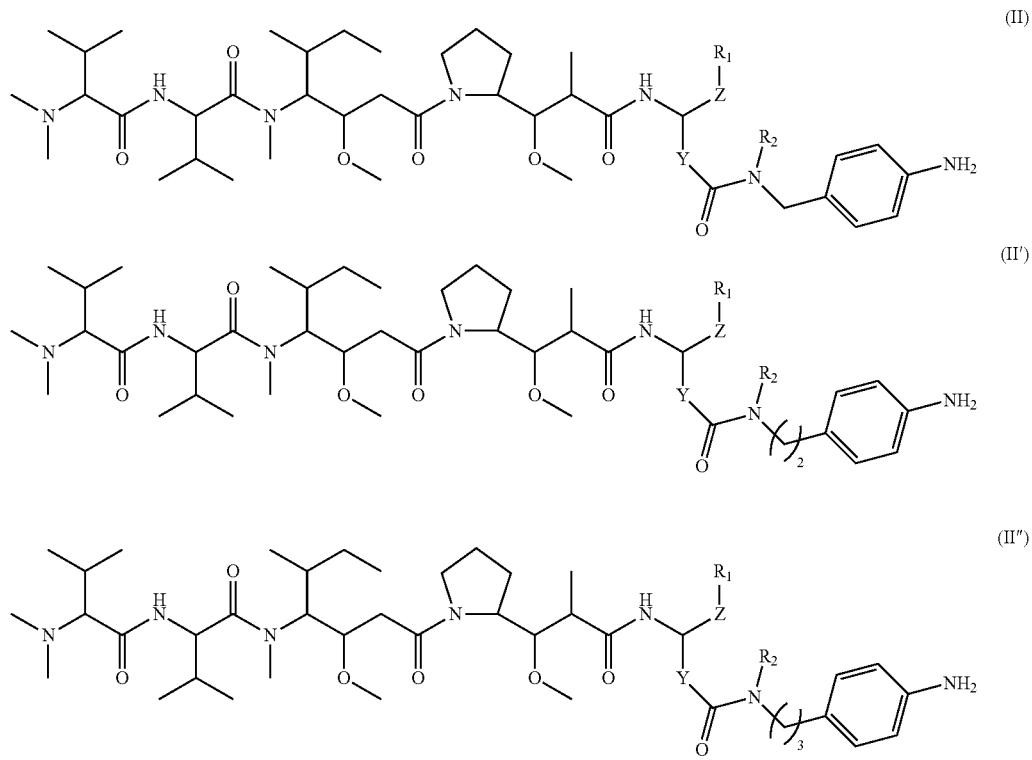

wherein:

Y is absent, or is methylene;

Z is absent, or is methylene or ethylene;

$R_1$ is selected from hydrogen, deuterium, $N_3$, CN, methyl, ethyl, propyl, isopropyl, cyclopropyl, ethynyl, methylsulfonyl, phenyl, p-hydroxyphenyl, p-(methylsulfonyl)phenyl

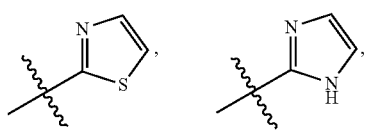 [SMILES: *c1nccs1 ; *c1ncc[nH]1]

oxazolyl, isoxazolyl, pyrazolyl, pyridyl, imidazolyl, pyridazinyl, morpholinyl optionally substituted by =O, piperazinyl optionally substituted by =O and/or C$_{1-6}$ alkyl, and thiomorpholinyl optionally substituted by =O;

R$_2$ is hydrogen, deuterium or methyl.

2. The compound of claim 1, or a pharmaceutically acceptable salt, solvate, hydrate, isomer thereof, or crystalline form or racemate thereof, wherein the compound is selected from:

T001
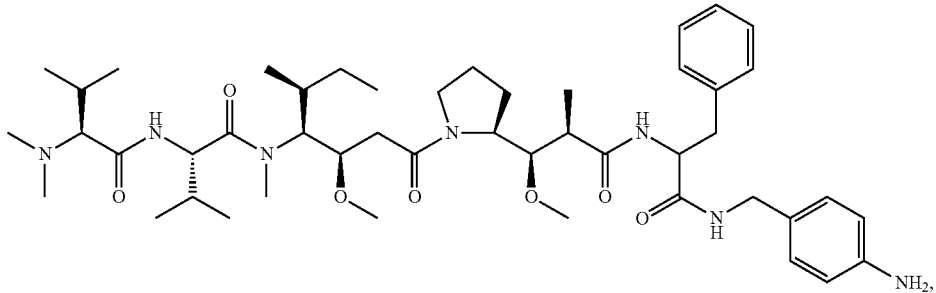

T002
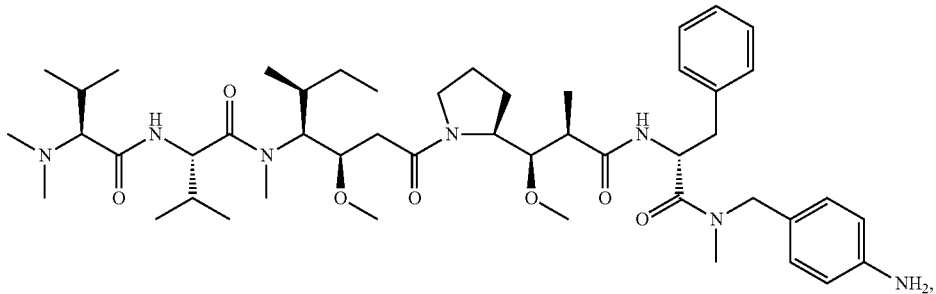

T003
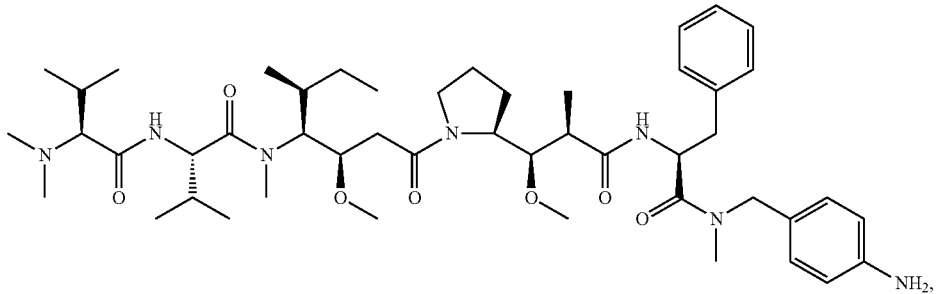

T004
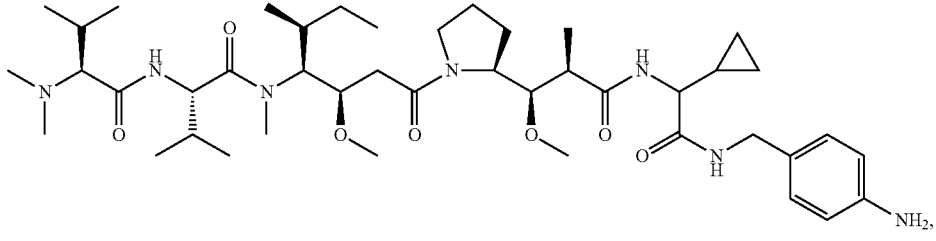

T005
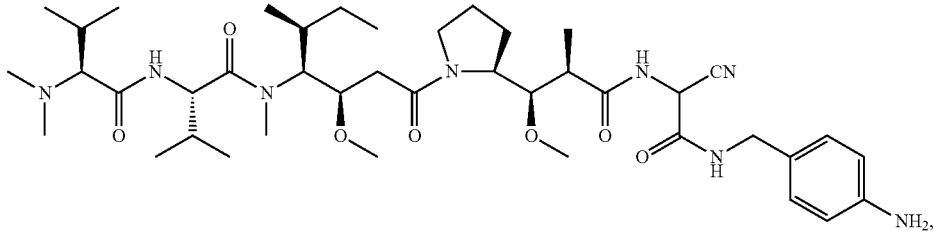

-continued
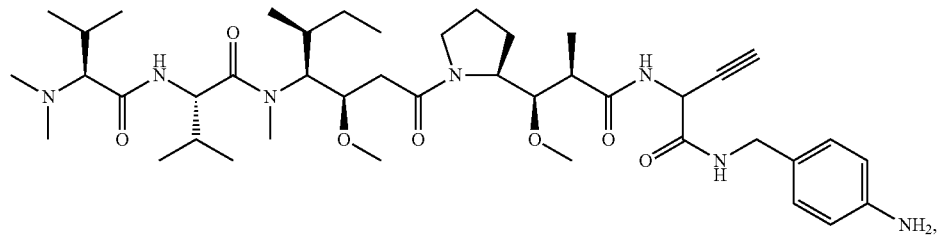
T006
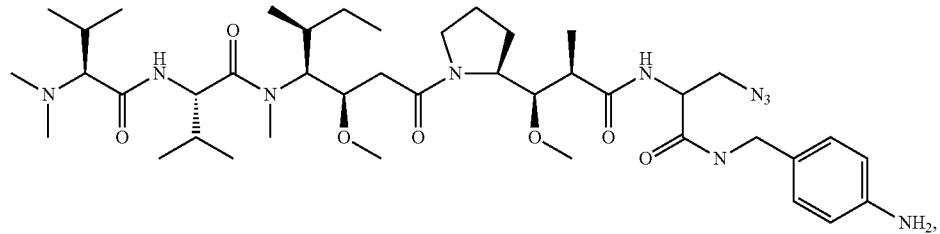
T007
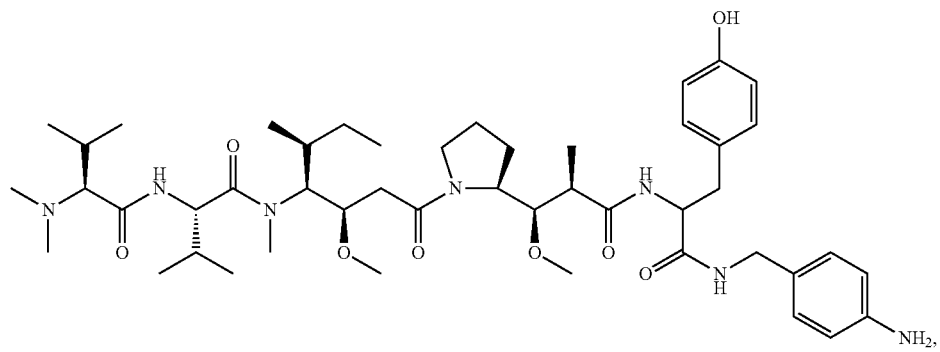
T008
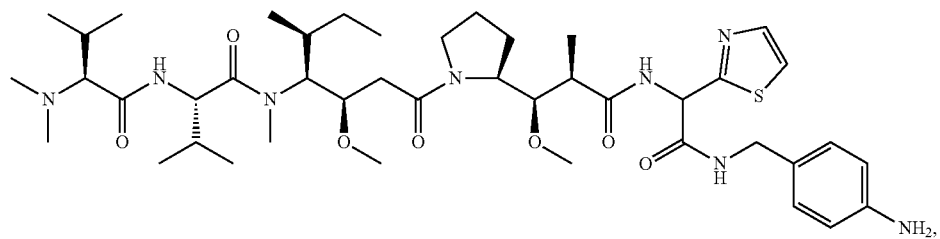
T009
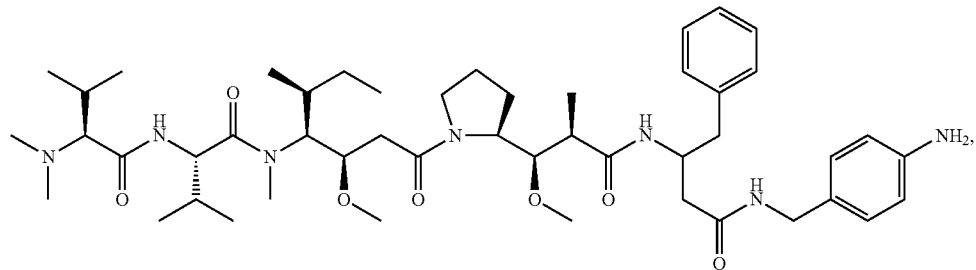
T010

T011
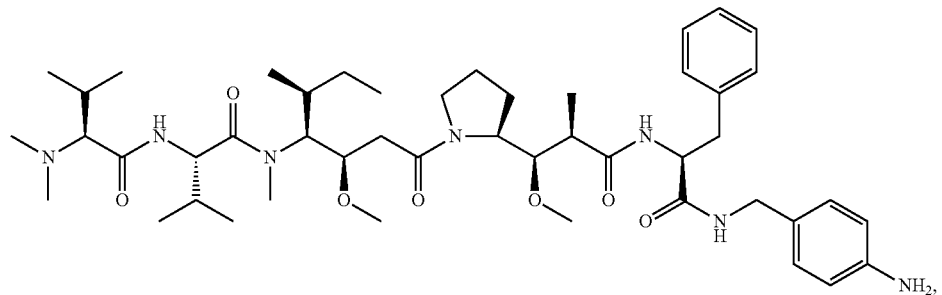
T012
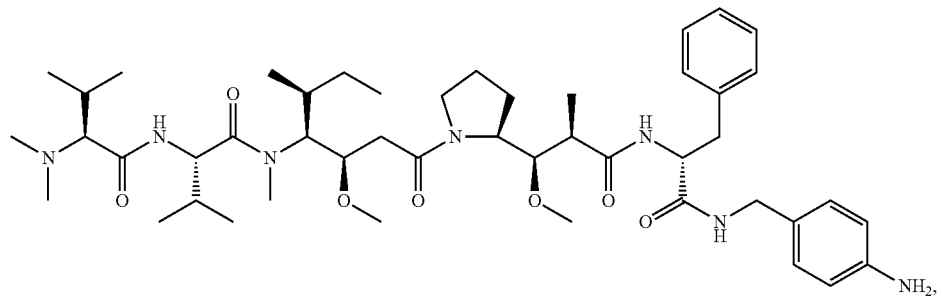
T013
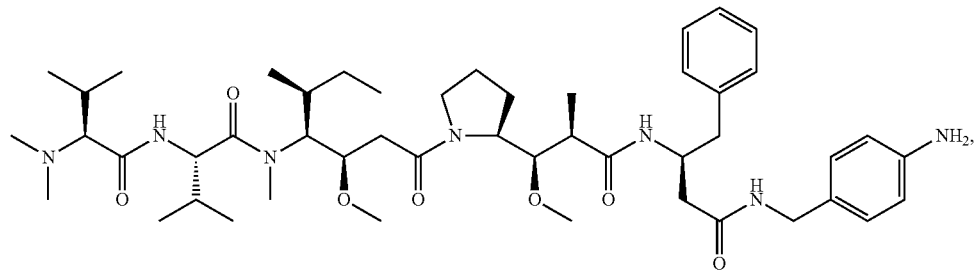
T014
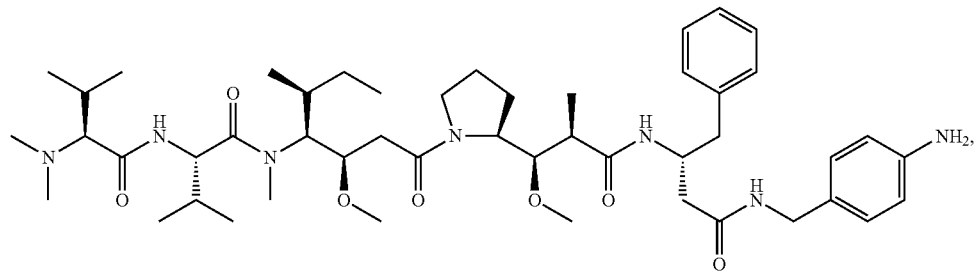
T015
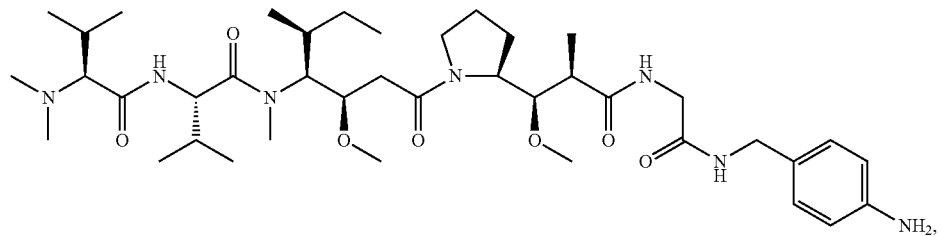

-continued
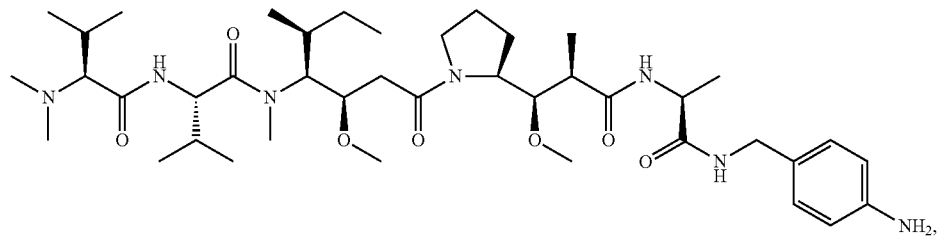
T016
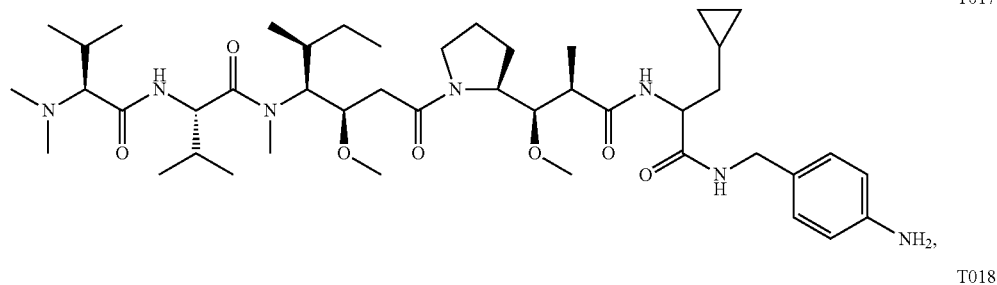
T017
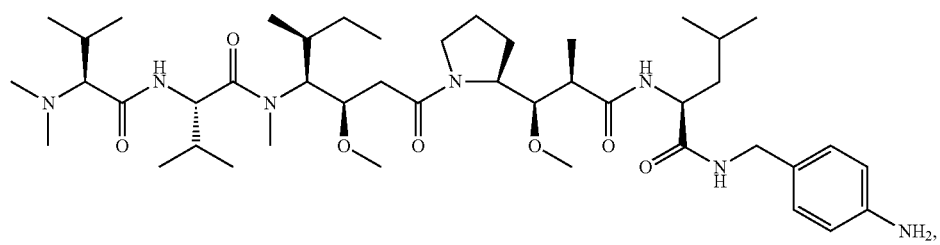
T018
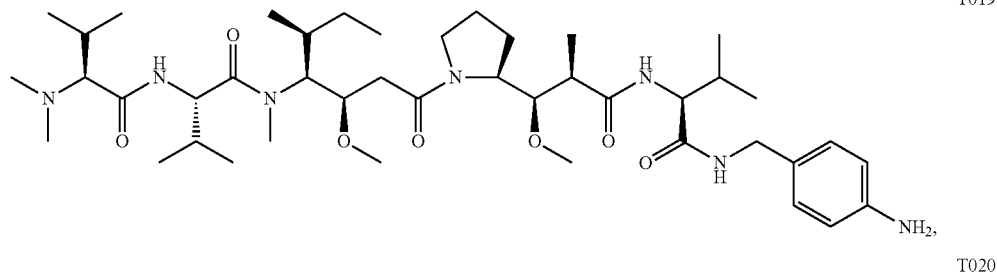
T019
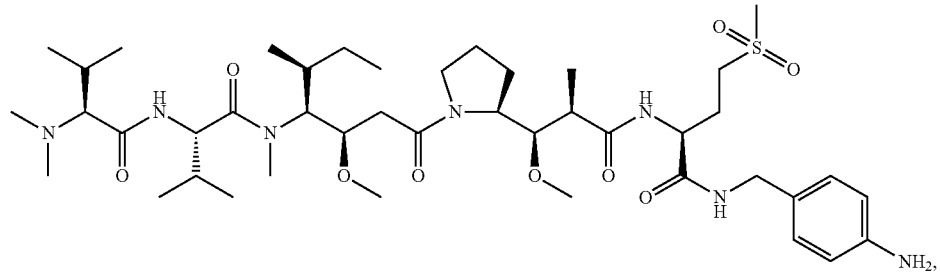
T020
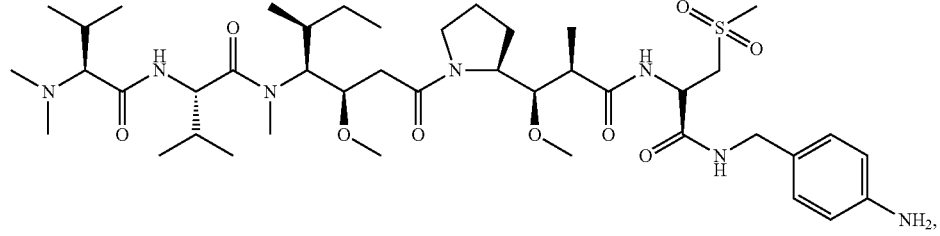
T021

-continued
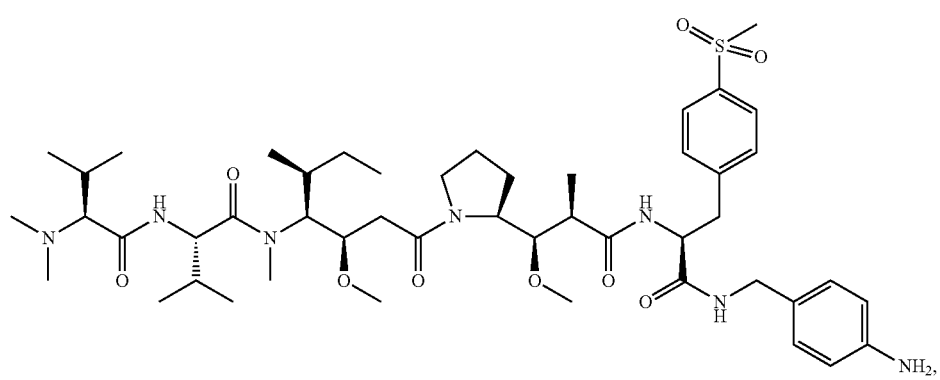
T022
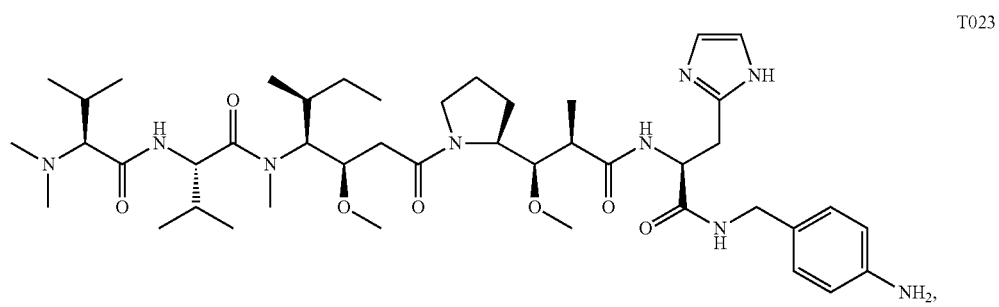
T023
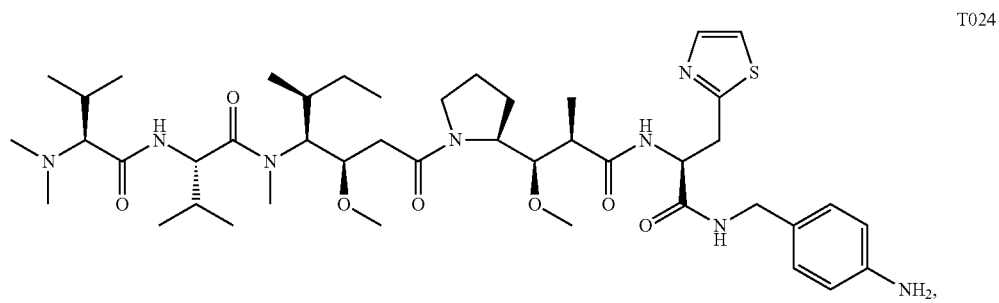
T024
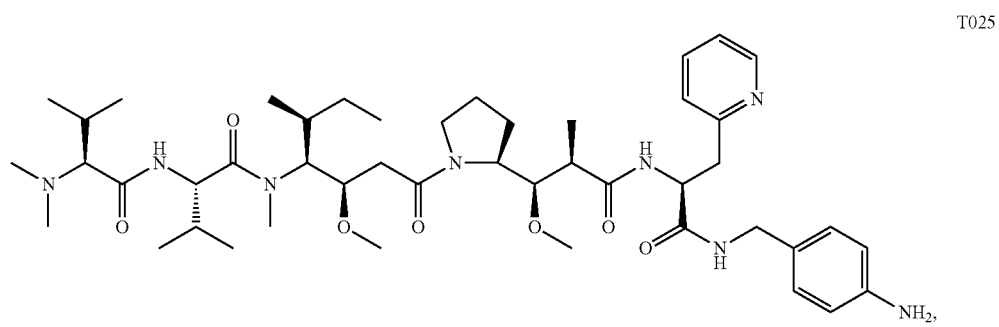
T025
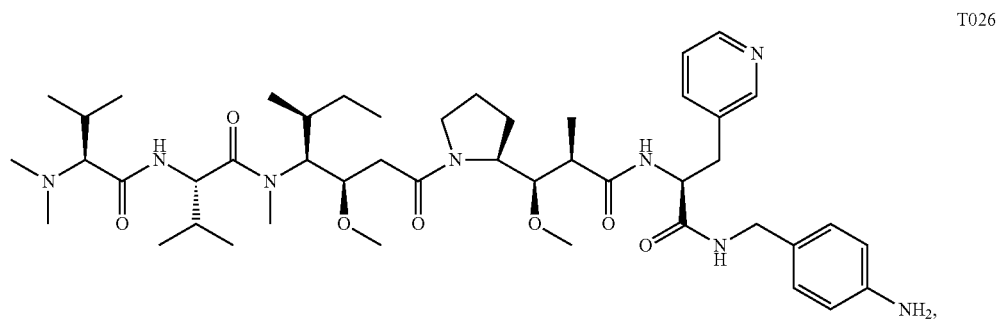
T026

T027
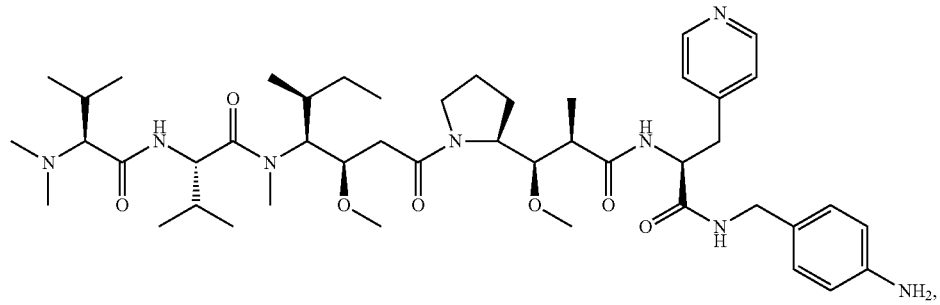
T028
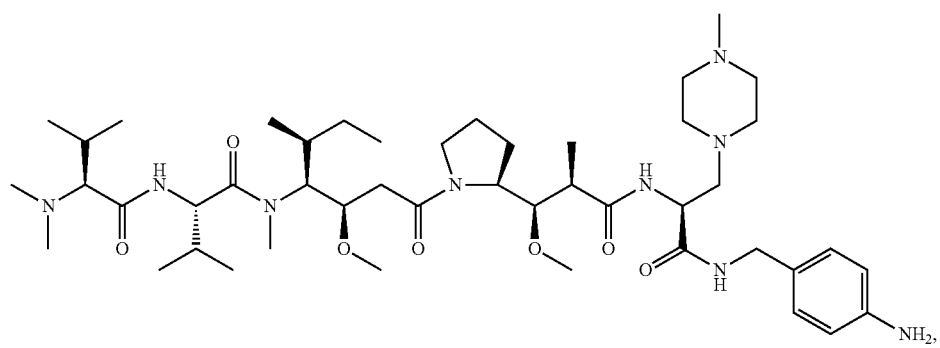
T029
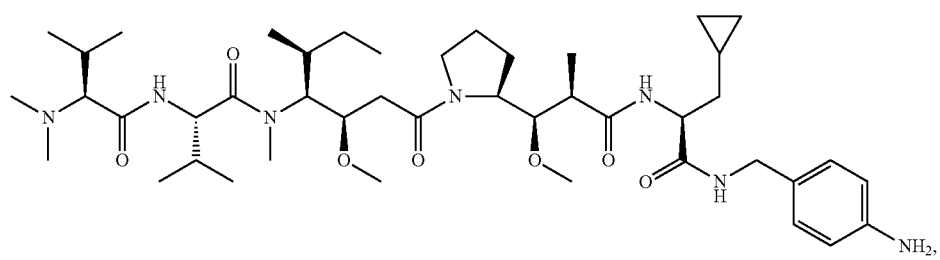
T030
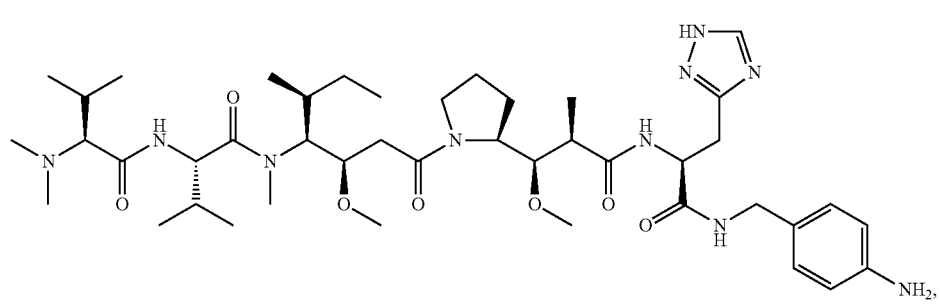
T031
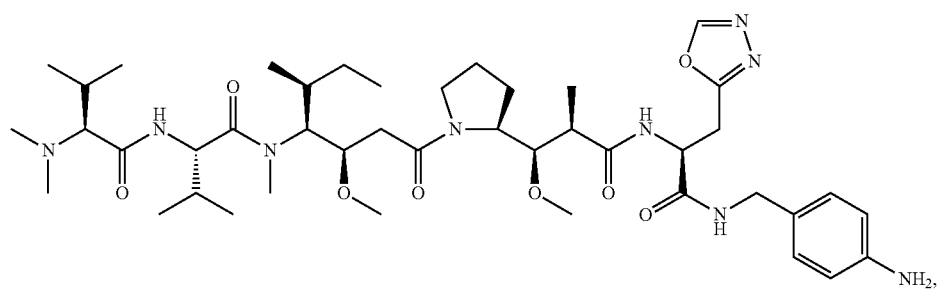

-continued
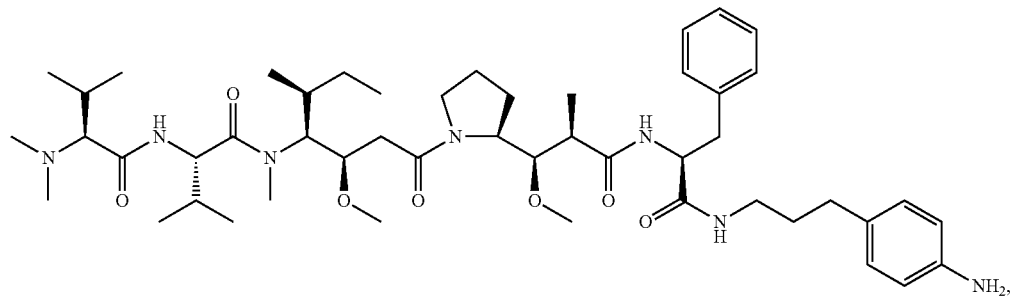
T032
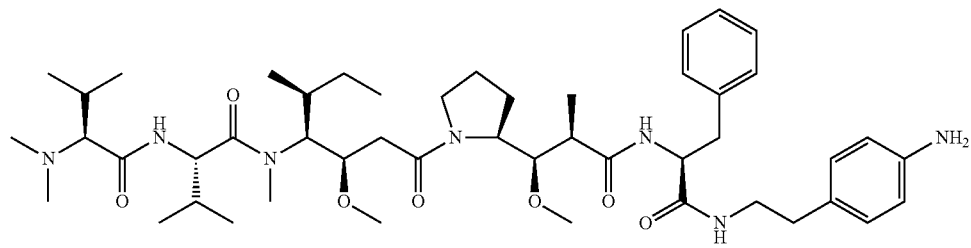
T033
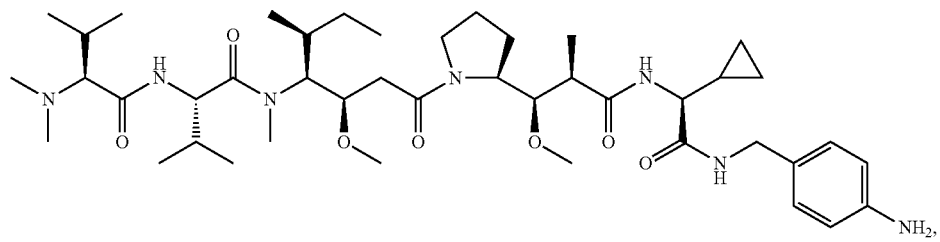
T034
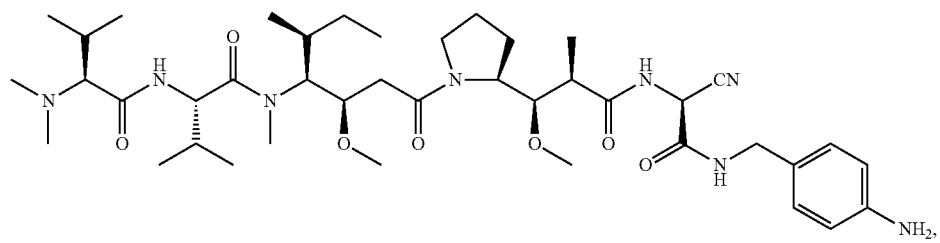
T035
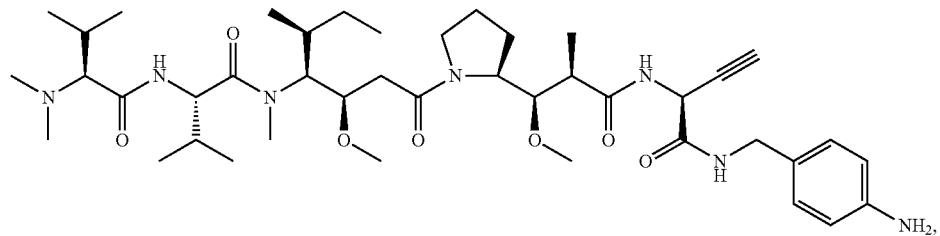
T036
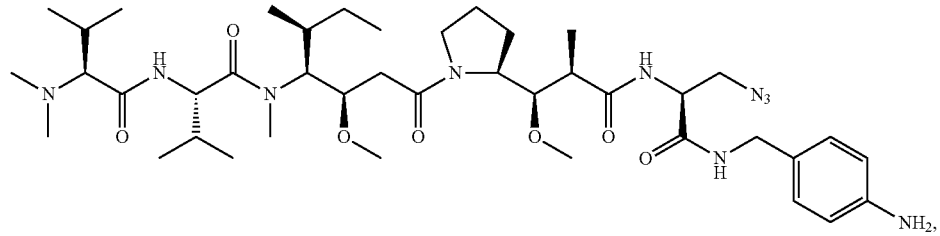
T037

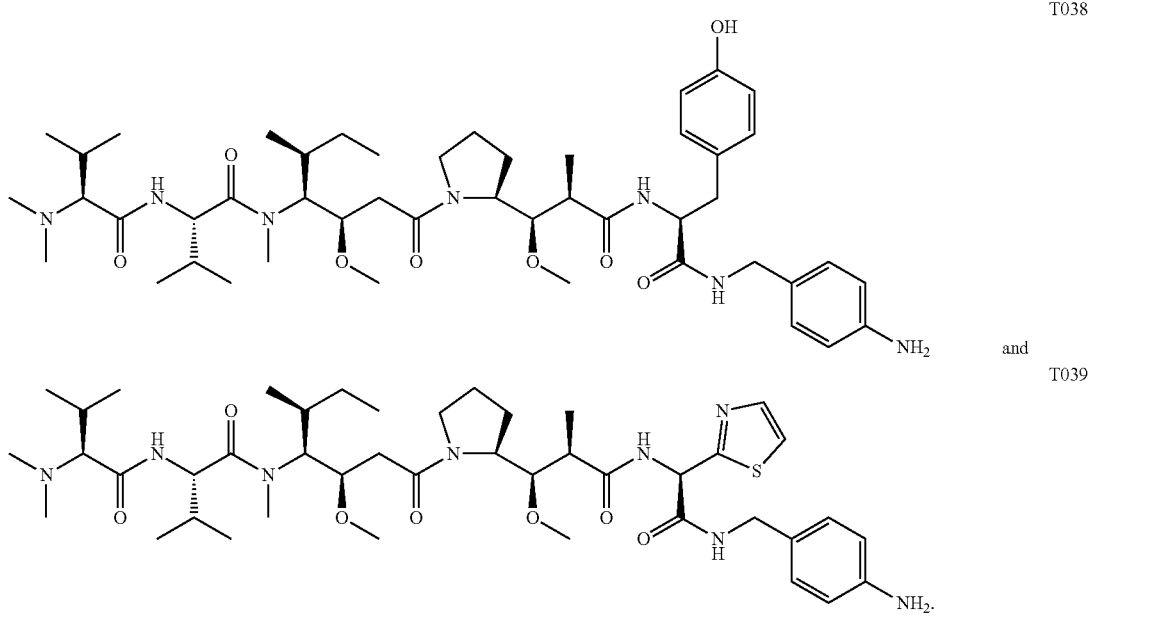

T038 and

T039

3. A conjugate comprising one or more compounds of claim 1, or a pharmaceutically acceptable salt, solvate, hydrate, isomer thereof, or crystalline form or racemate thereof, and one or more linkers, which has the structure:

G-B wherein G is the compound as defined in claim 1, or a pharmaceutically acceptable salt, solvate, hydrate, isomer thereof, or crystalline form or racemate thereof, which is linked to B via $M_8$;

B is a linker, which has the structure:

$(L_1)_s\text{-}(L_2)_w\text{-}(D)\text{-}L_3$;

wherein $L_1$ is selected from: peptide, oligose, Val-Cit, Val-Ala, Val-Lys(Ac), Phe-Lys, Phe-Lys(Ac), D-Val-Leu-Lys, Gly-Gly-Arg, and Ala-Ala-Asn;

$L_2$ is selected from:

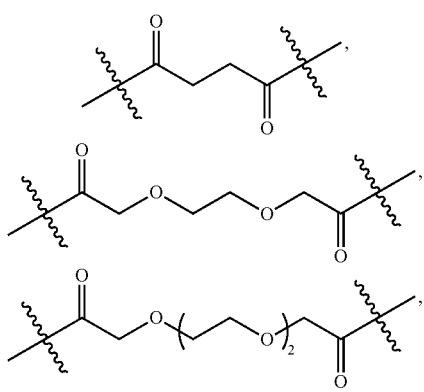

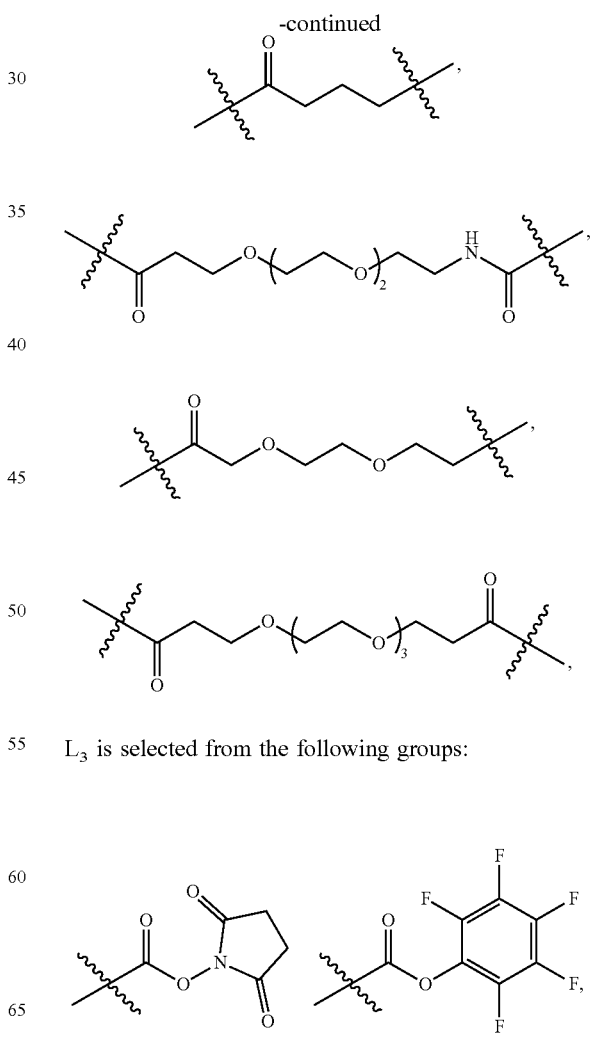

$L_3$ is selected from the following groups:

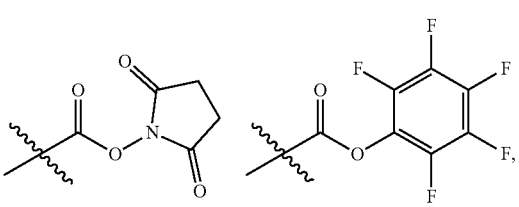 [SMILES: *C(=O)ON1C(=O)CCC1=O ; *C(=O)Oc1c(F)c(F)c(F)c(F)c1F]

449

D is selected from the following groups optionally substituted by one or more $R_i$:

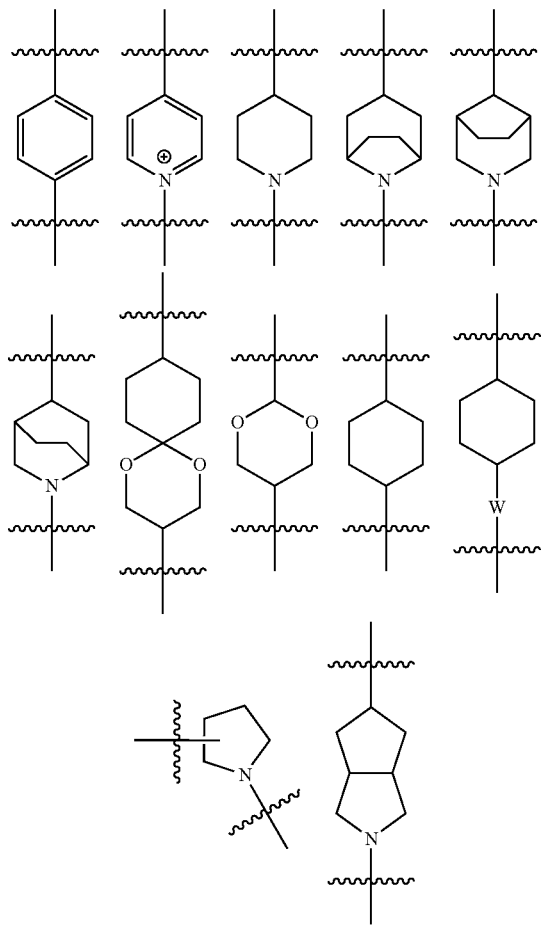

$R_i$ is independently selected from hydrogen, deuterium, =O, CN, CH2CN, methyl, and CF3; W is O or $NR_j$, $R_j$; is independently selected from hydrogen, deuterium, $C_{1-6}$ alkyl, $C_{3-6}$ cycloalkyl, $C_{1-6}$ alkoxy, cyano $C_{1-2}$ alkyl;

s, w, independently of each other, are selected from 1 or 2;

or a conjugate comprising one or more compounds of claim 1, or a pharmaceutically acceptable salt, solvate, hydrate, isomer thereof, or crystalline form or racemate thereof, and one or more linkers, the linker is also covalently linked to a targeting moiety;

which has the structure:

$(G-B)_\alpha-E$, wherein, G is the compound as defined in claim 1, or a pharmaceutically acceptable salt, solvate, hydrate, isomer thereof, or crystalline form or racemate thereof, which is linked to B via $M_8$;

B is a linker having the structure:

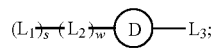

450 wherein $L_1$ is selected from: peptide, oligose, Val-Cit, Val-Ala, Val-Lys(Ac), Phe-Lys, Phe-Lys(Ac), D-Val-Leu-Lys, Gly-Gly-Arg, and Ala-Ala-Asn;

$L_2$ is selected from:

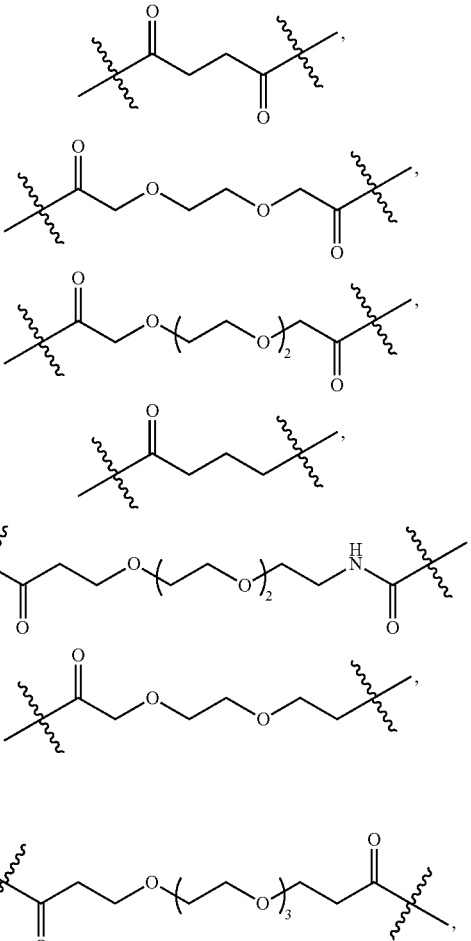

$L_3$ is selected from the following groups:

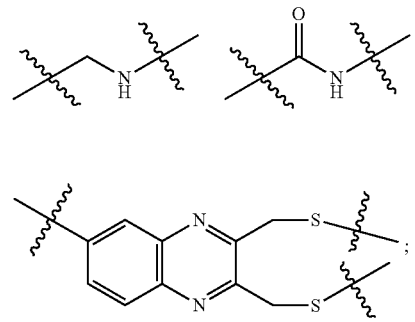

s, w, independently of each other, are selected from 1 or 2;

D is selected from the following groups optionally substituted by one or more $R_i$:

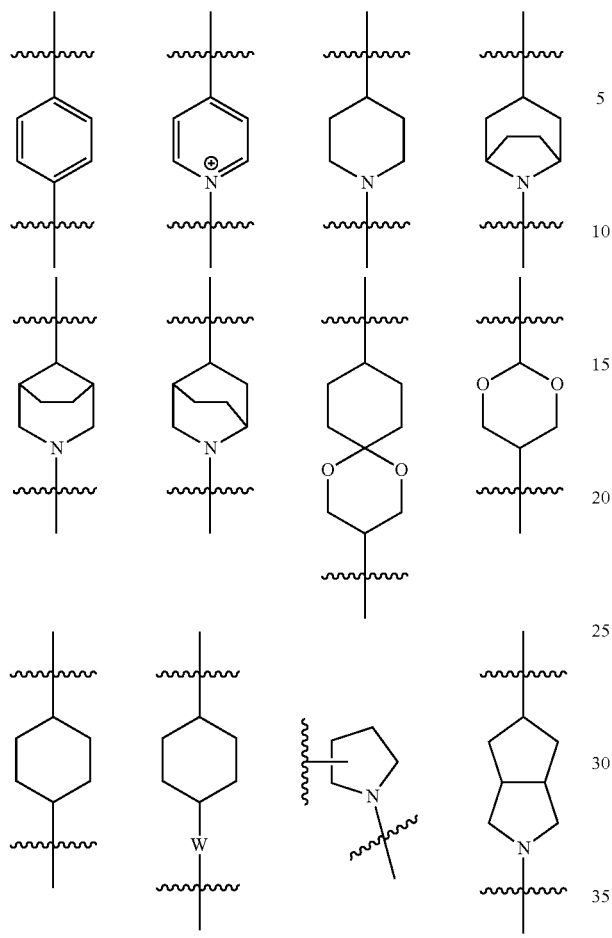

R$_i$ is independently selected from hydrogen, deuterium, =O, CN, CH2CN, methyl, CF$_3$; W is O or NR$_j$, R$_j$ is independently selected from hydrogen, deuterium, C$_{1-6}$ alkyl, C$_{3-6}$ cycloalkyl, C$_{1-6}$ alkoxy, cyano C$_{1-2}$ alkyl;

E is a targeting moiety;

α is a number between 1-20.

4. The conjugate of claim 3, wherein in the linker, L$_1$ is selected from Val-Cit, Val-Ala.

5. The conjugate of claim 3, wherein in the linker, L$_2$ is selected from:

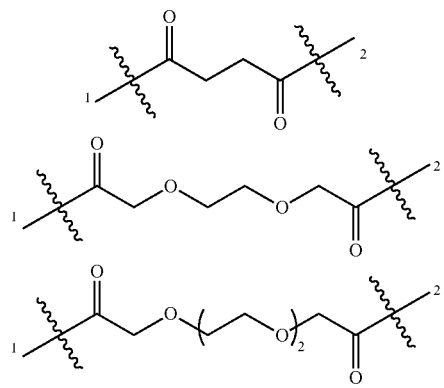

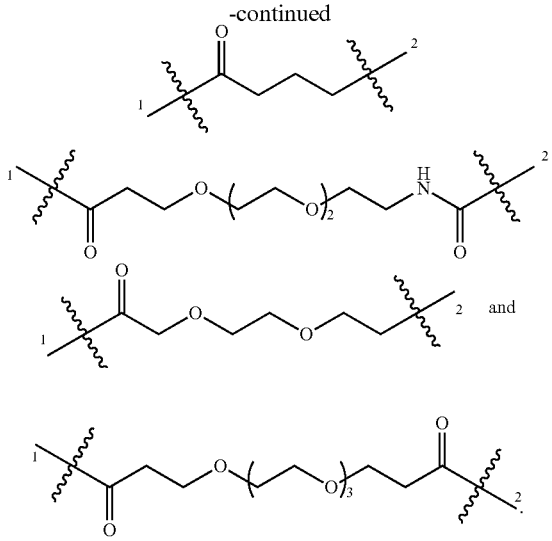

wherein the group L$_2$ is linked to L$_1$ at the position marked by 1, and linked to D at the position marked by 2.

6. The conjugate of claim 3, wherein in the linker, L$_3$ is selected from:

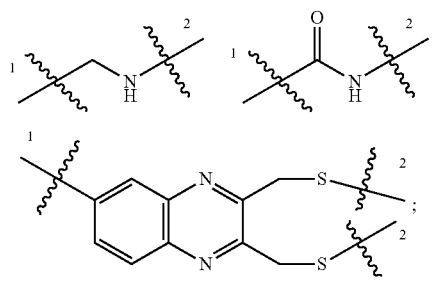

wherein the group
L$_3$ is linked to D at the position marked by 1, and linked to E at the position marked by 2.

7. The conjugate of claim 3, wherein in the linker, L$_3$ is

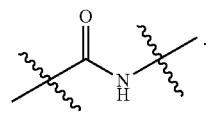 [SMILES: *NC(*)=O]

8. The conjugate of claim 3, wherein in the linker, D is selected from:

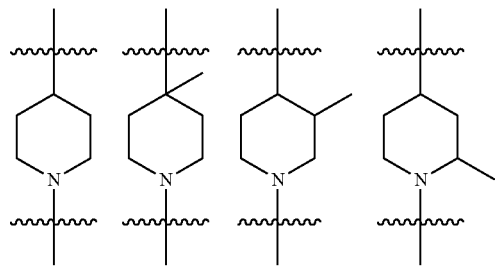

-continued
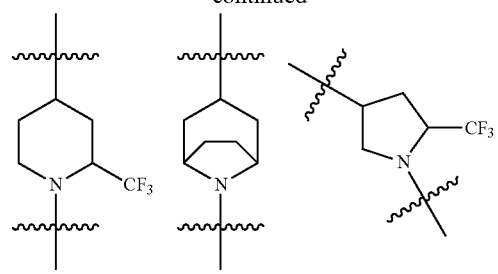
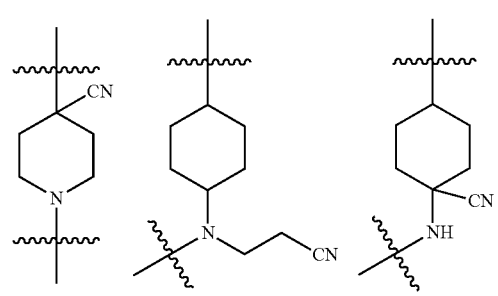
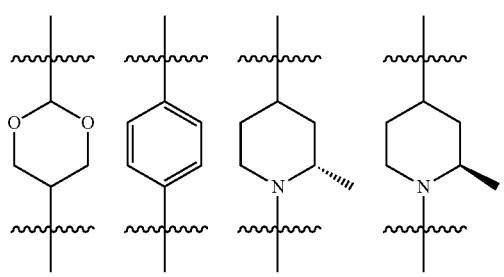
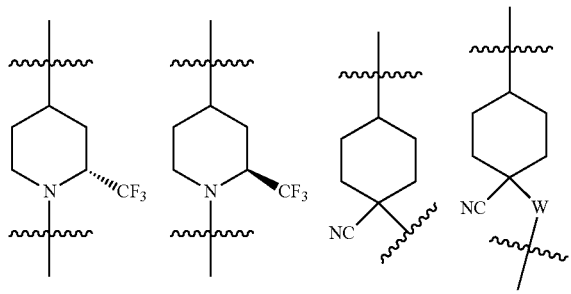
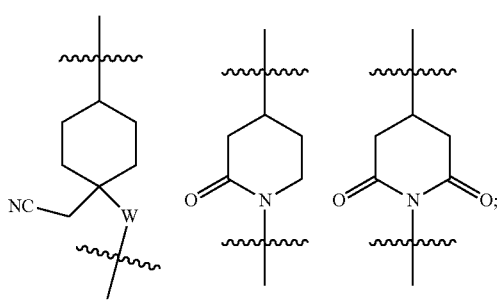
optionally, D is selected from:
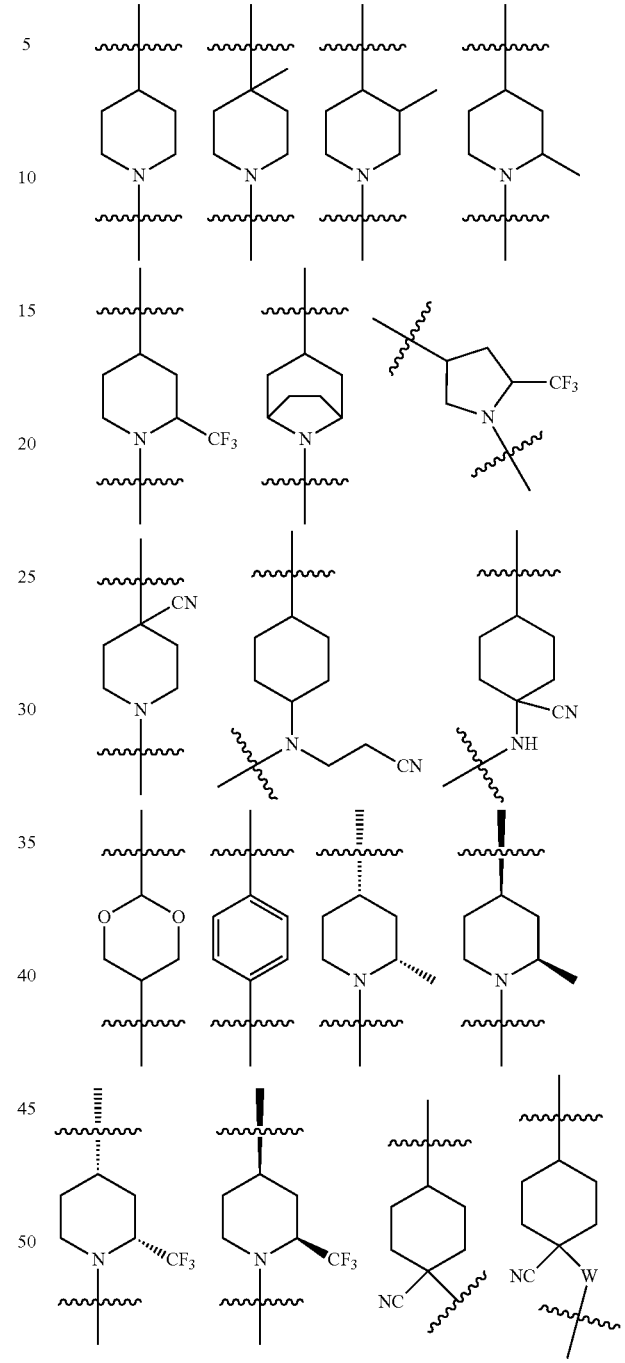
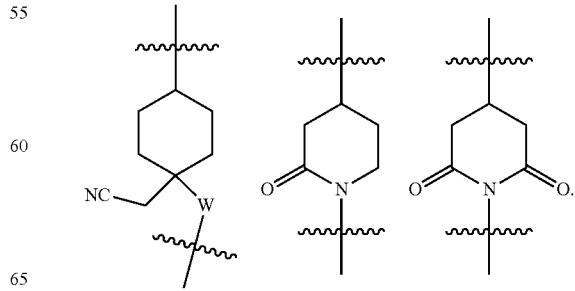

9. The conjugate of claim 3, wherein in the linker, D is selected from:
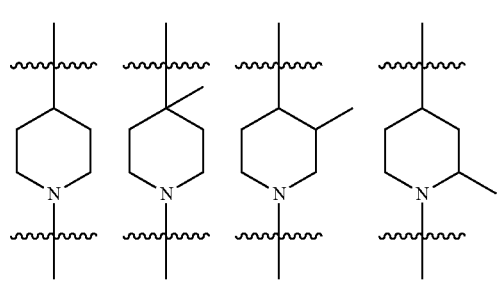
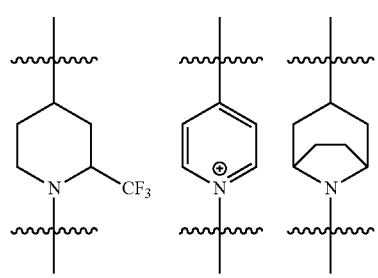
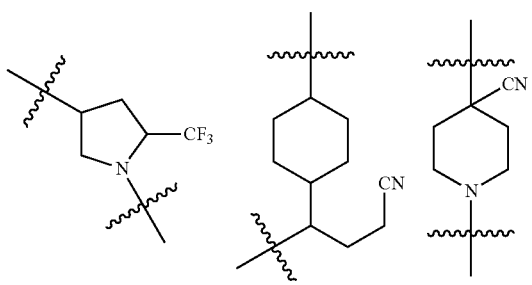
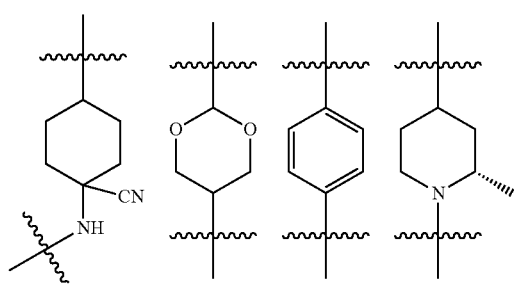
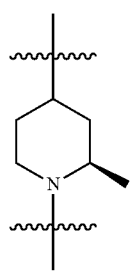
;
optionally, D is selected from:
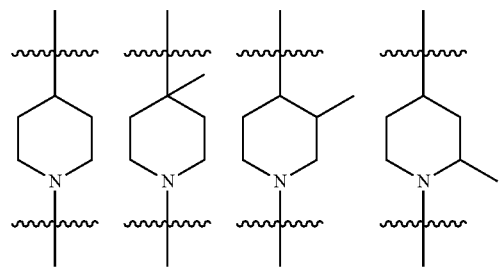
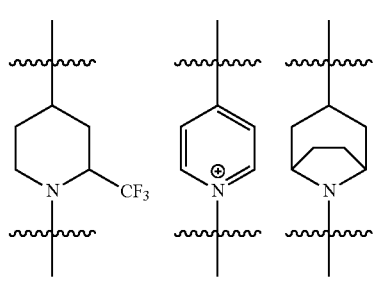
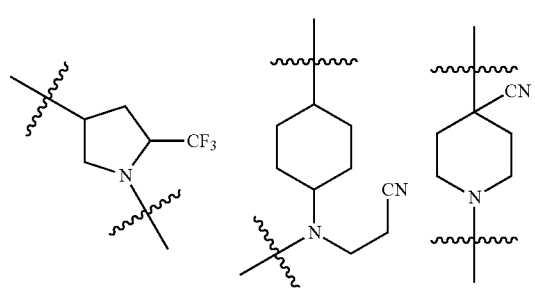
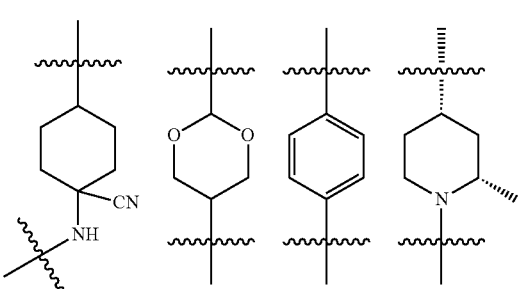
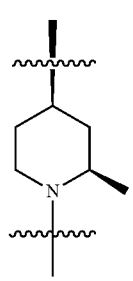

10. The conjugate of claim 3, wherein in the linker, D is selected from:
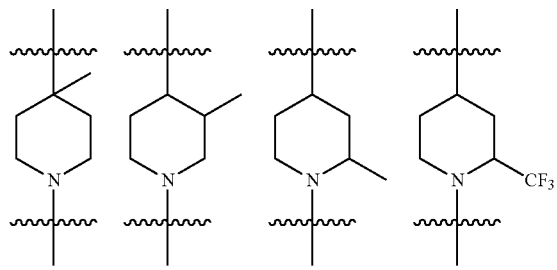
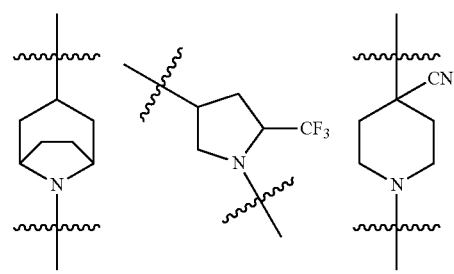
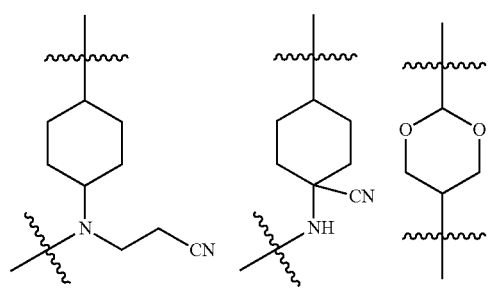
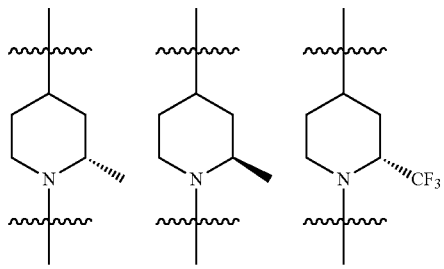
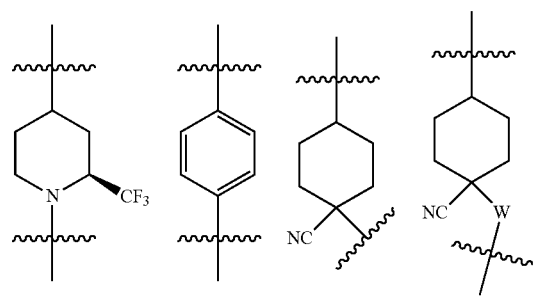
-continued
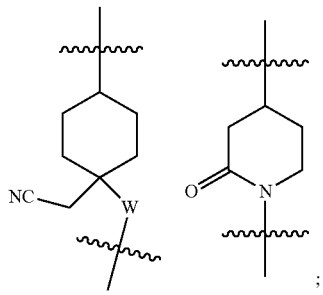
optionally, D is selected from:
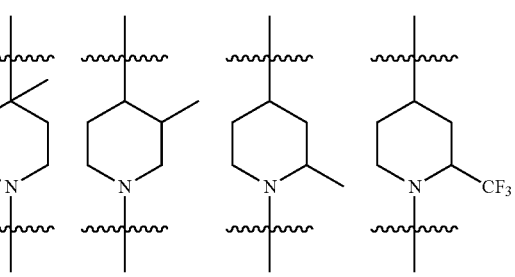
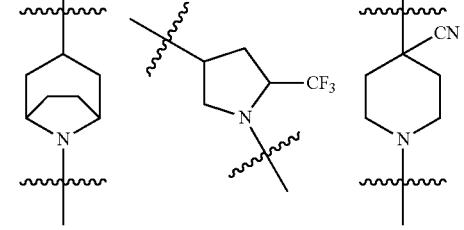
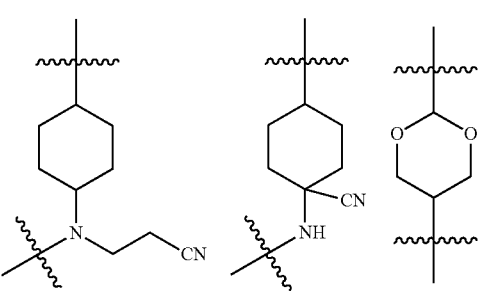
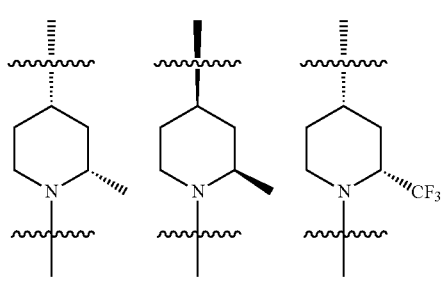

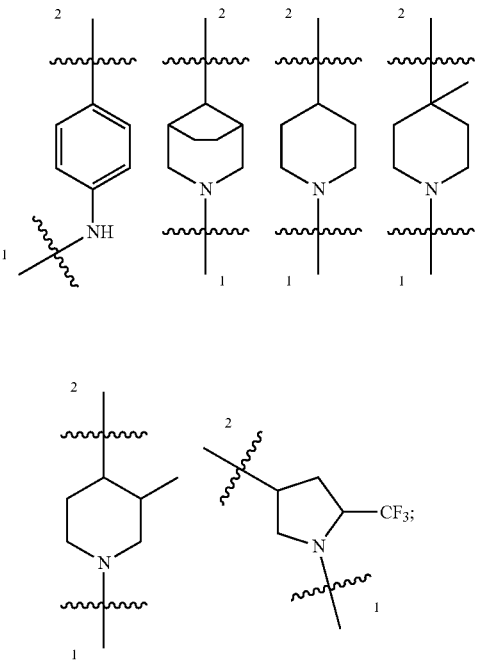
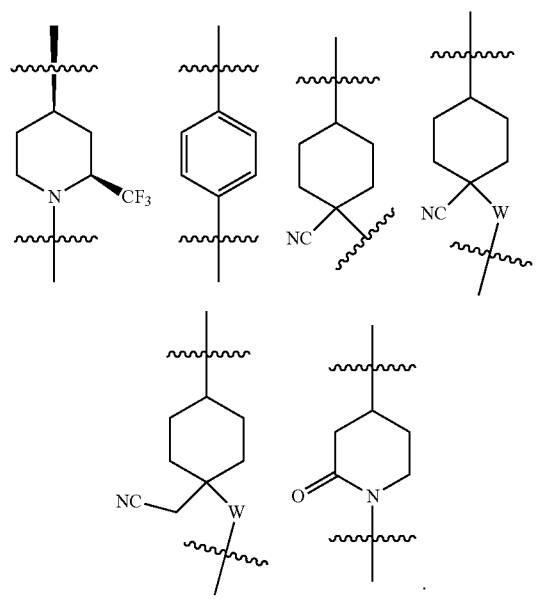
11. The conjugate of claim 3, wherein in the linker, D is selected from the following groups:
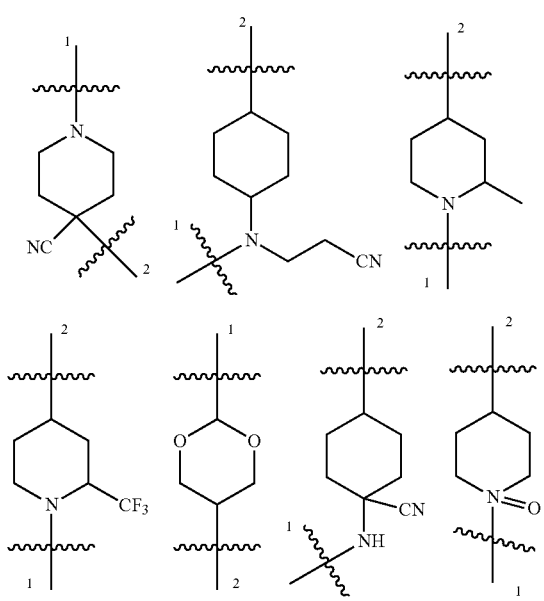
wherein,
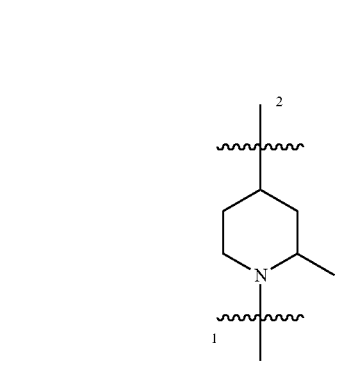
is optionally further selected from
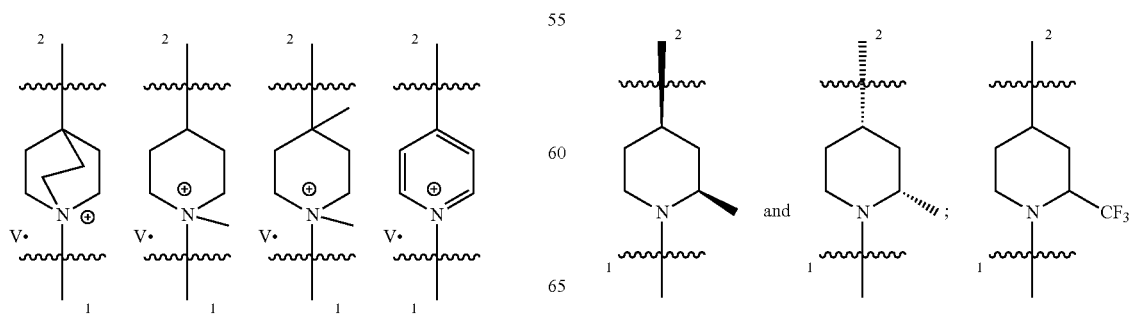

is optionally further selected from

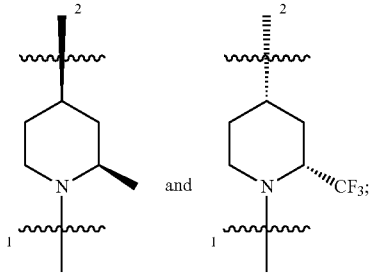

and the above group is linked to $L_2$ at one of the two positions marked by 1 or 2, and linked to $L_3$ at the other position;
V. is a counterion.

12. The conjugate of claim 3, wherein in the linker, $L_2$ is selected from:

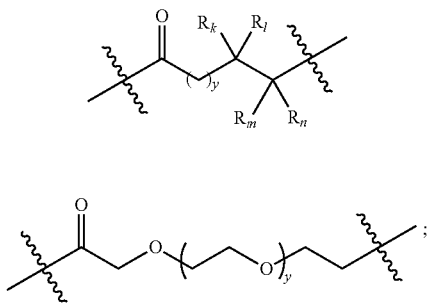

wherein y=1;
$R_k$, $R_l$, $R_m$, and $R_n$ are all hydrogen.

13. A conjugate comprising a drug and a linker, and optionally a targeting moiety, wherein the linker is as defined in claim 3;
the drug is selected from the compounds as defined in claim 1, or a pharmaceutically acceptable salt, solvate, hydrate, isomer thereof, or crystalline form or racemate thereof.

14. The conjugate of claim 3, wherein the targeting moiety (E) is an antibody.

15. The conjugate of claim 3, wherein the targeting moiety (E) is directed to a target selected from: epidermal growth factor, CD37, HER2, CD70, EGFRvIII, Mesothelin, Folate eceoptor1, Mucin 1, CD138, CD20, CD19, CD30, SLTRK6, Nectin 4, Tissue factor, Mucin16, Endothelinreceoptor, STEAP1, SLC39A6, Guanylylcyclase C, PSMA, CCD79b, CD22, Sodium phosphate cotransporter 2B, GPNMB, Trophoblast glycoprotein, AGS-16, EGFR, CD33, CD66e, CD74, CD56, PD-L1, TACSTD2, DR5, BMPR1B, E16, STEAP1, 0772P, MPF, Napi3b, Sema 5b, PSCA hlg, ETBR, MSG783, STEAP2, TrpM4, CRIPTO, CD21, CD79b, FcRH2, NCA, MDP, IL20Rα, Brevican, EphB2R, ASLG659, PSCA, GEDA, BAFF-R, CD22, CD79a, CXCR5, HLA-DOB, P2X5, CD72, LY64, FcRH1, IRTA2, TENB2, integrin α5β6, α4β7, FGF2, FGFR2, Her3, CD70, CA6, DLL3, EpCAM, pCAD, CD223, LYPD3, LY6E, EFNA4, ROR1, SLITRK6, 5T4, ENPP3, SLC39A6, Claudin18.2, BMPR1B, E16, STEAP1, 0772P, MPF, Napi3b, Sema 5b, PSCA hlg, ETBR, MSG783, STEAP2, TrpM4, CRIPTO, CD21, CD79b, FcRH2, NCA, MDP, IL20Rα, Brevican, EphB2R, ASLG659, PSCA, GEDA, CD22, CD79a, CXCR5, HLA-DOB, P2X5, CD72, LY64, FcRH1, IRTA2, and TENB2.

16. The conjugate of claim 3, wherein the conjugate comprises a targeting moiety (E), wherein the targeting moiety (E) comprises a lysine residue or a cysteine residue and is linked to the linker via the lysine residue or the cysteine residue.

17. The conjugate of claim 3, which is selected from:

TL001

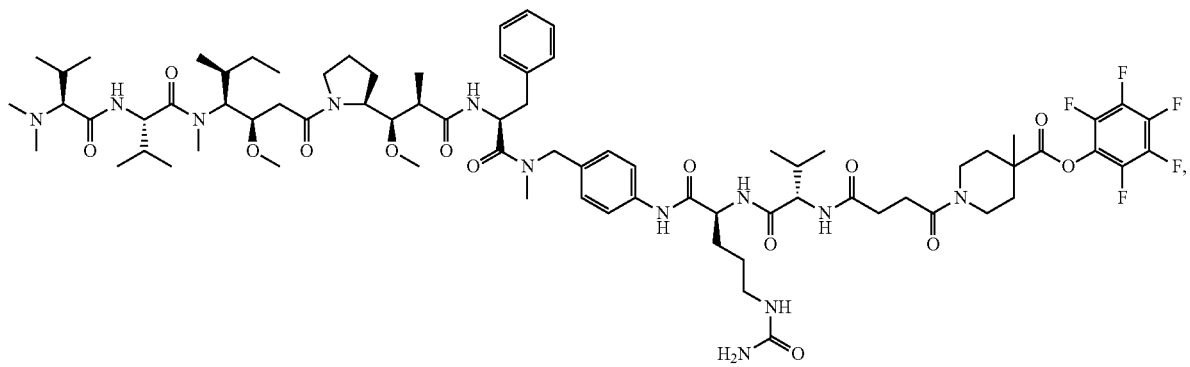

-continued
TL004
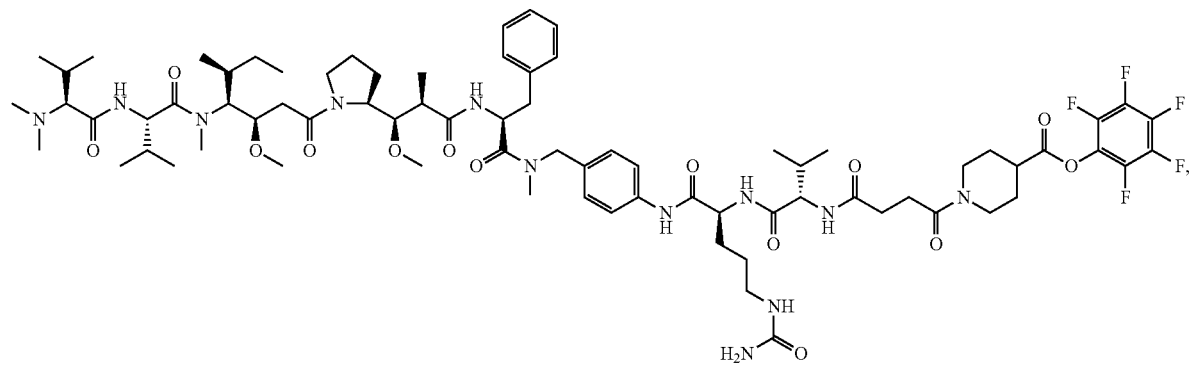
TL005
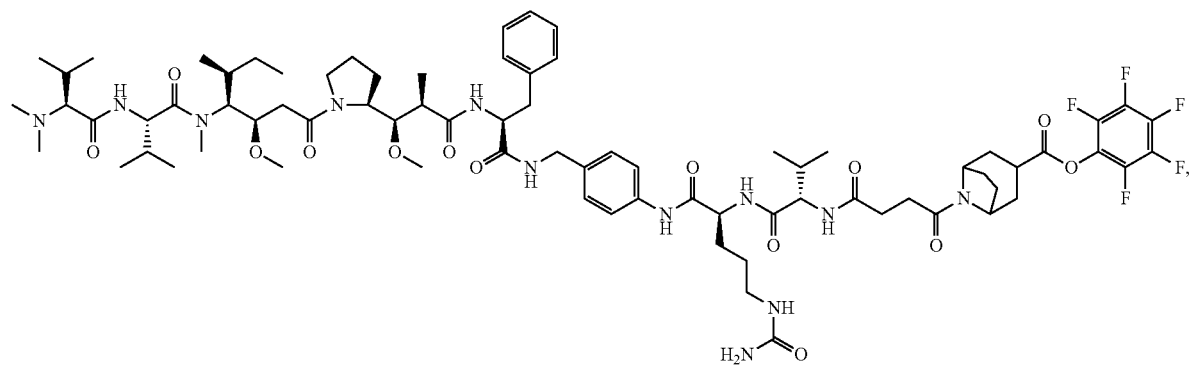
TL006
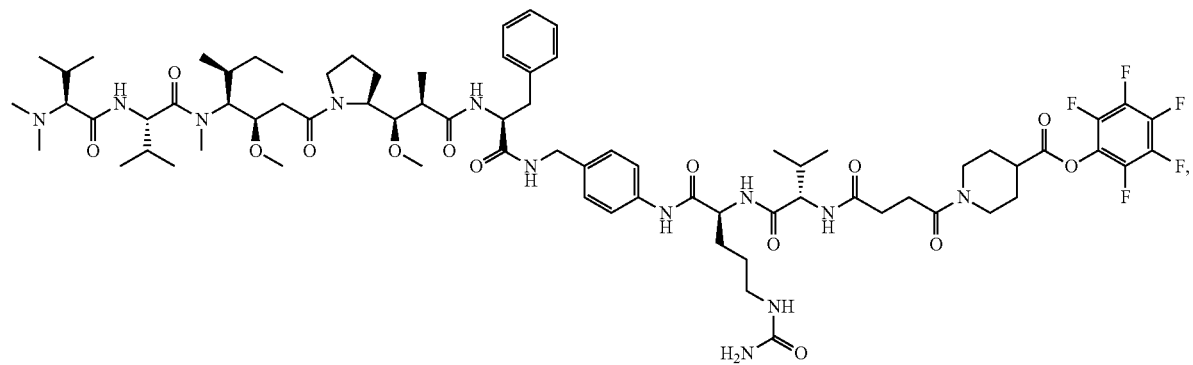
TL007
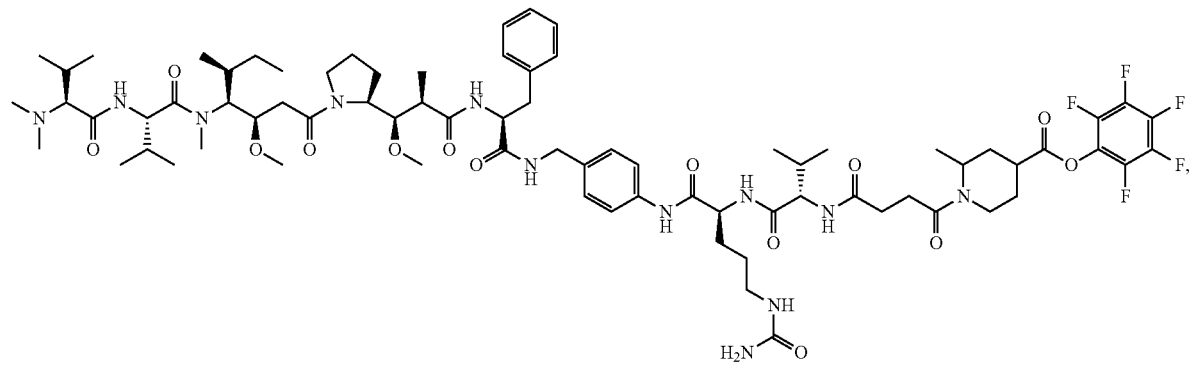

-continued
TL008
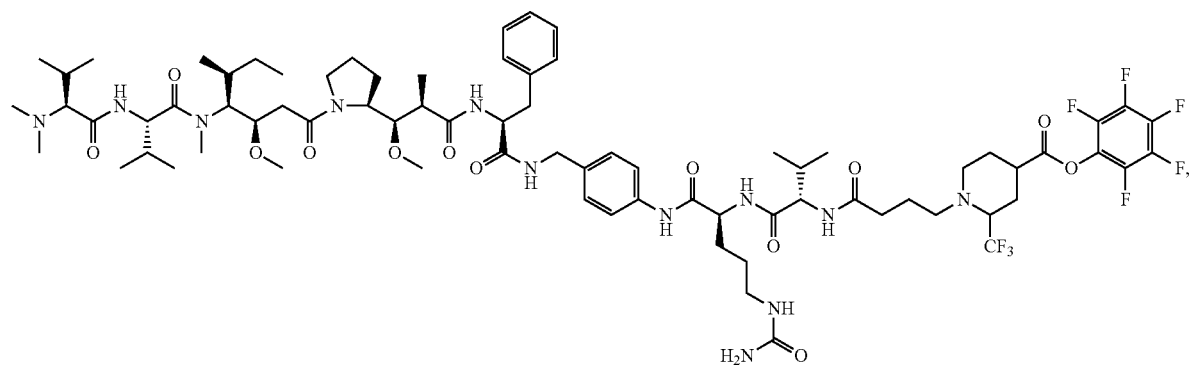
TL009
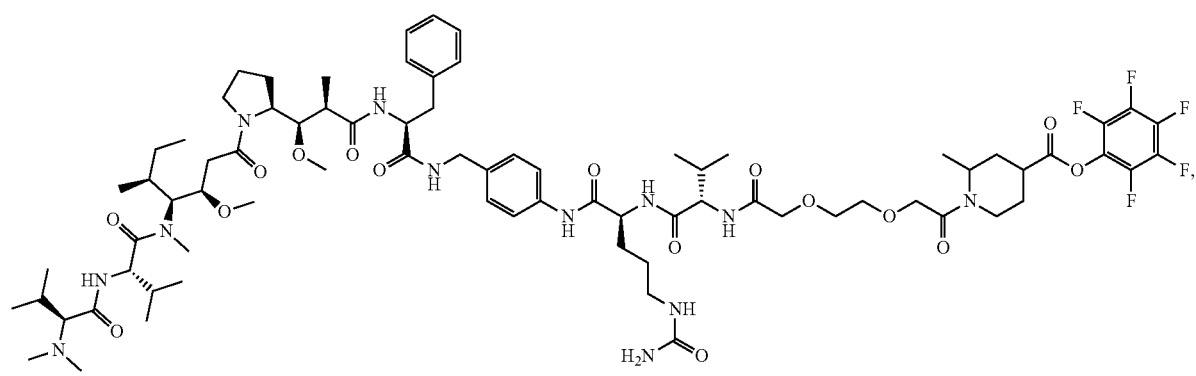
TL010
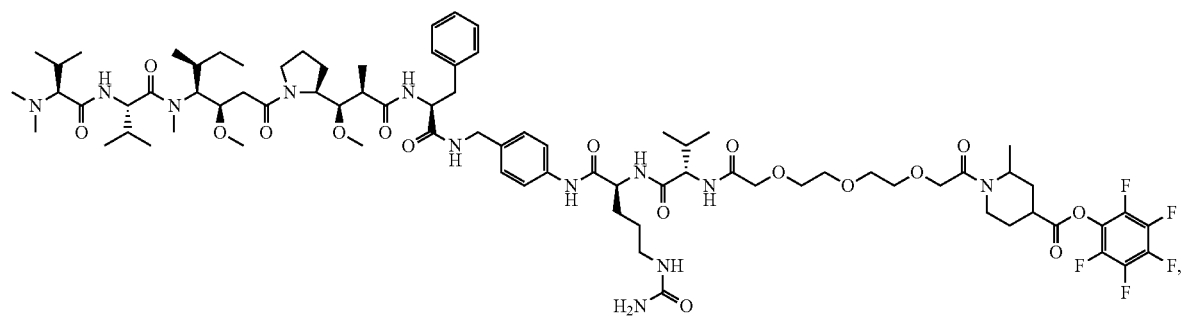
TL011
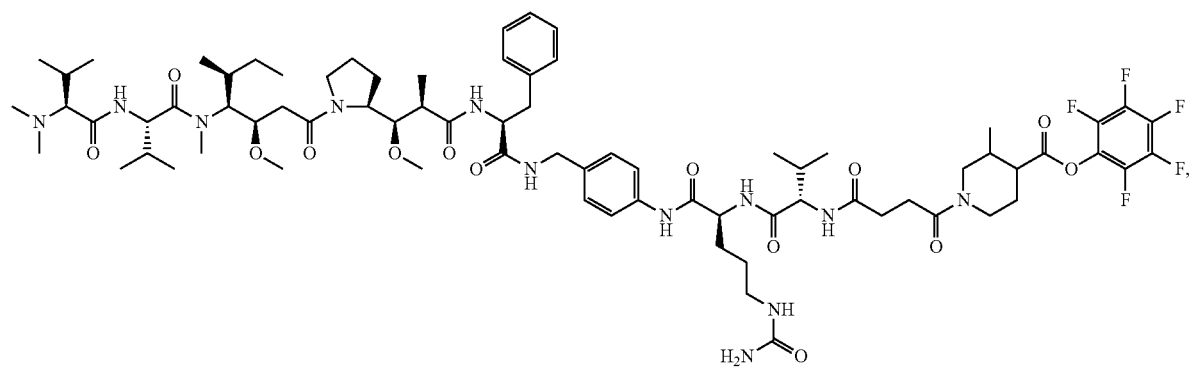

TL012
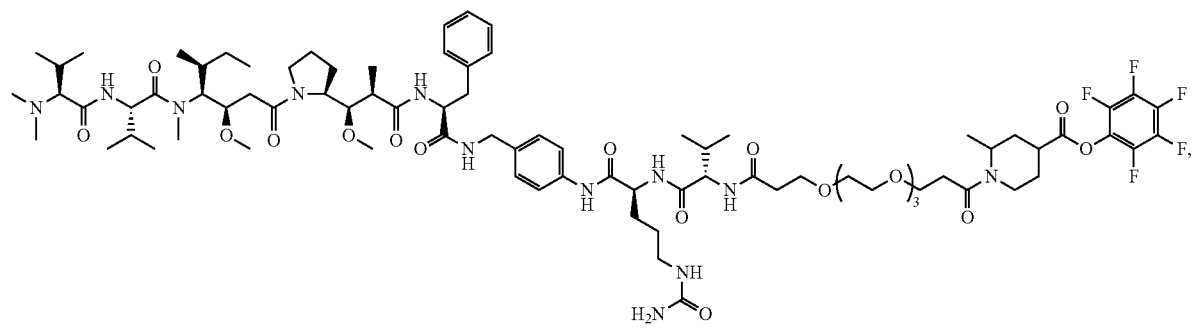
TL013
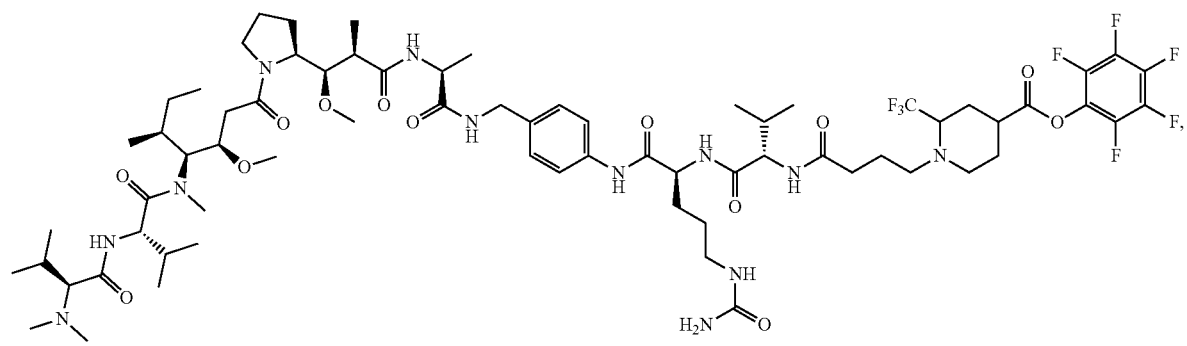
TL014
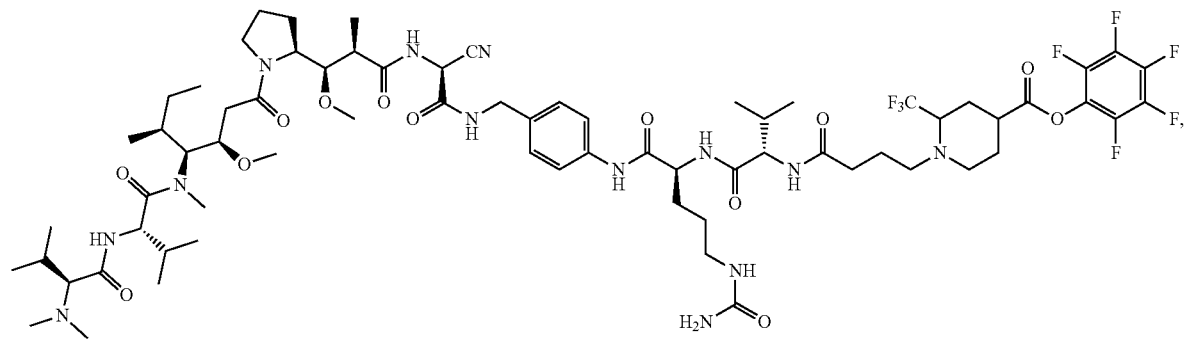
TL015
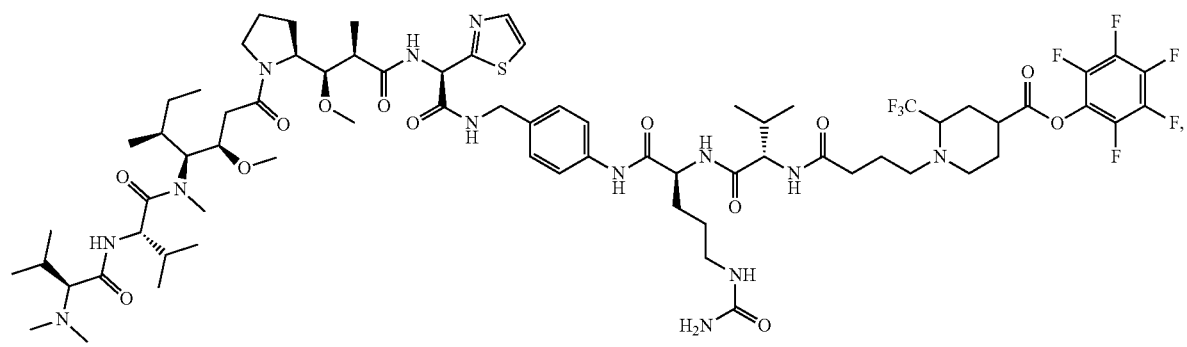

TL016
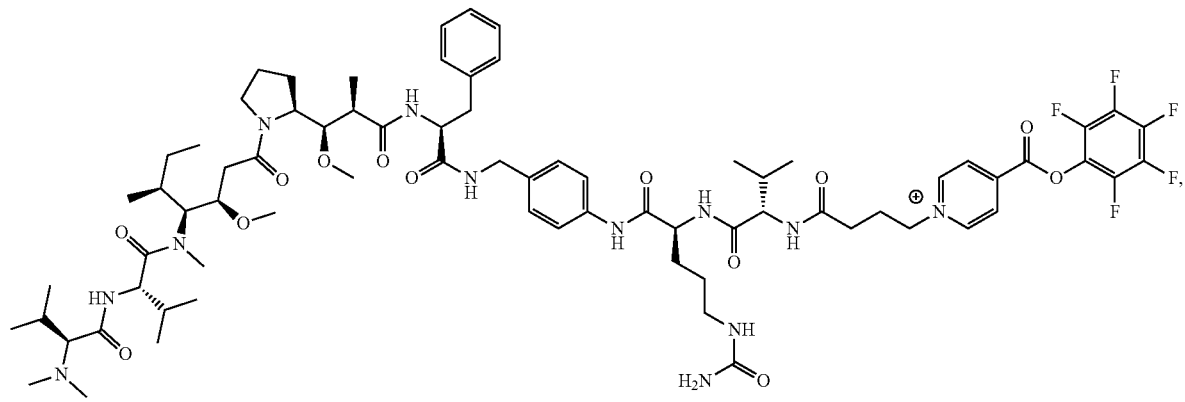
TL017
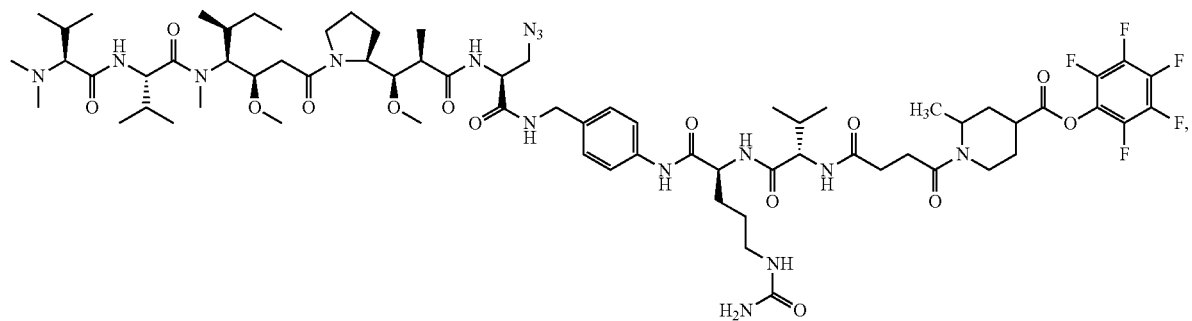
TL018
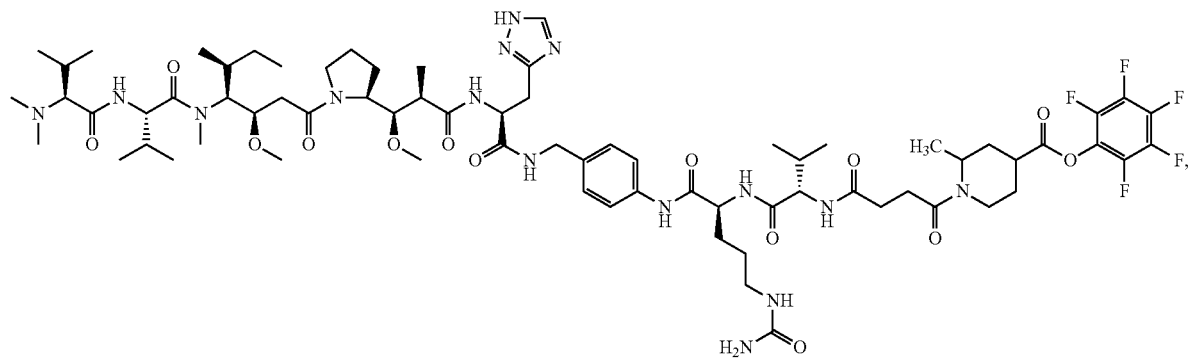
TL019
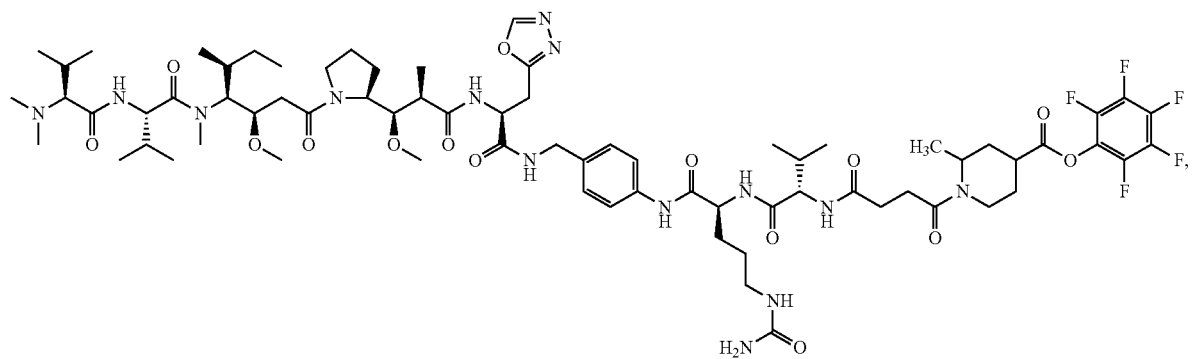

-continued
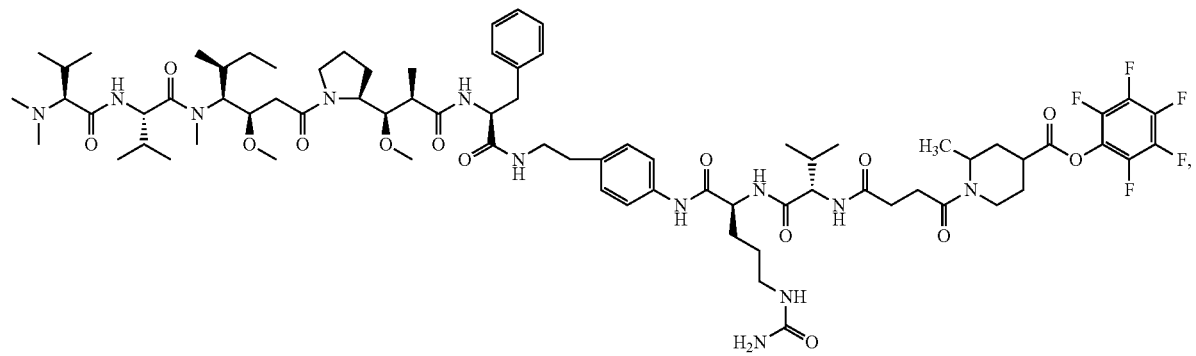
TL020
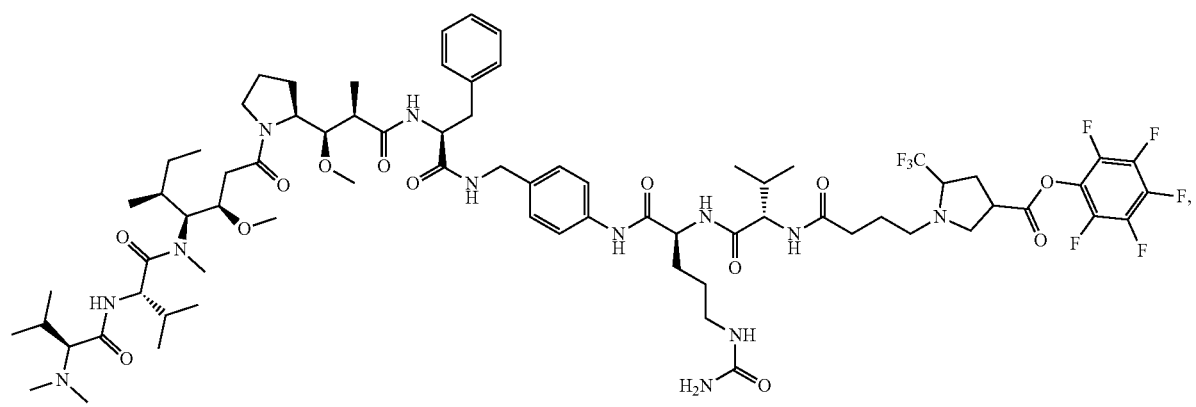
TL021
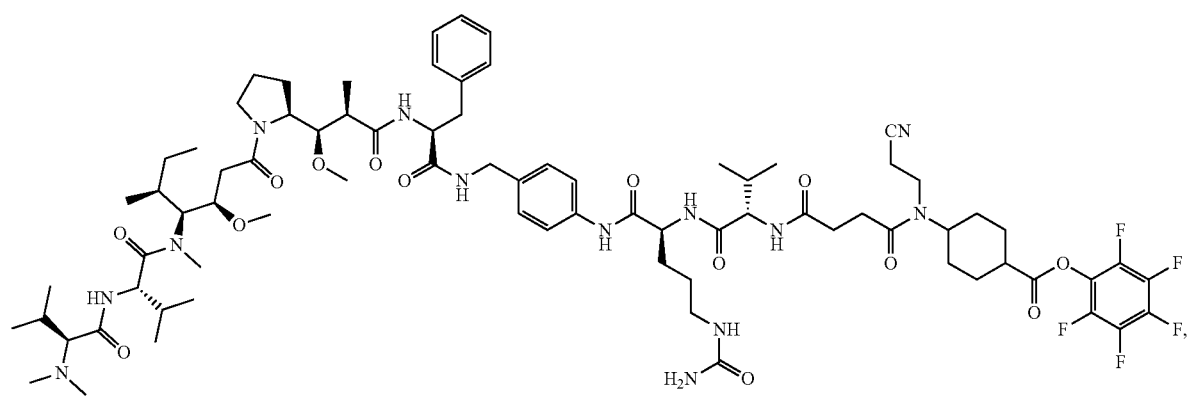
TL022
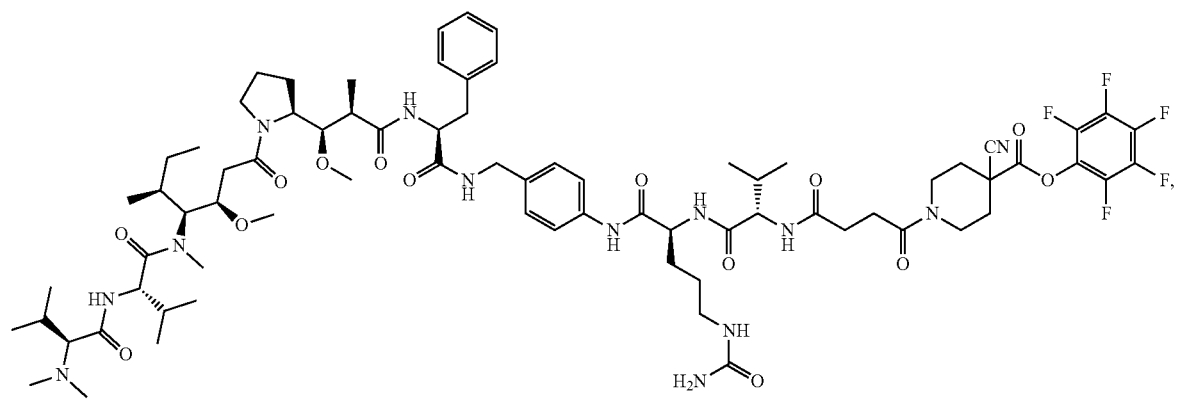
TL023

-continued
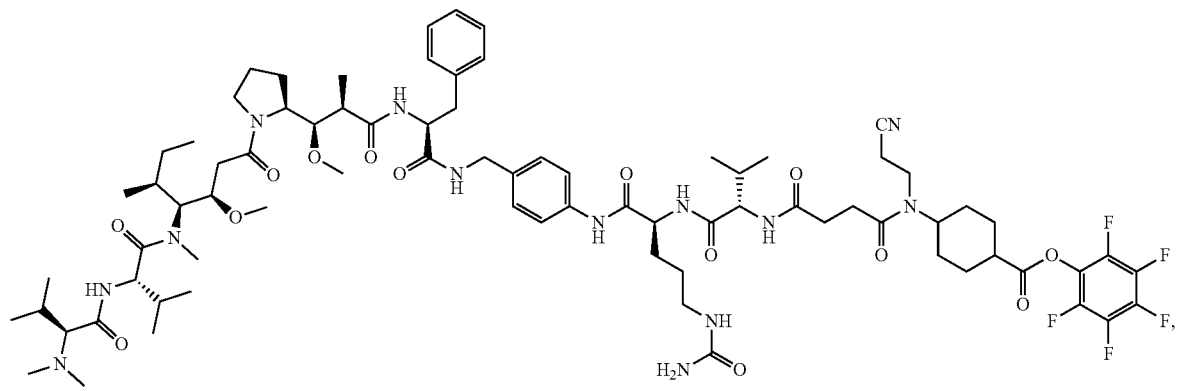
TL024
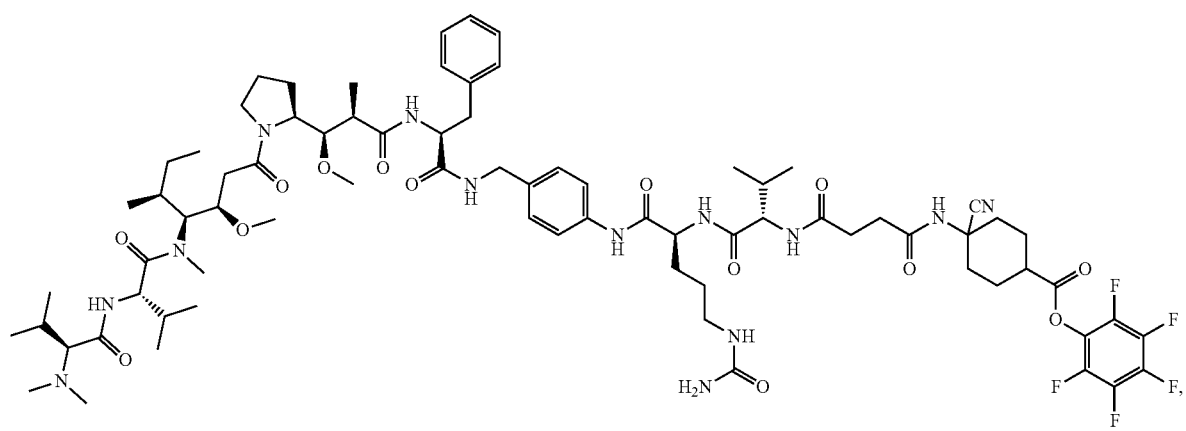
TL025
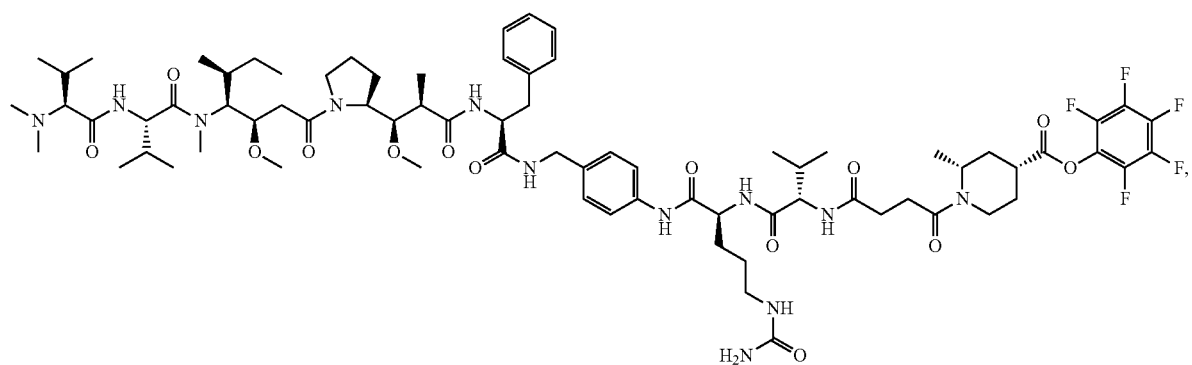
TL030
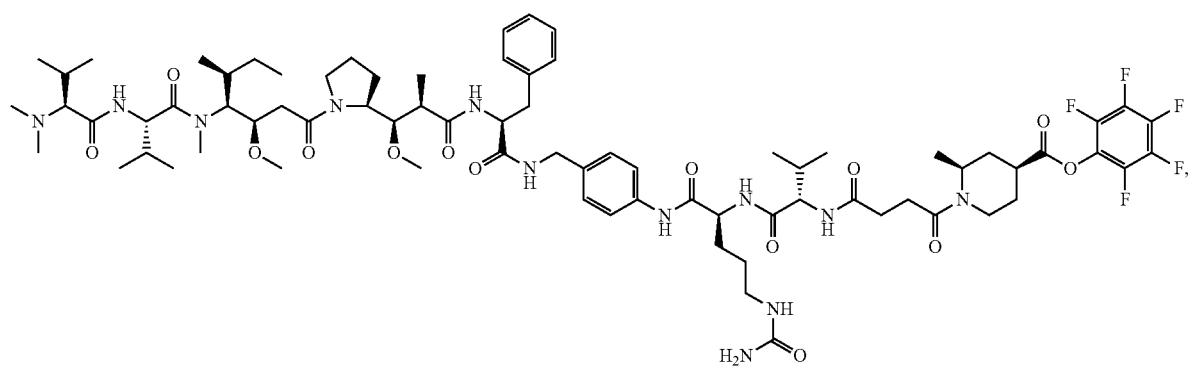
TL031

-continued
TL033
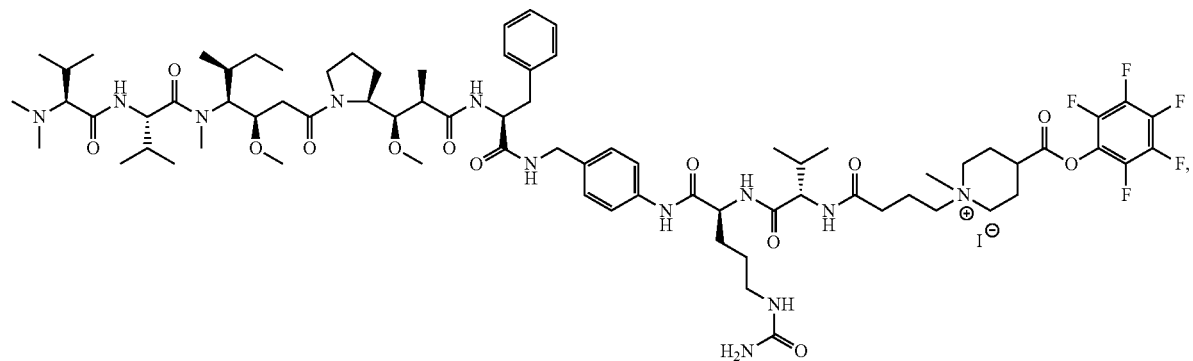
TL034
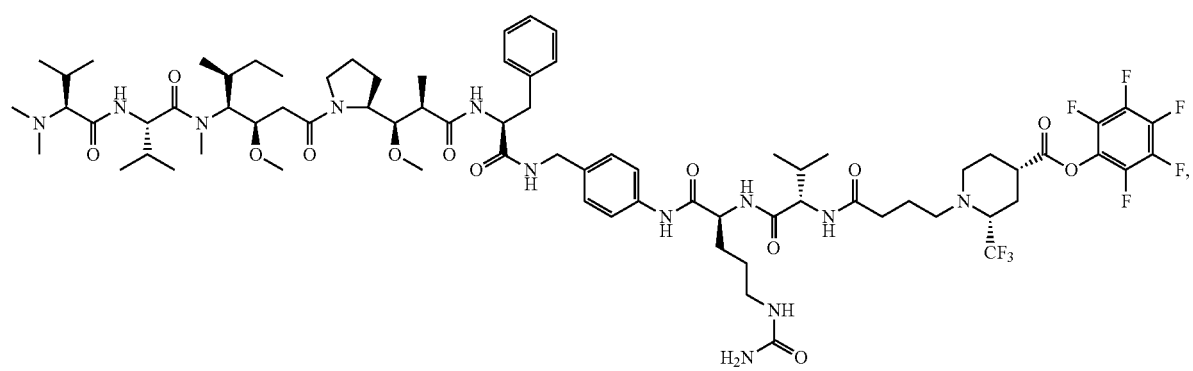
TL035
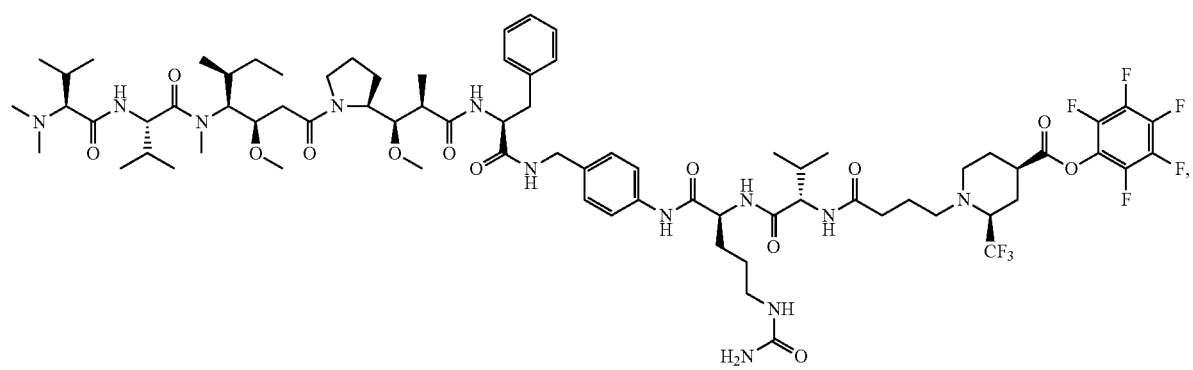
TL036
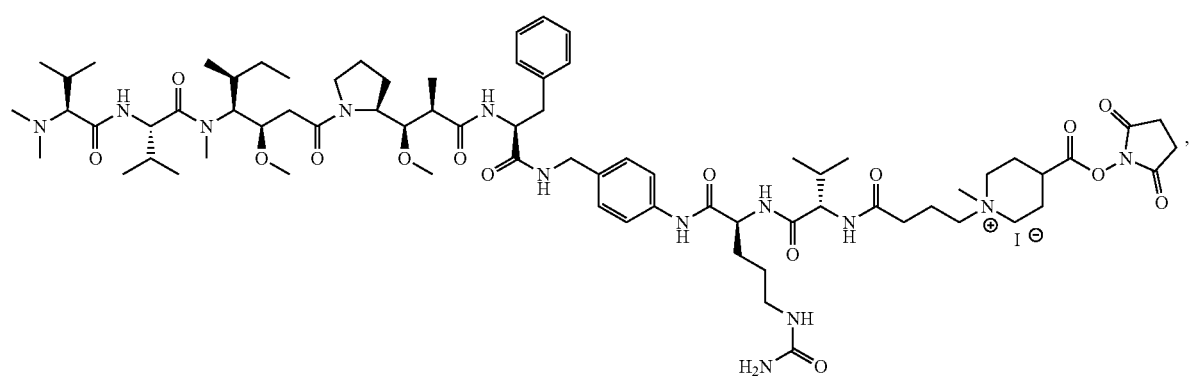

-continued
TL037
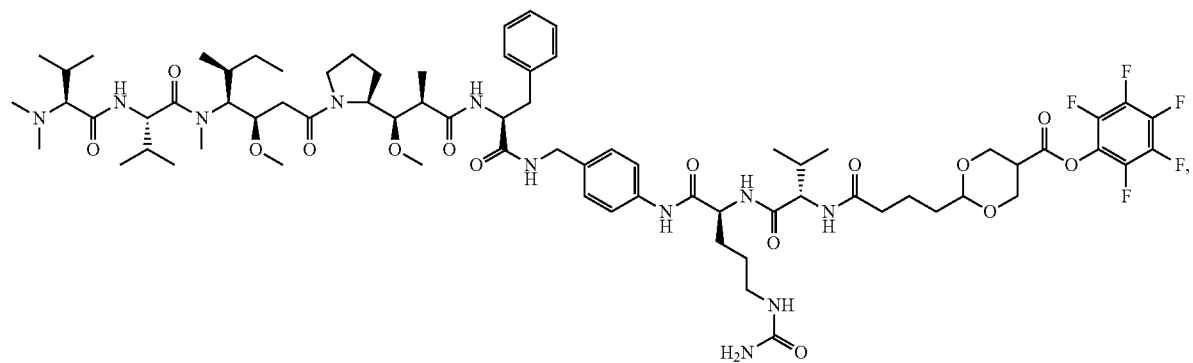
TL042
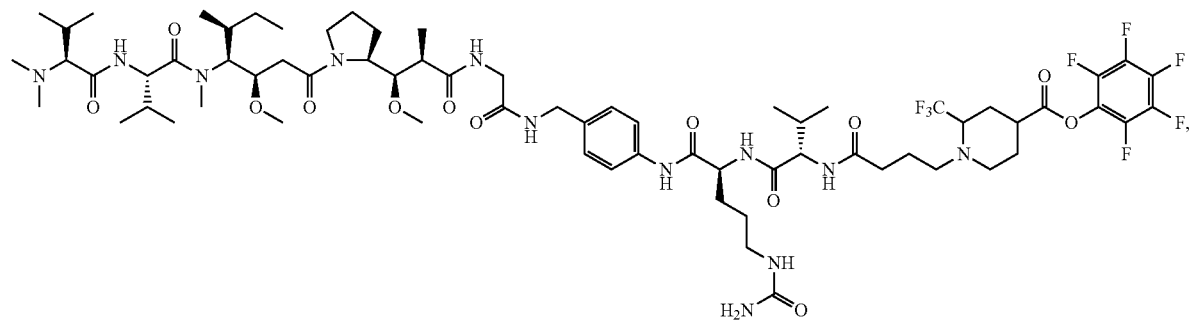
TL059
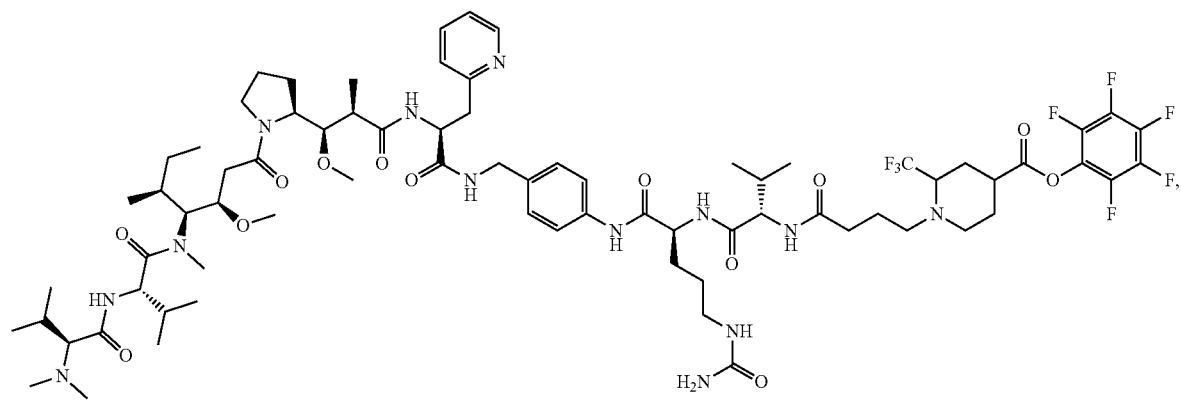
TL060
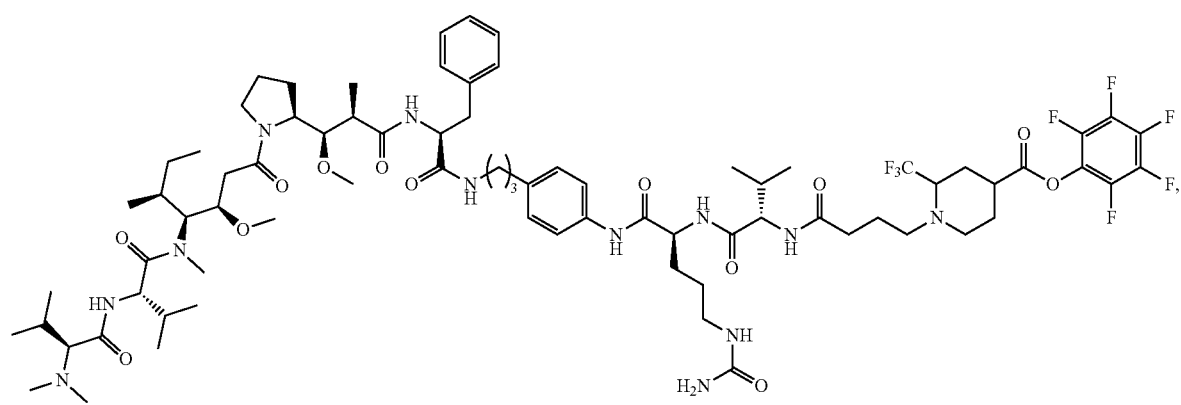

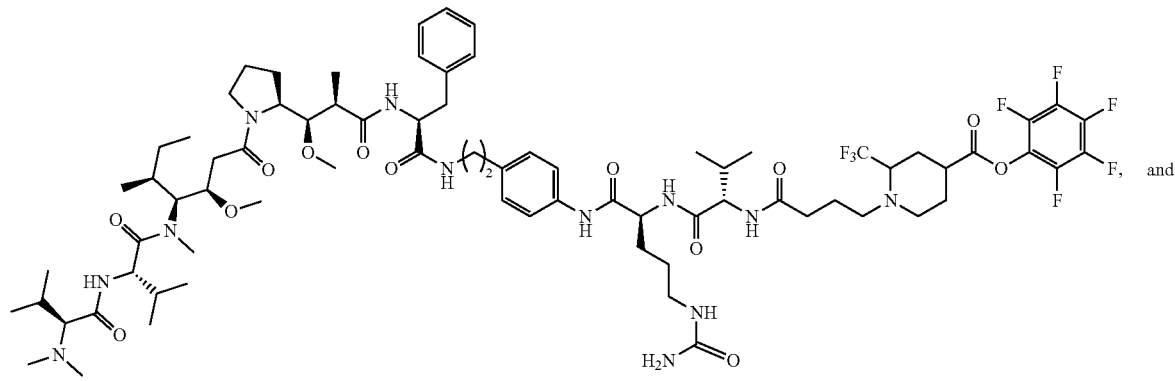
TL061
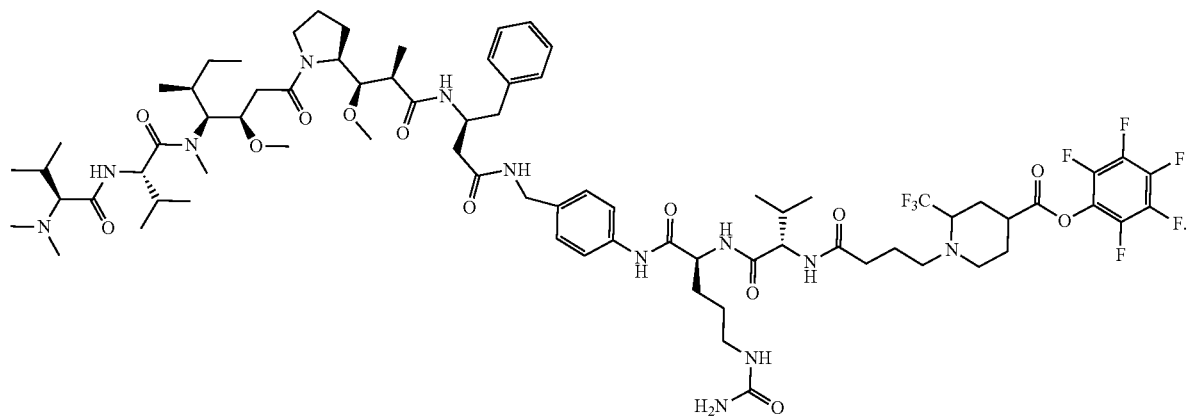
TL065
18. The conjugate of claim 3, which is selected from:
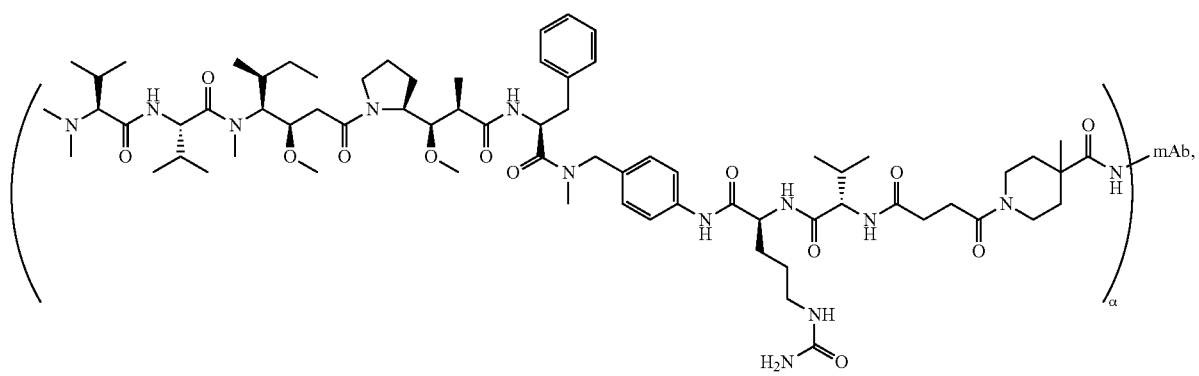

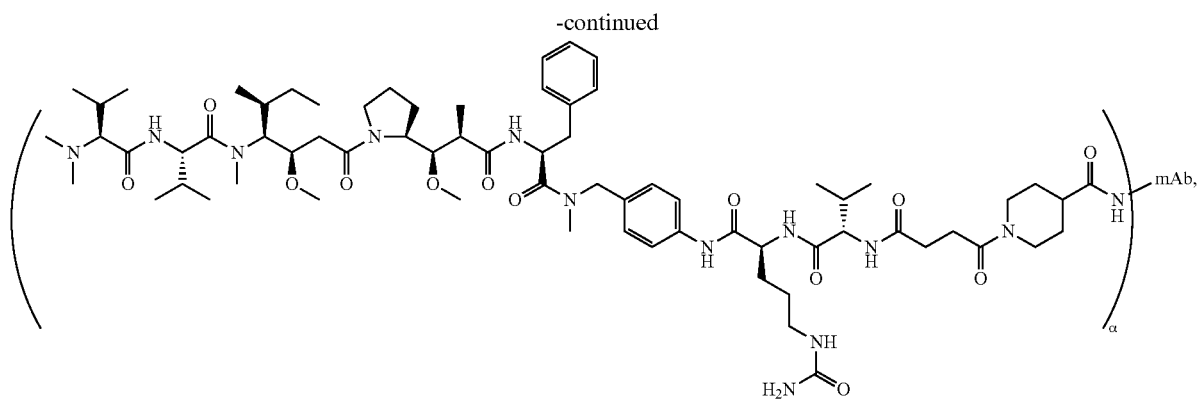
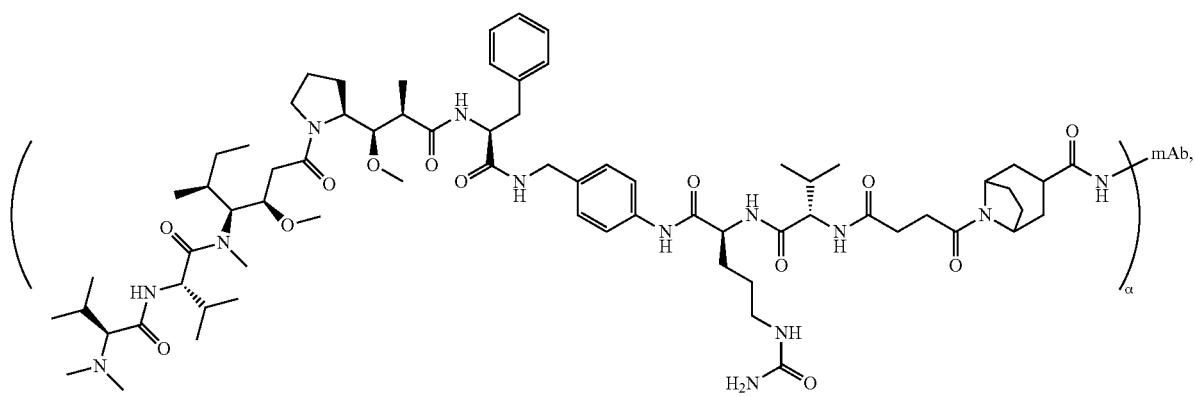
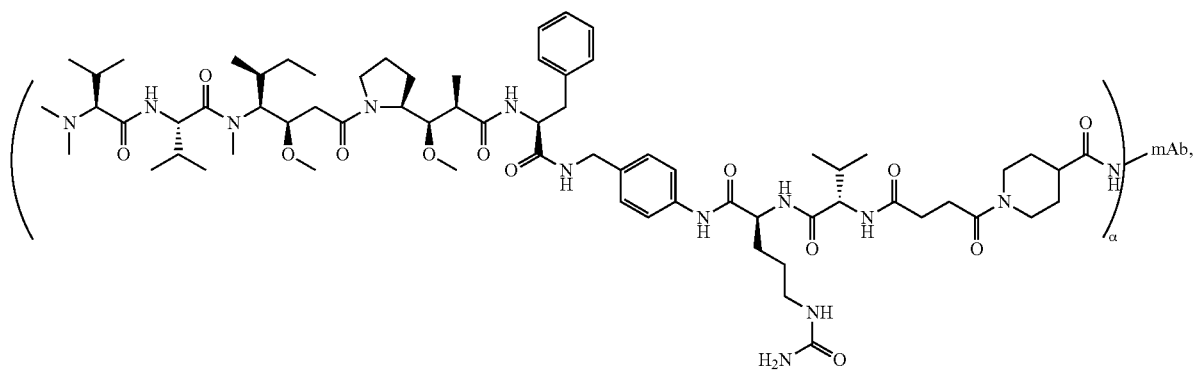
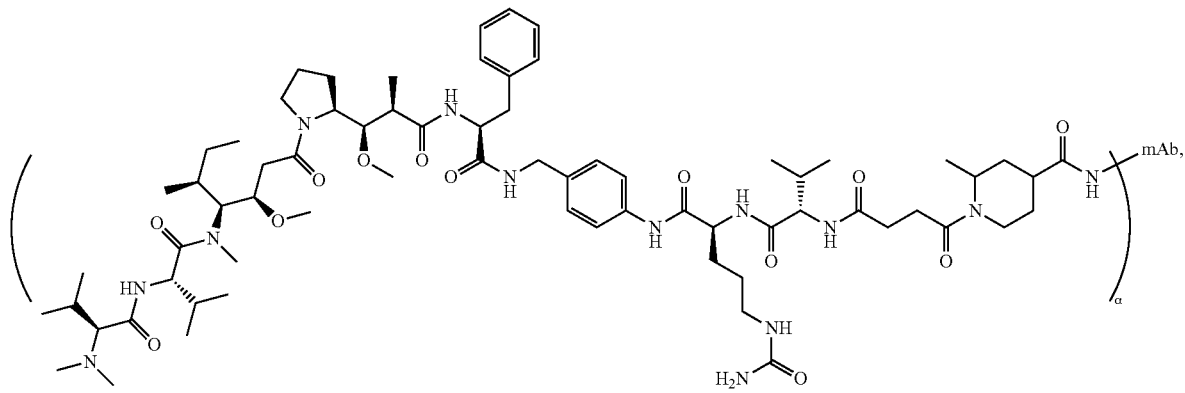

483
484
-continued
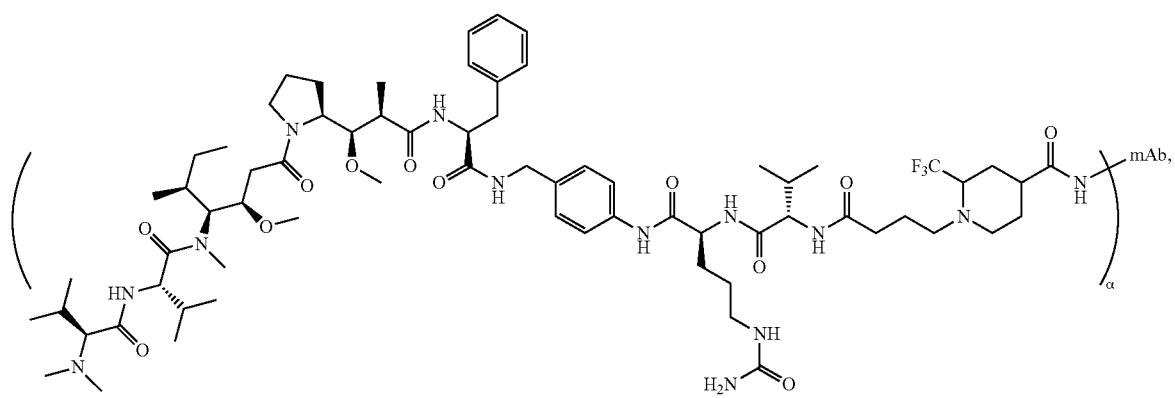
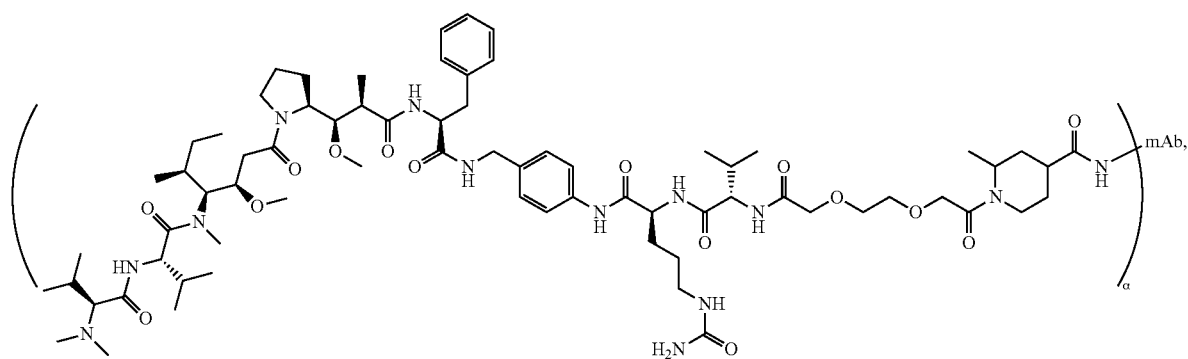
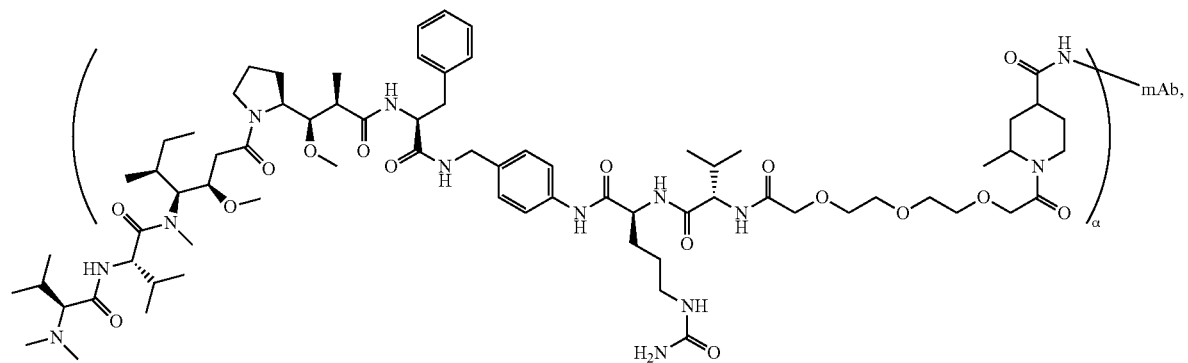
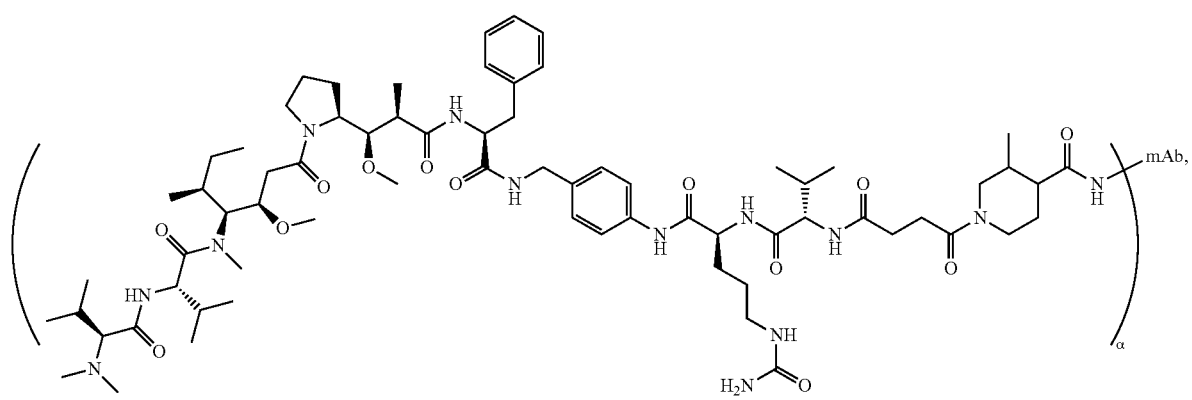

485 486
-continued
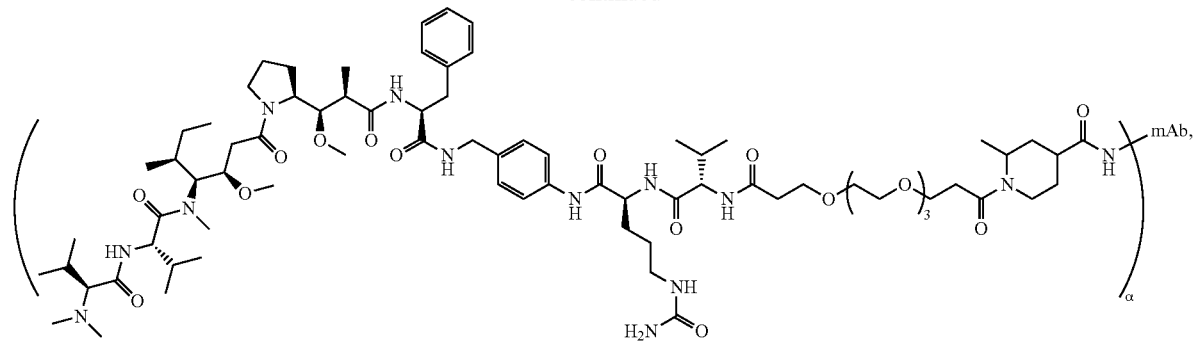
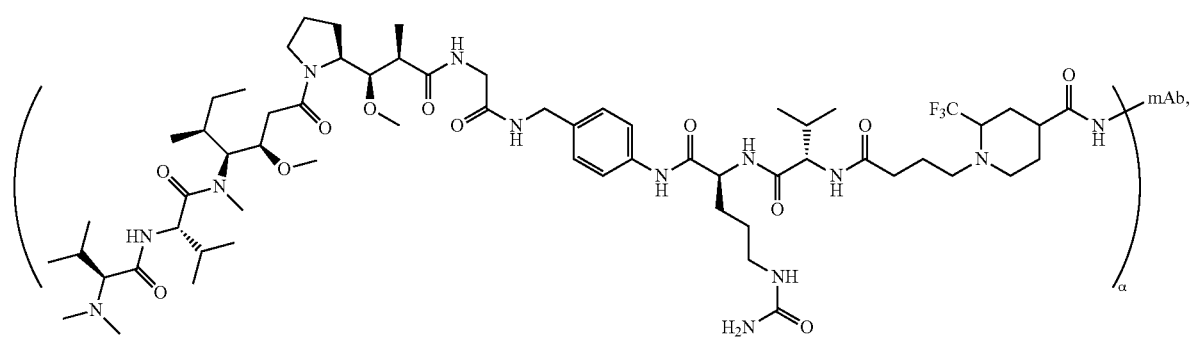
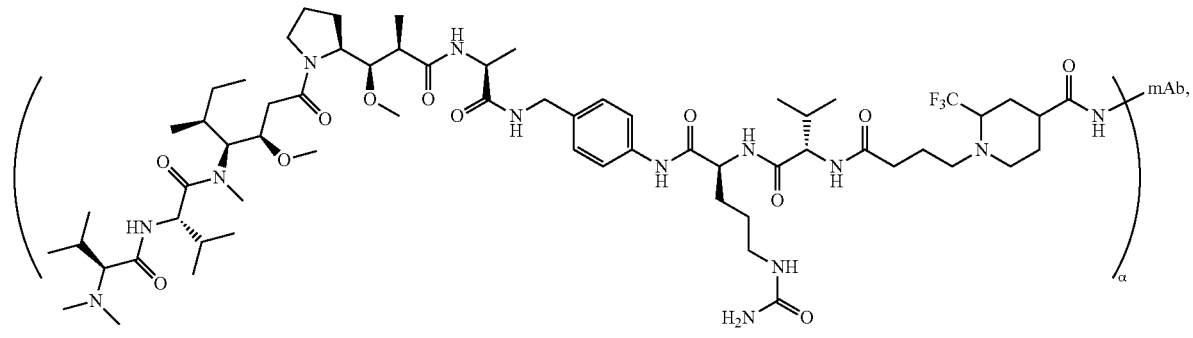
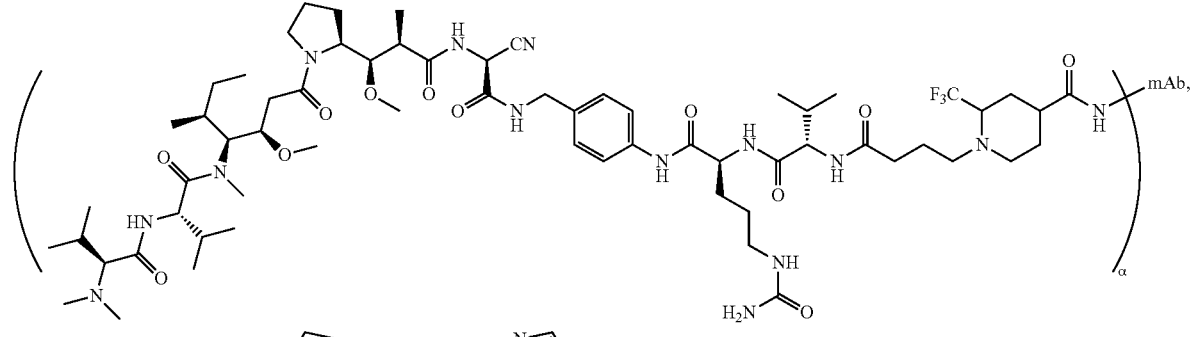
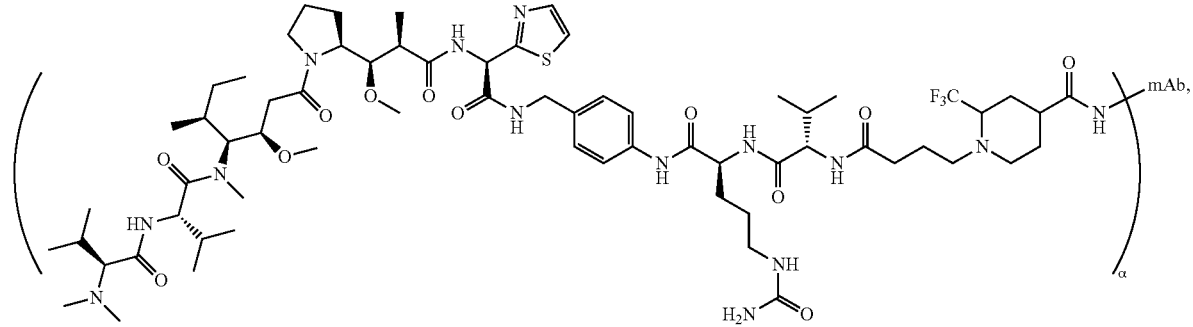

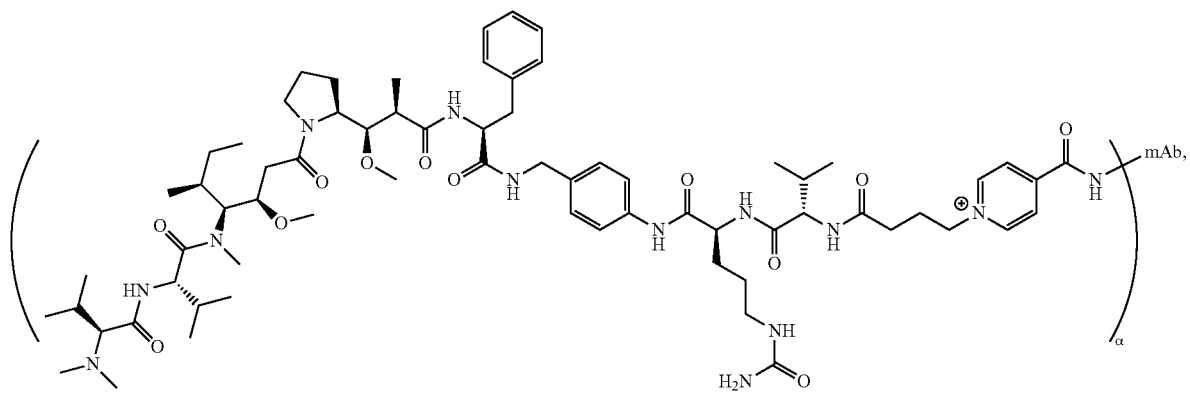
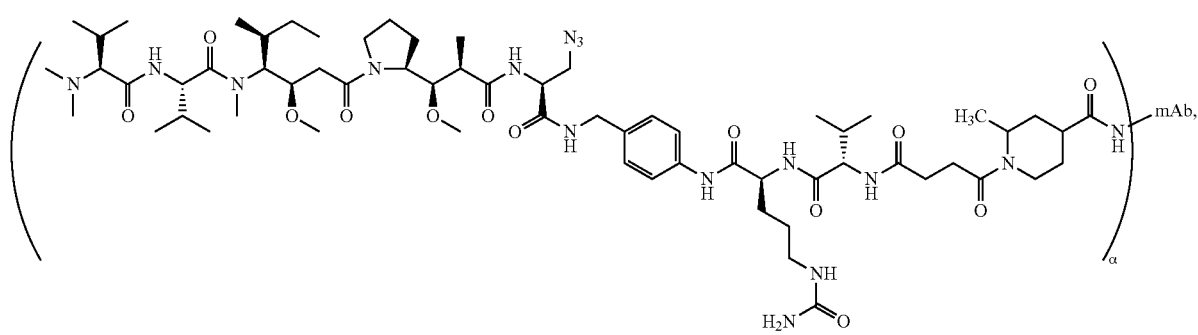
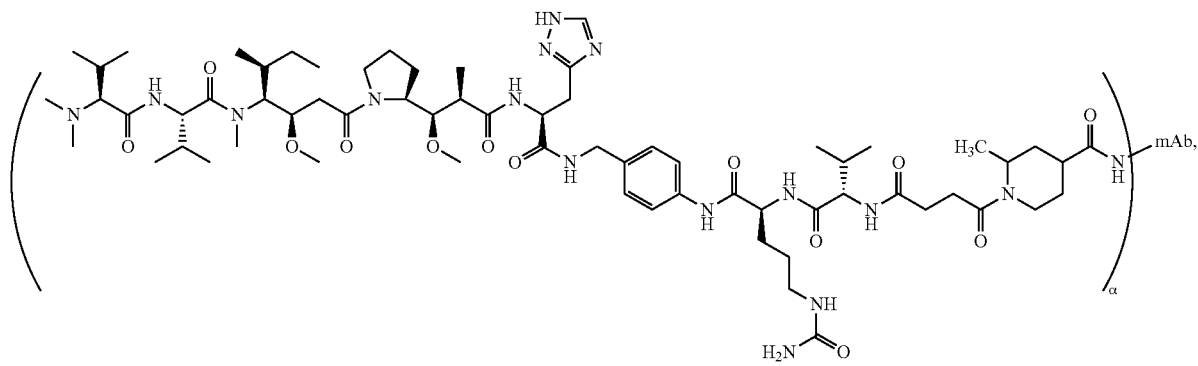
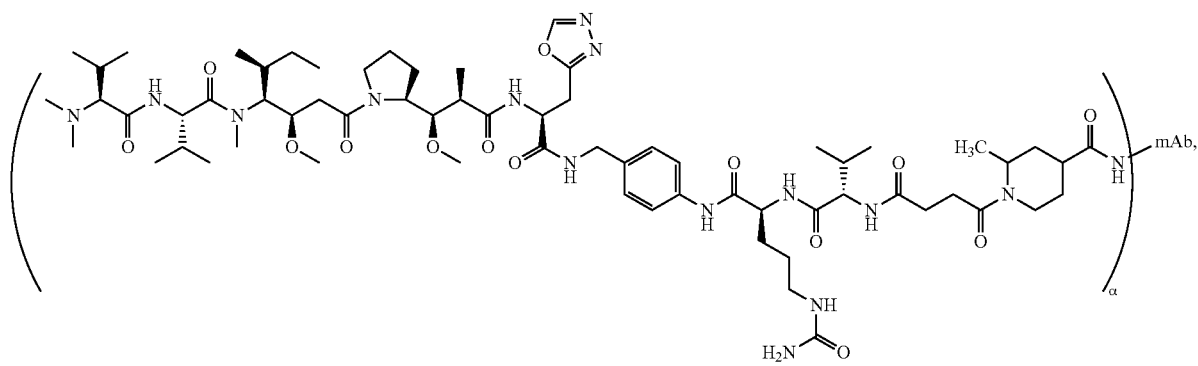

489                                                                 490
-continued
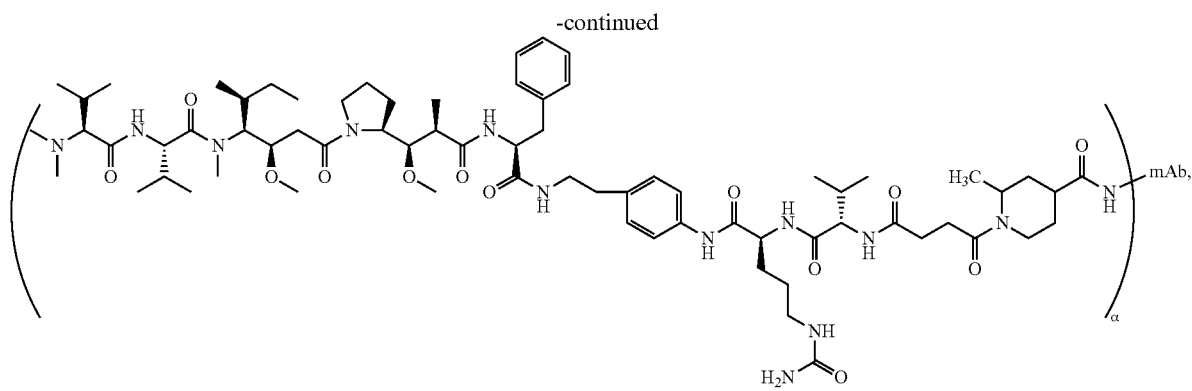
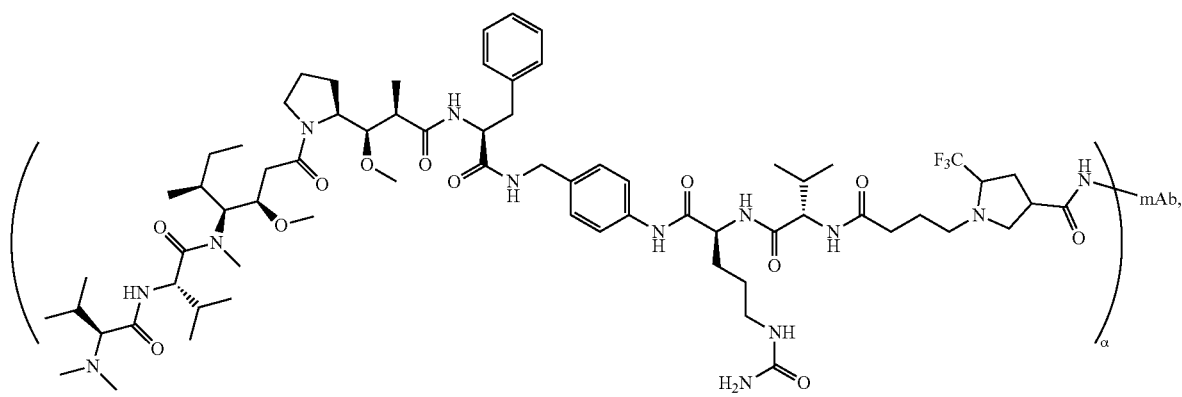
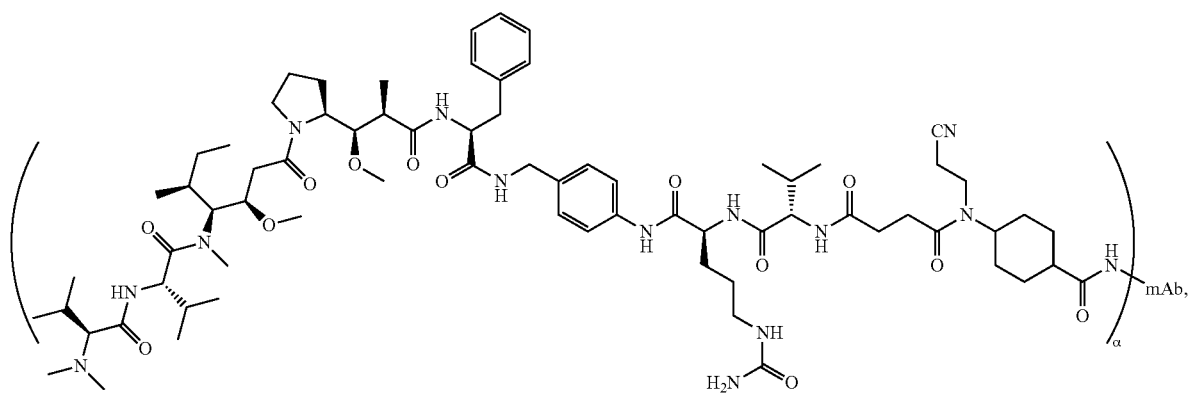
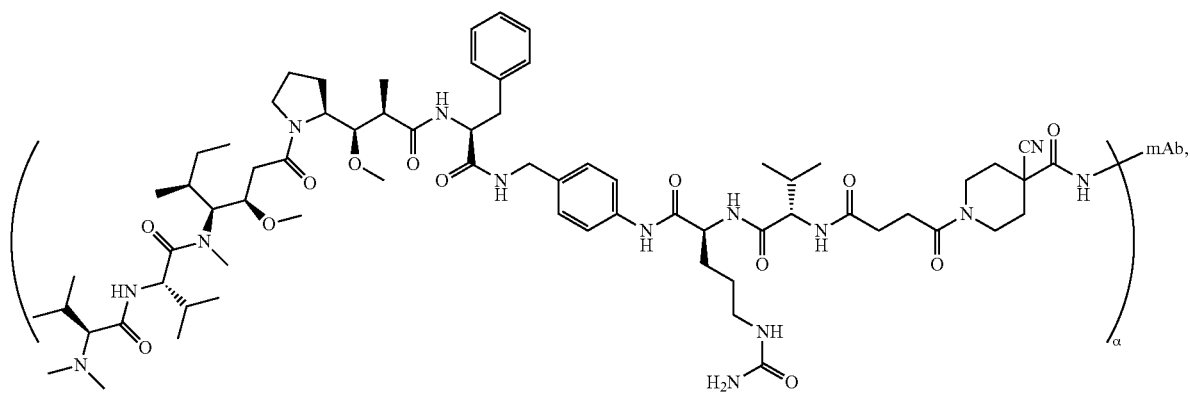

-continued
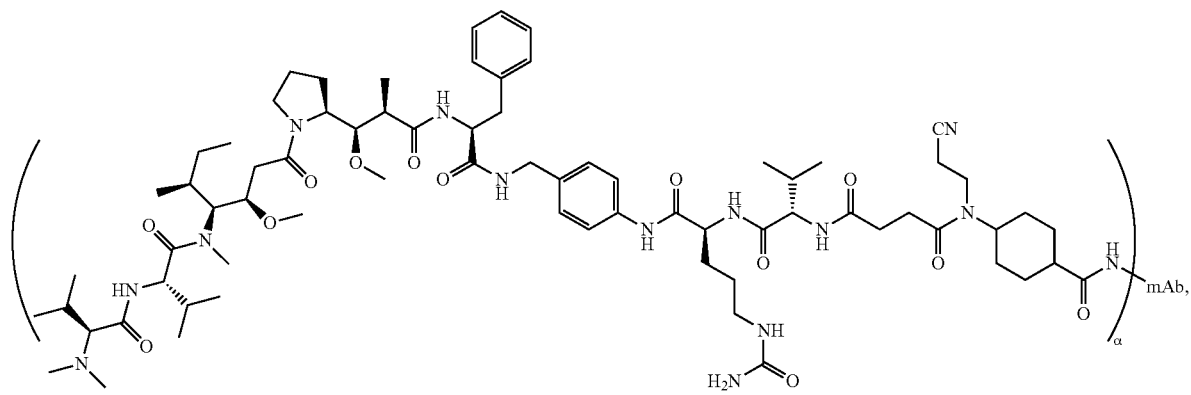
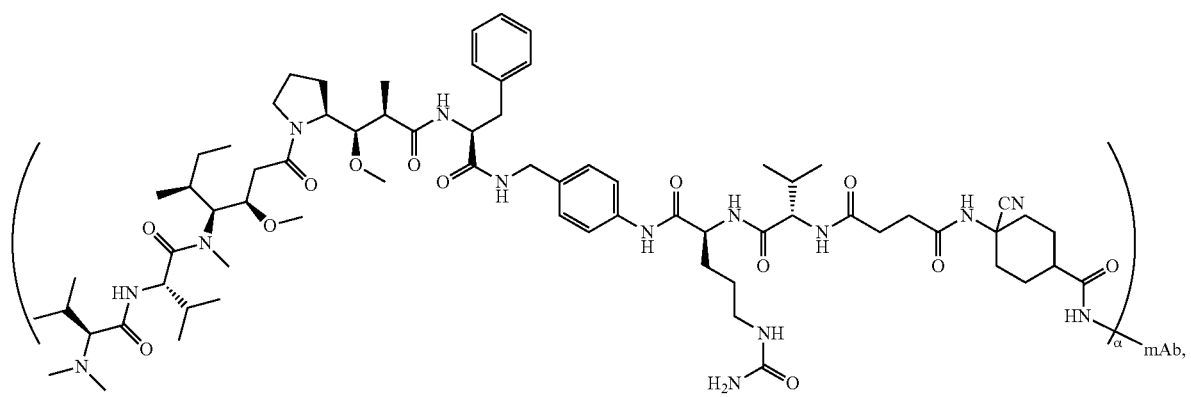
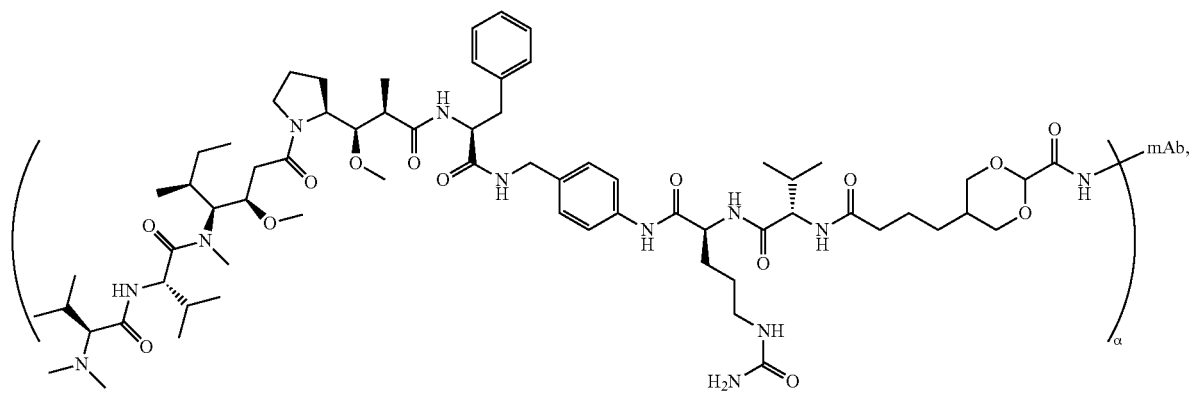
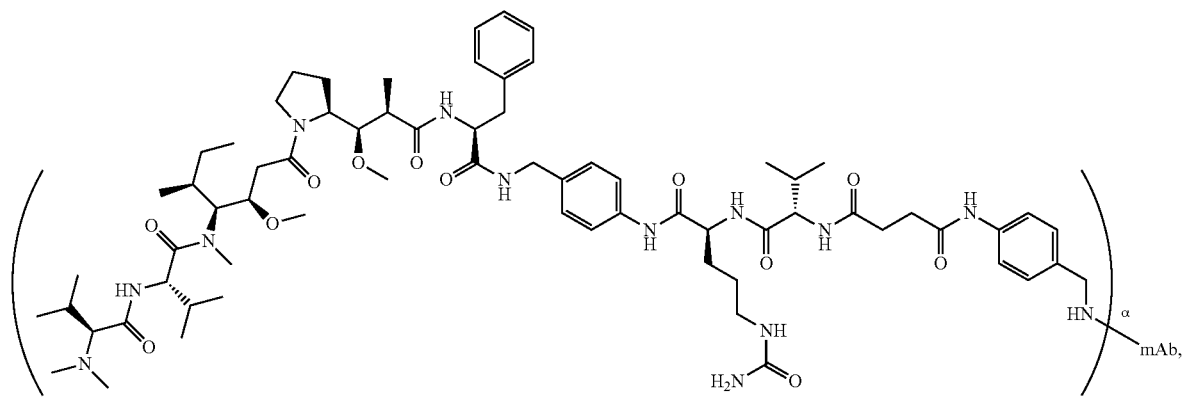

493 494
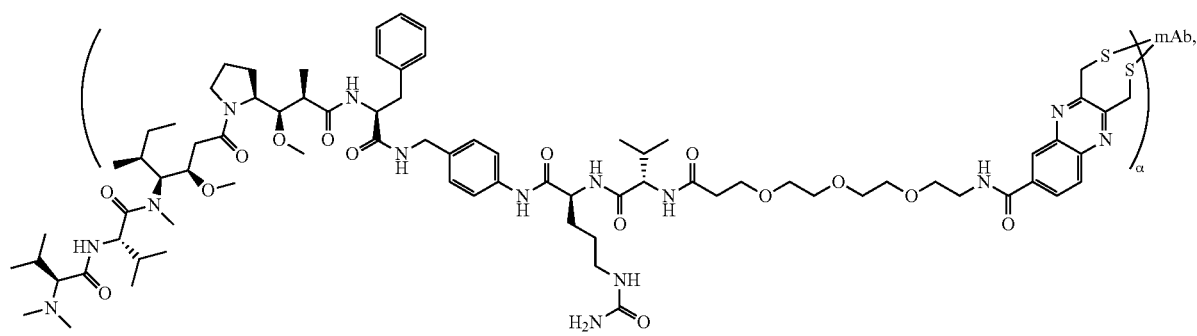
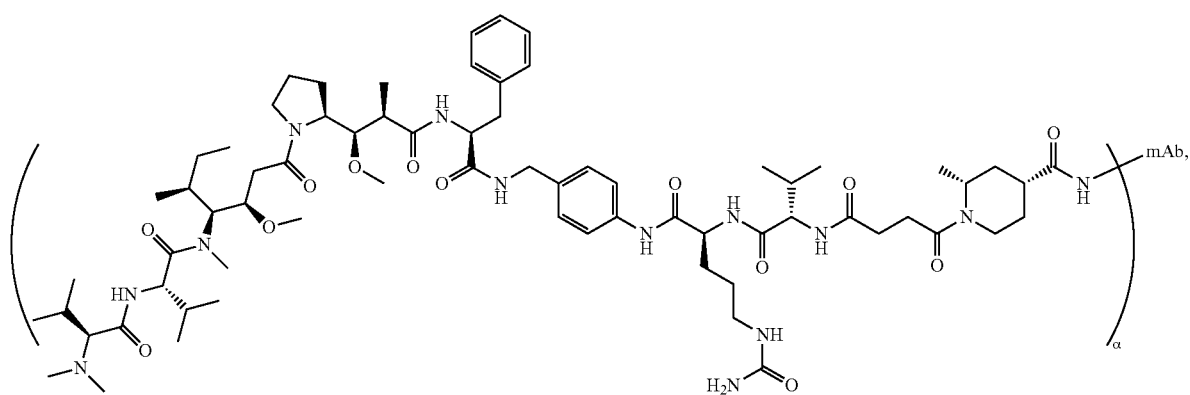
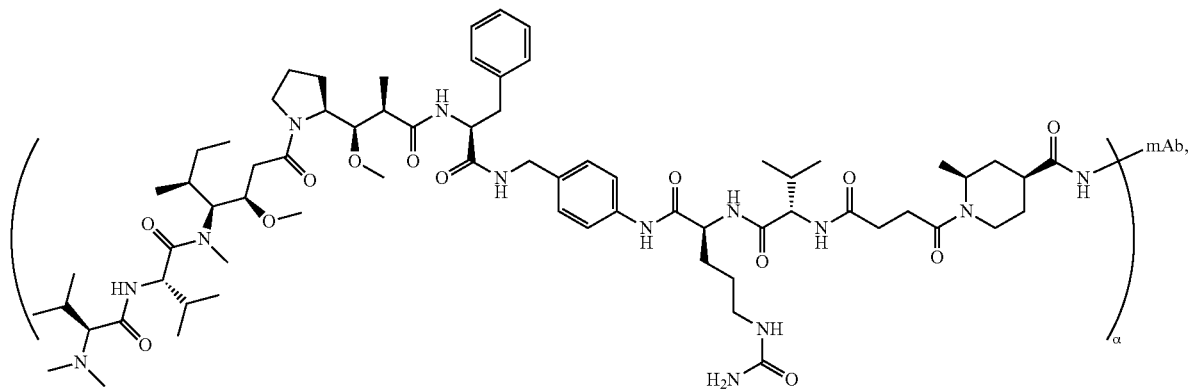
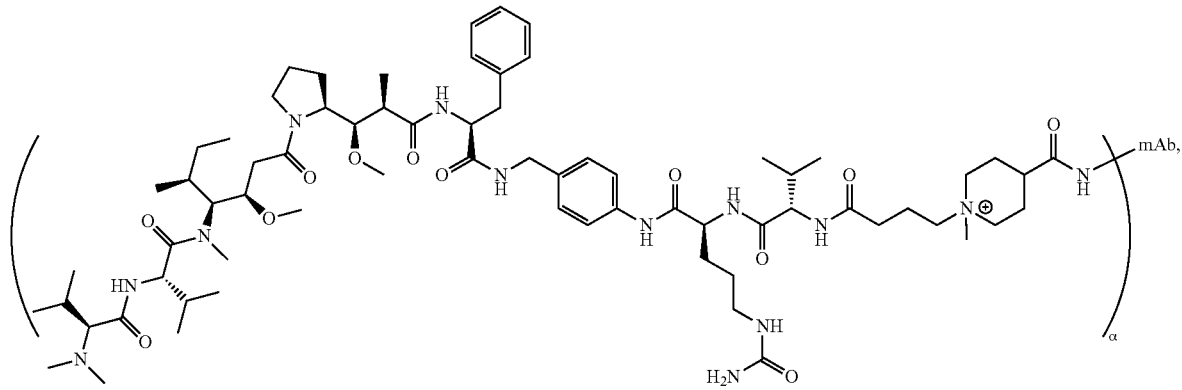

-continued
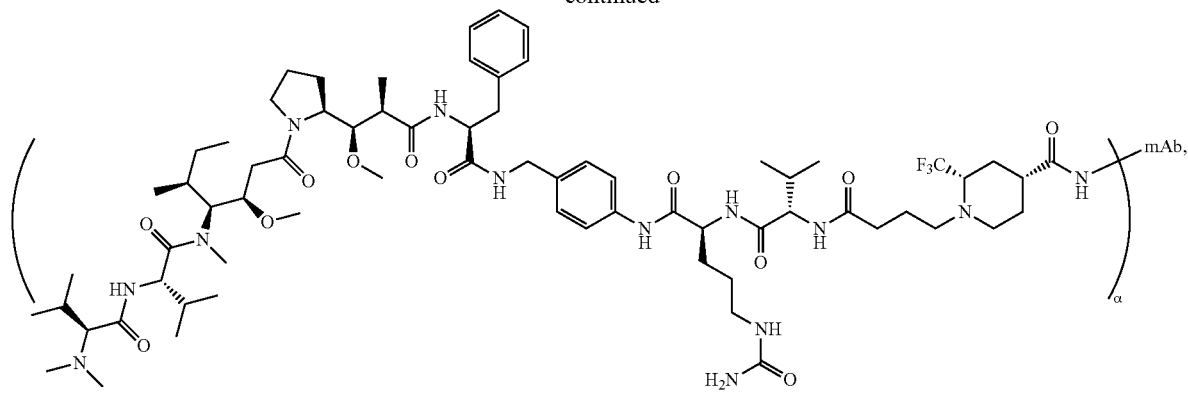
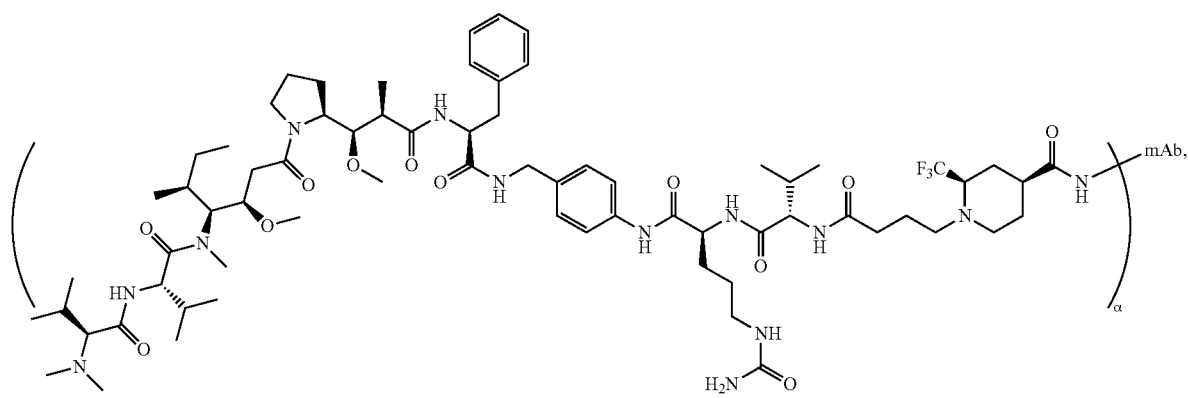
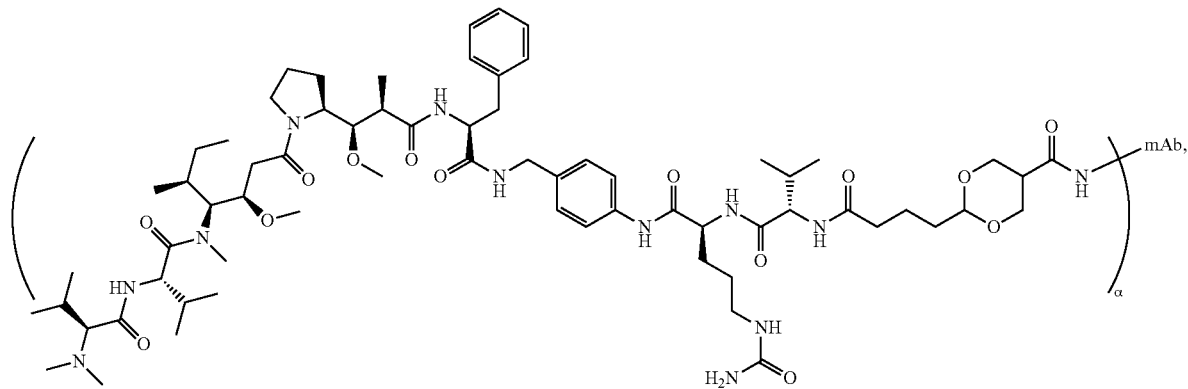
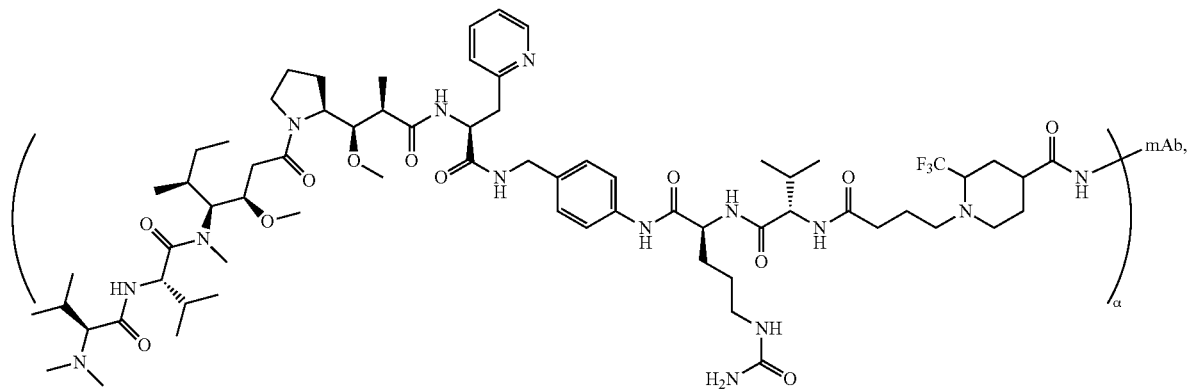

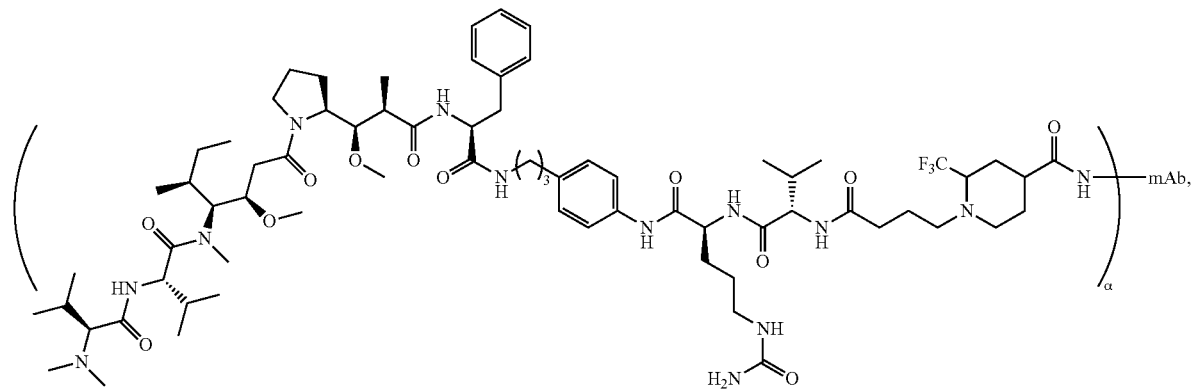
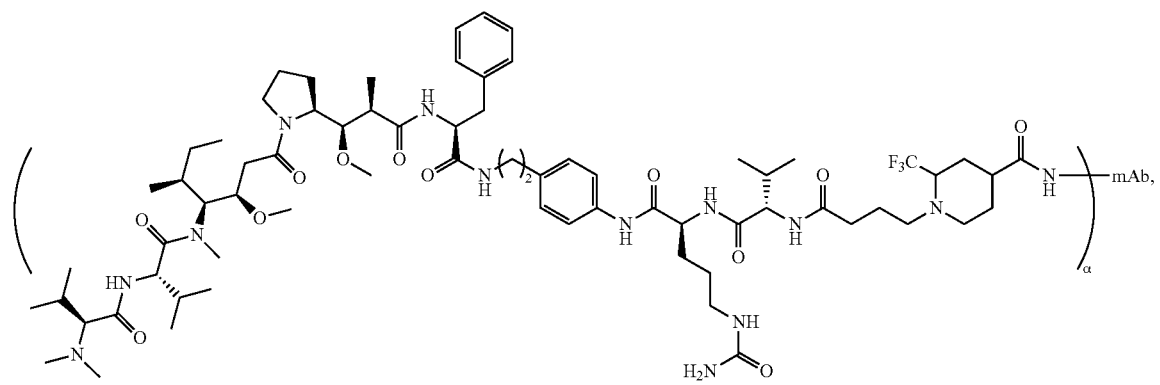
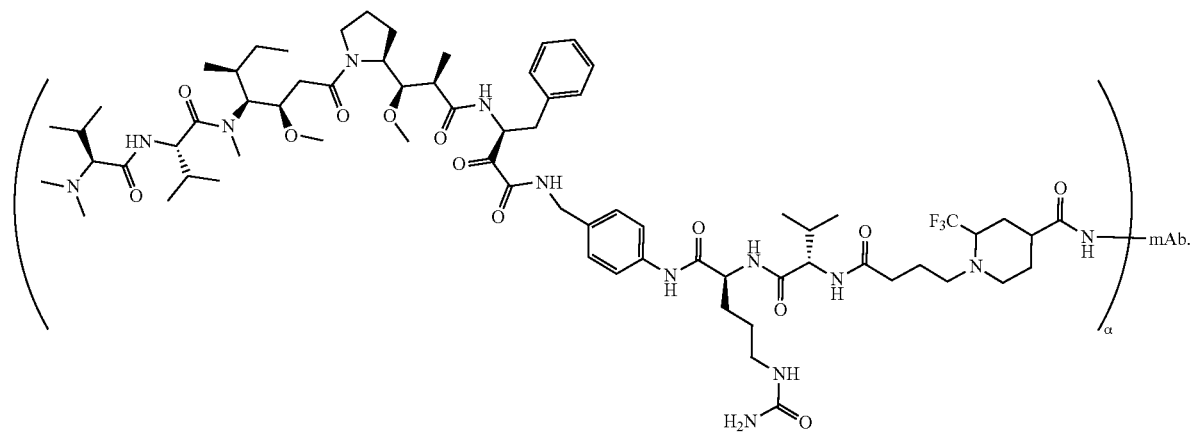

19. The conjugate of claim 3, which is selected from:
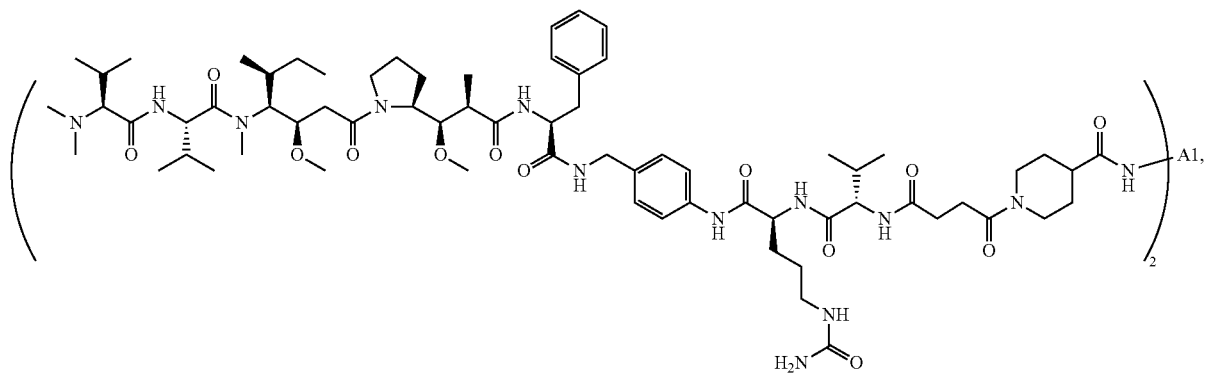
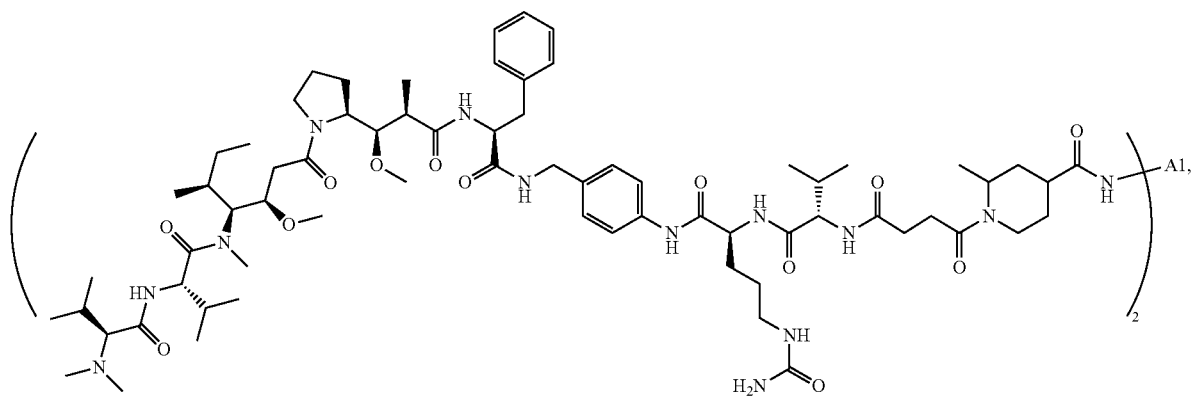
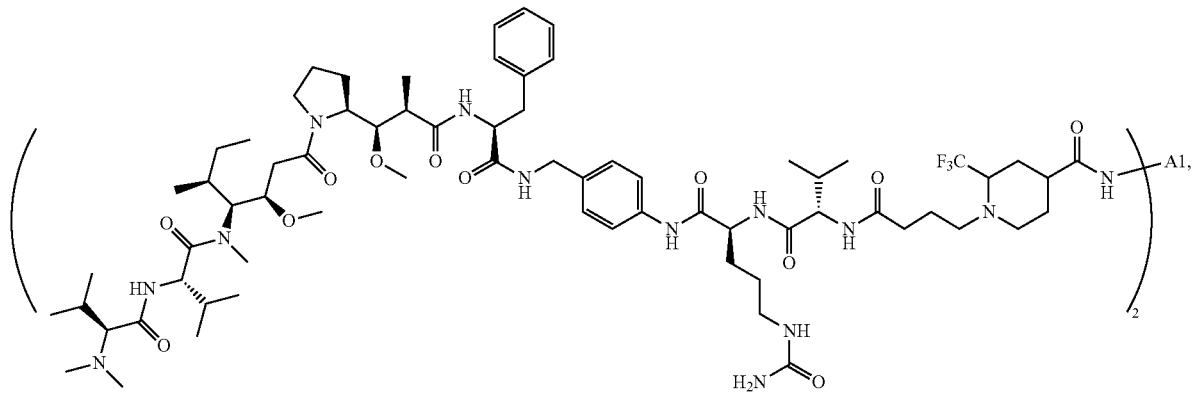
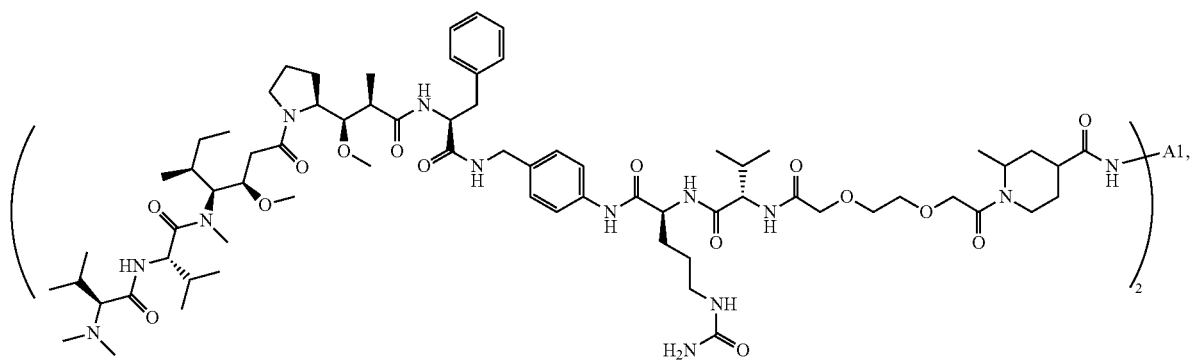

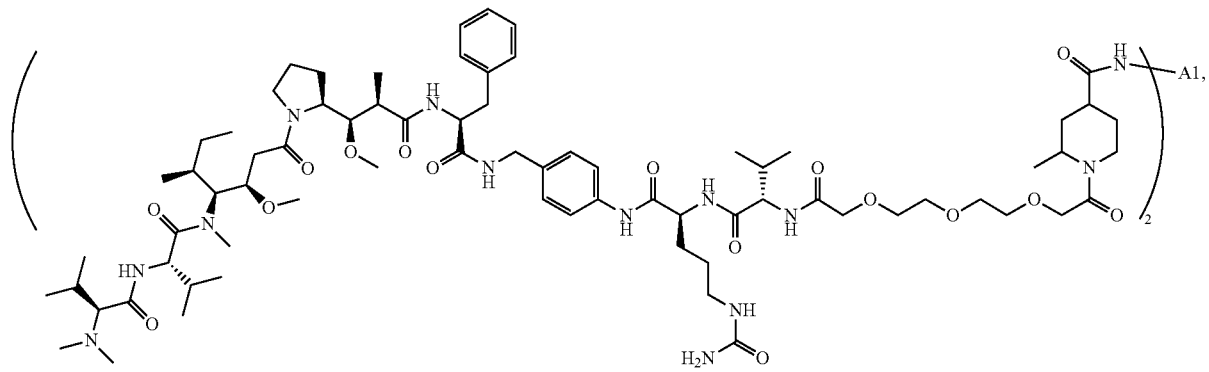
BT001009
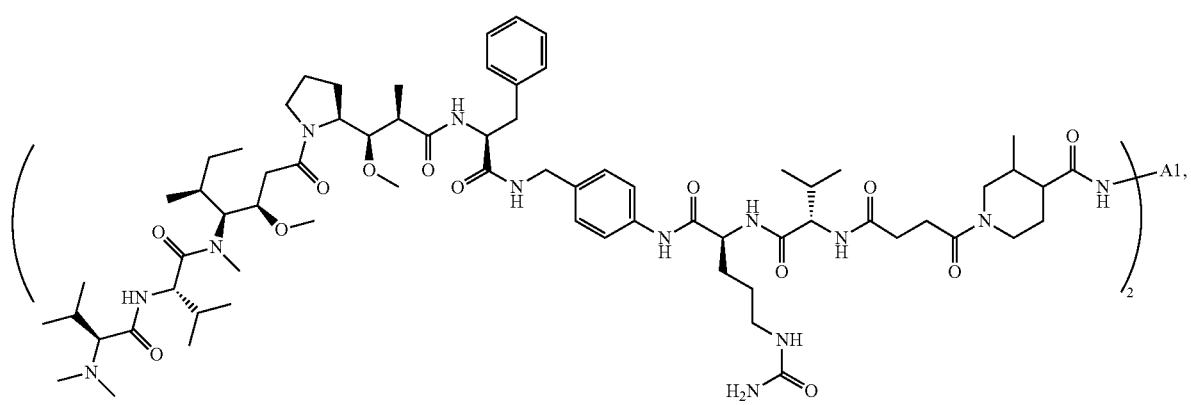
BT001010
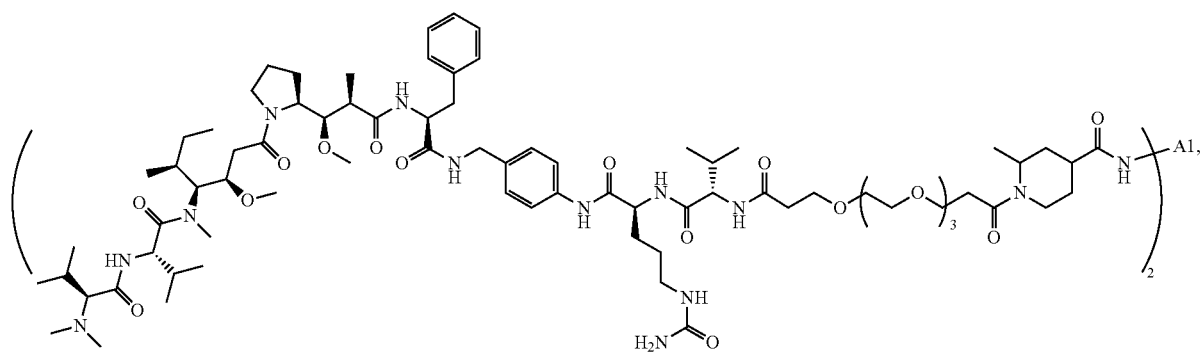
BT001011
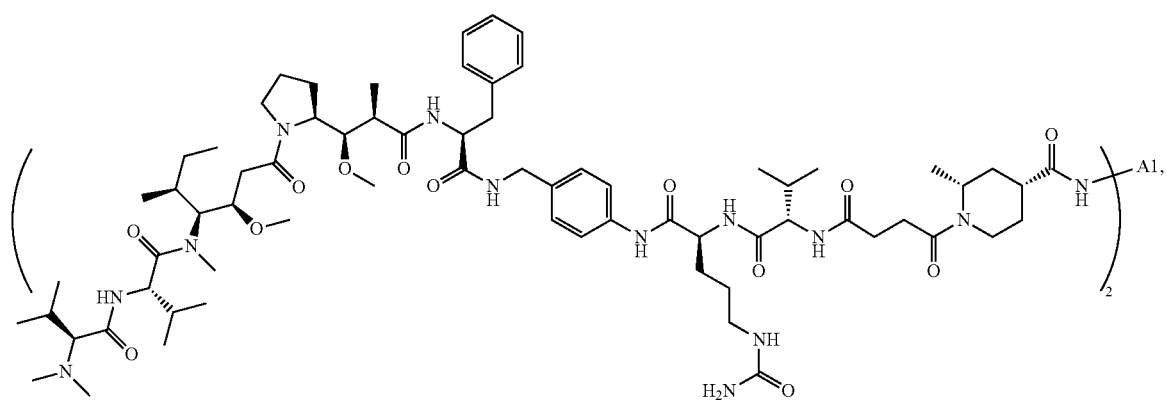
BT001012

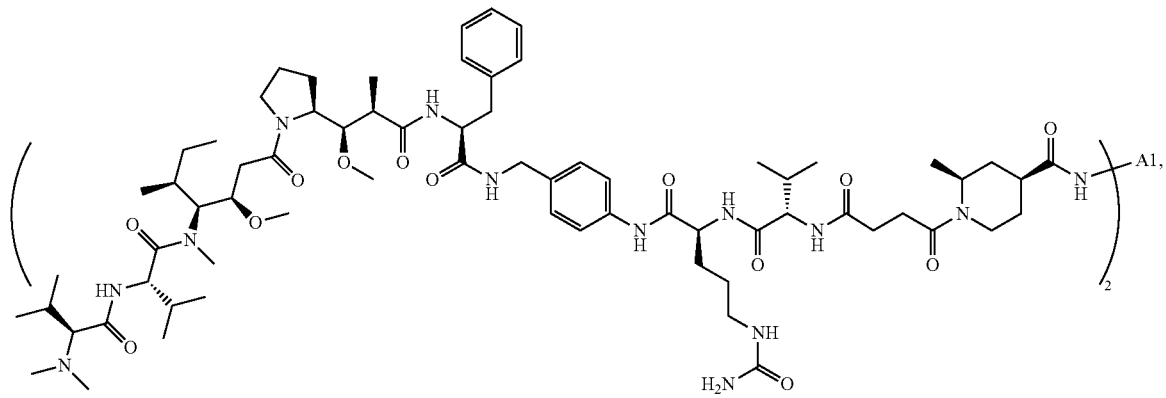
BT001013
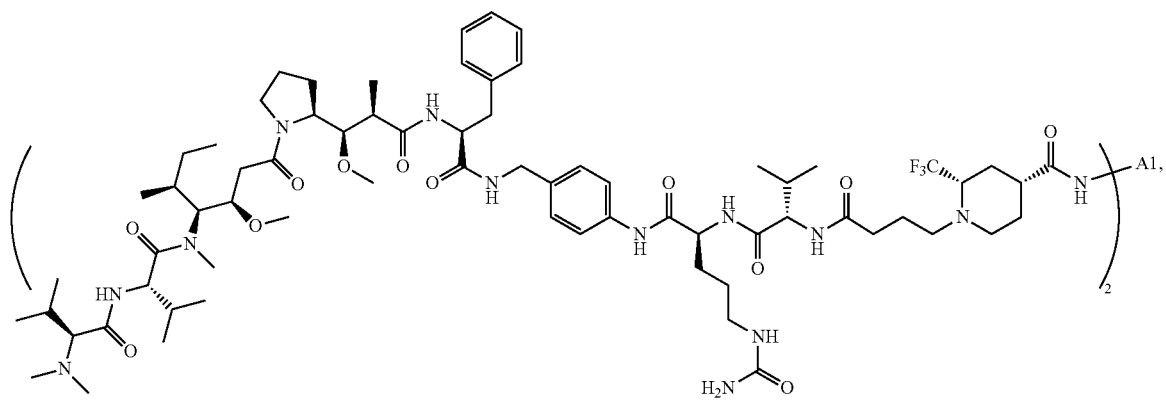
BT001016
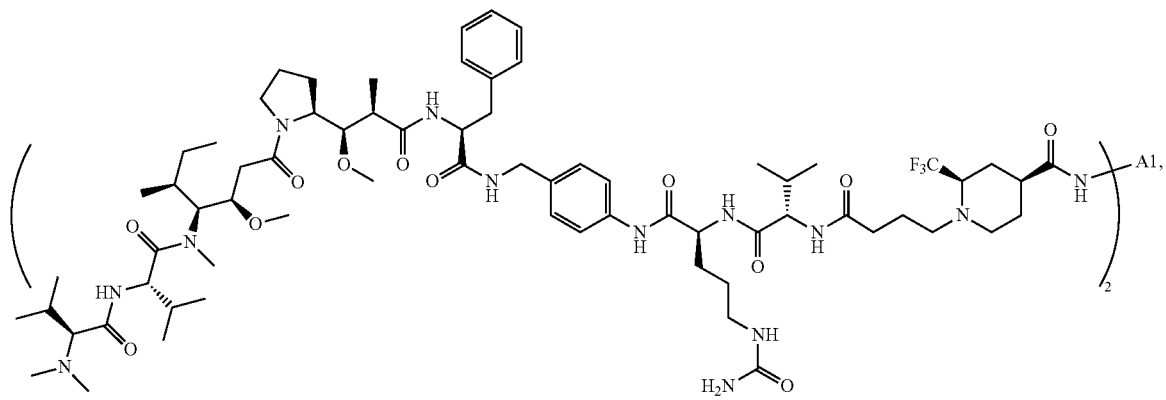
BT001017

-continued
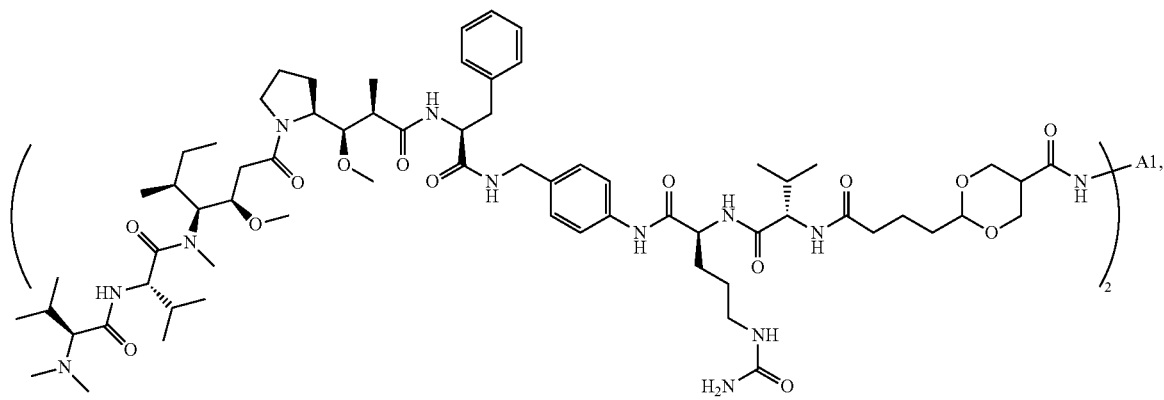
BT001018
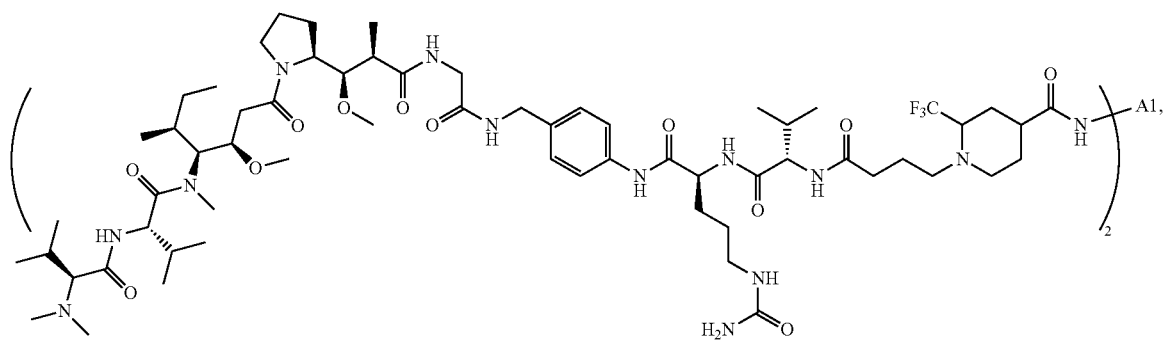
BT001019
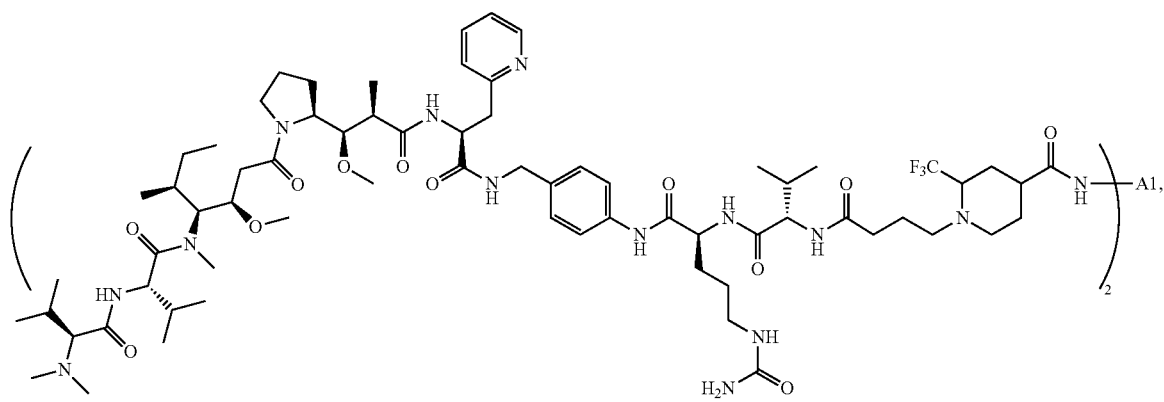
BT001021
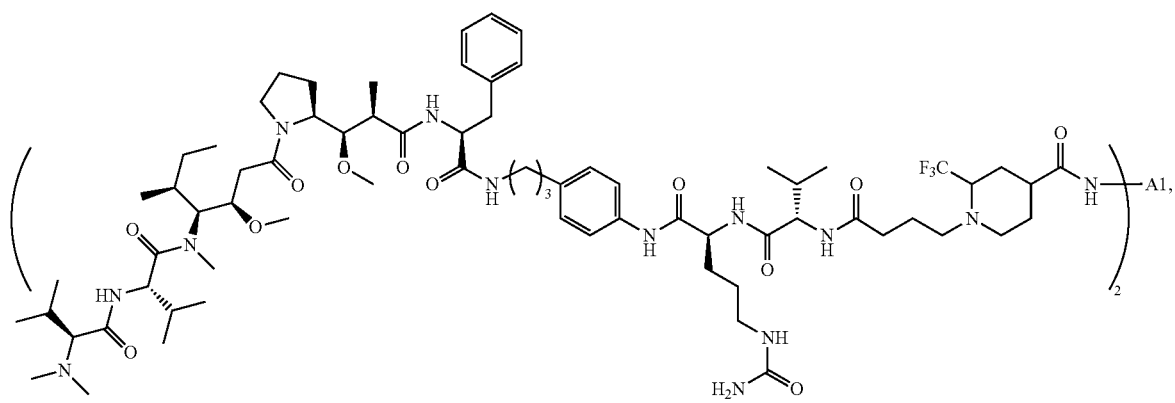
BT001022

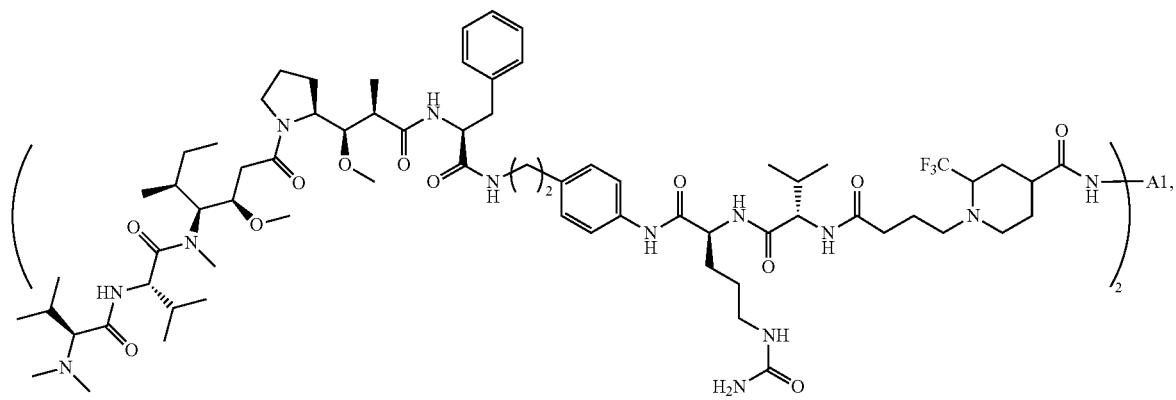
BT001023
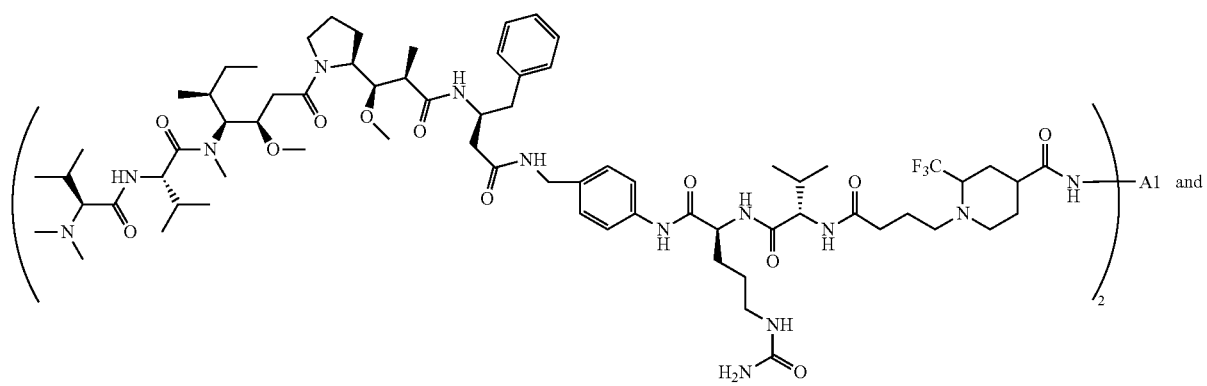
BT001024 and
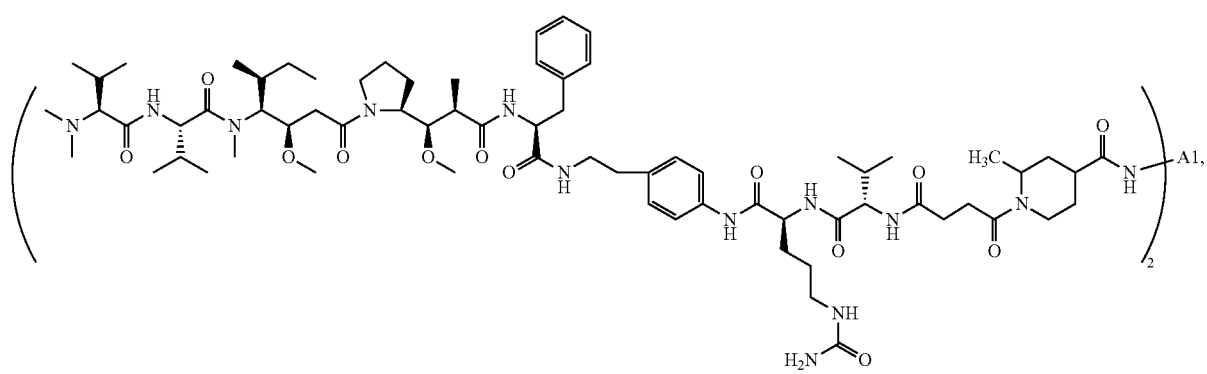
BT001025 wherein A1 is a group obtained after removing 2 amino groups from trastuzumab; or
the conjugate is selected from:
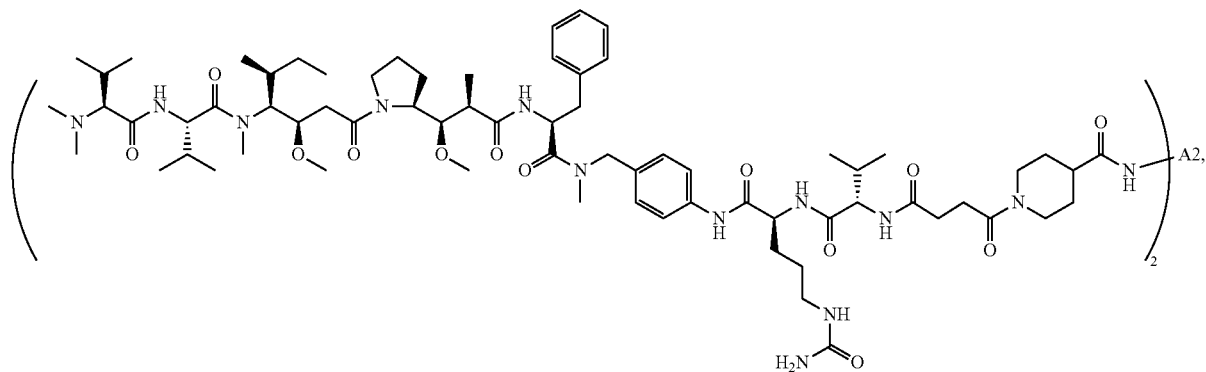
BT001026
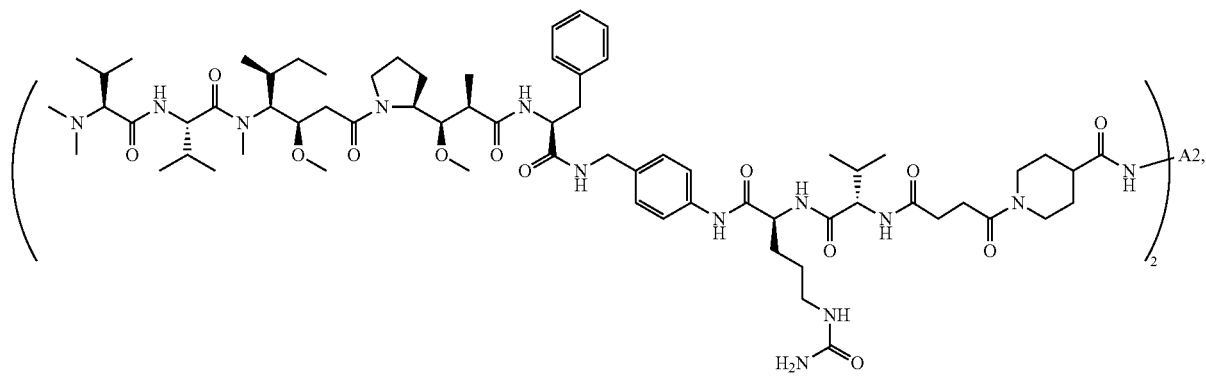
BT001027
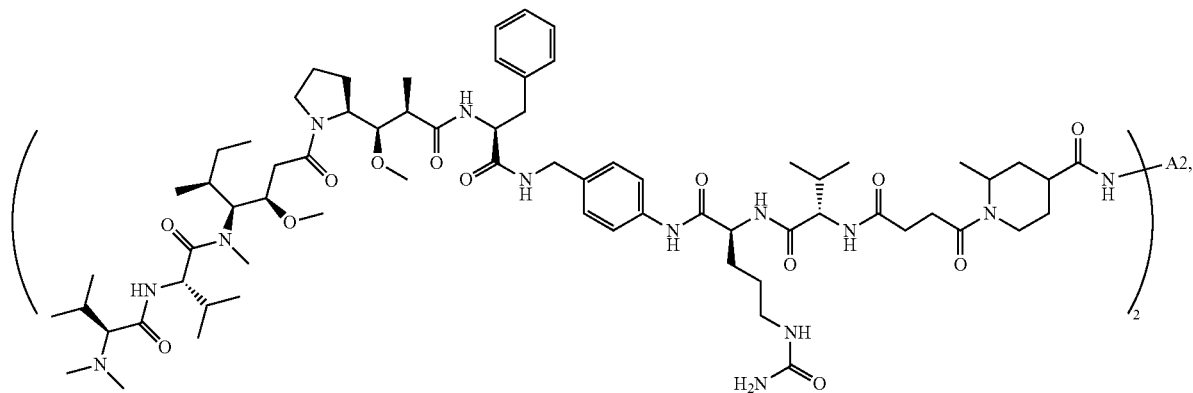
BT001028

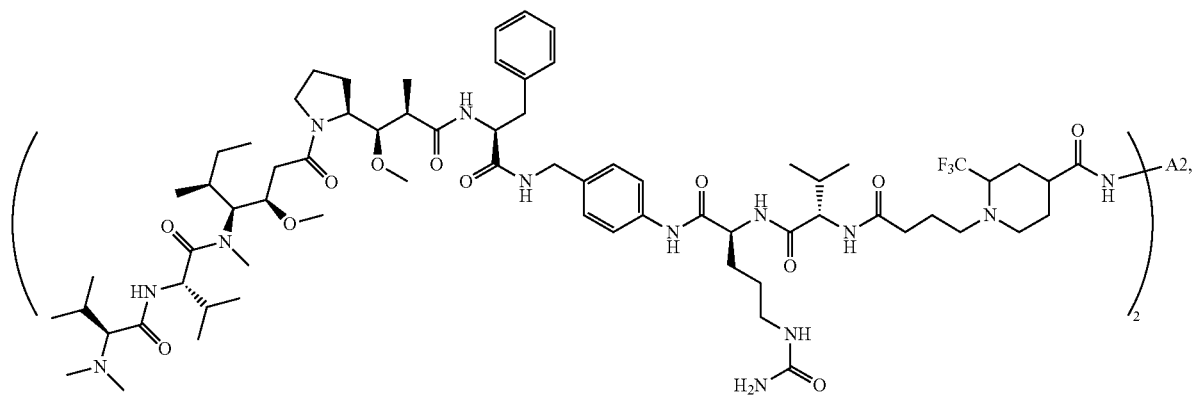
BT001029
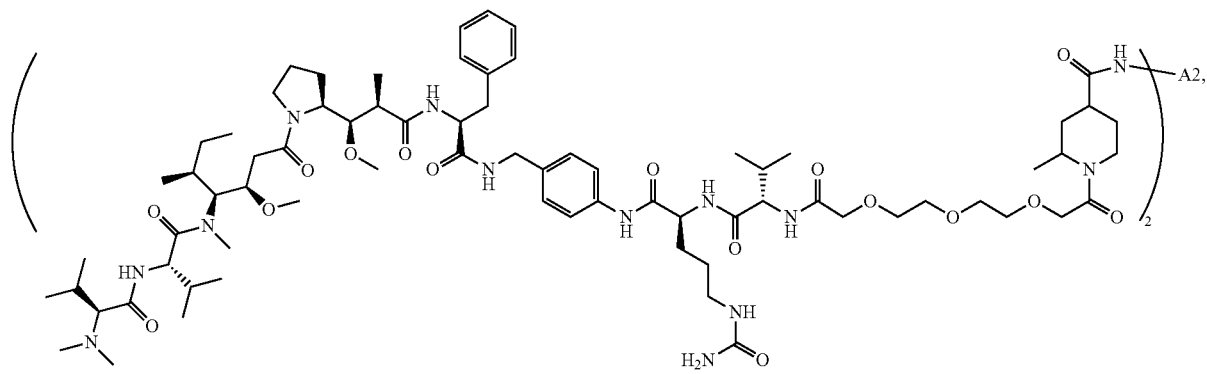
BT001030
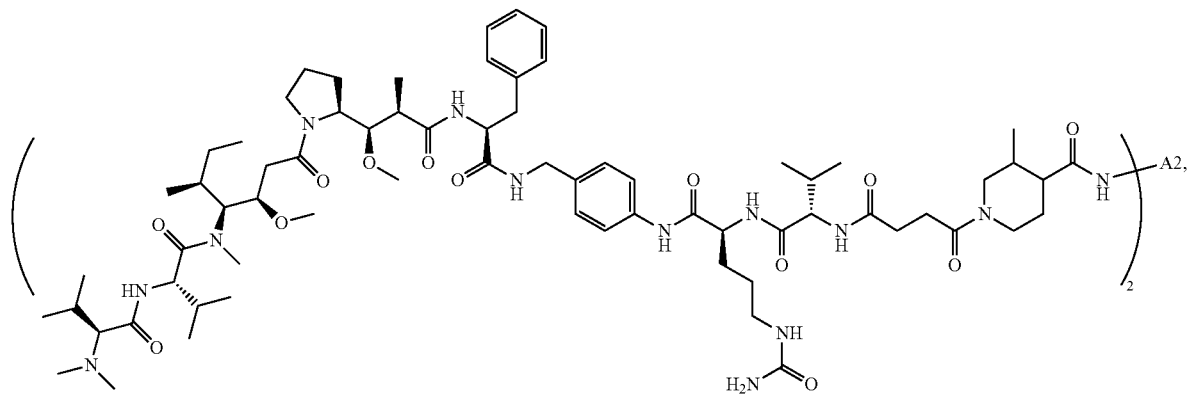
BT001031
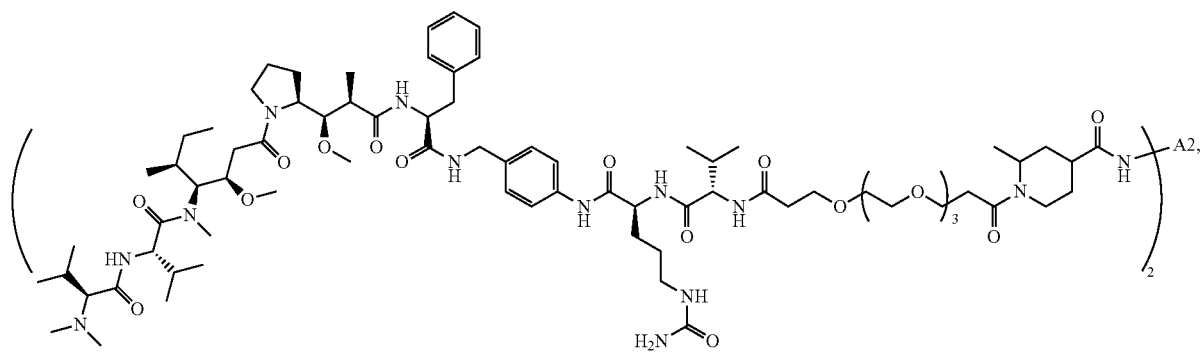
BT001032

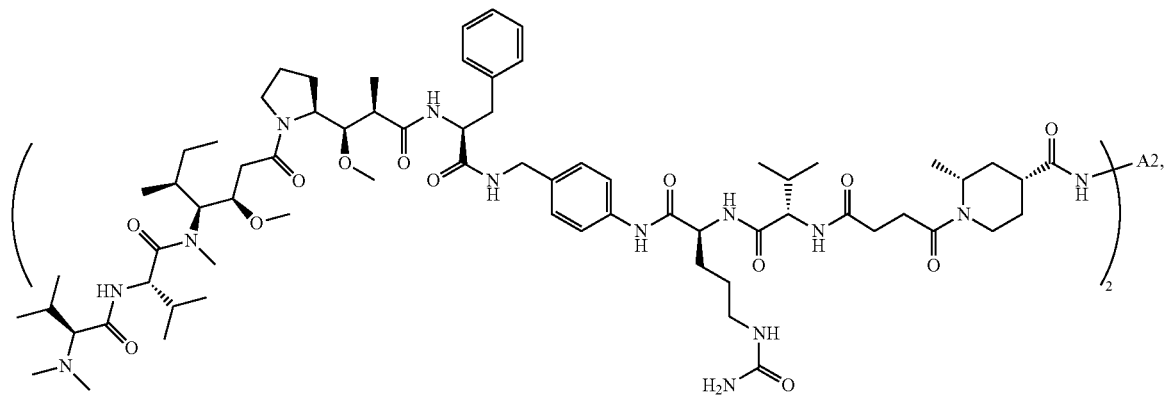
BT001033
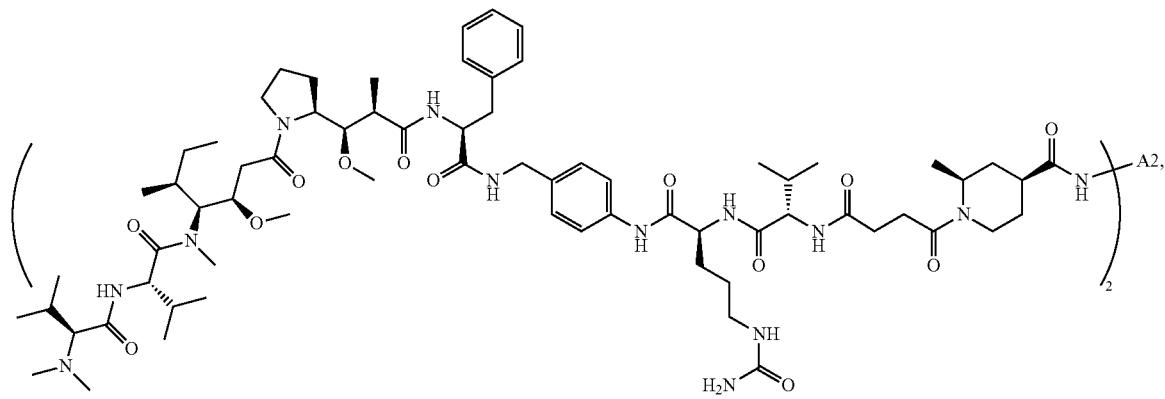
BT001034
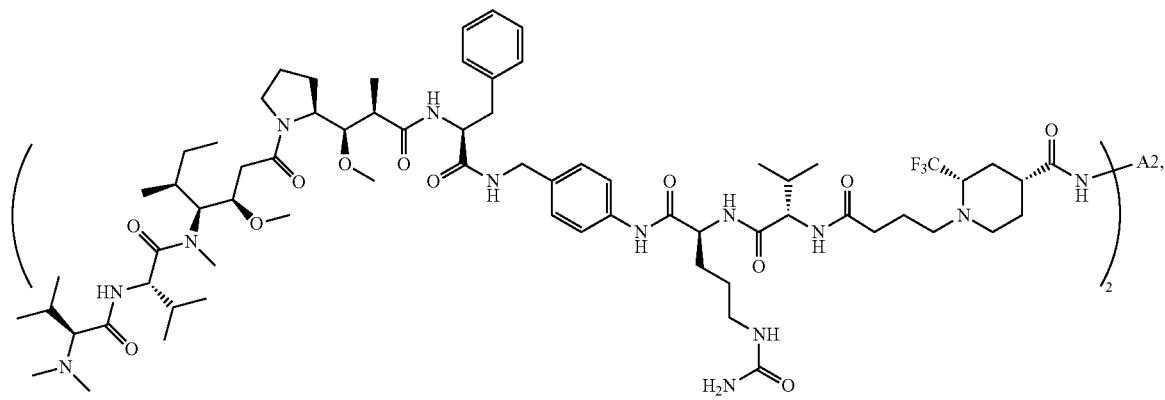
BT001035

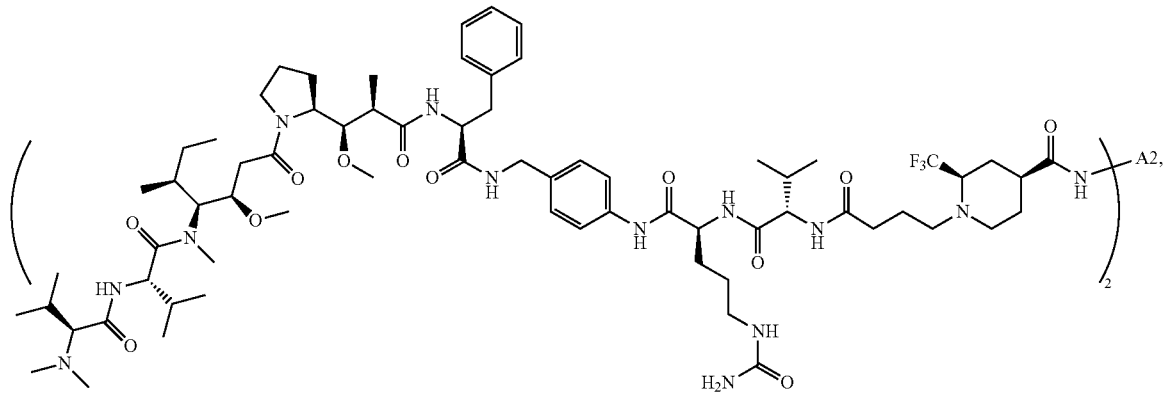
BT001036
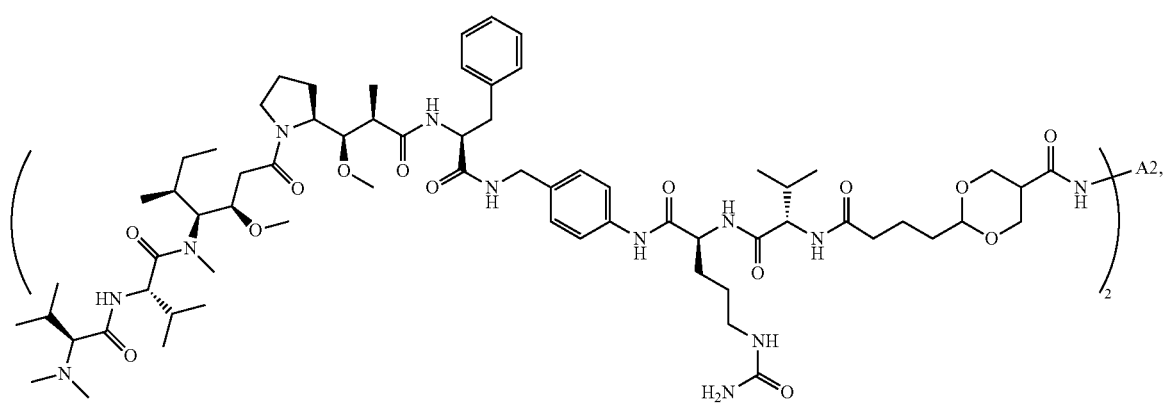
BT001037
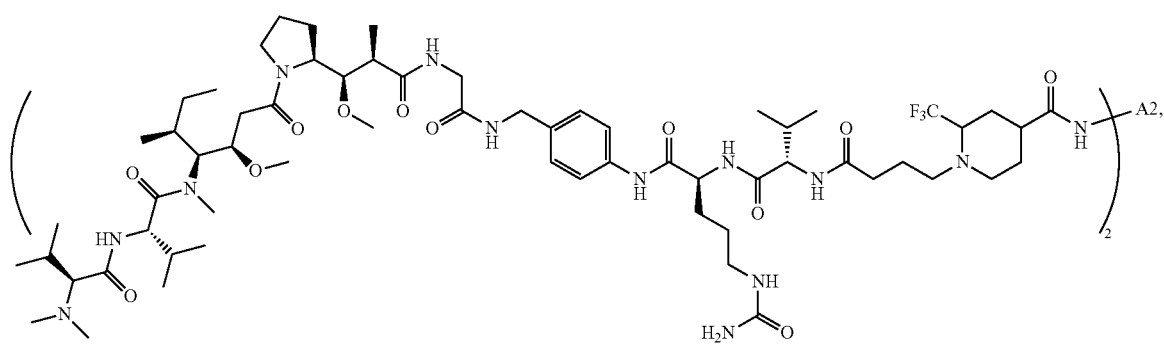
BT001038
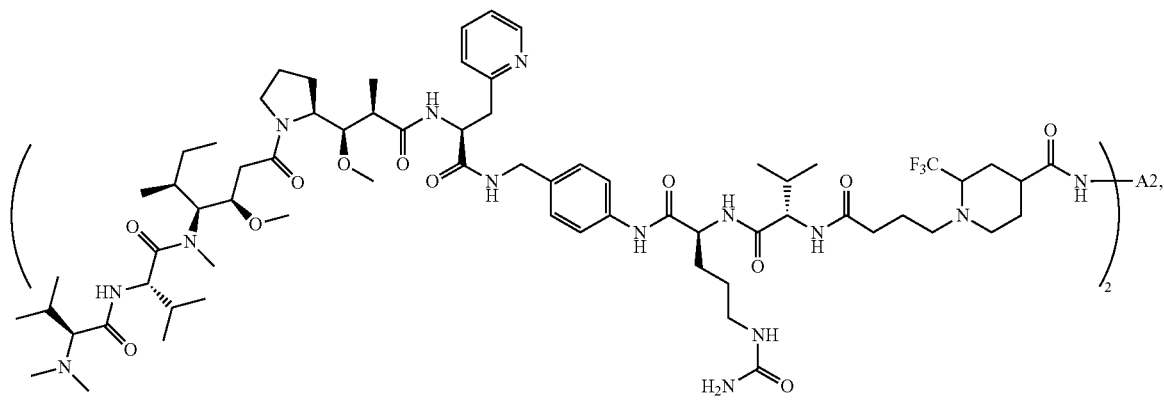
BT001039

-continued
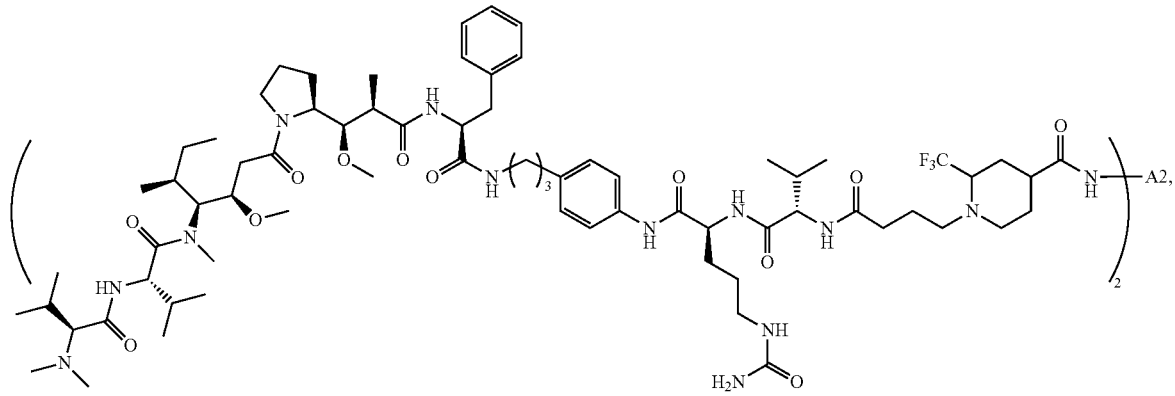
BT001040
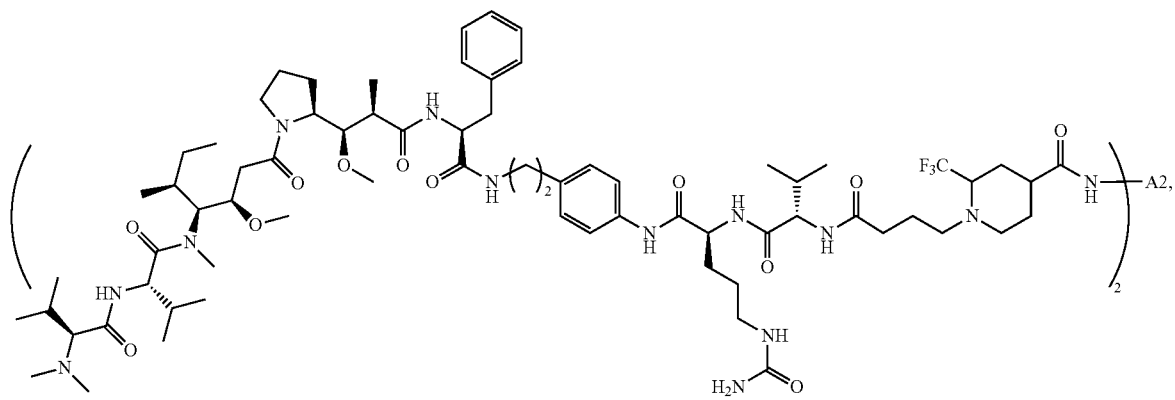
BT001041
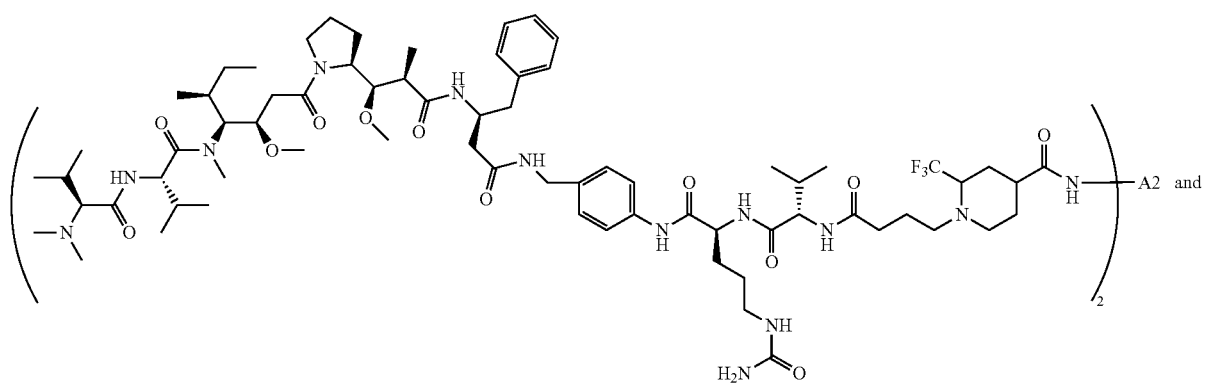
BT001042 and
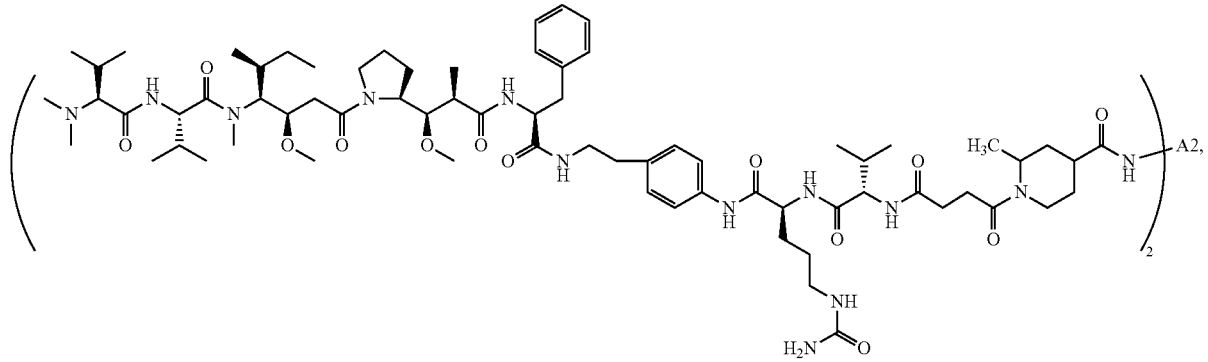
BT001043 wherein A2 is a group obtained after removing 2 amino groups from pertuzumab; or
the conjugate is selected from:
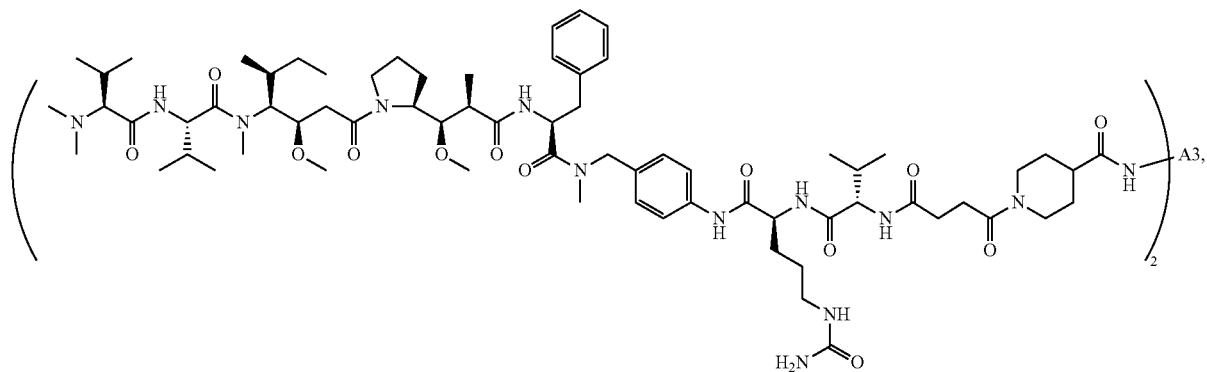
BT001044
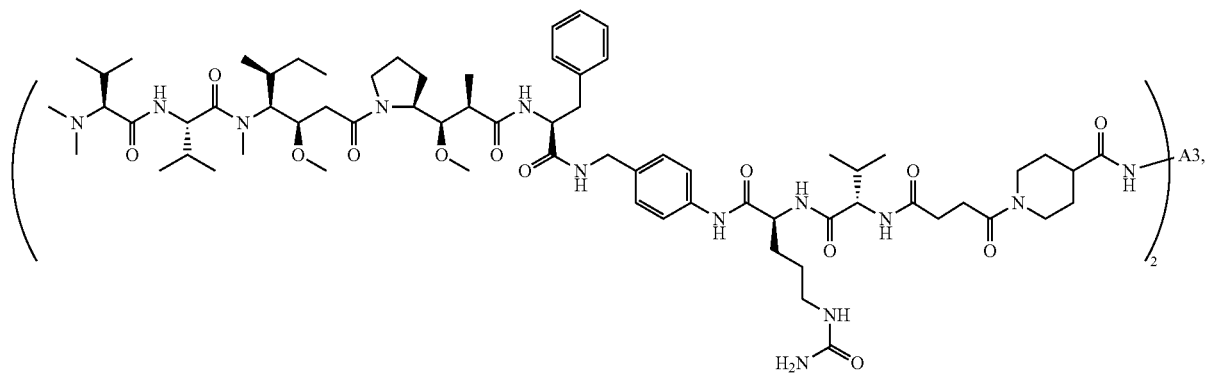
BT001045
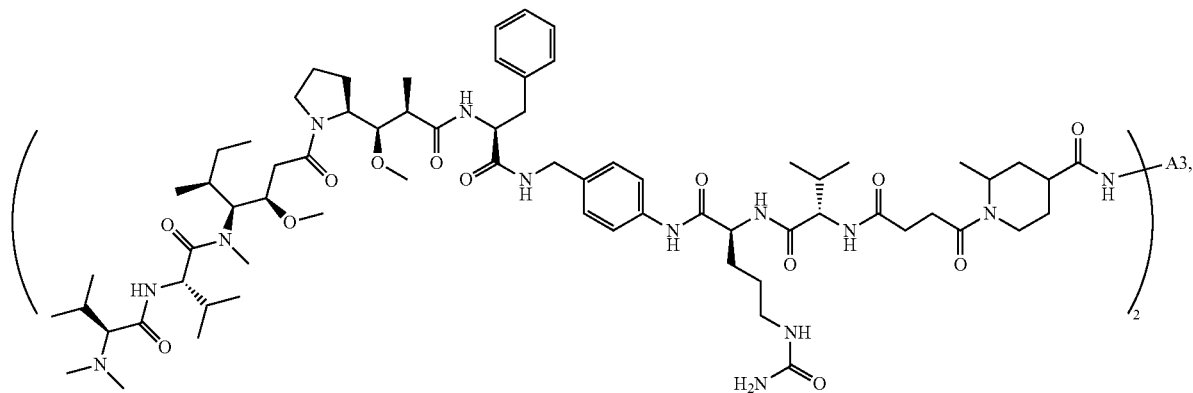
BT001014

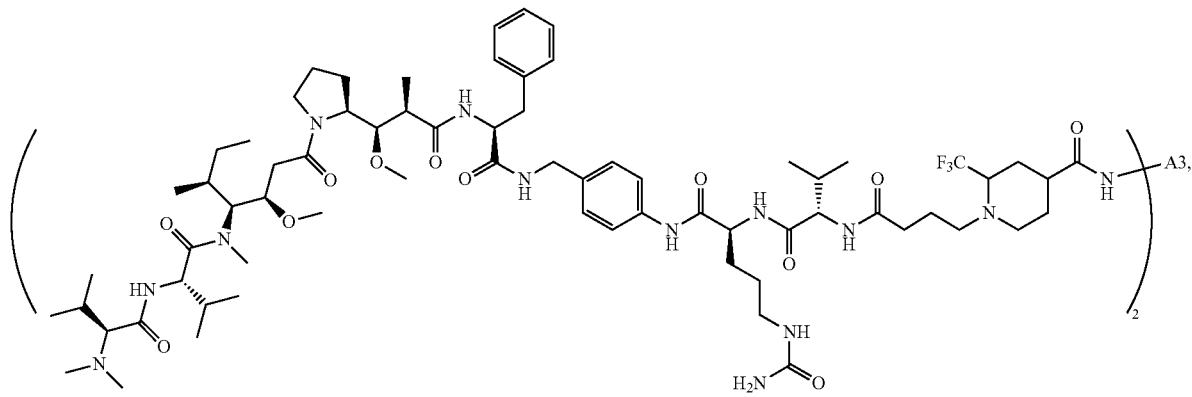
BT001015
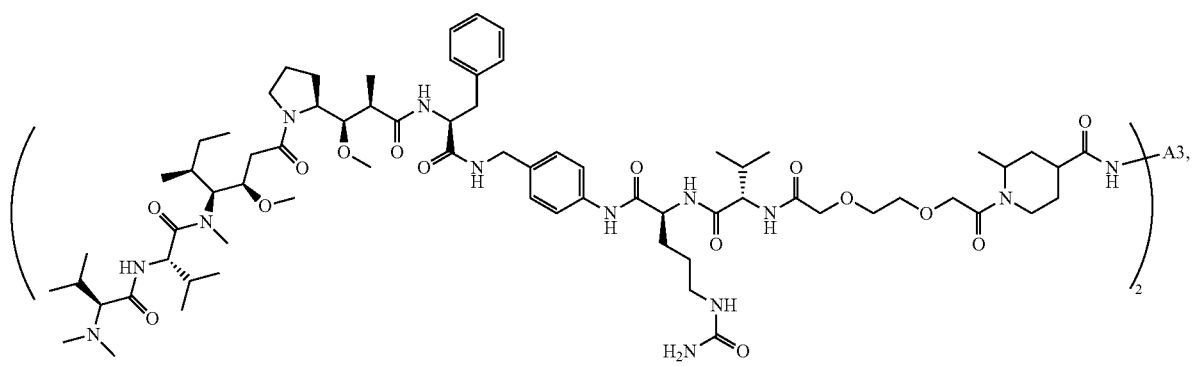
BT001046
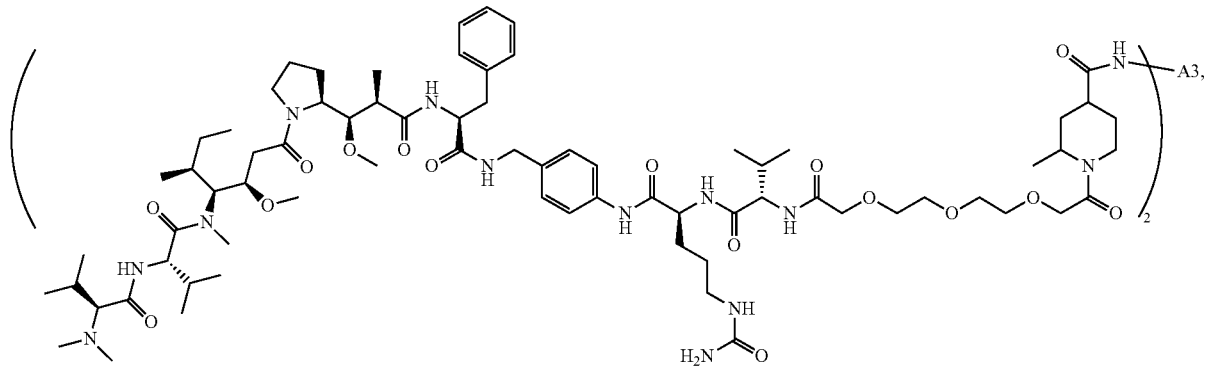
BT001047
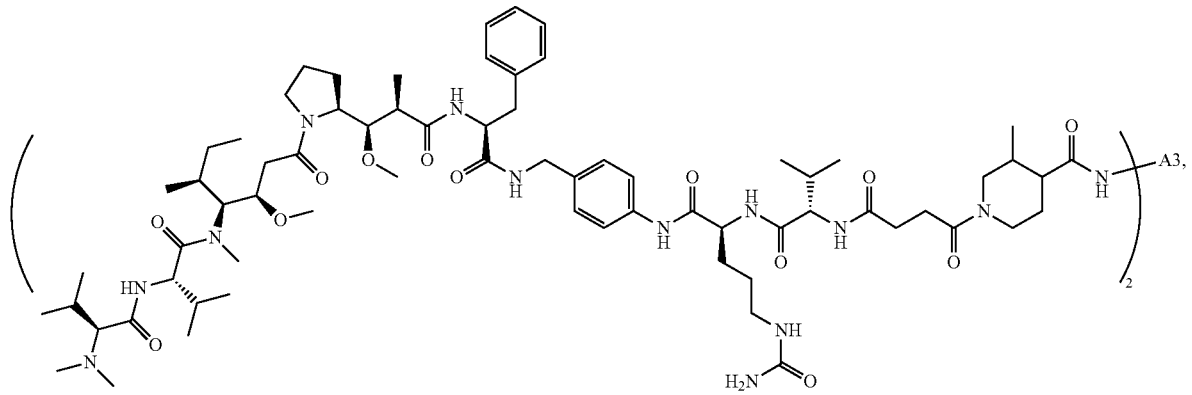
BT001048

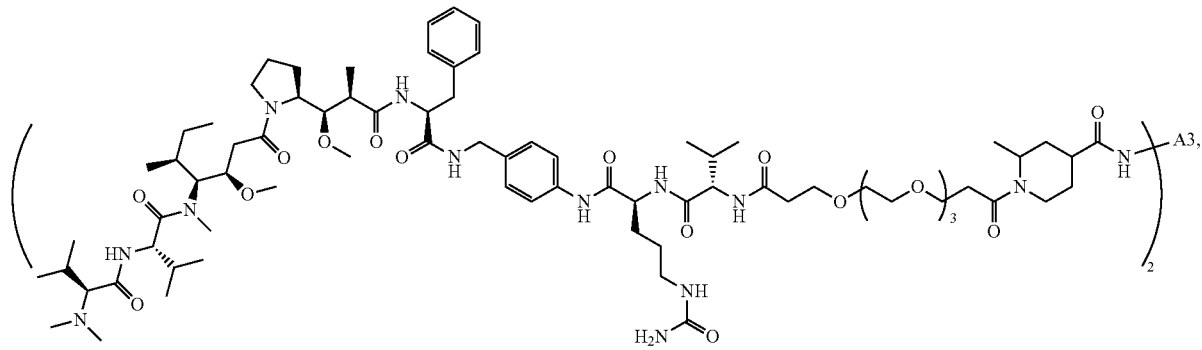
BT001049
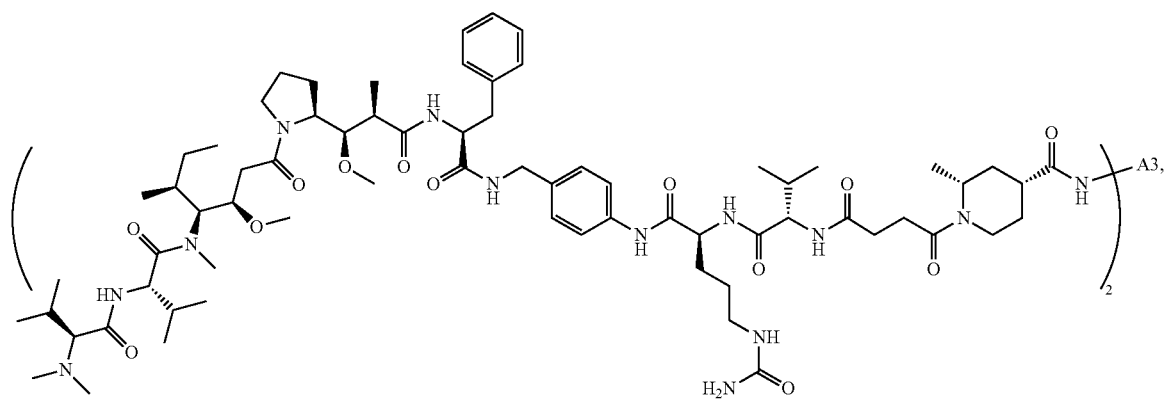
BT001050
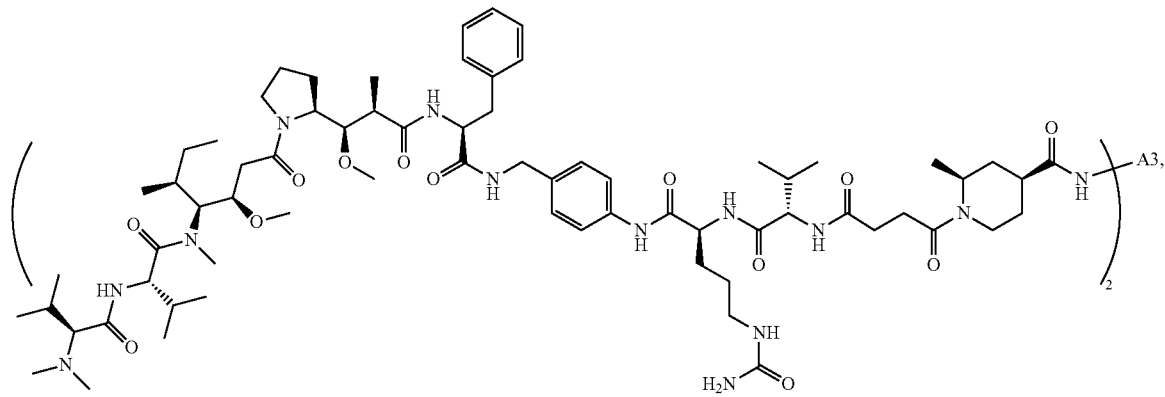
BT001051
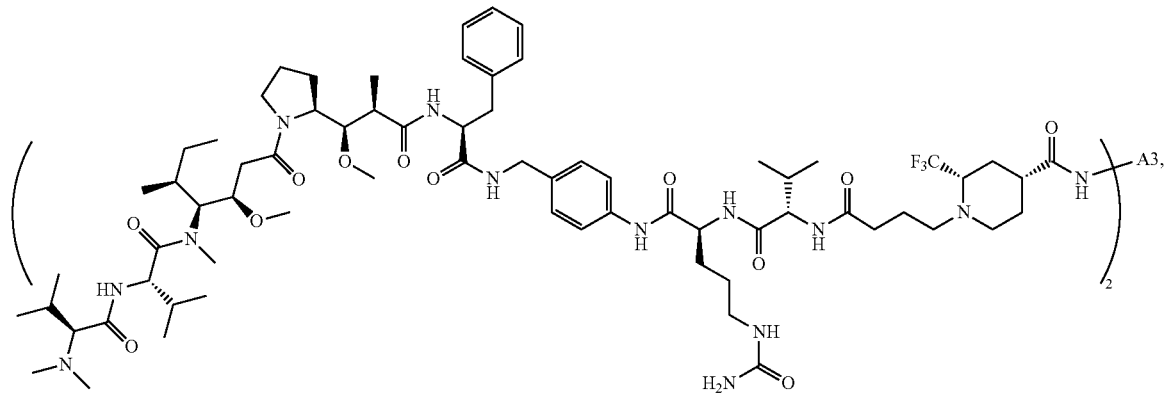
BT001052

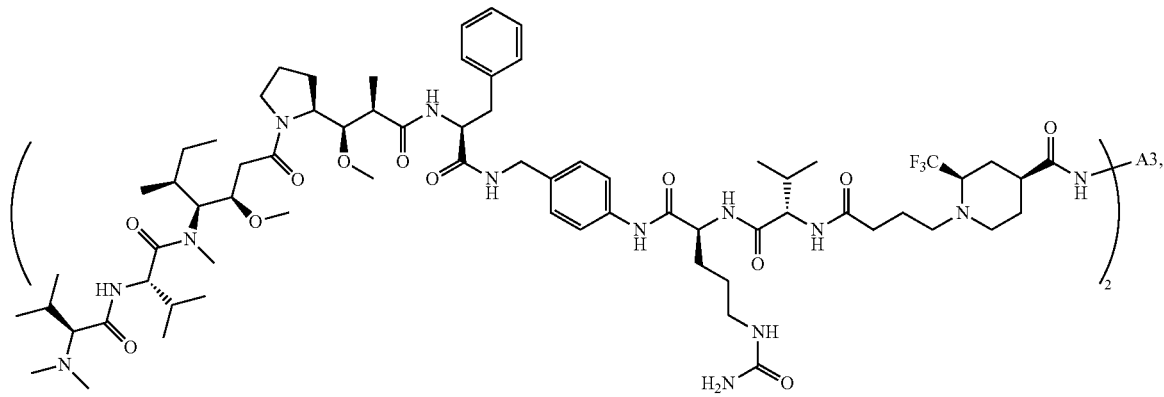
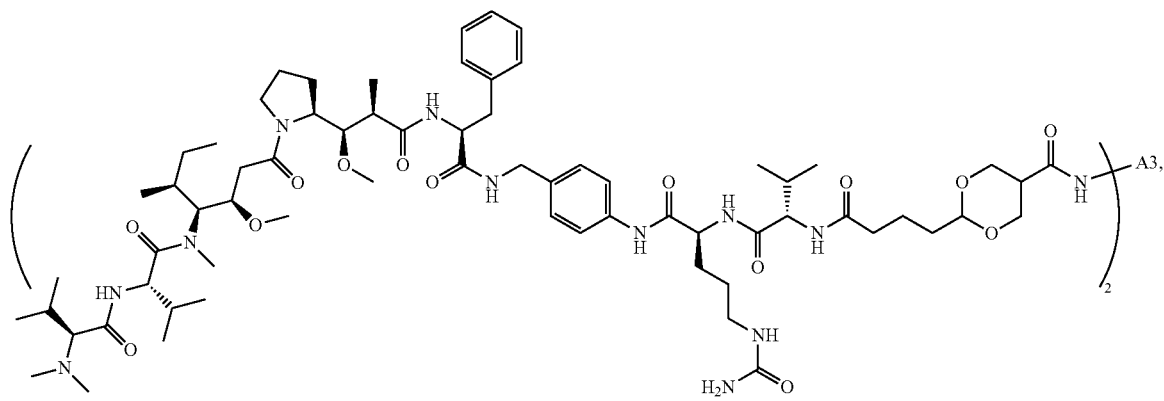
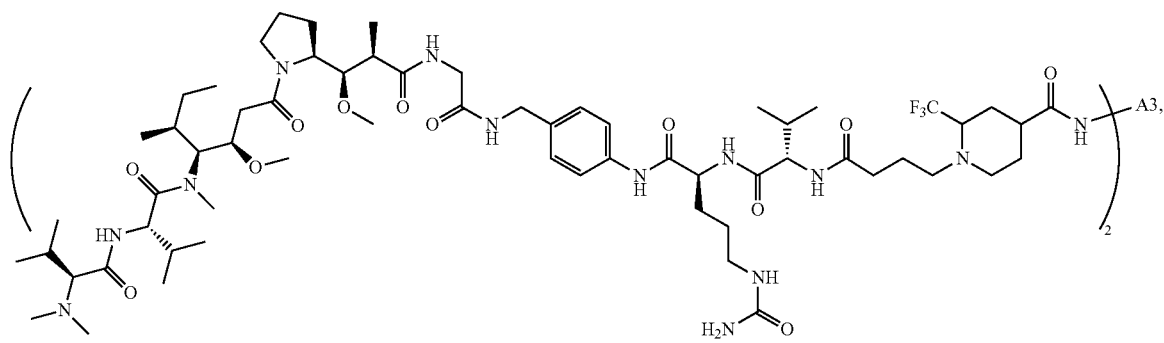
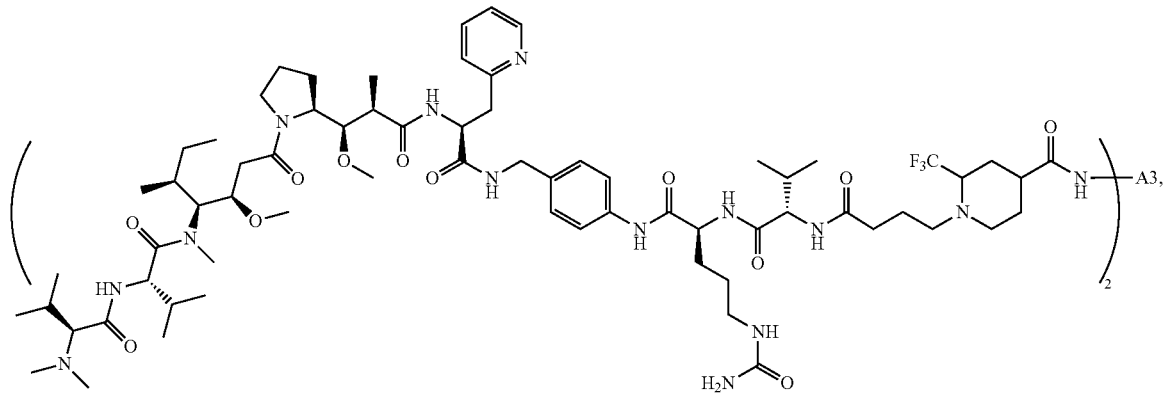

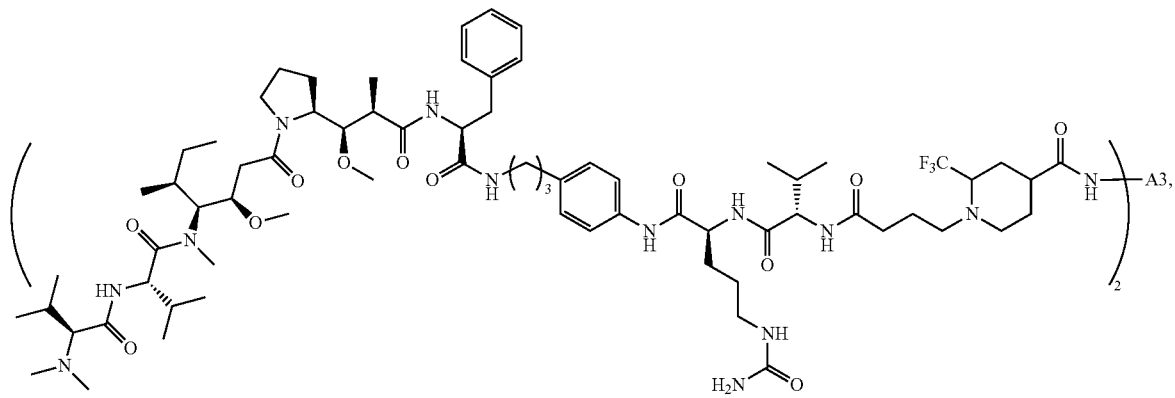
BT001057
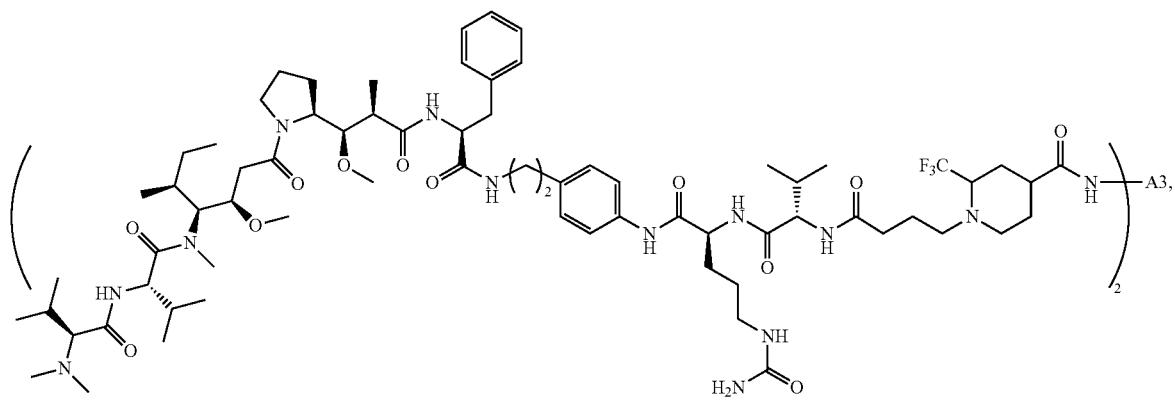
BT001058
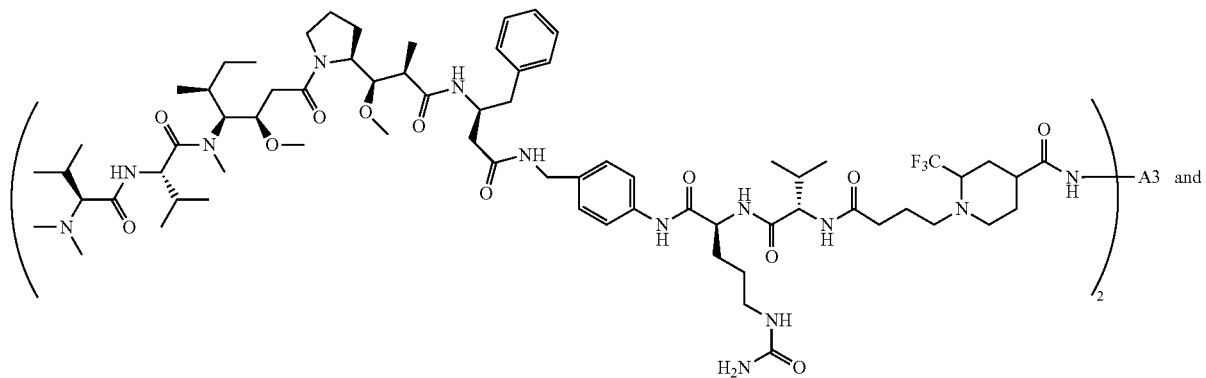
BT001059
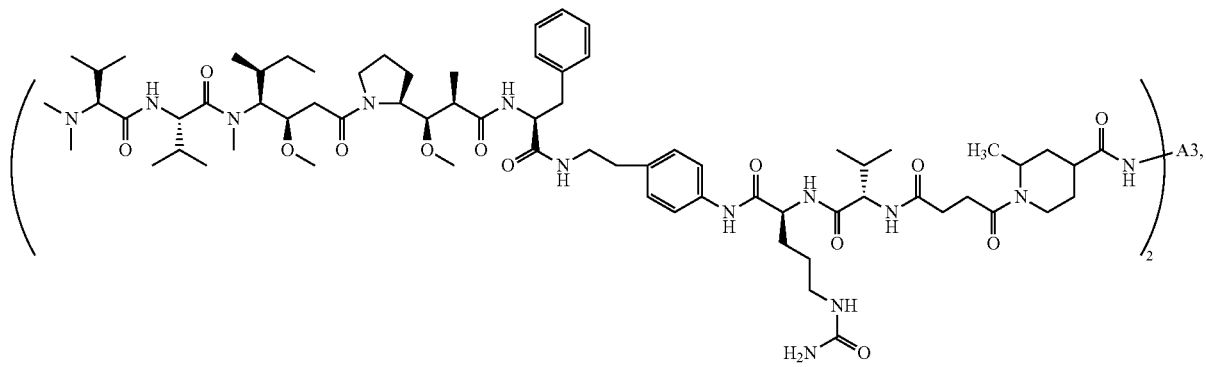
BT001060 wherein A3 is a group obtained after removing 2 amino groups from sacituzumab; or
the conjugate is selected from:
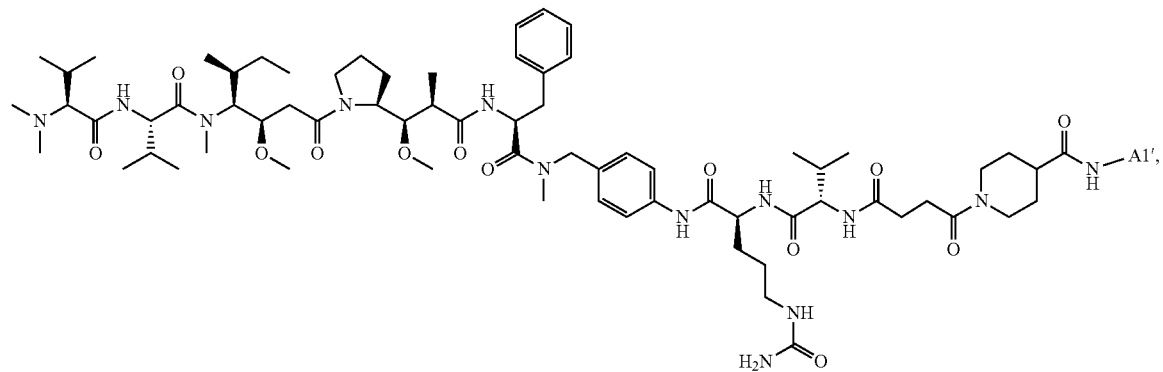
BT001061
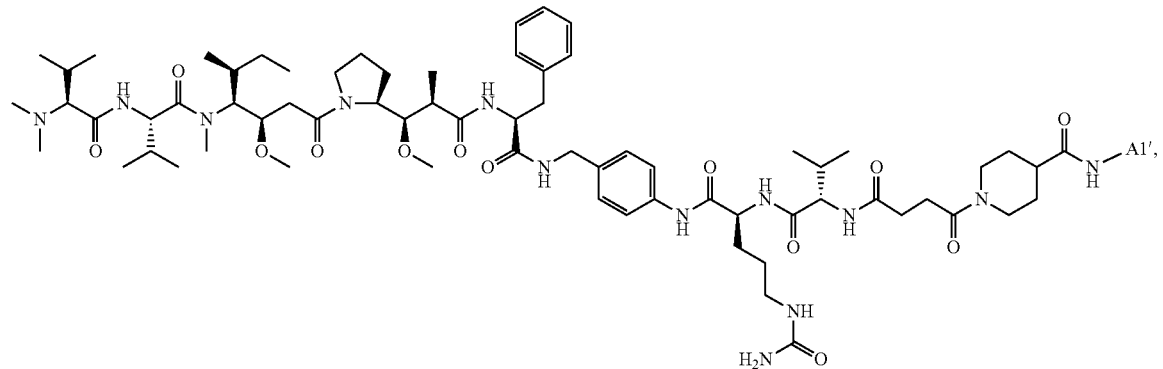
BT001062
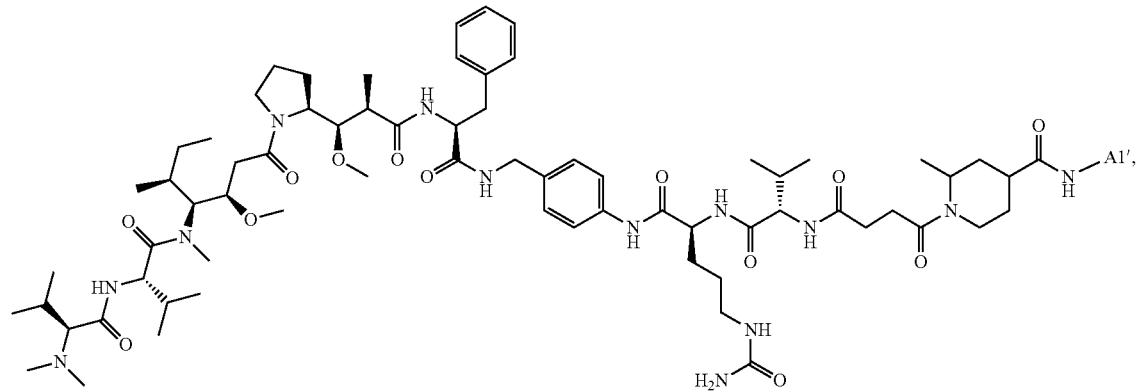
BT001063

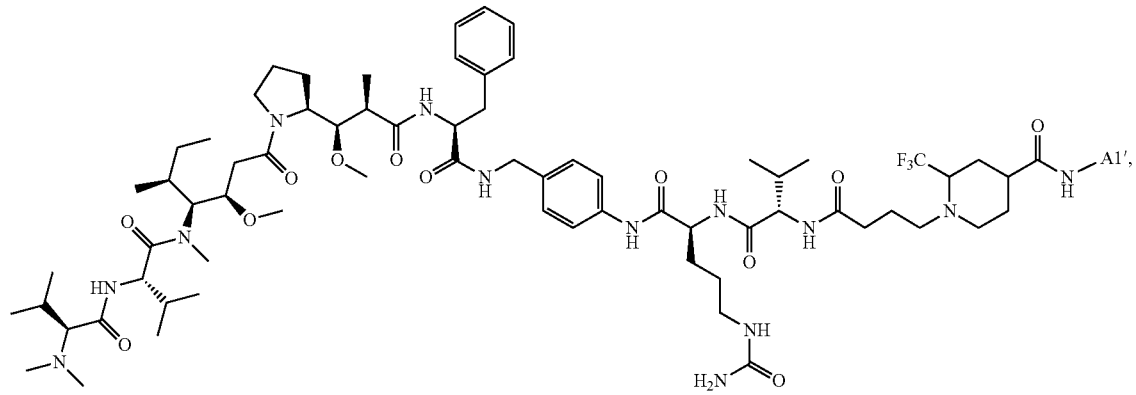
BT001064
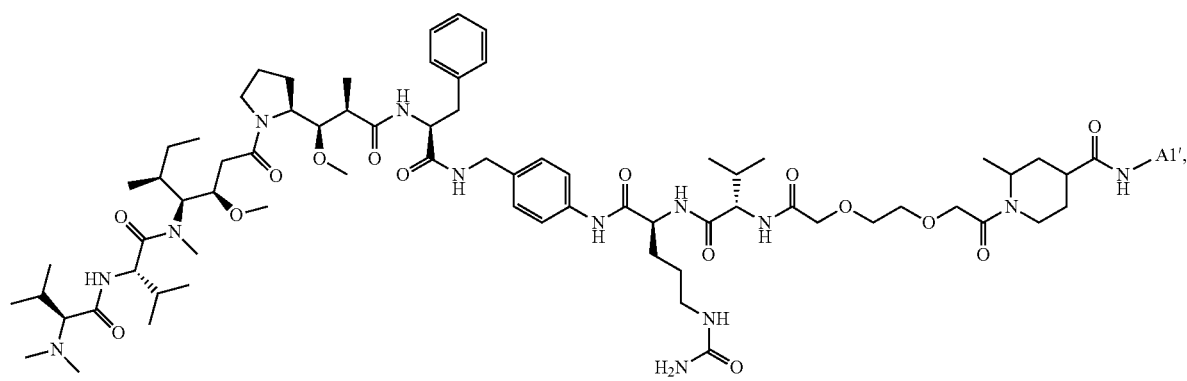
BT001065
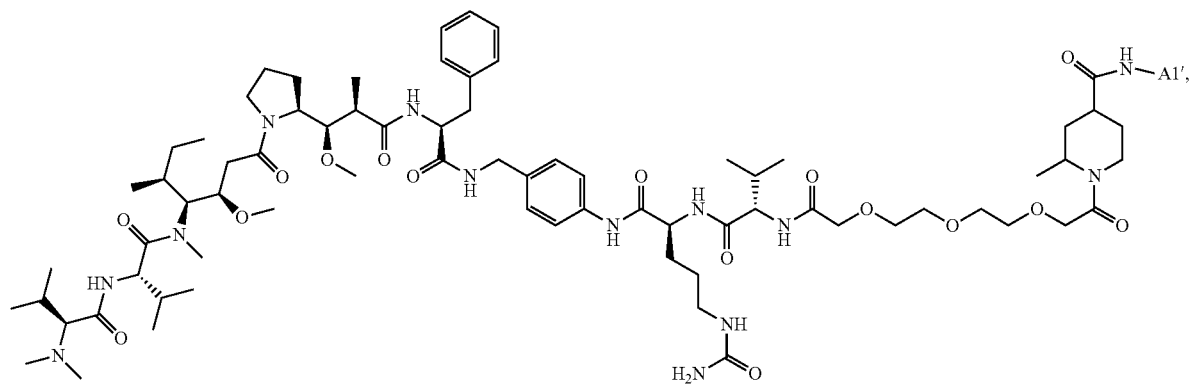
BT001066
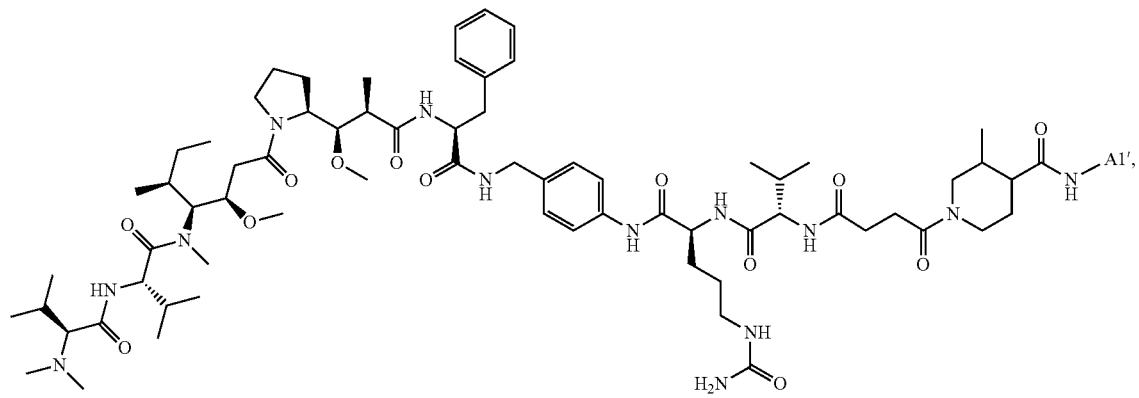
BT001067

-continued
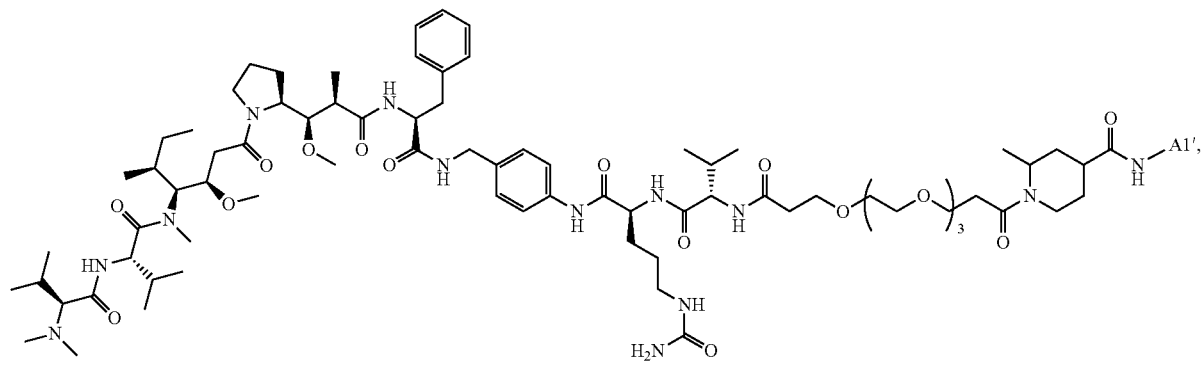
BT001068
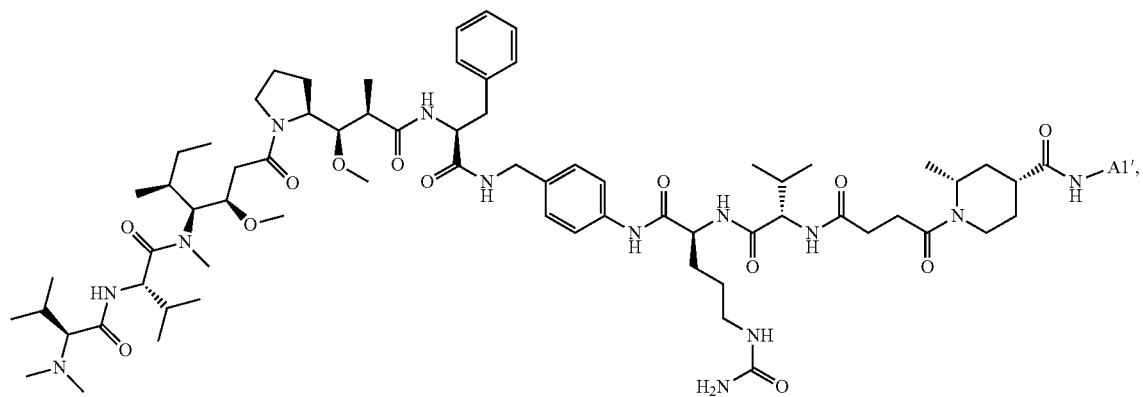
BT001072
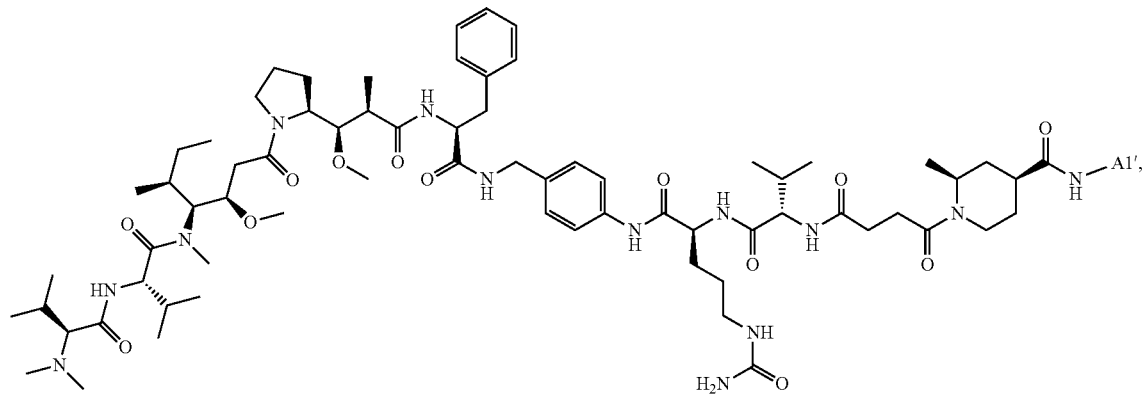
BT001073
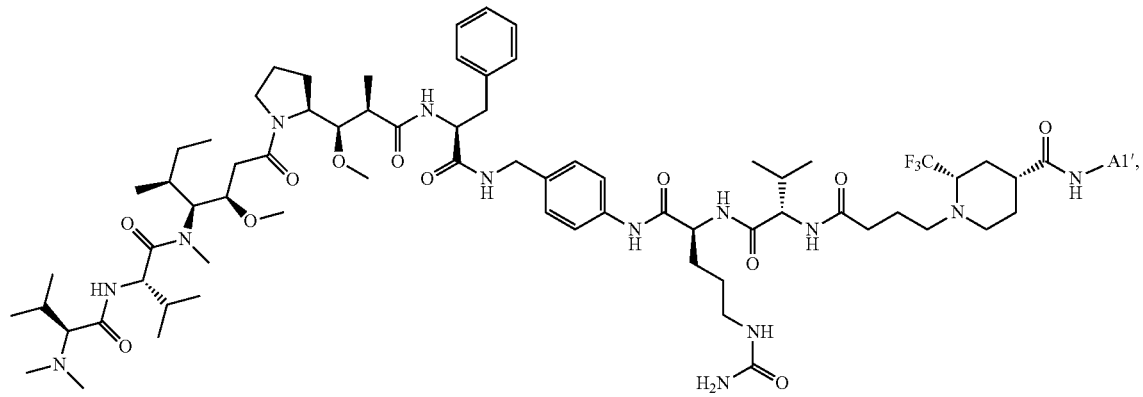
BT001074

-continued
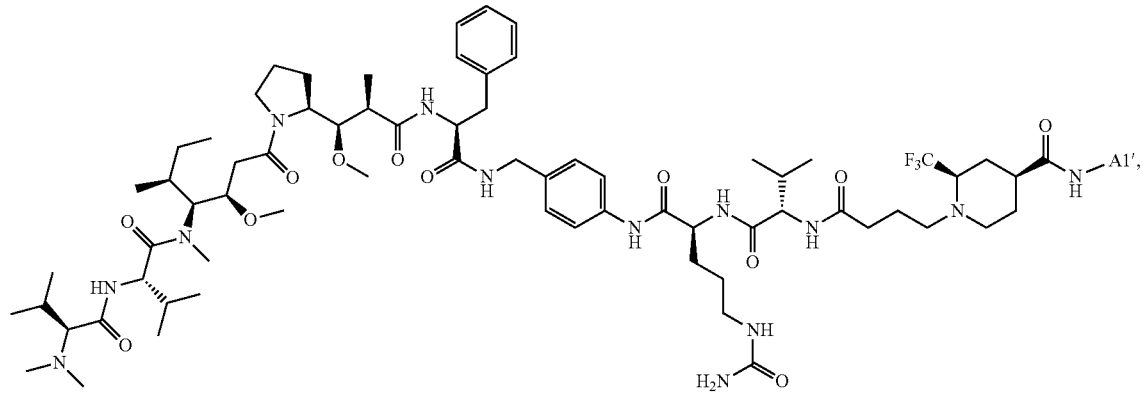
BT001075
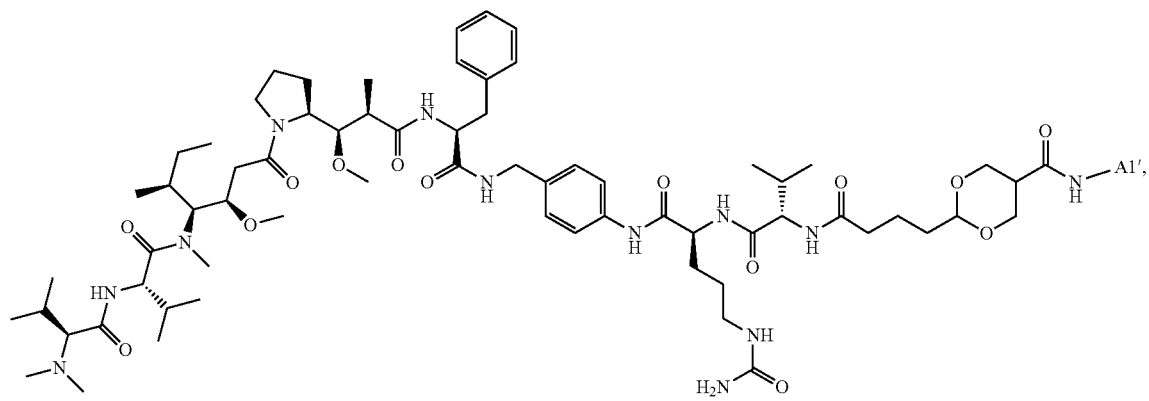
BT001076
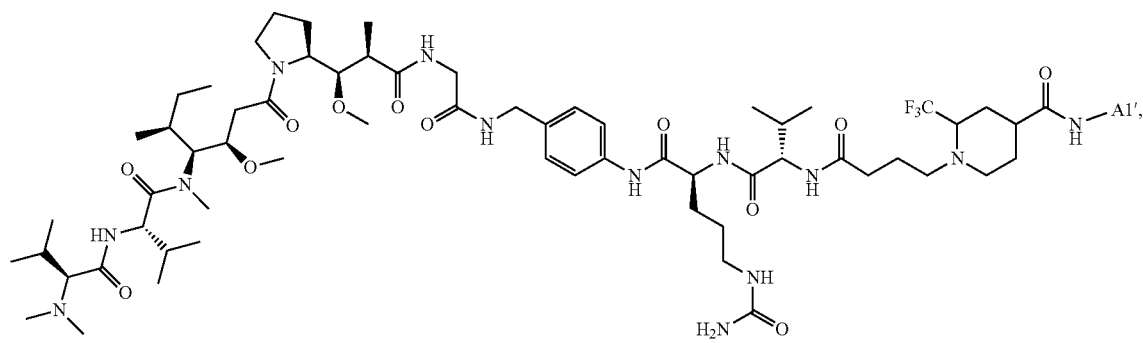
BT001077
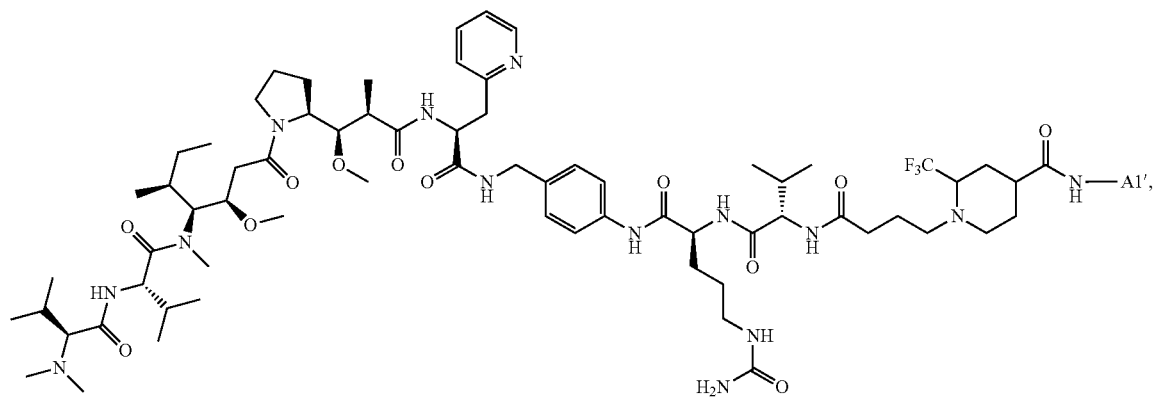
BT001078

-continued
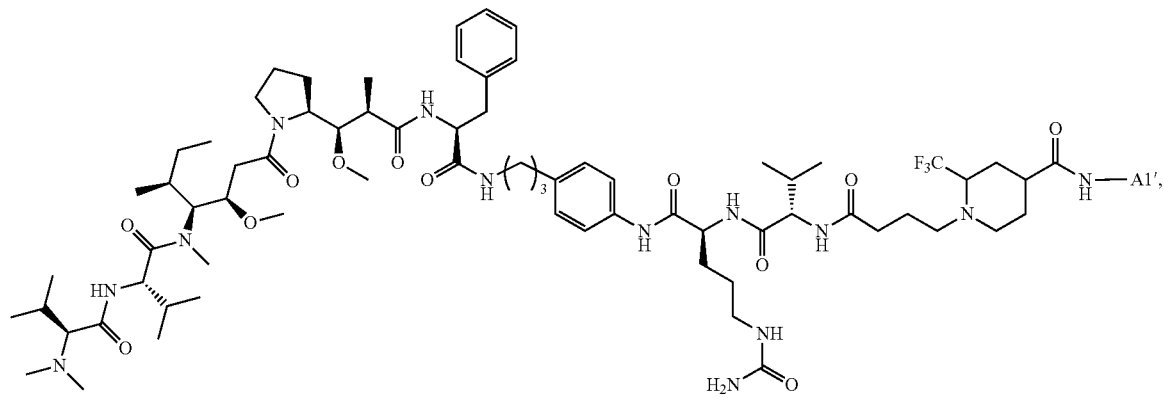
BT001079
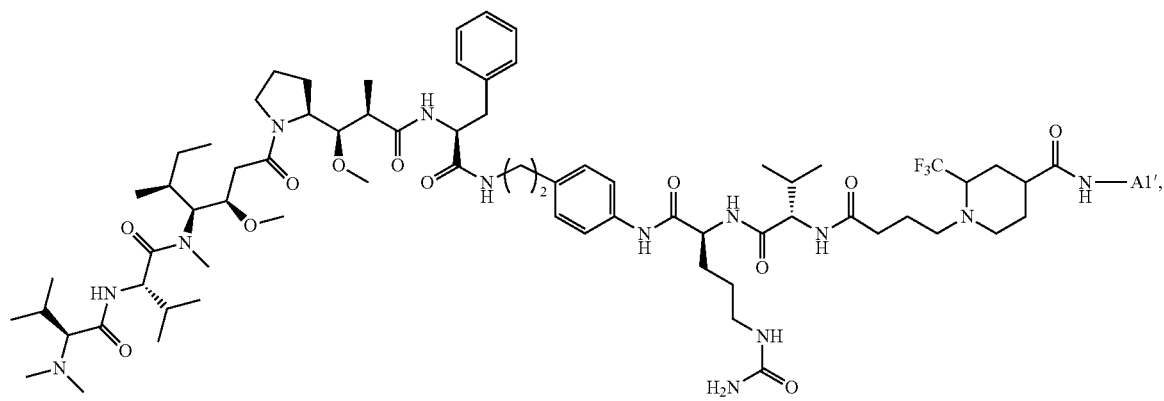
BT001080
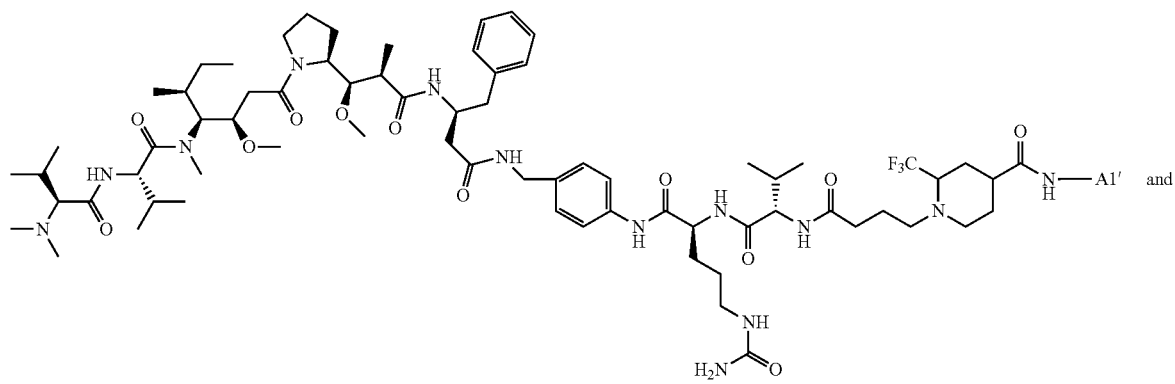
BT001092
and
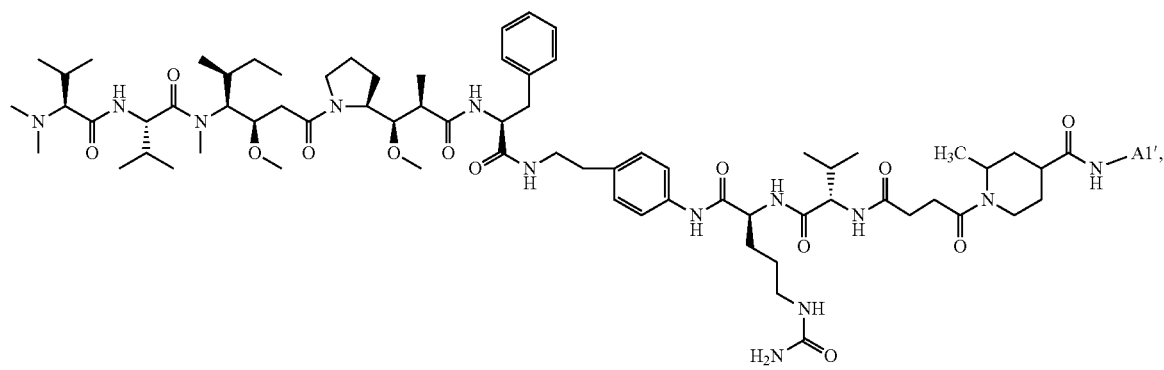
BT001093 wherein A1' is a group obtained after removing 1 amino group from trastuzumab; or
the conjugate is selected from:
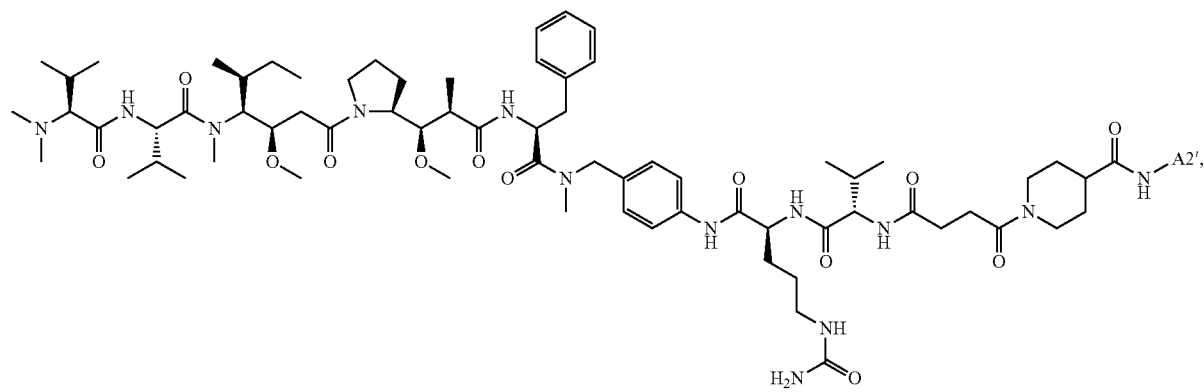
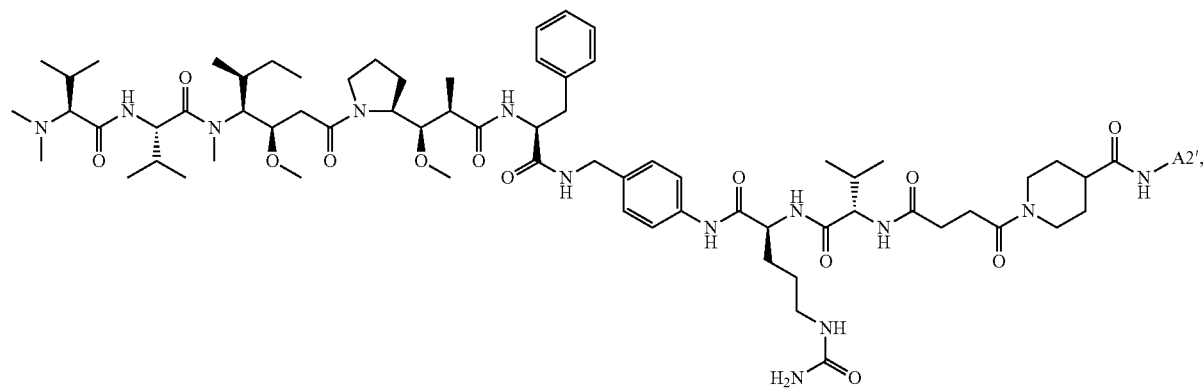
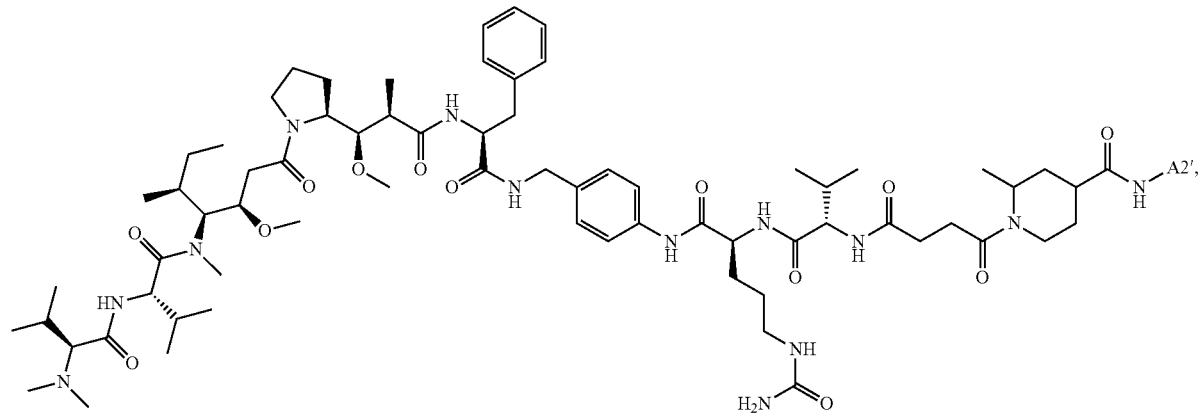

-continued
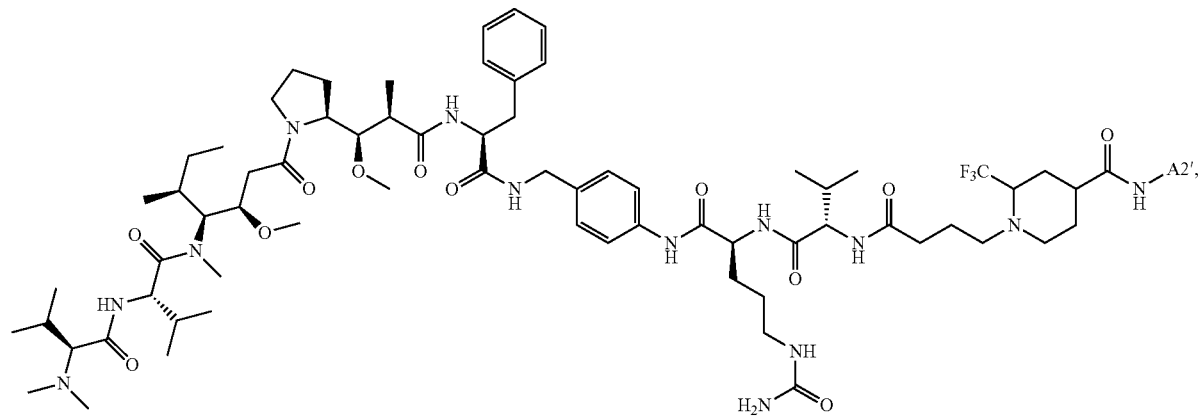
BT001097
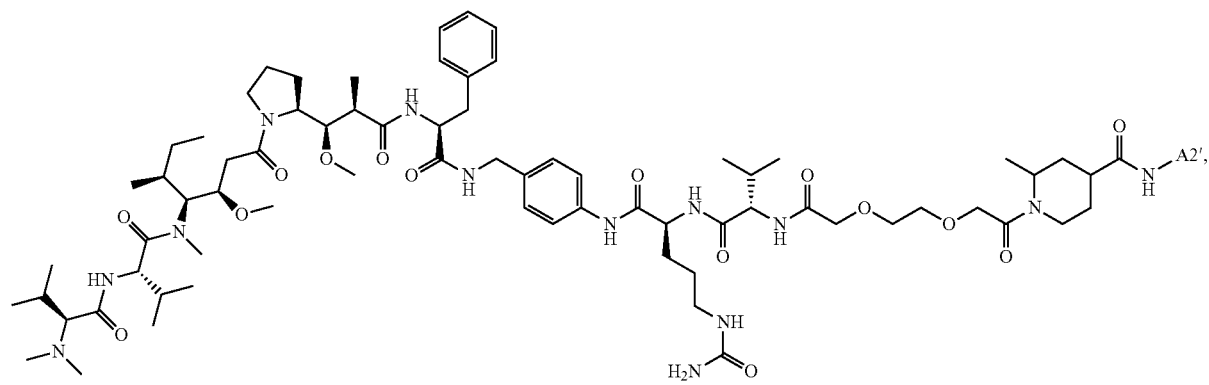
BT001098
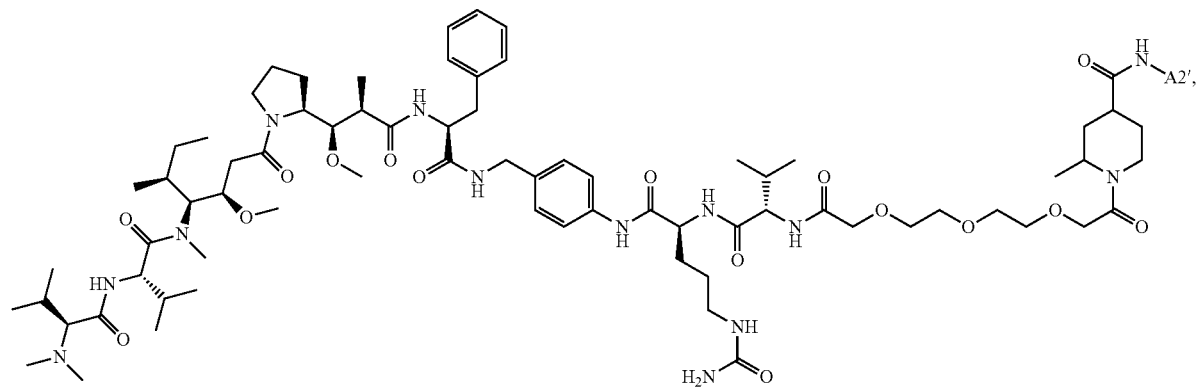
BT001099

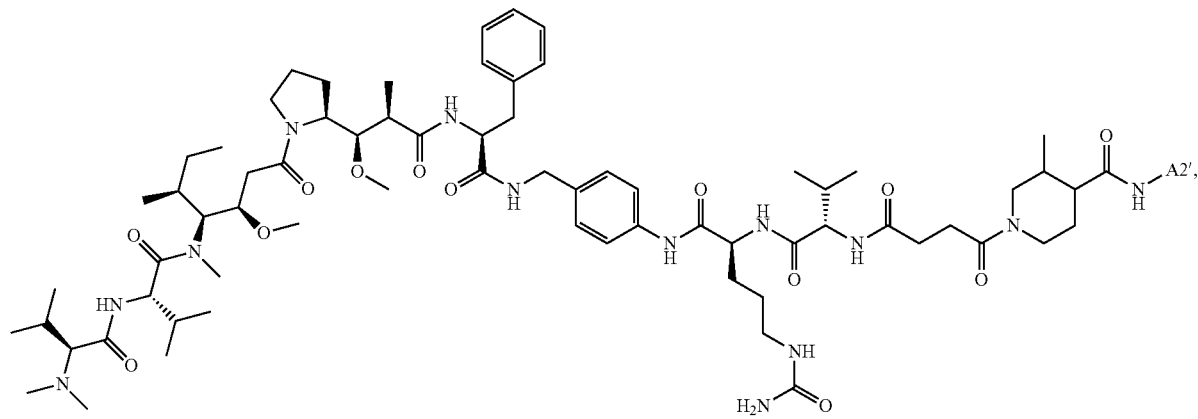
BT001100
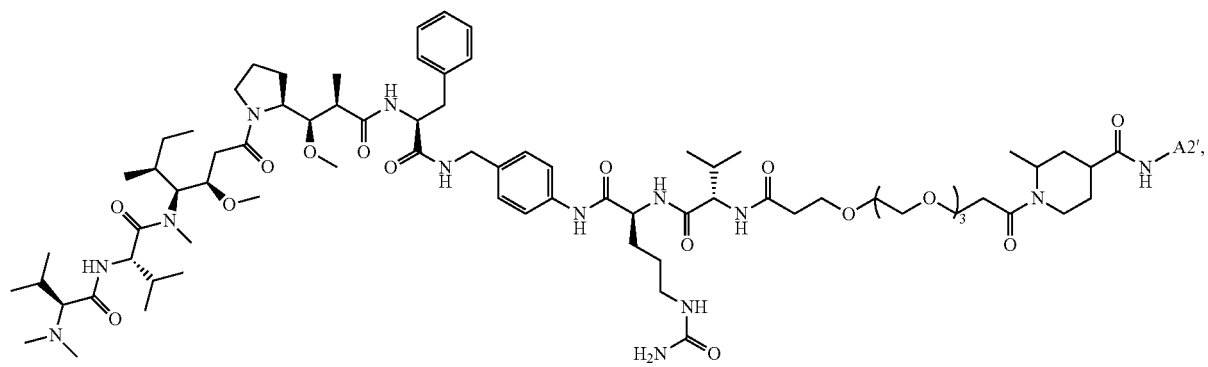
BT001101
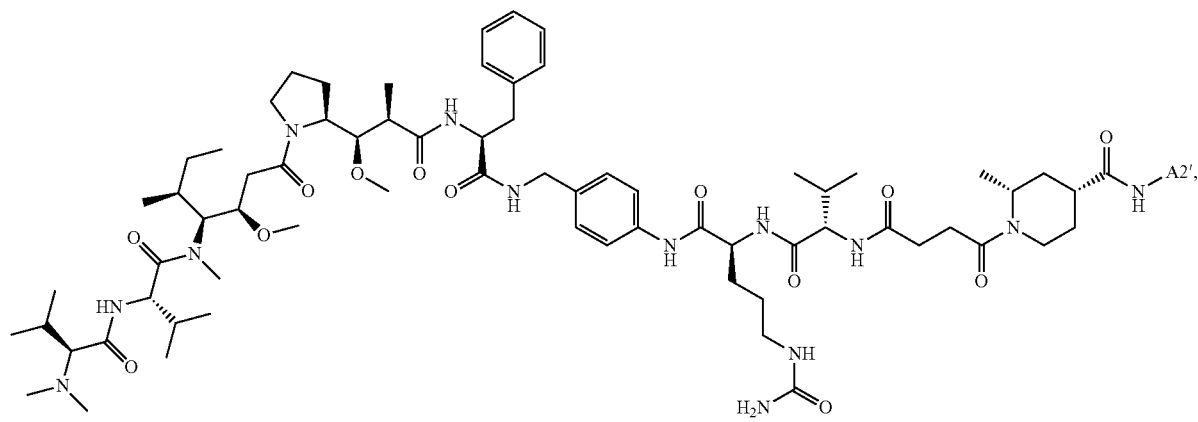
BT001102

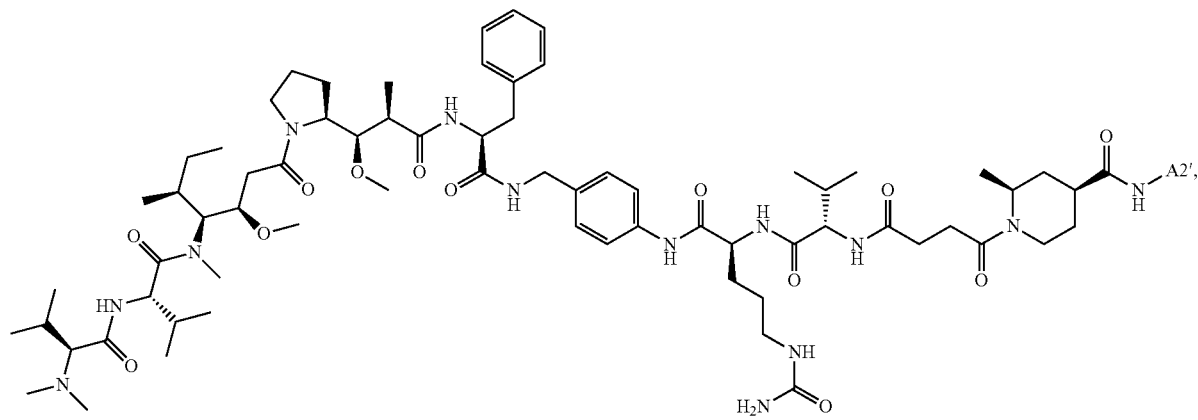
BT001103
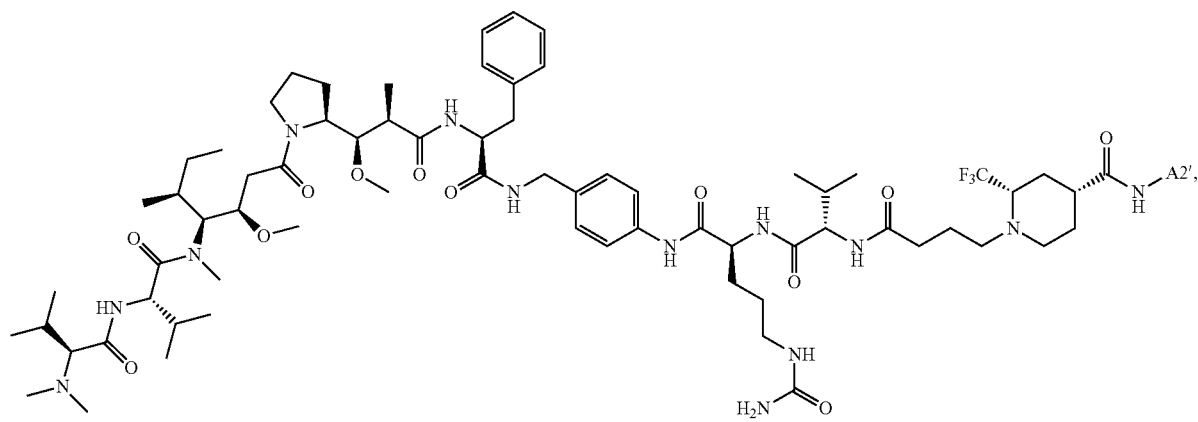
BT001104
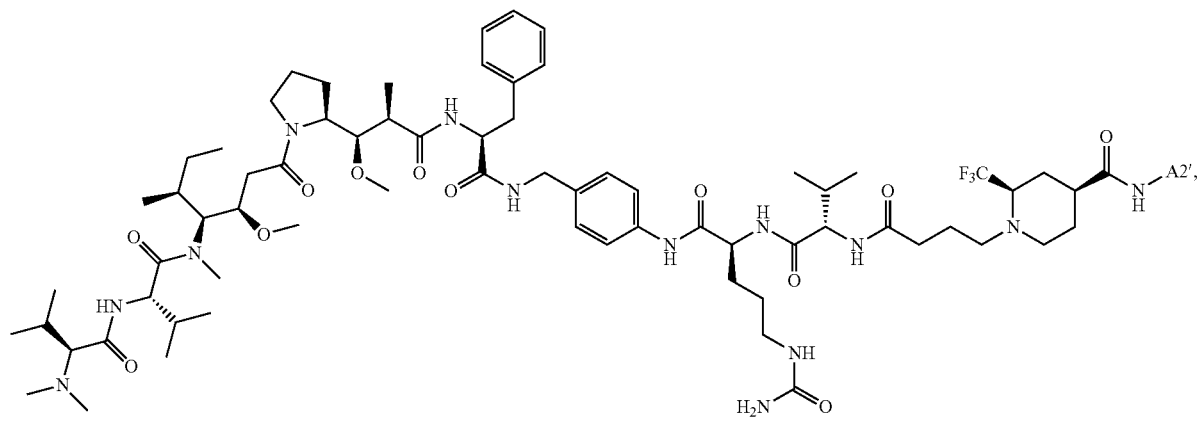
BT001105

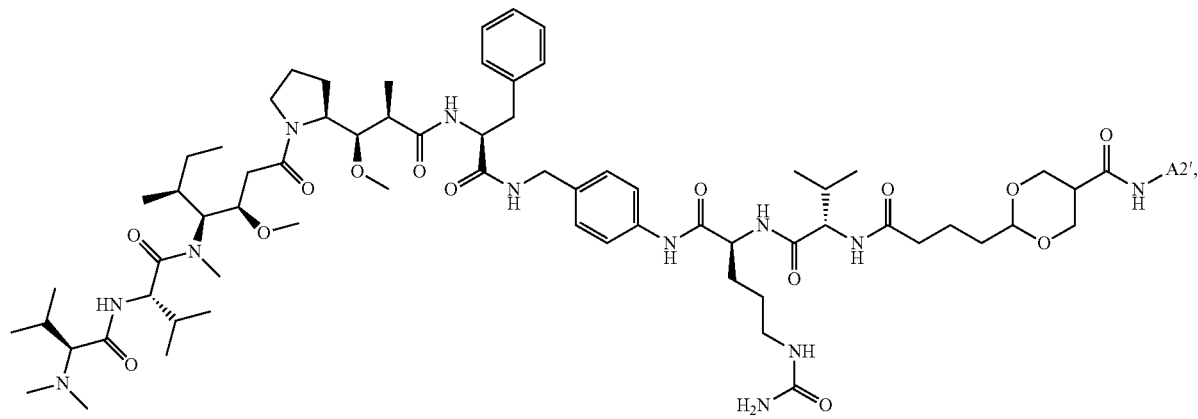
BT001106
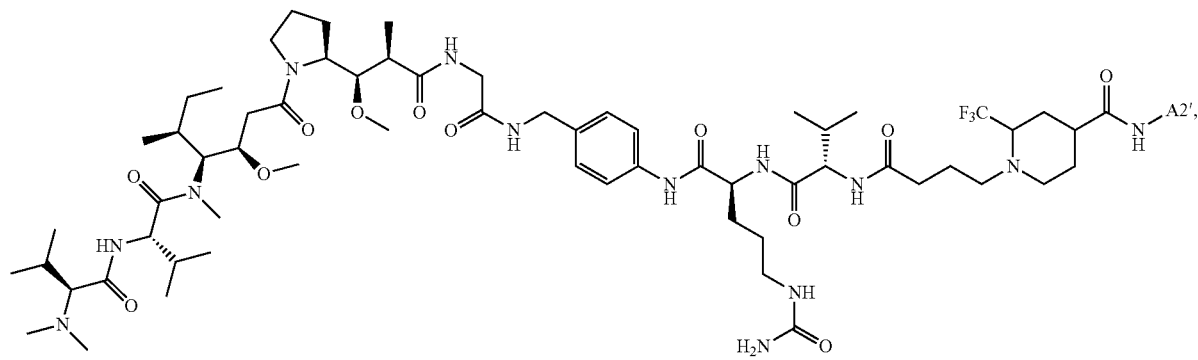
BT001107
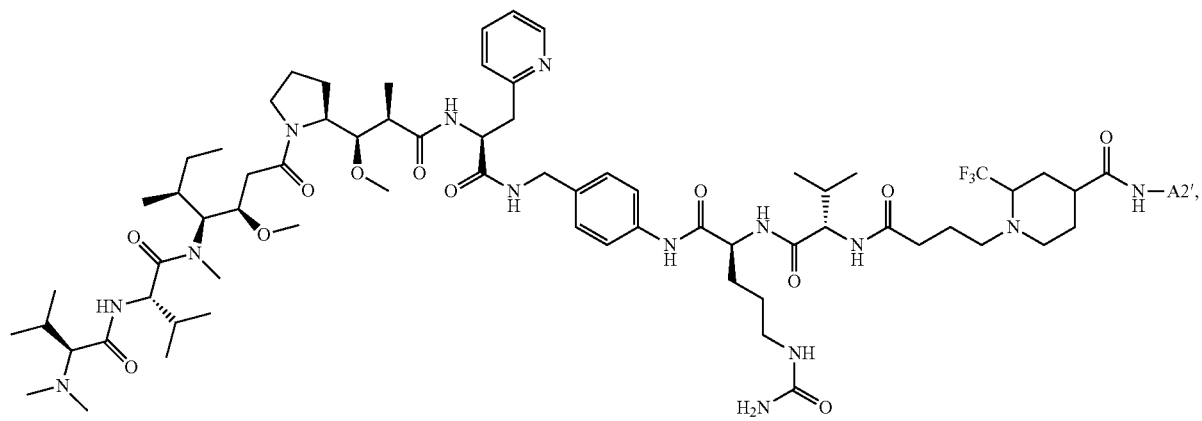
BT001108

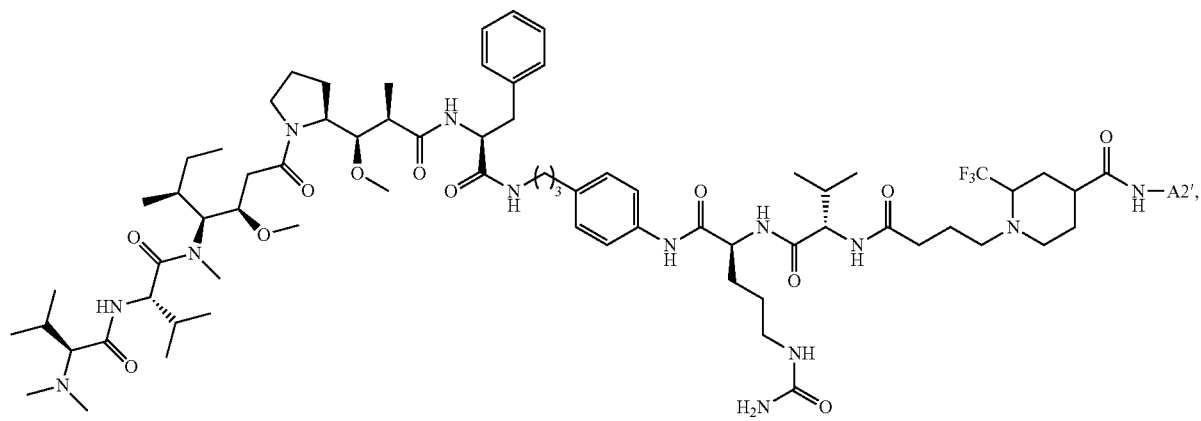
BT001109
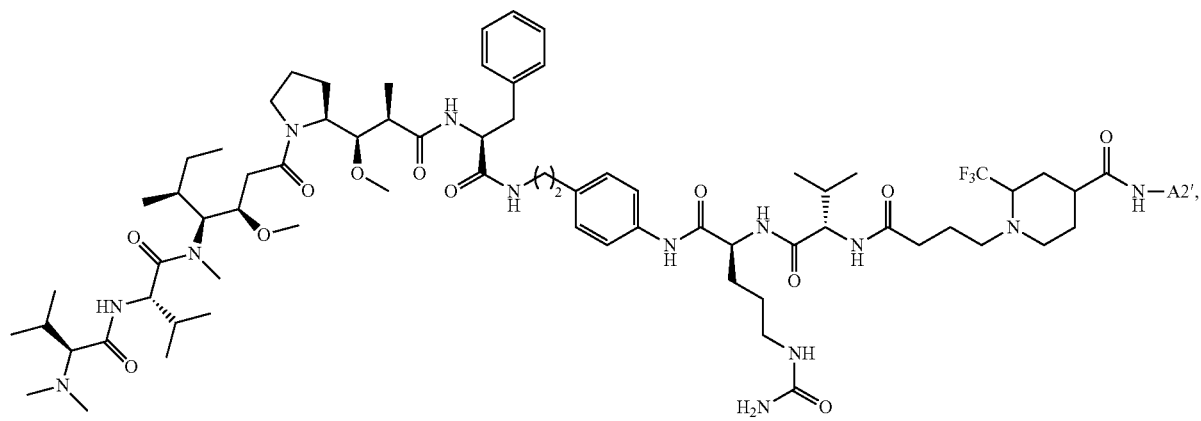
BT001110
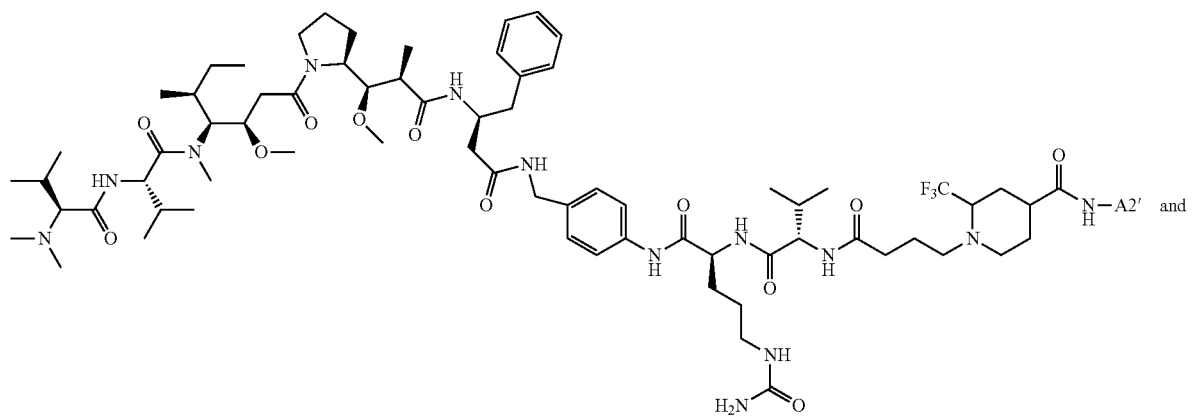
BT001111
and

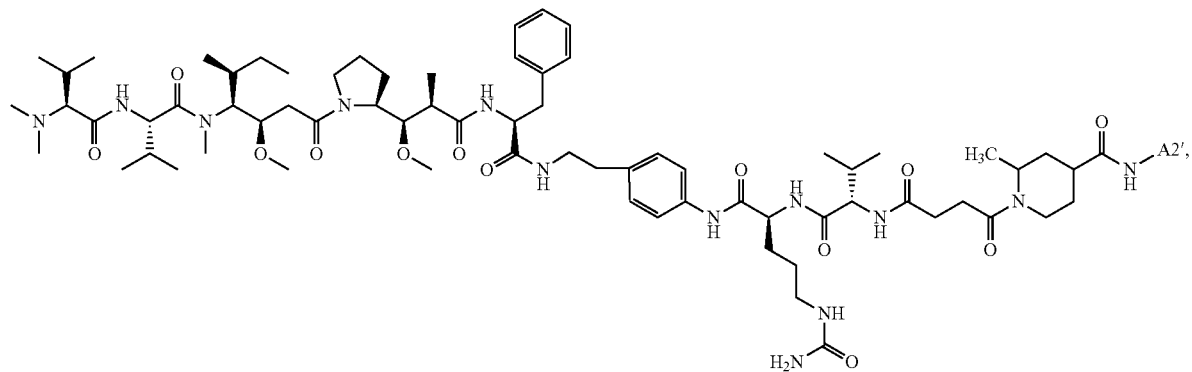
wherein A2' is a group obtained after removing 1 amino group from pertuzumab; or
the conjugate is selected from:
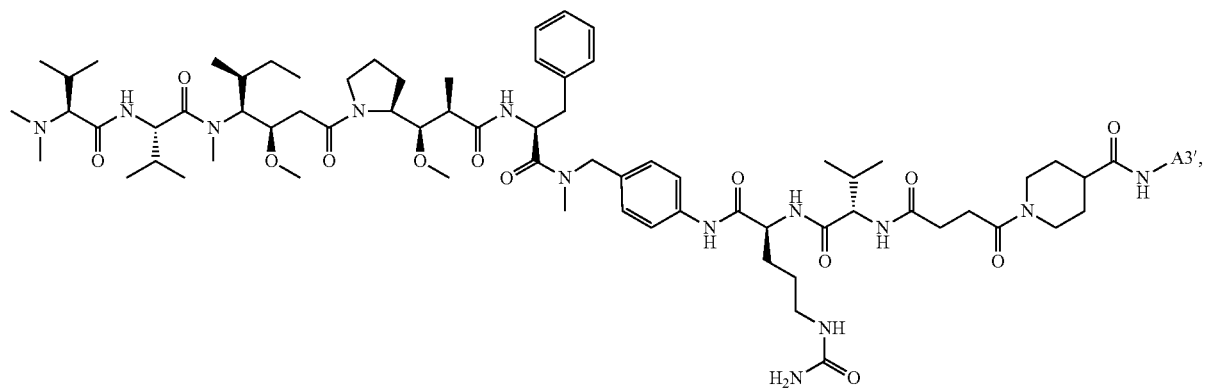
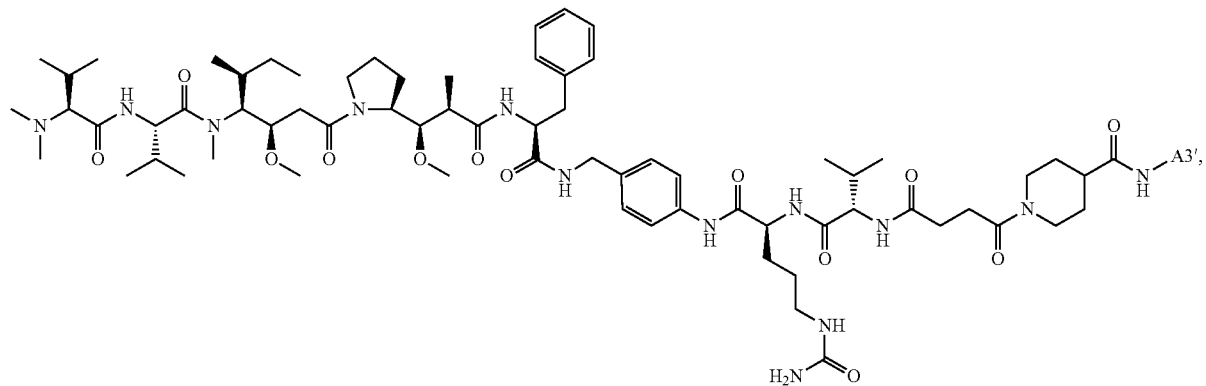

-continued
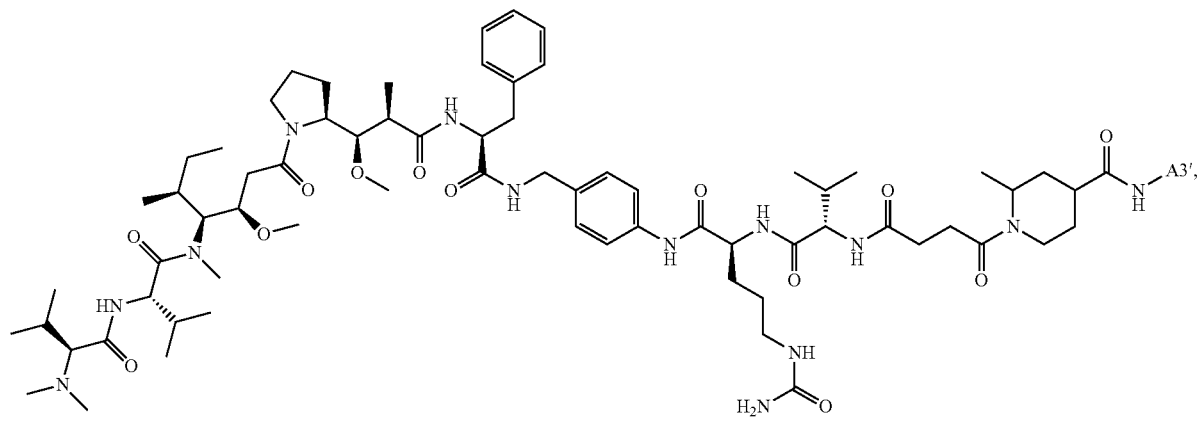
BT001069
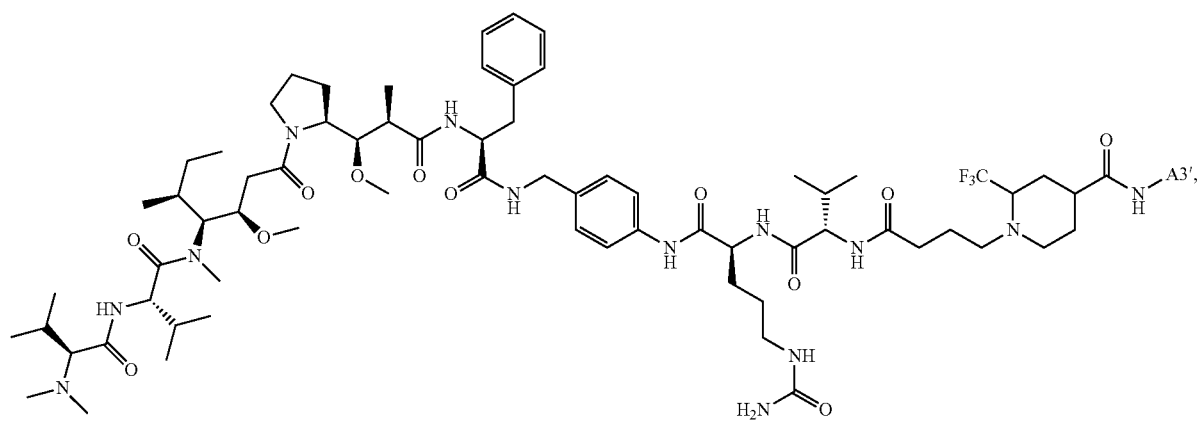
BT001070
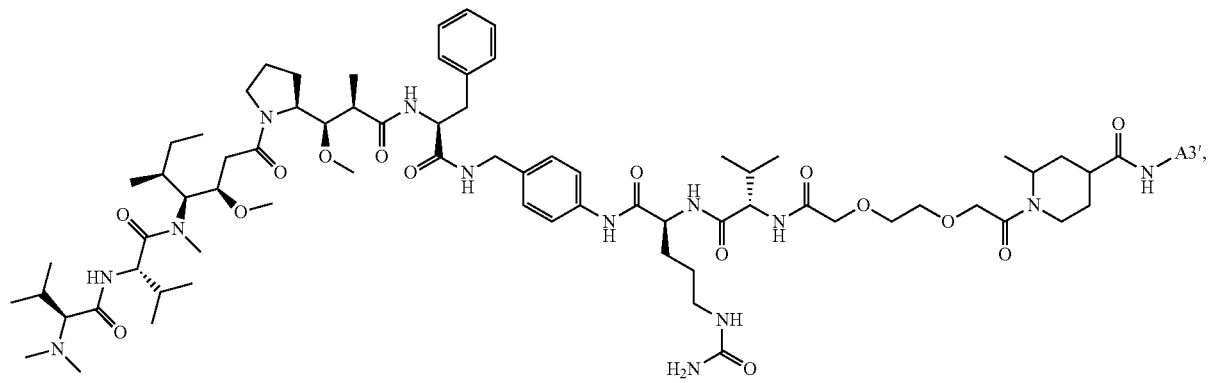
BT001115

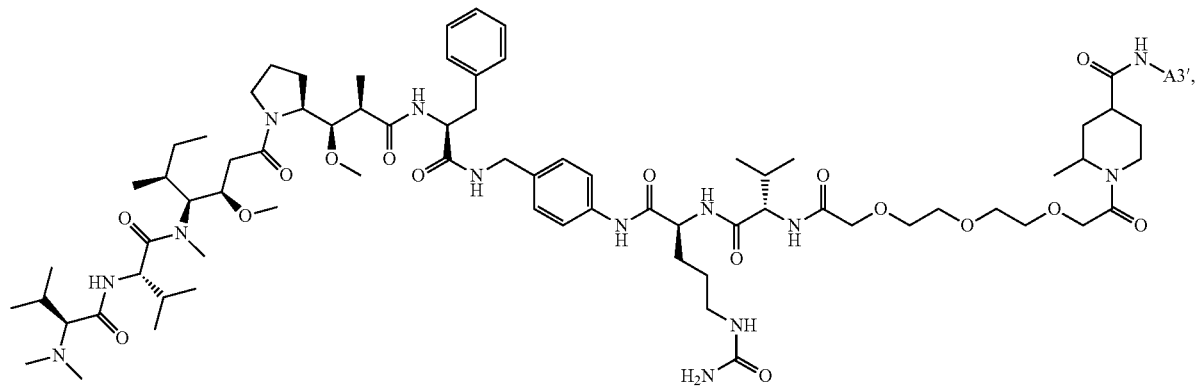
BT001116
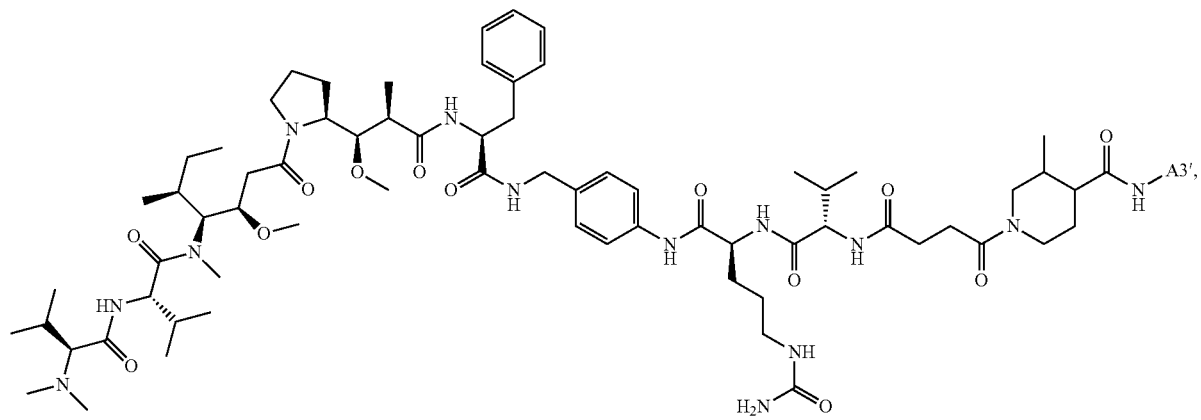
BT001117
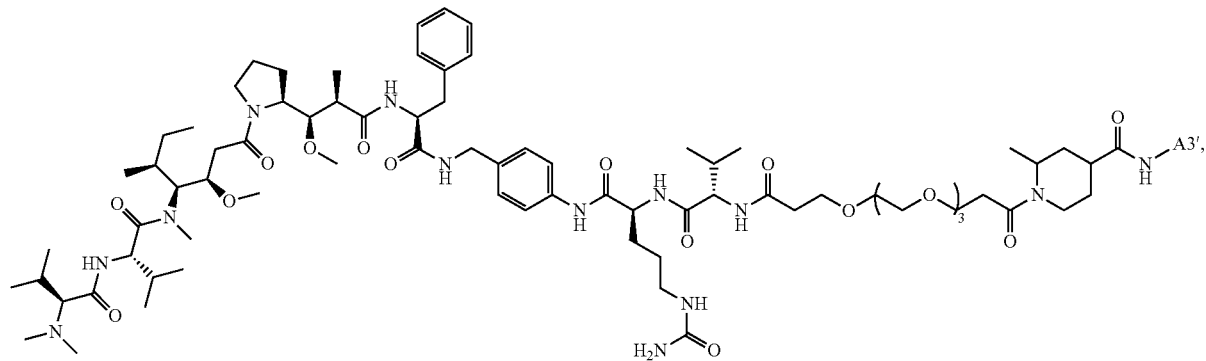
BT001118

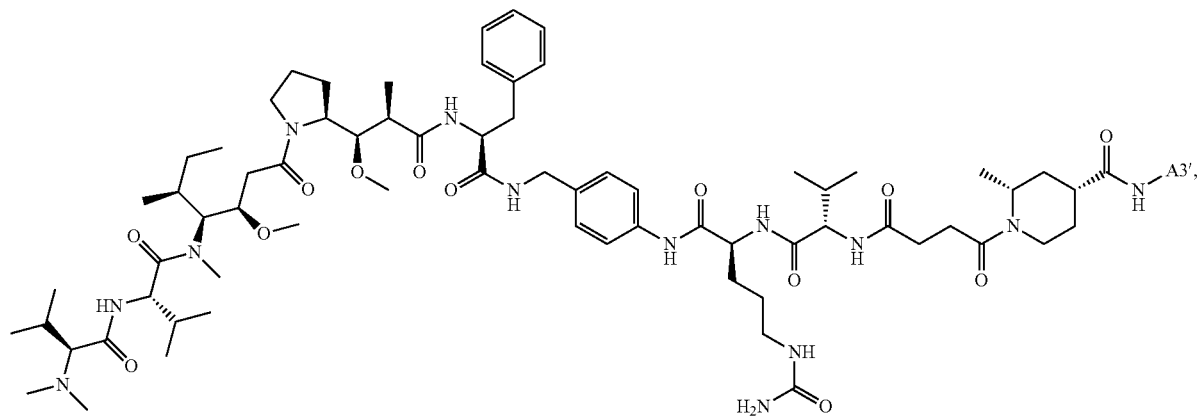
BT001119
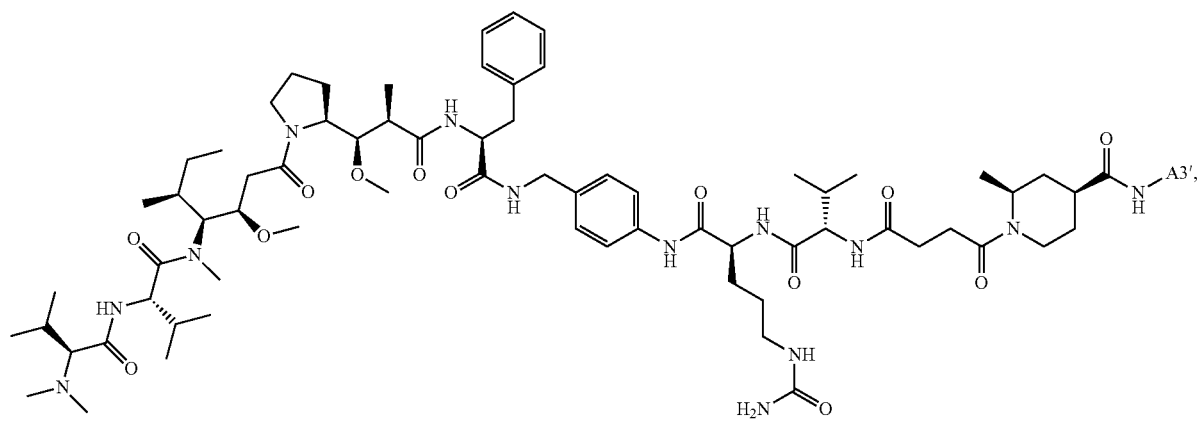
BT001120
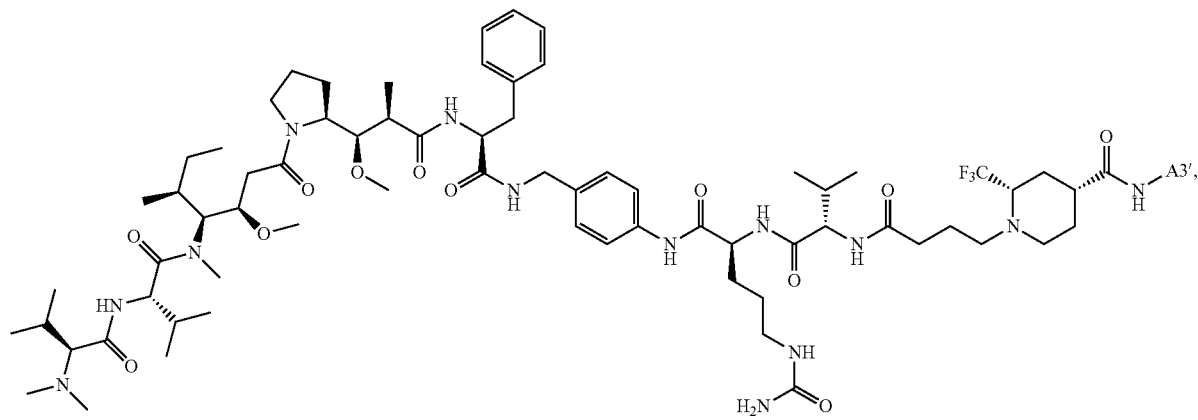
BT001121

-continued
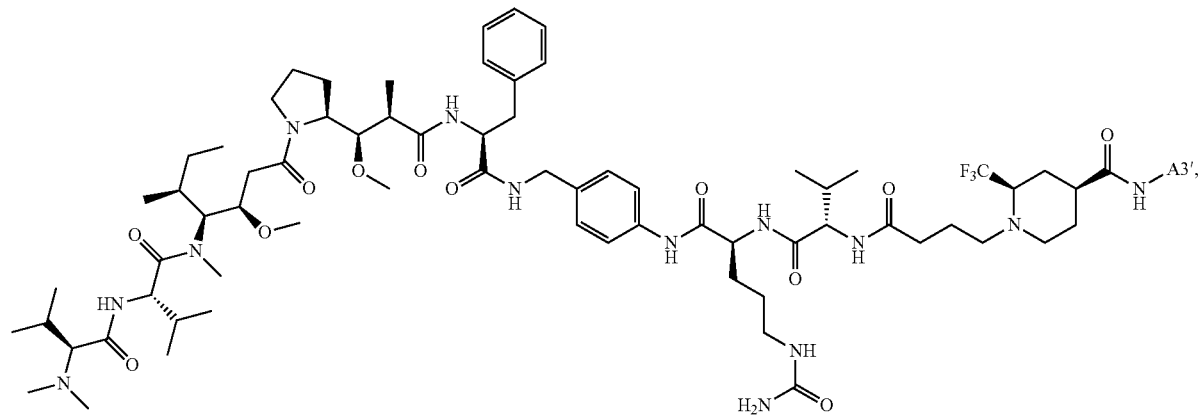
BT001122
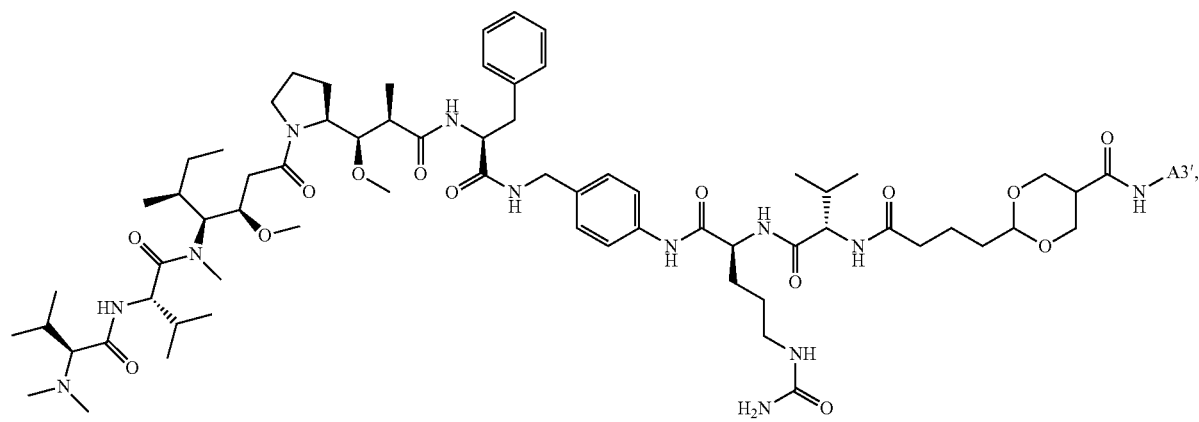
BT001123
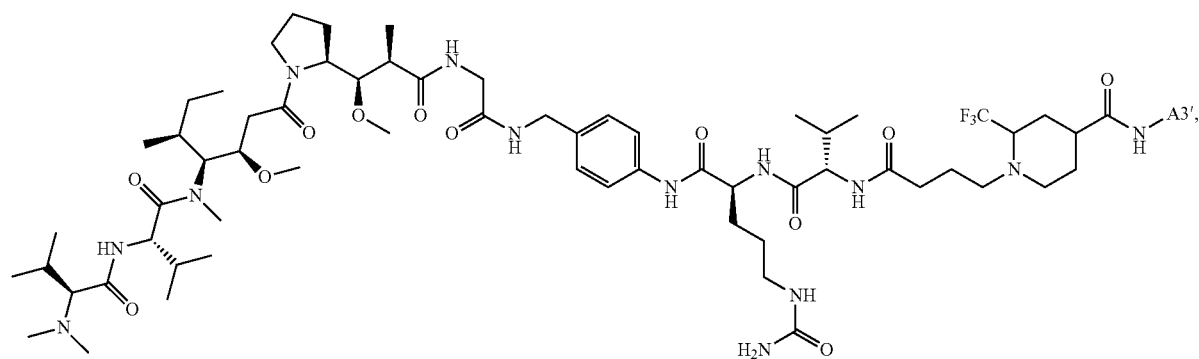
BT001124

-continued
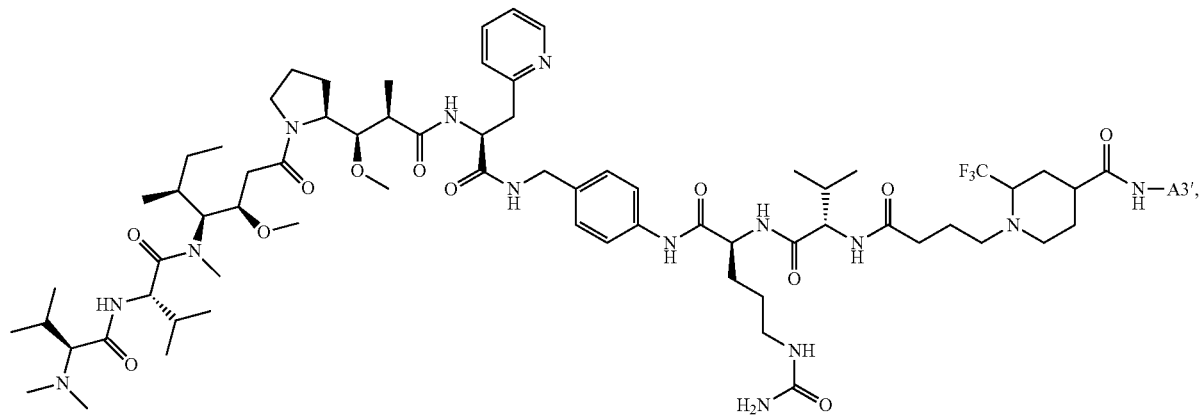
BT001125
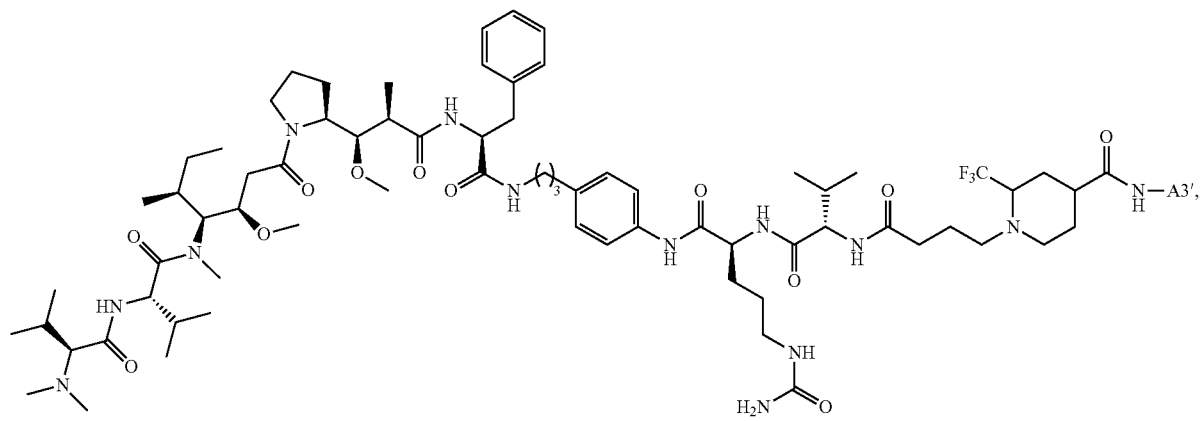
BT001126
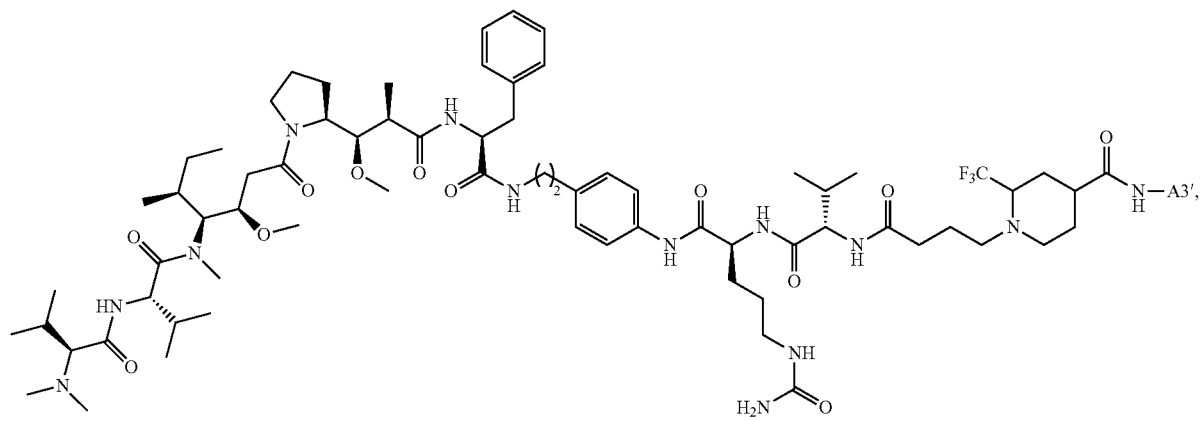
BT001127

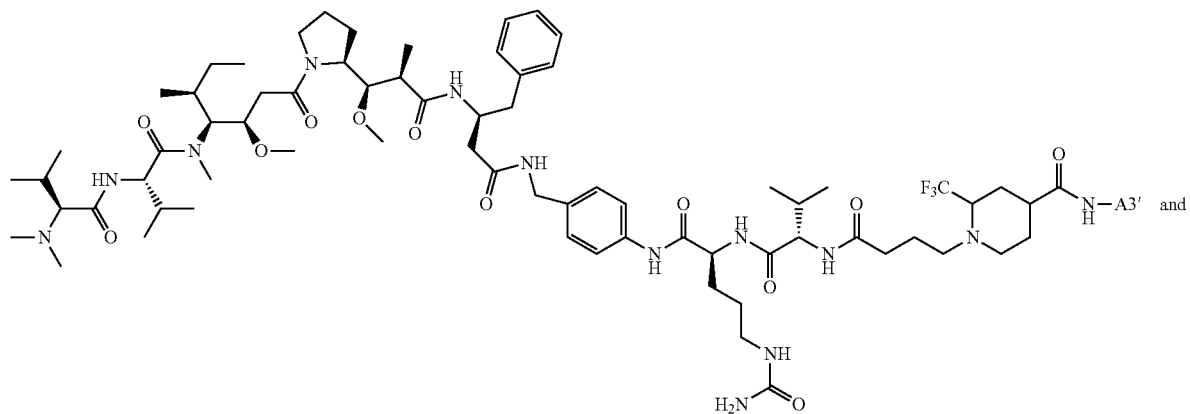
BT001128
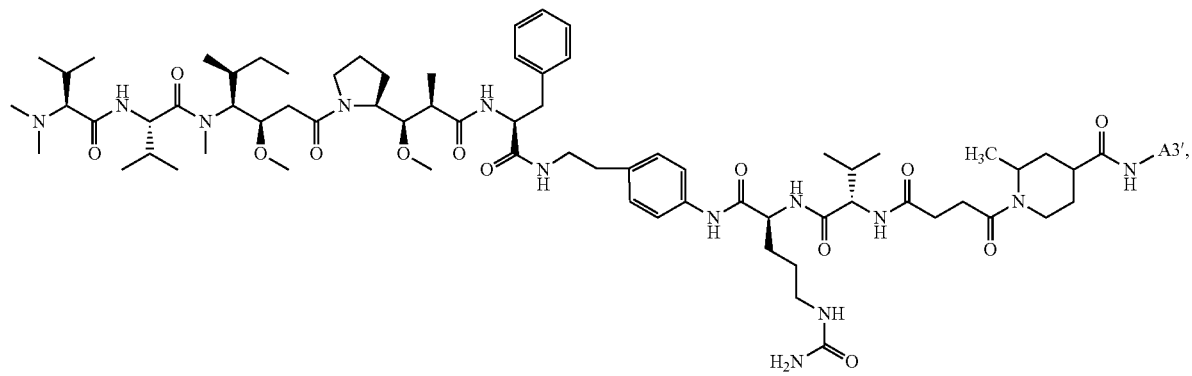
BT001129
wherein A3' is a group obtained after removing 1 amino group from sacituzumab; or
the conjugate is selected from:
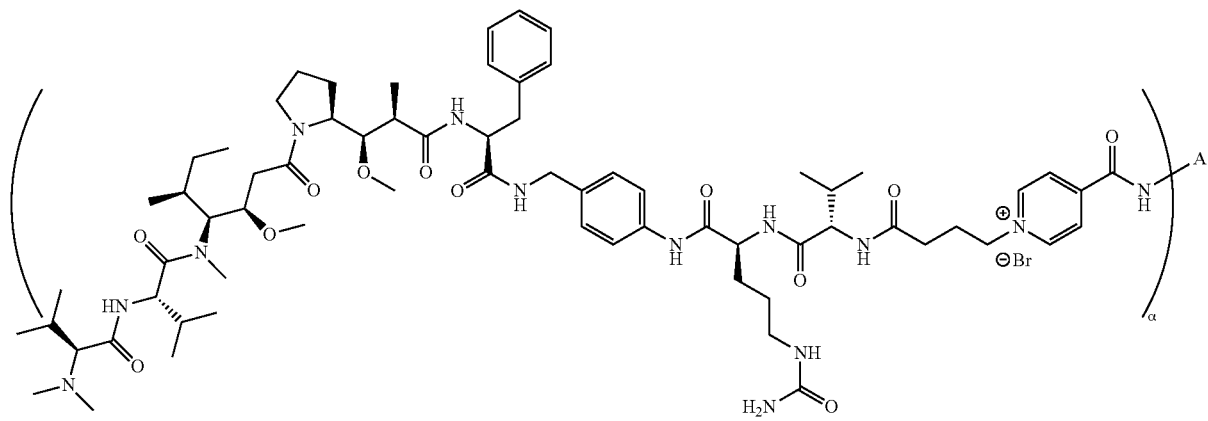

-continued
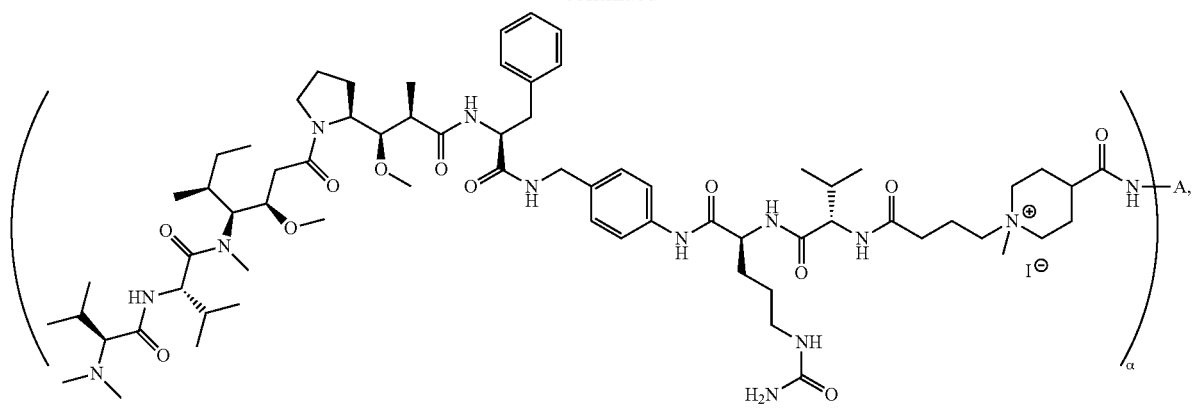
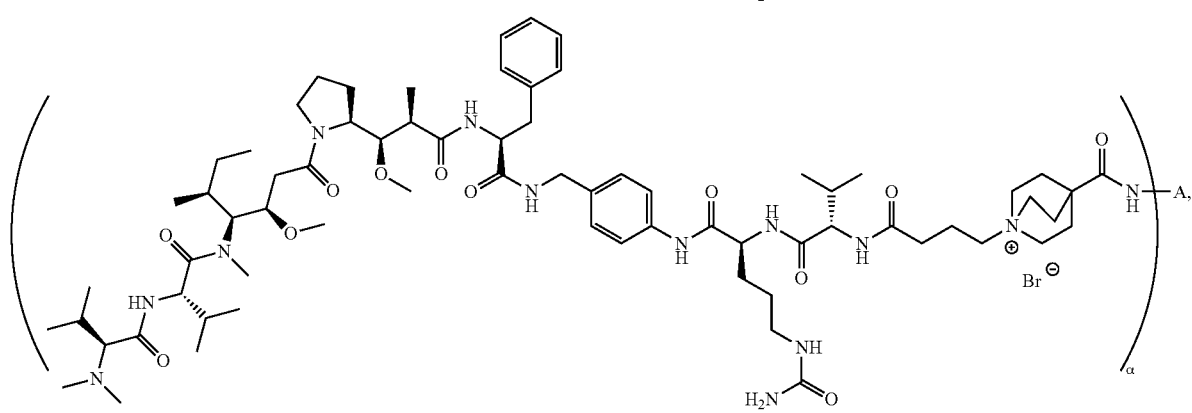
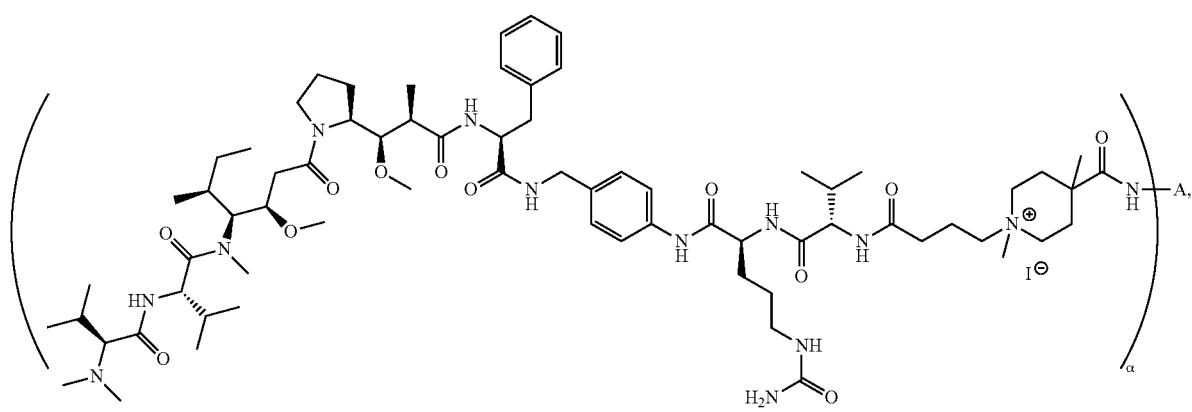
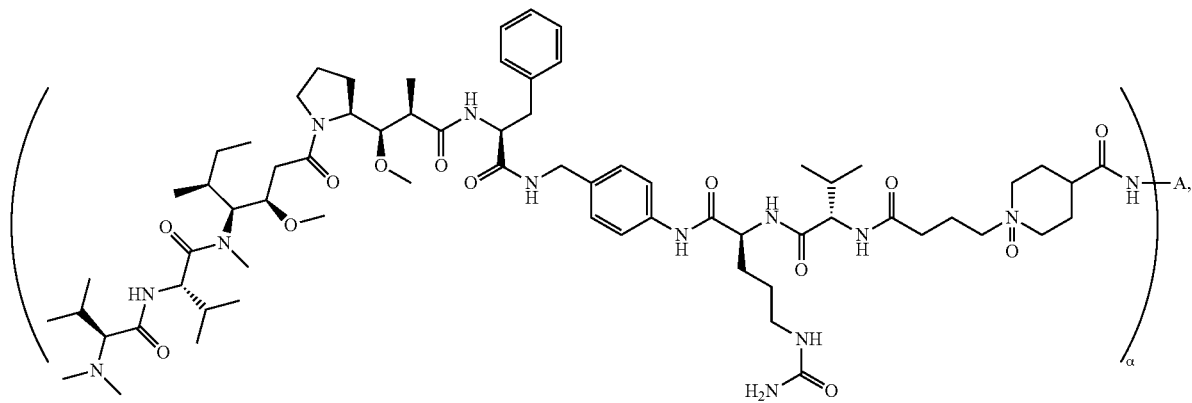

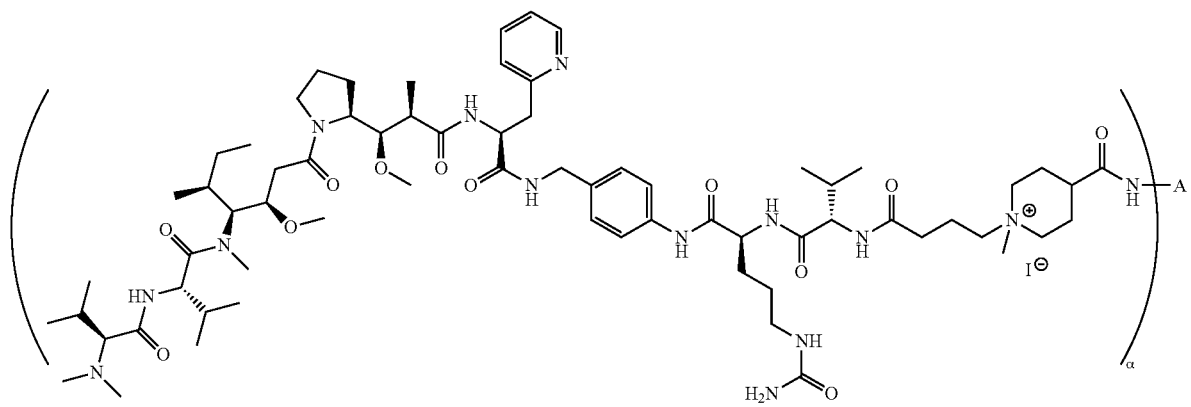
and
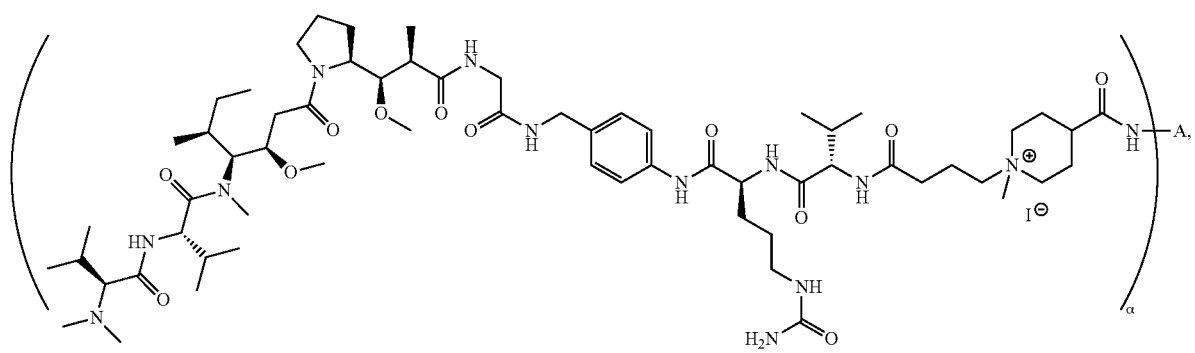
wherein α is an integer of 1, 2, 3 or 4; and A is a group obtained after removing α amino groups from trastuzumab, pertuzumab or sacituzumab;
the conjugate is selected from:
BT001130
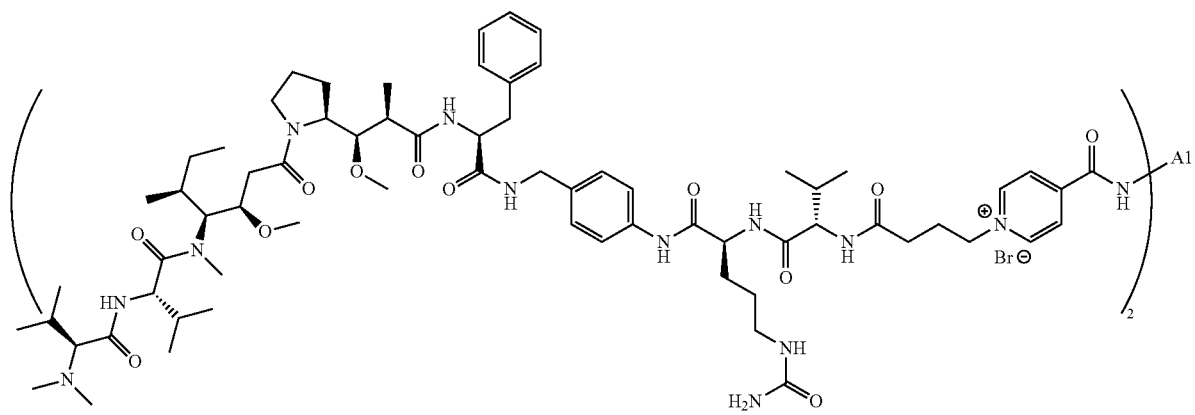

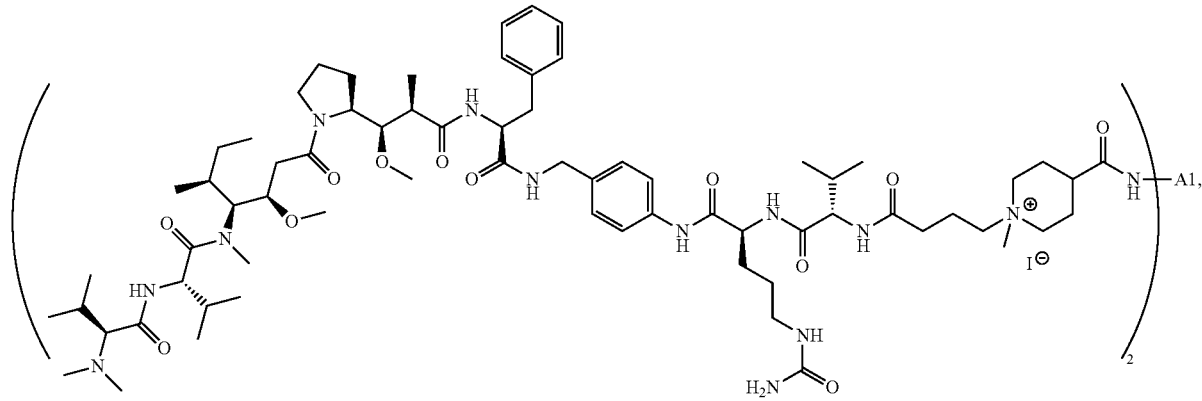
BT001020
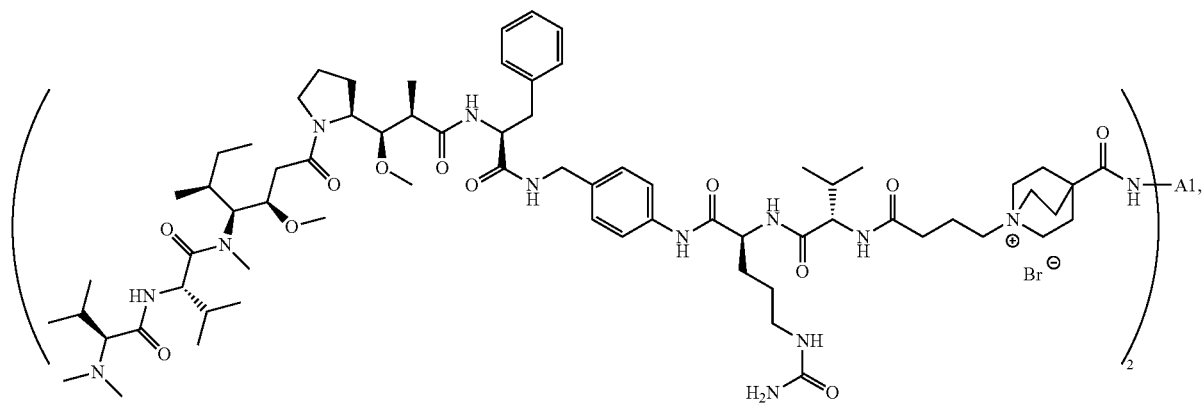
BT001131
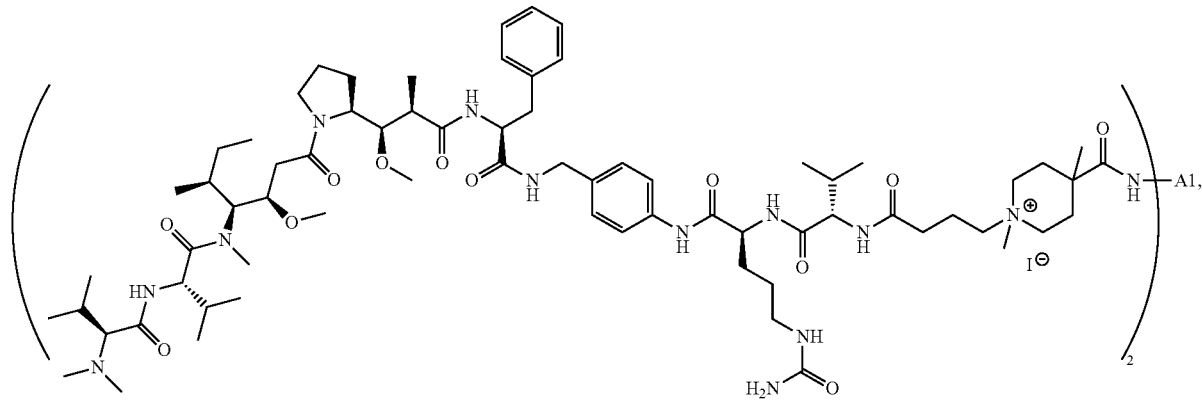
BT001132

-continued
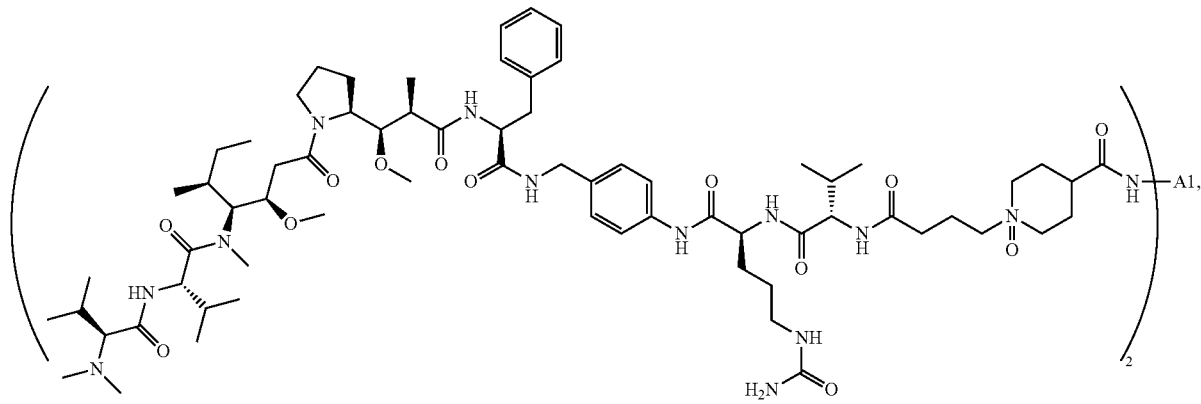
BT001133
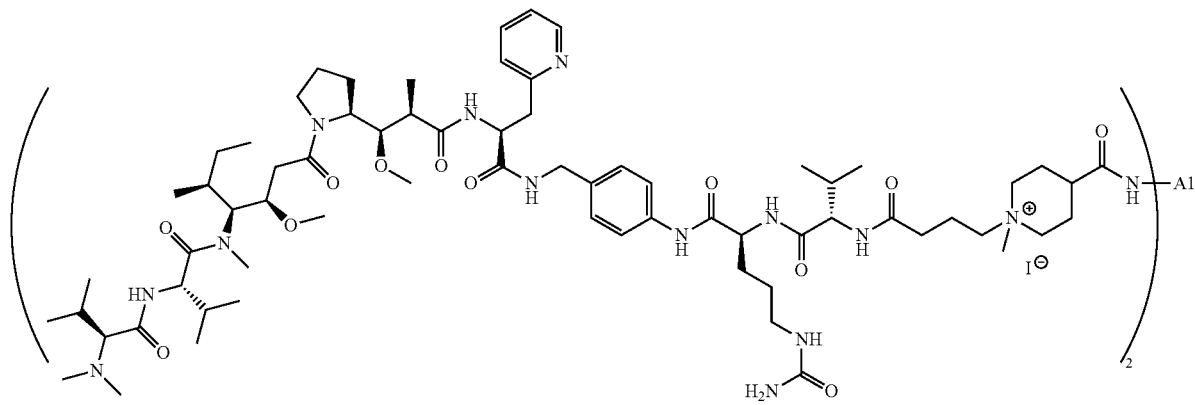
BT001134
and
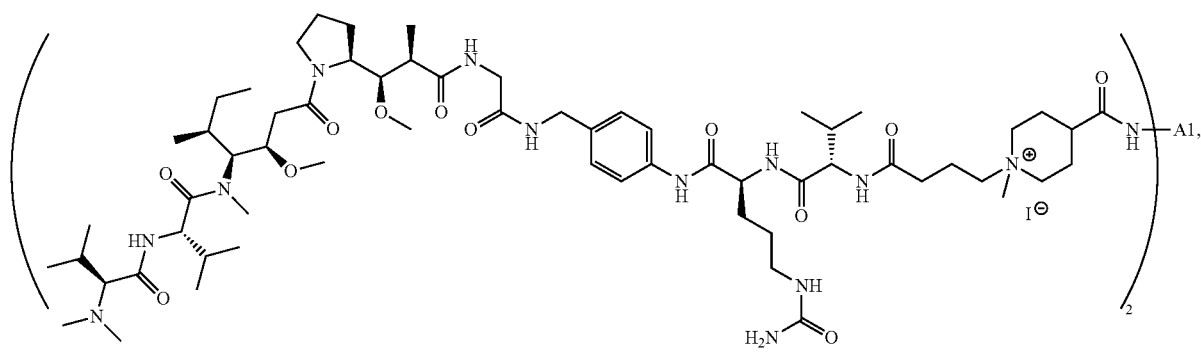
BT001135 wherein A1 is a group obtained after removing 2 amino groups from trastuzumab; or;
the conjugate is selected from:
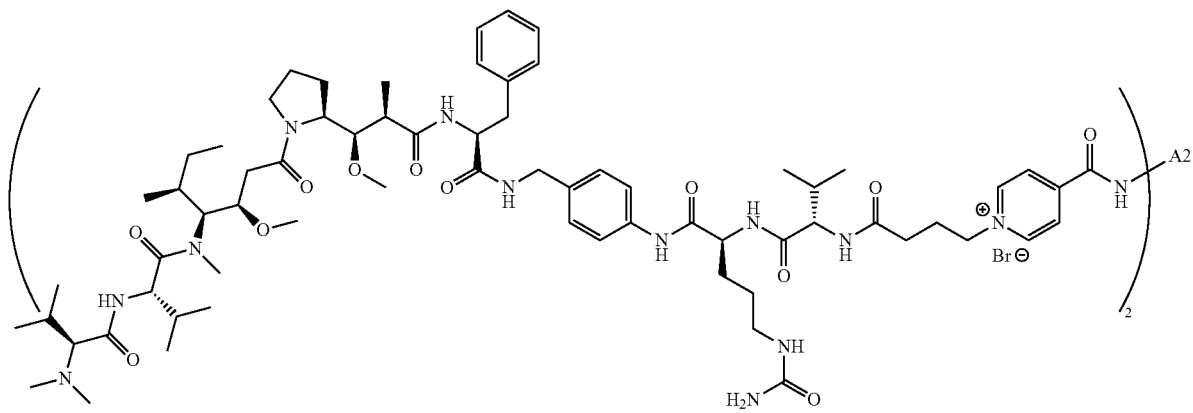
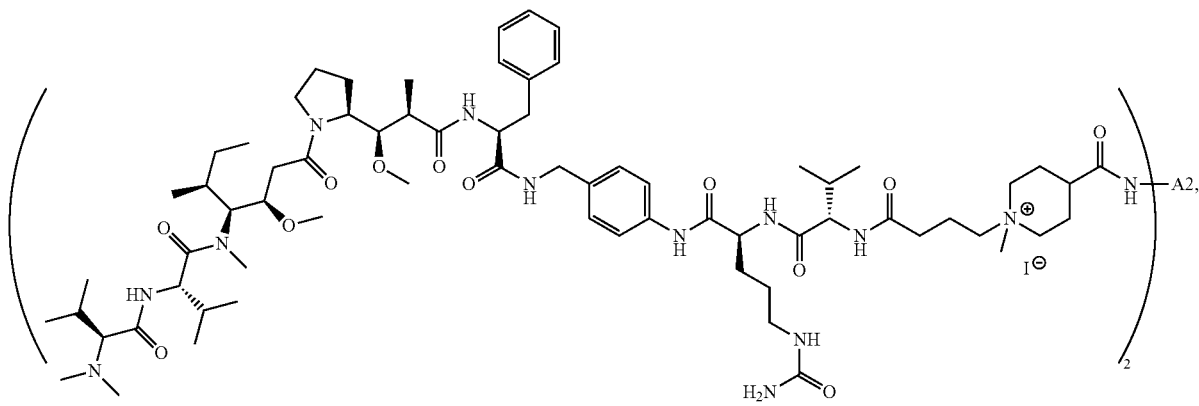
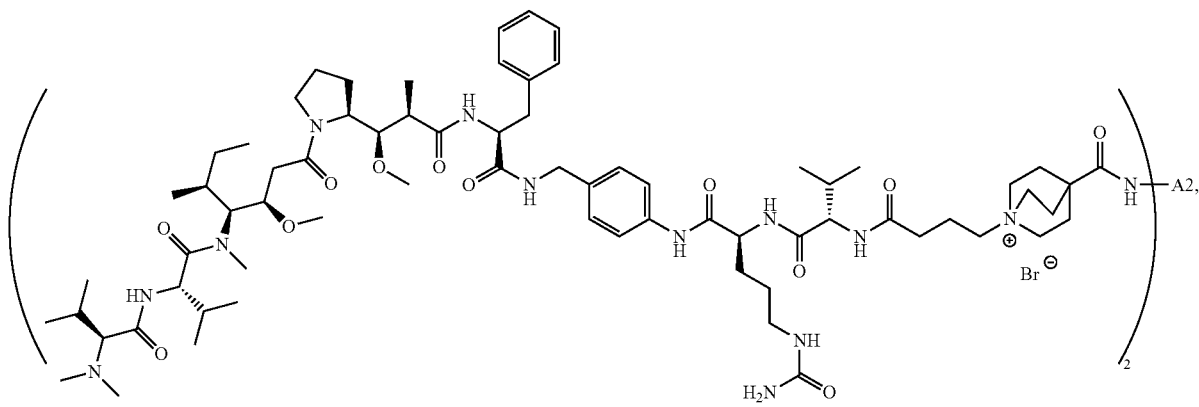

-continued
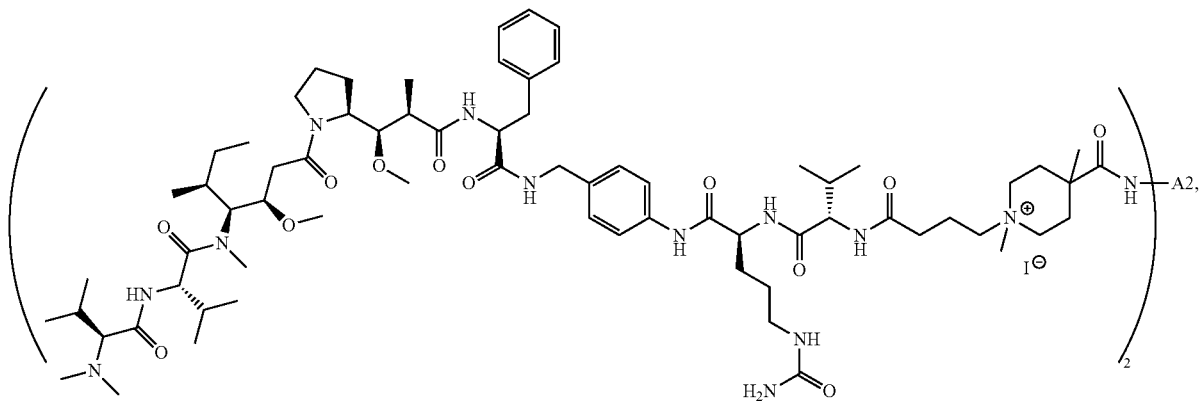
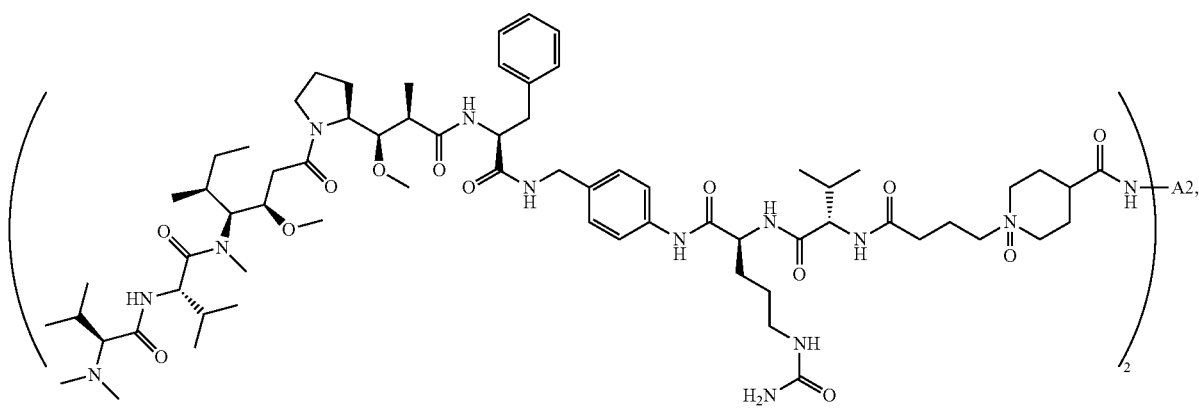
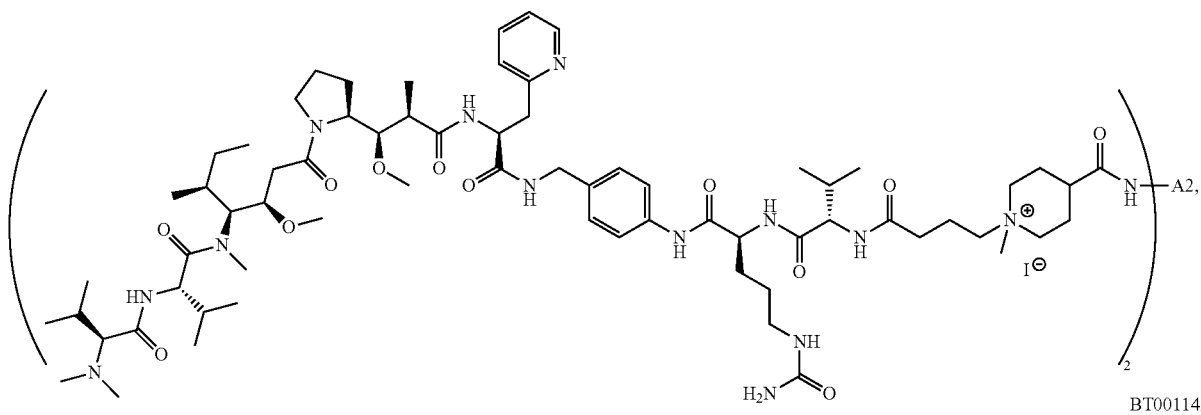
and
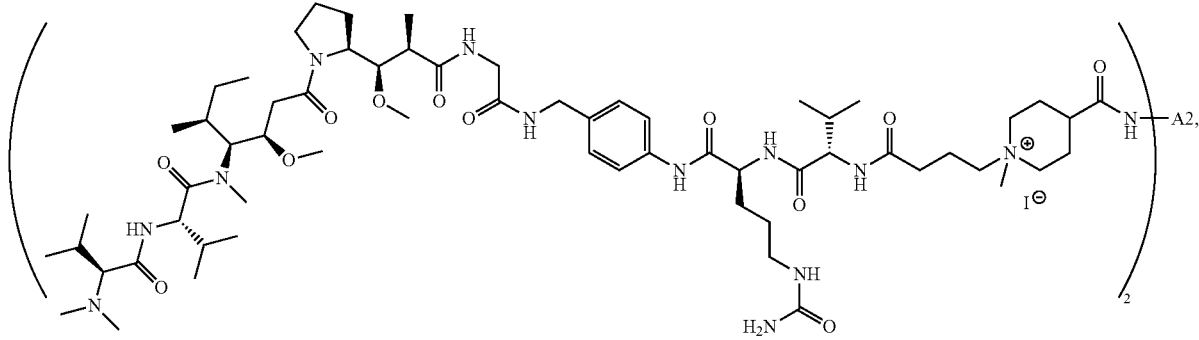

wherein A2 is a group obtained after removing 2 amino groups from pertuzumab; or
the conjugate is selected from:
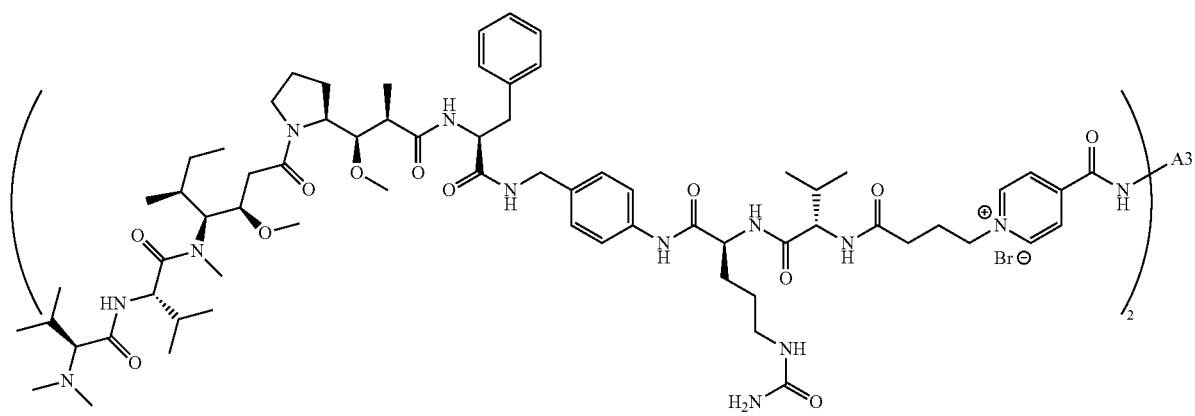
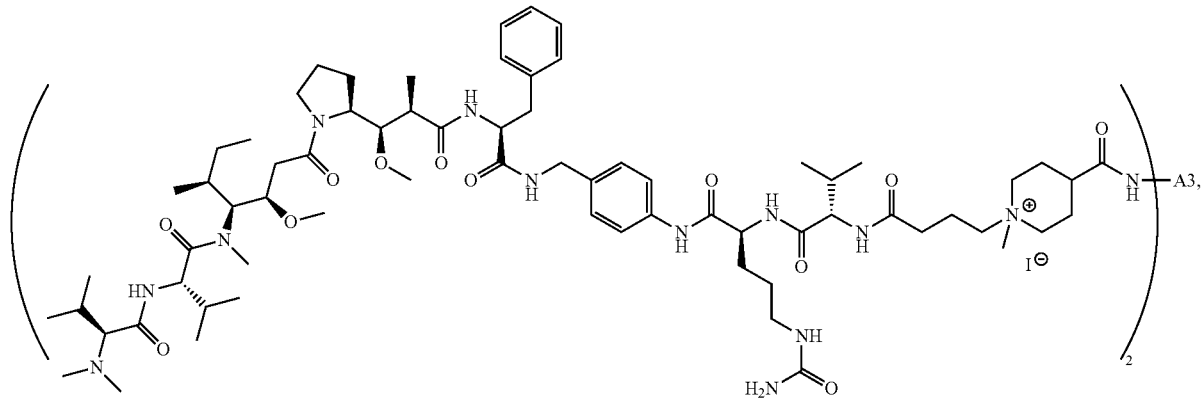
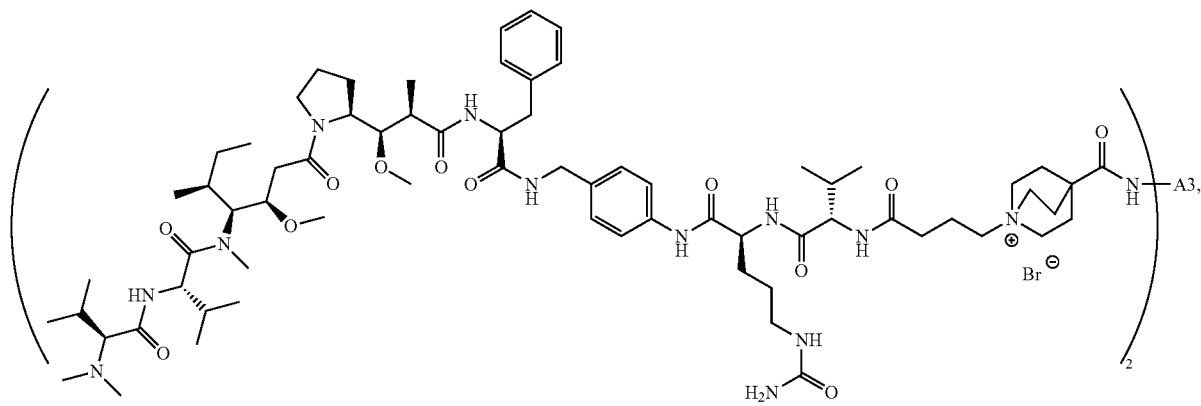

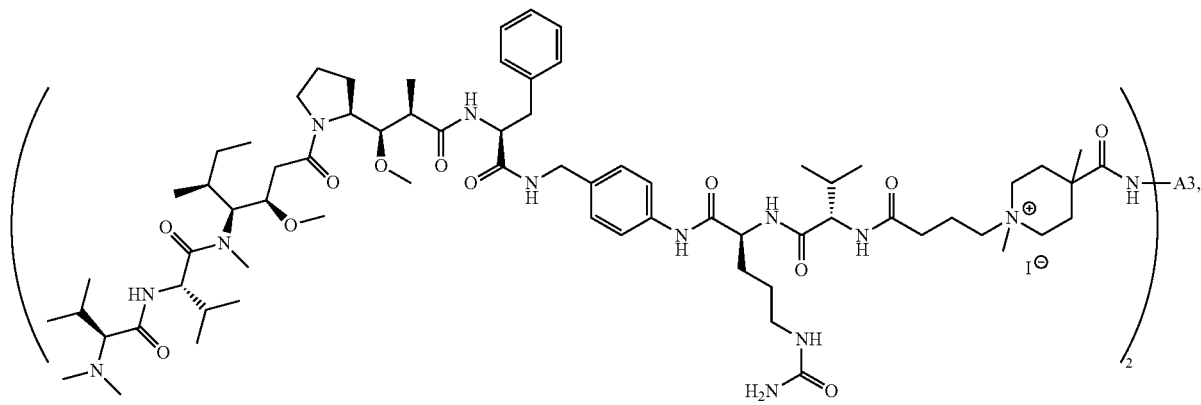
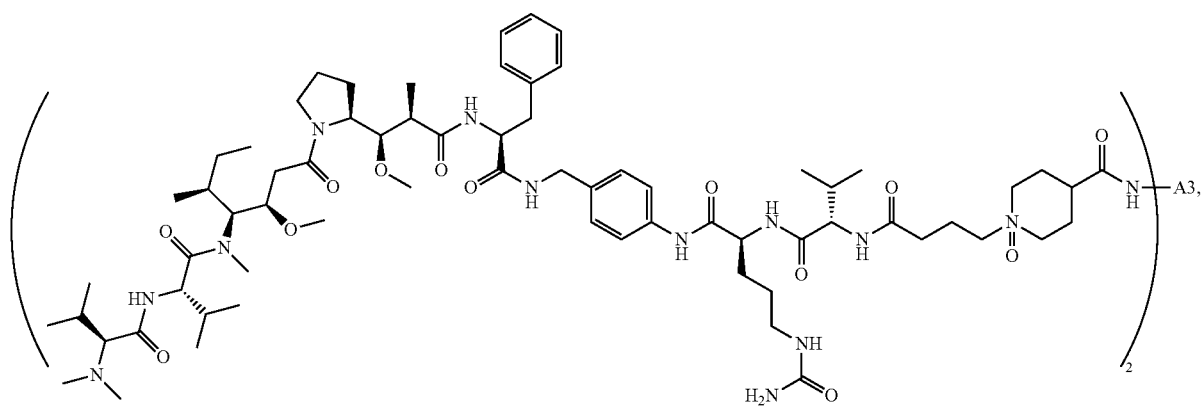
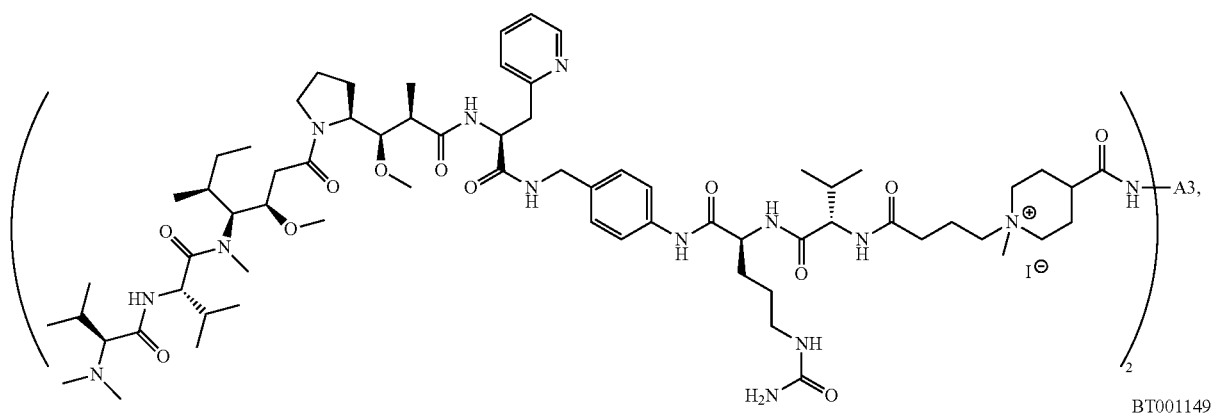
and
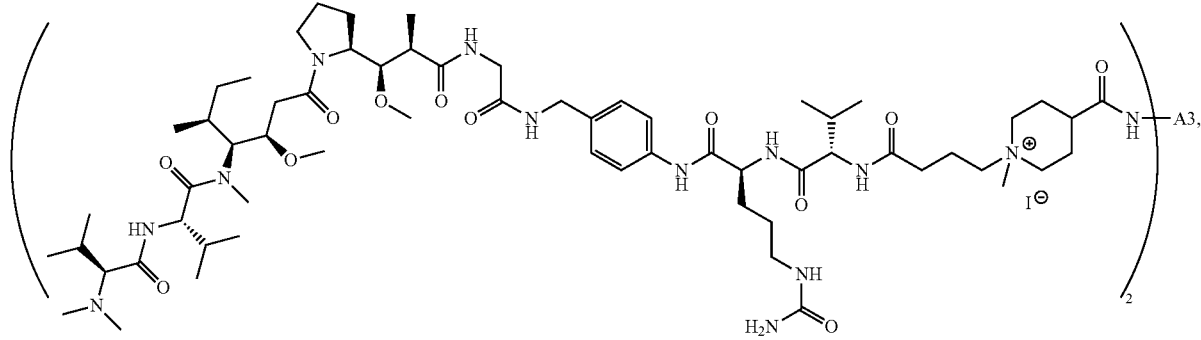

wherein A3 is a group obtained after removing 2 amino groups from sacituzumab; or
the conjugate is selected from:
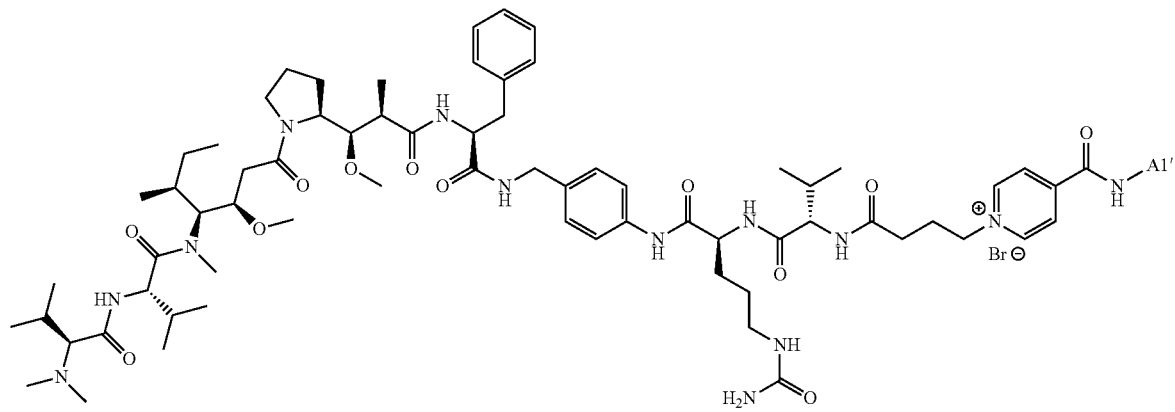
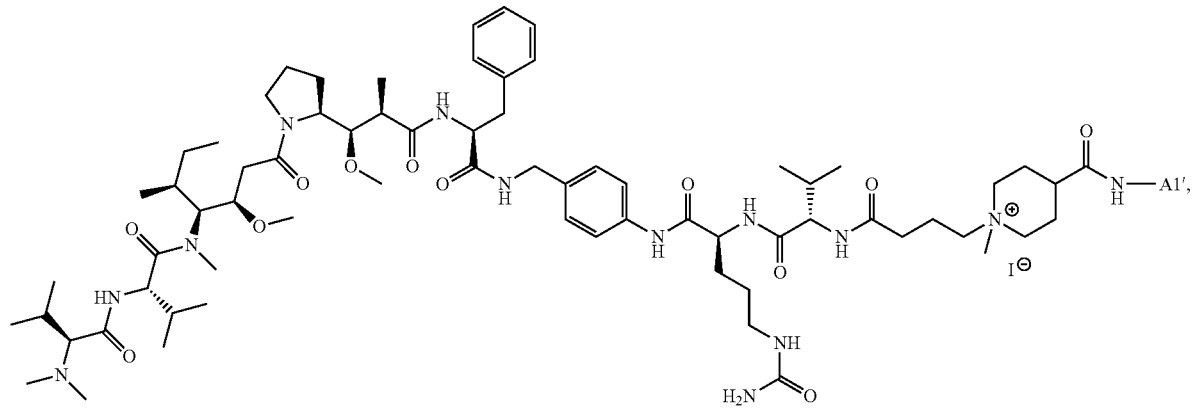
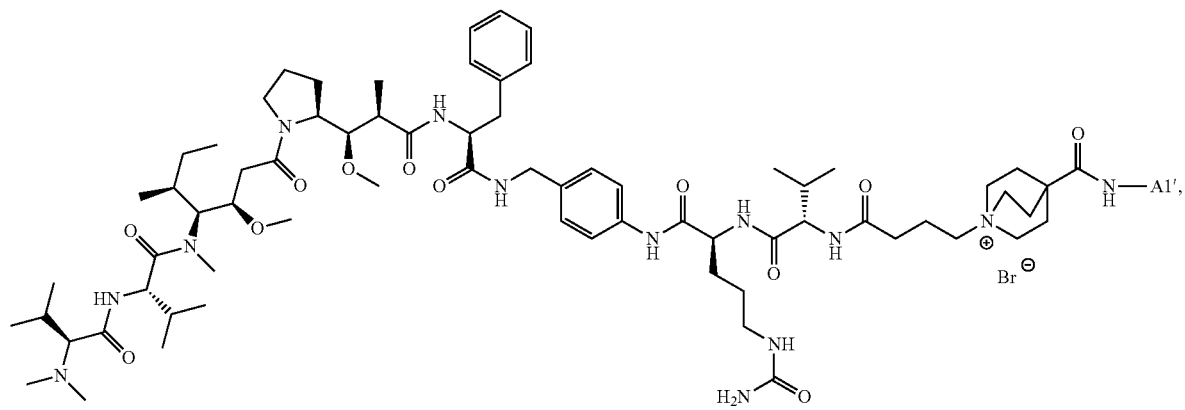

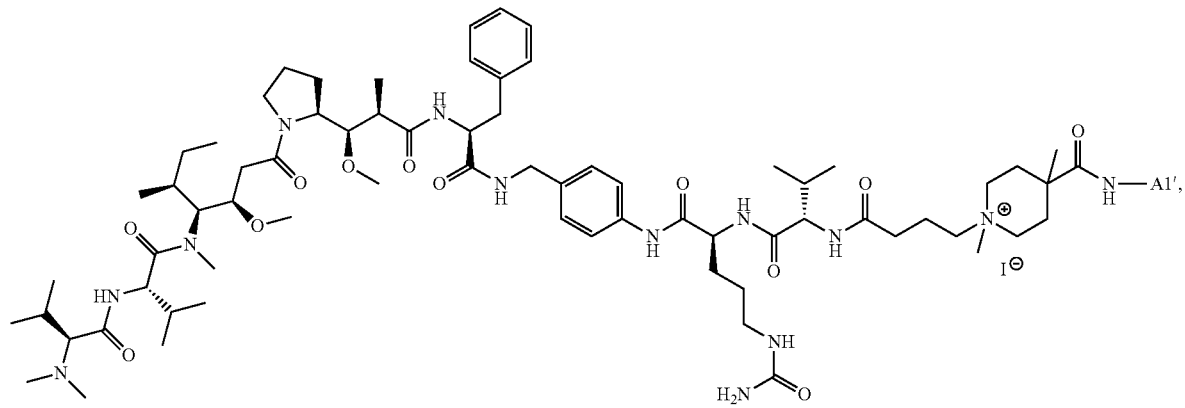
BT001152
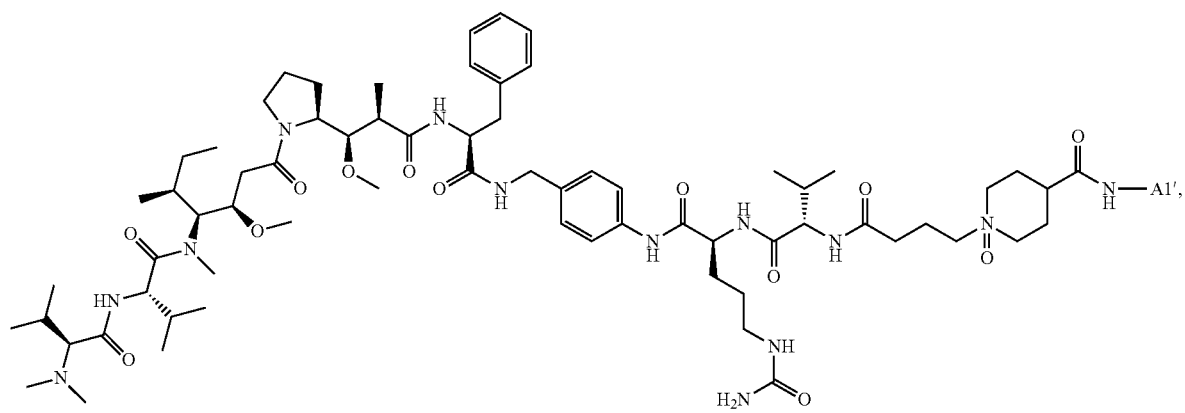
BT001153
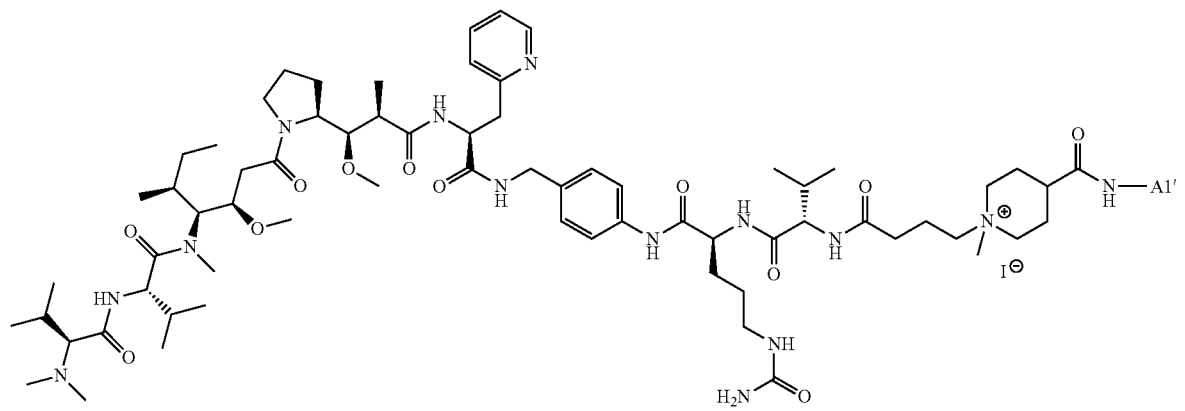
BT001154
and

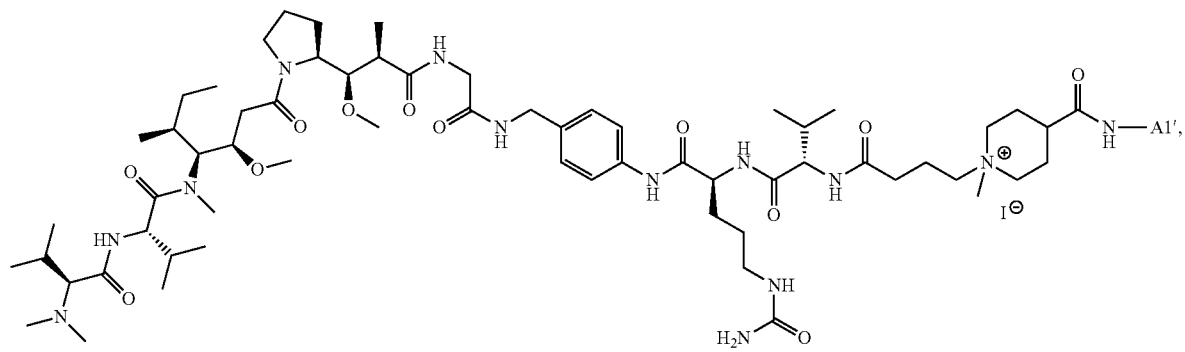
wherein A1' is a group obtained after removing 1 amino group from trastuzumab; or
the conjugate is selected from:
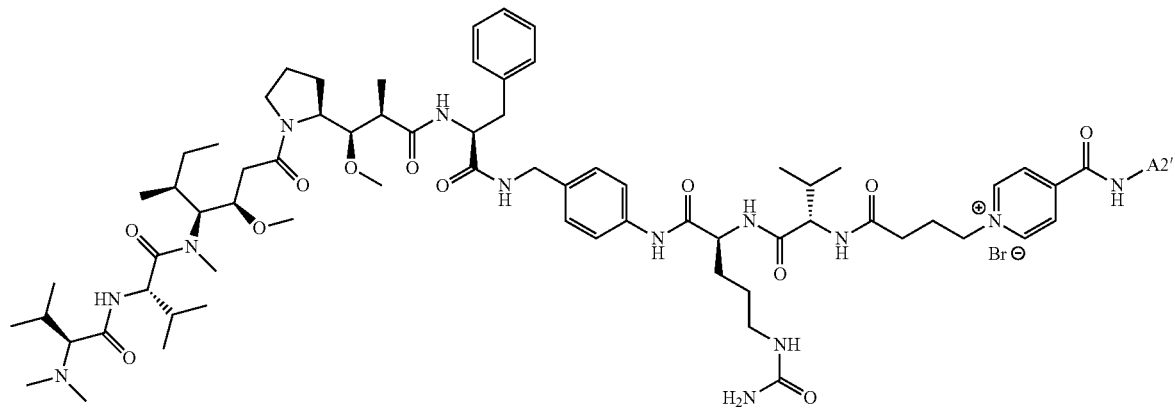
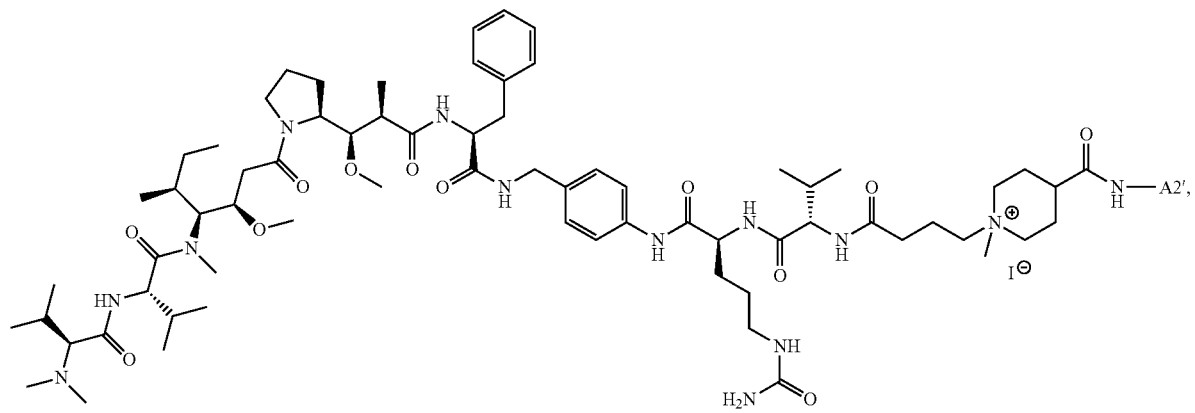

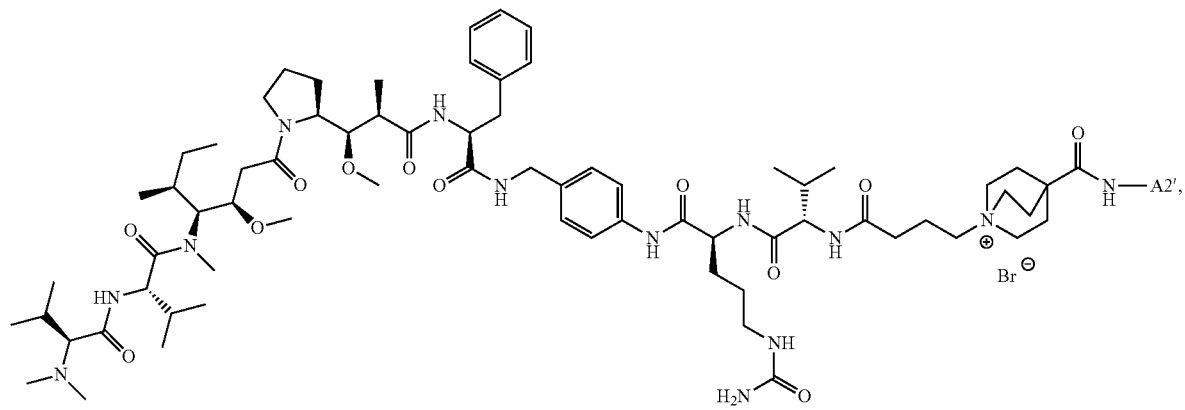
BT001158
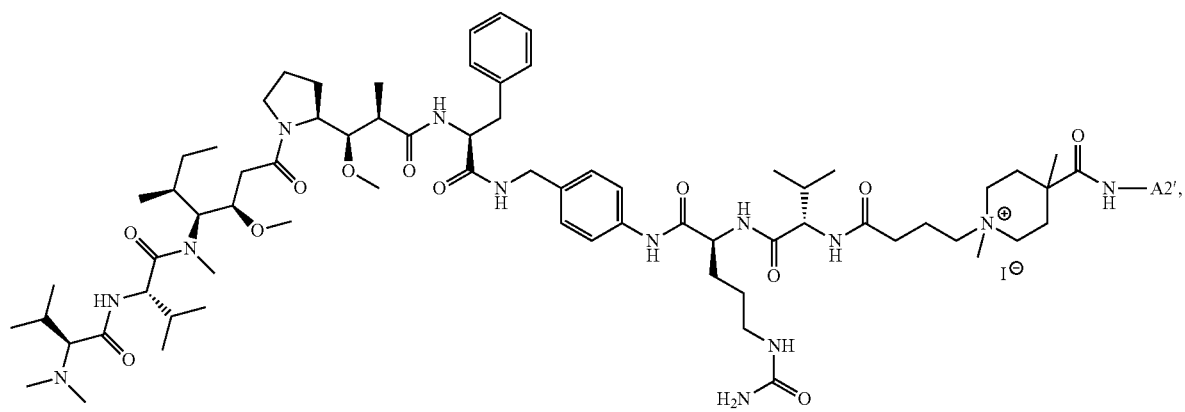
BT001159
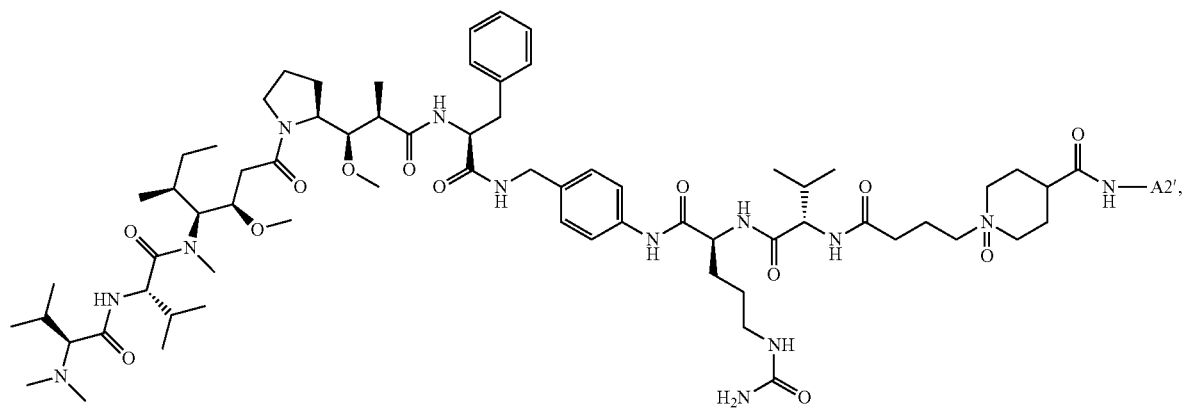
BT001160

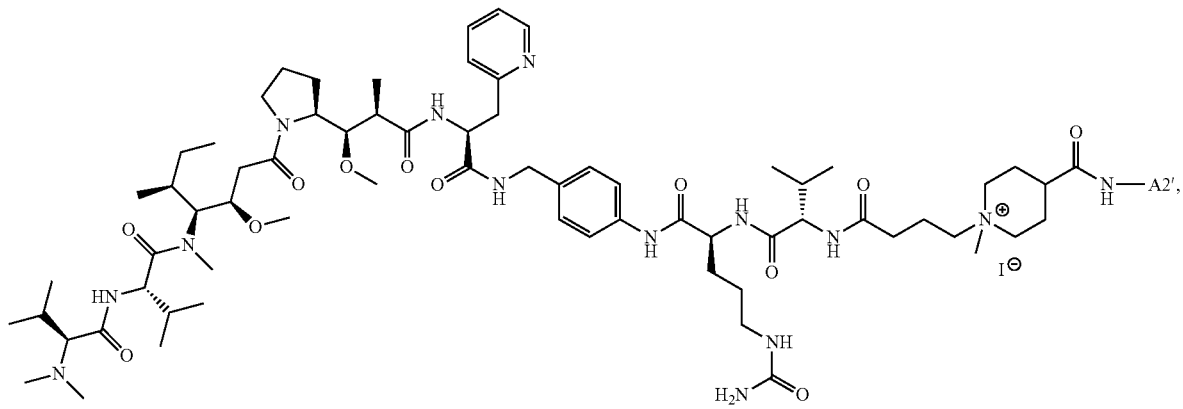
BT001161
and
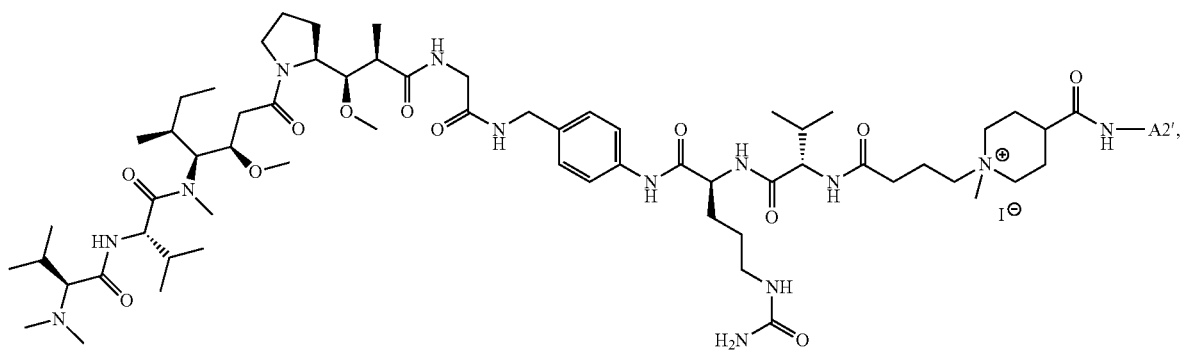
BT001162
wherein A2' is a group obtained after removing 1 amino group from pertuzumab; or
the conjugate is selected from:
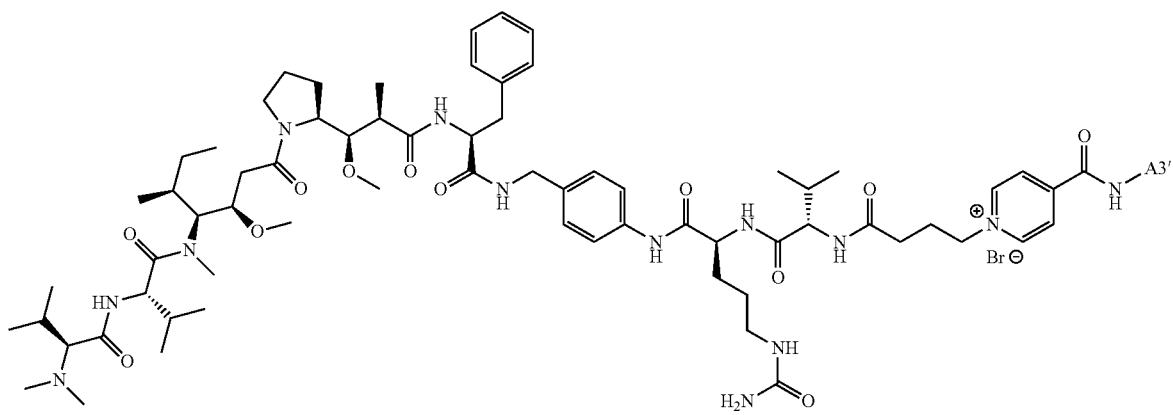
BT001163

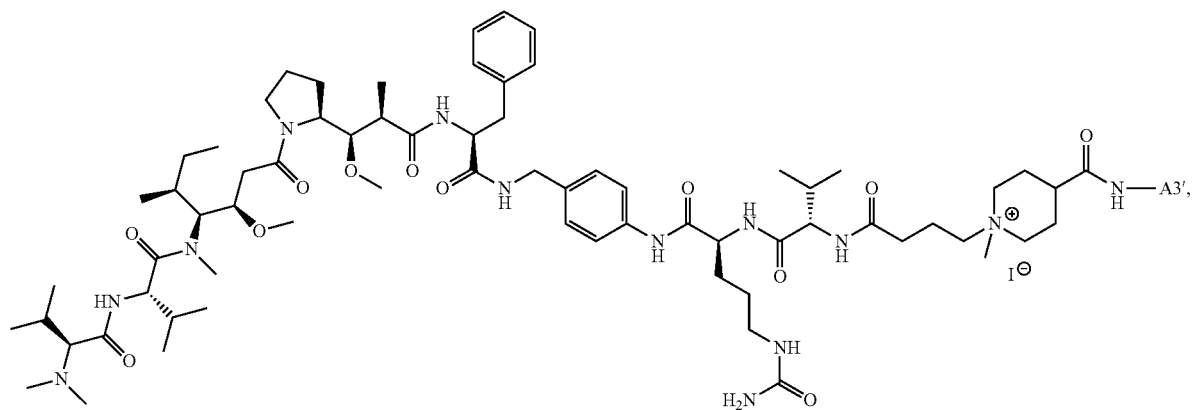
BT001164
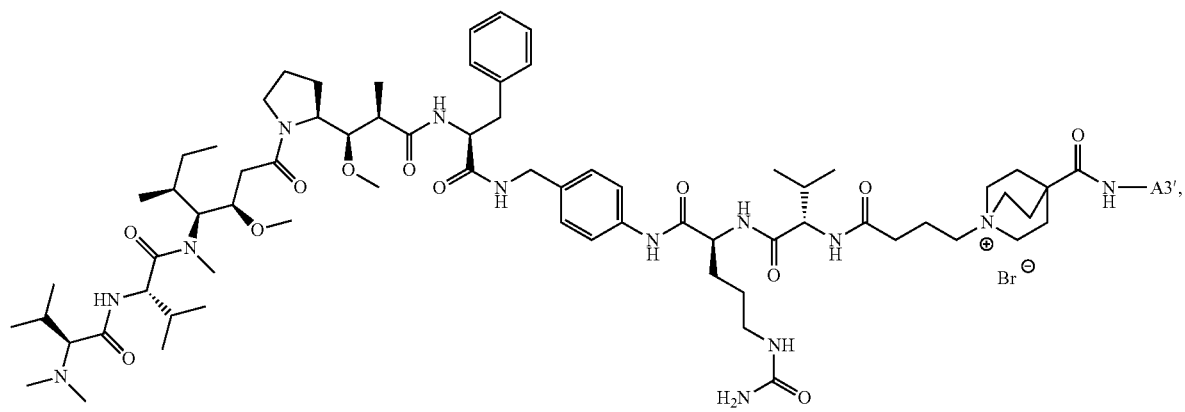
BT001165
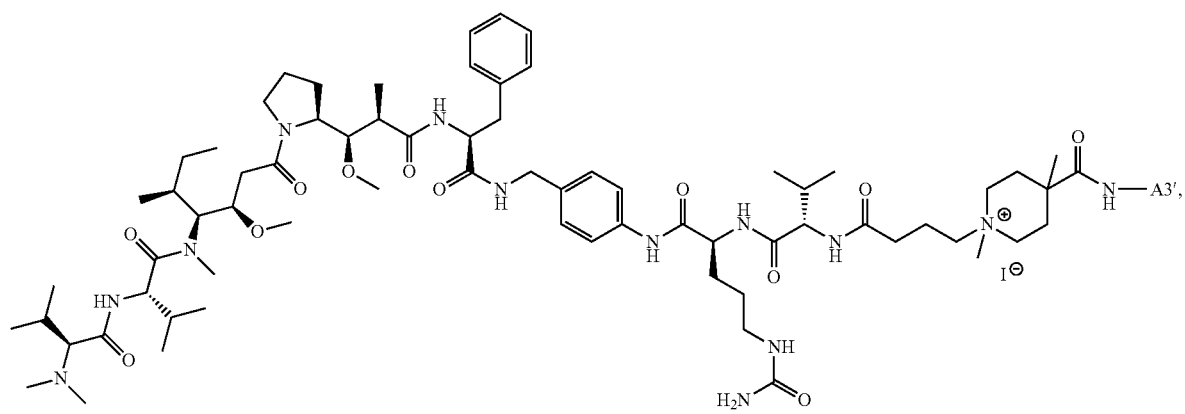
BT001166

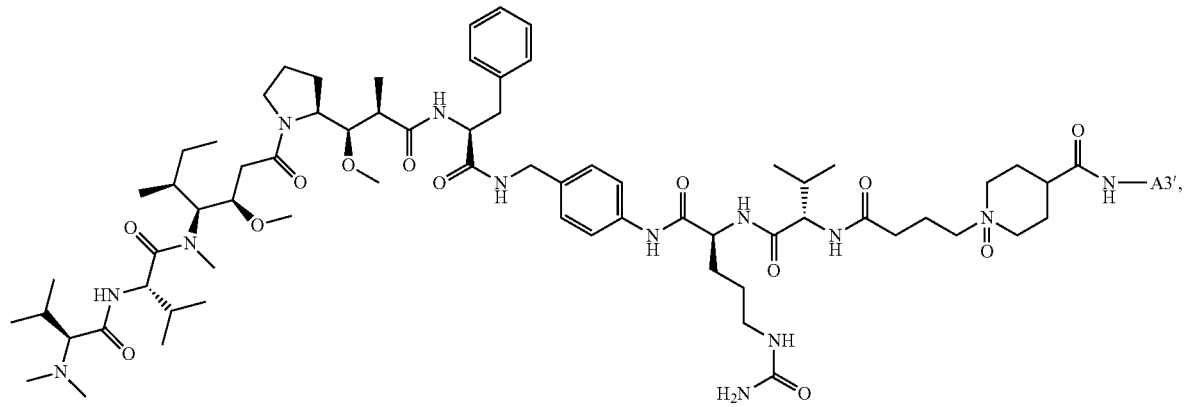

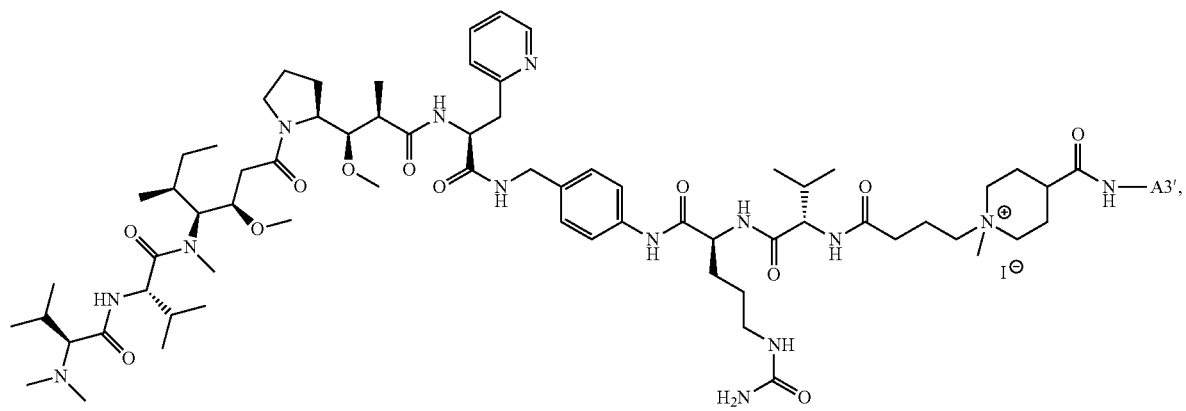

and

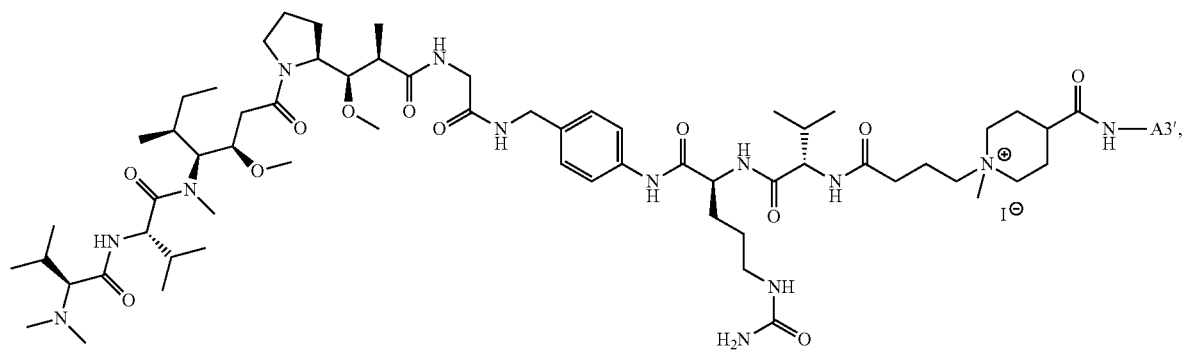

wherein A3' is a group obtained after removing 1 amino group from sacituzumab.

20. A pharmaceutical composition comprising the compound of claim 1 or the pharmaceutically acceptable salt, solvate, hydrate, isomer thereof, or crystalline form or racemate thereof, and comprising one or more medicinal excipients.

21. A method for treating a cancer disease in a subject, comprising the step of administrating the compound of claim 1 or a pharmaceutically acceptable salt, solvate, hydrate, isomer thereof, or crystalline form or racemate thereof, wherein the cancer disease is selected from breast cancer, non-small cell lung cancer, and pancreatic cancer.

22. A method for preparation of the compound of claim 1, or a pharmaceutically acceptable salt, solvate, hydrate, isomer thereof, or crystalline form or racemate thereof, wherein the method is illustrated by the following scheme:

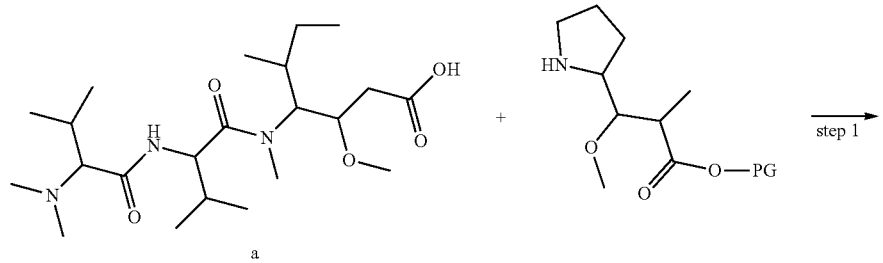

a

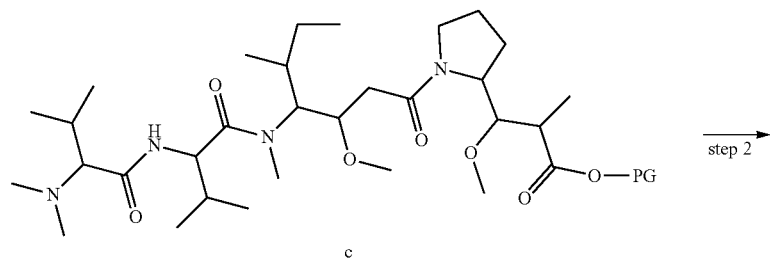

c

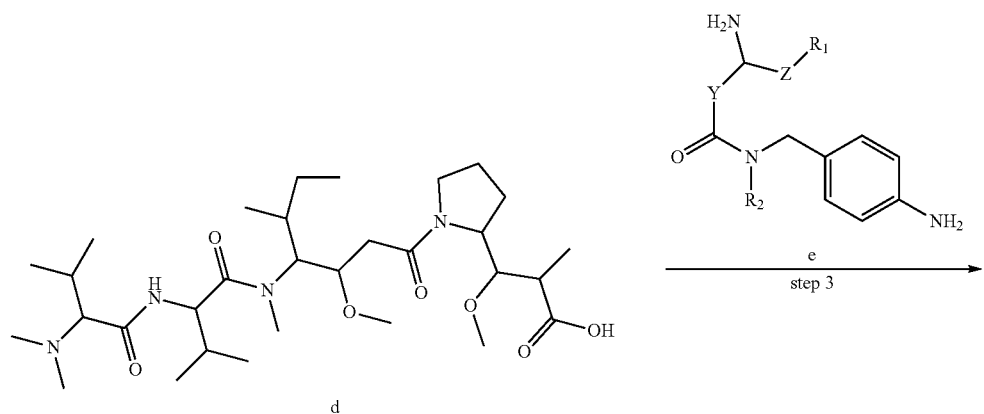

d

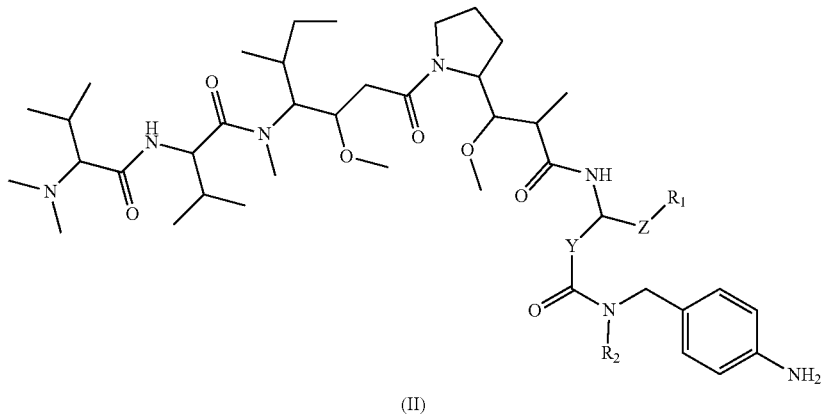

(II)

wherein $R_1$, R2, Y, and Z, are as defined in claim 1, PG is a protecting group;
the method comprises the following steps:
Step 1: reacting compound a with compound b in the presence of a base and/or a condensation reagent to obtain compound c;
Step 2: removing PG from compound c in the presence of hydrogen gas and a catalyst, to obtain compound d;
Step 3: reacting compound d with compound e in the presence of a base and/or a condensation reagent to obtain a compound of formula (I).

23. A method for preparation of the conjugate of claim 3, wherein the method is illustrated by the following scheme:

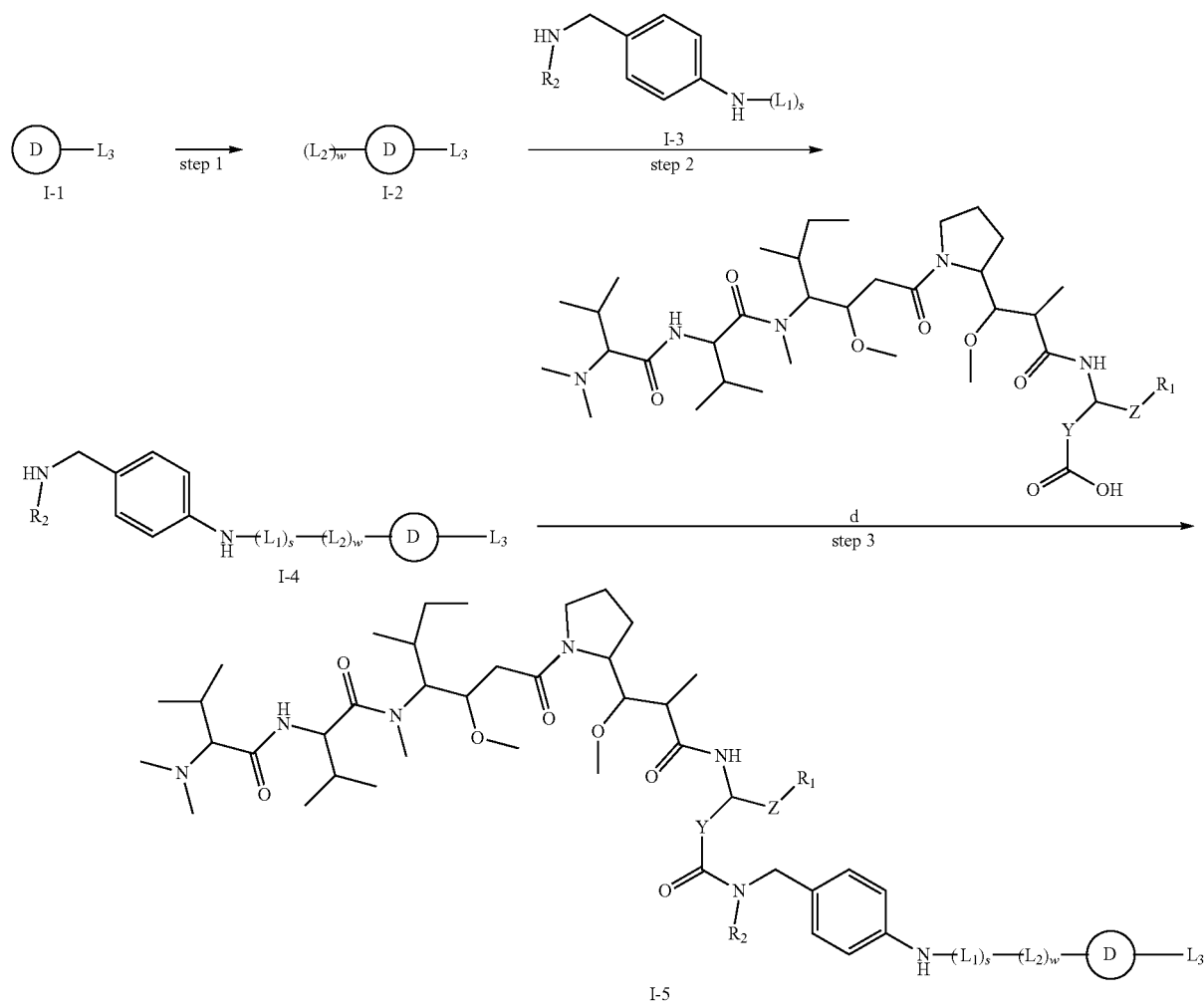

wherein, $R_1$, $R_2$, Y, Z $L_1$, $L_2$, $L_3$, D, s, and w are as defined in claim 3;

the method comprises the following steps:

Step 1: reacting compound I-1 with compound $L_2'$ in the presence of a base and/or a condensation reagent to obtain compound I-2, wherein the compound $L_2'$ is $CH_2Br_2$, $CH_2I_2$, $CH_2BrI$, $Br—(CH_2CH_2O)_y$—$(CH_2)_y$—Br, $Br—(CH_2CH_2O)_y$—$(CH_2)_y$—I, $I—(CH_2CH_2O)_y$—$(CH_2)_y$Br, $I—(CH_2CH_2O)_y$—$(CH_2)_y$—I, or

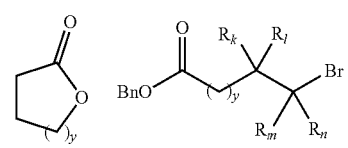

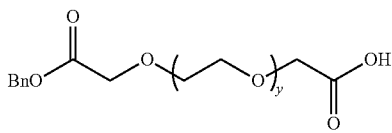

-continued

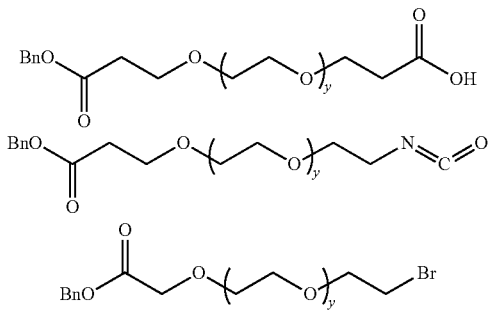

wherein:

$R_k$, $R_l$, $R_m$, and $R_n$, independently of each other, are selected from hydrogen, deuterium, halogen, $CF_3$, CN, $CH_2CN$, $C_{1-6}$ alkyl, $C_{1-6}$ alkoxy, $C_{2-10}$ alkynyl, and $C_{3-6}$ cycloalkyl;

y, independently of each other, is 0, 1, 2, 3, 4, 5, 6, 7, 8, 9 or 10;

Step 2: reacting compound 1-2 with compound 1-3 in the presence of a base and/or a condensation reagent to obtain compound 1-4;

Step 3: reacting compound 1-4 with compound d in the presence of a base and/or a condensation reagent to obtain compound 1-5.

24. The method of claim 23, which further comprises step 4: coupling the compound I-5 with a targeting moiety (E).

25. A method for preparation of the conjugate of claim 3, wherein the method is illustrated by the following scheme:

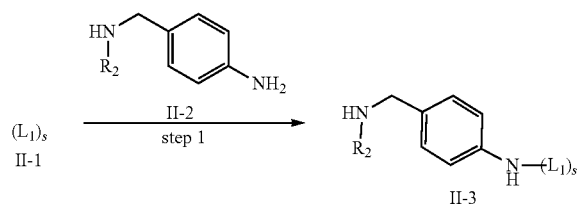
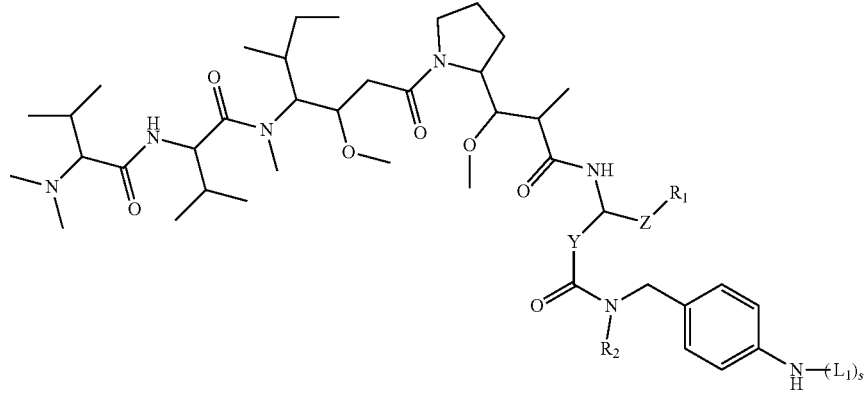
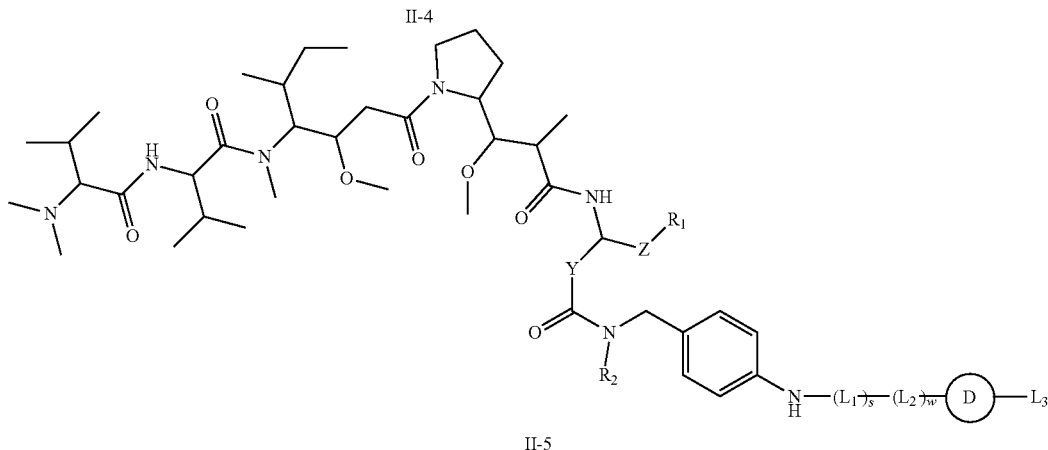

Step 3: reacting compound II-4 with compound I-2 in the presence of a base and/or a condensation reagent to obtain compound II-5.

26. The method of claim 25, which further comprises step 4: coupling the compound II-5 with a targeting moiety (E).

27. A pharmaceutical composition comprising the compound of claim 2 or the pharmaceutically acceptable salt,

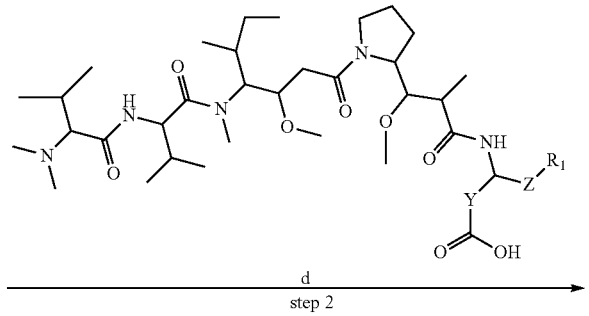
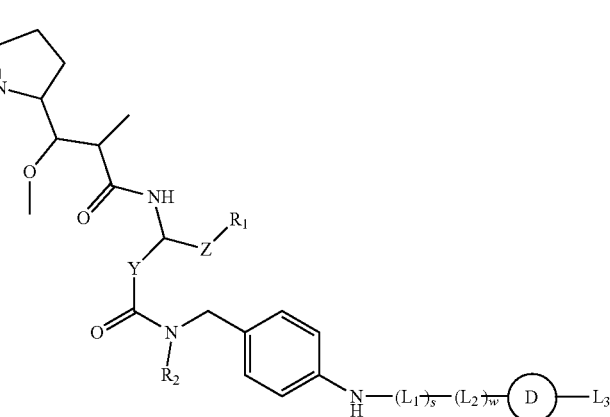

wherein, $R_1$, $R_2$, Y, Z, $L_1$, $L_2$, $L_3$, D, s, and w are as defined in claim 3;

the method comprises the following steps:

Step 1: reacting compound II-1 with compound II-2 in the presence of a base and/or a condensation reagent to obtain compound II-3;

Step 2: reacting compound II-3 with compound d in the presence of a base and/or a condensation reagent to obtain compound II-4;

solvate, hydrate, isomer thereof, or crystalline form or racemate thereof, and comprising one or more medicinal excipients.

28. A pharmaceutical composition comprising the conjugate of claim 3, and comprising one or more medicinal excipients.

29. A pharmaceutical composition comprising the conjugate of claim 19, and comprising one or more medicinal excipients.

30. A method for treating a cancer disease in a subject, comprising the step of administrating the compound of claim 2 or a pharmaceutically acceptable salt, solvate, hydrate, isomer thereof, or crystalline form or racemate thereof, wherein the cancer disease is selected from breast cancer, non-small cell lung cancer, and pancreatic cancer.

31. A method for treating a cancer disease in a subject, comprising the step of administrating the conjugate of claim 3, wherein the cancer disease is selected from breast cancer, non-small cell lung cancer, and pancreatic cancer.

32. A method for treating a cancer disease in a subject, comprising the step of administrating the conjugate of claim 19, wherein the cancer disease is selected from breast cancer, non-small cell lune cancer, and pancreatic cancer.

33. A method for treating a cancer disease in a subject, comprising the step of administrating the pharmaceutical composition of claim 20, wherein the cancer disease is selected from breast cancer, non-small cell lung cancer, and pancreatic cancer.

34. A method for treating a cancer disease in a subject, comprising the step of administrating the pharmaceutical composition of claim 27, wherein the cancer disease is selected from breast cancer, non-small cell lung cancer, and pancreatic cancer.

35. A method for treating a cancer disease in a subject, comprising the step of administrating the pharmaceutical composition of claim 28, wherein the cancer disease is selected from breast cancer, non-small cell lung cancer, and pancreatic cancer.

36. A method for treating a cancer disease in a subject, comprising the step of administrating the pharmaceutical composition of claim 29, wherein the cancer disease is selected from breast cancer, non-small cell lung cancer, and pancreatic cancer.

* * * * *

UNITED STATES PATENT AND TRADEMARK OFFICE
CERTIFICATE OF CORRECTION

PATENT NO. : 11,207,420 B2
APPLICATION NO. : 16/497415
DATED : December 28, 2021
INVENTOR(S) : Jiaqiang Cai et al.

It is certified that error appears in the above-identified patent and that said Letters Patent is hereby corrected as shown below:

In the Claims

In Claim 1, Columns 431-432, delete the structures for formulas (II') and (II") that appear beneath the structure for formula (II).

In Claim 2, Columns 435-436, in the structure for compound T007 (second structure from the top),

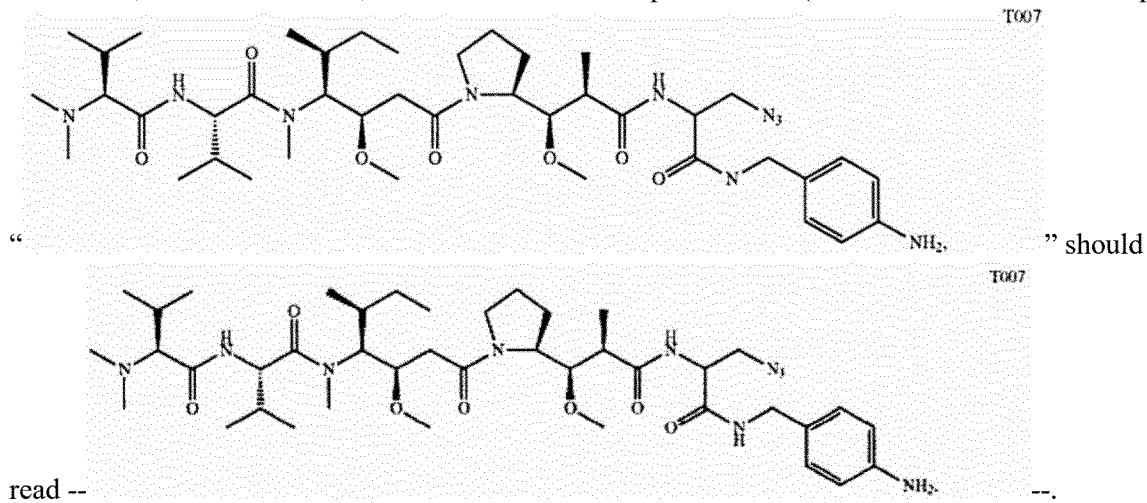

" should read --

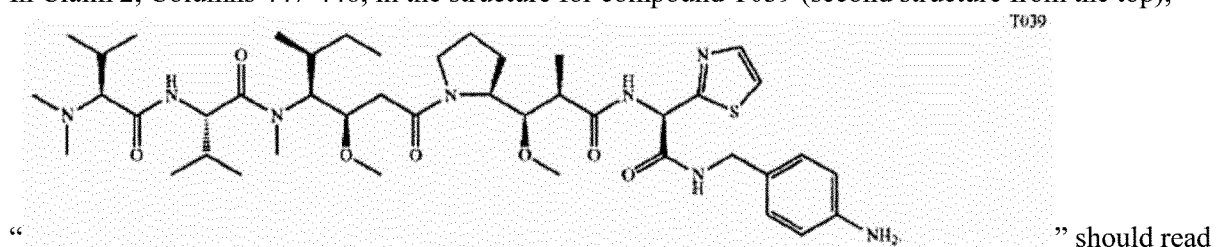

--.

In Claim 2, Columns 447-448, in the structure for compound T039 (second structure from the top),

" should read

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*

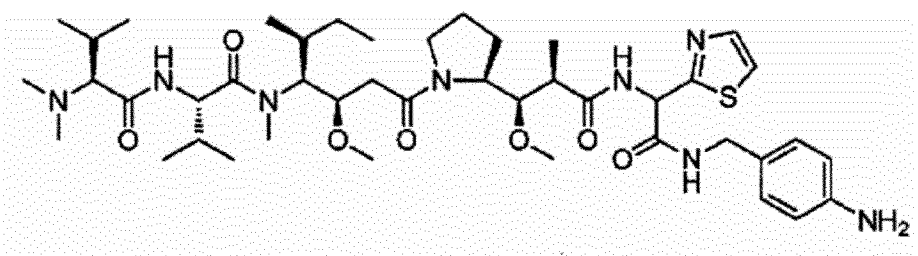
-- T039 --.
In Claim 3, Column 451, Lines 25-37, in the third structure from the left,
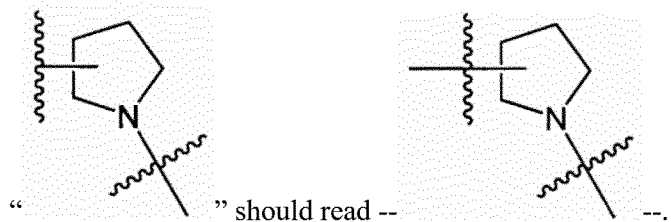
" " should read -- --.
In Claim 5, Column 452, Lines 16-21, after the structure
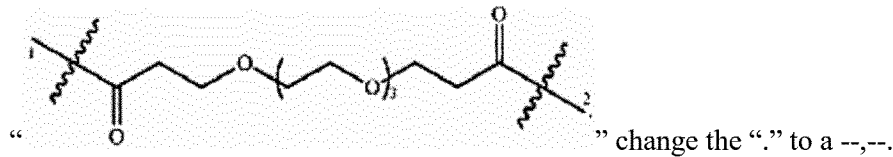
" " change the "." to a --,--.
In Claim 8, Column 453, Lines 40-51, in the third structure from the left,
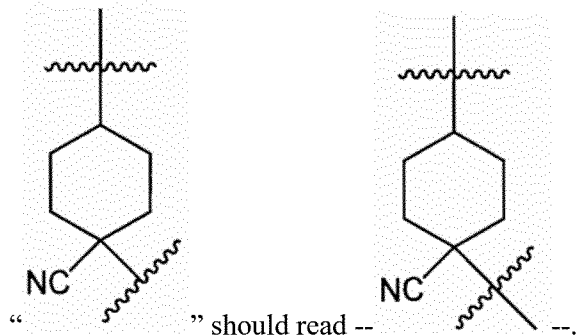
" " should read -- --.
In Claim 8, Column 454, Lines 44-54, in the third structure from the left,
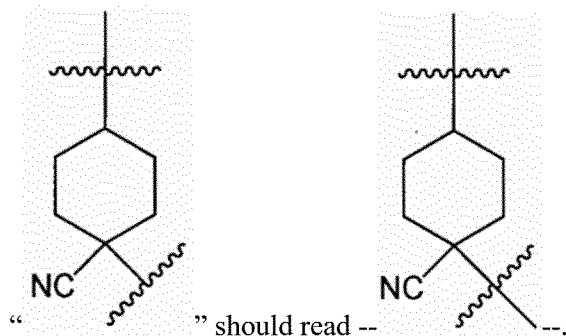
" " should read -- --.

In Claim 9, Column 455, Lines 30-40, in the second structure from the left,
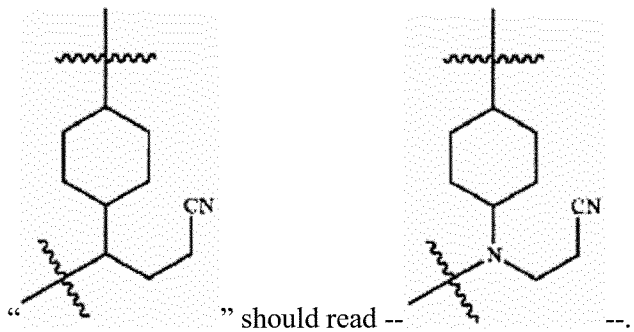
In Claim 10, Column 457, Lines 55-67, in the third structure from the left,
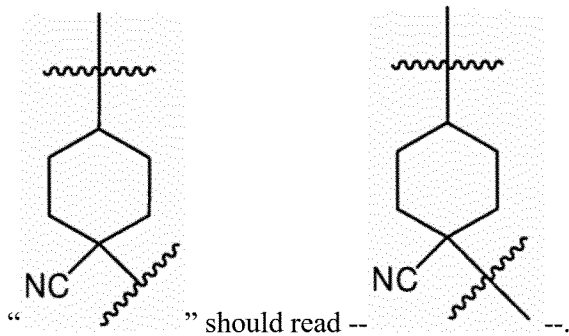
In Claim 10, Column 459, Lines 1-13, in the third structure from the left,
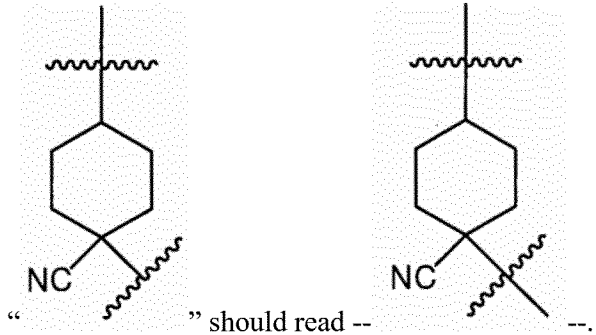
In Claim 11, Column 461, Lines 6-16, in the first structure on the left,
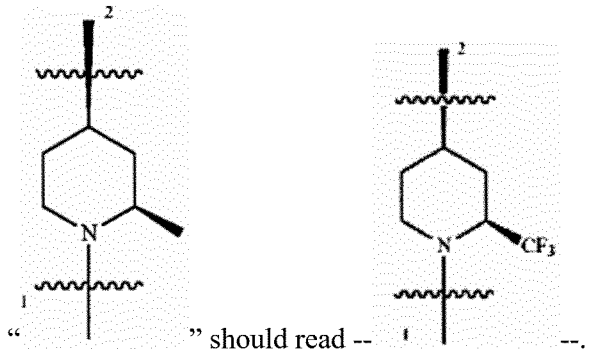
In Claim 11, Column 461, Line 20, "V. is a counterion." should read --V · is a counterion.--.

In Claim 17, Columns 477-478, in the structure for compound TL042 (second structure from the top),
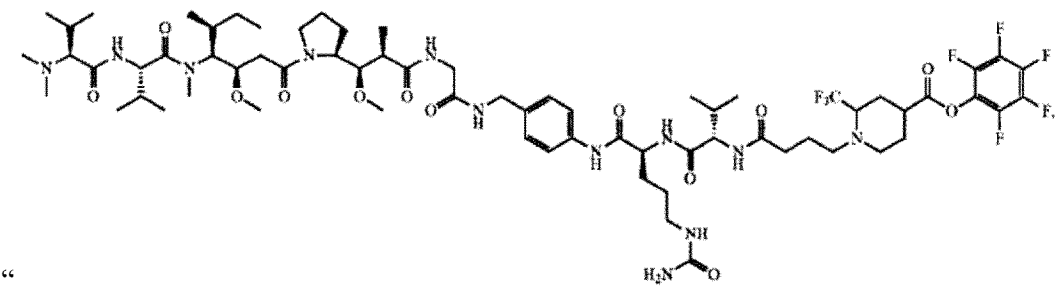
" 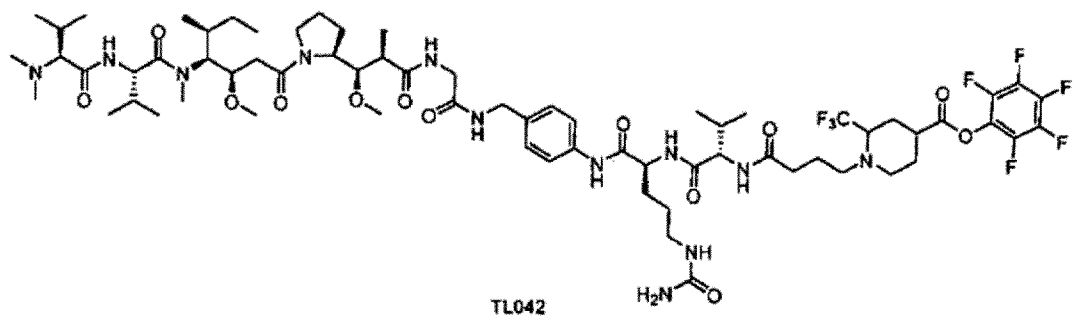 " should read -- -- .
In Claim 18, Columns 497-498, after the second structure from the top and before the third structure from the top, insert --and--.
In Claim 18, Columns 497-498, in the third structure from the top,
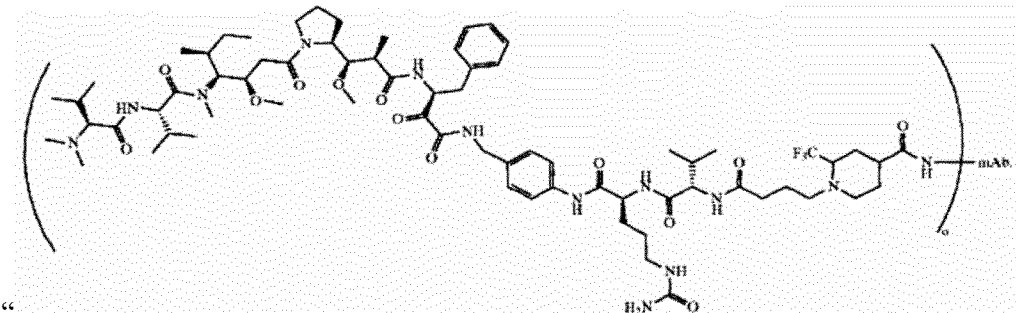
" " should read -- 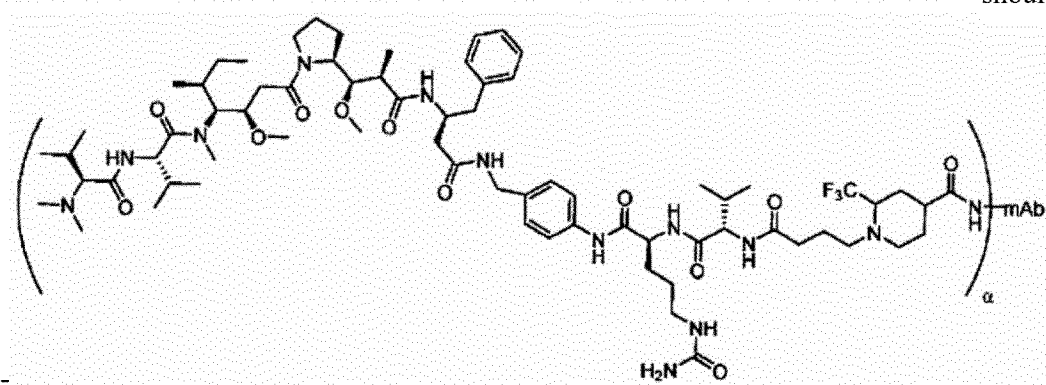 -- .

In Claim 19, Column 499, Line 1, after "which is selected from:" and before the structure for compound BT001005, insert the following missing structure for compound BT001003:

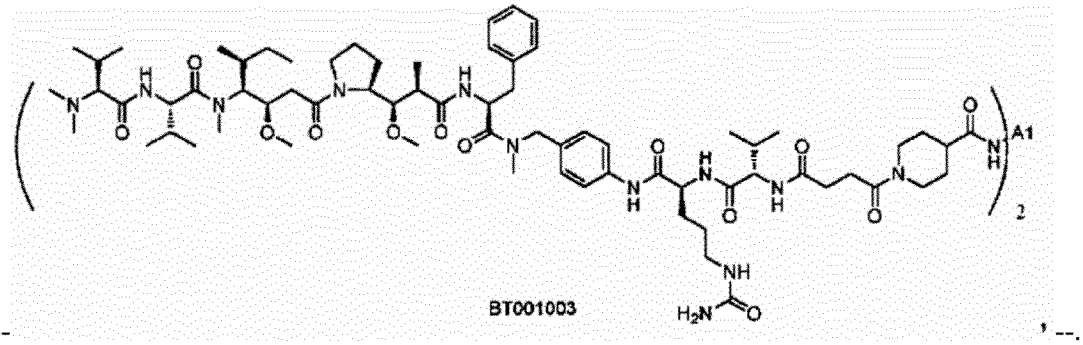
--                                                                                   , --.

In Claim 22, Columns 595-596, in the top row of the scheme, underneath the second structure from the left, "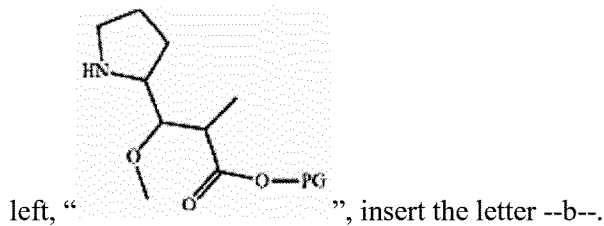", insert the letter --b--.

In Claim 22, Column 595, Line 62, "R2, Y, and Z, are as defined" should read --$R_2$, Y, and Z are as defined--.

In Claim 23, Column 597, Line 42, "Z $L_1$," should read --Z, $L_1$,--.

In Claim 23, Column 598, Line 65, "compound 1-2 with compound 1-3" should read --compound I-2 with compound I-3--.

In Claim 23, Column 598, Line 67, "compound 1-4;" should read --compound I-4;--.

In Claim 23, Column 599, Line 1, "compound 1-4" should read --compound I-4--.

In Claim 23, Column 599, Line 3, "compound 1-5." should read --compound I-5.--.

In Claim 32, Column 601, Line 14, "non-small cell lune cancer," should read --non-small cell lung cancer,--.